(12) United States Patent
Wrona et al.

(10) Patent No.: US 10,919,885 B2
(45) Date of Patent: Feb. 16, 2021

(54) COMPOUNDS AND USES THEREOF

(71) Applicant: Yumanity Therapeutics, Inc., Cambridge, MA (US)

(72) Inventors: Iwona Wrona, Sharon, MA (US); Parcharee Tivitmahaisoon, Boston, MA (US); Daniel Tardiff, Arlington, MA (US); Bhaumik Pandya, Bedford, MA (US); Kerem Ozboya, Cambridge, MA (US); Matthew Lucas, Lexington, MA (US); Bertrand Le Bourdonnec, Northborough, MA (US)

(73) Assignee: Yumanity Therapeutics, Inc., Boston, MA (US)

( * ) Notice: Subject to any disclaimer, the term of this patent is extended or adjusted under 35 U.S.C. 154(b) by 0 days.

(21) Appl. No.: 16/393,183

(22) Filed: Apr. 24, 2019

(65) Prior Publication Data
US 2019/0330198 A1 Oct. 31, 2019

Related U.S. Application Data

(60) Provisional application No. 62/662,673, filed on Apr. 25, 2018.

(51) Int. Cl.

| | | |
|---|---|---|
| *C07D 413/14* | (2006.01) | |
| *C07D 413/06* | (2006.01) | |
| *C07D 413/12* | (2006.01) | |
| *C07D 487/10* | (2006.01) | |
| *C07D 491/107* | (2006.01) | |
| *C07D 487/04* | (2006.01) | |
| *C07D 417/14* | (2006.01) | |
| *C07D 261/08* | (2006.01) | |

(52) U.S. Cl.
CPC ......... *C07D 413/14* (2013.01); *C07D 261/08* (2013.01); *C07D 413/06* (2013.01); *C07D 413/12* (2013.01); *C07D 417/14* (2013.01); *C07D 487/04* (2013.01); *C07D 487/10* (2013.01); *C07D 491/107* (2013.01)

(58) Field of Classification Search
CPC .................................................. C07D 413/14
See application file for complete search history.

(56) References Cited

U.S. PATENT DOCUMENTS

| | | |
|---|---|---|
| 7,074,809 B2 | 7/2006 | Arora et al. |
| 7,767,677 B2 | 8/2010 | Kamboj et al. |
| 8,207,147 B2 | 6/2012 | Fyfe et al. |
| 8,207,199 B2 | 6/2012 | Aoki et al. |
| 8,563,539 B2 | 10/2013 | Baldino et al. |
| 2008/0021028 A1 | 1/2008 | Swinnen et al. |
| 2008/0207587 A1 | 8/2008 | Kamboj et al. |
| 2009/0170828 A1 | 7/2009 | Isabel et al. |
| 2009/0239810 A1 | 9/2009 | Sundaresan et al. |
| 2010/0029722 A1 | 2/2010 | Dales et al. |
| 2012/0010186 A1 | 1/2012 | Lachance et al. |
| 2012/0196844 A1 | 8/2012 | Alper et al. |
| 2013/0225529 A1 | 8/2013 | Rigas |
| 2015/0051206 A1 | 2/2015 | Loren et al. |
| 2015/0252032 A1 | 9/2015 | Bolli et al. |

FOREIGN PATENT DOCUMENTS

| | | |
|---|---|---|
| WO | WO-2006/130986 A1 | 12/2006 |
| WO | WO-2007/120702 A2 | 10/2007 |
| WO | WO-2009/060053 A1 | 5/2009 |
| WO | WO-2010/022055 A2 | 2/2010 |
| WO | WO-2010/039186 A2 | 4/2010 |
| WO | WO-2010/108268 A1 | 9/2010 |
| WO | WO-2013/056148 A2 | 4/2013 |
| WO | WO-2018/081167 A1 | 5/2018 |

OTHER PUBLICATIONS

Huestis et al., "The Vinyl Moiety as a Handle for regiocontrol in the Preparation of Unsymmetrical 2,3-Aliphatic-Substituted Indoles and Pyrroles," Agnew Chem Int Edit 50(6):1338-41 (2011).
Jarvis et al., "A-803467, a potent and selective Nav1.8 sodium channel blocker, attenuates neuropathic and inflammatory pain in the rat," Proc Natl Acad Sci U.S.A. 104(20):8520-5 (2007).
International Search Report and Written Opinion for International Application No. PCT/US2019/28928, dated Sep. 30, 2019 (15 pages).
PubChem Compound Summary for CID 126485826, dated Apr. 22, 2017 (6 pages).
PubChem Compound Summary for CID 127012056, dated Jun. 2, 2017 (12 pages).
PubChem Compound Summary for CID 127868748, dated Jun. 18, 2017 (9 pages).
PubChem Compound Summary for CID 53003909, dated Jun. 21, 2011 (7 pages).
PubChem Compound Summary for CID 56980069, dated Jun. 13, 2012 (11 pages).
PubChem Compound Summary for CID 7059272, dated Jul. 29, 2006 (12 pages).
PubChem Compound Summary for CID 15985883, "5-[5-[4-[(4-Chlorophenyl)methyl]piperidin-1-yl]-5-oxopentyl]-1 H-pyridin-2-one," created Mar. 27, 2007, retrieved Mar. 25, 2020 (7 pages).

*Primary Examiner* — Paul V Ward
(74) *Attorney, Agent, or Firm* — Clark & Elbing LLP

(57) ABSTRACT

The present invention features compounds useful in the treatment of neurological disorders. The compounds of the invention, alone or in combination with other pharmaceutically active agents, can be used for treating or preventing neurological disorders.

16 Claims, No Drawings

COMPOUNDS AND USES THEREOF

BACKGROUND

An incomplete understanding of the molecular perturbations that cause disease, as well as a limited arsenal of robust model systems, has contributed to a failure to generate successful disease-modifying therapies against common and progressive neurological disorders, such as Parkinson's Disease (PD) and Alzheimer's Disease (AD). Progress is being made on many fronts to find agents that can arrest the progress of these disorders. However, the present therapies for most, if not all, of these diseases provide very little relief. Accordingly, a need exists to develop therapies that can alter the course of neurodegenerative diseases. More generally, a need exists for better methods and compositions for the treatment of neurodegenerative diseases in order to improve the quality of the lives of those afflicted by such diseases.

SUMMARY OF THE INVENTION

In an aspect, this disclosure provides a compound having the structure of Formula I:

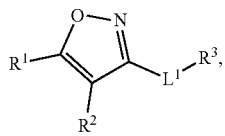

Formula I where
$R^1$ is H, halo, CN, $NO_2$, hydroxyl, optionally substituted amino, optionally substituted $C_1$-$C_6$ alkyl, optionally substituted $C_1$-$C_6$ heteroalkyl, optionally substituted $C_1$-$C_6$ alkenyl, optionally substituted $C_1$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl, $R^2$ is H or optionally substituted $C_1$-$C_6$ alkyl, or $R^1$ and $R^2$, together with the atoms to which each is attached, combine to form an optionally substituted $C_3$-$C_{10}$ carbocyclylene, optionally substituted $C_2$-$C_9$ heterocyclylene, optionally substituted $C_6$-$C_{10}$ arylene, or optionally substituted $C_2$-$C_9$ heteroarylene;

$L^1$ is optionally substituted $C_1$-$C_6$ alkylene or optionally substituted $C_1$-$C_6$ heteroalkylene; and $R^3$ is optionally substituted $C_2$-$C_9$ heteroaryl, or a pharmaceutically acceptable salt thereof.

In some embodiments, $R^3$ is a heteroaryl having the structure of Formula Ia:

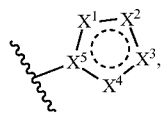

Formula Ia, where
each of $X^1$, $X^2$, $X^3$, and $X^4$ is, independently, O, $NR^4$, or $CR^5$, where
each $R^4$ is, independently, H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl, each $R^5$ is, independently, H, CN, optionally substituted $C_1$-$C_6$ alkyl, or optionally substituted $C_1$-$C_6$ heteroalkyl, and if one of $X^1$, $X^2$, $X^3$, or $X^4$ is O, then the adjacent atoms are N or $CR^5$; and $X^5$ is N or C, where 1, 2, or 3 of $X^1$, $X^2$, $X^3$, $X^4$, or $X^5$ is O or N.

In some embodiments, $R^3$ is

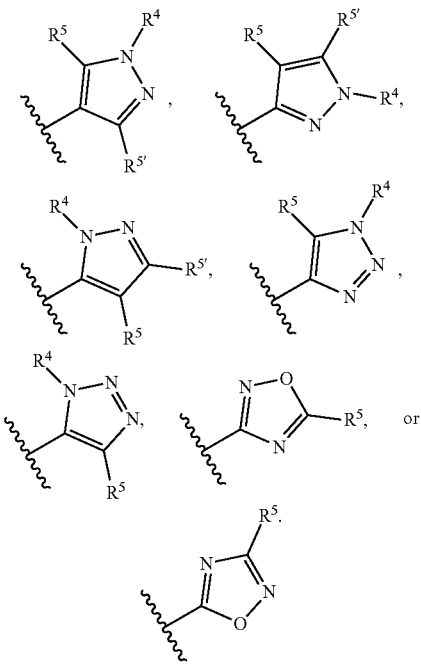

In some embodiments, $R^3$ is

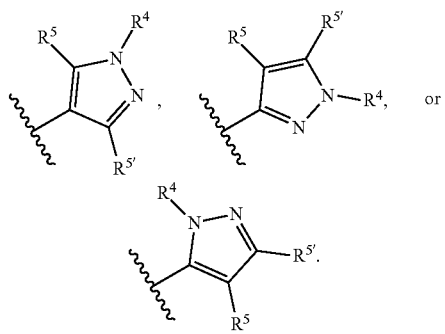

In some embodiments, $R^3$ is

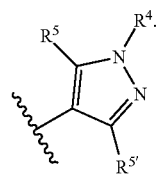

In some embodiments, each $R^5$ is, independently, H, CN, or optionally substituted $C_1$-$C_6$ alkyl.

In some embodiments, each $R^5$ is, independently, H, CN,

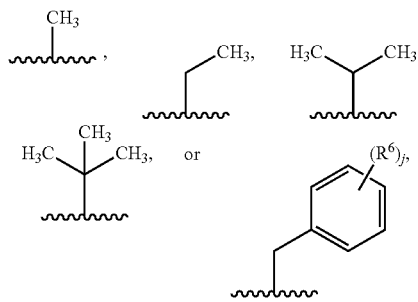

where j is 0, 1, 2, 3, 4, or 5; and each $R^6$ is, independently, halo, CN, optionally substituted $C_1$-$C_6$ alkyl, or optionally substituted $C_1$-$C_6$ heteroalkyl.

In some embodiments, each $R^6$ is, independently, F, Cl, Br, I, CN,

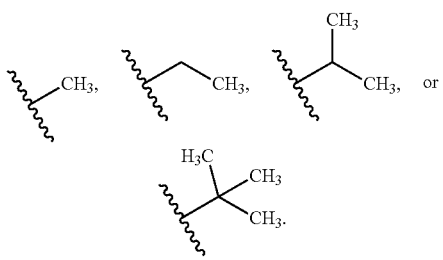

In some embodiments, j is 0, 1, 2, or 3.

In some embodiments, j is 2.

In some embodiments, each of $R^5$ is, independently, H, CN,

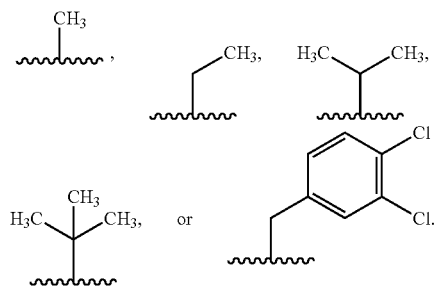

In some embodiments, $R^4$ is H.

In some embodiments, $R^4$ is optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, $R^4$ is optionally substituted $C_1$-$C_6$ heteroalkyl.

In some embodiments, $R^4$ is

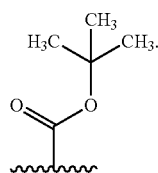

In some embodiments, $R^4$ is optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, $R^4$ is

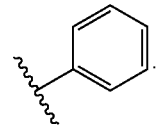 [SMILES: *c1ccccc1]

In some embodiments, $R^4$ is optionally substituted $C_1$-$C_6$ alkyl.

In some embodiments, $R^4$ is

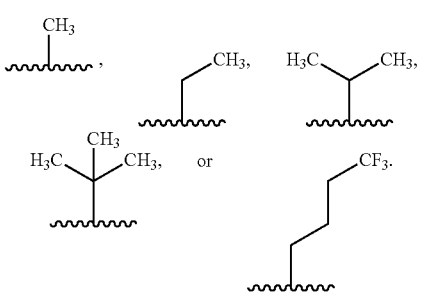

In some embodiments, $R^4$ is

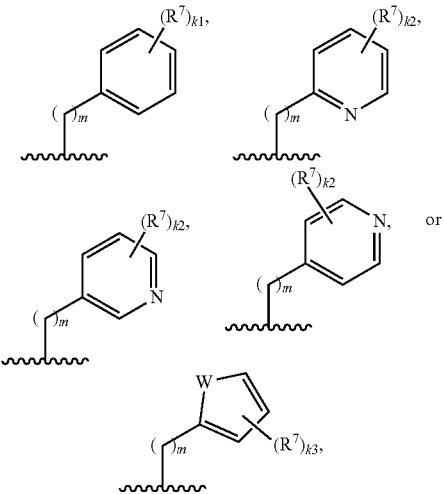

where k1 is 0, 1, 2, 3, 4, or 5;

k2 is 0, 1, 2, 3, or 4;

k3 is 0, 1, 2, or 3;

W is O or S;

m is 1 or 2; and each $R^7$ is, independently, halo, CN, $NO_2$, hydroxyl, optionally substituted $C_1$-$C_6$ alkyl, or optionally substituted $C_1$-$C_6$ heteroalkyl.

In some embodiments, m is 2. In some embodiments, m is 1.

In some embodiments, each $R^7$ is, independently, halo, CN, optionally substituted $C_1$-$C_6$ alkyl, or optionally substituted $C_1$-$C_6$ heteroalkyl.

In some embodiments, each of $R^7$ is, independently, F, Cl, Br, I, CN, —$CF_3$,

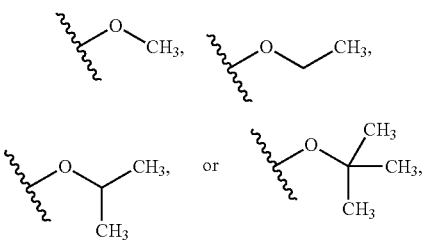

In some embodiments, k1 is 0. In some embodiments, k1 is 1.

In some embodiments, $R^4$ is

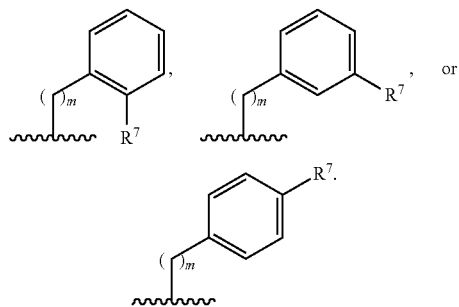

In some embodiments, k1 is 2.

In some embodiments, $R^4$ is

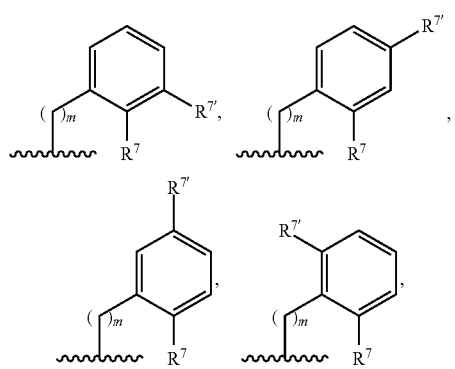

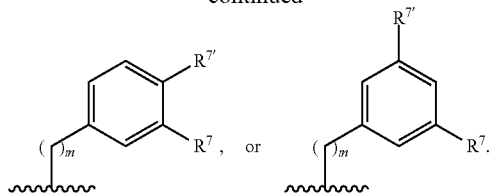

In some embodiments, k2 is 0. In some embodiments, k2 is 1.

In some embodiments, $R^4$ is

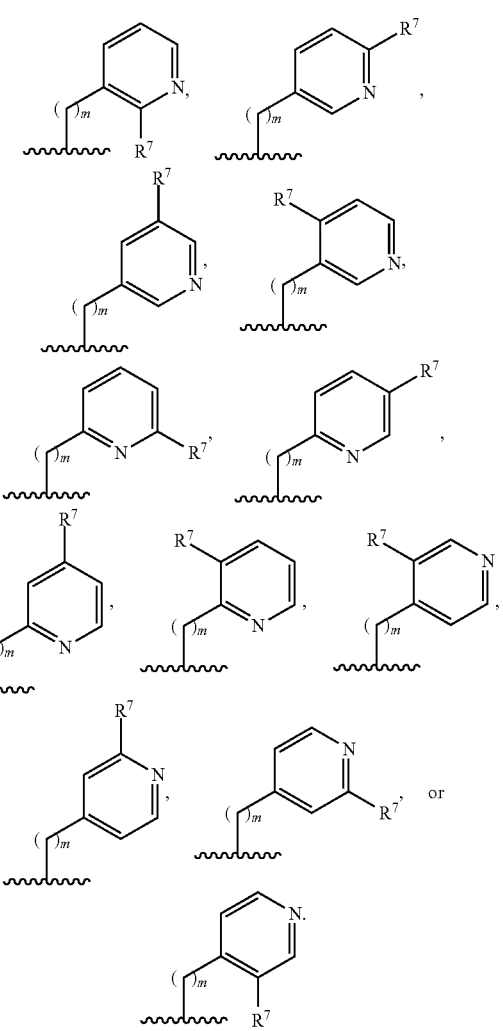

In some embodiments, k3 is 0. In some embodiments, k3 is 1.

In some embodiments, $R^4$ is

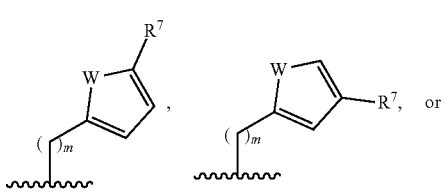

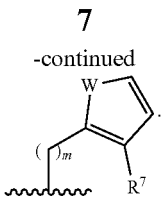
In some embodiments, W is S.
In some embodiments, $R^4$ is
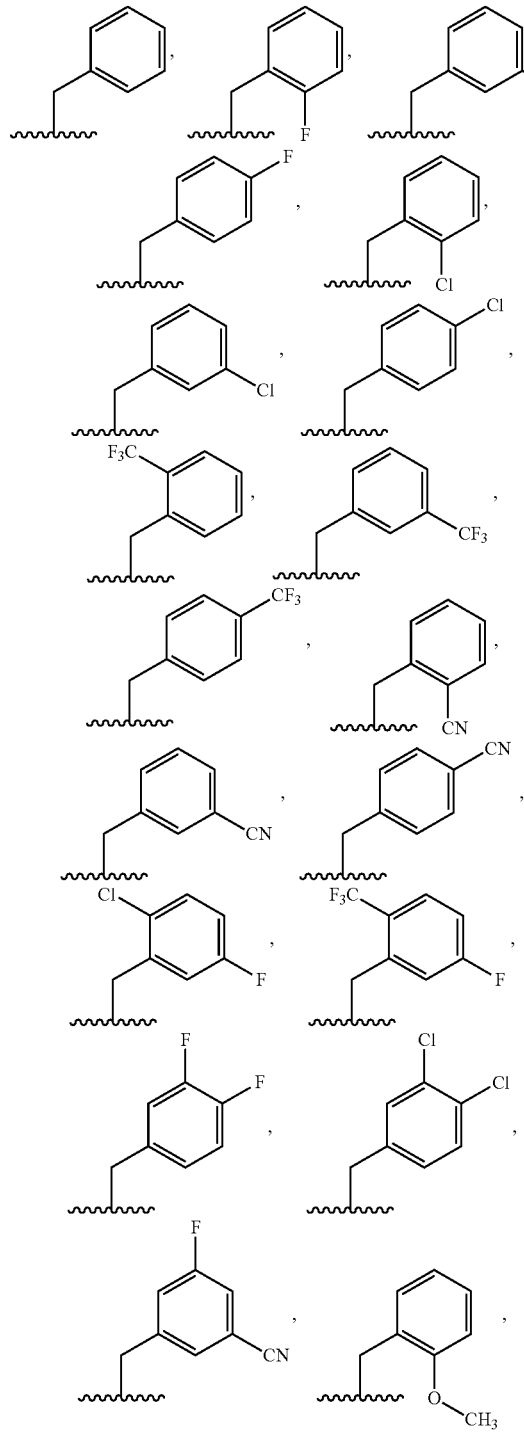
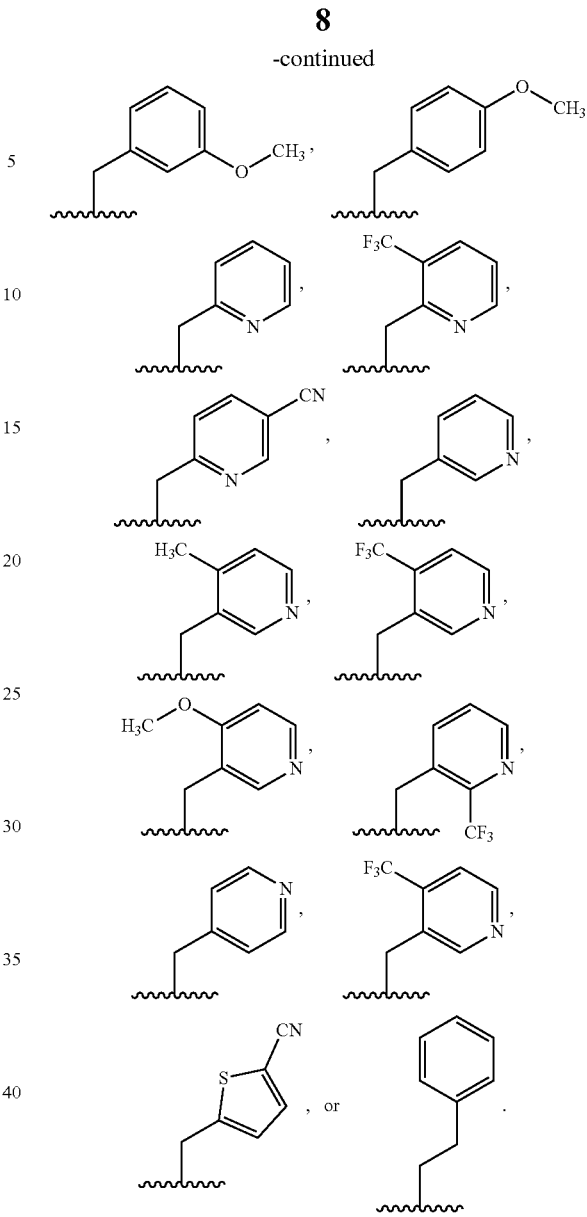
In some embodiments, $R^4$ is
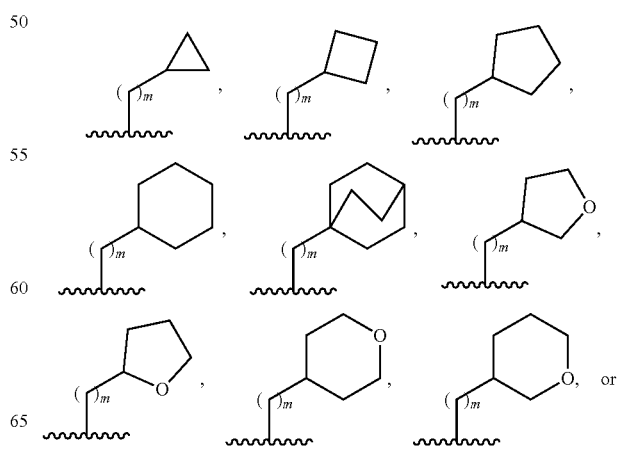

-continued

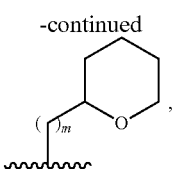

where m is 1 or 2.

In some embodiments, m is 1. In some embodiments, m is 2.

In some embodiments, $R^4$ is

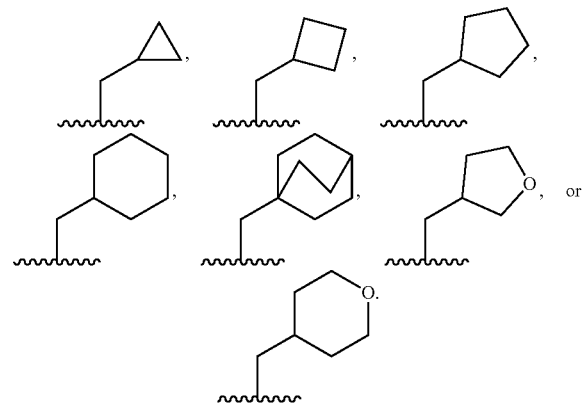

In some embodiments, $R^4$ is

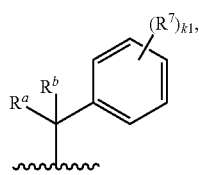

where
k1 is 0, 1, 2, 3, 4, or 5;
each $R^7$ is, independently, halo, CN, $NO_2$, hydroxyl, optionally substituted $C_1$-$C_6$ alkyl, or optionally substituted $C_1$-$C_6$ heteroalkyl;

$R^a$ is H, optionally substituted $C_1$-$C_6$ alkyl, or optionally substituted $C_1$-$C_6$ heteroalkyl; and $R^b$ is optionally substituted $C_1$-$C_6$ alkyl or optionally substituted $C_1$-$C_6$ heteroalkyl.

In some embodiments, each $R^7$ is, independently, halo, CN, optionally substituted $C_1$-$C_6$ alkyl, or optionally substituted $C_1$-$C_6$ heteroalkyl.

In some embodiments, each $R^7$ is, independently, F, Cl, Br, I, CN, —$CF_3$,

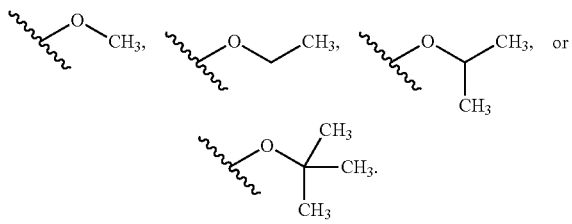

In some embodiments, k1 is 0. In some embodiments, k1 is 1.

In some embodiments, $R^4$ is

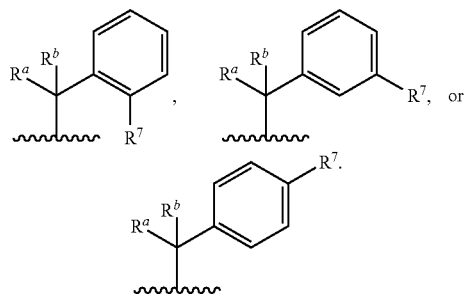

In some embodiments, k1 is 2.
In some embodiments, $R^4$ is

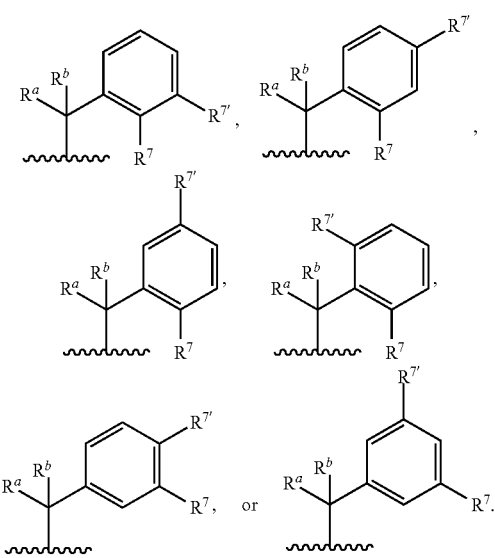

In some embodiments, $R^a$ is H or —$CH_3$.
In some embodiments, $R^b$ is optionally substituted $C_1$-$C_6$ alkyl.
In some embodiments, $R^b$ is

where
b is 1 or 2; and
$R^c$ is optionally substituted amino, optionally substituted thiol, optionally substituted sulfone, or optionally substituted sulfoxide.

In some embodiments, $R^c$ is

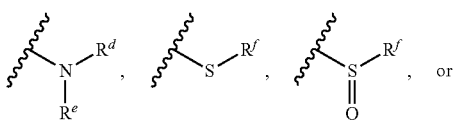

-continued

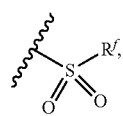

where each of $R^d$, $R^e$, and $R^f$ is, independently, H, optionally substituted $C_1$-$C_6$ alkyl, or optionally substituted $C_1$-$C_6$ alkyl.

In some embodiments, $R^4$ is

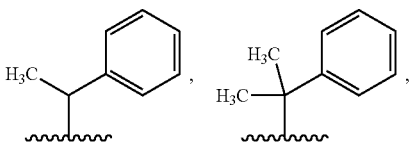

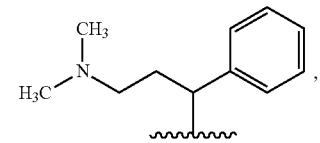

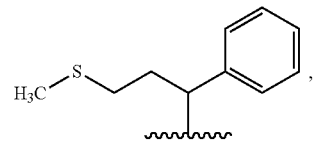

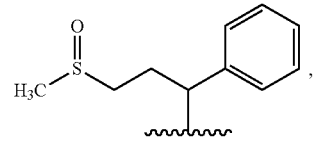

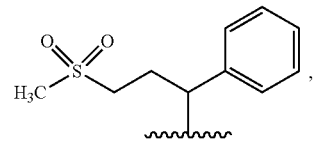

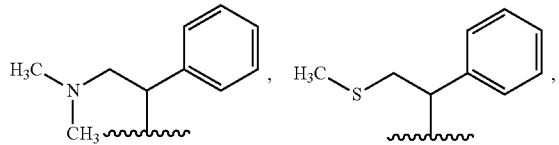

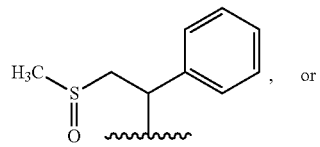

, or

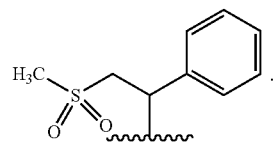

In some embodiments, $R^2$ is H or optionally substituted $C_1$-$C_6$ alkyl.

In some embodiments, $R^2$ is H,

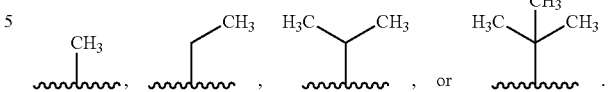

In some embodiments, $R^2$ is H.

In some embodiments, $R^1$ is H, halo, CN, $NO_2$, hydroxyl, optionally substituted amino, optionally substituted $C_1$-$C_6$ alkyl, optionally substituted $C_1$-$C_6$ heteroalkyl, optionally substituted $C_1$-$C_6$ alkenyl, optionally substituted $C_1$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, $R^1$ is H, halo, CN, optionally substituted $C_1$-$C_6$ alkyl, optionally substituted $C_1$-$C_6$ heteroalkyl, optionally substituted $C_1$-$C_6$ alkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, $R^1$ is H, halo, CN, optionally substituted $C_1$-$C_6$ alkyl, optionally substituted $C_1$-$C_6$ heteroalkyl, or optionally substituted $C_1$-$C_6$ alkenyl.

In some embodiments, $R^1$ is H, F, Cl, Br, I, CN,

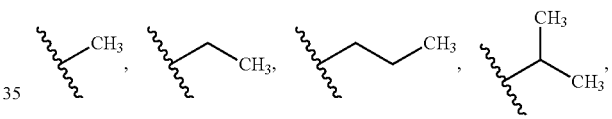

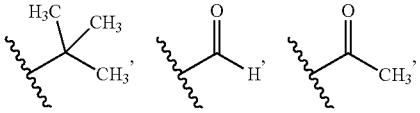

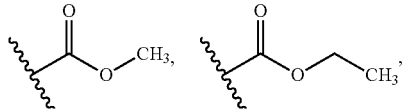

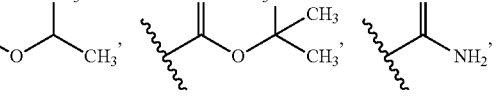

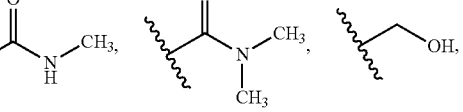

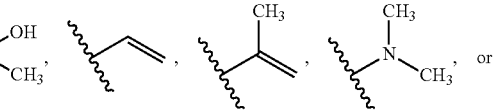

or

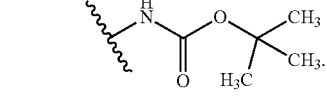

In some embodiments, $R^1$ is optionally substituted $C_3$-$C_{10}$ carbocyclyl.

In some embodiments, $R^1$ is

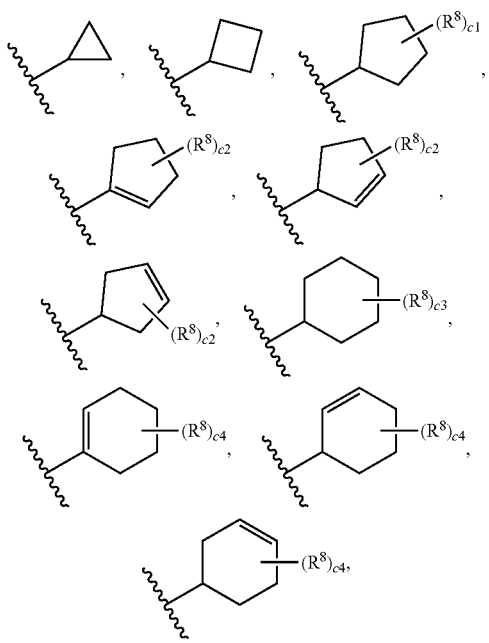

where
c1 is 0, 1, 2, 3, 4, or 5;
c2 is 0, 1, 2, 3, or 4;
c3 is 0, 1, 2, 3, 4, 5, or 6;
c4 is 0, 1, 2, 3, 4, or 5; and
each $R^8$ is, independently, halo, optionally substituted $C_1$-$C_6$ alkyl, or optionally substituted $C_1$-$C_6$ heteroalkyl.

In some embodiments, c1 is 0.
In some embodiments, c2 is 0.
In some embodiments, c3 is 0.
In some embodiments, c4 is 0.
In some embodiments, $R^1$ is optionally substituted $C_2$-$C_9$ heterocyclyl.
In some embodiments, $R^1$ is

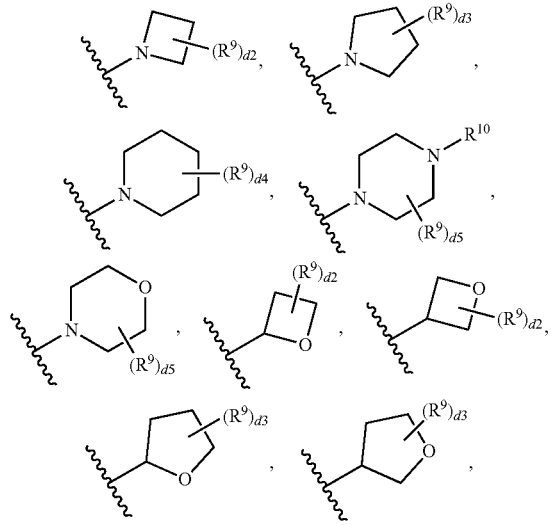

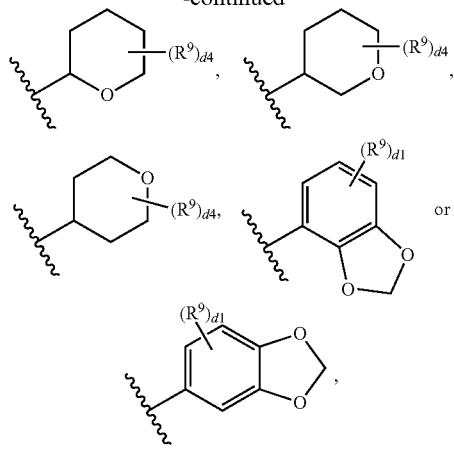

where
d1 is 0, 1, 2, or 3;
d2 is 0, 1, 2, or 3;
d3 is 0, 1, 2, 3, or 4;
d4 is 0, 1, 2, 3, 4, or 5;
d5 is 0, 1, 2, 3, or 4;
each $R^9$ is, independently, halo, hydroxyl, optionally substituted $C_1$-$C_6$ alkyl, or optionally substituted $C_1$-$C_6$ heteroalkyl; and
$R^{10}$ is H, optionally substituted $C_1$-$C_6$ alkyl, or optionally substituted $C_1$-$C_6$ heteroalkyl.

In some embodiments, d1 is 0 or 1. In some embodiments, d1 is 0. In some embodiments, d1 is 1.
In some embodiments, d2 is 0, 1, or 2. In some embodiments, d2 is 0. In some embodiments, d2 is 1.
In some embodiments, d3 is 0, 1, or 2. In some embodiments, d3 is 0. In some embodiments, d3 is 1.
In some embodiments, d4 is 0, 1, or 2. In some embodiments, d4 is 0. In some embodiments, d4 is 1.
In some embodiments, d5 is 0, 1, or 2. In some embodiments, d5 is 0. In some embodiments, d5 is 1.
In some embodiments, $R^9$ is hydroxyl or optionally substituted $C_1$-$C_6$ heteroalkyl.
In some embodiments, $R^9$ is hydroxyl,

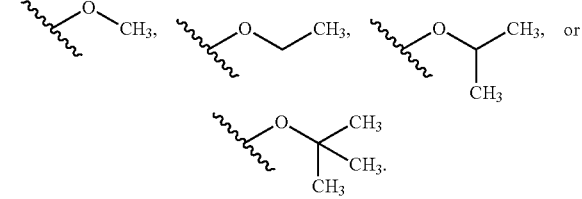

In some embodiments, $R^{10}$ is H,

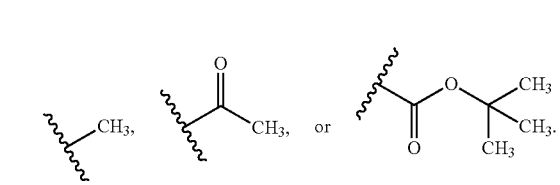

In some embodiments, $R^1$ is optionally substituted $C_6$-$C_{10}$ aryl.

In some embodiments, $R^1$

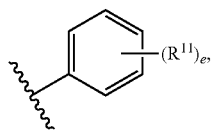

where e is 0, 1, 2, 3, 4, or 5; and each $R^{11}$ is, independently, halo, CN, $NO_2$, hydroxyl, optionally substituted $C_1$-$C_6$ alkyl, or optionally substituted $C_1$-$C_6$ heteroalkyl.

In some embodiments, e is 0. In some embodiments, e is 1.

In some embodiments, $R^1$ is

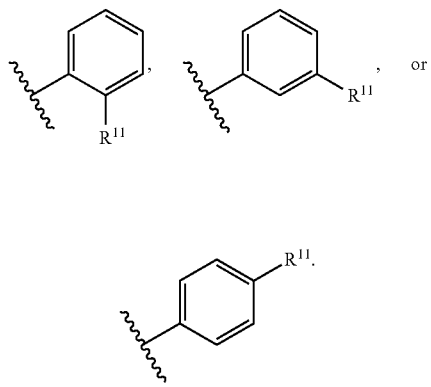

In some embodiments, e is 2.

In some embodiments, $R^1$ is

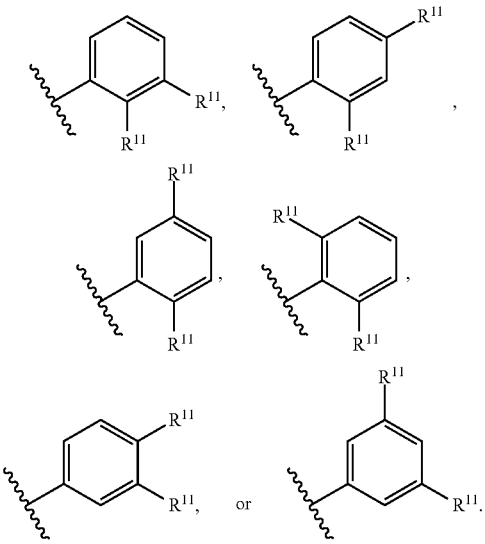

In some embodiments, $R^1$ is optionally substituted $C_2$-$C_9$ heteroaryl.

In some embodiments, $R^1$ is

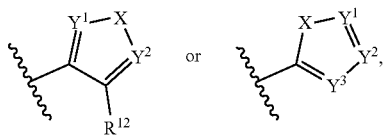

where

X is O, S, or $NR^{N1}$, where $R^{N1}$ is H, optionally substituted $C_1$-$C_6$ alkyl, or optionally substituted $C_1$-$C_6$ heteroalkyl;

each of $Y^1$, $Y^2$, and, and $Y^3$ is, independently, N or $CR^{C1}$, where $R^{C1}$ is H, halo, CN, optionally substituted $C_1$-$C_6$ alkyl, or optionally substituted $C_1$-$C_6$ heteroalkyl; and $R^{12}$ is H, halo, CN, optionally substituted $C_1$-$C_6$ alkyl, or optionally substituted $C_1$-$C_6$ heteroalkyl.

In some embodiments, X is S. In some embodiments, X is O.

In some embodiments, $Y^1$ is N. In some embodiments, $Y^1$ is $CR^{C1}$.

In some embodiments, $Y^2$ is N. In some embodiments, $Y^2$ is $CR^{C1}$.

In some embodiments, $Y^3$ is N. In some embodiments, $Y^3$ is $CR^{C1}$.

In some embodiments, $R^{C1}$ is H,

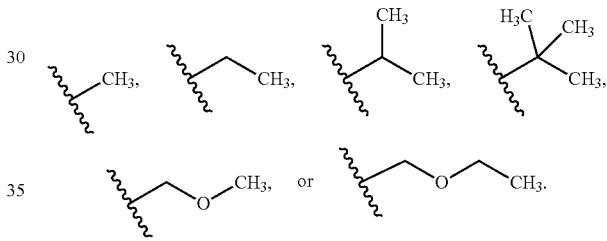

In some embodiments, $R^{12}$ is H,

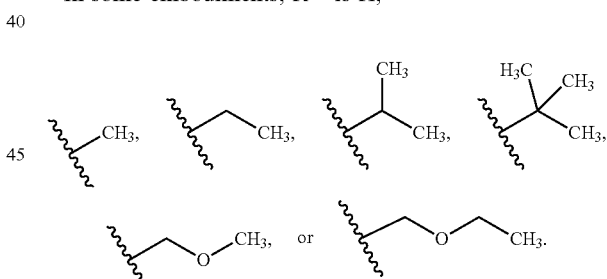

In some embodiments, $R^1$ is

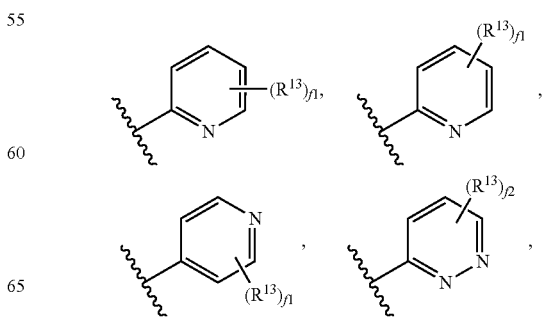

-continued

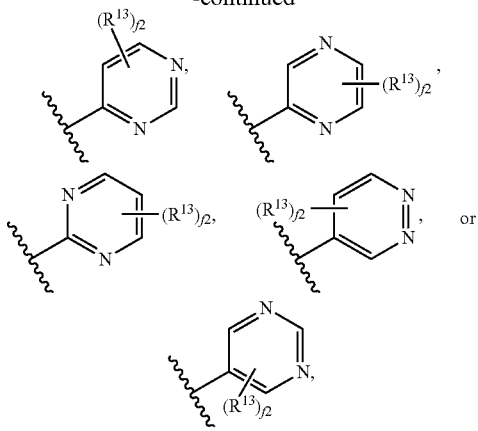

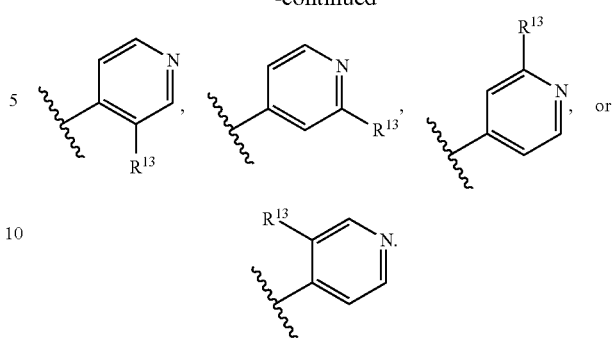

where
f1 is 0, 1, 2, 3, or 4;
f2 is 0, 1, 2, or 3; and
each $R^{13}$ is, independently, halo, CN, optionally substituted $C_1$-$C_6$ alkyl, or optionally substituted $C_1$-$C_6$ heteroalkyl.

In some embodiments, $R^1$ is

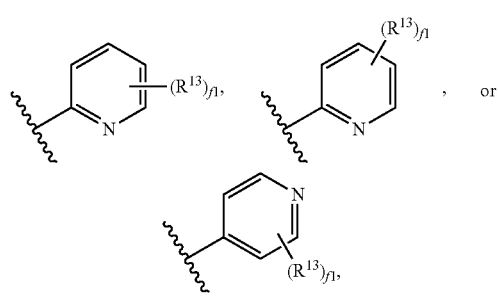

In some embodiments, f1 is 0. In some embodiments, f1 is 1.

In some embodiments, $R^1$ is

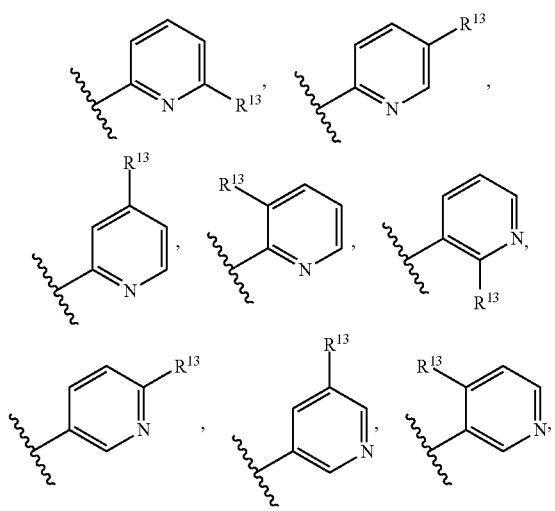

-continued

In some embodiments, f2 is 0.
In some embodiments, $R^1$ is

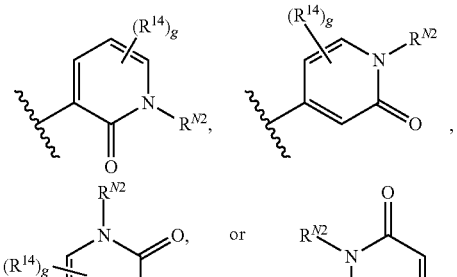

where
g is 0, 1, 2, 3, or 4;
$R^{N2}$ is H, optionally substituted $C_1$-$C_6$ alkyl, or optionally substituted $C_1$-$C_6$ heteroalkyl; and
each $R^{14}$ is H, halo, CN, optionally substituted $C_1$-$C_6$ alkyl, or optionally substituted $C_1$-$C_6$ heteroalkyl.

In some embodiments, $R^1$ is

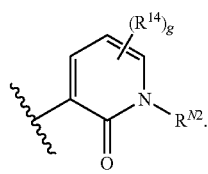

In some embodiments, g is 0.
In some embodiments, $R^1$ is

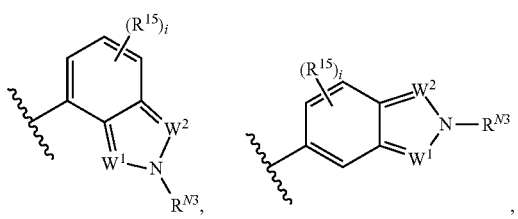

-continued where
i is 0, 1, 2, or 3;
each of $W^1$ and $W^2$ is, independently, N or $CR^{C2}$, where $R^{C2}$ is H, halo, CN, optionally substituted $C_1$-$C_6$ alkyl, or optionally substituted $C_1$-$C_6$ heteroalkyl;
$R^{N3}$ is H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, or optionally substituted $C_2$-$C_9$ heteroaryl; and
each of $R^{15}$ is, independently, halo, CN, optionally substituted $C_1$-$C_6$ alkyl, or optionally substituted $C_1$-$C_6$ heteroalkyl.

In some embodiments, i is 0.
In some embodiments, $W^1$ is N. In some embodiments, $W^1$ is $CR^{C2}$.
In some embodiments, $W^2$ is N. In some embodiments, $W^2$ is $CR^{C2}$.
In some embodiments, $R^{N3}$ is H, optionally substituted $C_1$-$C_6$ alkyl, optionally substituted $C_1$-$C_6$ heteroalkyl, or optionally substituted $C_2$-$C_9$ heterocyclyl.
In some embodiments, $R^{N3}$ is In some embodiments, $R^1$ is F, Cl, Br, I, CN, $NO_2$, $NH_2$, -continued

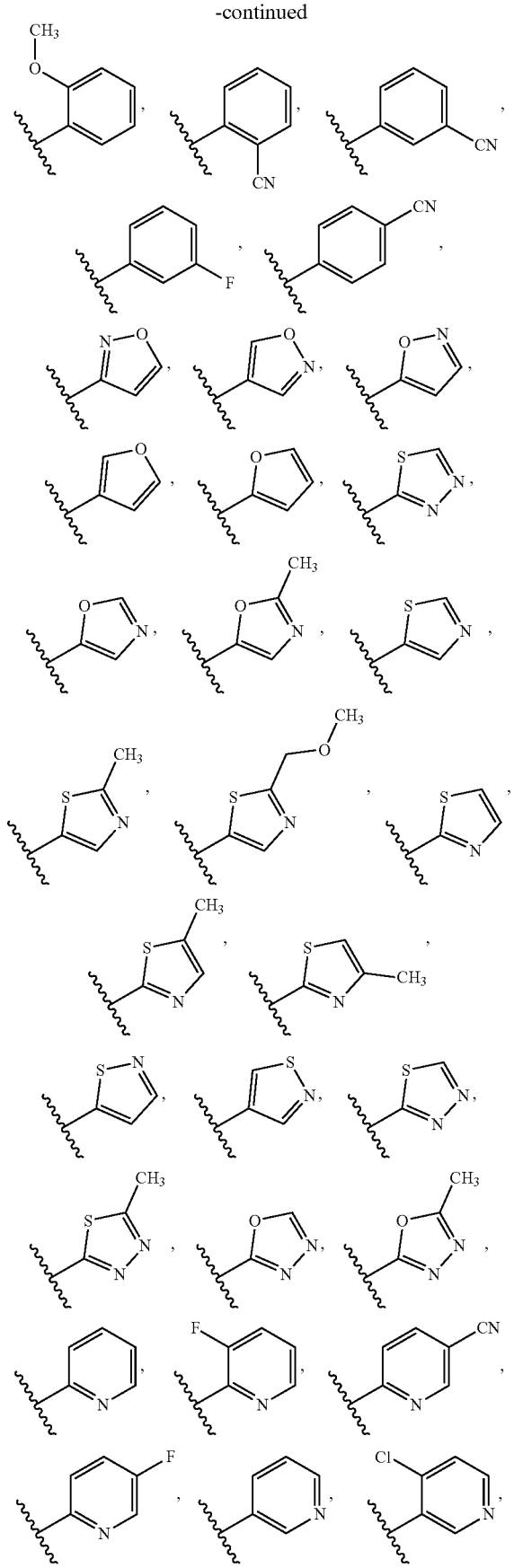

-continued

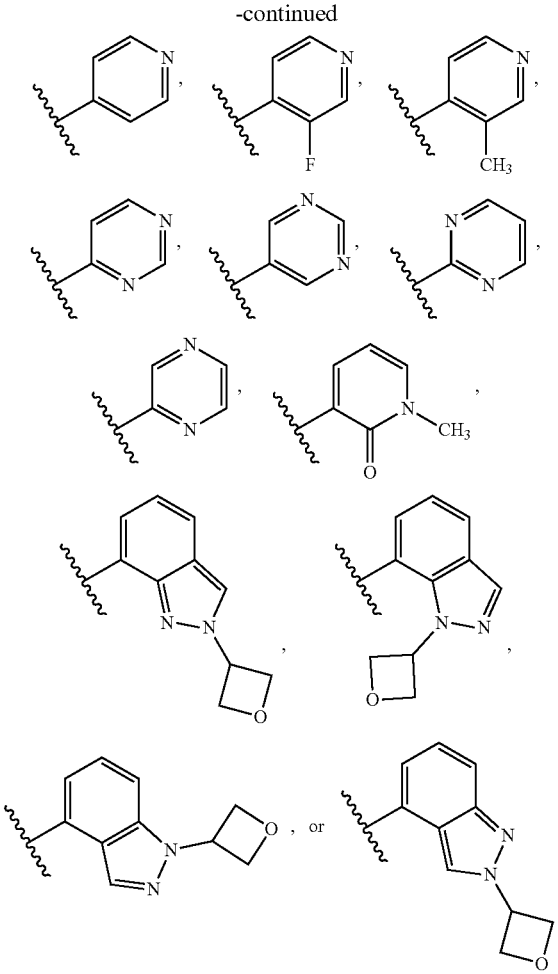

In some embodiments, R¹ and R², together with the atoms to which each is attached, combine to form an optionally substituted $C_3$-$C_{10}$ carbocyclylene, optionally substituted $C_2$-$C_9$ heterocyclylene, optionally substituted $C_6$-$C_{10}$ arylene, or optionally substituted $C_2$-$C_9$ heteroarylene.

In some embodiments, R¹ and R², together with the atoms to which each is attached, combine to form an optionally substituted $C_3$-$C_{10}$ carbocyclylene.

In some embodiments, the compound has the structure of Formula Ib:

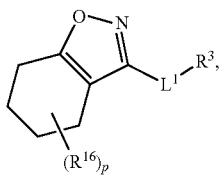

Formula Ib or a pharmaceutically acceptable salt thereof.

In some embodiments, L¹ is optionally substituted $C_1$-$C_6$ heteroalkylene.

In some embodiments, $L^1$ is

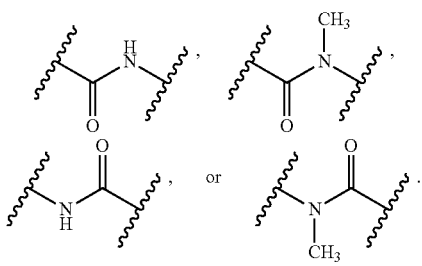

In some embodiments, $L^1$ is

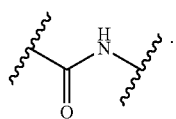

In an aspect, this disclosure provides a compound having the structure of Formula II:

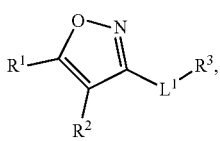

Formula II where $R^1$ is H, halo, CN, $NO_2$, hydroxyl, optionally substituted amino, optionally substituted $C_1$-$C_6$ alkyl, optionally substituted $C_1$-$C_6$ heteroalkyl, optionally substituted $C_1$-$C_6$ alkenyl, optionally substituted $C_1$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl; and $R^2$ is H or optionally substituted $C_1$-$C_6$ alkyl; or $R^1$ and $R^2$, together with the atoms to which each is attached, combine to form an optionally substituted $C_3$-$C_{10}$ carbocyclylene, optionally substituted $C_2$-$C_9$ heterocyclylene, optionally substituted $C_6$-$C_{10}$ arylene, or optionally substituted $C_2$-$C_9$ heteroarylene;

$L^1$ is optionally substituted $C_1$-$C_6$ alkylene or optionally substituted $C_1$-$C_6$ heteroalkylene; and $R^3$ is optionally substituted $C_2$-$C_9$ heterocyclyl, or a pharmaceutically acceptable salt thereof.

In some embodiments, $R^3$ is a heterocyclyl having the structure of Formula IIa:

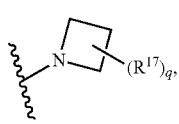

Formula IIa where n is 0, 1, 2, 3, 4, 5, or 6; and
each $R^{17}$ is

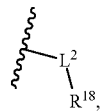

where each $L^2$ is, independently, absent, O, S, optionally substituted amino, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl; and each $R^{18}$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $L^2$ is, independently, absent, O, S, optionally substituted amino, optionally substituted $C_1$-$C_6$ alkyl, or optionally substituted $C_1$-$C_6$ heteroalkyl.

In some embodiments, each $R^{18}$ is, independently, halo, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $R^{18}$ is, independently, halo, optionally substituted $C_6$-$C_{10}$ aryl, or optionally substituted $C_2$-$C_9$ heteroaryl.

In some embodiments, each $R^{18}$ is, independently, F, Cl, Br, I, or

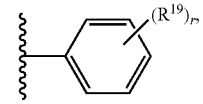

where r is 0, 1, 2, 3, 4, or 5; and each $R^{19}$ is, independently, halo, CN, hydroxyl, optionally substituted $C_1$-$C_6$ alkyl, or optionally substituted $C_1$-$C_6$ heteroalkyl.

In some embodiments, each $R^{19}$ is, independently, F, Cl, Br, I, CN, hydroxyl,

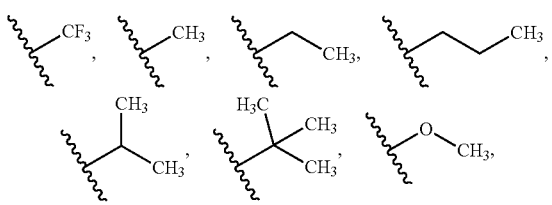

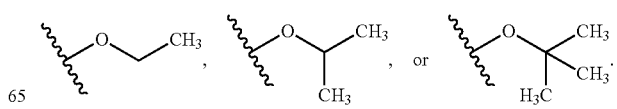

In some embodiments, r is 0, 1, or 2. In some embodiments r is 0. In some embodiments, r is 1.

In some embodiments r is 2.

In some embodiments, $R^{18}$ is

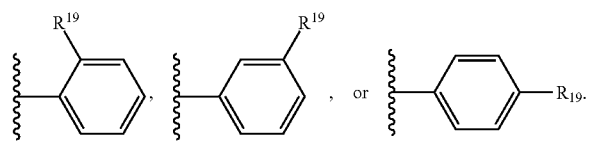

In some embodiments, $R^{18}$ is

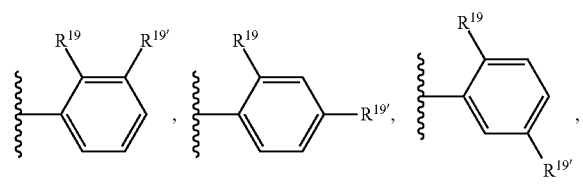

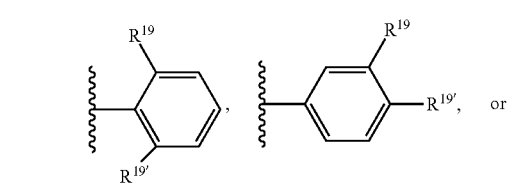

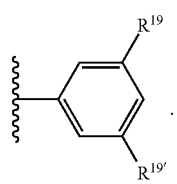

In some embodiments, q is 0, 1, 2, or 3. In some embodiments, q is 1.

In some embodiments, $L^2$ is absent. In some embodiments, $L^2$ is O. In some embodiments, $L^2$ is

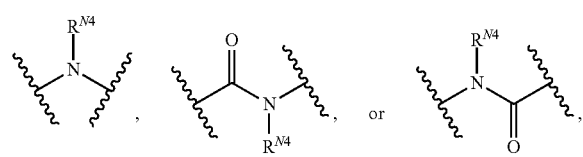

where $R^{N4}$ is H, optionally substituted $C_1$-$C_6$ alkyl, or optionally substituted $C_1$-$C_6$ heteroalkyl. In some embodiments, $L^2$ is

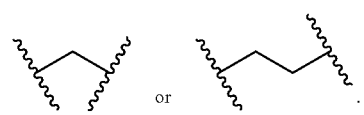

In some embodiments, $R^{N4}$ is H or —$CH_3$.

In some embodiments, $R^3$ is

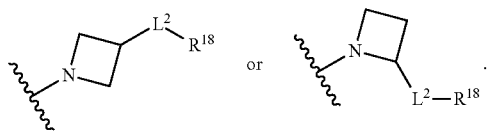

In some embodiments, $R^{17}$ is

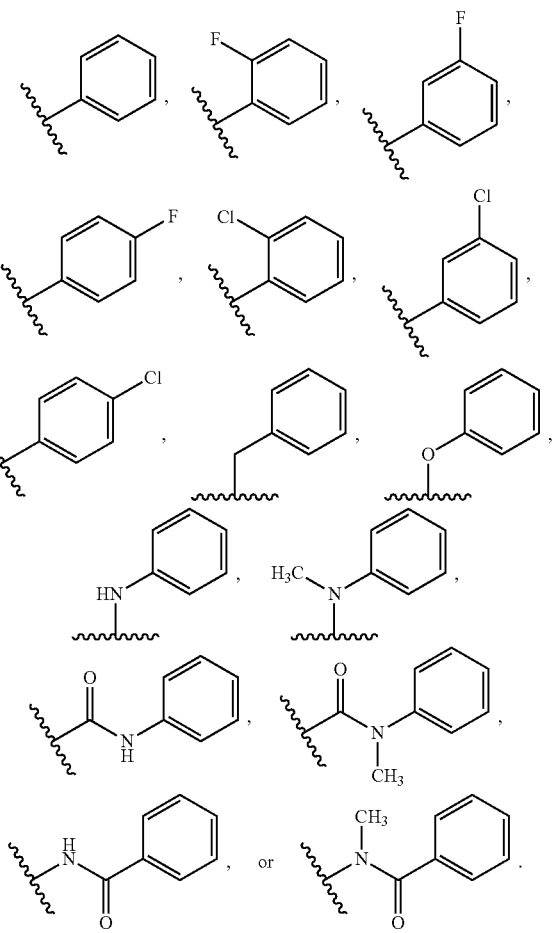

In some embodiments, $R^3$ is a heterocyclyl having the structure of Formula IIb:

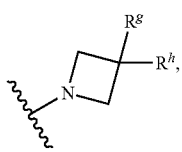

Formula IIb where $R^g$ and $R^h$, together with the atom to which each is attached, combine to form an optionally substituted $C_3$-$C_{10}$ carbocyclylene or optionally substituted $C_2$-$C_9$ heterocyclylene.

In some embodiments, $R^g$ and $R^h$, together with the atom to which each is attached, combine to form an optionally substituted $C_3$-$C_{10}$ carbocyclylene.

In some embodiments, $R^g$ and $R^h$, together with the atom to which each is attached, combine to form an optionally substituted $C_2$-$C_9$ heterocyclylene.

In some embodiments, $R^3$ is

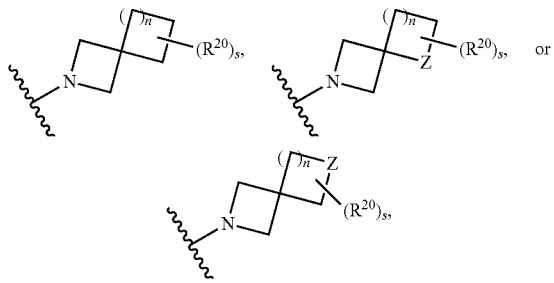

where
n is 1, 2, 3, or 4;
s is 0, 1, 2, 3, 4, 5, 6, or 7;
Z is O, S,

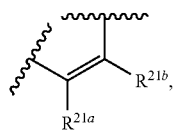

or $NR^{N5}$, where $R^{N5}$ is H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl; and each of $R^{21a}$ and $R^{21b}$ is, independently, H, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl; and each $R^{20}$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $R^{20}$ is, independently, optionally substituted $C_1$-$C_6$ alkyl, optionally substituted $C_1$-$C_6$ heteroalkyl, optionally substituted $C_6$-$C_{10}$ aryl, or optionally substituted $C_2$-$C_9$ heteroaryl.

In some embodiments, $R^{N5}$ is H, optionally substituted $C_1$-$C_6$ alkyl, optionally substituted $C_1$-$C_6$ heteroalkyl, optionally substituted $C_6$-$C_{10}$ aryl, or optionally substituted $C_2$-$C_9$ heteroaryl.

In some embodiments, n is 1. In some embodiments, n is 2.

In some embodiments, s is 0. In some embodiments, s is 1. In some embodiments, s is 2.

In some embodiments, Z is O. In some embodiments, $NR^{N5}$. In some embodiments, Z is

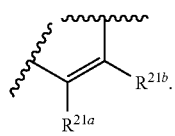

In some embodiments, each of $R^{21a}$ and $R^{21b}$ is, independently, H, optionally substituted $C_1$-$C_6$ alkyl, or optionally substituted $C_1$-$C_6$ heteroalkyl.

In some embodiments, $R^{21a}$ is H.

In some embodiments, $R^{21b}$ is H.

In some embodiments, $R^{21a}$ is H and $R^{21b}$ is H.

In some embodiments, $R^{20}$ is

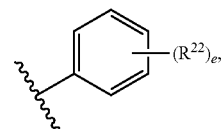

where
e is 0, 1, 2, 3, 4, or 5; and
each $R^{22}$ is, independently, halo, CN, $NO_2$, hydroxyl, optionally substituted $C_1$-$C_6$ alkyl, or optionally substituted $C_1$-$C_6$ heteroalkyl.

In some embodiments, e is 0. In some embodiments, e is 1.

In some embodiments, $R^{20}$ is

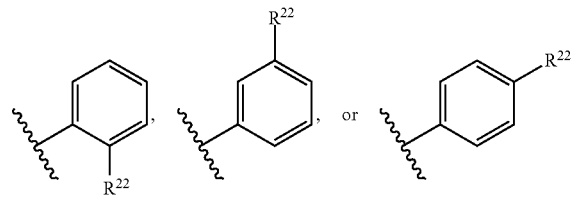

In some embodiments, e is 2.

In some embodiments, $R^{20}$ is

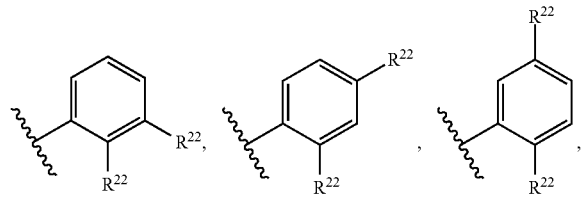

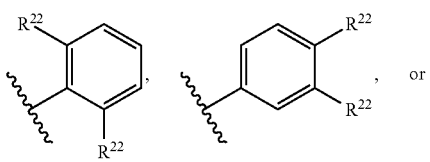

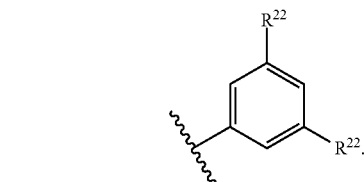

In some embodiments, $R^3$ is

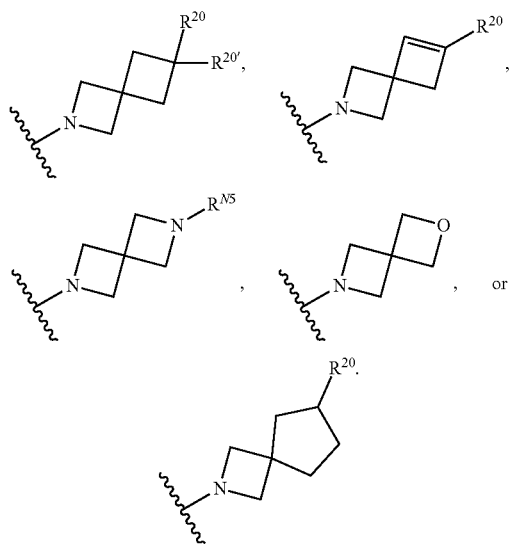

In some embodiments, $R^3$ is

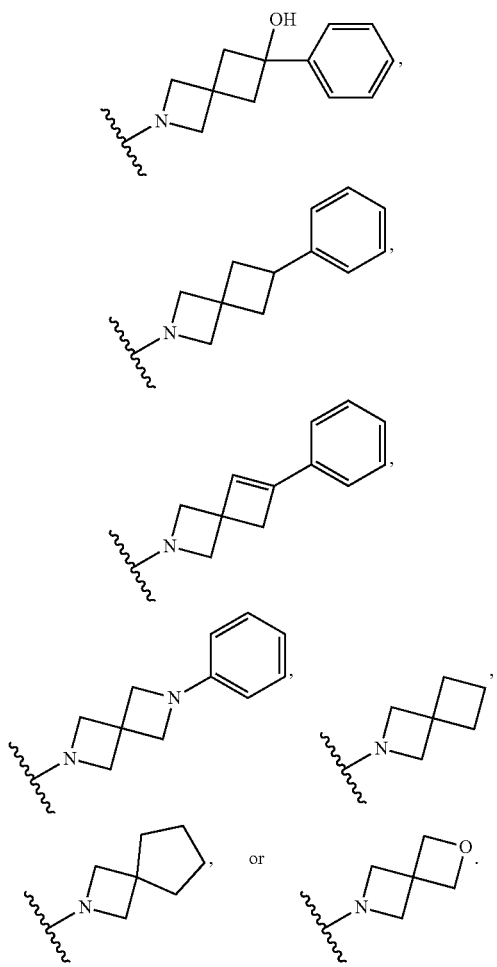

In some embodiments, $R^3$ is a heterocyclyl having the structure of Formula IIc, Formula IId, or Formula IIe:

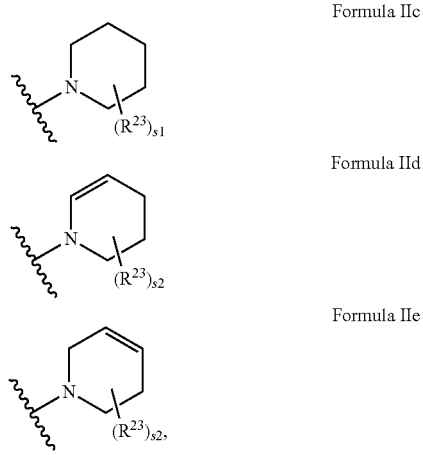

Formula IIc

Formula IId

Formula IIe where
s1 is 0, 1, 2, 3, 4, 5, or 6;
s2 is 0, 1, 2, 3, or 4; and
each $R^{23}$ is

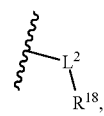

where
each $L^2$ is, independently, absent, O, S, optionally substituted amino, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl; and each $R^{18}$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $L^2$ is, independently, absent, O, S, optionally substituted amino, optionally substituted $C_1$-$C_6$ alkyl, or optionally substituted $C_1$-$C_6$ heteroalkyl.

In some embodiments, each $R^{18}$ is, independently, halo, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $R^{18}$ is, independently, F, Cl, Br, I,

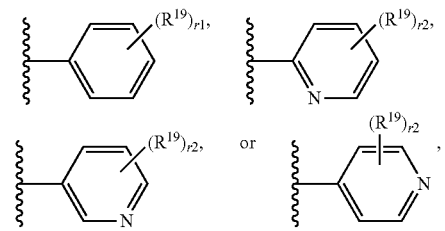

where r1 is 0, 1, 2, 3, 4, or 5;

r2 is 0, 1, 2, 3, or 4; and each $R^{19}$ is, independently, halo, hydroxyl, optionally substituted $C_1$-$C_6$ alkyl, or optionally substituted $C_1$-$C_6$ heteroalkyl.

In some embodiments, each $R^{19}$ is, independently, F, Cl, Br, I, CN, hydroxyl,

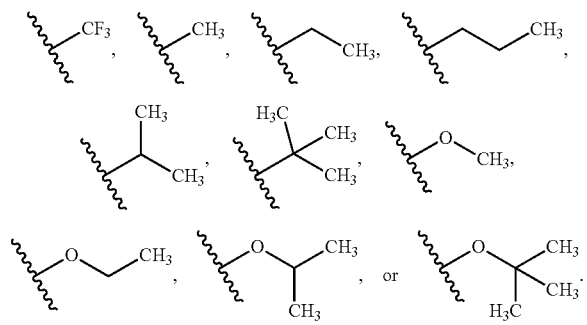

In some embodiments, r1 is 0, 1, or 2. In some embodiments r1 is 0. In some embodiments, r1 is 1. In some embodiments r1 is 2.

In some embodiments, $R^{18}$ is

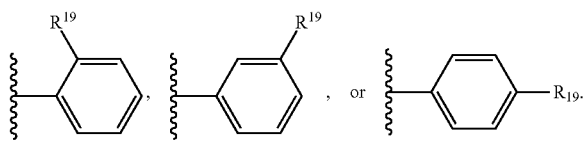

In some embodiments, $R^{18}$ is

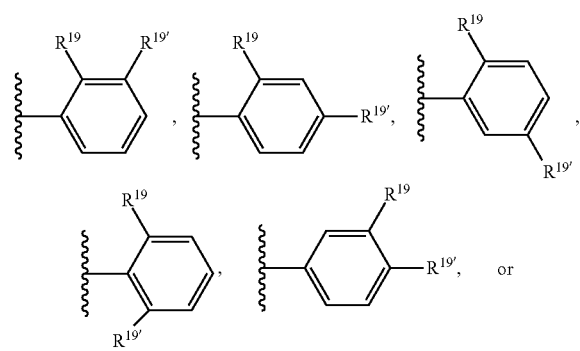

In some embodiments, r2 is 0, 1, or 2. In some embodiments r2 is 0. In some embodiments, r2 is 1.

In some embodiments, $R^{18}$ is

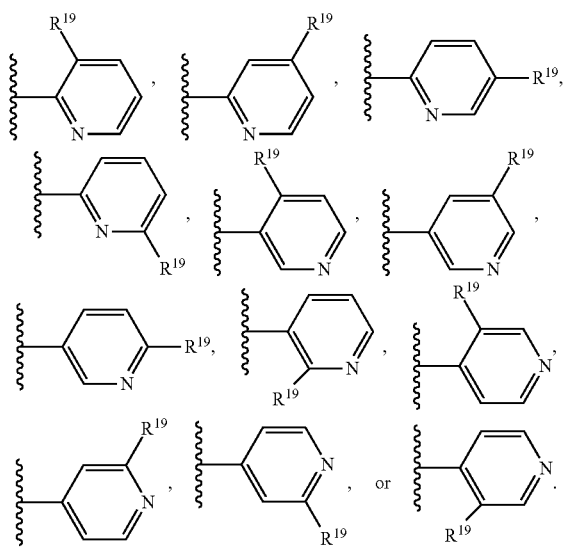

In some embodiments, $R^{18}$ is

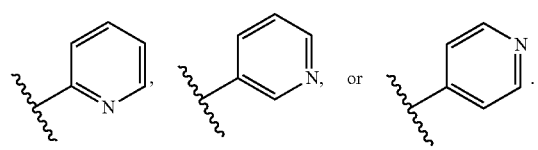

In some embodiments, $L^2$ is absent. In some embodiments, $L^2$ is O. In some embodiments, $L^2$ is

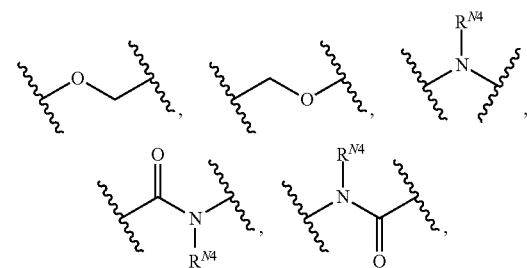

where $R^{N4}$ is H, optionally substituted $C_1$-$C_6$ alkyl, or optionally substituted $C_1$-$C_6$ heteroalkyl. In some embodiments, $L^2$ is

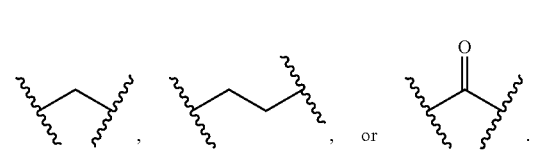

In some embodiments, $R^{N4}$ is H or —CH$_3$.

In some embodiments, s1 is 0 or 1. In some embodiments, s1 is 0. In some embodiments, s1 is 1.

In some embodiments, s2 is 0 or 1. In some embodiments, s2 is 0. In some embodiments, s2 is 1.

In some embodiments, $R^3$ is

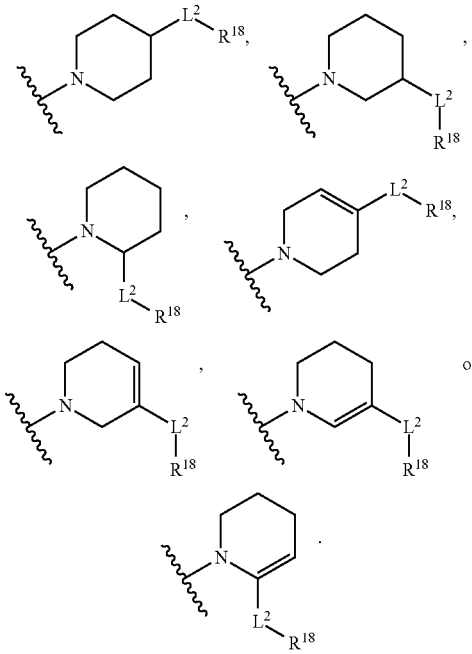

In some embodiments, $R^{23}$ is

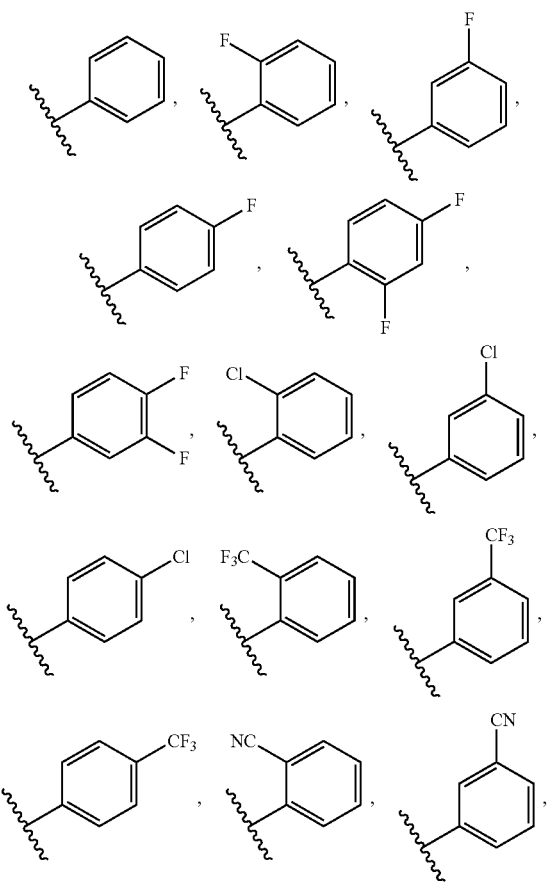

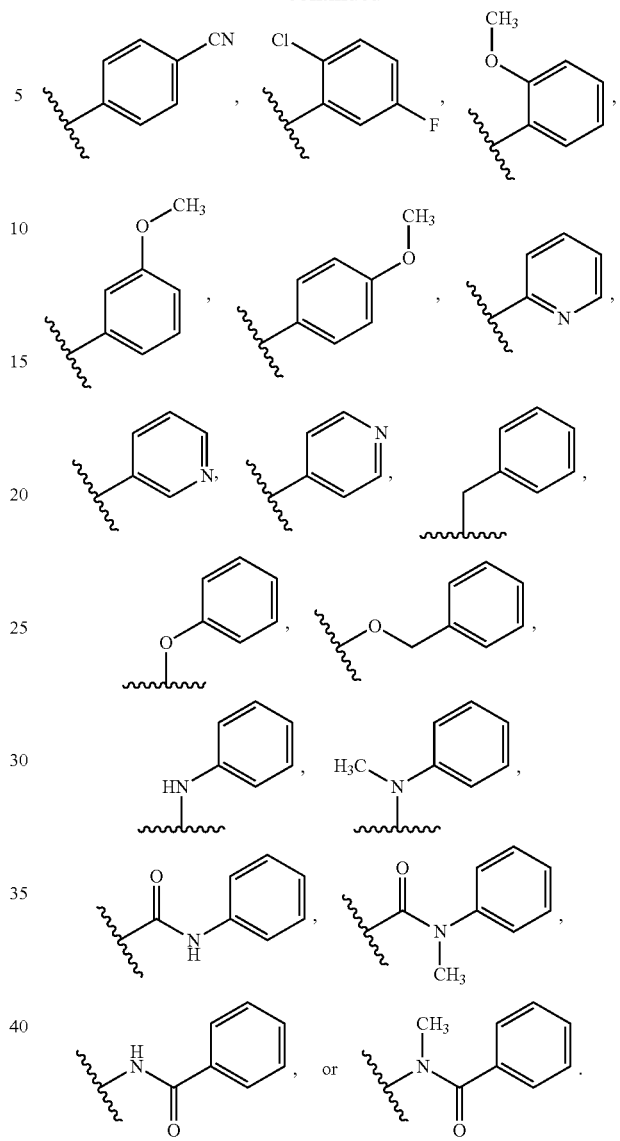

In some embodiments, $R^3$ is a heterocyclyl having the structure of Formula IIf:

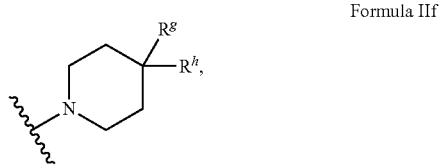

Formula IIf where $R^g$ and $R^h$, together with the atom to which each is attached, combine to form an optionally substituted $C_3$-$C_{10}$ carbocyclylene or optionally substituted $C_2$-$C_9$ heterocyclylene.

In some embodiments, $R^g$ and $R^h$, together with the atom to which each is attached, combine to form an optionally substituted $C_3$-$C_{10}$ heterocyclylene.

In some embodiments, $R^3$ is

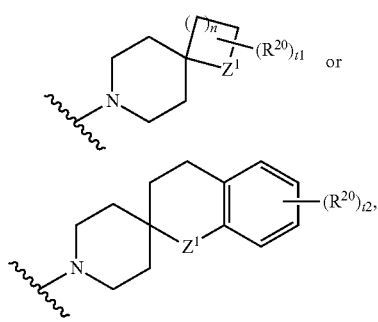

or

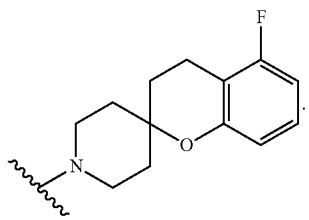 [SMILES: *N1CCC2(CCc3c(F)cccc3O2)CC1]

In some embodiments, $R^3$ is

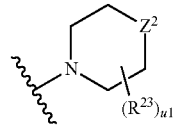

In some embodiments, $R^3$ is a heterocyclyl having the structure of Formula IIg or Formula IIh:

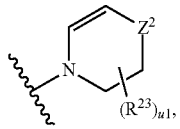  Formula IIg

Formula IIh where
n is 1, 2, 3, 4, or 5;
t1 is 0, 1, 2, 3, 4, 5, 6, or 7;
t2 is 0, 1, 2, 3, or 4;
$Z^1$ is O, S, or $NR^{N5}$, where $R^{N5}$ is H, optionally substituted $C_1$-$C_6$ alkyl, or optionally substituted $C_1$-$C_6$ heteroalkyl; and
each $R^{20}$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $R^{20}$ is, independently, halo optionally substituted $C_1$-$C_6$ alkyl, optionally substituted $C_1$-$C_6$ heteroalkyl, optionally substituted $C_6$-$C_{10}$ aryl, or optionally substituted $C_2$-$C_9$ heteroaryl.

In some embodiments, each $R^{20}$ is F, Cl, Br, I, CN, hydroxyl,

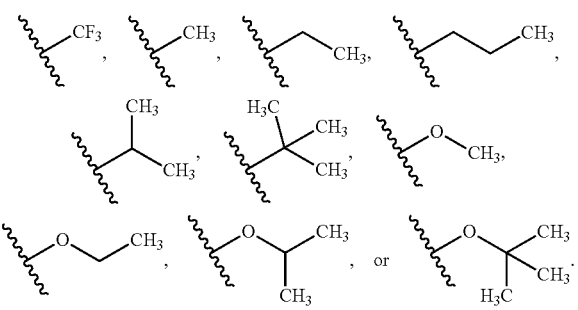

In some embodiments, each $R^{20}$ is F, Cl, Br, I, or CN.
In some embodiments, $R^{N5}$ is H, optionally substituted $C_1$-$C_6$ alkyl, optionally substituted $C_1$-$C_6$ heteroalkyl, optionally substituted $C_6$-$C_{10}$ aryl, or optionally substituted $C_2$-$C_9$ heteroaryl.

In some embodiments, n is 1, 2, or 3.

In some embodiments, n is 1. In some embodiments, n is 2. In some embodiments, n is 3.

In some embodiments, t1 is 0 or 1. In some embodiments, t1 is 0. In some embodiments, t1 is 1.

In some embodiments, t2 is 0 or 1. In some embodiments, t2 is 0. In some embodiments, t2 is 1.

In some embodiments, $Z^1$ is O.

where
u1 is 0, 1, 2, 3, 4, or 5;
u2 is 0, 1, 2, 3, or 4;
$Z^2$ is O, S, or $NR^{24}$,
where
$R^{24}$ is H, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl; and
each $R^{23}$ is where
each $L^2$ is, independently, absent, O, S, optionally substituted amino, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl; and
each $R^{18}$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $L^2$ is, independently, absent, O, S, optionally substituted amino, optionally substituted $C_1$-$C_6$ alkyl, or optionally substituted $C_1$-$C_6$ heteroalkyl.

In some embodiments, each $R^{18}$ is, independently, halo, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, $Z^2$ is O or $NR^{24}$. In some embodiments, $Z^2$ is O. In some embodiments, $Z^2$ is $NR^{24}$.

In some embodiments, u1 is 0 or 1. In some embodiments, u1 is 0. In some embodiments, u1 is 1.

In some embodiments, u2 is 0 or 1. In some embodiments, u2 is 0. In some embodiments, u2 is 1.

In some embodiments, $R^3$ is

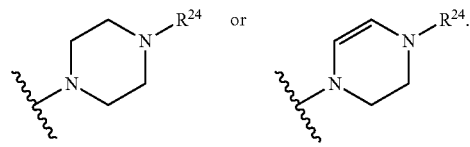

In some embodiments, $R^{24}$ is

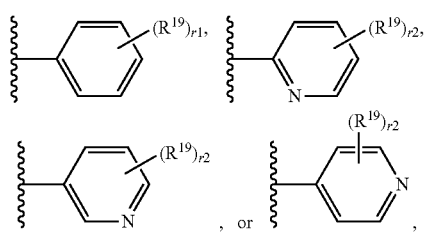

where
r1 is 0, 1, 2, 3, 4, or 5;
r2 is 0, 1, 2, 3, or 4; and
each $R^{19}$ is, independently, halo, optionally substituted $C_1$-$C_6$ alkyl, or optionally substituted $C_1$-$C_6$ heteroalkyl.

In some embodiments, each $R^{19}$ is, independently, F, Cl, Br, I, CN, hydroxyl,

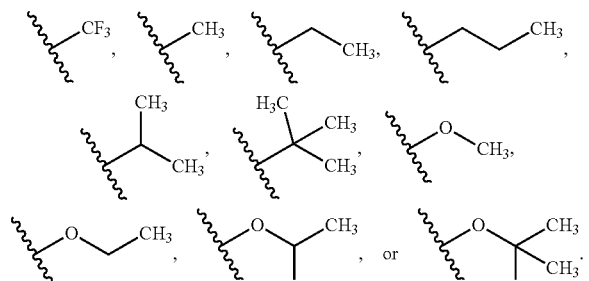

In some embodiments, r1 is 0, 1, or 2. In some embodiments r1 is 0. In some embodiments, r1 is 1. In some embodiments r1 is 2.

In some embodiments, $R^{24}$ is

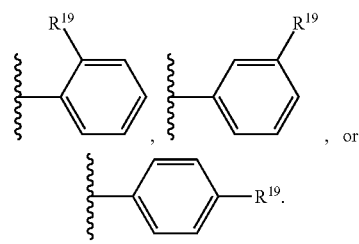

In some embodiments, $R^{24}$ is

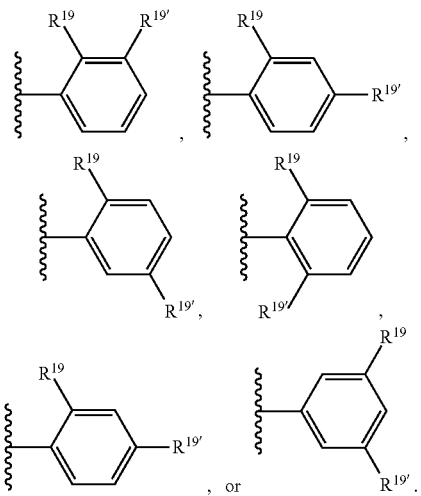

In some embodiments, r2 is 0, 1, or 2. In some embodiments r2 is 0. In some embodiments, r2 is 1.

In some embodiments, $R^{24}$ is

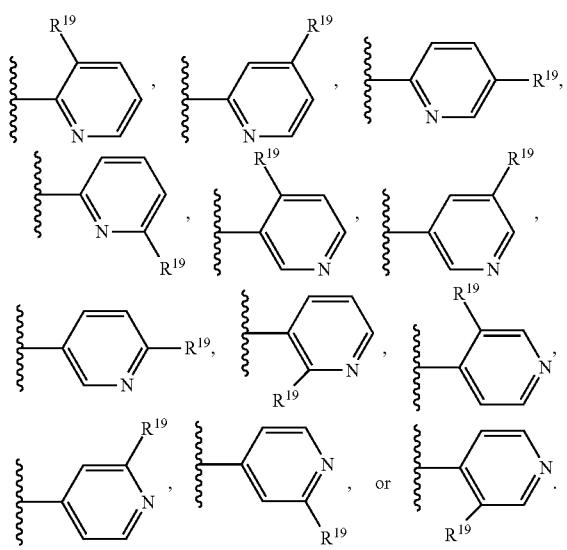

In some embodiments, $R^{24}$ is

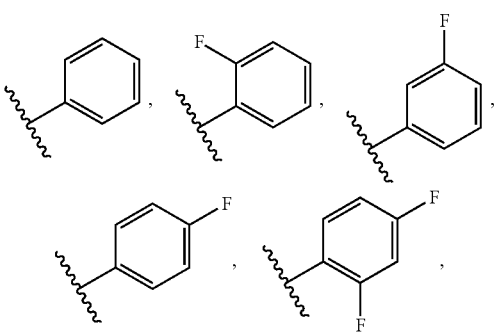

-continued

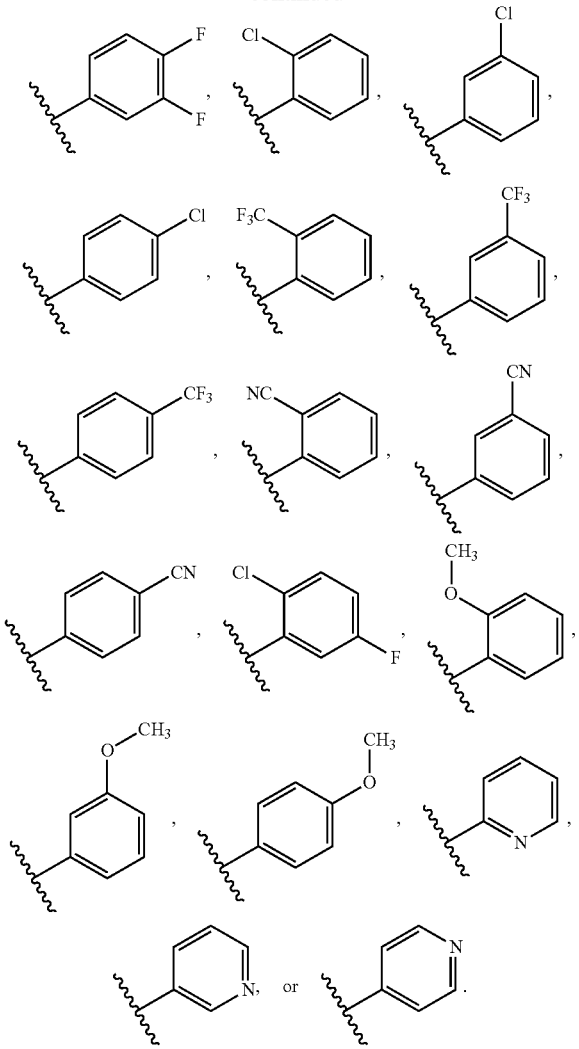

In some embodiments, $R^3$ is a heterocyclyl having the structure of Formula IIi, Formula IIj, or Formula IIk:

Formula IIi

Formula IIj

Formula IIk

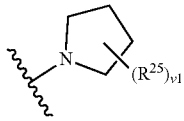
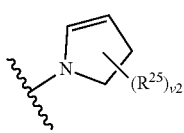
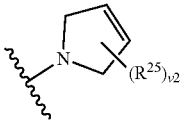

where
v1 is 0, 1, 2, 3, 4, 5, or 6;
v2 is 0, 1, 2, 3, or 4; and each $R^{25}$ is

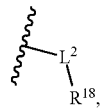

where
each $L^2$ is, independently, absent, O, S, optionally substituted amino, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl; and each $R^{18}$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, $L^2$ is, independently, absent, O, S, optionally substituted amino, optionally substituted $C_1$-$C_6$ alkyl, or optionally substituted $C_1$-$C_6$ heteroalkyl.

In some embodiments, each $R^{18}$ is, independently, halo, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $R^{18}$ is, independently, halo, optionally substituted $C_6$-$C_{10}$ aryl, or optionally substituted $C_2$-$C_9$ heteroaryl.

In some embodiments, each $R^{18}$ is F, Cl, Br, I,

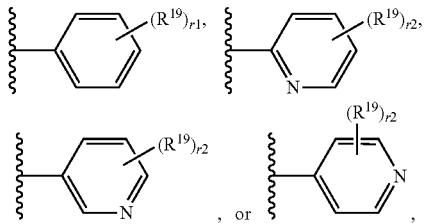

, or where
r1 is 0, 1, 2, 3, 4, or 5;
r2 is 0, 1, 2, 3, or 4; and
each $R^{19}$ is, independently, halo, optionally substituted $C_1$-$C_6$ alkyl, or optionally substituted $C_1$-$C_6$ heteroalkyl.

In some embodiments, each $R^{19}$ is, independently, F, Cl, Br, I, CN, hydroxyl,

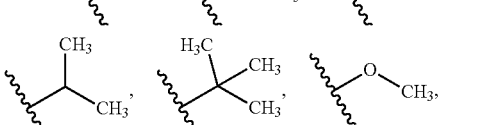

In some embodiments, r is 0, 1, or 2. In some embodiments r is 0. In some embodiments, r is 1. In some embodiments r is 2.

In some embodiments, $R^{18}$ is

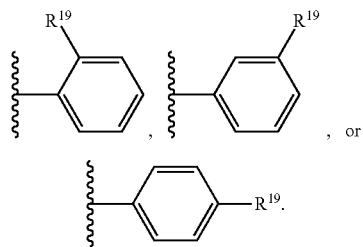

In some embodiments, $R^{18}$ is

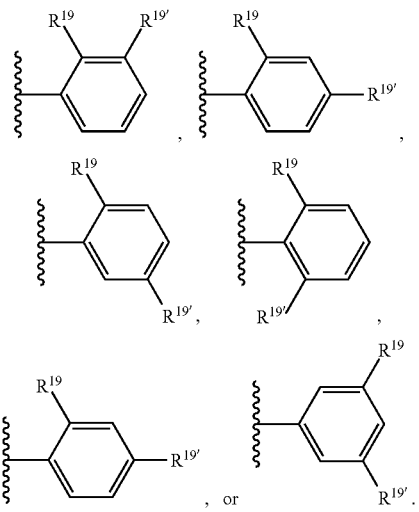

In some embodiments, v1 is 0 or 1. In some embodiments, v1 is 0. In some embodiments, v1 is 1.

In some embodiments, v2 is 0 or 1. In some embodiments, v2 is 0. In some embodiments, v2 is 1.

In some embodiments, $L^2$ is absent.

In some embodiments, $L^2$ is O.

In some embodiments, $L^2$ is

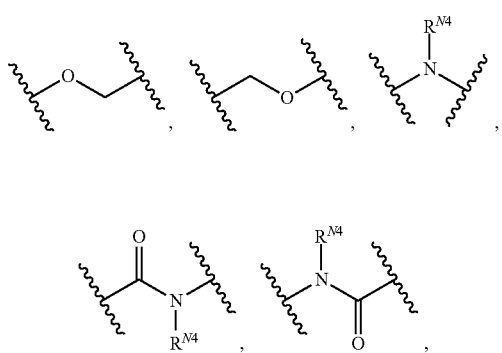

where $R^{N4}$ is H, optionally substituted $C_1$-$C_6$ alkyl, or optionally substituted $C_1$-$C_6$ heteroalkyl.

In some embodiments, $R^{N4}$ is H or —$CH_3$.

In some embodiments, $L^2$ is

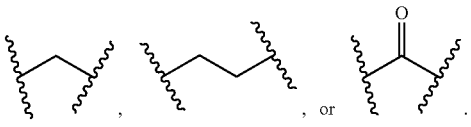

In some embodiments, $R^3$ is

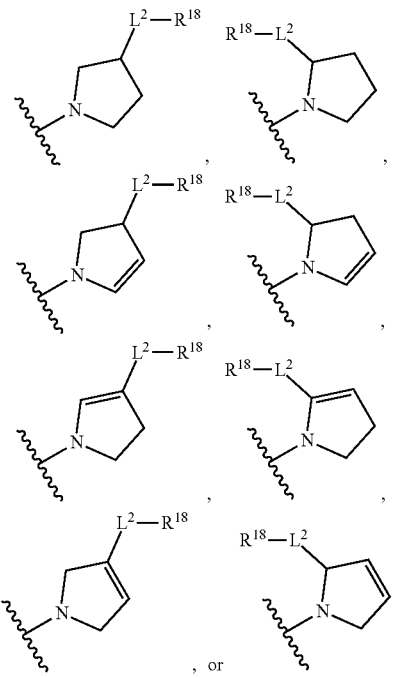

In some embodiments, $R^{25}$ is

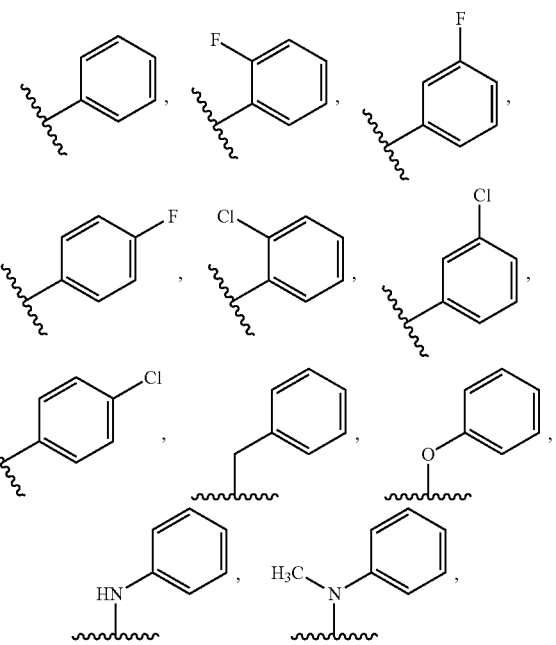

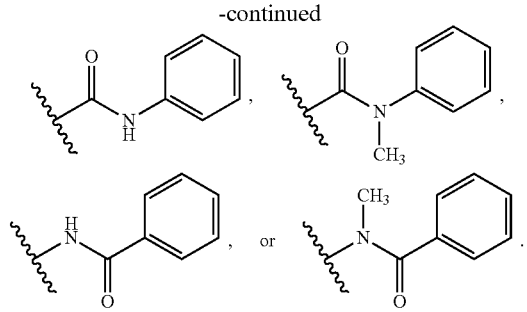

In some embodiments, R³ is a heterocyclyl having the structure of Formula IIm:

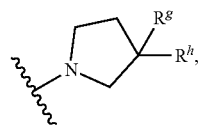

Formula IIm where
R$^g$ and R$^h$, together with the atom to which each is attached, combine to form an optionally substituted $C_3$-$C_{10}$ carbocyclylene or optionally substituted $C_2$-$C_9$ heterocyclylene.

In some embodiments, R$^g$ and R$^h$, together with the atom to which each is attached, combine to form an optionally substituted $C_3$-$C_{10}$ heterocyclylene.

In some embodiments, R³ is

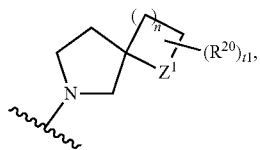

where
n is 1, 2, 3, 4, or 5;
t1 is 0, 1, 2, 3, 4, 5, 6, or 7;
$Z^1$ is O, S, or NR$^{N5}$, where R$^{N5}$ is H, optionally substituted $C_1$-$C_6$ alkyl, or optionally substituted $C_1$-$C_6$ heteroalkyl; and
each $R^{20}$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, each $R^{20}$ is, independently, optionally substituted $C_1$-$C_6$ alkyl, optionally substituted $C_1$-$C_6$ heteroalkyl, optionally substituted $C_6$-$C_{10}$ aryl, or optionally substituted $C_2$-$C_9$ heteroaryl.

In some embodiments, R$^{N5}$ is H, optionally substituted $C_1$-$C_6$ alkyl, optionally substituted $C_1$-$C_6$ heteroalkyl, optionally substituted $C_6$-$C_{10}$ aryl, or optionally substituted $C_2$-$C_9$ heteroaryl.

In some embodiments, n is 1, 2, or 3. In some embodiments, n is 2. In some embodiments, n is 3.

In some embodiments, t1 is 0, 1, or 2. In some embodiments, t1 is 1. In some embodiments, t1 is 2.

In some embodiments, $Z^1$ is O.

In some embodiments, R² is H or optionally substituted $C_1$-$C_6$ alkyl.

In some embodiments, R² is H or —CH₃.

In some embodiments, R² is H.

In some embodiments, R¹ is H, halo, CN, NO₂, hydroxyl, optionally substituted amino, optionally substituted $C_1$-$C_6$ alkyl, optionally substituted $C_1$-$C_6$ heteroalkyl, optionally substituted $C_1$-$C_6$ alkenyl, optionally substituted $C_1$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, R¹ is H, halo, CN, optionally substituted $C_1$-$C_6$ alkyl, optionally substituted $C_1$-$C_6$ heteroalkyl, optionally substituted $C_1$-$C_6$ alkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, R¹ is H, halo, CN, optionally substituted $C_1$-$C_6$ alkyl, optionally substituted $C_1$-$C_6$ heteroalkyl, or optionally substituted $C_1$-$C_6$ alkenyl.

In some embodiments, R¹ is H, F, Cl, Br, I, CN,

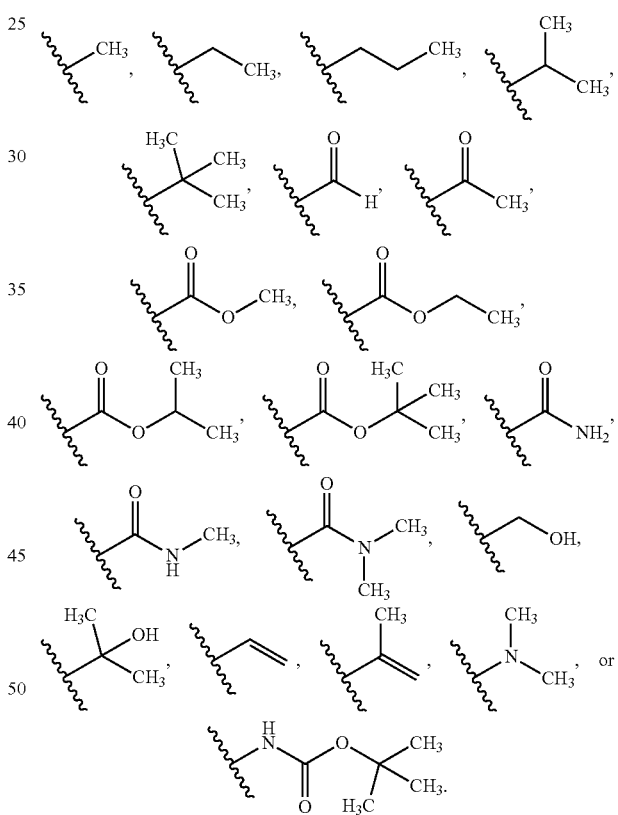

In some embodiments, R¹ is optionally substituted $C_3$-$C_{10}$ carbocyclyl.

In some embodiments, R¹ is

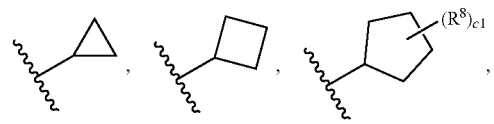

-continued

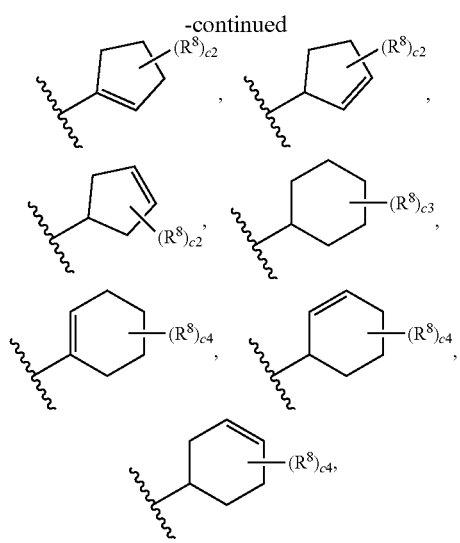

where
c1 is 0, 1, 2, 3, 4, or 5;
c2 is 0, 1, 2, 3, or 4;
c3 is 0, 1, 2, 3, 4, 5, or 6;
c4 is 0, 1, 2, 3, 4, or 5; and
each $R^8$ is, independently, halo, optionally substituted $C_1$-$C_6$ alkyl, or optionally substituted $C_1$-$C_6$ heteroalkyl.

In some embodiments, c1 is 0.
In some embodiments, c2 is 0.
In some embodiments, c3 is 0.
In some embodiments, c4 is 0.

In some embodiments, $R^1$ is optionally substituted $C_2$-$C_9$ heterocyclyl.

In some embodiments, $R^1$ is

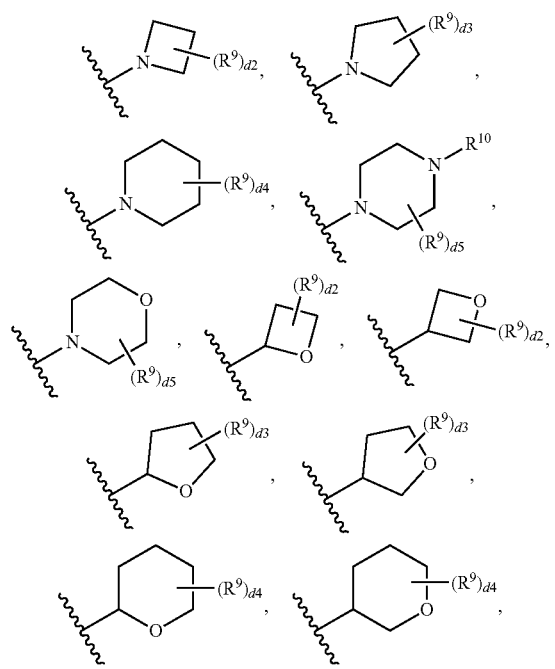

-continued

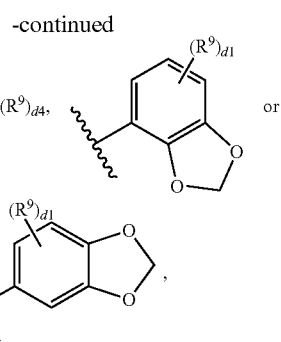

where
d1 is 0, 1, 2, or 3;
d2 is 0, 1, 2, or 3;
d3 is 0, 1, 2, 3, or 4;
d4 is 0, 1, 2, 3, 4, or 5;
d5 is 0, 1, 2, 3, or 4;
each $R^9$ is, independently, halo, hydroxyl, optionally substituted $C_1$-$C_6$ alkyl, or optionally substituted $C_1$-$C_6$ heteroalkyl; and
$R^{10}$ is H, optionally substituted $C_1$-$C_6$ alkyl, or optionally substituted $C_1$-$C_6$ heteroalkyl.

In some embodiments, d1 is 0 or 1. In some embodiments, d1 is 0. In some embodiments, d1 is 1.

In some embodiments, d2 is 0, 1, or 2. In some embodiments, d2 is 0. In some embodiments, d2 is 1.

In some embodiments, d3 is 0, 1, or 2. In some embodiments, d3 is 0. In some embodiments, d3 is 1.

In some embodiments, d4 is 0, 1, or 2. In some embodiments, d4 is 0. In some embodiments, d4 is 1.

In some embodiments, d5 is 0, 1, or 2. In some embodiments, d5 is 0. In some embodiments, d5 is 1.

In some embodiments, $R^9$ is hydroxyl or optionally substituted $C_1$-$C_6$ heteroalkyl.

In some embodiments, $R^9$ is hydroxyl,

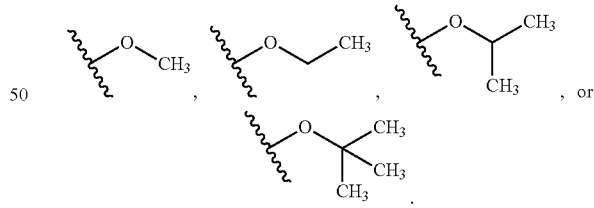

In some embodiments, $R^{10}$ is H,

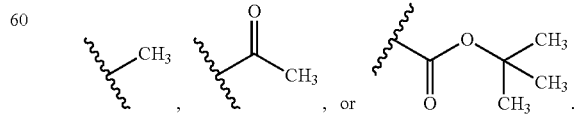

In some embodiments, $R^1$ is optionally substituted $C_6$-$C_{10}$ aryl.

In some embodiments, $R^1$

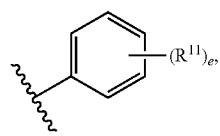

where
e is 0, 1, 2, 3, 4, or 5; and
each $R^{11}$ is, independently, halo, CN, $NO_2$, hydroxyl, optionally substituted $C_1$-$C_6$ alkyl, or optionally substituted $C_1$-$C_6$ heteroalkyl.

In some embodiments, e is 0. In some embodiments, e is 1.

In some embodiments, $R^1$ is

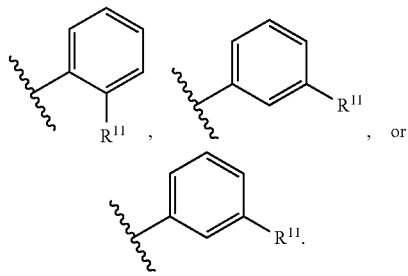

In some embodiments, e is 2.
In some embodiments, $R^1$ is

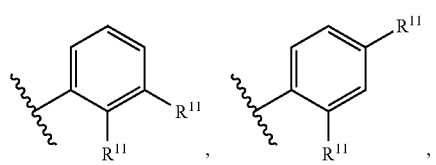

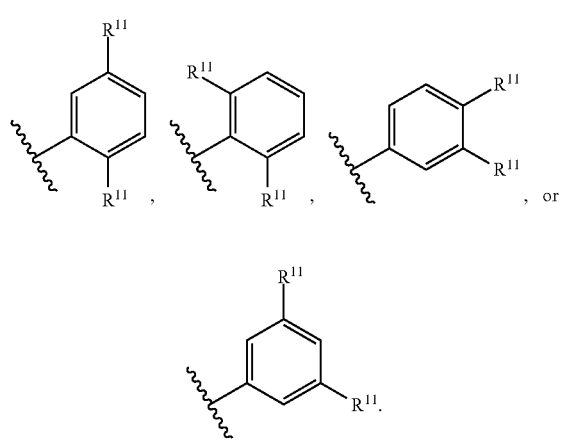

In some embodiments, $R^1$ is optionally substituted $C_2$-$C_9$ heteroaryl.

In some embodiments, $R^1$ is

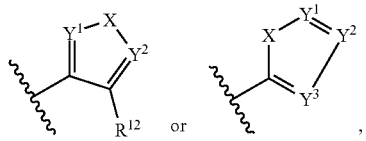

where
X is O, S, or $NR^{N1}$, where $R^{N1}$ is H, optionally substituted $C_1$-$C_6$ alkyl, or optionally substituted $C_1$-$C_6$ heteroalkyl;
each of $Y^1$, $Y^2$, and, and $Y^3$ is, independently, N or $CR^{C1}$, where $R^{C1}$ is H, halo, CN, optionally substituted $C_1$-$C_6$ alkyl, or optionally substituted $C_1$-$C_6$ heteroalkyl; and $R^{12}$ is H, halo, CN, optionally substituted $C_1$-$C_6$ alkyl, or optionally substituted $C_1$-$C_6$ heteroalkyl.

In some embodiments, X is S. In some embodiments, X is O.

In some embodiments, $Y^1$ is N. In some embodiments, $Y^1$ is $CR^{C1}$.

In some embodiments, $Y^2$ is N. In some embodiments, $Y^2$ is $CR^{C1}$.

In some embodiments, $Y^3$ is N. In some embodiments, $Y^3$ is $CR^{C1}$.

In some embodiments, $R^{C1}$ is H,

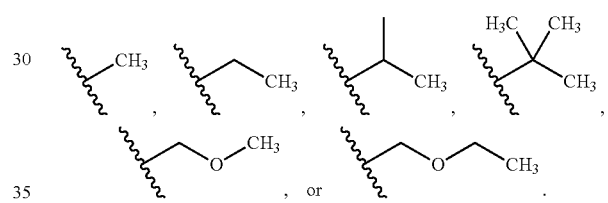

In some embodiments, $R^{12}$ is H,

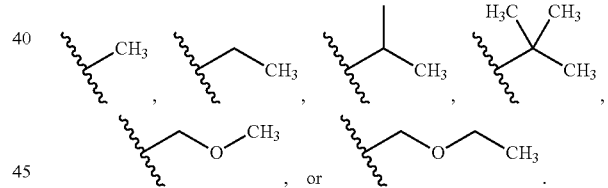

In some embodiments, $R^1$ is

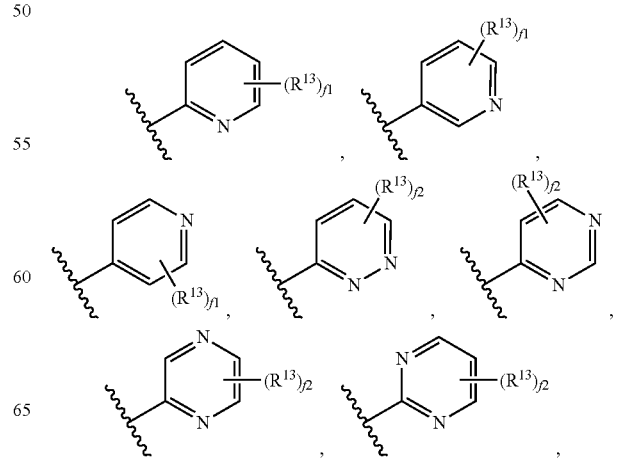

-continued

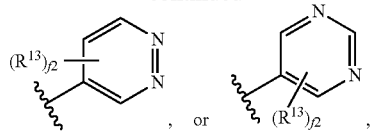

where
f1 is 0, 1, 2, 3, or 4;
f2 is 0, 1, 2, or 3; and
each $R^{13}$ is, independently, halo, CN, optionally substituted $C_1$-$C_6$ alkyl, or optionally substituted $C_1$-$C_6$ heteroalkyl.

In some embodiments, $R^1$ is

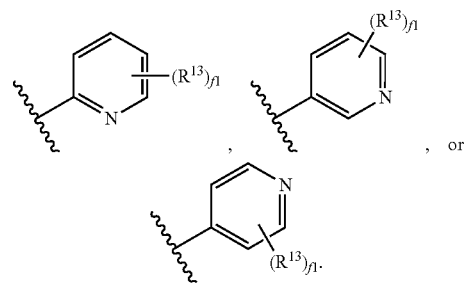

In some embodiments, f1 is 0. In some embodiments, f1 is 1.

In some embodiments, $R^1$ is

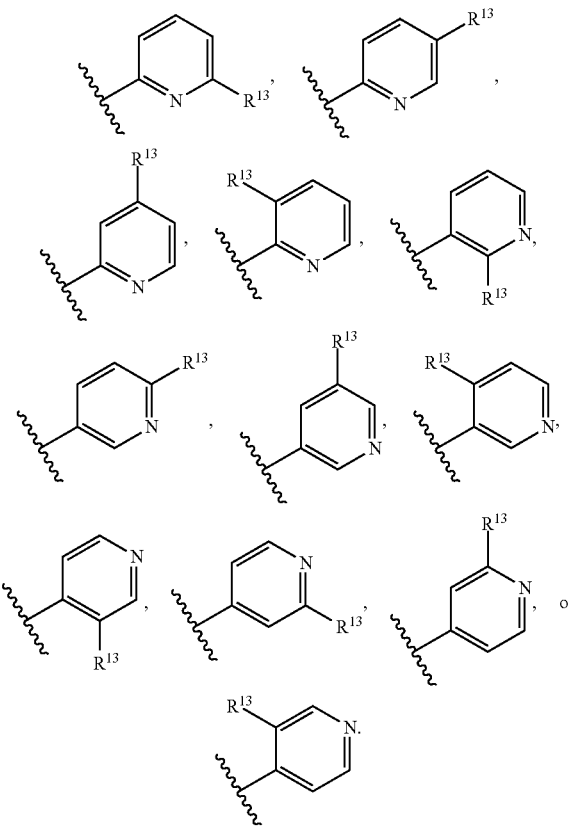

In some embodiments, f2 is 0.

In some embodiments, $R^1$ is

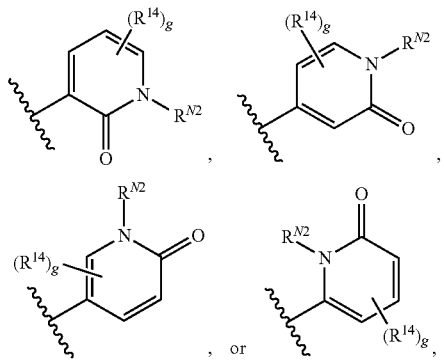

where
g is 0, 1, 2, 3, or 4;
$R^{N2}$ is H, optionally substituted $C_1$-$C_6$ alkyl, or optionally substituted $C_1$-$C_6$ heteroalkyl; and
each $R^{14}$ is H, halo, CN, optionally substituted $C_1$-$C_6$ alkyl, or optionally substituted $C_1$-$C_6$ heteroalkyl.

In some embodiments, $R^1$ is

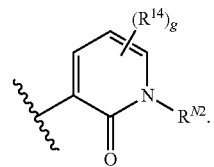

In some embodiments, g is 0.
In some embodiments, $R^1$ is

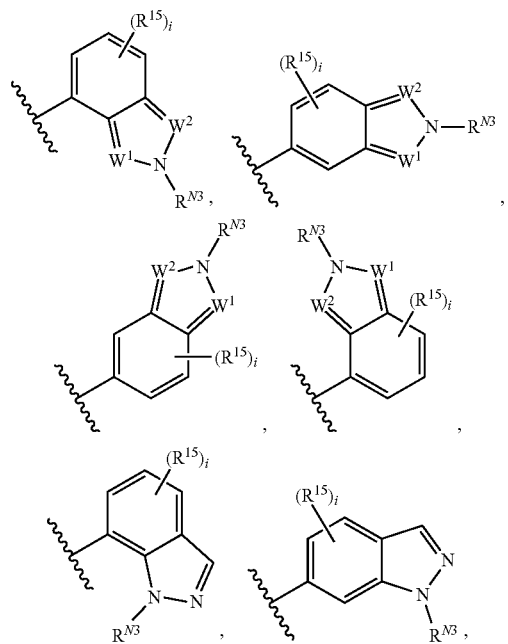

-continued

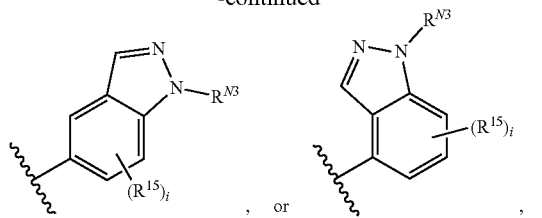

where
i is 0, 1, 2, or 3;
each of $W^1$ and $W^2$ is, independently, N or $CR^{C2}$, where $R^{C2}$ is H, halo, CN, optionally substituted $C_1$-$C_6$ alkyl, or optionally substituted $C_1$-$C_6$ heteroalkyl;

$R^{N3}$ is H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, or optionally substituted $C_2$-$C_9$ heteroaryl; and each of $R^{15}$ is, independently, halo, CN, optionally substituted $C_1$-$C_6$ alkyl, or optionally substituted $C_1$-$C_6$ heteroalkyl.

In some embodiments, i is 0.

In some embodiments, $W^1$ is N. In some embodiments, $W^1$ is $CR^{C2}$.

In some embodiments, $W^2$ is N. In some embodiments, $W^2$ is $CR^{C2}$.

In some embodiments, $R^{N3}$ is H, optionally substituted $C_1$-$C_6$ alkyl, optionally substituted $C_1$-$C_6$ heteroalkyl, or optionally substituted $C_2$-$C_9$ heterocyclyl.

In some embodiments, $R^{N3}$ is

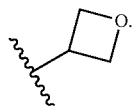 [SMILES: *C1COC1]

In some embodiments, $R^1$ is F, Cl, Br, I, CN, $NO_2$, $NH_2$,

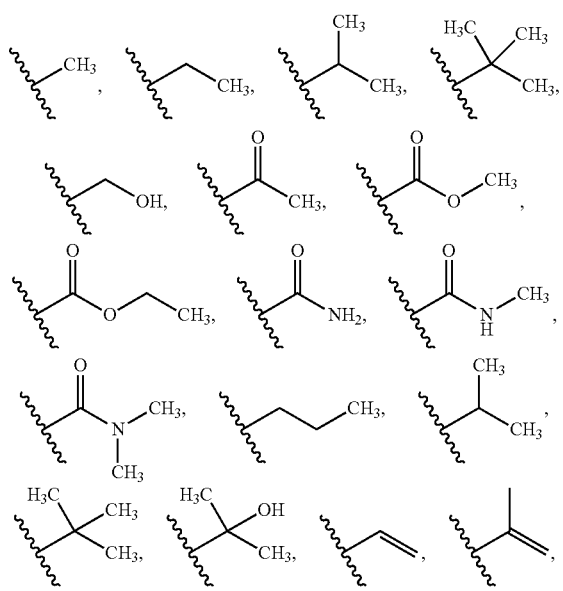

-continued

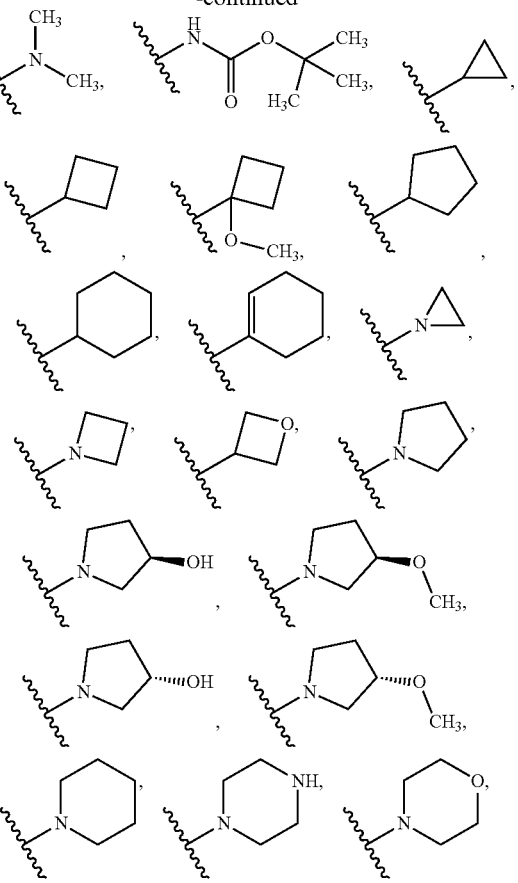

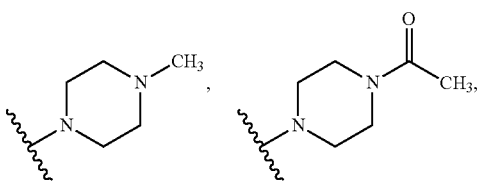

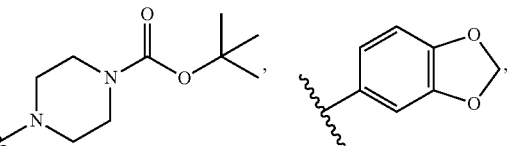

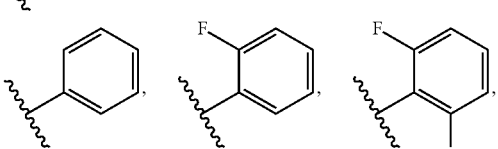

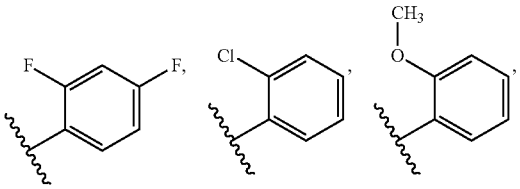

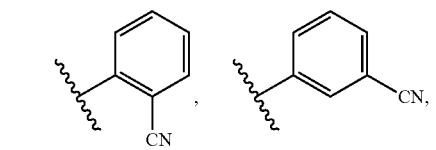

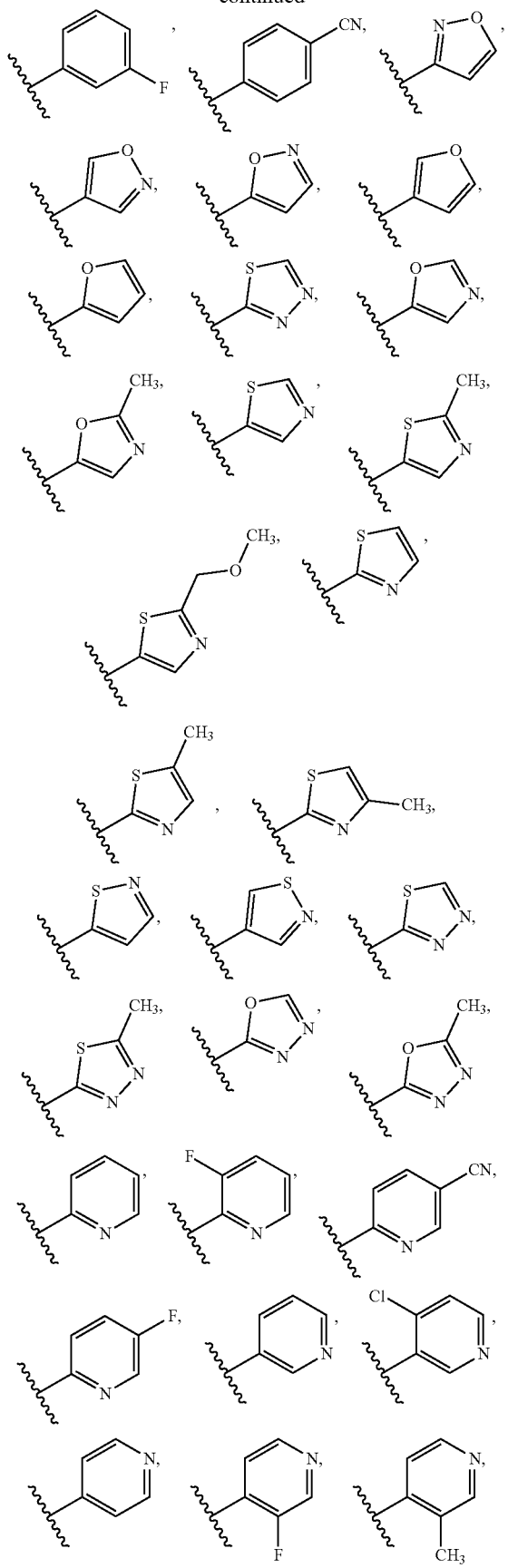

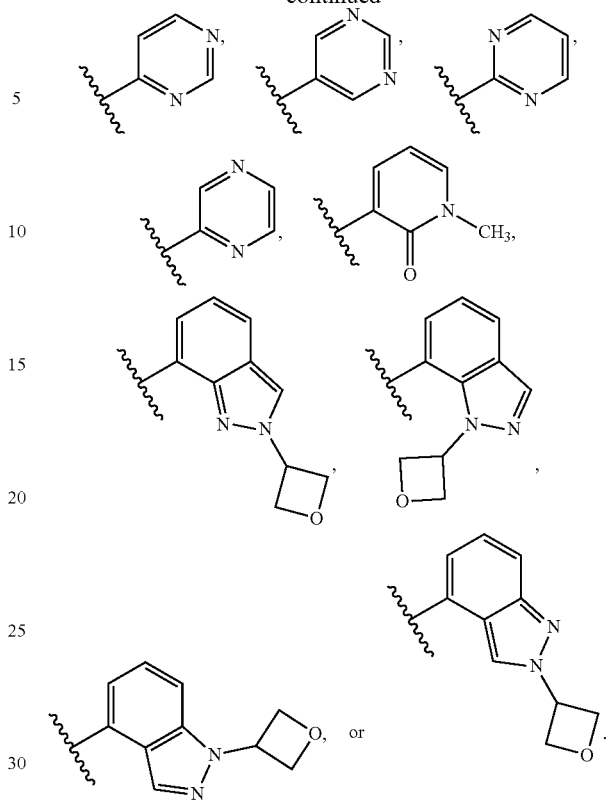

In some embodiments, R¹ and R², together with the atoms to which each is attached, combine to form an optionally substituted $C_3$-$C_{10}$ carbocyclylene, optionally substituted $C_2$-$C_9$ heterocyclylene, optionally substituted $C_6$-$C_{10}$ arylene, or optionally substituted $C_2$-$C_9$ heteroarylene.

In some embodiments, R¹ and R², together with the atoms to which each is attached, combine to form an optionally substituted $C_3$-$C_{10}$ carbocyclylene.

In some embodiments, the compound has the structure of Formula Ib:

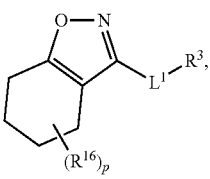

Formula Ib or a pharmaceutically acceptable salt thereof.

In some embodiments, L¹ is optionally substituted $C_1$-$C_6$ heteroalkylene.

In some embodiments, L¹ is

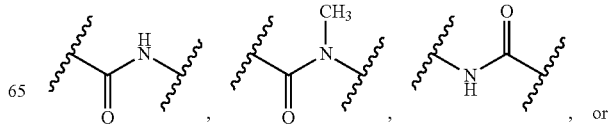

, or

-continued
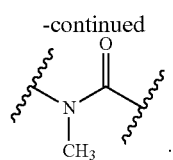
5
In some embodiments, $L^1$ is
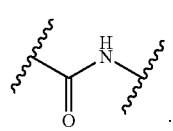
In an aspect, this disclosure provides a compound, or pharmaceutically acceptable salt thereof, having the structure of any one of compounds 1-464 in Table 1.
TABLE 1
Compounds of the Invention
| No. | Structure |
|---|---|
| 1 | 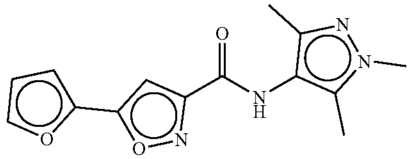 |
| 2 | 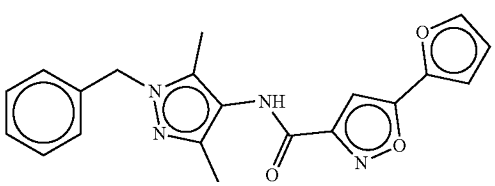 |
| 3 | 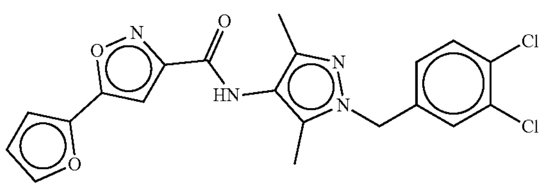 |
| 4 | 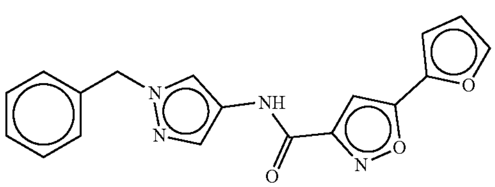 |
| 5 | 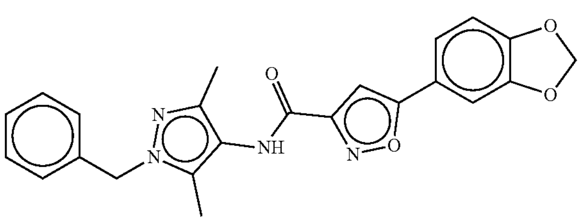 |

TABLE 1-continued
Compounds of the Invention
| No. | Structure |
|---|---|
| 6 | 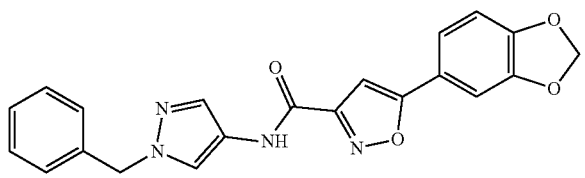 [SMILES: O=C(Nc1cnn(Cc2ccccc2)c1)c1cc(-c2ccc3c(c2)OCO3)on1] |
| 7 | 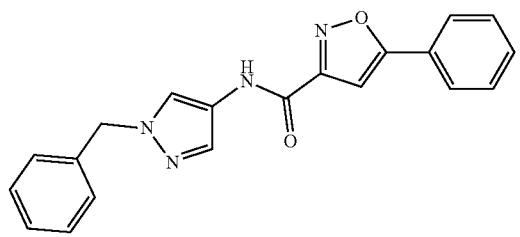 [SMILES: O=C(Nc1cnn(Cc2ccccc2)c1)c1cc(-c2ccccc2)on1] |
| 8 | 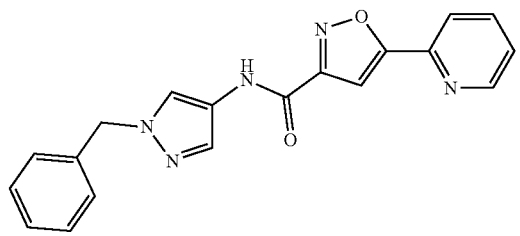 [SMILES: O=C(Nc1cnn(Cc2ccccc2)c1)c1cc(-c2ccccn2)on1] |
| 9 | 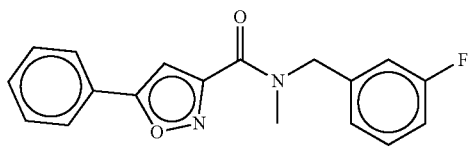 |
| 10 | 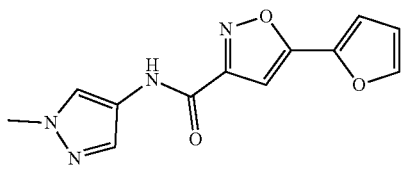 [SMILES: Cn1cc(NC(=O)c2cc(-c3ccco3)on2)cn1] |
| 11 | 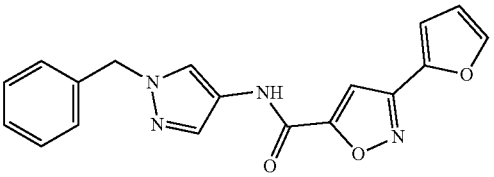 [SMILES: O=C(Nc1cnn(Cc2ccccc2)c1)c1cc(-c2ccco2)no1] |
| 12 | 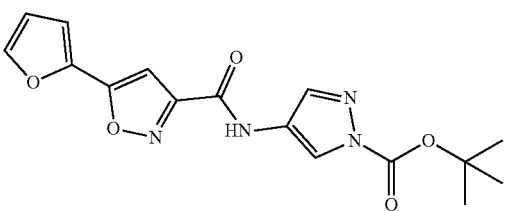 [SMILES: CC(C)(C)OC(=O)n1cc(NC(=O)c2cc(-c3ccco3)on2)cn1] |
| 13 | 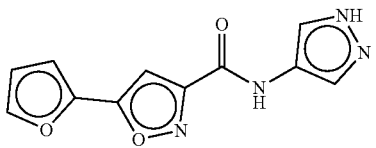 |

TABLE 1-continued

Compounds of the Invention

| No. | Structure |
|-----|-----------|
| 14  | 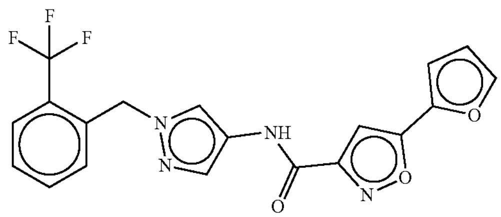 |
| 15  | 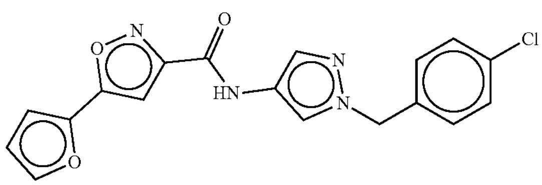 |
| 16  | 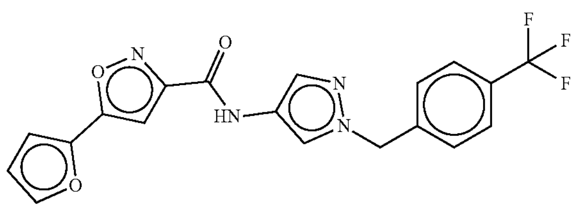 |
| 17  | 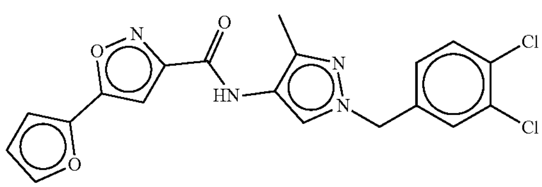 |
| 18  | 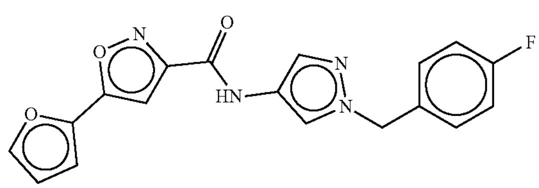 |
| 19  | 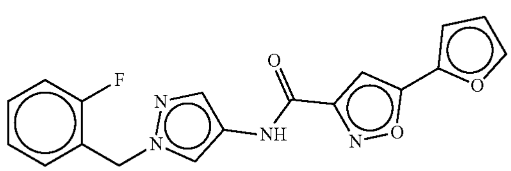 |
| 20  | 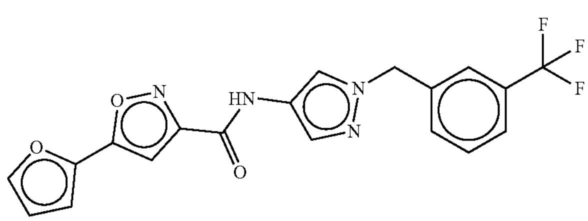 |

TABLE 1-continued

Compounds of the Invention

| No. | Structure |
|---|---|
| 21 | 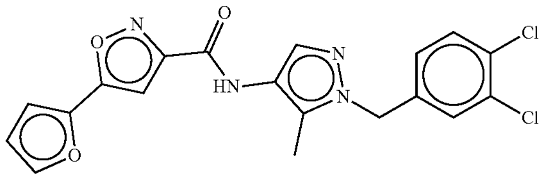 |
| 22 | 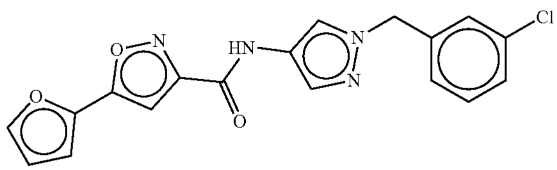 |
| 23 | 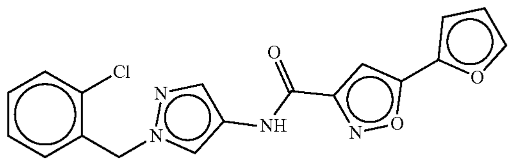 |
| 24 | 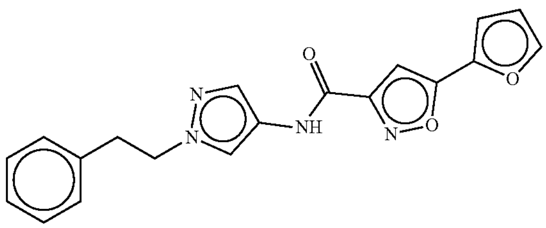 |
| 25 | 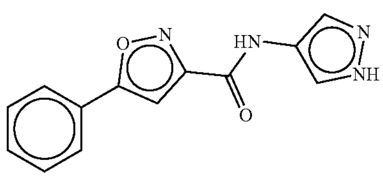 |
| 26 | 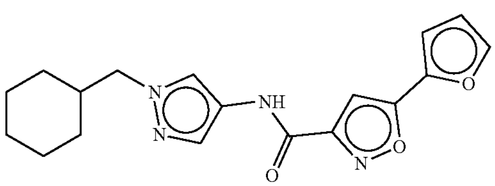 |
| 27 | 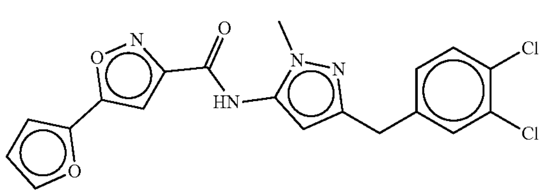 |
| 28 | 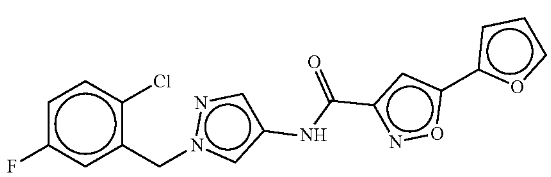 |

TABLE 1-continued

Compounds of the Invention

| No. | Structure |
|---|---|
| 29 | 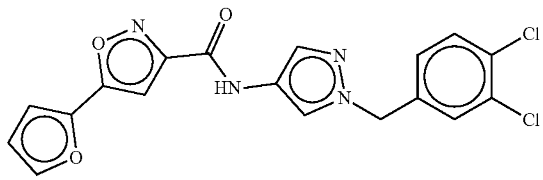 |
| 30 | 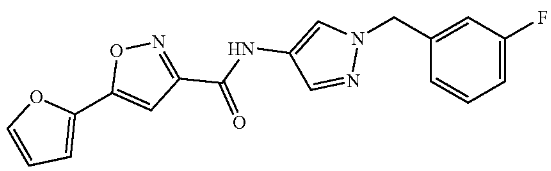 [SMILES: O=C(Nc1cnn(Cc2cccc(F)c2)c1)c1cc(-c2ccco2)on1] |
| 31 | 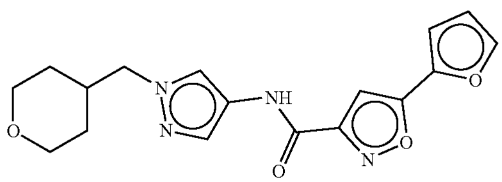 |
| 32 | 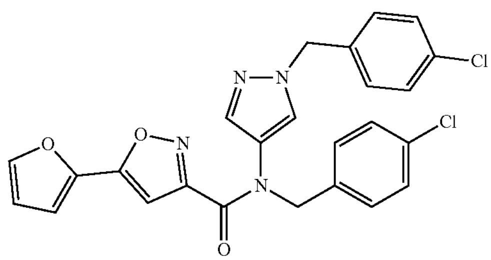 [SMILES: O=C(c1cc(-c2ccco2)on1)N(Cc1ccc(Cl)cc1)c1cnn(Cc2ccc(Cl)cc2)c1] |
| 33 | 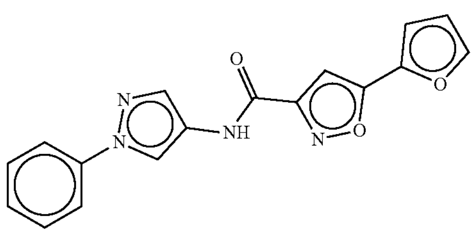 |
| 34 | 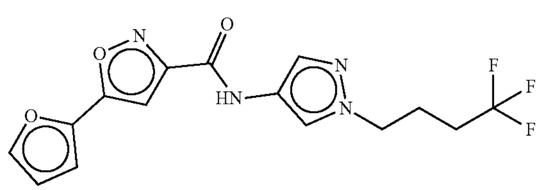 |
| 35 | 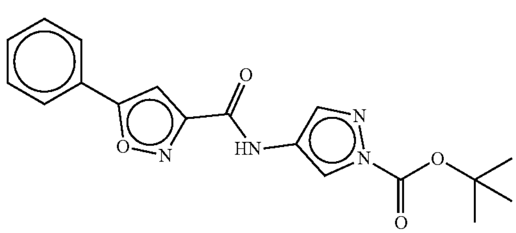 |

TABLE 1-continued

Compounds of the Invention

| No. | Structure |
|---|---|
| 36 | (2-fluoro-5-(trifluoromethyl)benzyl)triazole-pyrazole amide linked to isoxazole-furan |
| 37 | benzyl-triazole-NH-C(O)-isoxazole-thiazole |
| 38 | 5-(2-fluorophenyl)isoxazole-3-carboxamide-N-(1-benzylpyrazol-4-yl) |
| 39 | 5-phenylisoxazole-3-carboxamide-N-(1-(pyridin-3-ylmethyl)pyrazol-4-yl) |
| 40 | 5-phenylisoxazole-3-carboxamide-N-(1-(pyridin-2-ylmethyl)pyrazol-4-yl) |
| 41 | 5-phenylisoxazole-3-carboxamide-N-(1-(cyclopropylmethyl)pyrazol-4-yl) |
| 42 | 1-(4-cyanobenzyl)triazole-NH-C(O)-5-phenylisoxazole |
| 43 | 5-phenylisoxazole-3-carboxamide-N-(1-((5-cyanothiophen-2-yl)methyl)pyrazol-4-yl) |

TABLE 1-continued

Compounds of the Invention

| No. | Structure |
|-----|-----------|
| 44 | 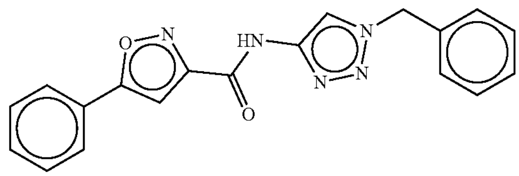 |
| 45 | 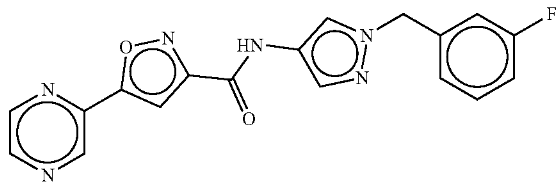 |
| 46 | 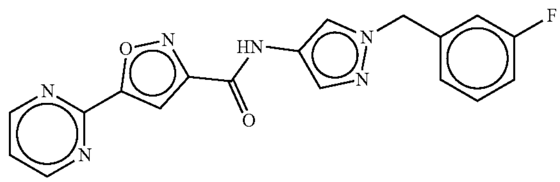 |
| 47 | 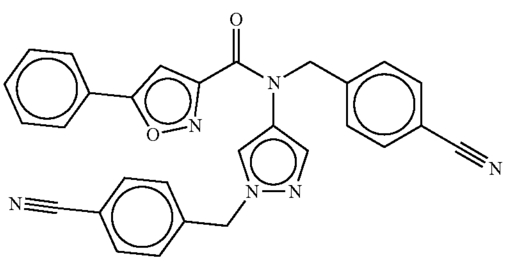 |
| 48 | 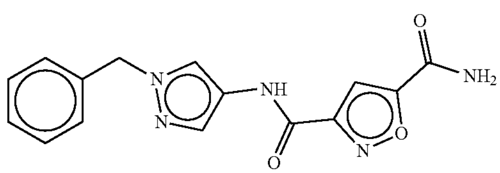 |
| 49 | 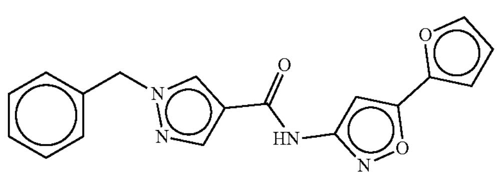 |
| 50 | 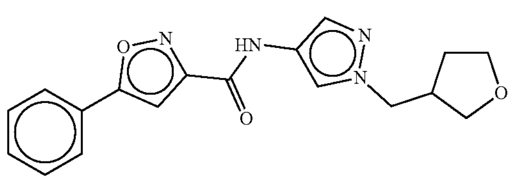 |
| 51 | 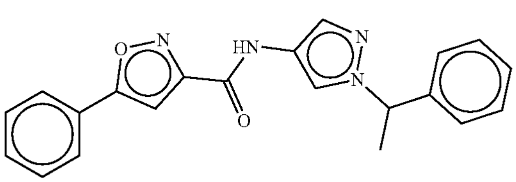 |

TABLE 1-continued
Compounds of the Invention
| No. | Structure |
|---|---|
| 52 | 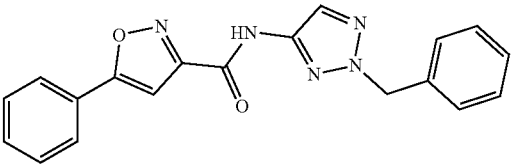 [SMILES: O=C(Nc1cnn(Cc2ccccc2)n1)c1cc(-c2ccccc2)on1] |
| 53 | 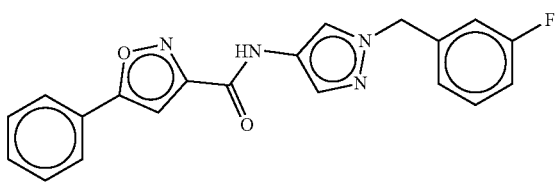 |
| 54 | 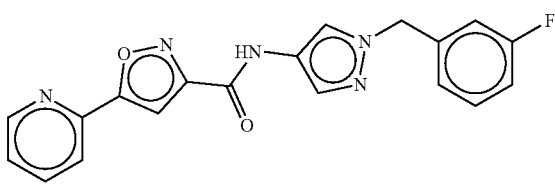 |
| 55 | 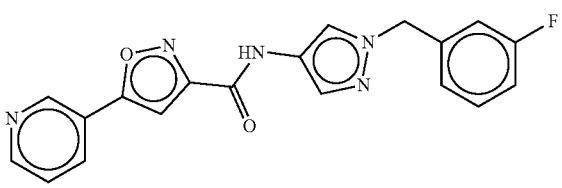 |
| 56 | 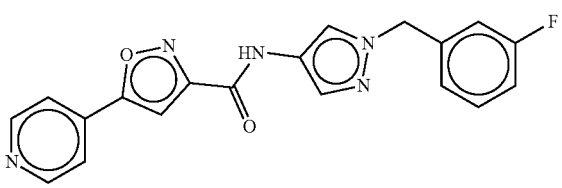 |
| 57 | 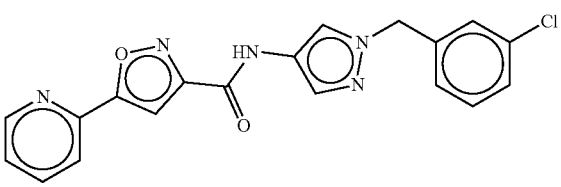 |
| 58 | 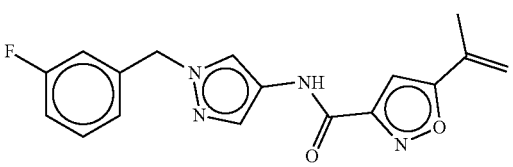 |
| 59 | 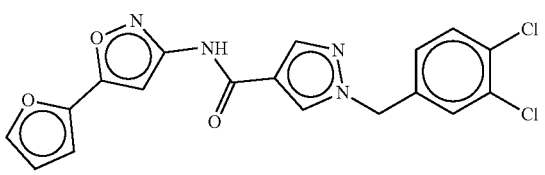 |

TABLE 1-continued
Compounds of the Invention
| No. | Structure |
|---|---|
| 60 | 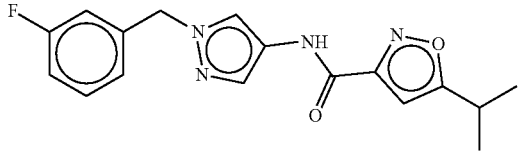 |
| 61 | 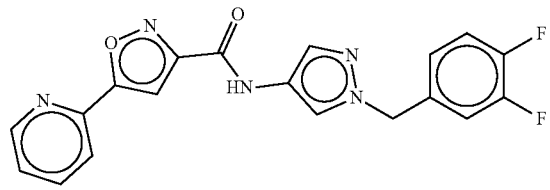 |
| 62 | 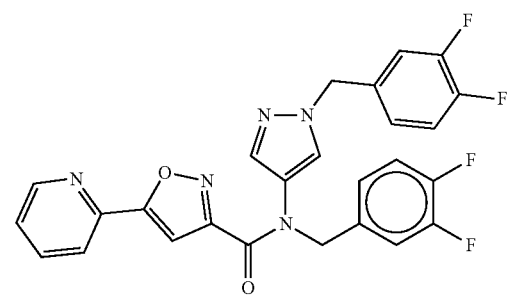 |
| 63 | 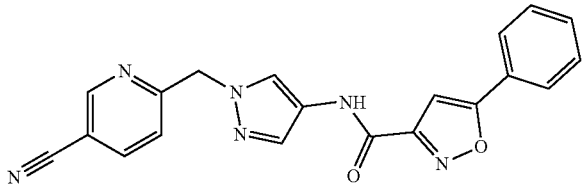 [SMILES: N#Cc1ccc(Cn2cc(NC(=O)c3cc(-c4ccccc4)on3)cn2)nc1] |
| 64 | 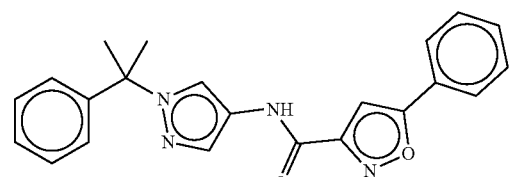 |
| 65 | 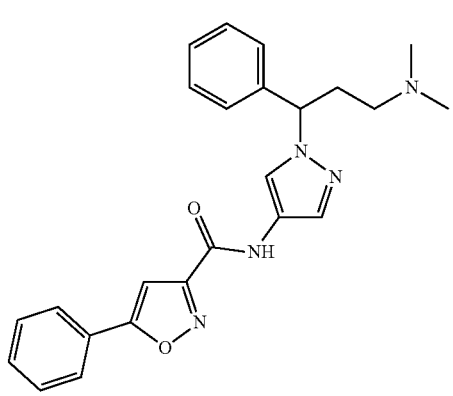 [SMILES: CN(C)CCC(c1ccccc1)n1cc(NC(=O)c2cc(-c3ccccc3)on2)cn1] |

TABLE 1-continued

Compounds of the Invention

| No. | Structure |
|---|---|
| 66 | 5-phenyl-N-(3-methyl-1-benzyl-1H-pyrazol-4-yl)isoxazole-3-carboxamide |
| 67 | N-(1-(3-fluorobenzyl)-1H-pyrazol-4-yl)-5-(2-methyloxazol-5-yl)isoxazole-3-carboxamide |
| 68 | 5-phenyl-N-(3-cyano-1-benzyl-1H-pyrazol-4-yl)isoxazole-3-carboxamide |
| 69 | N-(1-(3-fluorobenzyl)-1H-pyrazol-4-yl)-5-(thiazol-5-yl)isoxazole-3-carboxamide |
| 70 | 5-phenyl-N-(1-(3-(methylthio)-1-phenylpropyl)-1H-pyrazol-4-yl)isoxazole-3-carboxamide |
| 71 | 5-phenyl-N-(1-(3-(methylsulfinyl)-1-phenylpropyl)-1H-pyrazol-4-yl)isoxazole-3-carboxamide |

TABLE 1-continued

Compounds of the Invention

| No. | Structure |
|---|---|
| 72 | 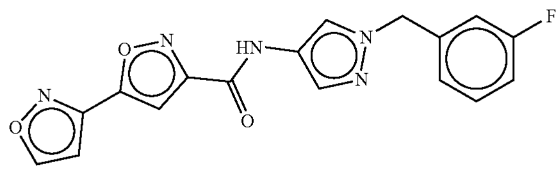 |
| 73 | 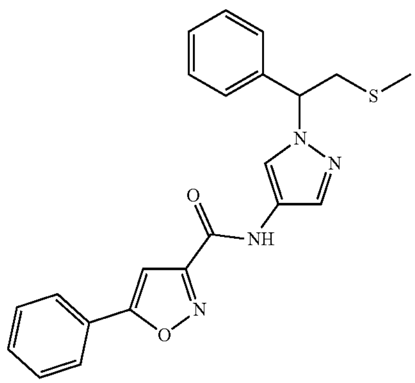 [SMILES: CSCC(c1ccccc1)n1cc(NC(=O)c2cc(-c3ccccc3)on2)cn1] |
| 74 | 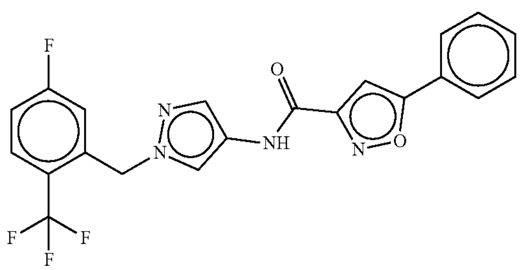 |
| 75 | 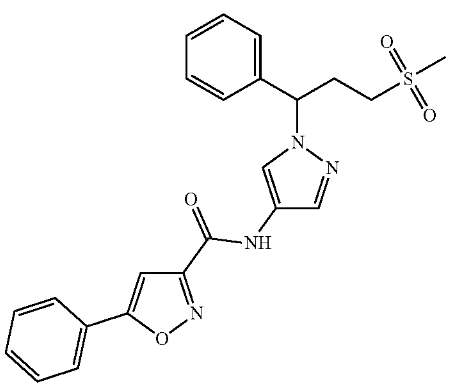 [SMILES: CS(=O)(=O)CCC(c1ccccc1)n1cc(NC(=O)c2cc(-c3ccccc3)on2)cn1] |
| 76 | 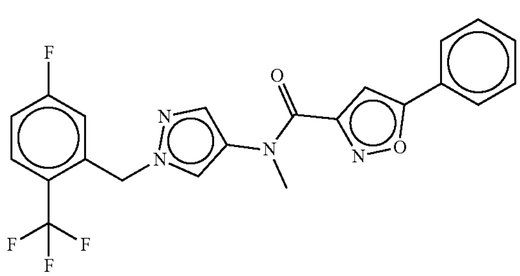 |

TABLE 1-continued

Compounds of the Invention

| No. | Structure |
|---|---|
| 77 | 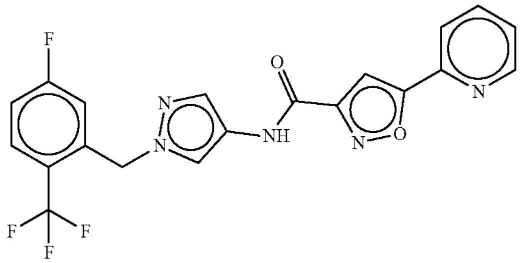 |
| 78 | 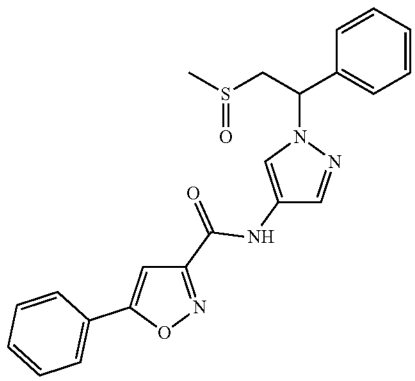 [SMILES: CS(=O)CC(c1ccccc1)n1cc(NC(=O)c2cc(-c3ccccc3)on2)cn1] |
| 79 | 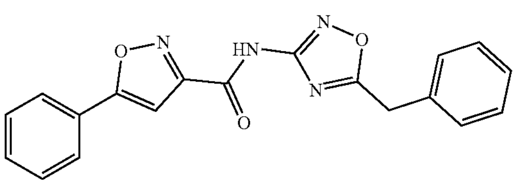 [SMILES: O=C(Nc1noc(Cc2ccccc2)n1)c1cc(-c2ccccc2)on1] |
| 80 | 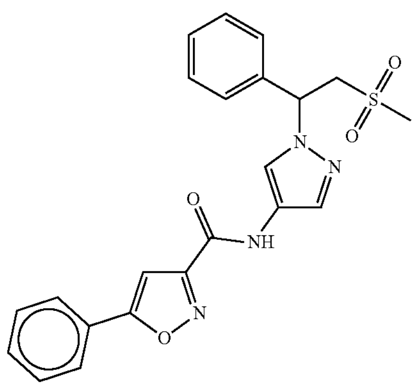 |
| 81 | 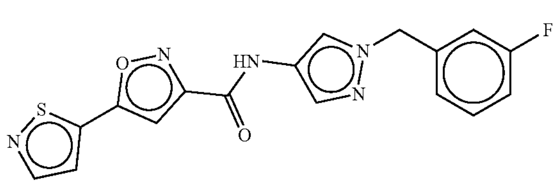 |

TABLE 1-continued
Compounds of the Invention
| No. | Structure |
|---|---|
| 82 | 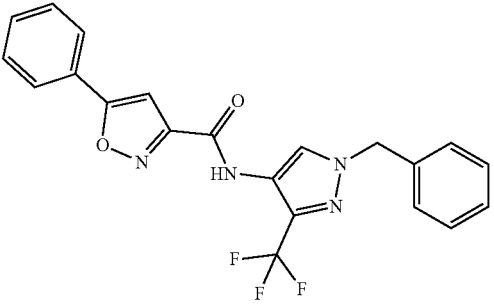 [SMILES: O=C(Nc1cn(Cc2ccccc2)nc1C(F)(F)F)c1cc(-c2ccccc2)on1] |
| 83 | 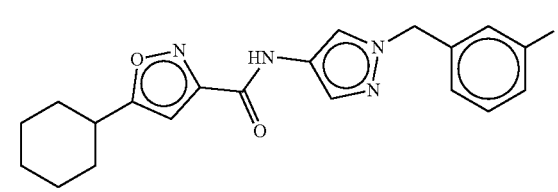 |
| 84 | 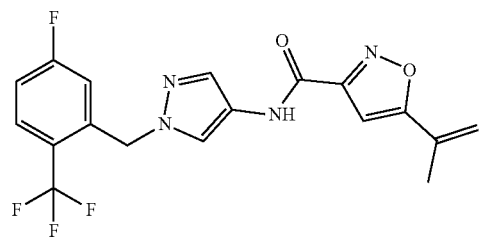 [SMILES: C=C(C)c1cc(C(=O)Nc2cnn(Cc3cc(F)ccc3C(F)(F)F)c2)no1] |
| 85 | 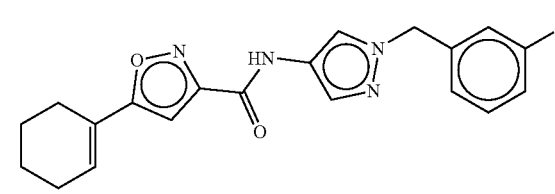 |
| 86 | 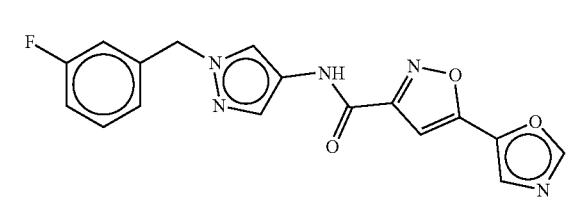 |
| 87 | 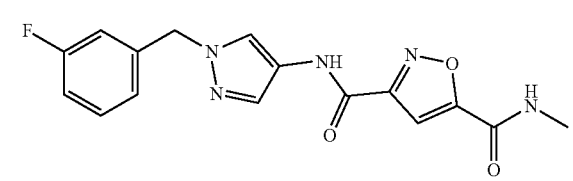 [SMILES: CNC(=O)c1cc(C(=O)Nc2cnn(Cc3cccc(F)c3)c2)no1] |
| 88 | 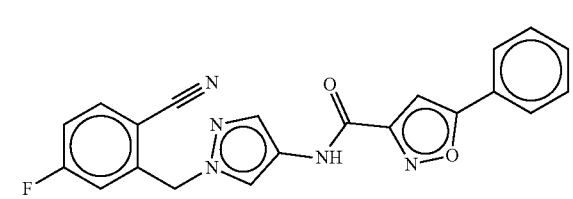 |

TABLE 1-continued
| | Compounds of the Invention |
|---|---|
| No. | Structure |
| 89 | 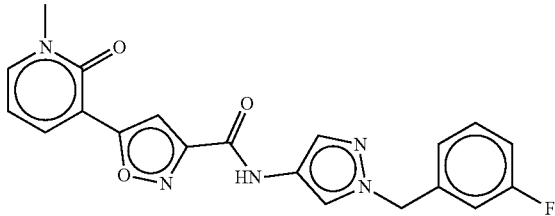 |
| 90 | 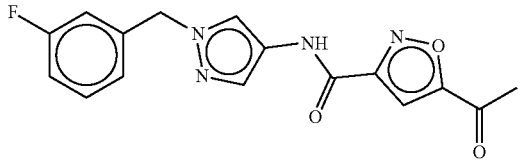 |
| 91 | 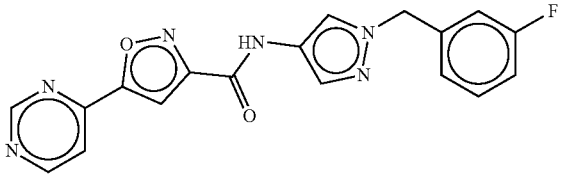 |
| 92 | 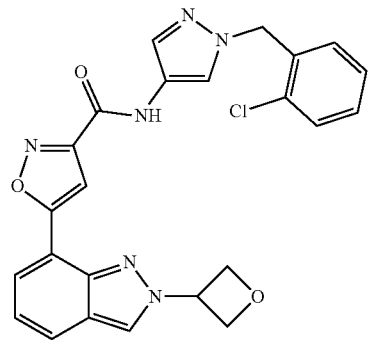 [SMILES: O=C(Nc1cnn(Cc2ccccc2Cl)c1)c1cc(-c2cccc3cn(C4COC4)nc23)on1] |
| 93 | 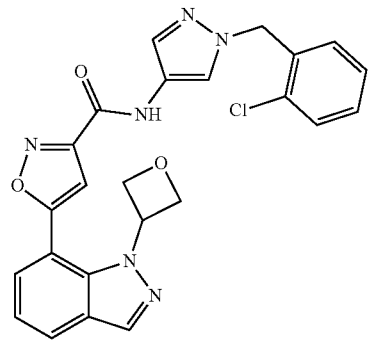 [SMILES: O=C(Nc1cnn(Cc2ccccc2Cl)c1)c1cc(-c2cccc3cnn(C4COC4)c23)on1] |

TABLE 1-continued

Compounds of the Invention

| No. | Structure |
|---|---|
| 94 | 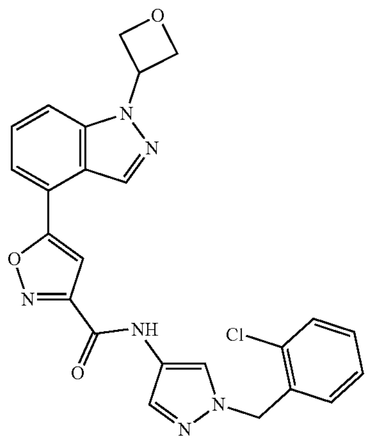 [SMILES: O=C(Nc1cnn(Cc2ccccc2Cl)c1)c1cc(-c2cccc3c2cnn3C2COC2)on1] |
| 95 | 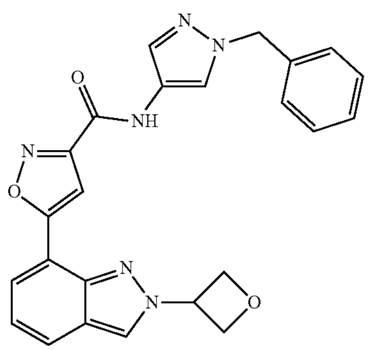 [SMILES: O=C(Nc1cnn(Cc2ccccc2)c1)c1cc(-c2cccc3cn(C4COC4)nc23)on1] |
| 96 | 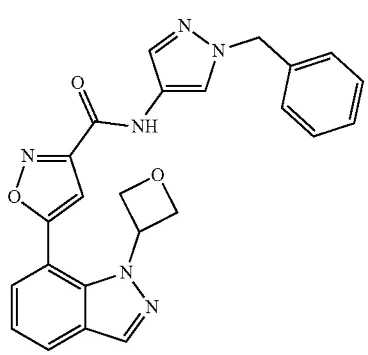 [SMILES: O=C(Nc1cnn(Cc2ccccc2)c1)c1cc(-c2cccc3cnn(C4COC4)c23)on1] |
| 97 | 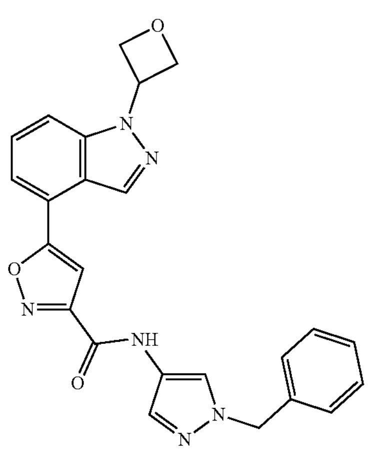 [SMILES: O=C(Nc1cnn(Cc2ccccc2)c1)c1cc(-c2cccc3c2cnn3C2COC2)on1] |

TABLE 1-continued

Compounds of the Invention

| No. | Structure |
|---|---|
| 98 | 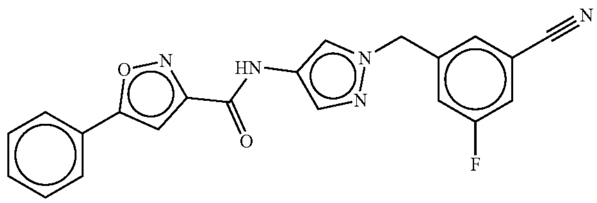 |
| 99 | 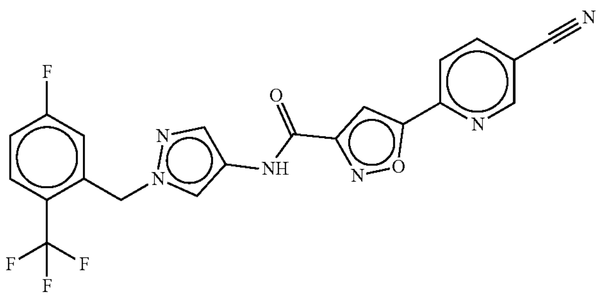 |
| 100 | 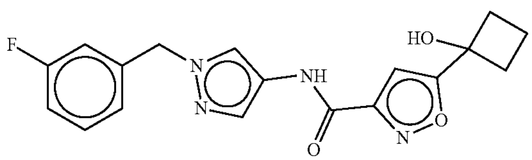 |
| 101 | 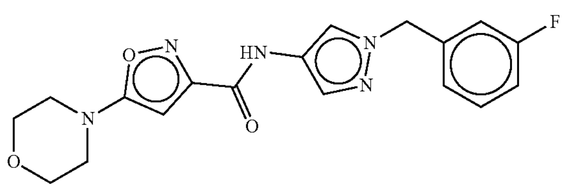 |
| 102 | 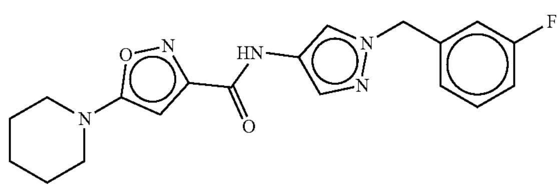 |
| 103 | 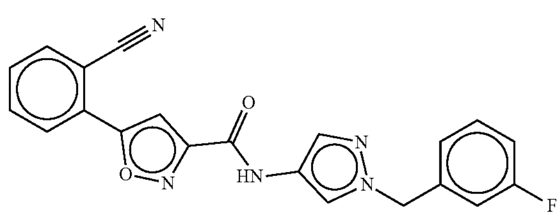 |
| 104 | 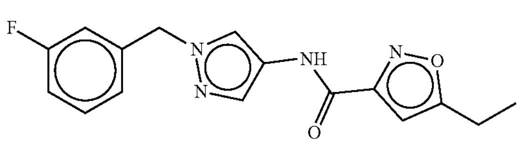 |
| 105 | 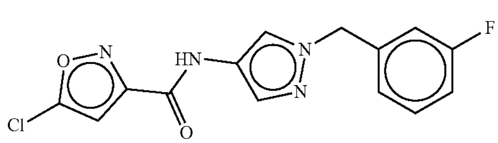 |

TABLE 1-continued

Compounds of the Invention

| No. | Structure |
|---|---|
| 106 | 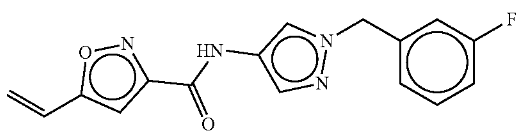 |
| 107 | 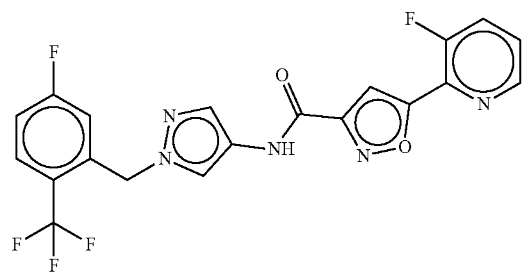 |
| 108 | 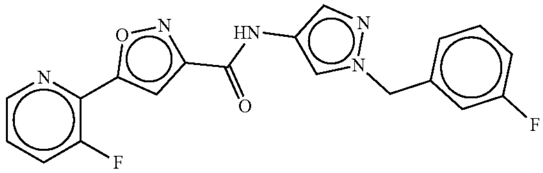 |
| 109 | 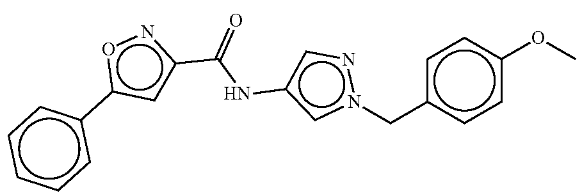 |
| 110 | 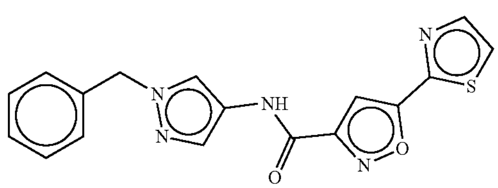 |
| 111 | 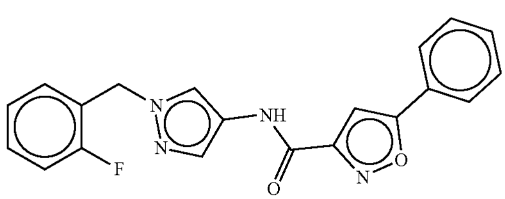 |
| 112 | 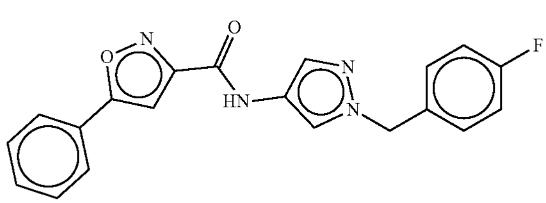 |

TABLE 1-continued

Compounds of the Invention

| No. | Structure |
|-----|-----------|
| 113 | 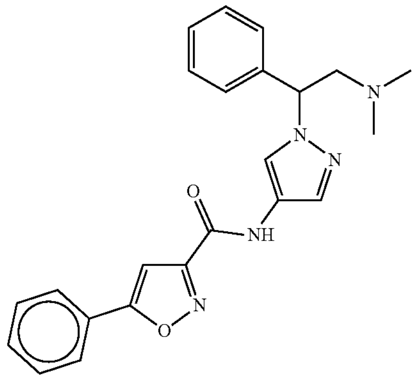 |
| 114 | 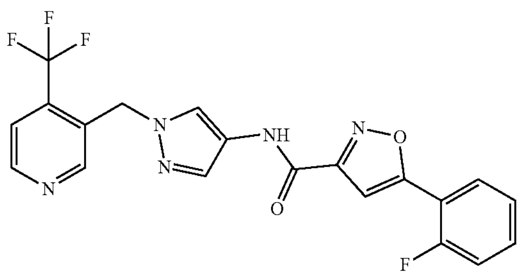 [SMILES: O=C(Nc1cnn(Cc2cnccc2C(F)(F)F)c1)c1cc(-c2ccccc2F)on1] |
| 115 | 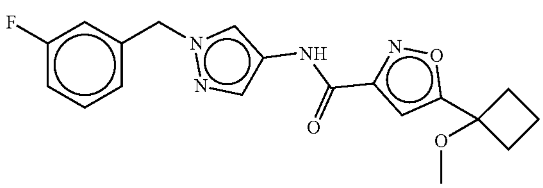 |
| 116 | 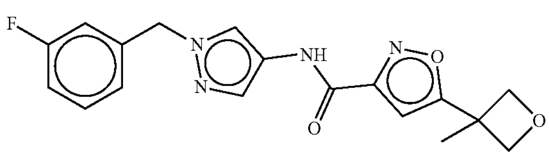 |
| 117 | 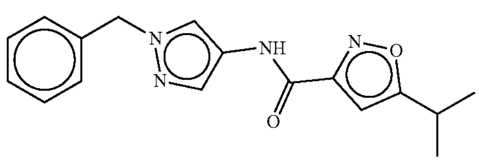 |
| 118 | 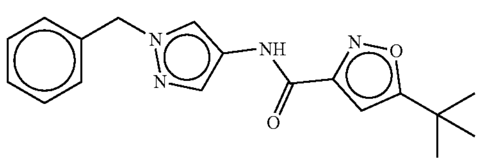 |
| 119 | 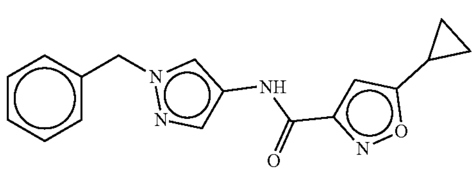 |

TABLE 1-continued

Compounds of the Invention

| No. | Structure |
|---|---|
| 120 | (structure) |
| 121 | (structure) |
| 122 | (structure) |
| 123 | (structure) |
| 124 | (structure) |
| 125 | (structure) |
| 126 | (structure) |
| 127 | (structure) |

TABLE 1-continued

Compounds of the Invention

| No. | Structure |
|-----|-----------|
| 128 | 5-(4-cyanophenyl)-N-(1-benzyl-1H-pyrazol-4-yl)isoxazole-3-carboxamide |
| 129 | 3-(pyridin-2-yl)-N-(1-benzyl-1H-pyrazol-4-yl)isoxazole-5-carboxamide |
| 130 | 3-(2-fluorophenyl)-N-(1-benzyl-1H-pyrazol-4-yl)isoxazole-5-carboxamide |
| 131 | N-(1-benzyl-1H-pyrazol-4-yl)-3-(thiazol-4-yl)isoxazole-5-carboxamide |
| 132 | N-(1-(3-cyanobenzyl)-1H-pyrazol-4-yl)-5-phenylisoxazole-3-carboxamide |
| 133 | N-(1-benzyl-1H-pyrazol-4-yl)-5-(2-methylthiazol-5-yl)isoxazole-3-carboxamide |
| 134 | 5-(3-chloropyridin-4-yl)-N-(1-benzyl-1H-pyrazol-4-yl)isoxazole-3-carboxamide |
| 135 | 5-(2-cyanophenyl)-N-(1-benzyl-1H-pyrazol-4-yl)isoxazole-3-carboxamide |

TABLE 1-continued

Compounds of the Invention

| No. | Structure |
|---|---|
| 136 | 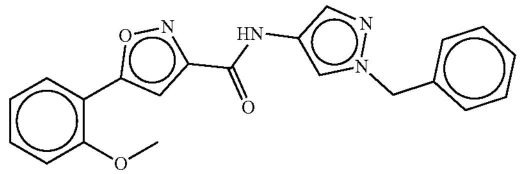 |
| 137 | 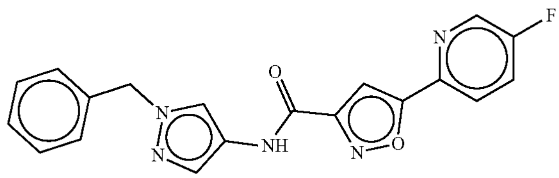 |
| 138 | 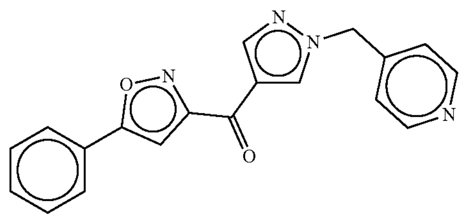 |
| 139 | 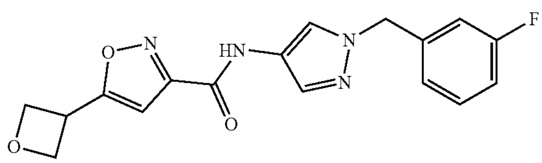 [SMILES: O=C(Nc1cnn(Cc2cccc(F)c2)c1)c1cc(C2COC2)on1] |
| 140 | 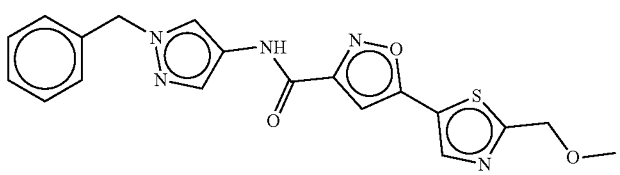 |
| 141 | 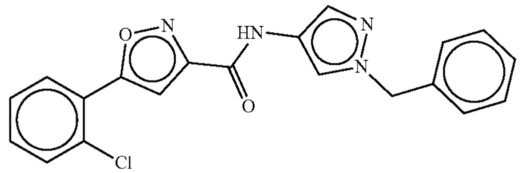 |
| 142 | 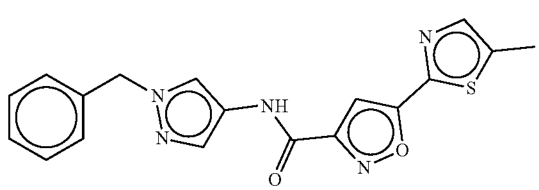 |
| 143 | 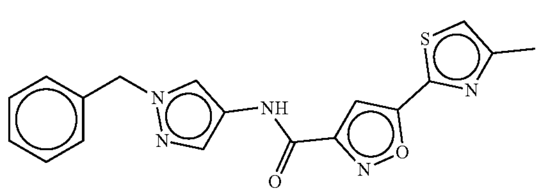 |

US 10,919,885 B2
TABLE 1-continued
Compounds of the Invention
| No. | Structure |
|---|---|
| 144 | 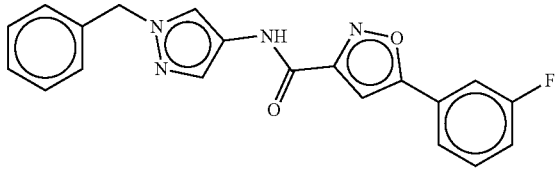 |
| 145 | 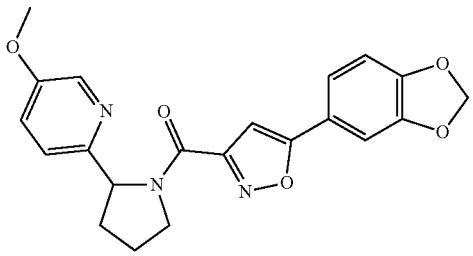 [SMILES: COc1ccc(C2CCCN2C(=O)c2cc(-c3ccc4c(c3)OCO4)on2)nc1] |
| 146 | 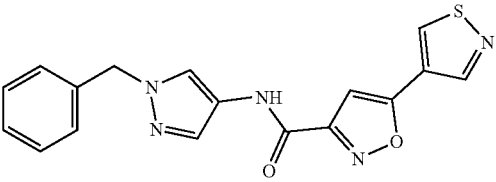 [SMILES: O=C(Nc1cnn(Cc2ccccc2)c1)c1cc(-c2cnsc2)on1] |
| 147 | 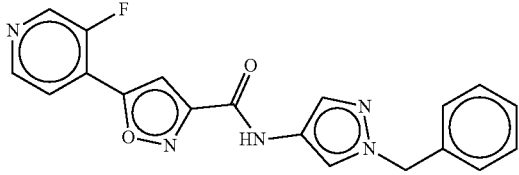 |
| 148 | 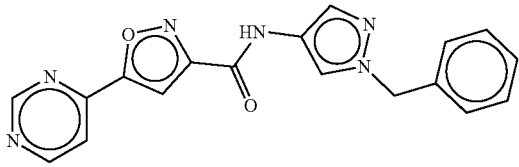 |
| 149 | 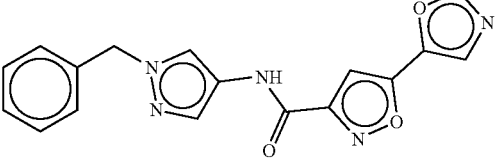 |
| 150 | 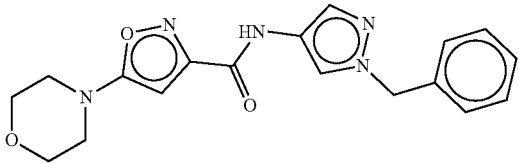 |
| 151 | 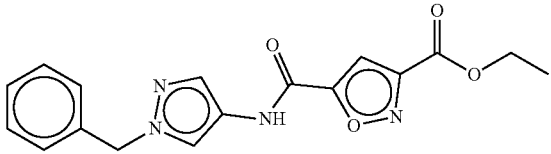 |

TABLE 1-continued

Compounds of the Invention

| No. | Structure |
|---|---|
| 152 | 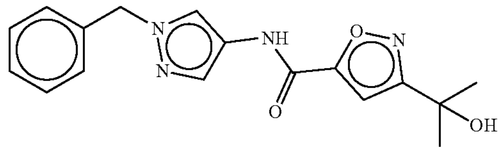 |
| 153 | 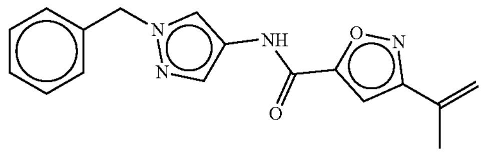 |
| 154 | 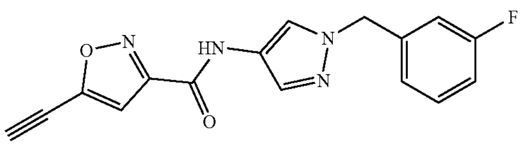 [SMILES: C#Cc1cc(C(=O)Nc2cnn(Cc3cccc(F)c3)c2)no1] |
| 155 | 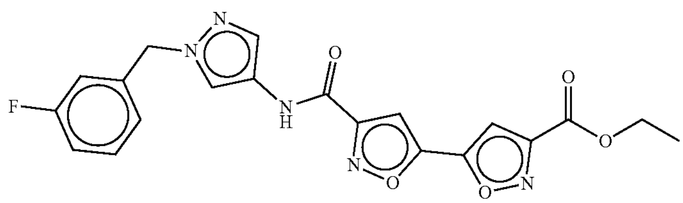 |
| 156 | 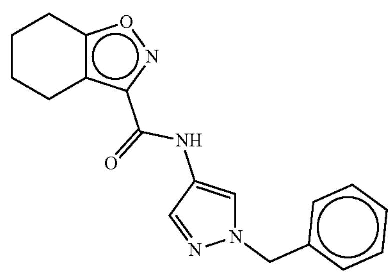 |
| 157 | 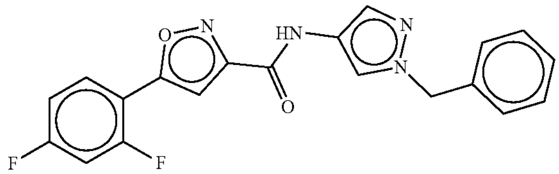 |
| 158 | 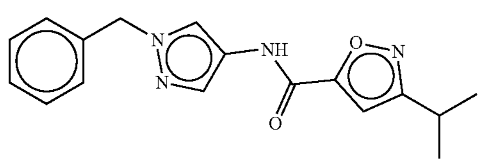 |
| 159 | 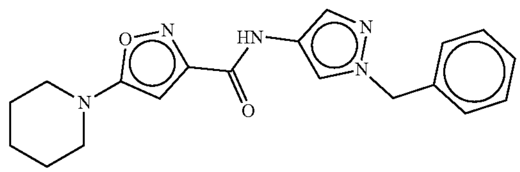 |

TABLE 1-continued

Compounds of the Invention

| No. | Structure |
|---|---|
| 160 | 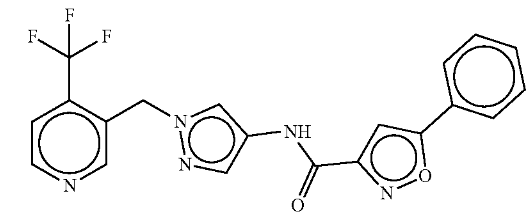 |
| 161 | 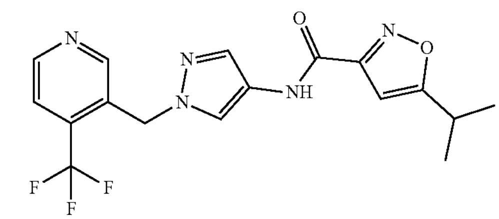 [SMILES: CC(C)c1cc(C(=O)Nc2cnn(Cc3cnccc3C(F)(F)F)c2)no1] |
| 162 | 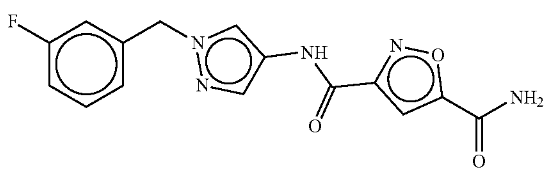 |
| 163 | 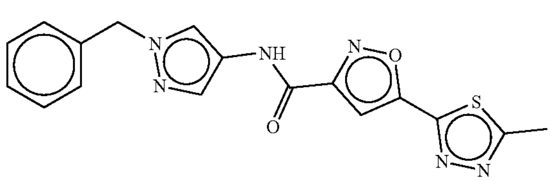 |
| 164 | 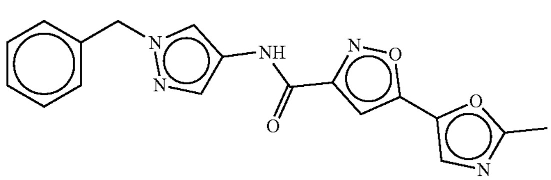 |
| 165 | 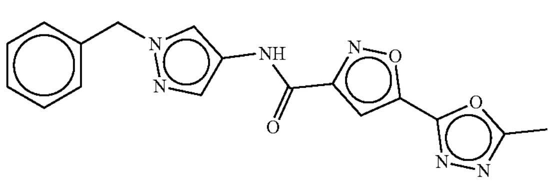 |
| 166 | 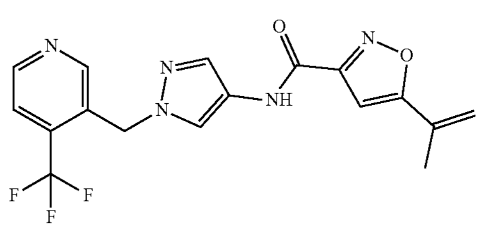 [SMILES: C=C(C)c1cc(C(=O)Nc2cnn(Cc3cnccc3C(F)(F)F)c2)no1] |

TABLE 1-continued

Compounds of the Invention

| No. | Structure |
|---|---|
| 167 | 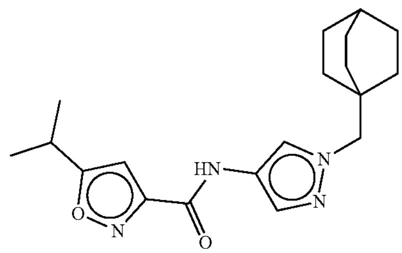 |
| 168 | 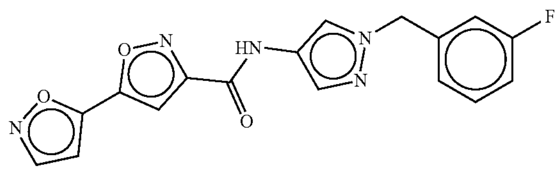 |
| 169 | 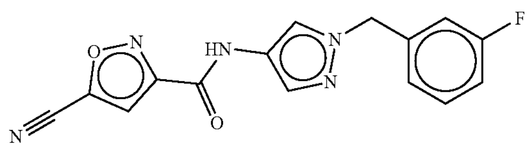 |
| 170 | 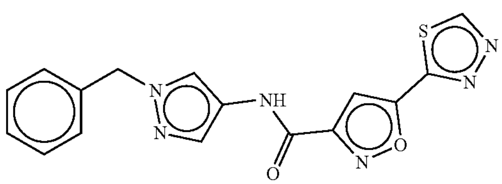 |
| 171 | 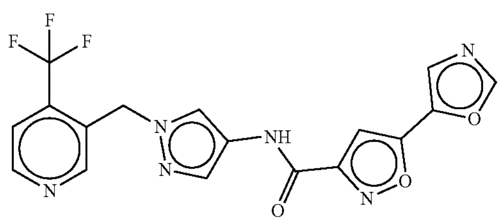 |
| 172 | 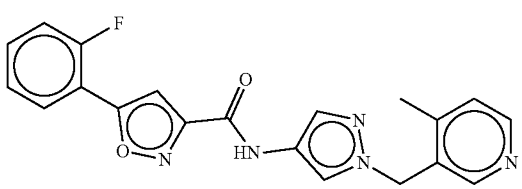 |
| 173 | 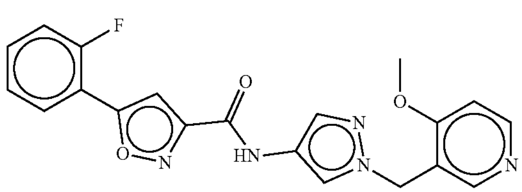 |
| 174 | 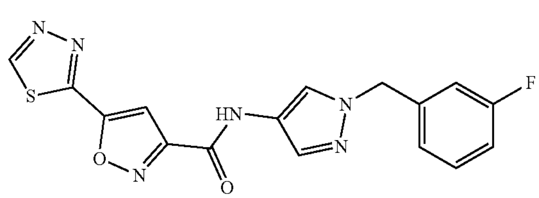 [SMILES: O=C(Nc1cnn(Cc2cccc(F)c2)c1)c1cc(-c2nncs2)on1] |

US 10,919,885 B2
105 106
TABLE 1-continued
Compounds of the Invention
| No. | Structure |
|---|---|
| 175 | 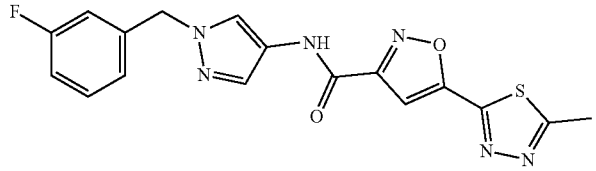 [SMILES: Cc1nnc(-c2cc(C(=O)Nc3cnn(Cc4cccc(F)c4)c3)no2)s1] |
| 176 | 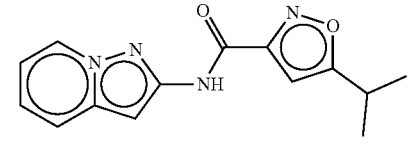 |
| 177 | 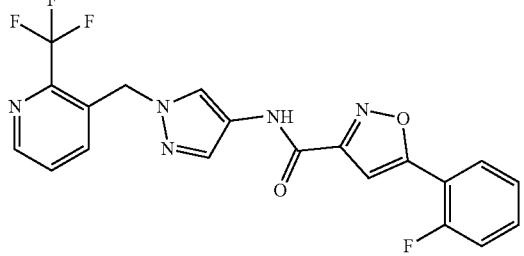 |
| 178 | 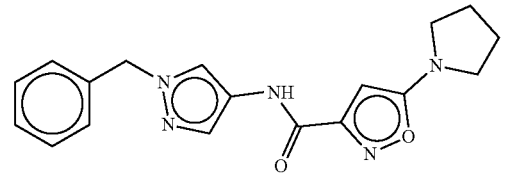 |
| 179 | 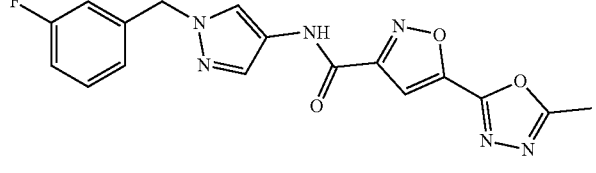 |
| 180 | 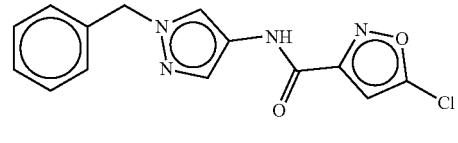 |
| 181 | 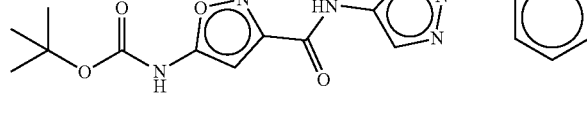 |
| 182 | 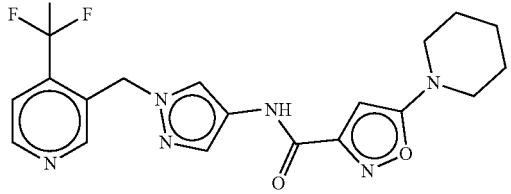 |

TABLE 1-continued
Compounds of the Invention
| No. | Structure |
|---|---|
| 183 | 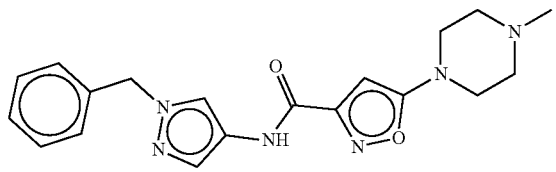 |
| 184 | 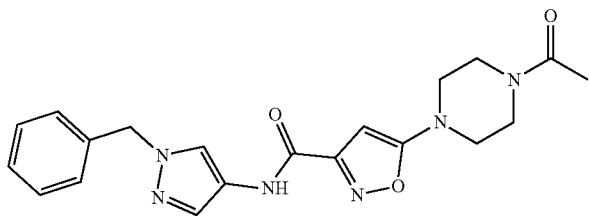 [SMILES: CC(=O)N1CCN(c2cc(C(=O)Nc3cnn(Cc4ccccc4)c3)no2)CC1] |
| 185 | 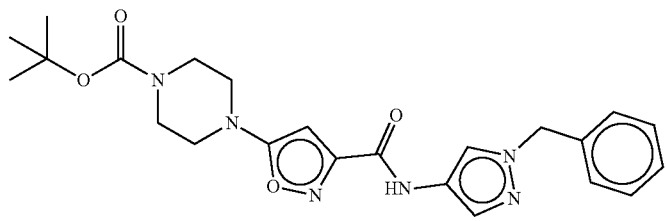 |
| 186 | 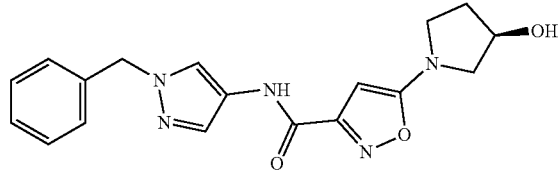 [SMILES: O=C(Nc1cnn(Cc2ccccc2)c1)c1cc(N2CC[C@@H](O)C2)on1] |
| 187 | 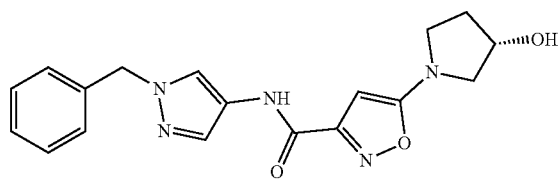 [SMILES: O=C(Nc1cnn(Cc2ccccc2)c1)c1cc(N2CC[C@H](O)C2)on1] |
| 188 | 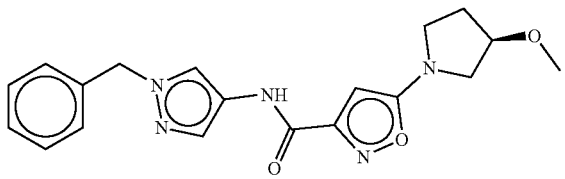 |
| 189 | 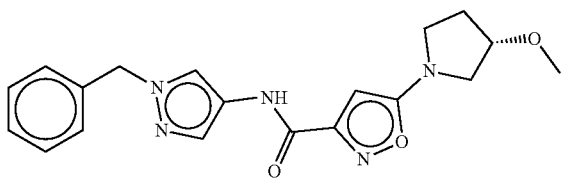 |
| 190 | 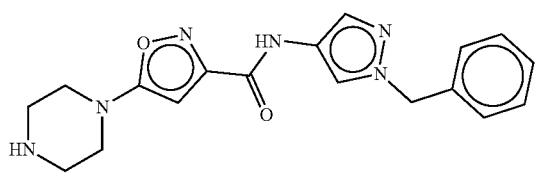 |

109

TABLE 1-continued

Compounds of the Invention

| No. | Structure |
|---|---|
| 191 | (3-fluorobenzyl-pyrazol-4-yl)-NH-C(O)-isoxazole-CH2OH |
| 192 | (benzyl-pyrazol-4-yl)-NH-C(O)-isoxazole-NH2 |
| 193 | 4,5,6,7-tetrahydrobenzo[d]isoxazole-3-C(O)-NH-(pyrazol-4-yl)-N-CH2-(3-fluorophenyl) |
| 194 | 4,5,6,7-tetrahydrobenzo[d]isoxazole-3-C(O)-NH-(pyrazol-4-yl)-N-CH2-(3-trifluoromethylpyridin-2-yl) |
| 195 | 5-(2,6-difluorophenyl)isoxazole-3-C(O)-NH-(1-benzylpyrazol-4-yl) |
| 196 | (3-trifluoromethylpyridin-2-yl)-CH2-(pyrazol-4-yl)-NH-C(O)-isoxazole-5-(2-fluorophenyl) |

110

TABLE 1-continued

Compounds of the Invention

| No. | Structure |
|---|---|
| 197 | 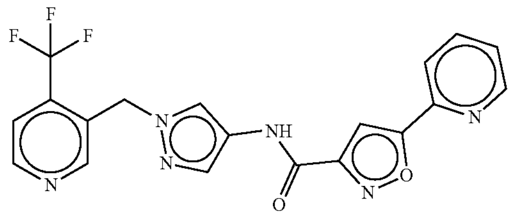 |
| 198 | 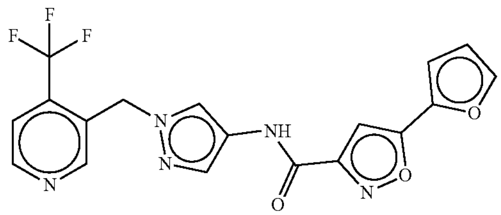 |
| 199 | 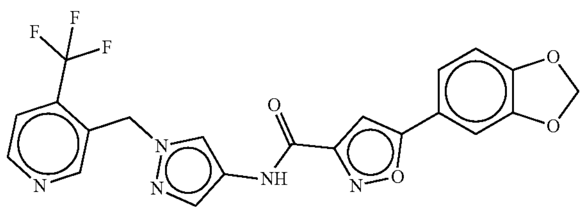 |
| 200 | 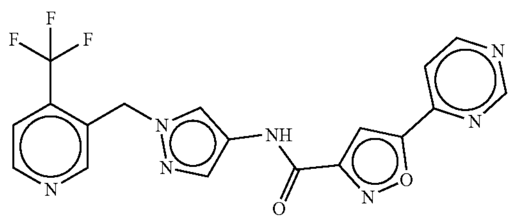 |
| 201 | 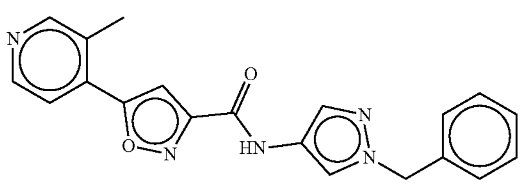 |
| 202 | 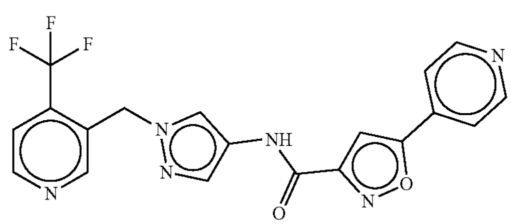 |
| 203 | 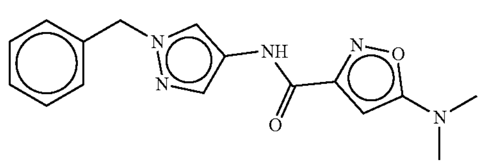 |

US 10,919,885 B2
113                                                                                                          114
TABLE 1-continued
Compounds of the Invention
| No. | Structure |
|---|---|
| 204 | 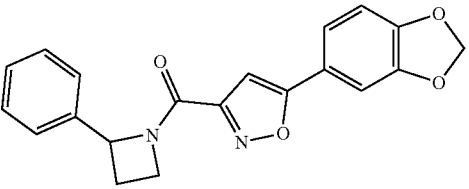 [SMILES: O=C(c1cc(-c2ccc3c(c2)OCO3)on1)N1CCC1c1ccccc1] |
| 205 | 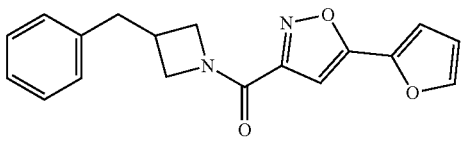 [SMILES: O=C(c1cc(-c2ccco2)on1)N1CC(Cc2ccccc2)C1] |
| 206 | 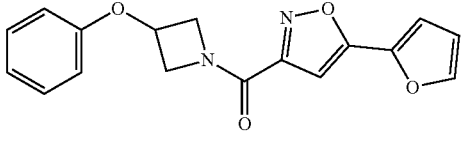 [SMILES: O=C(c1cc(-c2ccco2)on1)N1CC(Oc2ccccc2)C1] |
| 207 | 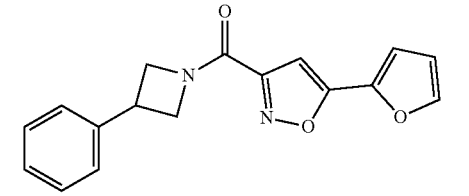 [SMILES: O=C(c1cc(-c2ccco2)on1)N1CC(c2ccccc2)C1] |
| 208 | 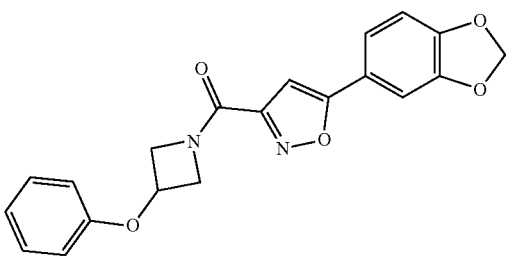 [SMILES: O=C(c1cc(-c2ccc3c(c2)OCO3)on1)N1CC(Oc2ccccc2)C1] |
| 209 | 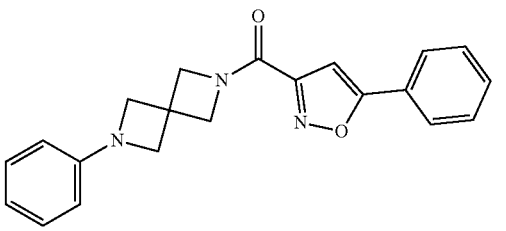 [SMILES: O=C(c1cc(-c2ccccc2)on1)N1CC2(C1)CN(c1ccccc1)C2] |
| 210 | 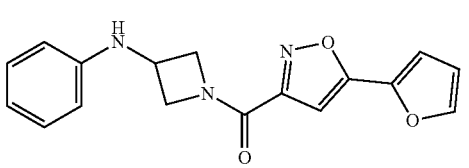 [SMILES: O=C(c1cc(-c2ccco2)on1)N1CC(Nc2ccccc2)C1] |

TABLE 1-continued

Compounds of the Invention

| No. | Structure |
|---|---|
| 211 | 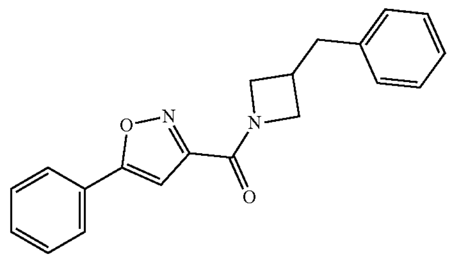 [SMILES: O=C(c1cc(-c2ccccc2)on1)N1CC(Cc2ccccc2)C1] |
| 212 | 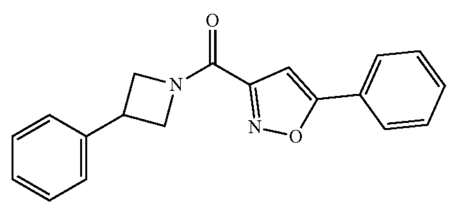 [SMILES: O=C(c1cc(-c2ccccc2)on1)N1CC(c2ccccc2)C1] |
| 213 | 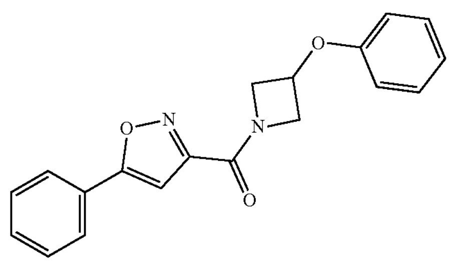 [SMILES: O=C(c1cc(-c2ccccc2)on1)N1CC(Oc2ccccc2)C1] |
| 214 | 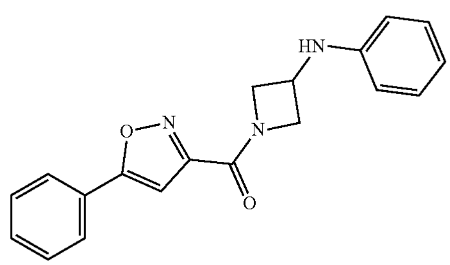 [SMILES: O=C(c1cc(-c2ccccc2)on1)N1CC(Nc2ccccc2)C1] |
| 215 | 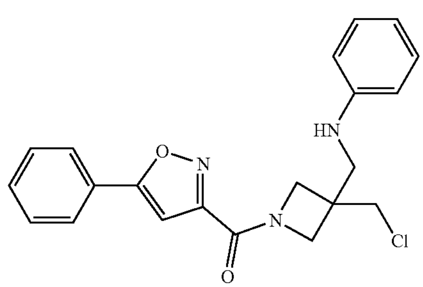 [SMILES: O=C(c1cc(-c2ccccc2)on1)N1CC(CCl)(CNc2ccccc2)C1] |
| 216 | 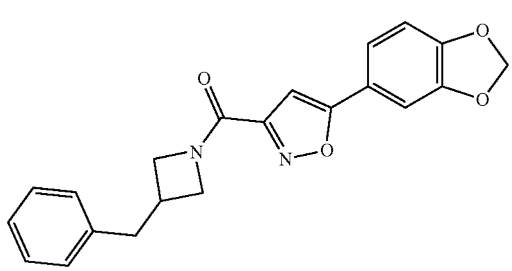 [SMILES: O=C(c1cc(-c2ccc3c(c2)OCO3)on1)N1CC(Cc2ccccc2)C1] |

TABLE 1-continued

| | Compounds of the Invention |
|---|---|
| No. | Structure |
| 217 | |
| 218 | |
| 219 | |
| 220 | |
| 221 | |

TABLE 1-continued

Compounds of the Invention

| No. | Structure |
|---|---|
| 222 | 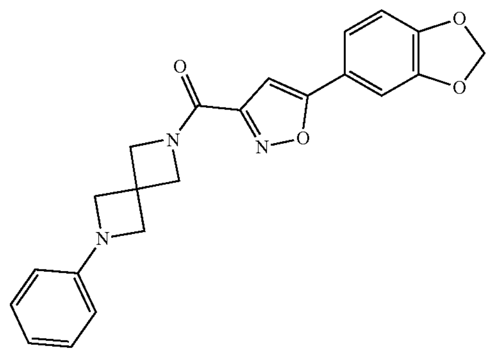 [SMILES: O=C(c1cc(-c2ccc3c(c2)OCO3)on1)N1CC2(C1)CN(c1ccccc1)C2] |
| 223 | 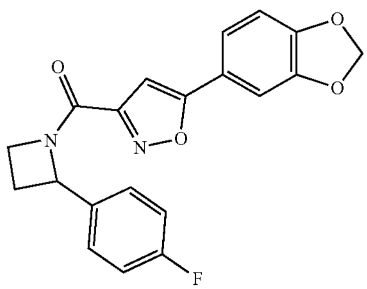 [SMILES: O=C(c1cc(-c2ccc3c(c2)OCO3)on1)N1CCC1c1ccc(F)cc1] |
| 224 | 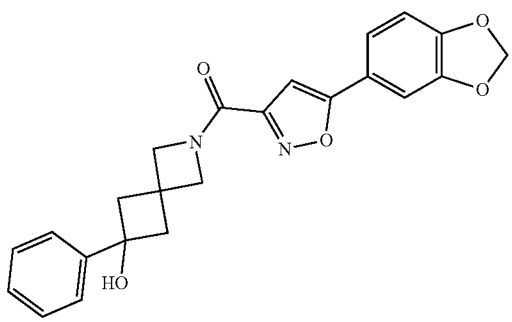 [SMILES: O=C(c1cc(-c2ccc3c(c2)OCO3)on1)N1CC2(C1)CC(O)(c1ccccc1)C2] |
| 225 | 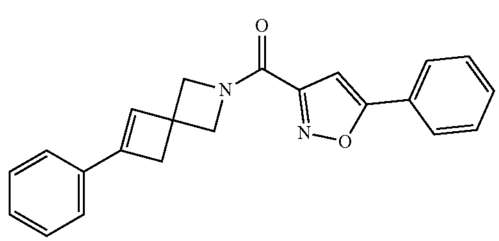 [SMILES: O=C(c1cc(-c2ccccc2)on1)N1CC2(C=C(c3ccccc3)C2)C1] |
| 226 | 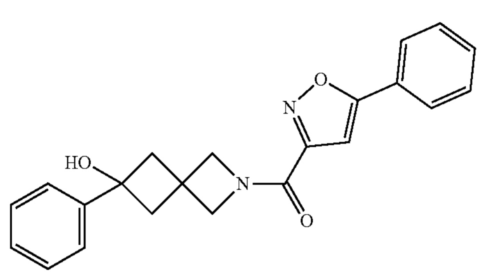 [SMILES: O=C(c1cc(-c2ccccc2)on1)N1CC2(C1)CC(O)(c1ccccc1)C2] |

121
TABLE 1-continued
Compounds of the Invention
| No. | Structure |
|---|---|
| 227 | 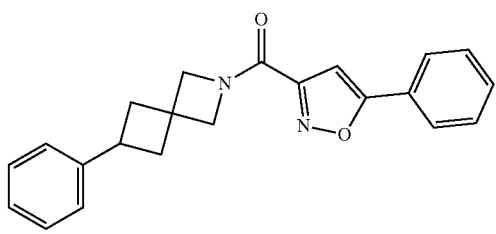 [SMILES: O=C(c1cc(-c2ccccc2)on1)N1CC2(CC(c3ccccc3)C2)C1] |
| 228 | 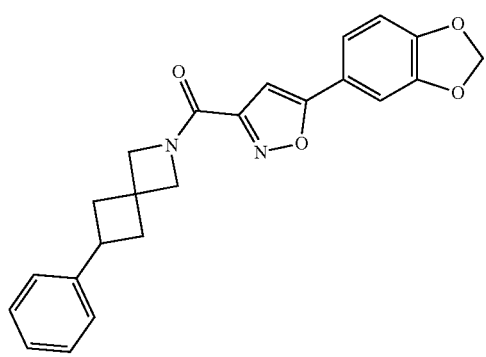 [SMILES: O=C(c1cc(-c2ccc3c(c2)OCO3)on1)N1CC2(CC(c3ccccc3)C2)C1] |
| 229 | 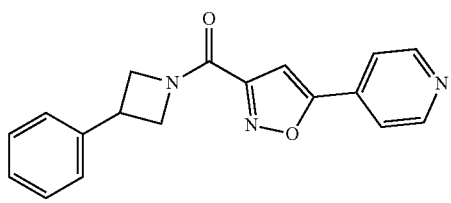 [SMILES: O=C(c1cc(-c2ccncc2)on1)N1CC(c2ccccc2)C1] |
| 230 | 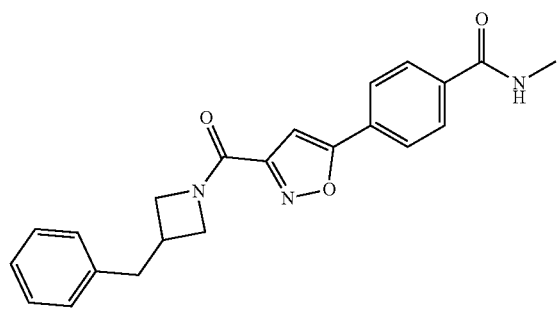 [SMILES: CNC(=O)c1ccc(-c2cc(C(=O)N3CC(Cc4ccccc4)C3)no2)cc1] |
| 231 | 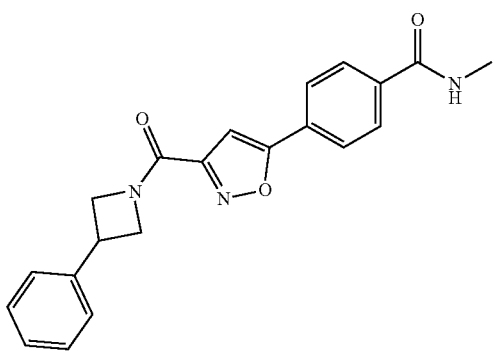 [SMILES: CNC(=O)c1ccc(-c2cc(C(=O)N3CC(c4ccccc4)C3)no2)cc1] |
122

123 124
TABLE 1-continued
Compounds of the Invention
| No. | Structure |
|---|---|
| 232 | 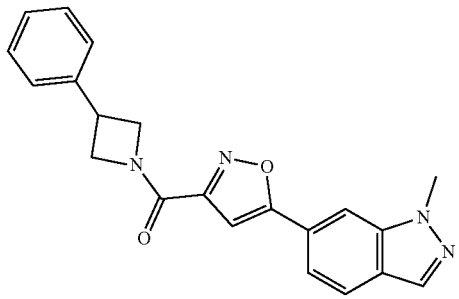 [SMILES: Cn1ncc2ccc(-c3cc(C(=O)N4CC(c5ccccc5)C4)no3)cc21] |
| 233 | 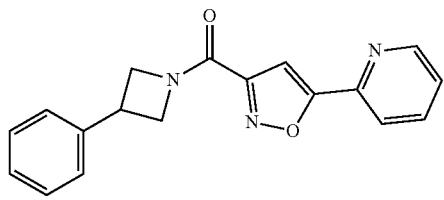 [SMILES: O=C(c1cc(-c2ccccn2)on1)N1CC(c2ccccc2)C1] |
| 234 | 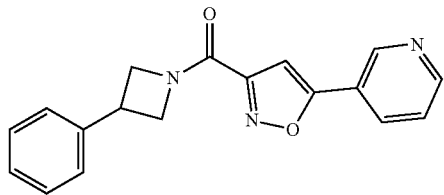 [SMILES: O=C(c1cc(-c2cccnc2)on1)N1CC(c2ccccc2)C1] |
| 235 | 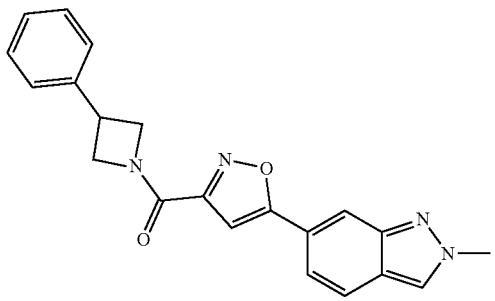 [SMILES: Cn1cc2ccc(-c3cc(C(=O)N4CC(c5ccccc5)C4)no3)cc2n1] |
| 236 | 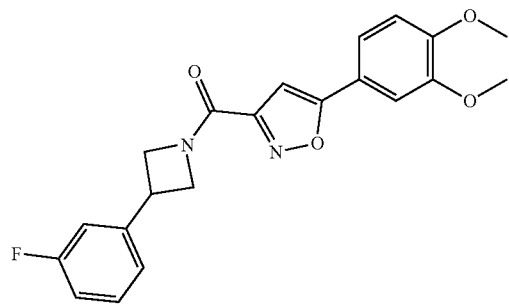 [SMILES: COc1ccc(-c2cc(C(=O)N3CC(c4cccc(F)c4)C3)no2)cc1OC] |

125
TABLE 1-continued
Compounds of the Invention
| No. | Structure |
|---|---|
| 237 | 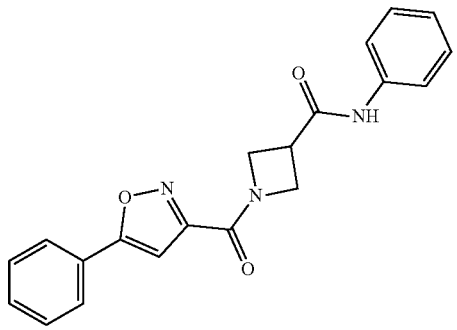 [SMILES: O=C(Nc1ccccc1)C1CN(C(=O)c2cc(-c3ccccc3)on2)C1] |
| 238 | 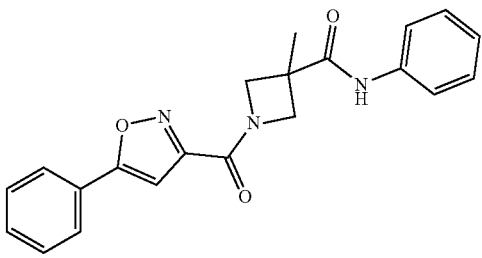 [SMILES: CC1(C(=O)Nc2ccccc2)CN(C(=O)c2cc(-c3ccccc3)on2)C1] |
| 239 | 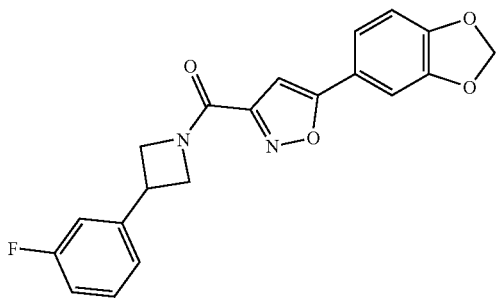 [SMILES: O=C(c1cc(-c2ccc3c(c2)OCO3)on1)N1CC(c2cccc(F)c2)C1] |
| 240 | 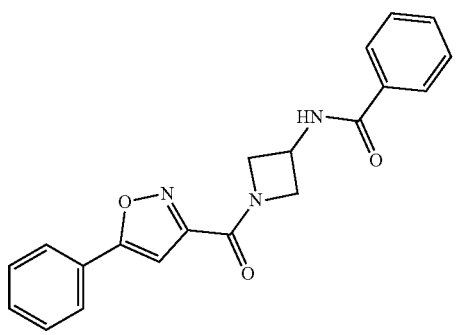 [SMILES: O=C(NC1CN(C(=O)c2cc(-c3ccccc3)on2)C1)c1ccccc1] |
| 241 | 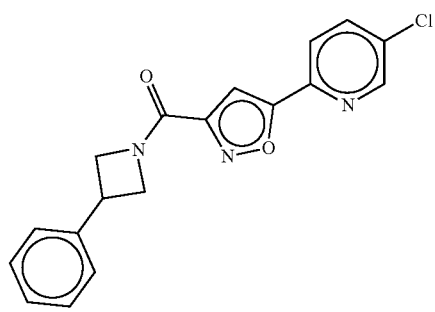 |

TABLE 1-continued
Compounds of the Invention
| No. | Structure |
|---|---|
| 242 | 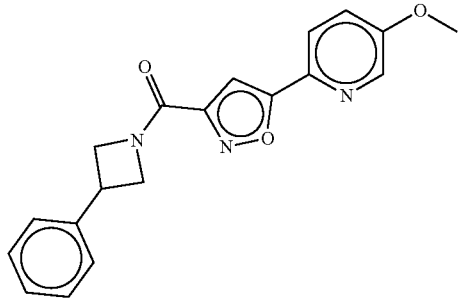 |
| 243 | 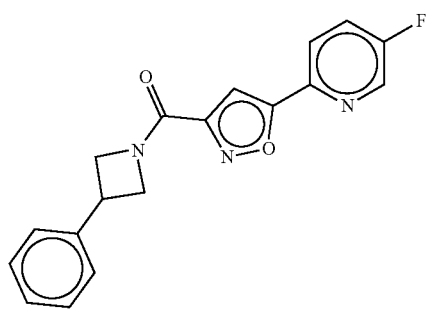 |
| 244 | 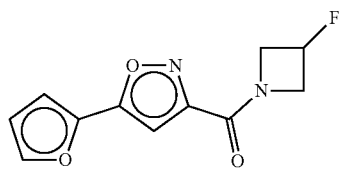 |
| 245 | 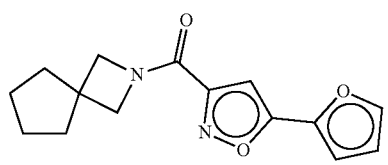 |
| 246 | 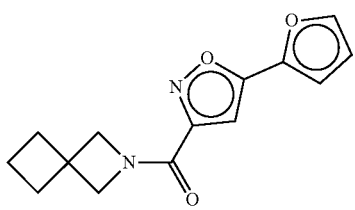 |
| 247 | 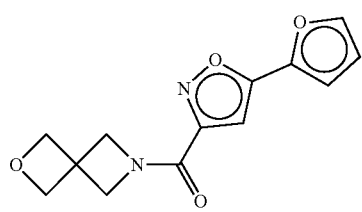 |

TABLE 1-continued
Compounds of the Invention
| No. | Structure |
|---|---|
| 248 | 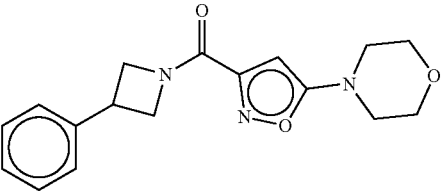 |
| 249 | 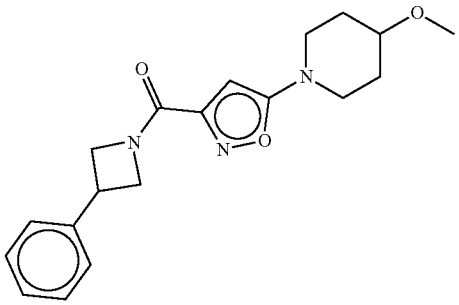 |
| 250 | 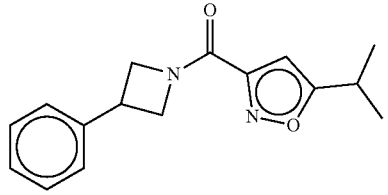 |
| 251 | 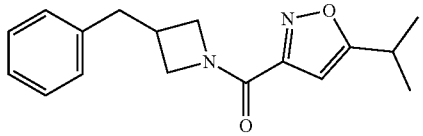 [SMILES: CC(C)c1cc(C(=O)N2CC(Cc3ccccc3)C2)no1] |
| 252 | 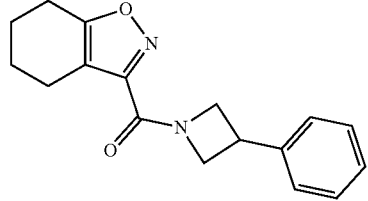 [SMILES: O=C(c1noc2c1CCCC2)N1CC(c2ccccc2)C1] |
| 253 | 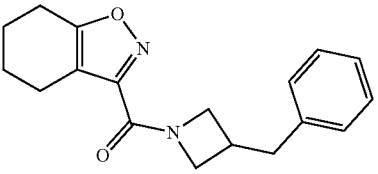 [SMILES: O=C(c1noc2c1CCCC2)N1CC(Cc2ccccc2)C1] |
| 254 | 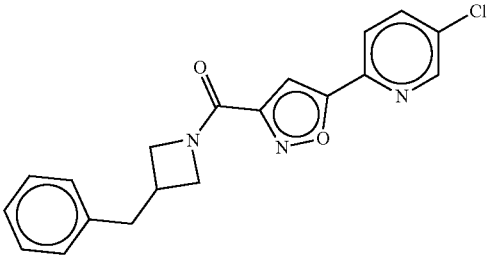 |

TABLE 1-continued
Compounds of the Invention
| No. | Structure |
|---|---|
| 255 | 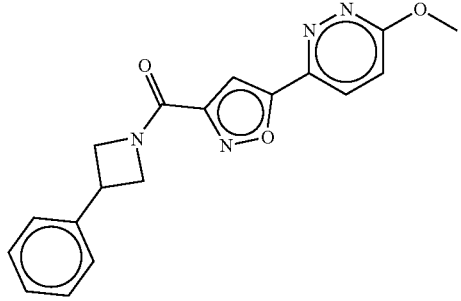 |
| 256 | 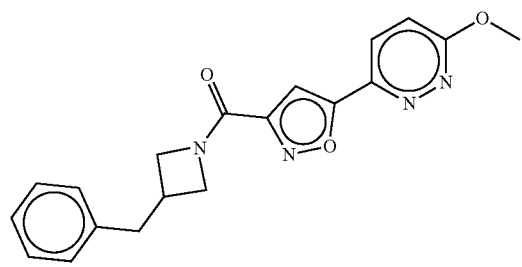 |
| 257 | 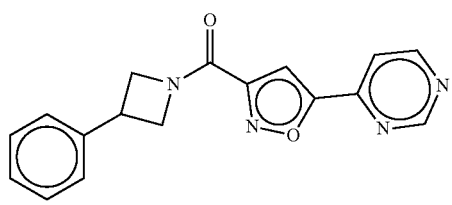 |
| 258 | 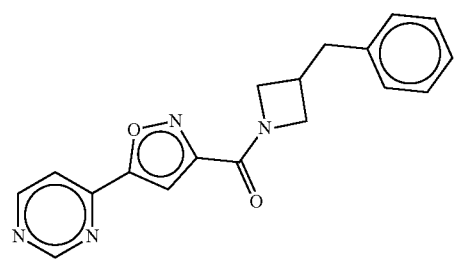 |
| 259 | 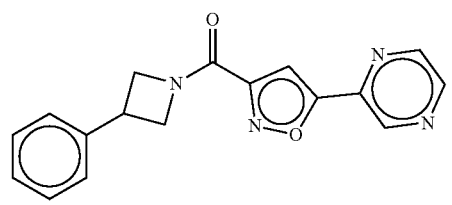 |
| 260 | 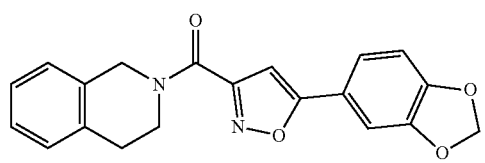 [SMILES: O=C(c1cc(-c2ccc3c(c2)OCO3)on1)N1CCc2ccccc2C1] |

TABLE 1-continued

Compounds of the Invention

| No. | Structure |
|---|---|
| 261 | 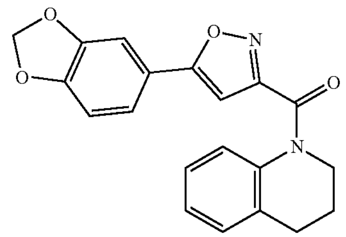 [SMILES: O=C(c1cc(-c2ccc3c(c2)OCO3)on1)N1CCCc2ccccc21] |
| 262 | 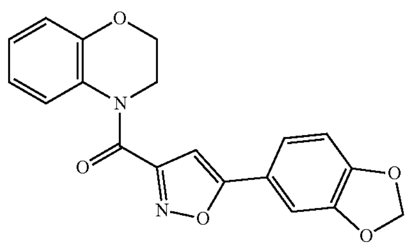 [SMILES: O=C(c1cc(-c2ccc3c(c2)OCO3)on1)N1CCOc2ccccc21] |
| 263 | 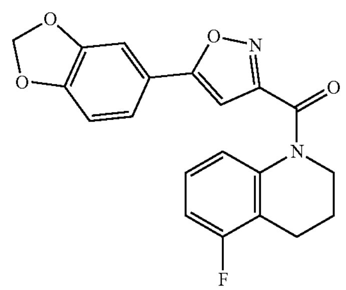 [SMILES: O=C(c1cc(-c2ccc3c(c2)OCO3)on1)N1CCCc2c(F)cccc21] |
| 264 | 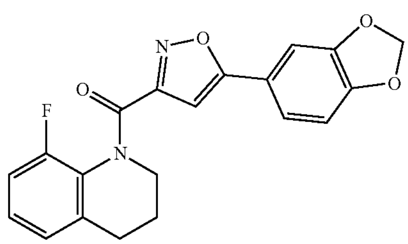 [SMILES: O=C(c1cc(-c2ccc3c(c2)OCO3)on1)N1CCCc2cccc(F)c21] |
| 265 | 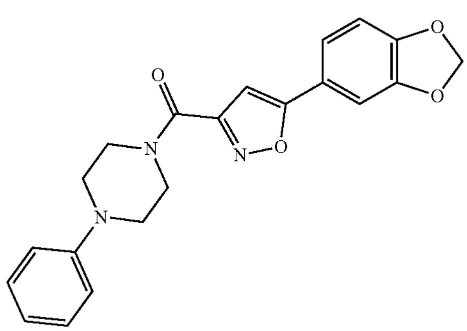 [SMILES: O=C(c1cc(-c2ccc3c(c2)OCO3)on1)N1CCN(c2ccccc2)CC1] |
| 266 | 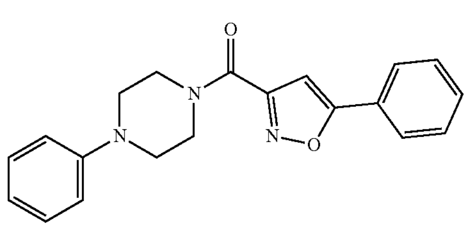 |

TABLE 1-continued

Compounds of the Invention

| No. | Structure |
|---|---|
| 267 | 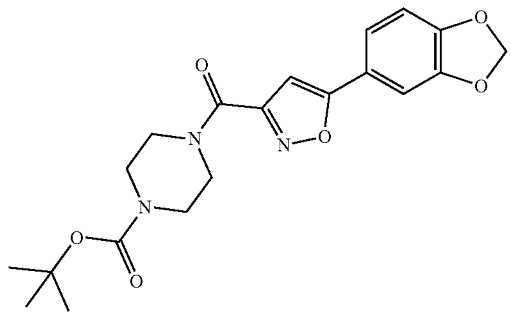 [SMILES: CC(C)(C)OC(=O)N1CCN(C(=O)c2cc(-c3ccc4c(c3)OCO4)on2)CC1] |
| 268 | 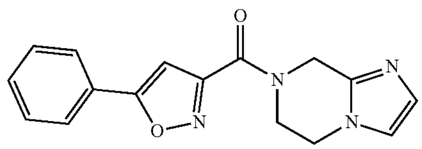 [SMILES: O=C(c1cc(-c2ccccc2)on1)N1CCn2ccnc2C1] |
| 269 | 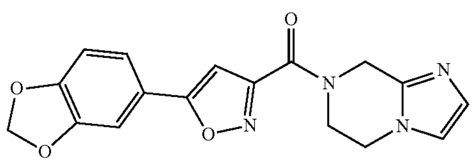 [SMILES: O=C(c1cc(-c2ccc3c(c2)OCO3)on1)N1CCn2ccnc2C1] |
| 270 | 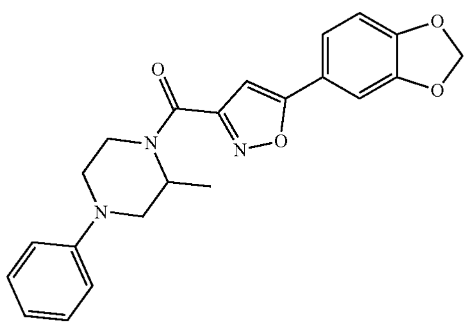 [SMILES: CC1CN(c2ccccc2)CCN1C(=O)c1cc(-c2ccc3c(c2)OCO3)on1] |
| 271 | 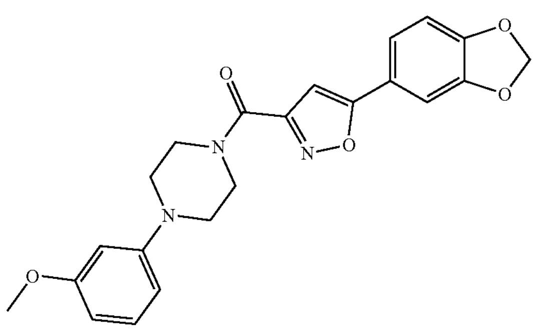 [SMILES: COc1cccc(N2CCN(C(=O)c3cc(-c4ccc5c(c4)OCO5)on3)CC2)c1] |
| 272 | 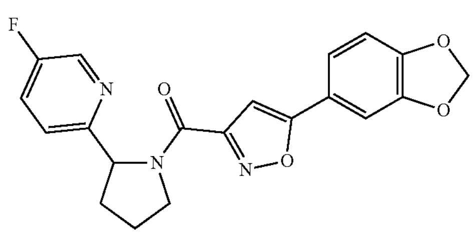 [SMILES: O=C(c1cc(-c2ccc3c(c2)OCO3)on1)N1CCCC1c1ccc(F)cn1] |

TABLE 1-continued
Compounds of the Invention
| No. | Structure |
|---|---|
| 273 | 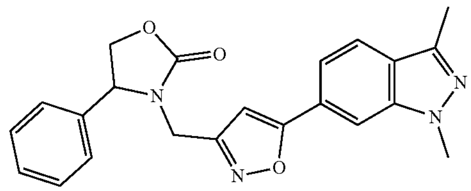 [SMILES: Cc1nn(C)c2cc(-c3cc(CN4C(=O)OCC4c4ccccc4)no3)ccc12] |
| 274 | 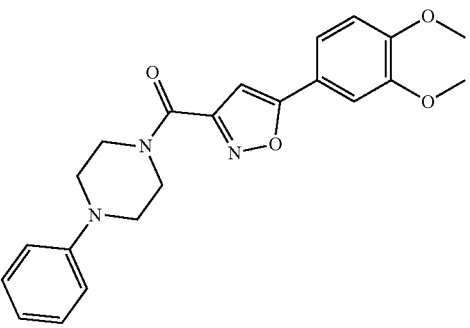 [SMILES: COc1ccc(-c2cc(C(=O)N3CCN(c4ccccc4)CC3)no2)cc1OC] |
| 275 | 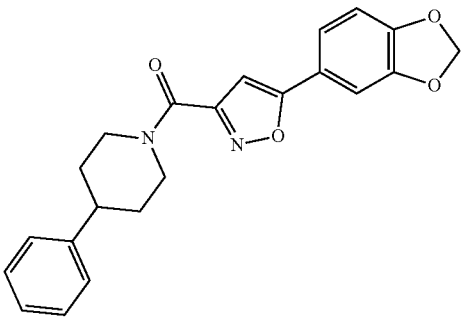 [SMILES: O=C(c1cc(-c2ccc3c(c2)OCO3)on1)N1CCC(c2ccccc2)CC1] |
| 276 | 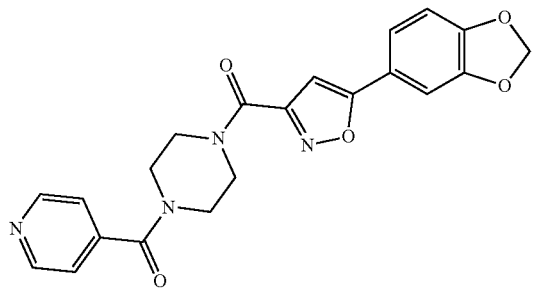 [SMILES: O=C(c1ccncc1)N1CCN(C(=O)c2cc(-c3ccc4c(c3)OCO4)on2)CC1] |
| 277 | 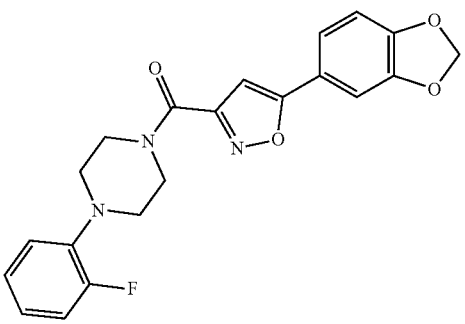 [SMILES: O=C(c1cc(-c2ccc3c(c2)OCO3)on1)N1CCN(c2ccccc2F)CC1] |

TABLE 1-continued
| | Compounds of the Invention |
|---|---|
| No. | Structure |
| 278 | 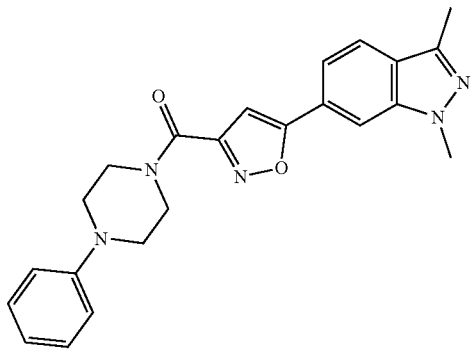 [SMILES: Cc1nn(C)c2cc(-c3cc(C(=O)N4CCN(c5ccccc5)CC4)no3)ccc12] |
| 279 | 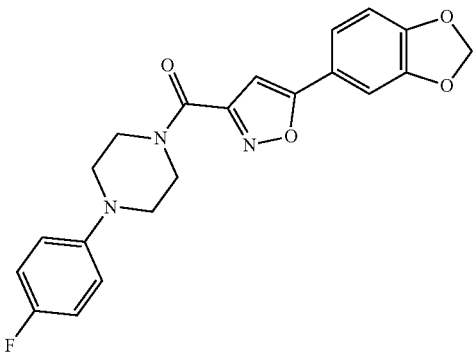 [SMILES: O=C(c1cc(-c2ccc3c(c2)OCO3)on1)N1CCN(c2ccc(F)cc2)CC1] |
| 280 | 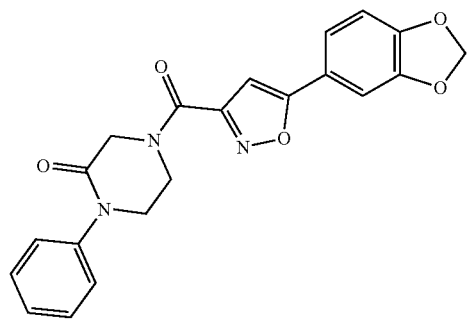 [SMILES: O=C(c1cc(-c2ccc3c(c2)OCO3)on1)N1CCN(c2ccccc2)C(=O)C1] |
| 281 | 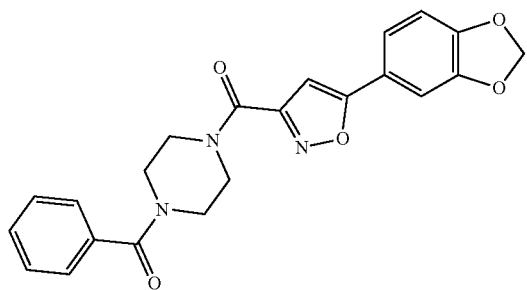 [SMILES: O=C(c1ccccc1)N1CCN(C(=O)c2cc(-c3ccc4c(c3)OCO4)on2)CC1] |

TABLE 1-continued

Compounds of the Invention

| No. | Structure |
|---|---|
| 282 | 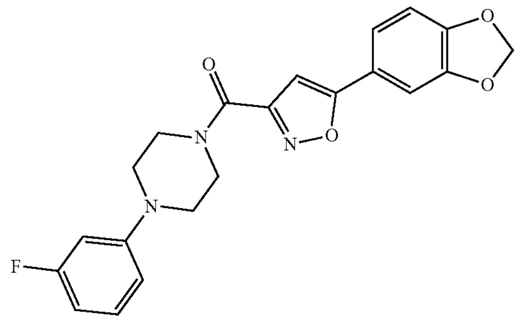 [SMILES: O=C(c1cc(-c2ccc3c(c2)OCO3)on1)N1CCN(c2cccc(F)c2)CC1] |
| 283 | 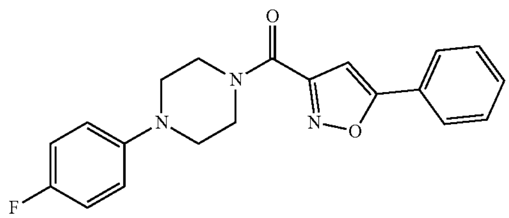 [SMILES: O=C(c1cc(-c2ccccc2)on1)N1CCN(c2ccc(F)cc2)CC1] |
| 284 | 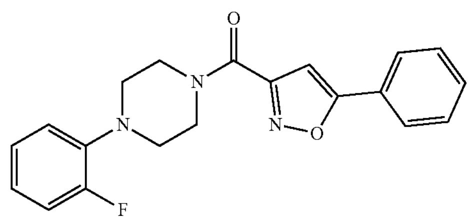 [SMILES: O=C(c1cc(-c2ccccc2)on1)N1CCN(c2ccccc2F)CC1] |
| 285 | 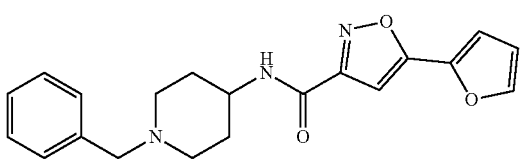 [SMILES: O=C(NC1CCN(Cc2ccccc2)CC1)c1cc(-c2ccco2)on1] |
| 286 | 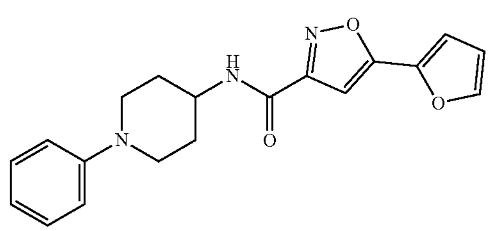 [SMILES: O=C(NC1CCN(c2ccccc2)CC1)c1cc(-c2ccco2)on1] |
| 287 | 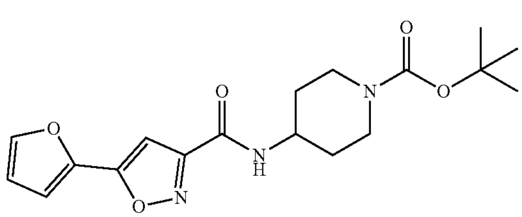 [SMILES: CC(C)(C)OC(=O)N1CCC(NC(=O)c2cc(-c3ccco3)on2)CC1] |
| 288 | 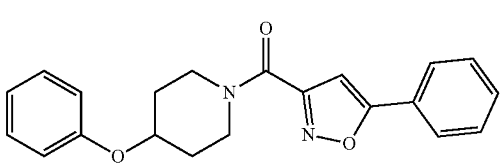 [SMILES: O=C(c1cc(-c2ccccc2)on1)N1CCC(Oc2ccccc2)CC1] |

143
TABLE 1-continued
| | Compounds of the Invention |
|---|---|
| No. | Structure |
| 289 | 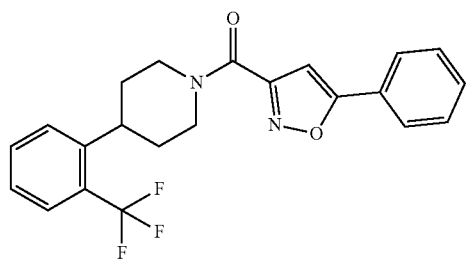 [SMILES: O=C(c1cc(-c2ccccc2)on1)N1CCC(c2ccccc2C(F)(F)F)CC1] |
| 290 | 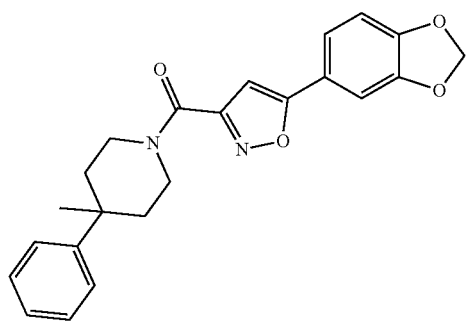 [SMILES: CC1(c2ccccc2)CCN(C(=O)c2cc(-c3ccc4c(c3)OCO4)on2)CC1] |
| 291 | 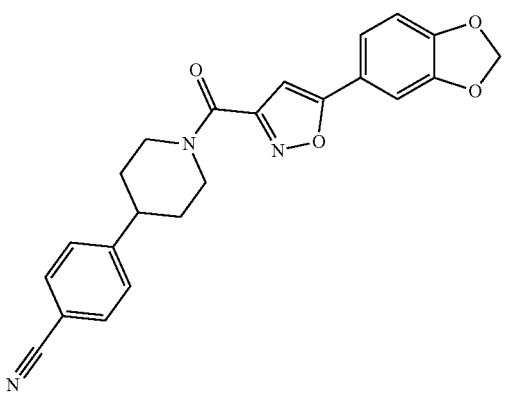 [SMILES: N#Cc1ccc(C2CCN(C(=O)c3cc(-c4ccc5c(c4)OCO5)on3)CC2)cc1] |
| 292 | 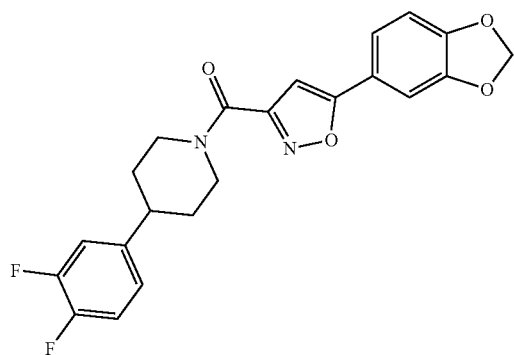 [SMILES: O=C(c1cc(-c2ccc3c(c2)OCO3)on1)N1CCC(c2ccc(F)c(F)c2)CC1] |

145
TABLE 1-continued
Compounds of the Invention
| No. | Structure |
|---|---|
| 293 | 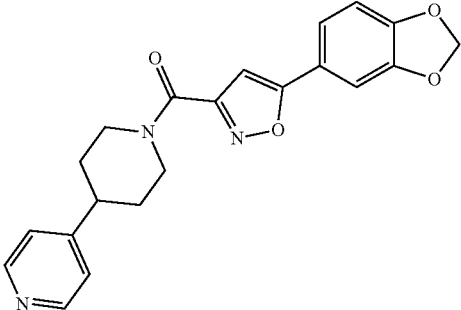 [SMILES: O=C(c1cc(-c2ccc3c(c2)OCO3)on1)N1CCC(c2ccncc2)CC1] |
| 294 | 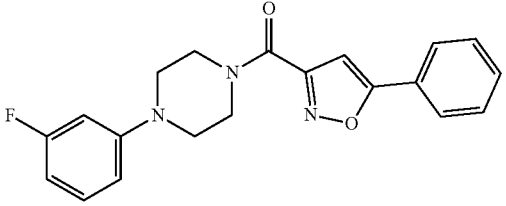 [SMILES: O=C(c1cc(-c2ccccc2)on1)N1CCN(c2cccc(F)c2)CC1] |
| 295 | 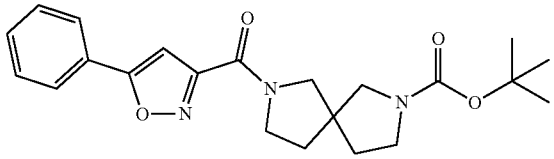 [SMILES: CC(C)(C)OC(=O)N1CCC2(CCN(C(=O)c3cc(-c4ccccc4)on3)C2)C1] |
| 296 | 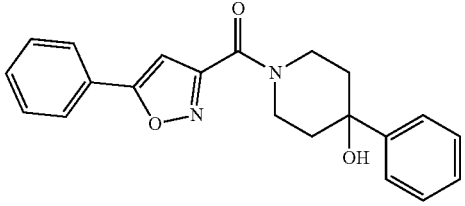 [SMILES: O=C(c1cc(-c2ccccc2)on1)N1CCC(O)(c2ccccc2)CC1] |
| 297 | 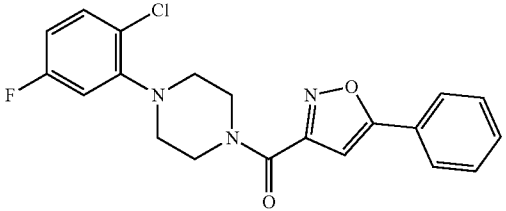 |
| 298 | 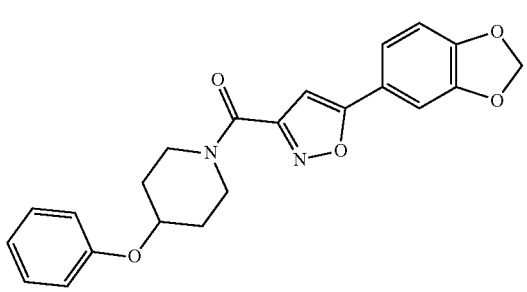 [SMILES: O=C(c1cc(-c2ccc3c(c2)OCO3)on1)N1CCC(Oc2ccccc2)CC1] |

TABLE 1-continued
Compounds of the Invention
| No. | Structure |
|---|---|
| 299 | 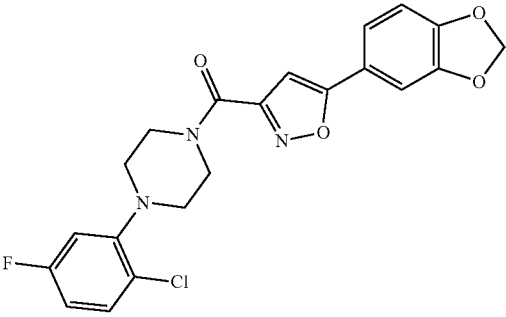 |
| 300 | 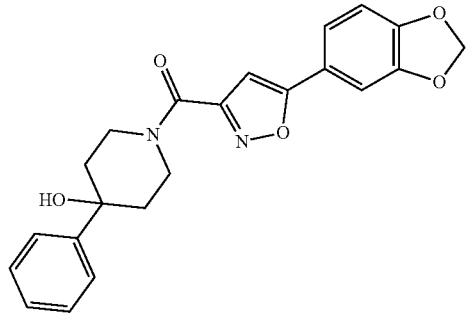 [SMILES: O=C(c1cc(-c2ccc3c(c2)OCO3)on1)N1CCC(O)(c2ccccc2)CC1] |
| 301 | 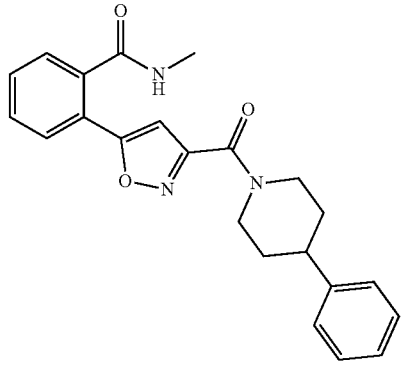 [SMILES: CNC(=O)c1ccccc1-c1cc(C(=O)N2CCC(c3ccccc3)CC2)no1] |
| 302 | 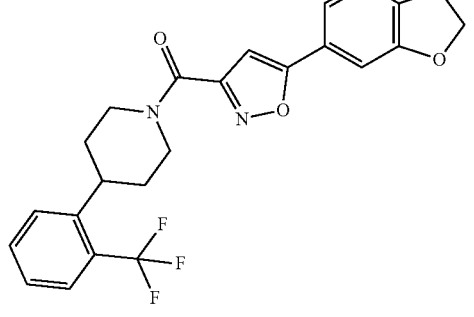 |

TABLE 1-continued
Compounds of the Invention
| No. | Structure |
|---|---|
| 303 | 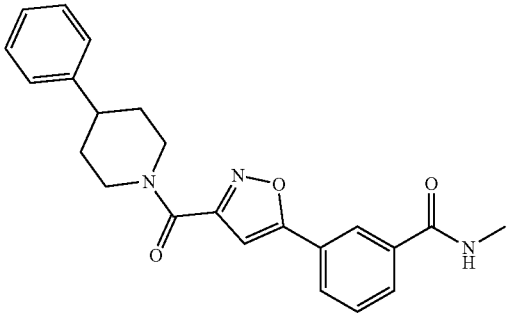 [SMILES: CNC(=O)c1cccc(-c2cc(C(=O)N3CCC(c4ccccc4)CC3)no2)c1] |
| 304 | 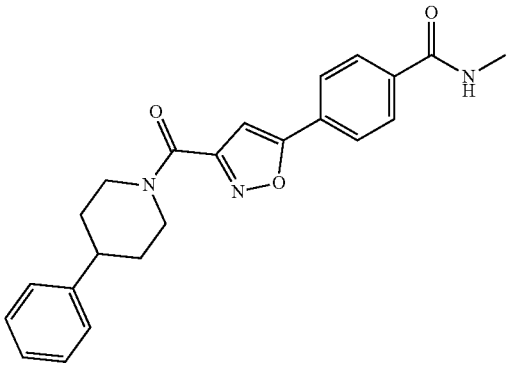 [SMILES: CNC(=O)c1ccc(-c2cc(C(=O)N3CCC(c4ccccc4)CC3)no2)cc1] |
| 305 | 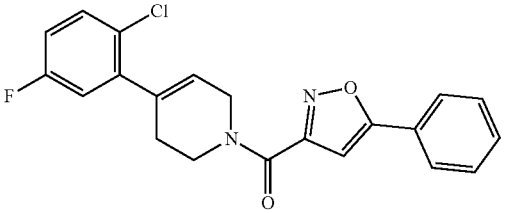 [SMILES: O=C(c1cc(-c2ccccc2)on1)N1CC=C(c2cc(F)ccc2Cl)CC1] |
| 306 | 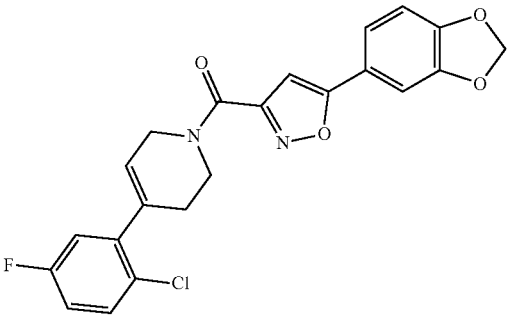 [SMILES: O=C(c1cc(-c2ccc3c(c2)OCO3)on1)N1CC=C(c2cc(F)ccc2Cl)CC1] |
| 307 | 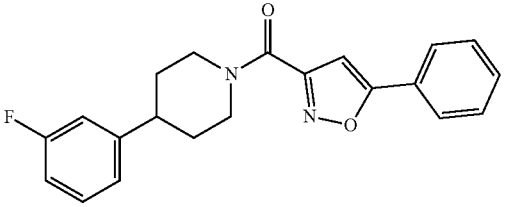 [SMILES: O=C(c1cc(-c2ccccc2)on1)N1CCC(c2cccc(F)c2)CC1] |

TABLE 1-continued
Compounds of the Invention
| No. | Structure |
|---|---|
| 308 | 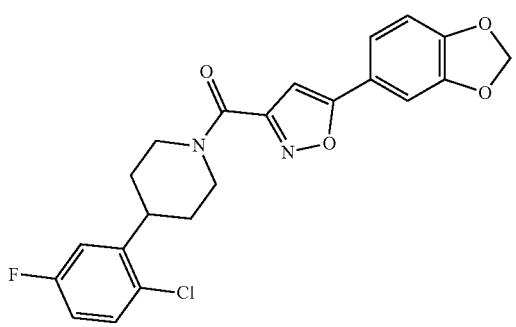 |
| 309 | 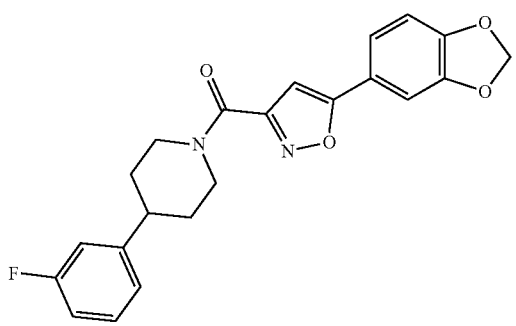 [SMILES: O=C(c1cc(-c2ccc3c(c2)OCO3)on1)N1CCC(c2cccc(F)c2)CC1] |
| 310 | 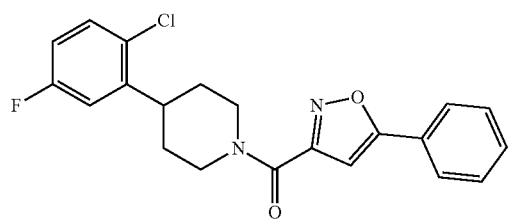 [SMILES: O=C(c1cc(-c2ccccc2)on1)N1CCC(c2cc(F)ccc2Cl)CC1] |
| 311 | 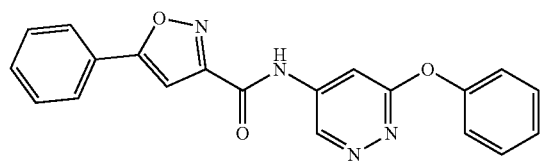 [SMILES: O=C(Nc1cnnc(Oc2ccccc2)c1)c1cc(-c2ccccc2)on1] |
| 312 | 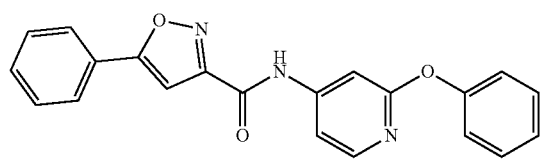 [SMILES: O=C(Nc1ccnc(Oc2ccccc2)c1)c1cc(-c2ccccc2)on1] |
| 313 | 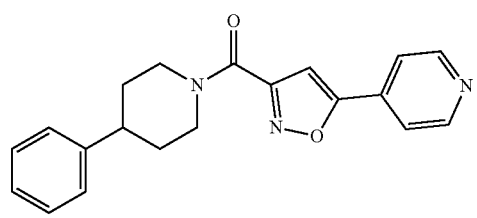 [SMILES: O=C(c1cc(-c2ccncc2)on1)N1CCC(c2ccccc2)CC1] |

TABLE 1-continued
Compounds of the Invention
| No. | Structure |
|---|---|
| 314 | 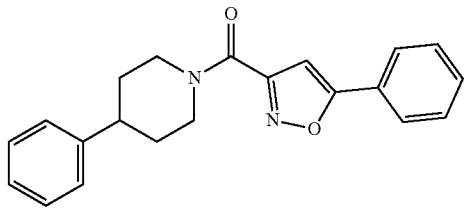 [SMILES: O=C(c1cc(-c2ccccc2)on1)N1CCC(c2ccccc2)CC1] |
| 315 | 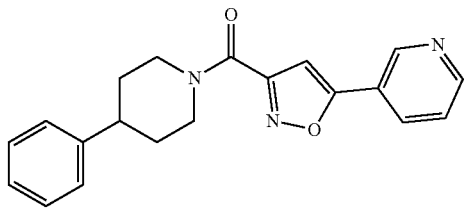 [SMILES: O=C(c1cc(-c2cccnc2)on1)N1CCC(c2ccccc2)CC1] |
| 316 | 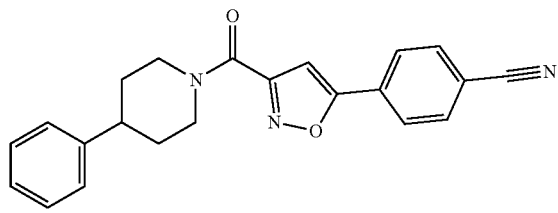 [SMILES: N#Cc1ccc(-c2cc(C(=O)N3CCC(c4ccccc4)CC3)no2)cc1] |
| 317 | 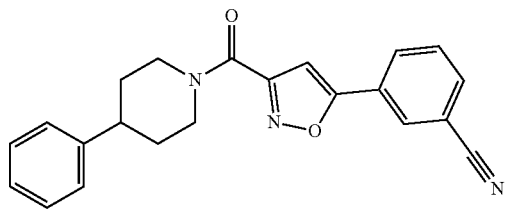 [SMILES: N#Cc1cccc(-c2cc(C(=O)N3CCC(c4ccccc4)CC3)no2)c1] |
| 318 | 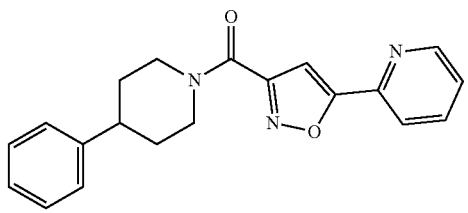 [SMILES: O=C(c1cc(-c2ccccn2)on1)N1CCC(c2ccccc2)CC1] |
| 319 | 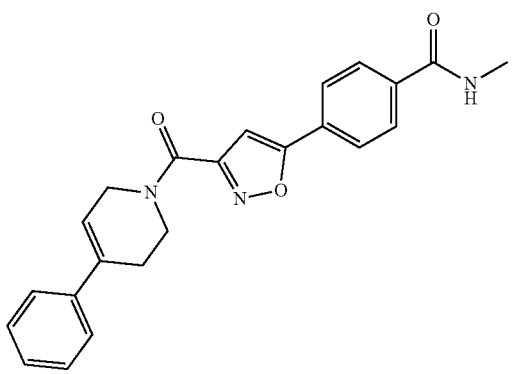 [SMILES: CNC(=O)c1ccc(-c2cc(C(=O)N3CC=C(c4ccccc4)CC3)no2)cc1] |

TABLE 1-continued
Compounds of the Invention
| No. | Structure |
|---|---|
| 320 | 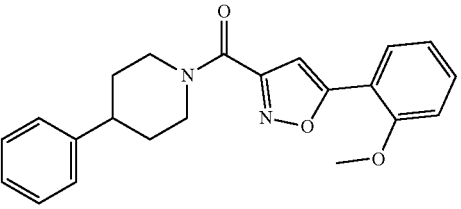 [SMILES: COc1ccccc1-c1cc(C(=O)N2CCC(c3ccccc3)CC2)no1] |
| 321 | 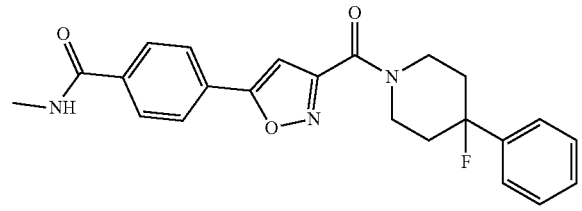 [SMILES: CNC(=O)c1ccc(-c2cc(C(=O)N3CCC(F)(c4ccccc4)CC3)no2)cc1] |
| 322 | 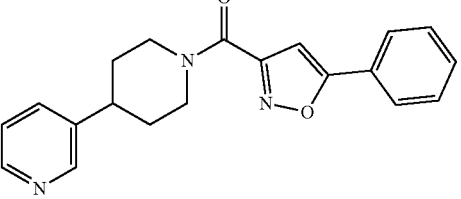 |
| 323 | 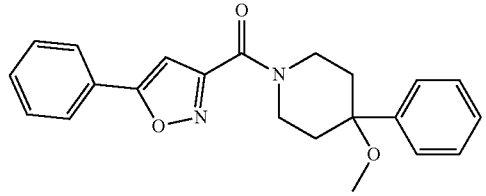 [SMILES: COC1(c2ccccc2)CCN(C(=O)c2cc(-c3ccccc3)on2)CC1] |
| 324 | 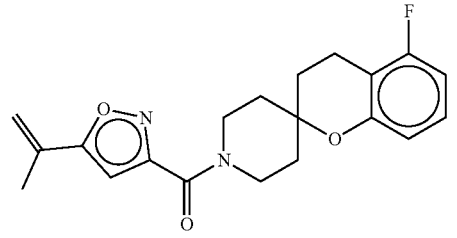 |
| 325 | 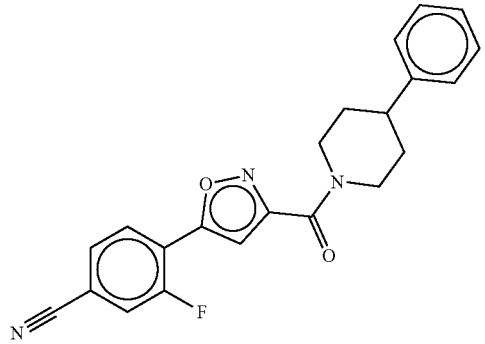 |

TABLE 1-continued

Compounds of the Invention

| No. | Structure |
|---|---|
| 326 | 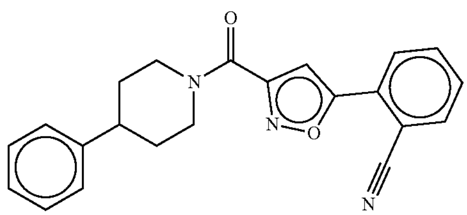 |
| 327 | 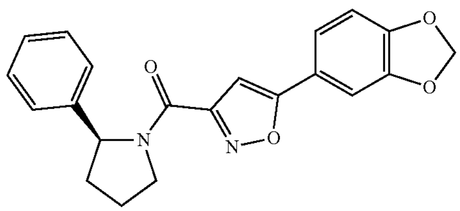 [SMILES: O=C(c1cc(-c2ccc3c(c2)OCO3)on1)N1CCC[C@H]1c1ccccc1] |
| 328 | 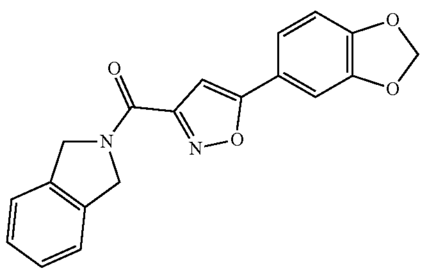 [SMILES: O=C(c1cc(-c2ccc3c(c2)OCO3)on1)N1Cc2ccccc2C1] |
| 329 | 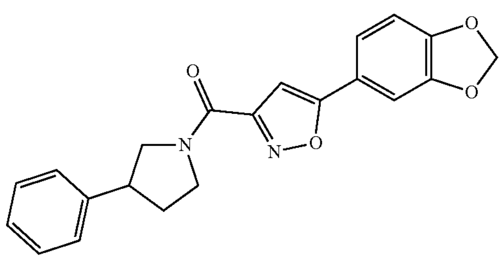 [SMILES: O=C(c1cc(-c2ccc3c(c2)OCO3)on1)N1CCC(c2ccccc2)C1] |
| 330 | 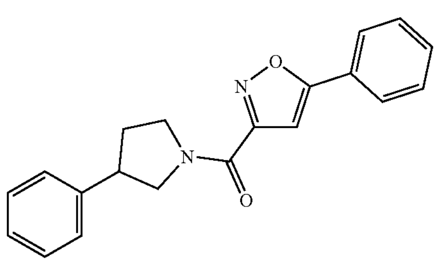 [SMILES: O=C(c1cc(-c2ccccc2)on1)N1CCC(c2ccccc2)C1] |
| 331 | 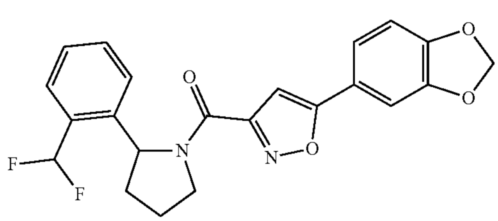 [SMILES: O=C(c1cc(-c2ccc3c(c2)OCO3)on1)N1CCCC1c1ccccc1C(F)F] |

TABLE 1-continued

Compounds of the Invention

| No. | Structure |
|-----|-----------|
| 332 | 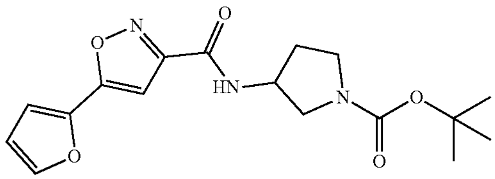 [SMILES: CC(C)(C)OC(=O)N1CCC(NC(=O)c2cc(-c3ccco3)on2)C1] |
| 333 | 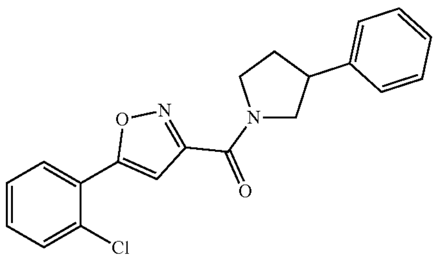 [SMILES: O=C(c1cc(-c2ccccc2Cl)on1)N1CCC(c2ccccc2)C1] |
| 334 | 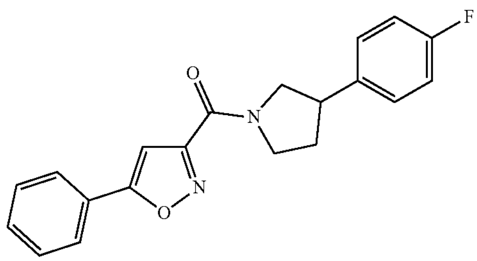 [SMILES: O=C(c1cc(-c2ccccc2)on1)N1CCC(c2ccc(F)cc2)C1] |
| 335 | 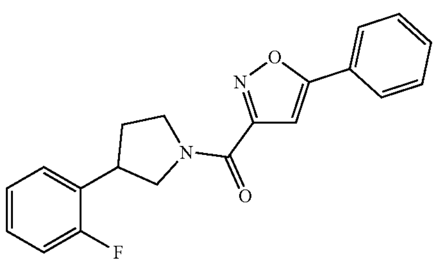 [SMILES: O=C(c1cc(-c2ccccc2)on1)N1CCC(c2ccccc2F)C1] |
| 336 | 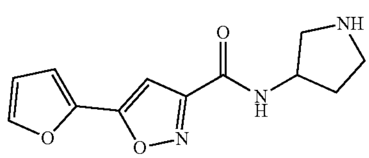 [SMILES: O=C(NC1CCNC1)c1cc(-c2ccco2)on1] |
| 337 | 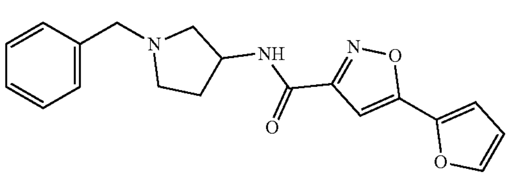 [SMILES: O=C(NC1CCN(Cc2ccccc2)C1)c1cc(-c2ccco2)on1] |
| 338 | 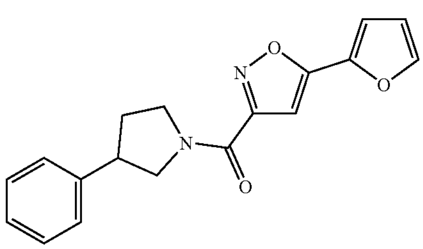 [SMILES: O=C(c1cc(-c2ccco2)on1)N1CCC(c2ccccc2)C1] |

TABLE 1-continued
Compounds of the Invention
| No. | Structure |
|---|---|
| 339 | 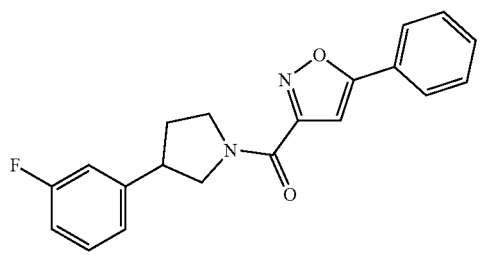 [SMILES: O=C(c1cc(-c2ccccc2)on1)N1CCC(c2cccc(F)c2)C1] |
| 340 | 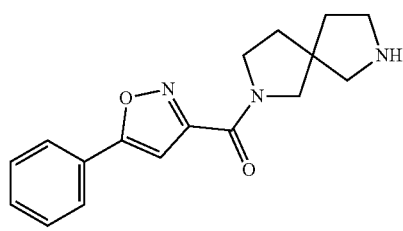 [SMILES: O=C(c1cc(-c2ccccc2)on1)N1CCC2(CCNC2)C1] |
| 341 | 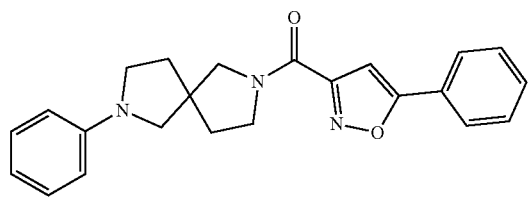 [SMILES: O=C(c1cc(-c2ccccc2)on1)N1CCC2(CCN(c3ccccc3)C2)C1] |
| 342 | 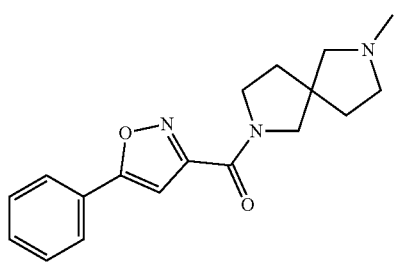 [SMILES: CN1CCC2(CCN(C(=O)c3cc(-c4ccccc4)on3)C2)C1] |
| 343 | 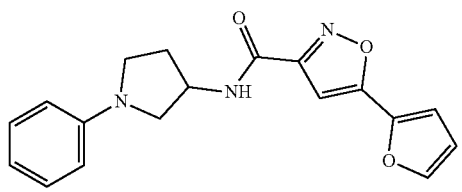 [SMILES: O=C(NC1CCN(c2ccccc2)C1)c1cc(-c2ccco2)on1] |
| 344 | 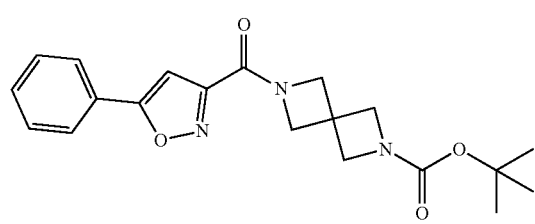 [SMILES: CC(C)(C)OC(=O)N1CC2(C1)CN(C(=O)c1cc(-c3ccccc3)on1)C2] |

TABLE 1-continued

Compounds of the Invention

| No. | Structure |
|---|---|
| 345 | 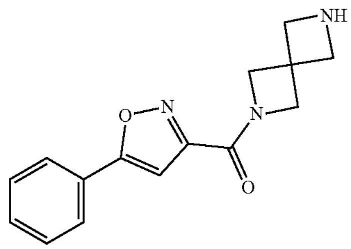 [SMILES: O=C(c1cc(-c2ccccc2)on1)N1CC2(CNC2)C1] |
| 346 | 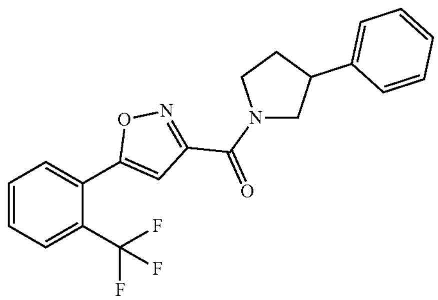 [SMILES: O=C(c1cc(-c2ccccc2C(F)(F)F)on1)N1CCC(c2ccccc2)C1] |
| 347 | 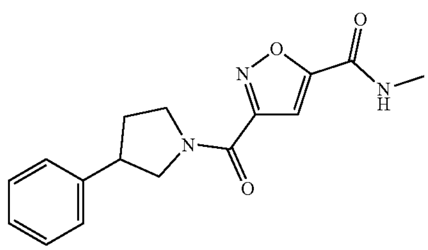 [SMILES: CNC(=O)c1cc(C(=O)N2CCC(c3ccccc3)C2)no1] |
| 348 | 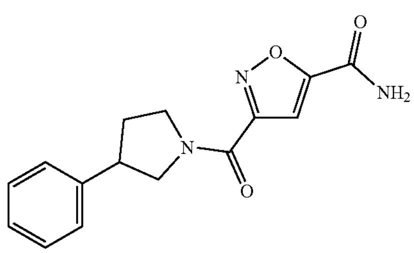 [SMILES: NC(=O)c1cc(C(=O)N2CCC(c3ccccc3)C2)no1] |
| 349 | 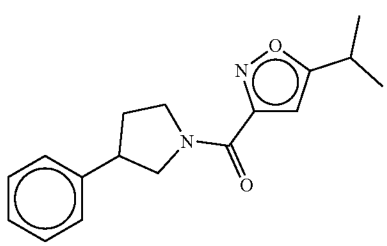 |
| 350 | 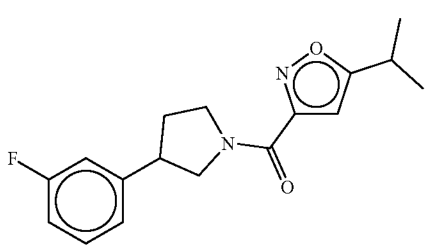 |

TABLE 1-continued
Compounds of the Invention
| No. | Structure |
|---|---|
| 351 | 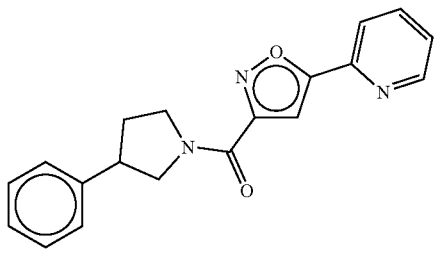 |
| 352 | 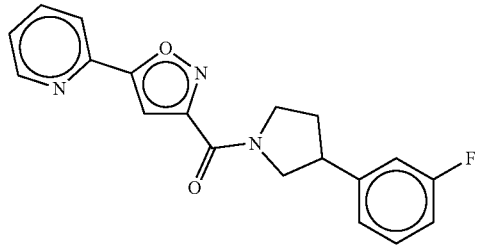 |
| 353 | 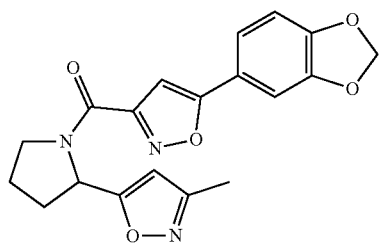 [SMILES: Cc1cc(C2CCCN2C(=O)c2cc(-c3ccc4c(c3)OCO4)on2)on1] |
| 354 | 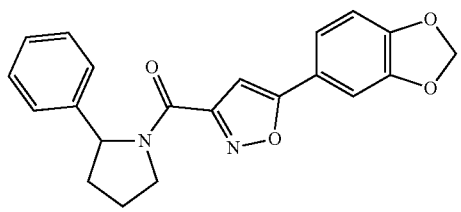 [SMILES: O=C(c1cc(-c2ccc3c(c2)OCO3)on1)N1CCCC1c1ccccc1] |
| 355 | 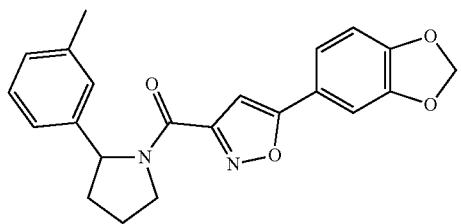 [SMILES: Cc1cccc(C2CCCN2C(=O)c2cc(-c3ccc4c(c3)OCO4)on2)c1] |
| 356 | 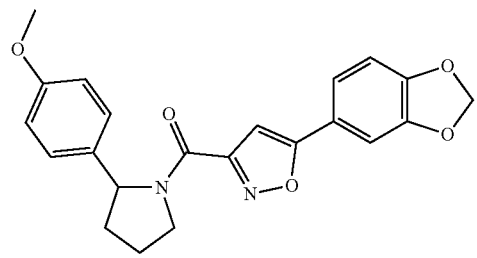 |

US 10,919,885 B2
167                                                              168
TABLE 1-continued
Compounds of the Invention
| No. | Structure |
|---|---|
| 357 | 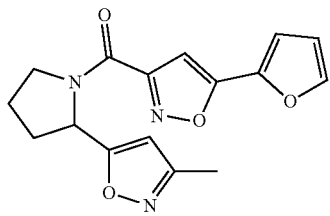 [SMILES: Cc1cc(C2CCCN2C(=O)c2cc(-c3ccco3)on2)on1] |
| 358 | 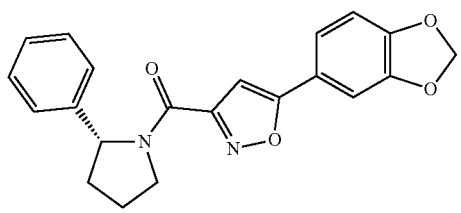 [SMILES: O=C(c1cc(-c2ccc3c(c2)OCO3)on1)N1CCC[C@@H]1c1ccccc1] |
| 359 | 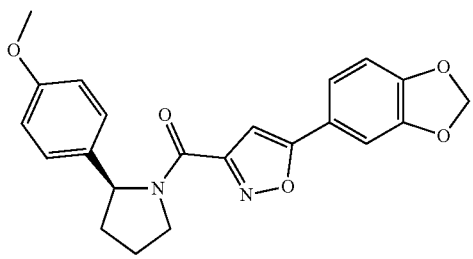 [SMILES: COc1ccc([C@@H]2CCCN2C(=O)c2cc(-c3ccc4c(c3)OCO4)on2)cc1] |
| 360 | 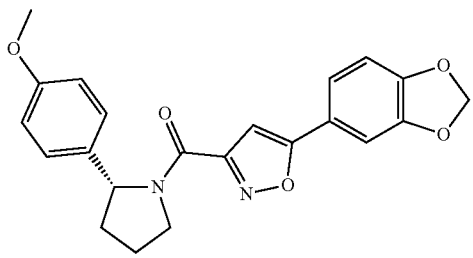 [SMILES: COc1ccc([C@H]2CCCN2C(=O)c2cc(-c3ccc4c(c3)OCO4)on2)cc1] |
| 361 | 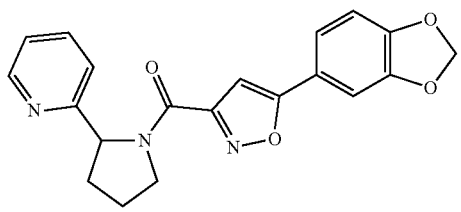 [SMILES: O=C(c1cc(-c2ccc3c(c2)OCO3)on1)N1CCCC1c1ccccn1] |
| 362 | 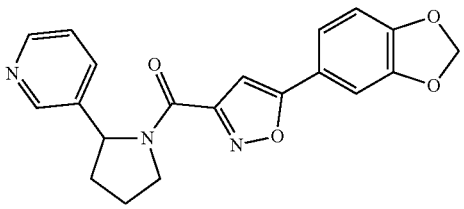 [SMILES: O=C(c1cc(-c2ccc3c(c2)OCO3)on1)N1CCCC1c1cccnc1] |

TABLE 1-continued
Compounds of the Invention
| No. | Structure |
|---|---|
| 363 | 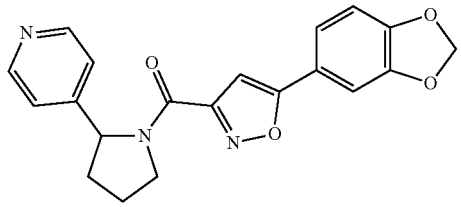 |
| 364 | 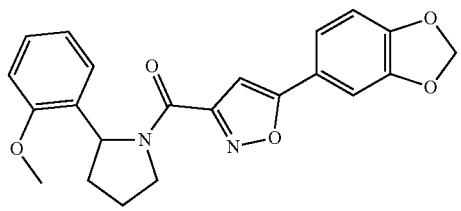 |
| 365 | 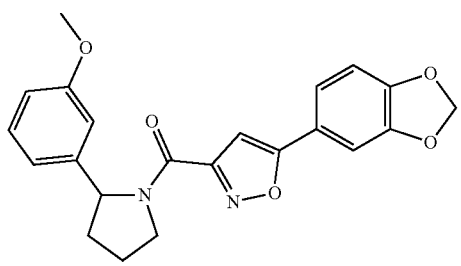 [SMILES: COc1cccc(C2CCCN2C(=O)c2cc(-c3ccc4c(c3)OCO4)on2)c1] |
| 366 | 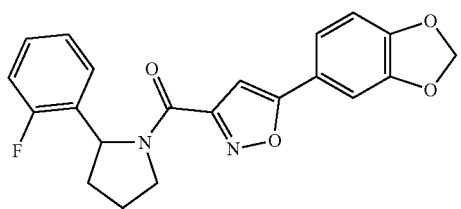 [SMILES: O=C(c1cc(-c2ccc3c(c2)OCO3)on1)N1CCCC1c1ccccc1F] |
| 367 | 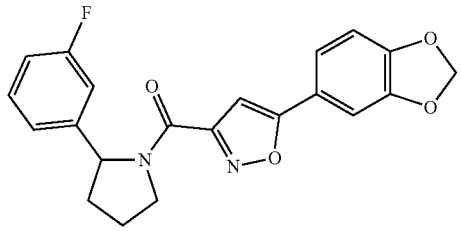 [SMILES: O=C(c1cc(-c2ccc3c(c2)OCO3)on1)N1CCCC1c1cccc(F)c1] |
| 368 | 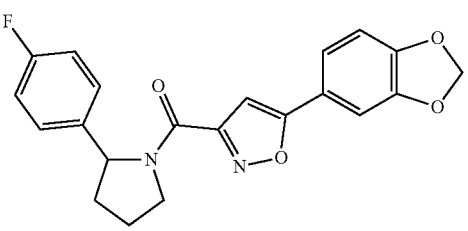 |

TABLE 1-continued

Compounds of the Invention

| No. | Structure |
|---|---|
| 369 | 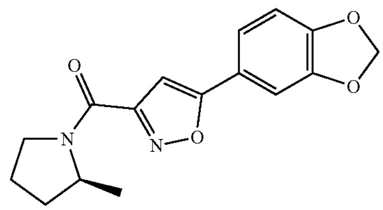 [SMILES: C[C@H]1CCCN1C(=O)c1cc(-c2ccc3c(c2)OCO3)on1] |
| 370 | 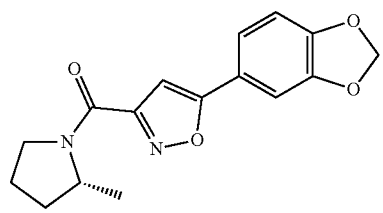 [SMILES: C[C@@H]1CCCN1C(=O)c1cc(-c2ccc3c(c2)OCO3)on1] |
| 371 | 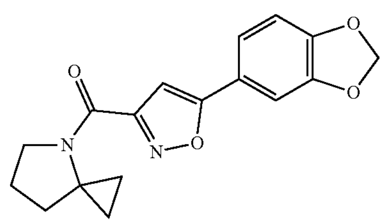 [SMILES: O=C(c1cc(-c2ccc3c(c2)OCO3)on1)N1CCCC12CC2] |
| 372 | 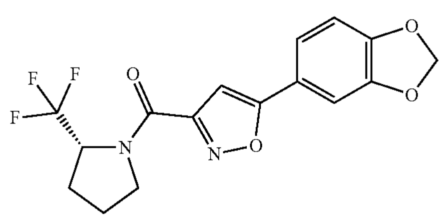 [SMILES: O=C(c1cc(-c2ccc3c(c2)OCO3)on1)N1CCC[C@@H]1C(F)(F)F] |
| 373 | 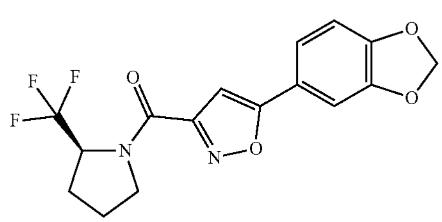 [SMILES: O=C(c1cc(-c2ccc3c(c2)OCO3)on1)N1CCC[C@H]1C(F)(F)F] |
| 374 | 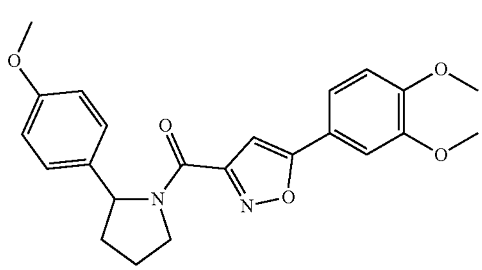 [SMILES: COc1ccc(C2CCCN2C(=O)c2cc(-c3ccc(OC)c(OC)c3)on2)cc1] |

TABLE 1-continued
Compounds of the Invention
| No. | Structure |
|-----|-----------|
| 375 | 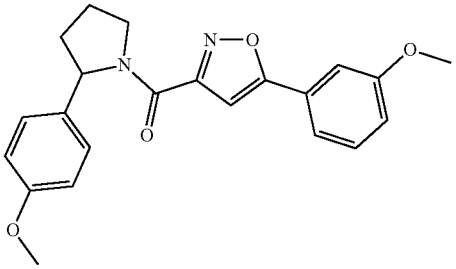 [SMILES: COc1ccc(C2CCCN2C(=O)c2cc(-c3cccc(OC)c3)on2)cc1] |
| 376 | 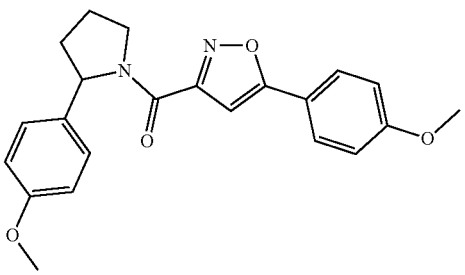 [SMILES: COc1ccc(-c2cc(C(=O)N3CCCC3c3ccc(OC)cc3)no2)cc1] |
| 377 | 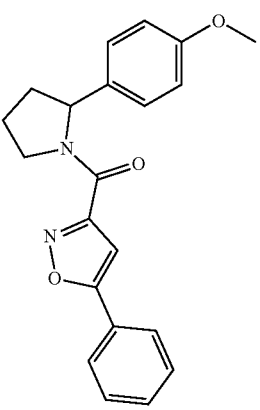 [SMILES: COc1ccc(C2CCCN2C(=O)c2cc(-c3ccccc3)on2)cc1] |
| 378 | 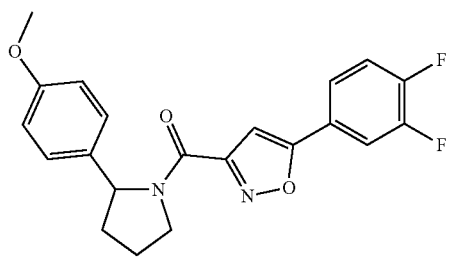 [SMILES: COc1ccc(C2CCCN2C(=O)c2cc(-c3ccc(F)c(F)c3)on2)cc1] |
| 379 | 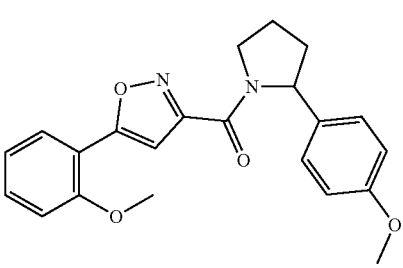 [SMILES: COc1ccc(C2CCCN2C(=O)c2cc(-c3ccccc3OC)on2)cc1] |

175
176
TABLE 1-continued
Compounds of the Invention
| No. | Structure |
|---|---|
| 380 | 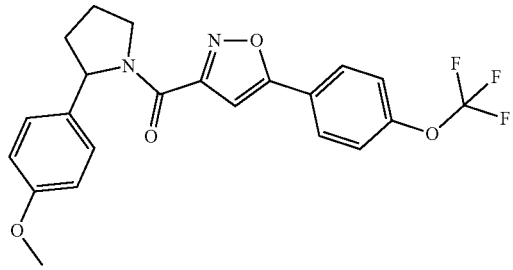 [SMILES: COc1ccc(C2CCCN2C(=O)c2cc(-c3ccc(OC(F)(F)F)cc3)on2)cc1] |
| 381 | 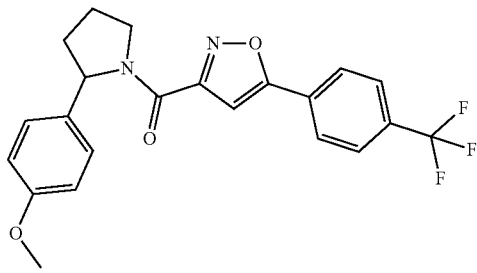 [SMILES: COc1ccc(C2CCCN2C(=O)c2cc(-c3ccc(C(F)(F)F)cc3)on2)cc1] |
| 382 | 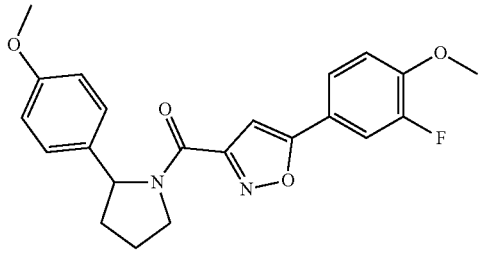 [SMILES: COc1ccc(C2CCCN2C(=O)c2cc(-c3ccc(OC)c(F)c3)on2)cc1] |
| 383 | 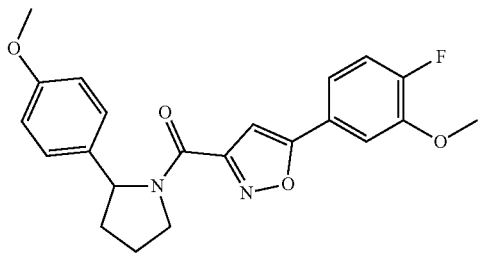 [SMILES: COc1ccc(C2CCCN2C(=O)c2cc(-c3ccc(F)c(OC)c3)on2)cc1] |
| 384 | 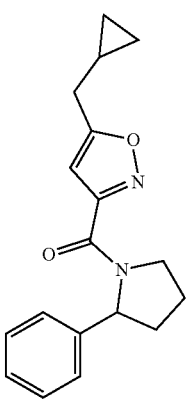 [SMILES: O=C(c1cc(CC2CC2)on1)N1CCCC1c1ccccc1] |

TABLE 1-continued
Compounds of the Invention
| No. | Structure |
|-----|-----------|
| 385 | 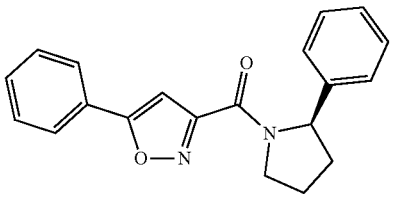 [SMILES: O=C(c1cc(-c2ccccc2)on1)N1CCC[C@@H]1c1ccccc1] |
| 386 | 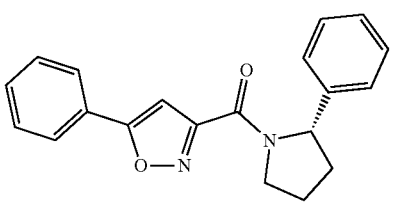 |
| 387 | 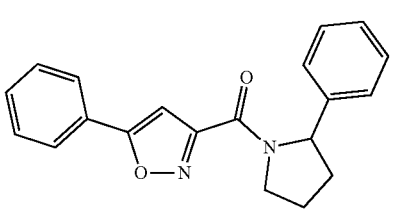 [SMILES: O=C(c1cc(-c2ccccc2)on1)N1CCCC1c1ccccc1] |
| 388 | 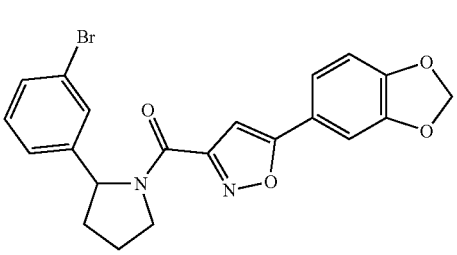 [SMILES: O=C(c1cc(-c2ccc3c(c2)OCO3)on1)N1CCCC1c1cccc(Br)c1] |
| 389 | 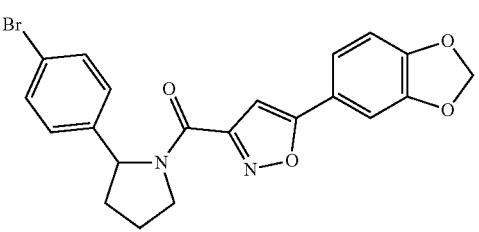 [SMILES: O=C(c1cc(-c2ccc3c(c2)OCO3)on1)N1CCCC1c1ccc(Br)cc1] |
| 390 | 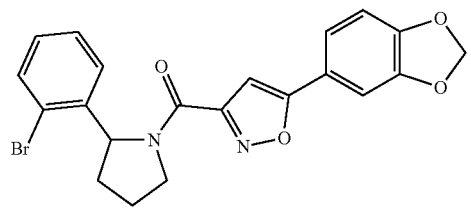 [SMILES: O=C(c1cc(-c2ccc3c(c2)OCO3)on1)N1CCCC1c1ccccc1Br] |
| 391 | 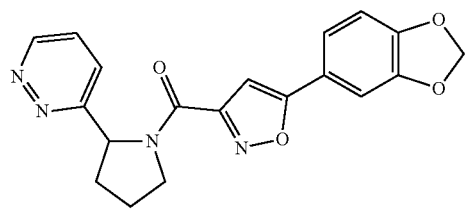 [SMILES: O=C(c1cc(-c2ccc3c(c2)OCO3)on1)N1CCCC1c1cccnn1] |

TABLE 1-continued

Compounds of the Invention

| No. | Structure |
|-----|-----------|
| 392 | 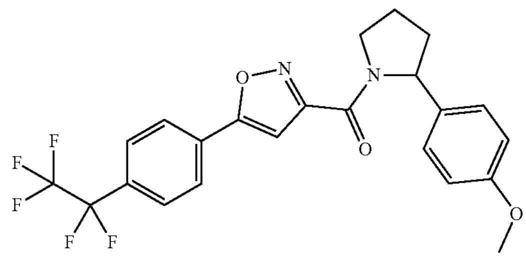 [SMILES: COc1ccc(C2CCCN2C(=O)c2cc(-c3ccc(C(F)(F)C(F)(F)F)cc3)on2)cc1] |
| 393 | 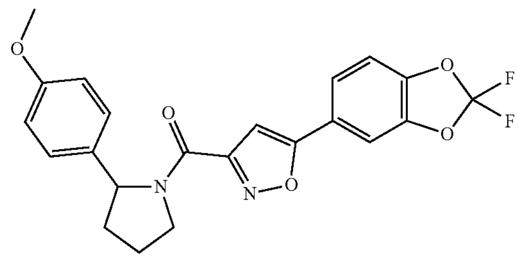 [SMILES: COc1ccc(C2CCCN2C(=O)c2cc(-c3ccc4c(c3)OC(F)(F)O4)on2)cc1] |
| 394 | 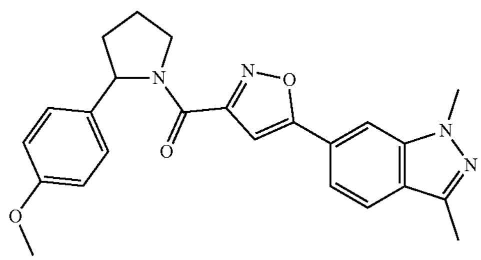 [SMILES: COc1ccc(C2CCCN2C(=O)c2cc(-c3ccc4c(C)nn(C)c4c3)on2)cc1] |
| 395 | 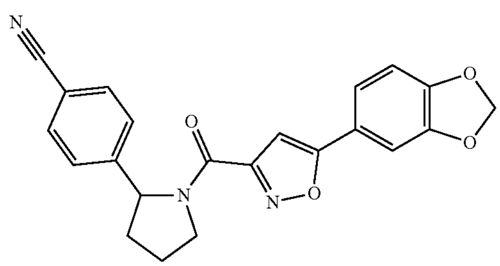 [SMILES: N#Cc1ccc(C2CCCN2C(=O)c2cc(-c3ccc4c(c3)OCO4)on2)cc1] |
| 396 | 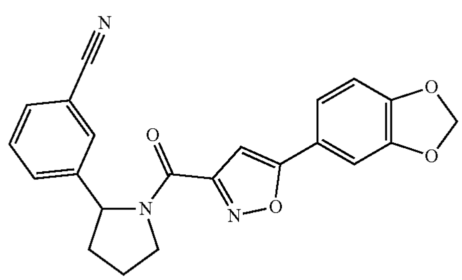 [SMILES: N#Cc1cccc(C2CCCN2C(=O)c2cc(-c3ccc4c(c3)OCO4)on2)c1] |
| 397 | 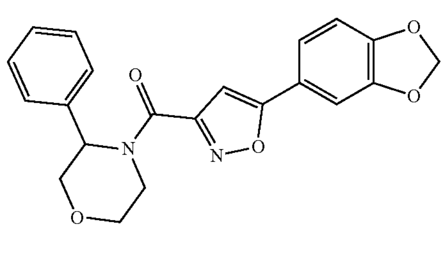 [SMILES: O=C(c1cc(-c2ccc3c(c2)OCO3)on1)N1CCOCC1c1ccccc1] |

TABLE 1-continued

Compounds of the Invention

| No. | Structure |
|---|---|
| 398 | 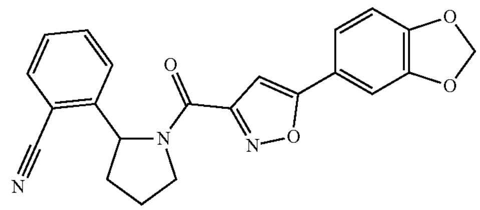 [SMILES: N#Cc1ccccc1C1CCCN1C(=O)c1cc(-c2ccc3c(c2)OCO3)on1] |
| 399 | 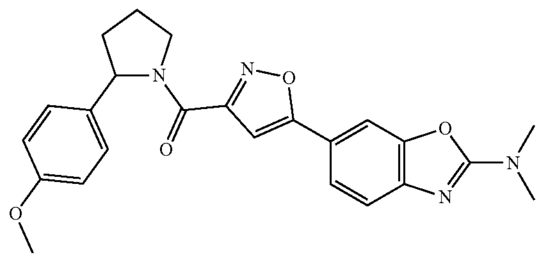 [SMILES: COc1ccc(C2CCCN2C(=O)c2cc(-c3ccc4nc(N(C)C)oc4c3)on2)cc1] |
| 400 | 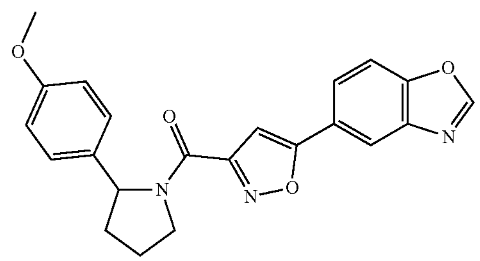 [SMILES: COc1ccc(C2CCCN2C(=O)c2cc(-c3ccc4ocnc4c3)on2)cc1] |
| 401 | 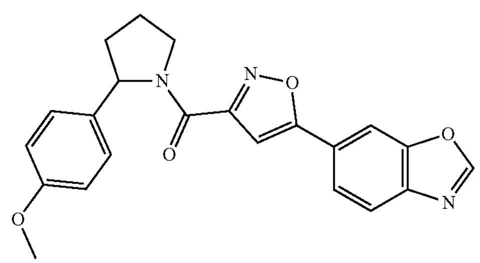 [SMILES: COc1ccc(C2CCCN2C(=O)c2cc(-c3ccc4ncoc4c3)on2)cc1] |
| 402 | 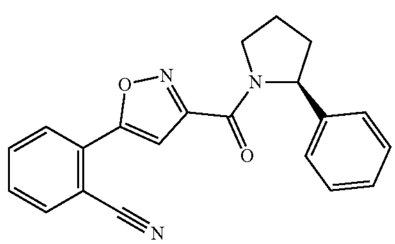 [SMILES: N#Cc1ccccc1-c1cc(C(=O)N2CCC[C@H]2c2ccccc2)no1] |
| 403 | 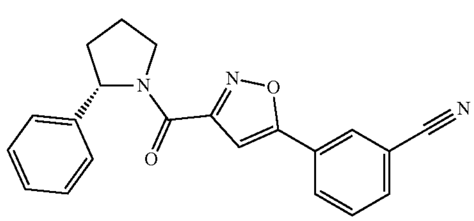 [SMILES: N#Cc1cccc(-c2cc(C(=O)N3CCC[C@H]3c3ccccc3)no2)c1] |

183

TABLE 1-continued

Compounds of the Invention

| No. | Structure |
|---|---|
| 404 | [Structure: 4-cyanophenyl-isoxazole-3-carbonyl-(2-phenyl)pyrrolidine] |
| 405 | [Structure: pyridin-3-yl-isoxazole-3-carbonyl-(2-phenyl)pyrrolidine] |
| 406 | [Structure: 4-phenyl-oxazolidine-N-carbonyl-isoxazole-5-(benzo[d][1,3]dioxol-5-yl)] |
| 407 | [Structure: 2-cyclopropylpyrrolidine-N-carbonyl-isoxazole-5-(benzo[d][1,3]dioxol-5-yl)] |
| 408 | [Structure: pyridin-2-yl-isoxazole-3-carbonyl-(2-phenyl)pyrrolidine] |
| 409 | [Structure: pyridin-4-yl-isoxazole-3-carbonyl-(2-phenyl)pyrrolidine] |
| 410 | [Structure: (2-phenyl)pyrrolidine-N-carbonyl-isoxazole-5-(6-methoxypyridin-3-yl)] |

TABLE 1-continued
Compounds of the Invention
| No. | Structure |
|---|---|
| 411 | 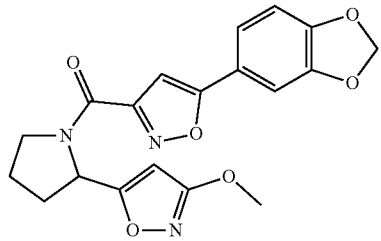 [SMILES: COc1cc(C2CCCN2C(=O)c2cc(-c3ccc4c(c3)OCO4)on2)on1] |
| 412 | 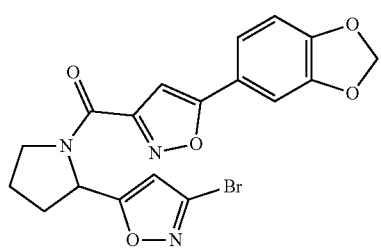 [SMILES: O=C(c1cc(-c2ccc3c(c2)OCO3)on1)N1CCCC1c1cc(Br)no1] |
| 413 | 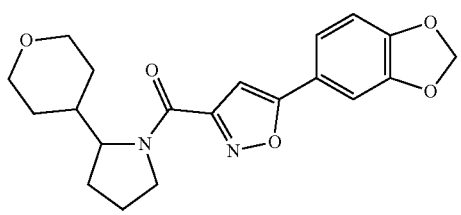 [SMILES: O=C(c1cc(-c2ccc3c(c2)OCO3)on1)N1CCCC1C1CCOCC1] |
| 414 | 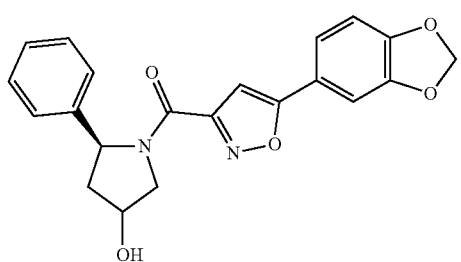 [SMILES: O=C(c1cc(-c2ccc3c(c2)OCO3)on1)N1CC(O)C[C@H]1c1ccccc1] |
| 415 | 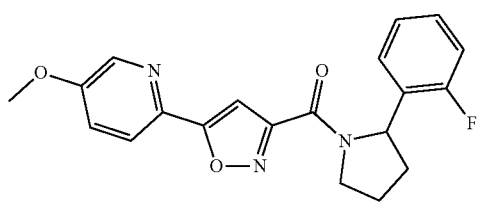 [SMILES: COc1ccc(-c2cc(C(=O)N3CCCC3c3ccccc3F)no2)nc1] |
| 416 | 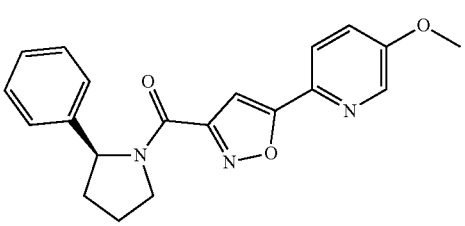 [SMILES: COc1ccc(-c2cc(C(=O)N3CCC[C@H]3c3ccccc3)no2)nc1] |

TABLE 1-continued

Compounds of the Invention

| No. | Structure |
|-----|-----------|
| 417 | 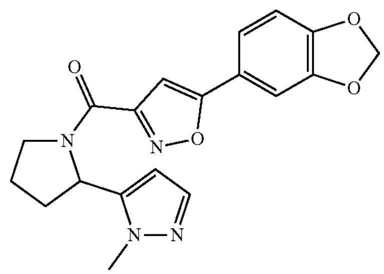 [SMILES: Cn1nccc1C1CCCN1C(=O)c1cc(-c2ccc3c(c2)OCO3)on1] |
| 418 | 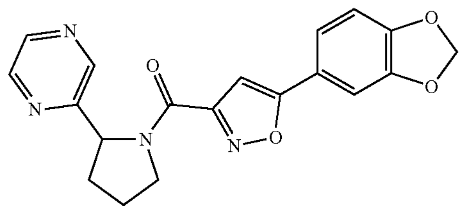 |
| 419 | 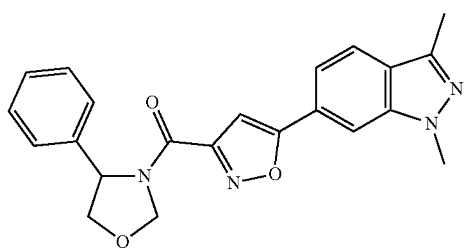 [SMILES: Cc1nn(C)c2cc(-c3cc(C(=O)N4COCC4c4ccccc4)no3)ccc12] |
| 420 | 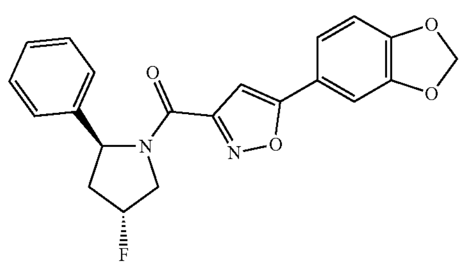 [SMILES: O=C(c1cc(-c2ccc3c(c2)OCO3)on1)N1C[C@H](F)C[C@H]1c1ccccc1] |
| 421 | 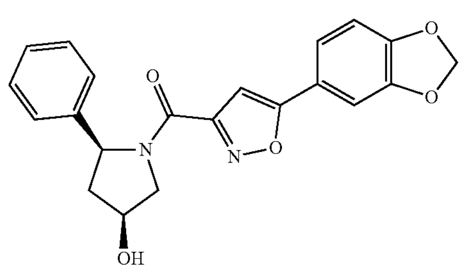 [SMILES: O=C(c1cc(-c2ccc3c(c2)OCO3)on1)N1C[C@@H](O)C[C@H]1c1ccccc1] |
| 422 | 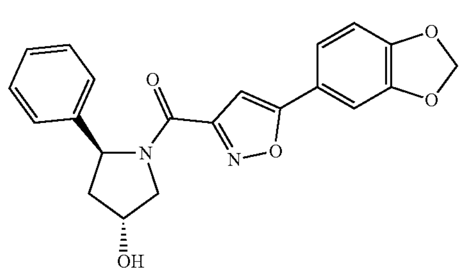 |

TABLE 1-continued

Compounds of the Invention

| No. | Structure |
|---|---|
| 423 | 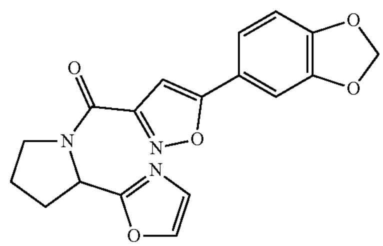 [SMILES: O=C(c1cc(-c2ccc3c(c2)OCO3)on1)N1CCCC1c1ncco1] |
| 424 | 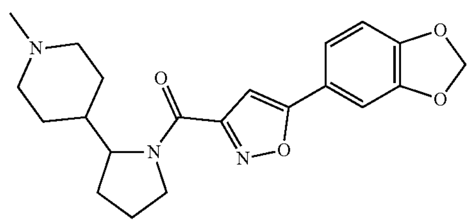 [SMILES: CN1CCC(C2CCCN2C(=O)c2cc(-c3ccc4c(c3)OCO4)on2)CC1] |
| 425 | 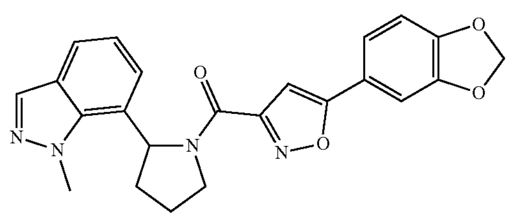 [SMILES: Cn1ncc2cccc(C3CCCN3C(=O)c3cc(-c4ccc5c(c4)OCO5)on3)c21] |
| 426 | 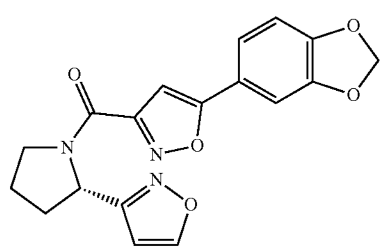 [SMILES: O=C(c1cc(-c2ccc3c(c2)OCO3)on1)N1CCC[C@H]1c1ccon1] |
| 427 | 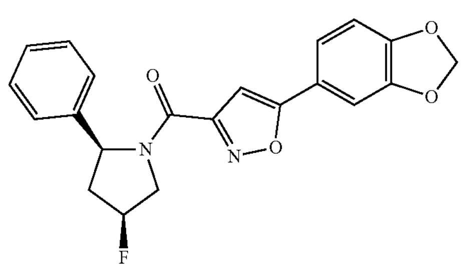 [SMILES: O=C(c1cc(-c2ccc3c(c2)OCO3)on1)N1C[C@@H](F)C[C@H]1c1ccccc1] |
| 428 | 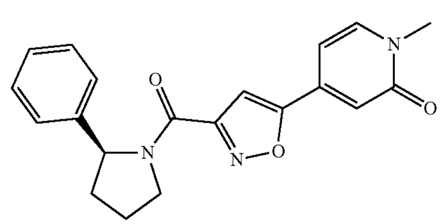 [SMILES: Cn1ccc(-c2cc(C(=O)N3CCC[C@H]3c3ccccc3)no2)cc1=O] |

TABLE 1-continued

Compounds of the Invention

| No. | Structure |
|---|---|
| 429 | 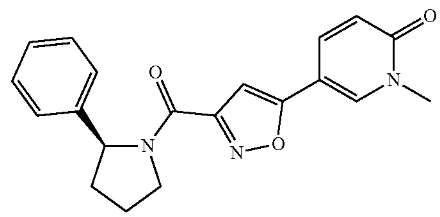 [SMILES: Cn1cc(-c2cc(C(=O)N3CCC[C@H]3c3ccccc3)no2)ccc1=O] |
| 430 | 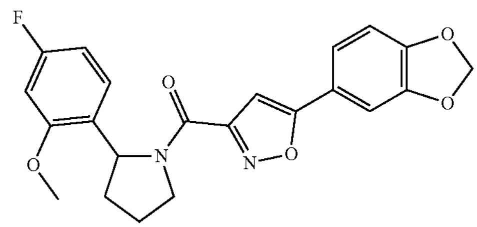 [SMILES: COc1cc(F)ccc1C1CCCN1C(=O)c1cc(-c2ccc3c(c2)OCO3)on1] |
| 431 | 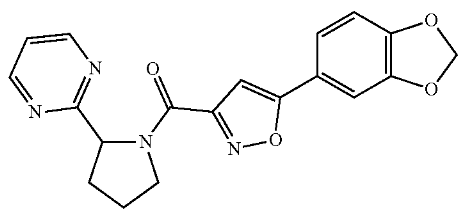 [SMILES: O=C(c1cc(-c2ccc3c(c2)OCO3)on1)N1CCCC1c1ncccn1] |
| 432 | 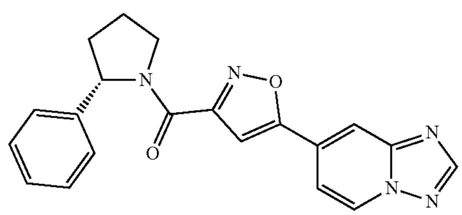 [SMILES: O=C(c1cc(-c2ccn3ncnc3c2)on1)N1CCC[C@H]1c1ccccc1] |
| 433 | 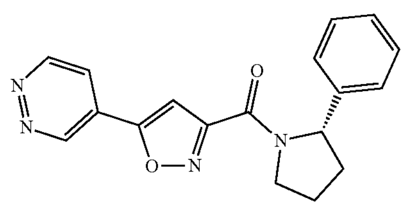 [SMILES: O=C(c1cc(-c2ccnnc2)on1)N1CCC[C@H]1c1ccccc1] |
| 434 | 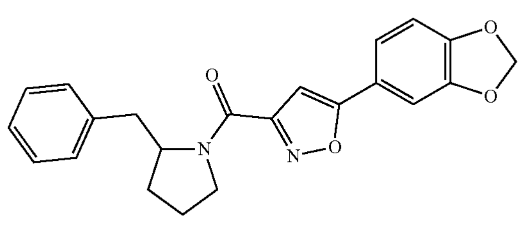 [SMILES: O=C(c1cc(-c2ccc3c(c2)OCO3)on1)N1CCCC1Cc1ccccc1] |
| 435 | 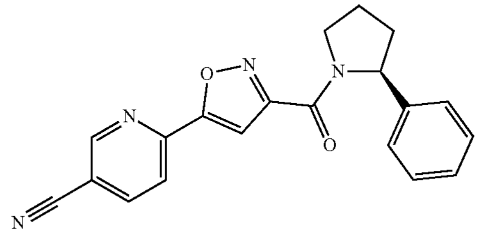 [SMILES: N#Cc1ccc(-c2cc(C(=O)N3CCC[C@H]3c3ccccc3)no2)nc1] |

TABLE 1-continued
Compounds of the Invention
| No. | Structure |
|---|---|
| 436 | 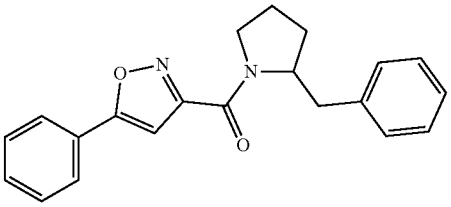 [SMILES: O=C(c1cc(-c2ccccc2)on1)N1CCCC1Cc1ccccc1] |
| 437 | 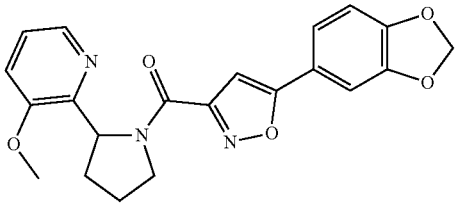 [SMILES: COc1cccnc1C1CCCN1C(=O)c1cc(-c2ccc3c(c2)OCO3)on1] |
| 438 | 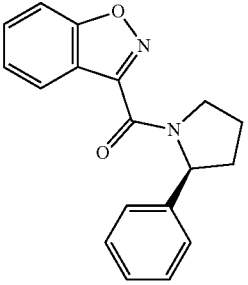 [SMILES: O=C(c1noc2ccccc12)N1CCC[C@H]1c1ccccc1] |
| 439 | 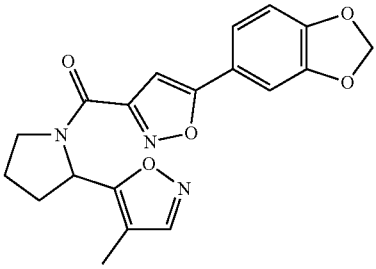 [SMILES: Cc1cnoc1C1CCCN1C(=O)c1cc(-c2ccc3c(c2)OCO3)on1] |
| 440 | 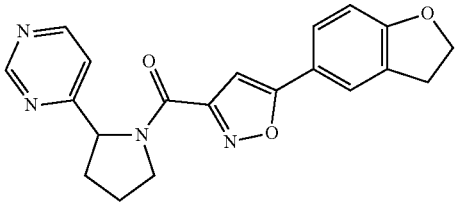 [SMILES: O=C(c1cc(-c2ccc3c(c2)CCO3)on1)N1CCCC1c1ccncn1] |
| 441 | 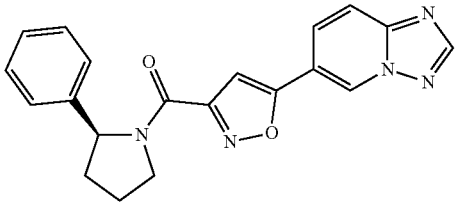 [SMILES: O=C(c1cc(-c2ccc3ncnn3c2)on1)N1CCC[C@H]1c1ccccc1] |

TABLE 1-continued

Compounds of the Invention

| No. | Structure |
|---|---|
| 442 | 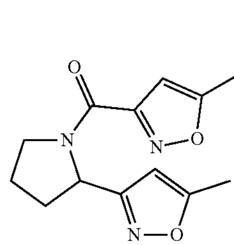 |
| 443 | 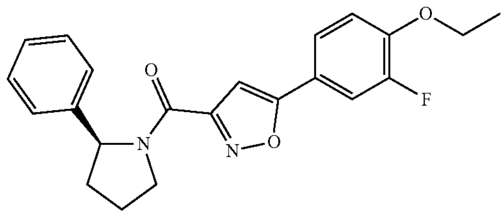 [SMILES: CCOc1ccc(-c2cc(C(=O)N3CCC[C@H]3c3ccccc3)no2)cc1F] |
| 444 | 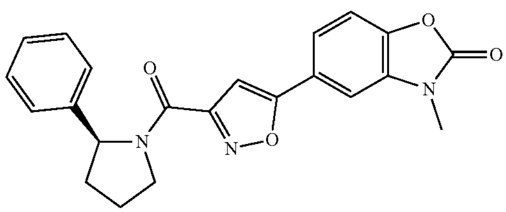 [SMILES: Cn1c(=O)oc2ccc(-c3cc(C(=O)N4CCC[C@H]4c4ccccc4)no3)cc21] |
| 445 | 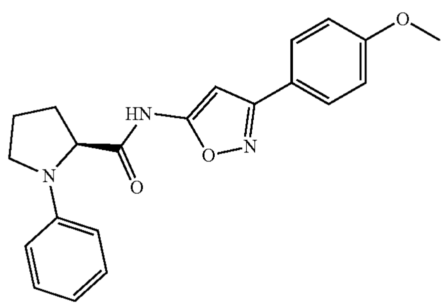 [SMILES: COc1ccc(-c2cc(NC(=O)[C@@H]3CCCN3c3ccccc3)on2)cc1] |
| 446 | 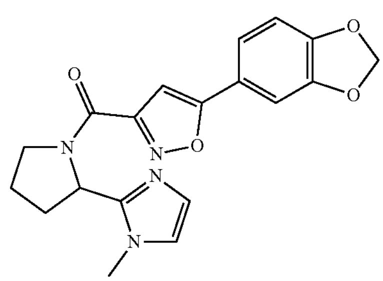 [SMILES: Cn1ccnc1C1CCCN1C(=O)c1cc(-c2ccc3c(c2)OCO3)on1] |
| 447 | 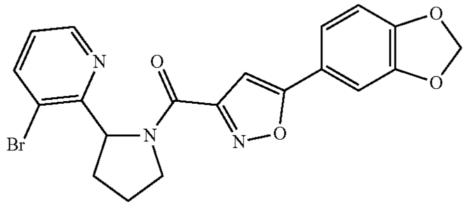 [SMILES: O=C(c1cc(-c2ccc3c(c2)OCO3)on1)N1CCCC1c1ncccc1Br] |

US 10,919,885 B2
197                                                                 198
TABLE 1-continued
Compounds of the Invention
| No. | Structure |
|---|---|
| 448 | 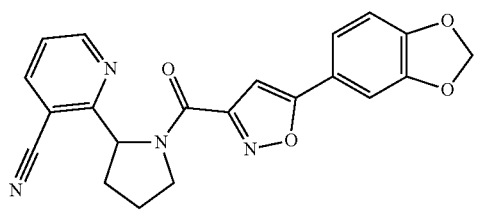 |
| 449 | 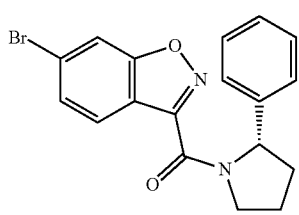 [SMILES: O=C(c1noc2cc(Br)ccc12)N1CCC[C@H]1c1ccccc1] |
| 450 | 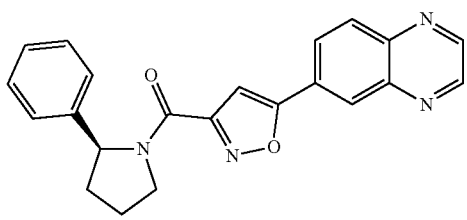 [SMILES: O=C(c1cc(-c2ccc3nccnc3c2)on1)N1CCC[C@H]1c1ccccc1] |
| 451 | 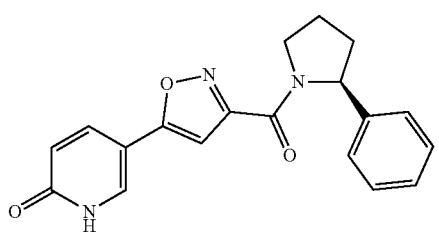 [SMILES: O=C(c1cc(-c2ccc(=O)[nH]c2)on1)N1CCC[C@H]1c1ccccc1] |
| 452 | 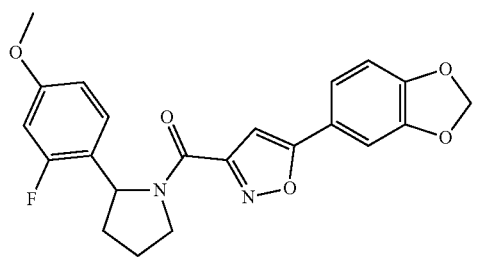 [SMILES: COc1ccc(C2CCCN2C(=O)c2cc(-c3ccc4c(c3)OCO4)on2)c(F)c1] |
| 453 | 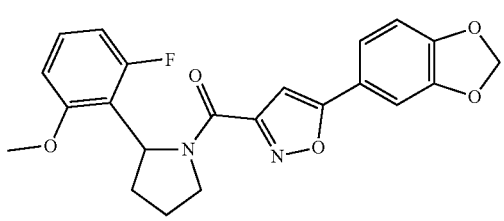 [SMILES: COc1cccc(F)c1C1CCCN1C(=O)c1cc(-c2ccc3c(c2)OCO3)on1] |

TABLE 1-continued
Compounds of the Invention
| No. | Structure |
|---|---|
| 454 | 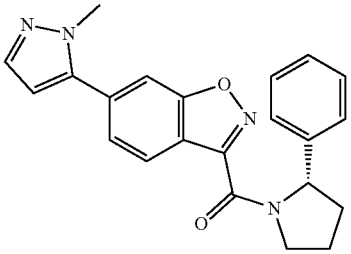 [SMILES: Cn1nccc1-c1ccc2c(C(=O)N3CCC[C@H]3c3ccccc3)noc2c1] |
| 455 | 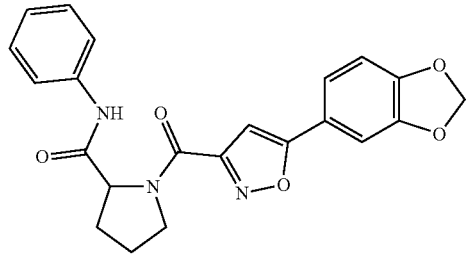 [SMILES: O=C(Nc1ccccc1)C1CCCN1C(=O)c1cc(-c2ccc3c(c2)OCO3)on1] |
| 456 | 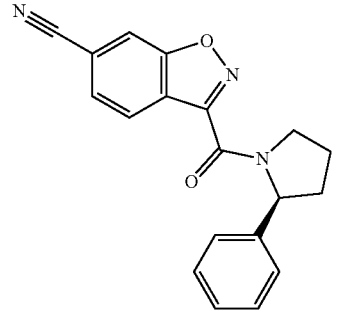 [SMILES: N#Cc1ccc2c(C(=O)N3CCC[C@H]3c3ccccc3)noc2c1] |
| 457 | 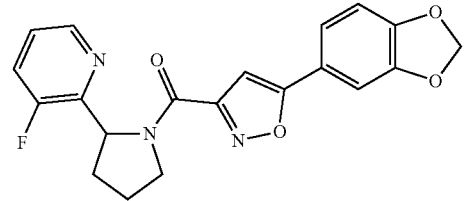 [SMILES: O=C(c1cc(-c2ccc3c(c2)OCO3)on1)N1CCCC1c1ncccc1F] |
| 458 | 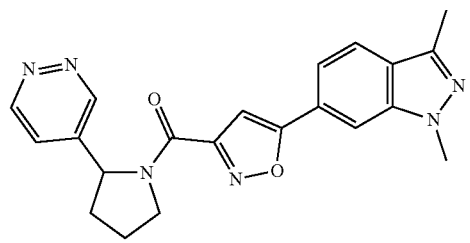 [SMILES: Cc1nn(C)c2cc(-c3cc(C(=O)N4CCCC4c4ccnnc4)no3)ccc12] |
| 459 | 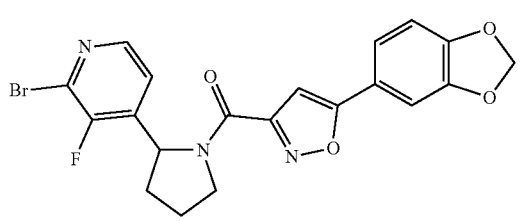 [SMILES: O=C(c1cc(-c2ccc3c(c2)OCO3)on1)N1CCCC1c1ccnc(Br)c1F] |

TABLE 1-continued

Compounds of the Invention

| No. | Structure |
|---|---|
| 460 | 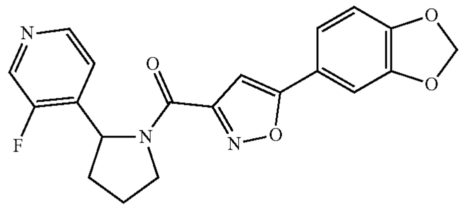 [SMILES: O=C(c1cc(-c2ccc3c(c2)OCO3)on1)N1CCCC1c1ccncc1F] |
| 461 | 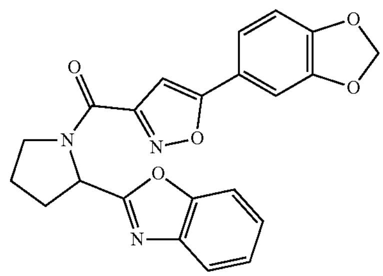 [SMILES: O=C(c1cc(-c2ccc3c(c2)OCO3)on1)N1CCCC1c1nc2ccccc2o1] |
| 462 | 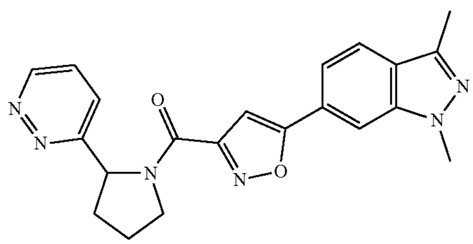 [SMILES: Cc1nn(C)c2cc(-c3cc(C(=O)N4CCCC4c4cccnn4)no3)ccc12] |
| 463 | 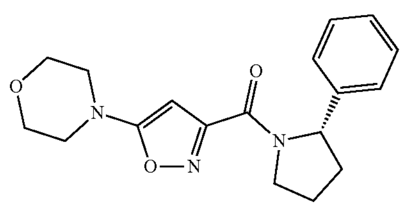 [SMILES: O=C(c1cc(N2CCOCC2)on1)N1CCC[C@H]1c1ccccc1] |
| 464 | 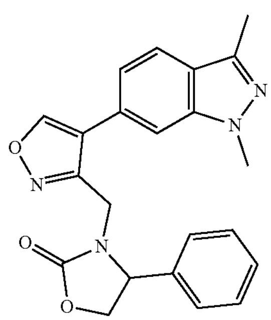 [SMILES: Cc1nn(C)c2cc(-c3conc3CN3C(=O)OCC3c3ccccc3)ccc12] |

In an aspect, this disclosure provides a pharmaceutical composition comprising a compound of any of the foregoing compounds, or pharmaceutically acceptable salt thereof, and a pharmaceutically acceptable excipient.

In some embodiments, the pharmaceutical composition includes a compound of Formula I or Formula II and a pharmaceutically acceptable excipient.

In an aspect, this disclosure provides a method of treating a neurological disorder in a subject in need thereof, the method comprising administering an effective amount of any of the foregoing compounds or a pharmaceutical composition thereof.

In an aspect, this disclosure provides a method of inhibiting toxicity in a cell related to a protein, the method comprising administering an effective amount of any of the foregoing compounds or a pharmaceutical composition thereof.

In some embodiments, the toxicity is α-synuclein-related toxicity. In some embodiments, the toxicity is ApoE4-related toxicity.

In some embodiments, the cell is a mammalian neural cell.

In an aspect, this disclosure provides a method of treating a stearoyl-CoA desaturase (SCD)-associated disorder in a subject in need thereof, the method comprising administering an effective amount of any of the foregoing compounds, or pharmaceutically acceptable salts thereof, or a pharmaceutical composition thereof.

Non-limiting exemplary SCD-associated disorders include, but are not limited to metabolic disorders (e.g., diabetes (e.g., Type I diabetes and Type II diabetes), hyperglycemia, metabolic syndrome, obesity, lipid disorders, fatty liver, nonalcoholic steatohepatitis (NASH), nonalcoholic fatty liver disease (NAFLD), and hypertension), cancer, cardiovascular diseases, cerebrovascular diseases, kidney diseases, liver diseases, skin disorders (e.g., acne (e.g., acne vulgaris)), central nervous system (CNS) disorders, dementia, multiple sclerosis, schizophrenia, mild cognitive impairment, Alzheimer's Disease, cerebral amyloid angiopathy, and dementia associated with Down Syndrome.

In some embodiments, the SCD-associated disorder is a SCD1-associated disorder.

In some embodiments, the SCD-associated disorder is a SCD5-associated disorder.

In an aspect, this disclosure provides a method of inhibiting SCD5, the method comprising contacting a cell with an effective amount of any of the foregoing compounds, or pharmaceutically acceptable salts thereof, or a pharmaceutical composition thereof.

In an aspect, this disclosure provides a method of inhibiting SCD1, the method comprising contacting a cell with an effective amount of any of the foregoing compounds, or pharmaceutically acceptable salts thereof, or a pharmaceutical composition thereof.

Chemical Terms

It is to be understood that the terminology employed herein is for the purpose of describing particular embodiments and is not intended to be limiting.

Those skilled in the art will appreciate that certain compounds described herein can exist in one or more different isomeric (e.g., stereoisomers, geometric isomers, tautomers) and/or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion, e.g., the interconversion illustrated in the scheme below:

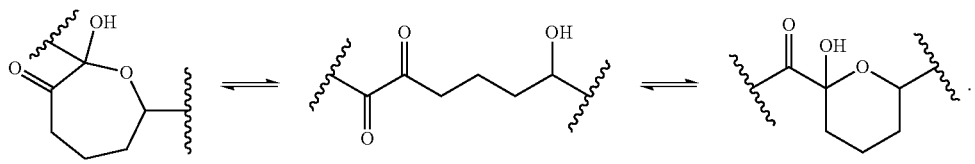

Those skilled in the art will appreciate that, in some embodiments, isotopes of compounds described herein may be prepared and/or utilized in accordance with the present invention. "Isotopes" refers to atoms having the same atomic number but different mass numbers resulting from a different number of neutrons in the nuclei. For example, isotopes of hydrogen include tritium and deuterium. In some embodiments, an isotopic substitution (e.g., substitution of hydrogen with deuterium) may alter the physicochemical properties of the molecules, such as metabolism and/or the rate of racemization of a chiral center.

As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized in any form, including in any solid form. In some embodiments, such entities are utilized in a particular form, for example in a particular solid form.

In some embodiments, compounds described and/or depicted herein may be provided and/or utilized in salt form.

In certain embodiments, compounds described and/or depicted herein may be provided and/or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

The term "acyl," as used herein, represents a hydrogen or an alkyl group, as defined herein that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group.

The term "alkenyl," as used herein, alone or in combination with other groups, refers to a straight-chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight-chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents $-N(R^{N1})_2$, wherein each $R^{N1}$ is, independently, H, OH, $NO_2$, $N(R^{N2})_2$, $SO_2OR^{N2}$, $SO_2RN^2$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., $-NH_2$) or a substituted amino (i.e., $-N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_{6-10}$ aryl, $C_1$-$C_{10}$ alkyl $C_{6-10}$ aryl, or $C_1$-$C_{20}$ alkyl $C_{6-10}$ aryl), such as, benzyl and phenethyl. In some embodiments, the akyl and the aryl each can be further substituted with 1, 2, 3, or 4 substituent groups as defined herein for the respective groups.

The term "azido," as used herein, represents a $-N_3$ group.

The term "cyano," as used herein, represents a CN group.

The terms "carbocyclyl," as used herein, refer to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, and adamantyl.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the akyl and the heteroaryl each can be further substituted with 1, 2, 3, or 4 substituent groups as defined herein for the respective groups.

The term "heterocyclyl," as used herein, denotes a mono- or polycyclic radical having 3 to 12 atoms having at least one ring containing one, two, three, or four ring heteroatoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the akyl and the heterocyclyl each can be further substituted with 1, 2, 3, or 4 substituent groups as defined herein for the respective groups.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an $NO_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "administration" refers to the administration of a composition (e.g., a compound, a complex or a preparation that includes a compound or complex as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population).

In the practice of the methods of the present invention, an "effective amount" of any one of the compounds of the invention or a combination of any of the compounds of the invention or a pharmaceutically acceptable salt thereof, is administered via any of the usual and acceptable methods known in the art, either singly or in combination.

As used herein, the term "combination therapy" refers to those situations in which a subject is simultaneously exposed to two or more therapeutic agents. In some embodiments, two or more compounds may be administered simultaneously; in some embodiments, such compounds may be administered sequentially; in some embodiments, such compounds are administered in overlapping dosing regimens.

As used herein, the term "dosage form" refers to a physically discrete unit of an active compound (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of formula (I). For example pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

The term "pure" means substantially pure or free of unwanted components (e.g., other compounds and/or other components of a cell lysate), material defilement, admixture or imperfection.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

As used herein, the term "stearoyl-CoA desaturase (SCD)-associated disorder" refers to an undesired physiological condition, disorder, or disease that is associated with and/or mediated at least in part by an SCD protein. In some instances, SCD-associated disorders are associated with excess SCD levels and/or activity. SCDs introduce a double bond in the C9-C10 position of saturated fatty acids such as palmitoyl-CoA and stearoyl-CoA which are converted to palmitoleoyl-CoA and oleoyl-CoA, respectively. One SCD gene, SCD1, has been characterized in humans for which there are two isoforms, SCD1 and SCD5. An SCD-associated disorder may be associated with and/or mediated at least in part by SCD1 and/or SCD5. Exemplary SCD-associated disorders include SCD-associated disorders include, but are not limited to metabolic disorders (e.g., diabetes (e.g., Type I diabetes and Type II diabetes), hyperglycemia, metabolic syndrome, obesity, lipid disorders, fatty liver, nonalcoholic steatohepatitis (NASH), nonalcoholic fatty liver disease (NAFLD), and hypertension), cancer, cardiovascular diseases, cerebrovascular diseases, kidney diseases, liver diseases, skin disorders (e.g., acne (e.g., acne vulgaris)), central nervous system (CNS) disorders, dementia, multiple sclerosis, schizophrenia, mild cognitive impairment, Alzheimer's Disease, cerebral amyloid angiopathy, and dementia associated with Down Syndrome. Additional SCD-associated disorders are described herein or known in the art.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

A "therapeutic regimen" refers to a dosing regimen whose administration across a relevant population is correlated with a desired or beneficial therapeutic outcome.

The term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

DETAILED DESCRIPTION

The invention features compounds useful for the treatment of neurological disorders, e.g., by inhibiting α-synuclein toxicity in a cell such as a neural cell, or by inhibiting SCD5 and/or SCD1 in a cell such as a neural cell. Exemplary compounds described herein include compounds having a structure according to Formula I:

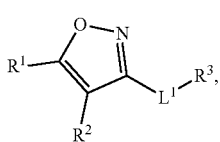

Formula I where
$R^1$ is H, halo, CN, $NO_2$, hydroxyl, optionally substituted amino, optionally substituted $C_1$-$C_6$ alkyl, optionally substituted $C_1$-$C_6$ heteroalkyl, optionally substituted $C_1$-$C_6$ alkenyl, optionally substituted $C_1$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl, $R^2$ is H or optionally substituted $C_1$-$C_6$ alkyl, or
$R^1$ and $R^2$, together with the atoms to which each is attached, combine to form an optionally substituted $C_3$-$C_{10}$ carbocyclylene, optionally substituted $C_2$-$C_9$ heterocyclylene, optionally substituted $C_6$-$C_{10}$ arylene, or optionally substituted $C_2$-$C_9$ heteroarylene;

$L^1$ is optionally substituted $C_1$-$C_6$ alkylene or optionally substituted $C_1$-$C_6$ heteroalkylene; and $R^3$ is optionally substituted $C_2$-$C_9$ heteroaryl, or according to Formula II:

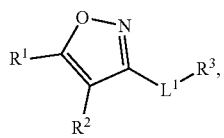

Formula II where
$R^1$ is H, halo, CN, $NO_2$, hydroxyl, optionally substituted amino, optionally substituted $C_1$-$C_6$ alkyl, optionally substituted $C_1$-$C_6$ heteroalkyl, optionally substituted $C_1$-$C_6$ alkenyl, optionally substituted $C_1$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl; and $R^2$ is H or optionally substituted $C_1$-$C_6$ alkyl; or
$R^1$ and $R^2$, together with the atoms to which each is attached, combine to form an optionally substituted $C_3$-$C_{10}$ carbocyclylene, optionally substituted $C_2$-$C_9$ heterocyclylene, optionally substituted $C_6$-$C_{10}$ arylene, or optionally substituted $C_2$-$C_9$ heteroarylene;

$L^1$ is optionally substituted $C_1$-$C_6$ alkylene or optionally substituted $C_1$-$C_6$ heteroalkylene; and $R^3$ is optionally substituted $C_2$-$C_9$ heterocyclyl,
or pharmaceutically acceptable salts thereof.

In some embodiments, the compound has the structure of any one of compounds 1-464 in Table 1.

Other embodiments, as well as exemplary methods for the synthesis or production of these compounds, are described herein.

Pharmaceutical Uses

The compounds described herein are useful in the methods of the invention and, while not bound by theory, are believed to exert their desirable effects through their ability to inhibit toxicity caused by protein aggregation, e.g., α-synuclein aggregation, in a cell.

Another aspect of the present invention relates to methods of treating and/or preventing neurological disorders such as neurodegenerative diseases in a subject in need thereof. The pathology of neurodegenerative disease may be characterized by the presence of inclusion bodies in brain tissue of affected patients.

In certain embodiments, neurological disorders that may be treated and/or prevented by the inventive methods include, but are not limited to, Alexander disease, Alper's disease, AD, amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, PD, Pelizaeus-Merzbacher disease, Pick's disease, primary lateral sclerosis, Ref sum's disease, Sandhoff disease, Schilder's disease, Steele-Richardson Olszewski disease, tabes dorsalis, and Guillain-Barre Syndrome.

The compounds described herein are useful as inhibitors of stearoyl-CoA desaturase (SCD), including SCD1 and/or SCD5. SCD inhibitors are known in the art to be useful in methods of treating and/or preventing SCD-associated disorders. SCD-associated disorders are described, for example, in U.S. Pat. No. 8,148,378, and in International Patent Application Publication Nos. WO 2011/047481, WO 2010/112520, WO 2010/045374, WO 2010/028761; WO 2009150196, and WO 2009/106991. Accordingly, another aspect of the present invention relates to methods of treating and/or preventing an SCD-associated disorder in a subject in need thereof.

SCD-associated disorders include metabolic disorders (e.g., insulin resistance, diabetes mellitus (e.g., Type I diabetes, Type II diabetes, non-insulin-dependent diabetes mellitus, gestational diabetes, and diabetic complications (e.g., diabetic peripheral neuropathy, diabetic nephropathy diseases, diabetic retinopathy, diabetic macroangiopathy, vascular complications of diabetes, and diabetic arteriosclerosis)), hyperglycemia, metabolic syndrome, hyperinsulinanemia, glucose intolerance, impaired glucose tolerance, body weight disorders (e.g., obesity (e.g., abdominal obesity), overweight, cachexia, body mass index, and anorexia), lipid disorders (e.g., abnormal lipid levels (e.g., elevated lipid levels, for example, in plasma), dyslipidemia (e.g., diabetic dyslipidemia), mixed dyslipidemia, hyperlipidemia, hypertriglyceridemia, hypoalphalipoproteinemia, hyperbetalipoproteinemia, atherosclerosis, hypercholesterolemia (e.g., familial hypercholesterolemia), low HDL, high LDL, diseases related to accumulation of lipids in liver, familial histiocytic reticulosis, lipoprotein lipase deficiency, polyunsaturated fatty acid (PUFA) disorder, fatty acid desaturation index (e.g. the ratio of 18:1/18:0 fatty acids, or other fatty acids), and abnormal lipid metabolism disorders), disorders of abnormal plasma lipoprotein, disorders of pancreatic beta cell regeneration, fatty liver, nonalcoholic steatohepatitis (NASH), nonalcoholic fatty liver disease (NAFLD), hypertension, and microalbuminemia, leptin related diseases, hyperleptinaemia, appetite disorder, essential fatty acid deficiency, and adverse weight gain associated with a drug therapy).

Additional SCD-associated disorders include cancer, including solid tumors or hematological malignancies (e.g., esophageal cancer, pancreatic cancer, endometrial cancer, kidney cancer, hepatoma, thyroid cancer, gallbladder cancer, prostate cancer, leukemia (e.g., lymphomas and myelomas), ENT-related cancer, brain cancer, colon cancer, rectal cancer, colorectal cancer, ovarian cancer, uterine cancer, breast cancer, skin cancer, and prostate cancer), neoplasia, malignancy, metastases, tumors (benign or malignant), carcinogenesis, and hepatomas.

Further SCD-associated disorders include cardiovascular disease (e.g., heart disease, atherosclerosis, hypertension, lipidemia, dyslipidemia, elevated blood pressure, microalbuminemia, hyperuricaemia, hypercholesterolemia, hyperlipidemias, hypertriglyceridemias, arteriosclerosis, coronary artery disease, myocardial infarction, vascular complications of diabetes, and diabetic arteriosclerosis), inflammation, sinusitis, asthma, pancreatitis, osteoarthritis, rheumatoid arthritis, hepatitis (e.g., sexual hepatitis), meibomitis, cystic fibrosis, pre-menstrual syndrome, osteoporosis, thrombosis, cardiovascular risks, weight loss, angina, high blood pressure, ischemia, cardiac ischemia, reperfusion injury, angioplastic restenosis, infertility, liver disease (e.g., fatty liver, cirrhosis, nonalcoholic steatohepatitis, liver fibrosis, and hepatitis C related steatosis), kidney disease (e.g., tubulointerstitial fibrosis, kidney lipid accumulation, glomerular sclerosis, and proteinuria), osteoarthritis (e.g., osteoarthritis of the knee), gastro-esophageal disease, sleep apnea, secondary hyperparathyroidism of renal osteodystrophy, peripheral vascular disease, cerebrovascular disease (e.g., stroke, ischemic stroke and transient ischemic attack (TIA), and ischemic retinopathy), hyperandrogenism, malignant syndrome, extrapyramidal symptoms, hyperuricemia, hypercoagulability, syndrome X, cataract, polycystic ovary syndrome, breathing abnormalities, sleep-disordered breathing, low back pain, gout, gallstone disease, myopathies, lipid myopathies (e.g., carnitine palmitoyltransferase deficiency (CPT I or CPT II)), autoimmune diseases (e.g., lupus, host versus graft rejection, and rejection of organ transplants), asthma, inflammatory bowel diseases, nephropathy, retinopathy, erythrohepatic protoporphyria, iron overload disorders, and hereditary hemochromatosis.

Still further SCD-associated disorders include central nervous system (CNS) disorders, dementia, schizophrenia, mild cognitive impairment, Alzheimer's Disease, cerebral amyloid angiopathy, dementia associated with Down Syndrome, other neurodegenerative diseases, psychiatric disorders, eye diseases, immune disorders, multiple sclerosis, neuropathy, and depression.

Additional SCD-associated disorders include skin disorders (e.g., acne (e.g., acne vulgaris), psoriasis, hirsutism, rosacea, seborrheic skin, oily skin (syn seborrhea), seborrheic dermatitis, hyperseborrhea, eczema, keloid scar, skin ageing, diseases related to production or secretions from mucous membranes, wrinkles, lack of adequate skin firmness, lack of adequate dermal hydration, insufficient sebum secretion, oily hair, shiny skin, greasy-looking skin, greasy-looking hair, and other skin conditions caused by lipid imbalance).

An SCD-associated disorder can also include a disease or condition which is, or is related to, viral diseases or infections.

In some embodiments, the SCD-associated disorder is acne (e.g., acne vulgaris). In some embodiments, the SCD-associated disorder is diabetes (e.g., type II diabetes, including diabetes with inadequate glycemic control). In some embodiments, the SCD-associated disorder is nonalcoholic fatty liver disease (NAFLD). In some embodiments, the SCD-associated disorder is nonalcoholic steatohepatitis (NASH). In some embodiments, the SCD-associated disorder is cancer. In some embodiments, the SCD-associated disorder is obesity. In some embodiments, the SCD-associated disorder is metabolic syndrome (e.g., dyslipidemia, obesity, insulin resistance, hypertension, microalbuminemia, hyperuricaemia, and hypercoagulability), syndrome X, diabetes, insulin resistance, decreased glucose tolerance, non-insulin-dependent diabetes mellitus, Type II diabetes, Type I diabetes, diabetic complications, body weight disorders (e.g., obesity, overweight, cachexia, and anorexia), weight loss, body mass index, leptin related diseases, or a skin disorder (e.g., eczema, acne, psoriasis, and keloid scar). In some embodiments, the SCD-associated disorder is diabetes, metabolic syndrome, insulin resistance, obesity, a cardiovascular disorder, a CNS disorder, schizophrenia, or Alzheimer's disease.

Combination Formulations and Uses Thereof

The compounds of the invention can be combined with one or more therapeutic agents. In particular, the therapeutic agent can be one that treats or prophylactically treats any neurological disorder described herein.

Combination Therapies

A compound of the invention can be used alone or in combination with other agents that treat neurological disorders or symptoms associated therewith, or in combination with other types of treatment to treat, prevent, and/or reduce the risk of any neurological disorders. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6, 2005). In this case, dosages of the compounds when combined should provide a therapeutic effect.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20$^{th}$ ed.) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered. Preferred dose ranges include, for example, between 0.05-15 mg/kg or between 0.5-15 mg/kg.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

General Scheme 1

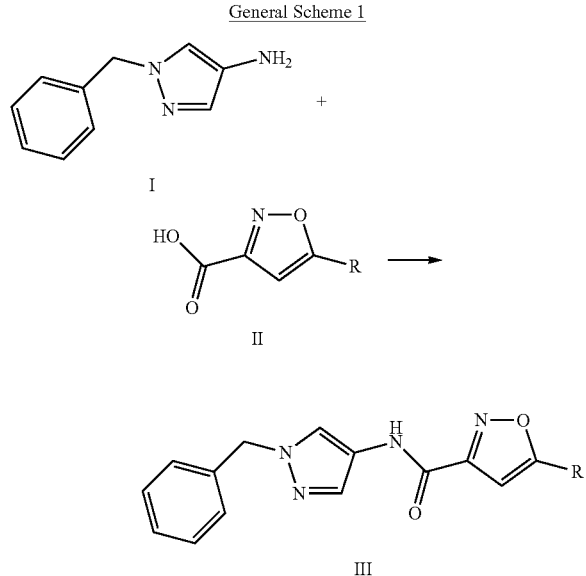

Benzyl pyrazole amine I can be coupled with acid II under a variety of peptide coupling conditions (e.g. HATU, HBTU or T3P) to provide the desired amide III.

General Scheme 2

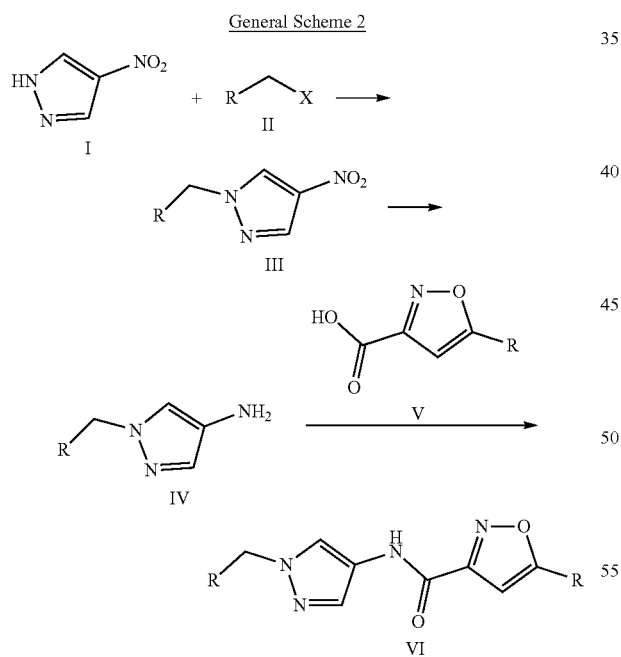

4-Nitro pyrazole I can be alkylated with appropriately substituted benzyl or alkyl halide II (X is a halogen, such as Cl or Br) in presence of an inorganic base (e.g. cesium carbonate) to give pyrazole III. Reduction of pyrazole III to amine IV is obtained with iron. This amine can be coupled with acid V under a variety of conditions to provide the desired amide VI.

General Scheme 3

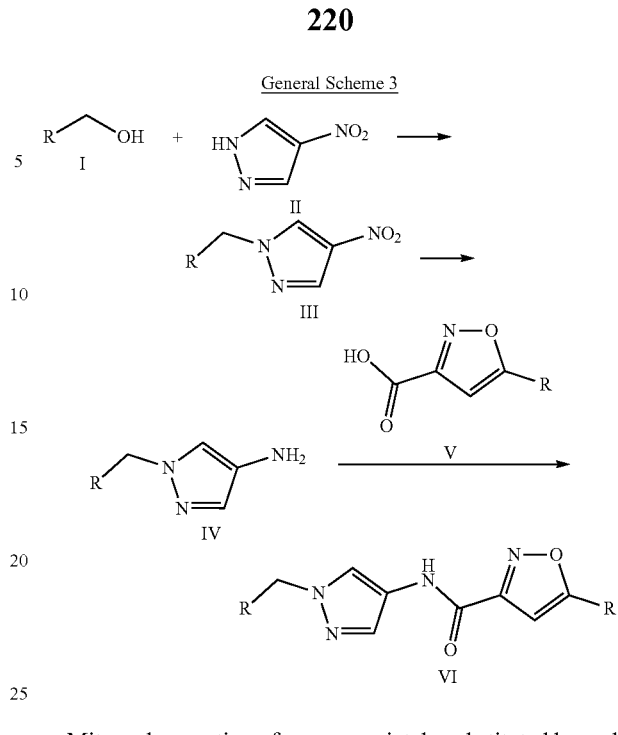

Mitsunobu reaction of an appropriately substituted benzyl alcohol I with 4-nitro pyrazole II gives alkylated pyrazole III. Reduction of pyrazole III to amine IV is obtained with iron or palladium on carbon. This amine can be coupled with acid V under a variety of peptide coupling conditions (e.g. HATU, HBTU or T3P) to provide the desired amide VI.

General Scheme 4

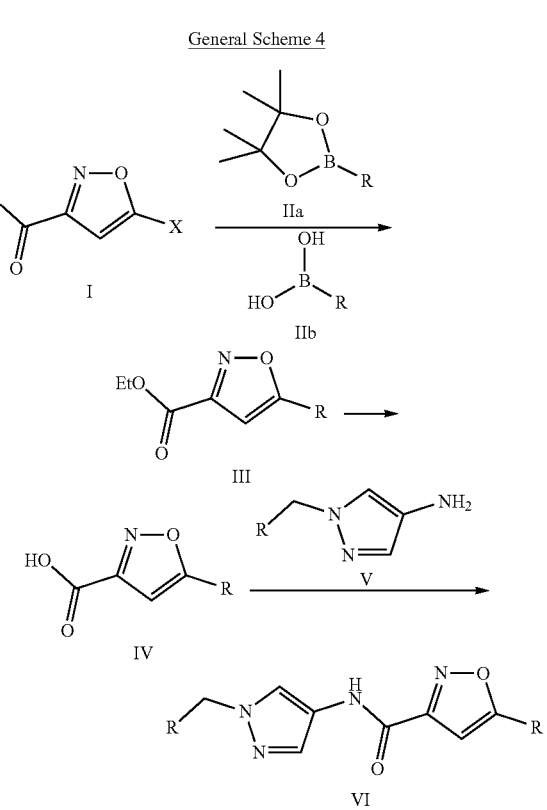

Halo substituted isoxazole ester I (where X is typically a bromine) can be reacted under metal catalysis conditions with appropriately substituted boronic ester IIa or boronic acid IIb to give intermediate III. Hydrolysis of III under various conditions gives acid IV which can be coupled with appropriately substituted amine V under a variety of peptide coupling conditions (e.g. HATU) to yield the desired amide VI.

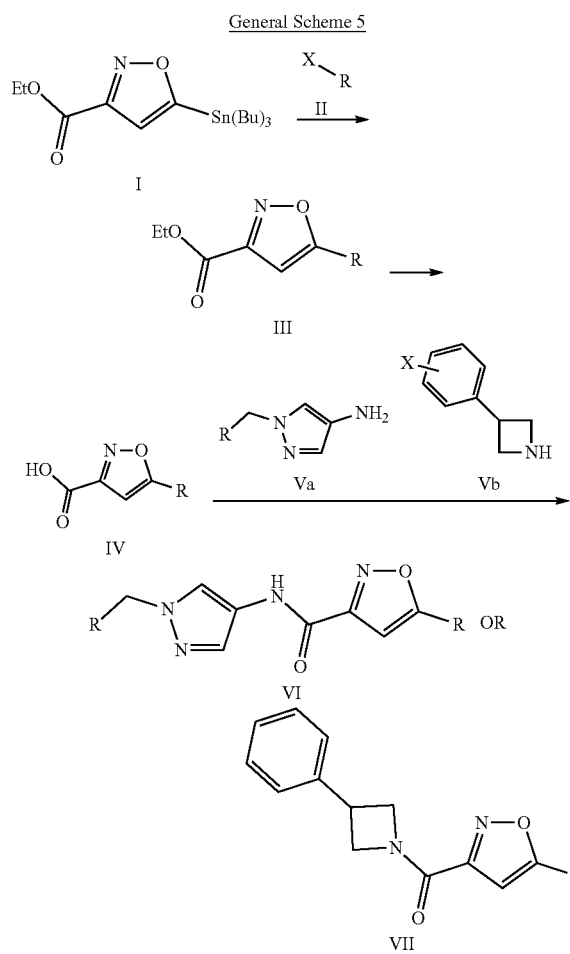

Stannyl isoxazole ester I can be reacted under metal catalysis conditions with appropriately substituted aromatic halide II (where X is typically a Br or Cl) to give intermediate III. Hydrolysis of ethyl ester III under various conditions gives isoxazole acid IV which can be coupled with appropriately substituted pyrazole amine Va or azetidine amine Vb under a variety of peptide coupling conditions (e.g. HATU) to yield the desired pyrazole amide VI or azetidine amide VII.

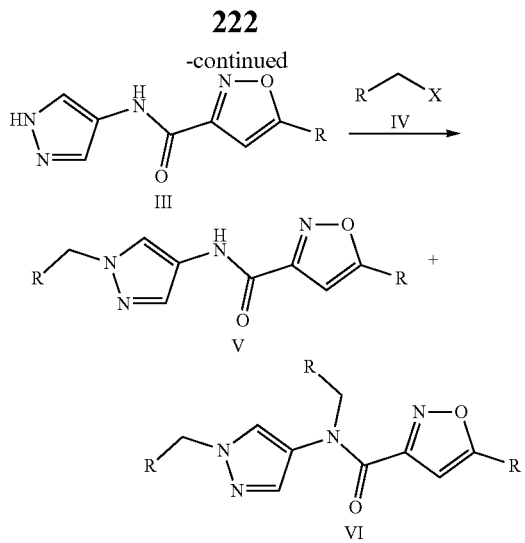

An appropriately substituted acid I can be coupled with pyrazole amine II under a variety of peptide coupling conditions (e.g. HATU) to give intermediate amide III. Alkylation of pyrazole amide III with appropriately substituted benzyl halide IV (where X is typically a Br or Cl) occurs in presence of inorganic base (e.g. potassium carbonate). to provide the desired amide V and doubly alkylated byproduct VI.

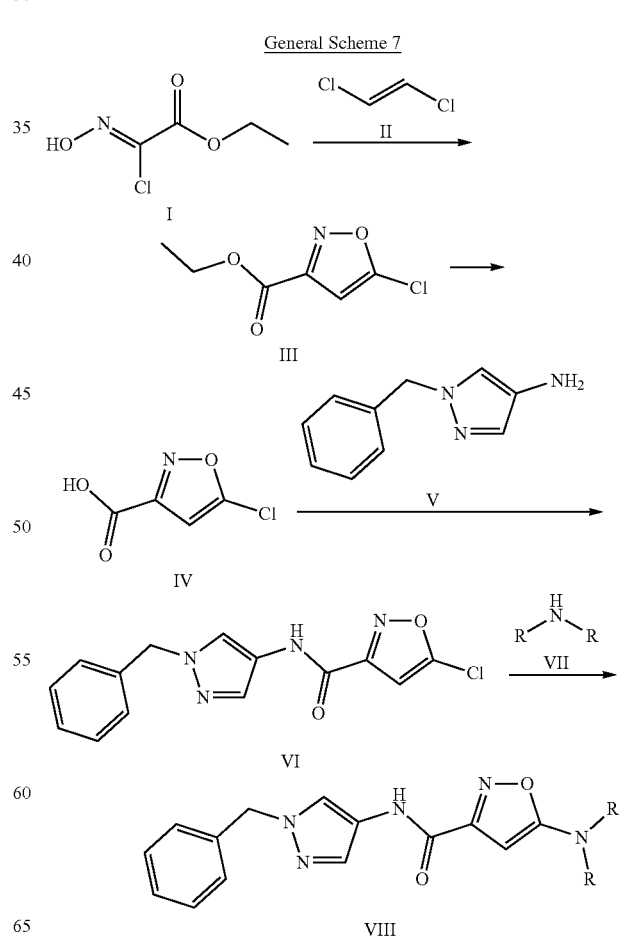

Cycloaddition of nitrile oxide, generated in situ from halo oxime I, with 1,2-dichloroethene II under basic conditions (e.g. triethylamine) gives isoxazole ester intermediate III. Hydrolysis of III under various conditions (e.g. lithium hydroxide) gives acid IV which can be coupled with appropriately substituted amine V under a variety of peptide coupling conditions (e.g. HATU) to yield intermediate amide VI. Displacement of chloride under basic conditions (e.g potassium carbonate) in presence of heat with appropriately selected amine VII affords amide VIII.

General Scheme 8

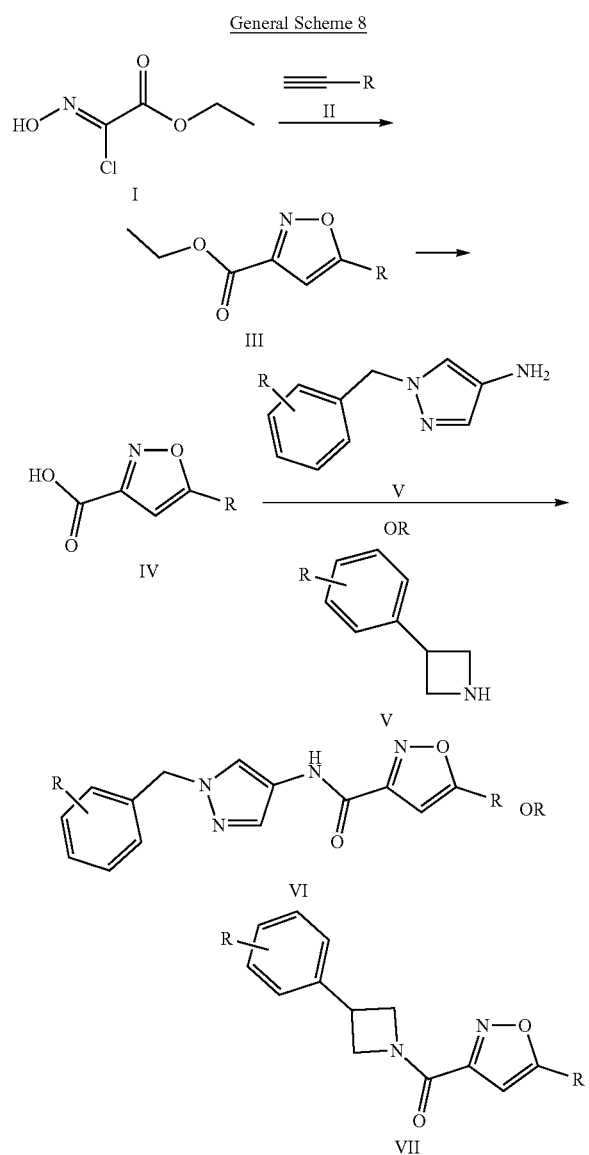

Cycloaddition of nitrile oxide, generated in situ from halo oxime I, with appropriately substituted alkynyl heterocycle II under basic conditions (e.g. triethylamine) gives isoxazole ester intermediate III. Hydrolysis of III under various conditions (e.g. lithium hydroxide) gives acid IV which can be coupled with appropriately substituted pyrazole amine Va or azetidine Vb under a variety of peptide coupling conditions (e.g. HATU) to yield pyrazole amide VI or azetidine amide VII.

General Scheme 9

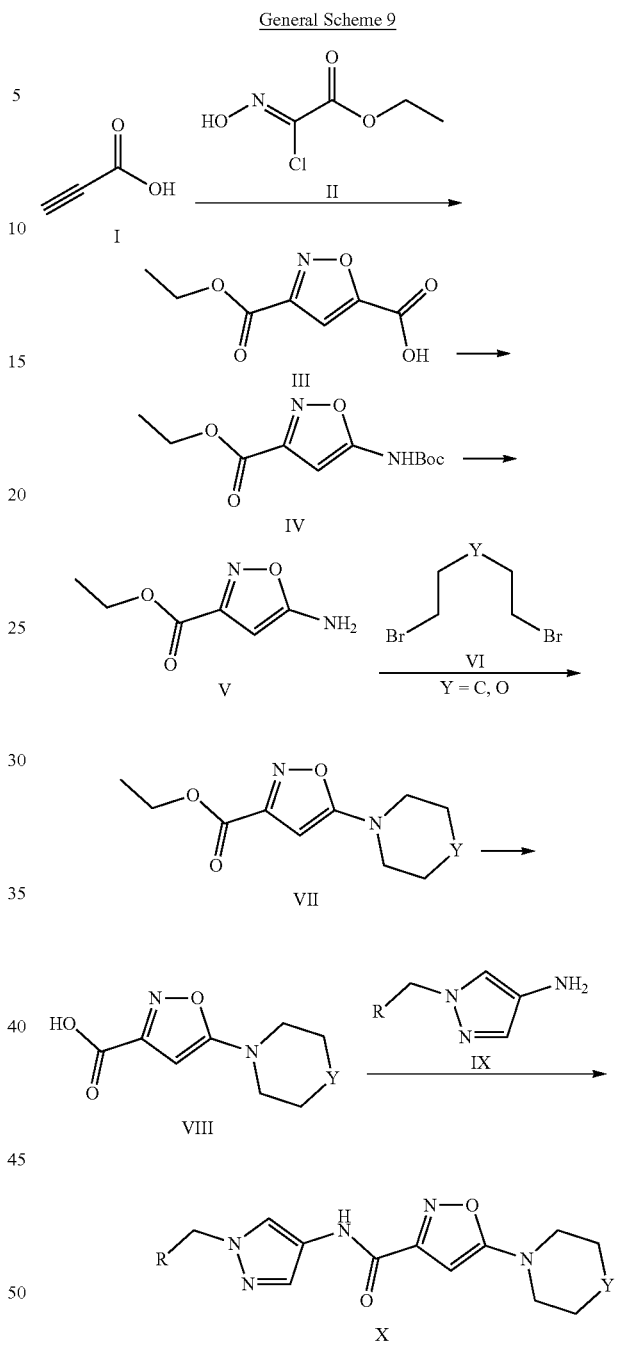

Cycloaddition of nitrile oxide, generated in situ from halo oxime II, with alkynyl acid I under basic conditions (e.g. triethylamine) gives isoxazole acid intermediate III. The Curtius rearrangement of III affords protected amine IV. Deprotection of IV under a variety of acidic conditions (e.g. trifluoroacetic acid) gives intermediate amine V which can be doubly alkylated with bis-bromoalkyl VI under basic conditions (e.g. potassium carbonate) in presence of heat to provide ester VII. Hydrolysis of VII under various conditions (e.g. lithium hydroxide) gives acid VIII which can be coupled with appropriately substituted pyrazole amine IX under a variety of peptide coupling conditions (e.g. HATU) to yield pyrazole amide X.

General Scheme 10

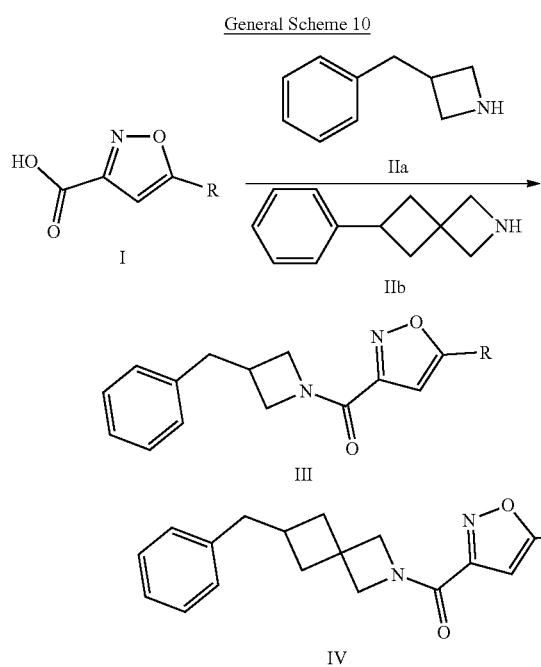

An appropriately substituted isoxazole acid I can be coupled with either benzyl azetidine IIa or spirocyclic amine IIb under a variety of peptide coupling conditions (e.g. HATU, HBTU or T3P) to give the desired benzyl azetidine amide III or spirocyclic amide IV, respectively.

General Scheme 11

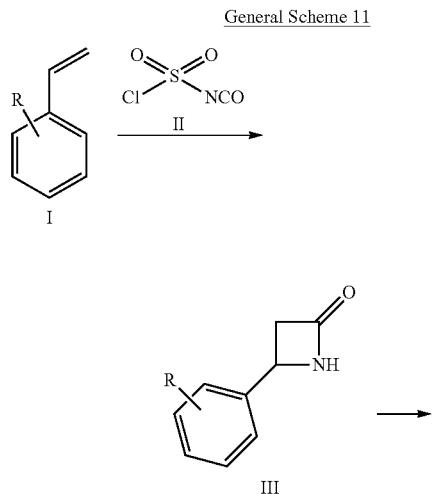

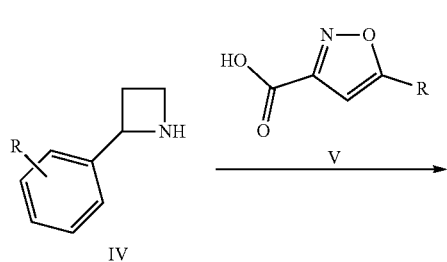

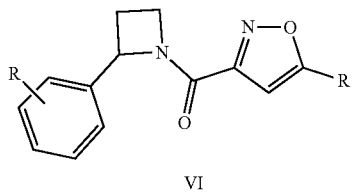

An appropriately substituted vinyl phenyl I can be reacted with chlorosulfonyl isocyanate II to give appropriately substituted phenyl azetidine-2-one III. Reduction of III with lithium aluminum hydride affords 2-substituted azetidine IV, which can be coupled with appropriately substituted acid V under a variety of conditions (e.g. HATU) to give the desired amide VI.

General Scheme 12

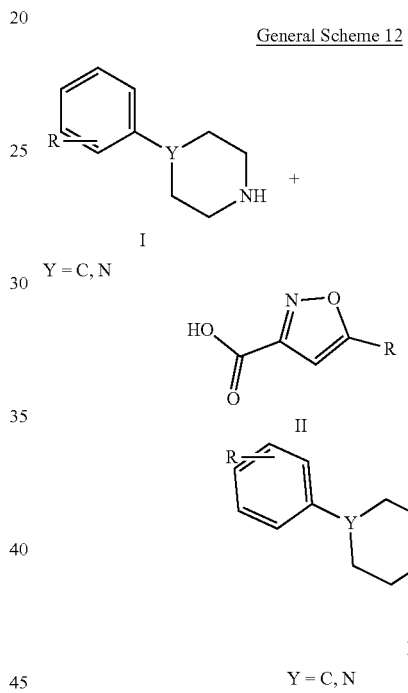

An appropriately substituted isoxazole acid piperidine or piperazine I can be coupled with appropriately substituted isoxazole acid II under a variety of peptide coupling conditions (e.g. HATU, HBTU or T3P) to give the desired amide III.

General Scheme 13

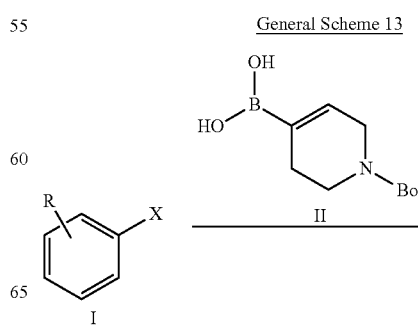

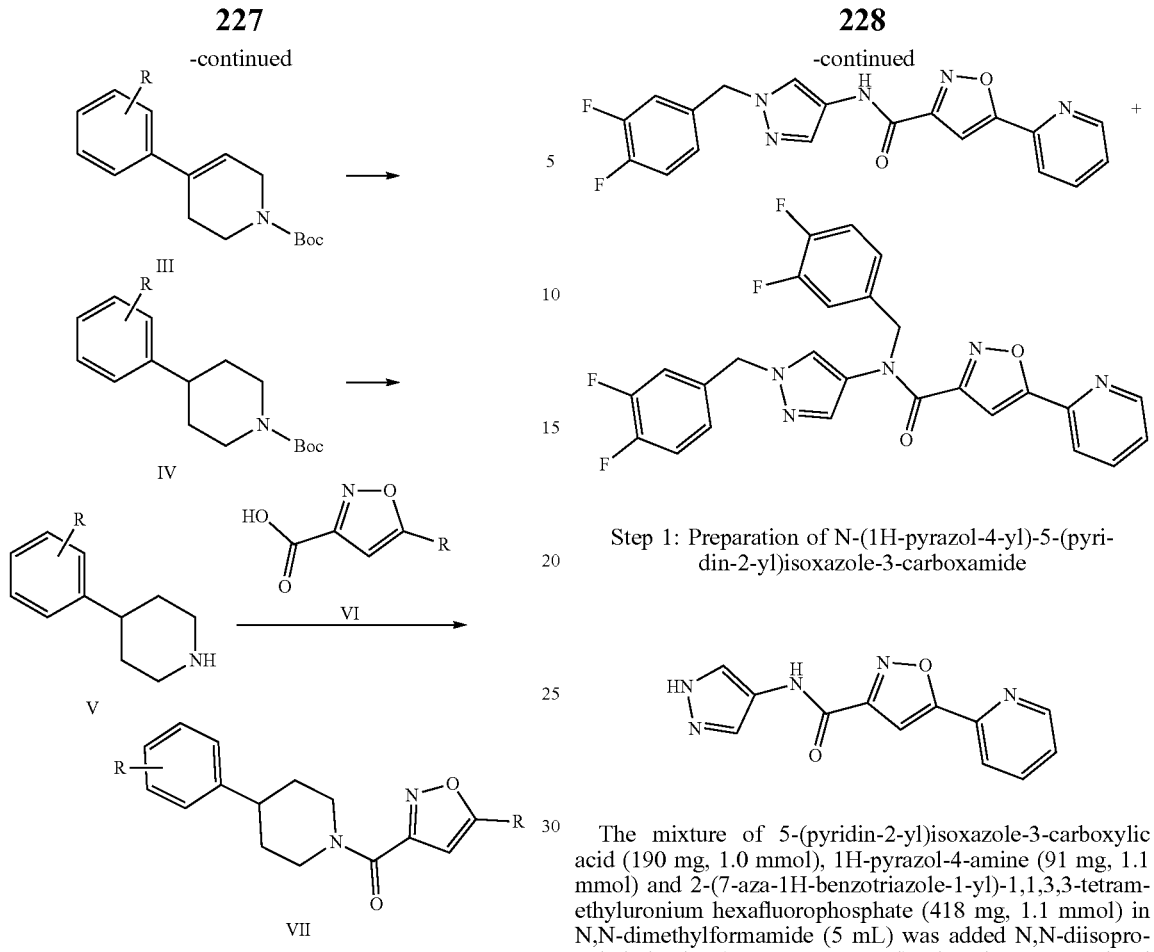

An appropriately substituted aromatic halide I (where X is typically a bromine) can be reacted under metal catalysis conditions with appropriately substituted boronic II to give intermediate III. Hydrogenation of III in presence of palladium on carbon and hydrogen atmosphere affords piperidine intermediate IV. Deprotection of IV under acidic conditions (e.g. hydrogen chloride) gives piperidine V, which can be coupled with an appropriately substituted acid VI under a variety of peptide coupling conditions (e.g. HATU) to yield the desired amide VII.

Example 1. Preparation of N-(3,4-difluorobenzyl)-N-(1-(3,4-difluorobenzyl)-1H-pyrazol-4-yl)-5-(pyridin-2-yl)isoxazole-3-carboxamide (62)

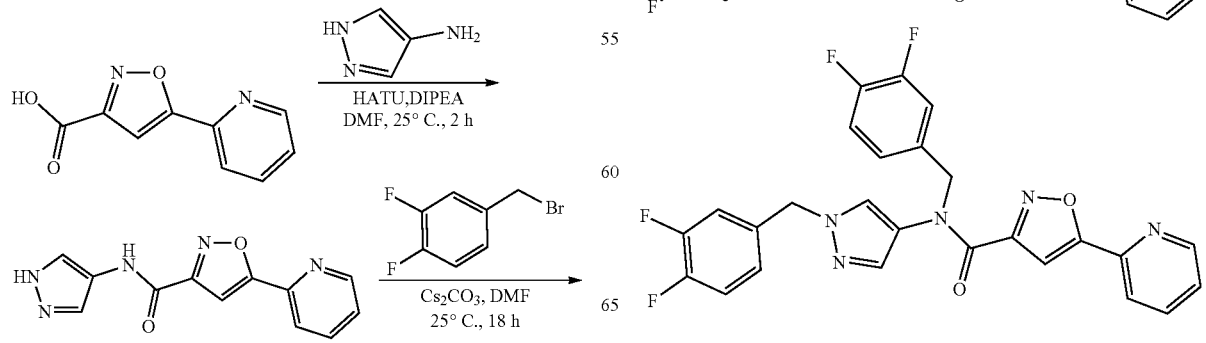

Step 1: Preparation of N-(1H-pyrazol-4-yl)-5-(pyridin-2-yl)isoxazole-3-carboxamide The mixture of 5-(pyridin-2-yl)isoxazole-3-carboxylic acid (190 mg, 1.0 mmol), 1H-pyrazol-4-amine (91 mg, 1.1 mmol) and 2-(7-aza-1H-benzotriazole-1-yl)-1,1,3,3-tetramethyluronium hexafluorophosphate (418 mg, 1.1 mmol) in N,N-dimethylformamide (5 mL) was added N,N-diisopropylethylamine (387 mg, 3.0 mmol). The mixture was stirred at 23° C. for 2 h. The reaction mixture was added dropwise to an ice-cooled solution of aqueous 0.5 hydrochloric acid (50 mL). The solid precipitate was collected by filtration and dried in vacuo to afford N-(1H-pyrazol-4-yl)-5-(pyridin-2-yl)isoxazole-3-carboxamide (215 mg, 0.84 mmol, 84%) as a pale-yellow solid. LCMS (ESI) m/z: 256.1 [M+H]$^+$.

Step 2: Preparation of N-(1-(3,4-difluorobenzyl)-1H-pyrazol-4-yl)-5-(pyridin-2-yl)isoxazole-3-carboxamide and N-(3,4-difluorobenzyl)-N-(1-(3,4-difluorobenzyl)-1H-pyrazol-4-yl)-5-(pyridin-2-yl)isoxazole-3-carboxamide To a suspension of N-(1H-pyrazol-4-yl)-5-(pyridin-2-yl)isoxazole-3-carboxamide (0.215 g, 0.84 mmol) and cesium carbonate (0.547 g, 1.68 mmol) in N,N-dimethylformamide (5 mL) at 0° C. was added dropwise 4-(bromomethyl)-1,2-difluorobenzene (0.173 g, 0.84 mmol). The mixture was stirred at 23° C. for 18 h. After filtration, the residue was purified by prep-HPLC (Sunfire prep C18 10 μm OBD 19*250 mm; mobile phase: [water (0.05% trifluoroacetic acid-acetonitrile]; B %: 60%-88%, 15 min) to offer N-(1-(3,4-difluorobenzyl)-1H-pyrazol-4-yl)-5-(pyridin-2-yl)isoxazole-3-carboxamide (76.4 mg, 0.20 mmol, 24%) as a white solid. H NMR (500 MHz, Dimethylsulfoxide-$d_6$) δ 11.08 (s, 1H), 8.77 (d, J=4.5 Hz, 1H), 8.24 (s, 1H), 8.16-7.95 (m, 2H), 7.70 (s, 1H), 7.57 (ddd, J=7.5, 4.8, 1.1 Hz, 1H), 7.49 (s, 1H), 7.43 (dd, J=8.5, 2.3 Hz, 1H), 7.34 (d, J=1.3 Hz, 1H), 7.17-6.99 (m, 1H), 5.34 (s, 2H). LCMS (ESI) m/z: 382.1 [M+H]$^+$. and N-(3,4-difluorobenzyl)-N-(1-(3,4-difluorobenzyl)-1H-pyrazol-4-yl)-5-(pyridin-2-yl)isoxazole-3-carboxamide (40.8 mg, 0.08 mmol, 10%) as a white solid. $^1$H NMR (500 MHz, Dimethylsulfoxide-$d_6$) δ 8.92-8.18 (m, 1H), 8.01 (ddd, J=9.4, 8.8, 2.7 Hz, 1H), 7.89 (d, J=7.9 Hz, 1H), 7.73 (d, J=57.1 Hz, 1H), 7.60-7.47 (m, 1H), 7.48-7.29 (m, 3H), 7.17 (s, 1H), 7.11-6.86 (m, 2H), 6.71 (s, 1H), 5.13 (dd, J=94.7, 71.8 Hz, 4H). LCMS (ESI) m/z: 508.0 [M+H]$^+$.

Example 2. Preparation of N-(1-benzylpyrazol-4-yl)-5-(2-fluorophenyl)isoxazole-3-carboxamide (38)

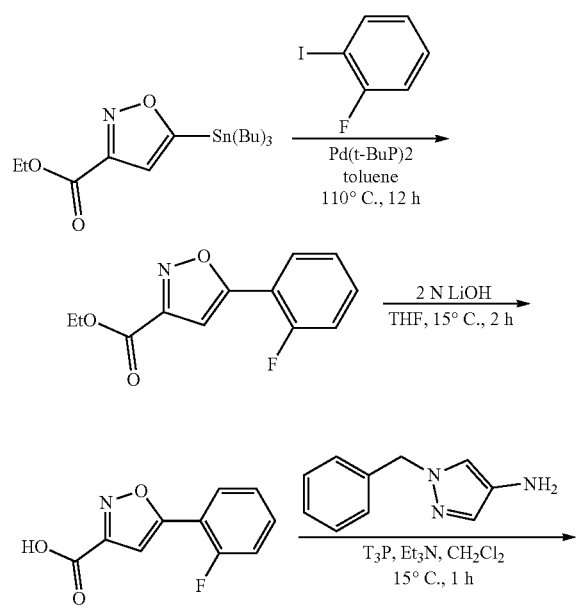

Step 1: Preparation of ethyl 5-(2-fluorophenyl)isoxazole-3-carboxylate

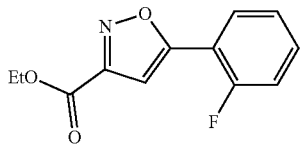 [SMILES: O=C(O)c1cc(-c2ccccc2F)on1]

A mixture of ethyl 5-tributylstannylisoxazole-3-carboxylate (0.500 g, 1.16 mmol), 1-fluoro-2-iodo-benzene (0.272 mL, 2.32 mmol), bis(triphenylphosphine)palladium(II) dichloride (0.041 g, 0.058 mmol) in toluene (5 mL) was purged with nitrogen (3×), and then the mixture was stirred at 110° C. for 12 h under nitrogen. The mixture was cooled to 15° C. and then poured into ice-water (5 mL). The aqueous phase was extracted with ethyl acetate (10 mL×3). The combined organic layers were washed with brine (5 mL), dried with anhydrous sodium sulfate, filtered and concentrated in vacuo to afford crude product. The crude residue was purified by column chromatography (ISCO, 12 g silica, 0-50% ethyl acetate in petroleum ether, gradient over 30 min) to give ethyl 5-(2-fluorophenyl)isoxazole-3-carboxylate (0.200 g, crude) as a white solid. LCMS (ESI) m/z: 236.1 [M+H]$^+$.

Step 2: Preparation of 5-(2-fluorophenyl)isoxazole-3-carboxylic Acid

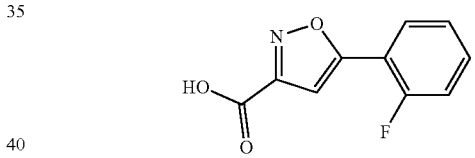

To a stirred solution of ethyl 5-(2-fluorophenyl)isoxazole-3-carboxylate (0.180 g, 0.765 mmol) in tetrahydrofuran (0.5 mL) was added lithium hydroxide (2 M, 0.77 mL). The mixture was stirred at 15° C. for 2 h. The mixture was diluted with water and the adjusted to pH=5 by addition of aqueous hydrogen chloride solution (2 M, 1 mL). The aqueous phase was extracted with ethyl acetate (5 mL×3). The combined organic phases were washed with brine (5 mL), dried with anhydrous sodium sulfate, filtered and concentrated in vacuo to afford 5-(2-fluorophenyl)isoxazole-3-carboxylic acid (0.150 g, crude) as a white solid. Used without additional purification in the next step.

Step 3: Preparation of ethyl N-(1-benzylpyrazol-4-yl)-5-(2-fluorophenyl)isoxazole-3-carboxamide

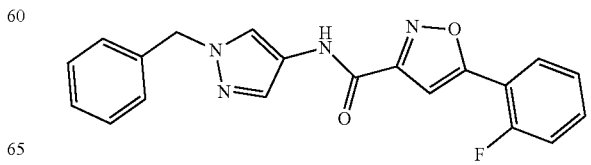

To a stirred solution of 5-(2-fluorophenyl)isoxazole-3-carboxylic acid (0.140 g, 0.676 mmol) in dichloromethane (2 mL) was added propylphosphonic anhydride (0.482 g, 0.811 mmol, 50% wt), triethylamine (0.188 mL, 1.35 mmol) and 1-benzylpyrazol-4-amine (0.117 g, 0.676 mmol). The mixture was stirred at 15° C. for 1 h. The crude residue was purified by prep-HPLC (YMC-Actus Triart C18 150×30 5 um column; 30-70% acetonitrile in a 10 mM ammonium acetate solution in water, 10 min gradient) to give N-(1-benzylpyrazol-4-yl)-5-(2-fluorophenyl)isoxazole-3-carboxamide (0.172 g, 0.469 mmol, 69%) as a white solid. $^1$H NMR (400 MHz, Dimethylsulfoxide-d6) δ 11.05 (s, 1H), 8.18 (s, 1H), 8.08-7.97 (m, 1H), 7.68 (s, 1H), 7.66-7.59 (m, 1H), 7.53-7.40 (m, 2H), 7.38-7.21 (m, 6H), 5.34 (s, 2H); LCMS (ESI) m/z: 363.0 [M+H]$^+$.

Example 3. Preparation of N-(1-benzylpyrazol-4-yl)-5-(2-pyridyl)isoxazole-3-carboxamide (8)

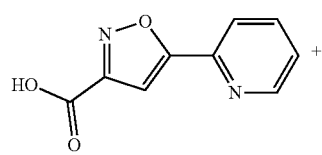

To a stirred solution of 1-benzylpyrazol-4-amine (0.120 g, 0.693 mmol) and 5-(pyridin-2-yl)isoxazole-3-carboxylic acid (0.157 g, 0.831 mmol) in N,N-dimethylformamide (1 mL) was added N,N,N',N'-tetramethyl-O-(1H-benzotriazol-1-yl)uronium hexafluorophosphate (0.315 g, 0.831 mmol) and diisopropylethylamine (0.242 mL, 1.39 mmol) at 15° C., then stirred at 15° C. for 3 h. The reaction mixture was purified directly by prep-HPLC (Agela Venusil XBP C18 150×25 5 um column; 50%-75% acetonitrile in a 10 mM 0.04% ammonium hydroxide, 10 min gradient) to give N-(1-benzylpyrazol-4-yl)-5-(2-pyridyl)isoxazole-3-carboxamide (0.068 g, 0.197 mmol, 29%) as a pale yellow solid. $^1$H NMR (400 MHz, Chloroform-d) δ 8.76 (d, J=4.5 Hz, 1H), 8.55 (br. s, 1H), 8.06 (s, 1H), 7.97-7.92 (m, 1H), 7.91-7.84 (m, 1H), 7.64 (s, 1H), 7.44-7.31 (m, 5H), 7.30-7.26 (m, 2H), 5.32 (s, 2H); LCMS (ESI) m/z: 346.0 [M+H]$^+$.

Example 4. Preparation of 5-(1,3-benzodioxol-5-yl)-N-(1-benzylpyrazol-4-yl)isoxazole-3-carboxamide (6)

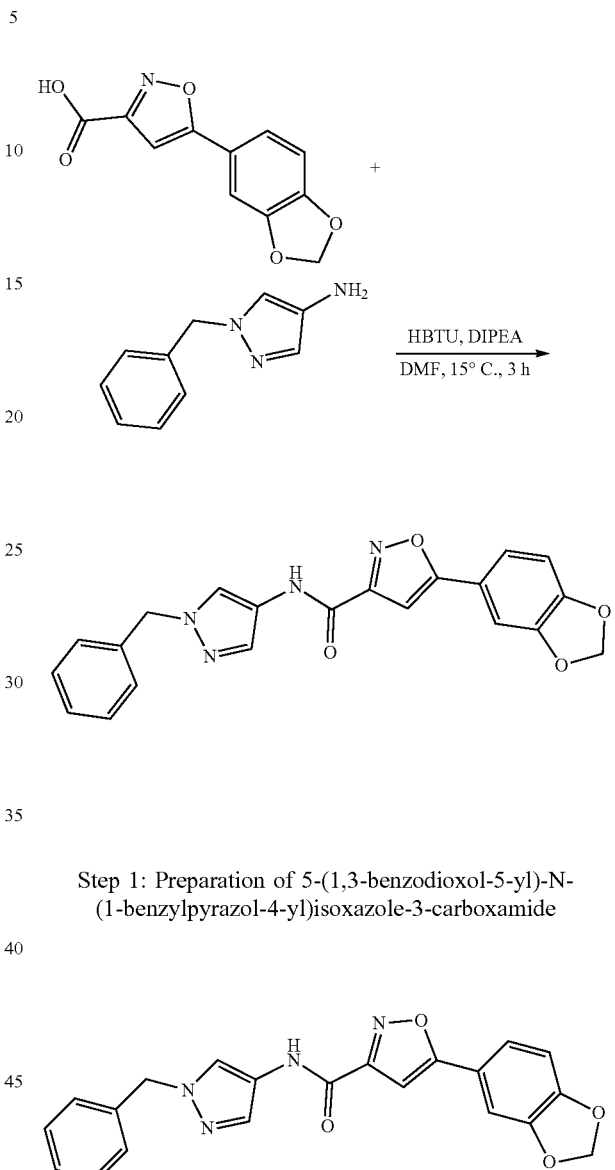

Step 1: Preparation of 5-(1,3-benzodioxol-5-yl)-N-(1-benzylpyrazol-4-yl)isoxazole-3-carboxamide To a stirred solution of 1-benzylpyrazol-4-amine (0.120 g, 0.693 mmol) and 5-(pyridin-2-yl)isoxazole-3-carboxylic acid (0.157 g, 0.831 mmol) in N,N-dimethylformamide (1 mL) was added N,N,N',N'-tetramethyl-O-(1H-benzotriazol-1-yl)uronium hexafluorophosphate (0.315 g, 0.831 mmol) and diisopropylethylamine (0.242 g, 1.39 mmol) at 15° C. The reaction mixture was stirred at 15° C. for 3 h then purified directly by prep-HPLC (Agela Venusil XBP C18 150×25 5 um column; 50%-75% acetonitrile in a 10 mM 0.04% ammonium hydroxide, 10 min gradient) to give 5-(1,3-benzodioxol-5-yl)-N-(1-benzylpyrazol-4-yl)isoxazole-3-carboxamide (0.070 g, 0.181 mmol, 31%) as a white solid. $^1$H NMR (400 MHz, Chloroform-d) δ 8.53 (s, 1H), 8.04 (s, 1H), 7.63 (s, 1H), 7.41-7.30 (m, 4H), 7.30-7.25 (m, 3H), 6.93 (d, J=8.2 Hz, 1H), 6.88 (s, 1H), 6.07 (s, 2H), 5.32 (s, 2H); LCMS (ESI) m/z: 389.1 [M+H]$^+$.

Example 5. Preparation of N-(1-benzylpyrazol-4-yl)-5-phenyl-isoxazole-3-carboxamide (7)

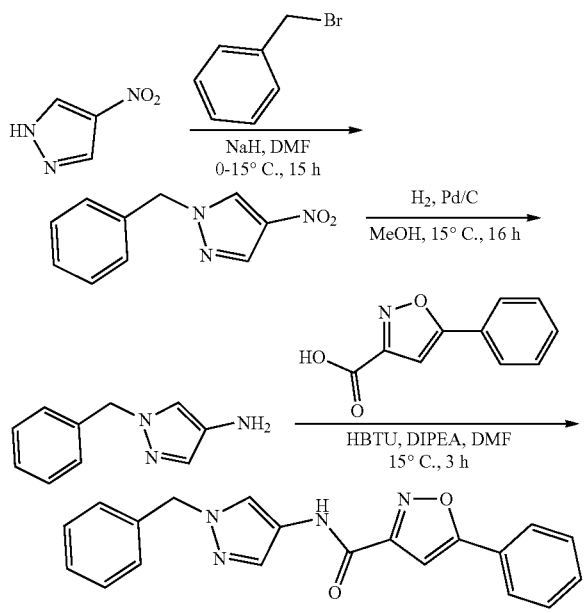

Step 1: Preparation of 1-benzyl-4-nitro-pyrazole

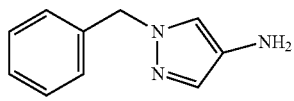 [SMILES: Nc1cnn(Cc2ccccc2)c1]

To a stirred solution of 4-nitro-1H-pyrazole (2.00 g, 17.7 mmol) in N,N-dimethylformamide (15 mL) was added sodium hydride (0.778 g, 19.0 mmol, 60% purity in mineral oil) at 0° C. The reaction mixture was stirred at 15° C. for 1 h and then cooled to 0° C. before benzyl bromide (2.10 mL, 17.7 mmol) was added. The reaction mixture was warmed to 15° C. and stirred for 15 h then quenched by adding ice water (5 mL) and extracted with ethyl acetate (15 mL×3). The combined organic layers were washed with water (10 mL×2) and brine (5 mL), dried over sodium sulfate, filtered and concentrated under reduced pressure to give a residue. The residue was purified by column chromatography (ISCO, 20 g silica, 0-30% ethyl acetate in petroleum ether, gradient over 20 min) to give 1-benzyl-4-nitro-pyrazole (2.80 g, 13.8 mmol, 78%) as a white solid. $^1$H NMR (400 MHz, Chloroform-d) δ 8.10 (s, 1H), 8.04 (s, 1H), 7.45-7.39 (m, 3H), 7.32-7.28 (m, 2H), 5.31 (s, 2H); LCMS (ESI) m/z: 204.1 [M+H]$^+$.

Step 2: Preparation of 1-benzylpyrazol-4-amine

To a solution of 1-benzyl-4-nitro-pyrazole (1.50 g, 7.38 mmol) in methanol (10 mL) was added palladium on activated carbon (0.500 g, 10% by weight) under nitrogen. The suspension was purged with hydrogen several times. The mixture was stirred under hydrogen balloon at 15° C. for 16 h, then purged with nitrogen and filtrated. The filtrate was concentrated in vacuo to give 1-benzylpyrazol-4-amine (1.10 g, 6.35 mmol, 86%) as a pink solid. LCMS (ESI) m/z: 174.1 [M+H]$^+$.

Step 3: Preparation of N-(1-benzylpyrazol-4-yl)-5-phenyl-isoxazole-3-carboxamide

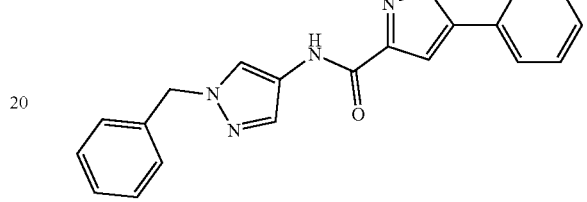

To a stirred solution of 1-benzylpyrazol-4-amine (0.120 g, 0.693 mmol) and 5-phenylisoxazole-3-carboxylic acid (0.157 g, 0.831 mmol) in N,N-dimethylformamide (1 mL) was added N,N,N',N'-tetramethyl-O-(1H-benzotriazol-1-yl)uronium hexafluorophosphate (0.315 g, 0.831 mmol) and diisopropylethylamine (0.242 mL, 1.39 mmol) at 15° C., then stirred at 15° C. for 3 h. The reaction was purified by prep-HPLC (Agela Venusil XBP C18 150×25 5 um column; 50%-75% acetonitrile in a 10 mM 0.04% ammonium hydroxide, 10 min gradient) to give N-(1-benzylpyrazol-4-yl)-5-phenyl-isoxazole-3-carboxamide (0.087 g, 0.253 mmol, 36%) as a pale yellow solid. $^1$H NMR (400 MHz, Chloroform-d) δ 8.57 (br. s, 1H), 8.05 (s, 1H), 7.86-7.82 (m, 2H), 7.65 (s, 1H), 7.54-7.50 (m, 3H), 7.41-7.33 (m, 3H), 7.30-7.27 (m, 2H), 7.03 (s, 1H), 5.32 (s, 2H); LCMS (ESI) m/z: 345.1 [M+H]$^+$.

Example 6. Preparation of 5-(benzo[d][1,3]dioxol-5-yl)-N-(1-benzyl-3,5-dimethyl-1H-pyrazol-4-yl)isoxazole-3-carboxamide (6)

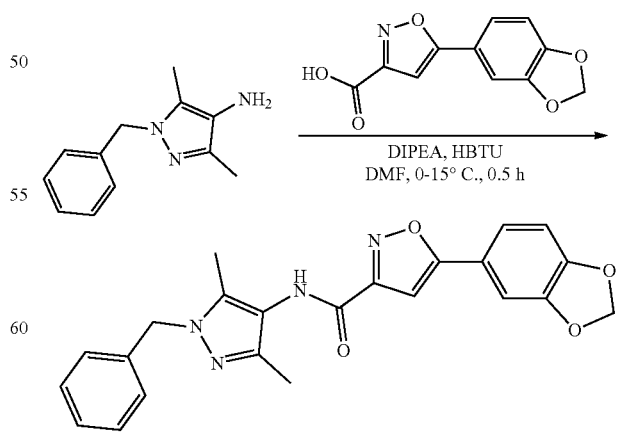

To a solution of 1-benzyl-3,5-dimethyl-1H-pyrazol-4-amine (0.700 g, 0.348 mmol), 5-(1,3-benzodioxol-5-yl)

isoxazole-3-carboxylic acid (0.0811 g, 0.348 mmol), N,N,N',N'-tetramethyl-O-(1H-benzotriazol-1-yl)uronium hexafluorophosphate (0.132 g, 0.348 mmol) in N,N-dimethylformamide (0.5 mL) was added diisopropylethylamine (121 mL, 0.696 mmol) at 0° C. Then the reaction mixture was stirred at 15° C. for 0.5 h. The mixture was purified by prep-HPLC (column: Waters Xbridge 150×25 5 u; mobile phase: [water (10 mM ammonium bicarbonate)-acetonitrile]; B %: 35%-65%, 12 min gradient) to afford 5-(benzo[d][1,3]dioxol-5-yl)-N-(1-benzyl-3,5-dimethyl-1H-pyrazol-4-yl)isoxazole-3-carboxamide (0.0892 g, 0.208 mmol, 60%) as a white solid. $^1$H NMR (400 MHz, Dimethylsulfoxide-d6) δ 9.93 (s, 1H), 7.52-7.45 (m, 2H), 7.36-7.23 (m, 4H), 7.15 (d, J=7.4 Hz, 2H), 7.08 (d, J=7.8 Hz, 1H), 6.12 (s, 2H), 5.21 (s, 2H), 2.06 (s, 3H), 2.03 (s, 3H); LCMS (ESI) m/z: 417.2 [M+H]$^+$.

Example 7. Preparation of N-(1-benzyl-1H-pyrazol-4-yl)-5-(furan-2-yl)isoxazole-3-carboxamide (4)

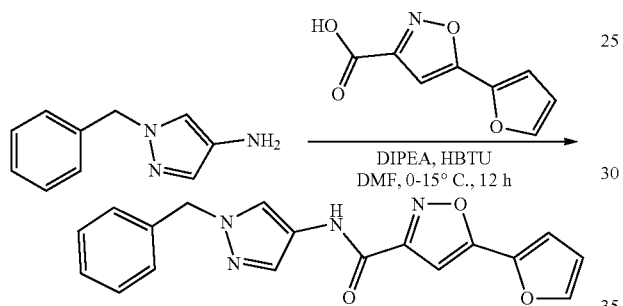

The mixture of 5-(furan-2-yl)isoxazole-3-carboxylic acid (0.090 g, 0.502 mmol), N,N,N',N'-tetramethyl-O-(1H-benzotriazol-1-yl)uronium hexafluorophosphate (0.191 g, 0.502 mmol) and diisopropylethylamine (0.176 mL, 1.00 mmol) in N,N-dimethylformamide (1 mL) at 0° C. was added 1-benzyl-1H-pyrazol-4-amine (0.087 g, 0.502 mmol). The reaction mixture was stirred at 15° C. for 12 h. The residue was purified by prep-HPLC (column: Luna C8 100×30 5 u; mobile phase: [water (10 mM ammonium bicarbonate)-acetonitrile]; B %: 36%-66%, 12 min gradient) to give N-(1-benzyl-1H-pyrazol-4-yl)-5-(furan-2-yl)isoxazole-3-carboxamide (0.055 g, 0.162 mmol, 32%) as a pink solid. $^1$H NMR (400 MHz, Chloroform-d) δ 8.47 (br. s., 1H), 8.02 (s, 1H), 7.61 (d, J=6.6 Hz, 2H), 7.40-7.31 (m, 3H), 7.26 (br. s., 1H), 6.99 (d, J=3.5 Hz, 1H), 6.91 (s, 1H), 6.65-6.53 (m, 1H), 5.31 (s, 2H); LCMS (ESI) m/z: 335.1 [M+H]$^+$.

Example 8. Preparation of (R)—N-(1-benzyl-1H-pyrazol-4-yl)-5-(3-hydroxypyrrolidin-1-yl)isoxazole-3-carboxamide (186)

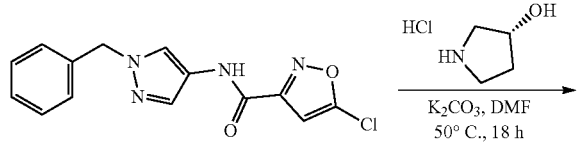

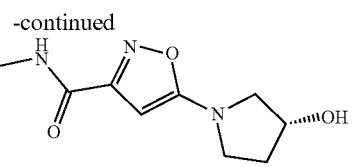

A mixture of N-(1-benzyl-1H-pyrazol-4-yl)-5-chloroisoxazole-3-carboxamide (130 mg, 0.43 mmol), (R)-pyrrolidin-3-ol hydrochloride (159 mg, 1.30 mmol) and potassium carbonate (90 mg, 0.64 mmol) in N,N-dimethylformamide (5 mL) in a sealed tube was heated at 50° C. for 18 h. After being filtered, the filtrate was purified by prep-HPLC (column: Sunfire prep C18 10 μm OBD 19*250 mm; mobile phase: [water (0.05% trifluoroacetic acid-acetonitrile]; B %: 60%-88%, 15 min) to offer N-(1-benzyl-1H-pyrazol-4-yl)-5-(pyrrolidin-1-yl)isoxazole-3-carboxamide (70 mg, 0.20 mmol, 46%) as a white solid. $^1$H NMR (500 MHz, Dimethylsulfoxide-d$_6$) δ 10.62 (s, 1H), 8.10 (s, 1H), 7.64 (s, 1H), 7.29 (ddd, J=33.7, 20.4, 7.0 Hz, 5H), 5.34 (d, J=37.2 Hz, 3H), 4.47-4.28 (m, 1H), 3.67-3.29 (m, 6H), 3.25 (d, J=10.5 Hz, 1H), 2.02 (dd, J=8.7, 4.4 Hz, 1H), 1.95-1.75 (m, 1H); LCMS (ESI) m/z: 354.1 [M+H]$^+$.

Example 9. Preparation of N-(1-benzyl-1H-pyrazol-4-yl)-5-(thiazol-2-yl)isoxazole-3-carboxamide (110)

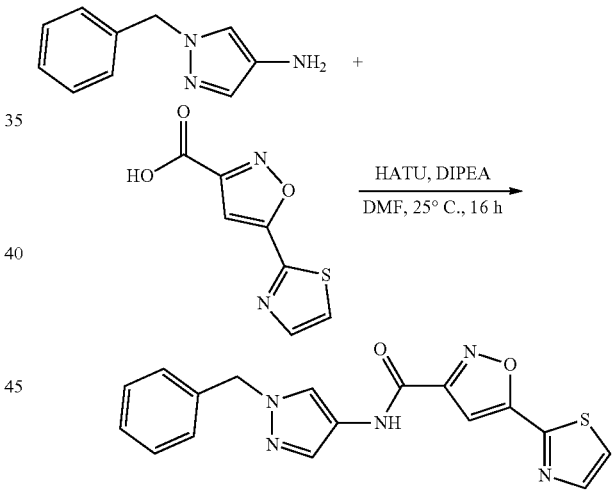

To a solution of 1-benzyl-1H-pyrazol-4-amine (0.033 g, 0.157 mmol), 5-(thiazol-2-yl)isoxazole-3-carboxylic acid (30.8 mg, 0.157 mmol) and diisopropylethylamine (50.8 mg, 0.393 mmol) in N,N'-dimethylformamide (0.5 mL) at 25° C. was added 1-[bis(dimethylamino)methylene]-1H-1,2,3-triazolo[4,5-b]pyridinium 3-oxide hexafluorophosphate (0.123 g, 0.157 mmol). The reaction mixture was stirred at 25° for 16 h. The reaction mixture was quenched with water (1 mL) and the aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 40% ethyl acetate/hexanes for 20 min) to give N-(1-benzyl-1H-pyrazol-4-yl)-5-(thiazol-2-yl)isoxazole-3-carboxamide (24.7 mg, 0.0704 mmol, 45%) as a yellow solid. $^1$H NMR (300 MHz, Dimethylsulfoxide-d$_6$) δ 11.10 (s, 1H), 8.24-8.03 (m, 3H), 7.67 (d, J=0.7 Hz, 1H), 7.49 (s, 1H), 7.46-7.17 (m, 5H), 5.34 (s, 2H); LCMS (ESI) m/z: 352.2 [M+H]⁺.

Example 10. Preparation of N-(1-benzyl-1H-pyrazol-4-yl)-5-isopropylisoxazole-3-carboxamide (117)

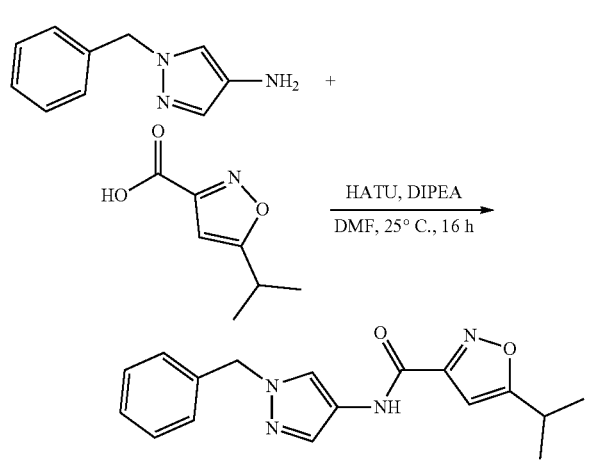

To a solution of 1-benzyl-1H-pyrazol-4-amine (0.050 g, 0.289 mmol), 5-isopropylisoxazole-3-carboxylic acid (44.7 mg, 0.289 mmol) and 1-[bis(dimethylamino)methylene]-1H-1,2,3-triazolo[4,5-b]pyridinium 3-oxide hexafluorophosphate (109 mg, 0.289 mmol) in N,N'-dimethylformamide (1 mL) at 25° C. was added diisopropylethylamine (0.075 mL, 0.433 mmol). The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 40% ethyl acetate/hexanes for 20 min) to give N-(1-benzyl-1H-pyrazol-4-yl)-5-isopropylisoxazole-3-carboxamide (63.3 mg, 0.204 mmol, 70%) as an off-white solid. ¹H NMR (300 MHz, Dimethylsulfoxide-d₆) δ 10.87 (s, 1H), 8.13 (d, J=1.6 Hz, 1H), 7.64 (d, J=1.7 Hz, 1H), 7.40-7.05 (m, 5H), 6.63 (t, J=1.2 Hz, 1H), 5.31 (d, J=1.6 Hz, 2H), 3.16 (p, J=6.8 Hz, 1H), 1.28 (dd, J=7.0, 1.7 Hz, 6H); LCMS (ESI) m/z: 311.3 [M+H]⁺.

Example 11. Preparation of N-(1-benzyl-1H-pyrazol-4-yl)-5-(tert-butyl)isoxazole-3-carboxamide (118)

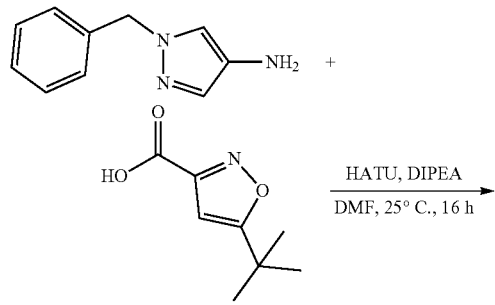

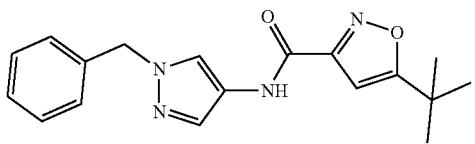

To a solution of 1-benzyl-1H-pyrazol-4-amine (0.050 g, 0.289 mmol), 5-(tert-butyl)isoxazole-3-carboxylic acid (48.8 mg, 0.289 mmol) and 1-[bis(dimethylamino)methylene]-1H-1,2,3-triazolo[4,5-b]pyridinium 3-oxide hexafluorophosphate (109 mg, 0.289 mmol) in N,N'-dimethylformamide (1 mL) at 25° C. was added diisopropylethylamine (0.075 mL, 0.433 mmol). The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 40% ethyl acetate/hexanes for 20 min) to give N-(1-benzyl-1H-pyrazol-4-yl)-5-(tert-butyl)isoxazole-3-carboxamide (65.3 mg, 0.201 mmol, 70%) as a yellow solid. ¹H NMR (300 MHz, Dimethylsulfoxide-d₆) δ 10.86 (s, 1H), 8.13 (s, 1H), 7.63 (s, 1H), 7.42-7.13 (m, 5H), 6.62 (d, J=1.2 Hz, 1H), 5.31 (s, 2H), 1.34 (d, J=1.1 Hz, 10H). M+H=325.3; LCMS (ESI) m/z: 325.3 [M+H]⁺.

Example 12. Preparation of N-(1-benzyl-1H-pyrazol-4-yl)-5-(pyrrolidin-1-yl)isoxazole-3-carboxamide (178)

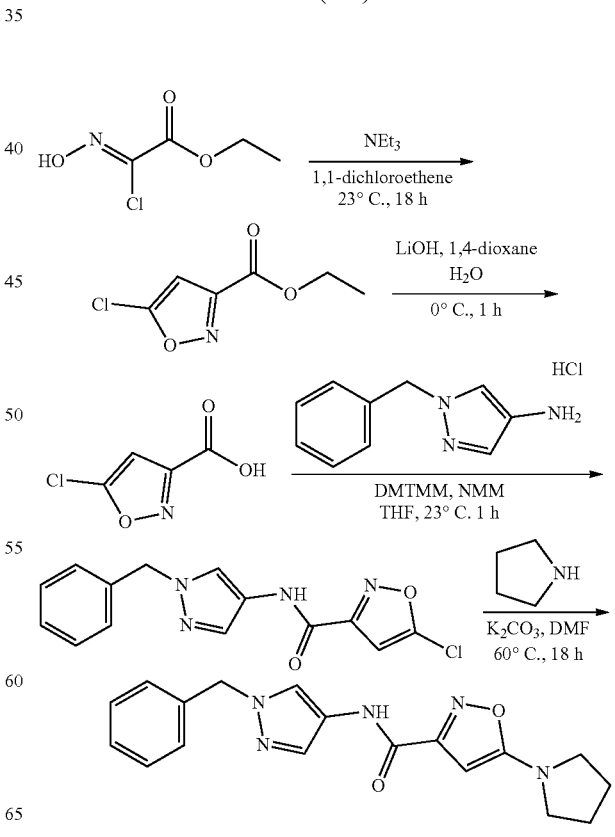

Step 1: Preparation of ethyl 5-chloroisoxazole-3-carboxylate

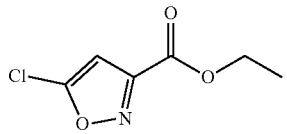

A solution of triethylamine (26.2 mL, 182 mmol) in 1,1-dichloroethene (150 mL) was added dropwise to a solution of (Z)-ethyl 2-chloro-2-(hydroxyimino)acetate (11.0 g, 72.9 mmol) in 1,1-dichloroethene (100 mL) over 2 h. The mixture was stirred at 23° C. for 18 h. After being concentrated, the residue was dissolved in ethyl acetate (300 mL) and washed with brine (100 mL), dried over sodium sulfate, filtered and concentrated in vacuo. The residue was purified by column chromatography (silica, petroleum ether/ethyl acetate=20/1) to afford ethyl 5-chloroisoxazole-3-carboxylate (1.40 g, 8.00 mmol, 11%) as a pale-yellow oil. LCMS (ESI) m/z: 176.1 [M+H]$^+$.

Step 2: Preparation of 5-chloroisoxazole-3-carboxylic Acid

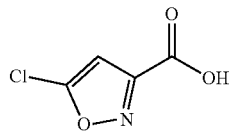

To an ice-cooled solution of ethyl 5-chloroisoxazole-3-carboxylate (2.80 g, 16.0 mmol) in 1,4-dioxane (18 mL) was added a solution of lithium hydroxide monohydrate (1.34 g, 32.0 mmol) in water (18 mL). The mixture was stirred at 0° C. for 1 h. After being concentrated, the residue was diluted with ethyl acetate/water (1/1, 250 mL) and adjusted to pH=5 with aqueous 0.5N hydrochloric acid. The aqueous layer was extracted with ethyl acetate (2×100 mL). The combined organic layers were washed with brine (100 mL), dried over sodium sulfate, filtered and concentrated to offer 5-chloroisoxazole-3-carboxylic acid (2.00 g, 13.6 mmol, 85%) as a pale-yellow solid. LCMS (ESI) m/z: 148.1 [M+H]$^+$. This material was used in the next step without further purification.

Step 3: Preparation of N-(1-benzyl-1H-pyrazol-4-yl)-5-chloroisoxazole-3-carboxamide

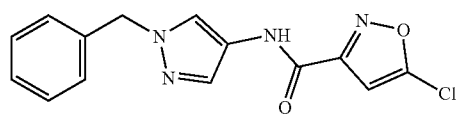 [SMILES: O=C(Nc1cnn(Cc2ccccc2)c1)c1cc(Cl)on1]

To a solution of 5-chloroisoxazole-3-carboxylic acid (2.00 g, 13.6 mmol), 1-benzyl-1H-pyrazol-4-amine hydrochloride (2.84 g, 13.6 mmol) and 4-(4,6-dimethoxy-1,3,5-triazin-2-yl)-4-methyl morpholinium chloride (4.01 g, 13.6 mmol) in tetrahydrofuran (50 mL) was added 4-methylmorpholine (4.12 g, 40.8 mmol). The mixture was stirred at 23° C. for 1 h. The reaction mixture was diluted with ethyl acetate (300 mL) and washed with aqueous 0.5N hydrochloric acid (100 mL), water (100 mL) and brine (100 mL). The combined organic layers were dried over sodium sulfate, filtered and concentrated in vacuo. The residue was purified by column chromatography (silica, petroleum ether/ethyl acetate=2/1) to afford N-(1-benzyl-1H-pyrazol-4-yl)-5-chloroisoxazole-3-carboxamide (2.38 g, 7.88 mmol, 58%) as a white yellow solid. LCMS (ESI) m/z: 303.1 [M+H]$^+$.

Step 4: Preparation of N-(1-benzyl-1H-pyrazol-4-yl)-5-(pyrrolidin-1-yl)isoxazole-3-carboxamide

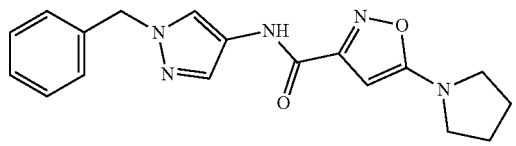 [SMILES: O=C(Nc1cnn(Cc2ccccc2)c1)c1cc(N2CCCC2)on1]

A mixture of N-(1-benzyl-1H-pyrazol-4-yl)-5-chloroisoxazole-3-carboxamide (130 mg, 0.43 mmol), pyrrolidine (180 mg, 1.30 mmol) and potassium carbonate (90 mg, 0.64 mmol) in N,N-dimethylformamide (5 mL) in a sealed tube was stirred at 60° C. for 18 h. After being filtered, the filtrate was purified by prep-HPLC (column: Sunfire prep C18 10 μm OBD 19×250 mm; mobile phase: [water (0.05% trifluoroacetic acid-acetonitrile]; B %: 60%-88%, 15 min) to offer N-(1-benzyl-1H-pyrazol-4-yl)-5-(pyrrolidin-1-yl)isoxazole-3-carboxamide (60 mg, 0.18 mmol, 41%) as a white solid. $^1$H NMR (500 MHz, Dimethylsulfoxide-d$_6$) δ 10.62 (s, 1H), 8.11 (s, 1H), 7.64 (s, 1H), 7.44-6.90 (m, 5H), 5.34 (d, J=34.0 Hz, 3H), 3.37 (t, J=6.6 Hz, 5H), 2.00-1.74 (m, 4H); LCMS (ESI) m/z: 338.1 [M+H]$^+$.

Example 13. Preparation of N-(1-benzyl-1H-pyrazol-4-yl)-5-(dimethylamino)isoxazole-3-carboxamide (203)

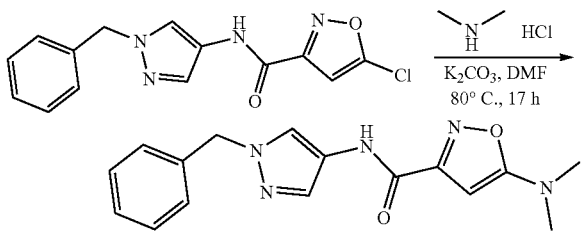

To a solution of N-(1-benzyl-1H-pyrazol-4-yl)-5-chloroisoxazole-3-carboxamide (0.160 g, 0.53 mmol) in N,N-dimethylformamide (15 mL) was added dimethylamine hydrochloride (0.130 g, 1.59 mmol) and potassium carbonate (0.219 g, 1.59 mmol). The reaction mixture was heated at 80° C. for 17 h. The reaction mixture was filtered and concentrated in vacuo. The crude sample was dissolved in minimum amount of N,N-dimethylformamide and purified via prep-HPLC (Boston C18 21×250 mm 10 μm column; acetonitrile/0.01% aqueous trifluoroacetic acid) to give N-(1-benzyl-1H-pyrazol-4-yl)-5-(dimethylamino)isoxazole-3-carboxamide (40.4 mg, 0.13 mmol, 25%) as a white solid. $^1$H NMR (400 MHz, Dimethylsulfoxide-d$_6$) δ 10.61

(s, 1H), 8.10 (s, 1H), 7.74-7.53 (m, 1H), 7.43-7.01 (m, 5H), 5.50 (s, 1H), 5.31 (s, 2H), 2.98 (s, 6H); LCMS (ESI) m/z: 312.1 [M+H]+.

Example 14. Preparation of N-(1-benzyl-1H-pyrazol-4-yl)-5-cyclopropylisoxazole-3-carboxamide (119)

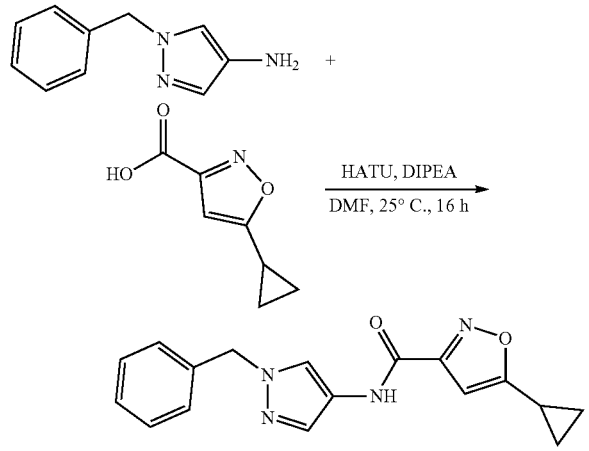

To a solution of 1-benzyl-1H-pyrazol-4-amine (0.050 g, 0.289 mmol), 5-cyclopropylisoxazole-3-carboxylic acid (44.1 mg, 0.289 mmol) and 1-[bis(dimethylamino)methylene]-1H-1,2,3-triazolo[4,5-b]pyridinium 3-oxide hexafluorophosphate (109 mg, 0.289 mmol) in N,N'-dimethylformamide (1 mL) at 25° C. was added diisopropylethylamine (0.075 mL, 0.433 mmol). The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 40% ethyl acetate/hexanes for 20 min) to give N-(1-benzyl-1H-pyrazol-4-yl)-5-cyclopropylisoxazole-3-carboxamide (12.4 mg, 0.041 mmol, 14%) as an off-white solid. $^1$H NMR (300 MHz, Chloroform-d) δ 8.42 (s, 1H), 8.00 (s, 1H), 7.59 (s, 1H), 7.37-7.18 (m, 5H), 6.39 (s, 1H), 5.30 (s, 2H), 2.11 (tt, J=8.5, 5.0 Hz, 1H), 1.23-1.08 (m, 2H), 1.08-0.92 (m, 2H); LCMS (ESI) m/z: 309.2 [M+H]+.

Example 15. Preparation of N-(1-benzyl-1H-pyrazol-4-yl)-5-(pyridin-4-yl)isoxazole-3-carboxamide (124)

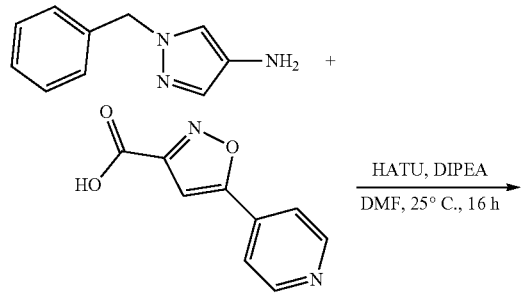

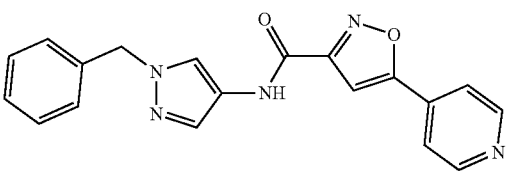

To a solution of 1-benzyl-1H-pyrazol-4-amine (0.050 g, 0.289 mmol), 5-(pyridin-4-yl)isoxazole-3-carboxylic acid (54.8 mg, 0.289 mmol) and 1-[bis(dimethylamino)methylene]-1H-1,2,3-triazolo[4,5-b]pyridinium 3-oxide hexafluorophosphate (109 mg, 0.289 mmol) in N,N'-dimethylformamide (1 mL) at 25° C. was added diisopropylethylamine (0.075 mL, 0.433 mmol). The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 60% ethyl acetate/hexanes for 20 min) to give N-(1-benzyl-1H-pyrazol-4-yl)-5-(pyridin-4-yl)isoxazole-3-carboxamide (26 mg, 0.075 mmol, 26%) as a pale orange solid. $^1$H NMR (300 MHz, Dimethylsulfoxide-d$_6$) δ 11.10 (s, 1H), 8.85-8.73 (m, 2H), 8.18 (s, 1H), 8.01-7.89 (m, 2H), 7.75 (s, 1H), 7.68 (s, 1H), 7.40-7.19 (m, 5H), 5.34 (s, 2H); LCMS (ESI) m/z: 346.3 [M+H]+.

Example 16. Preparation of N-(1-benzyl-1H-pyrazol-4-yl)-5-(2-(methoxymethyl)thiazol-5-yl)isoxazole-3-carboxamide (140)

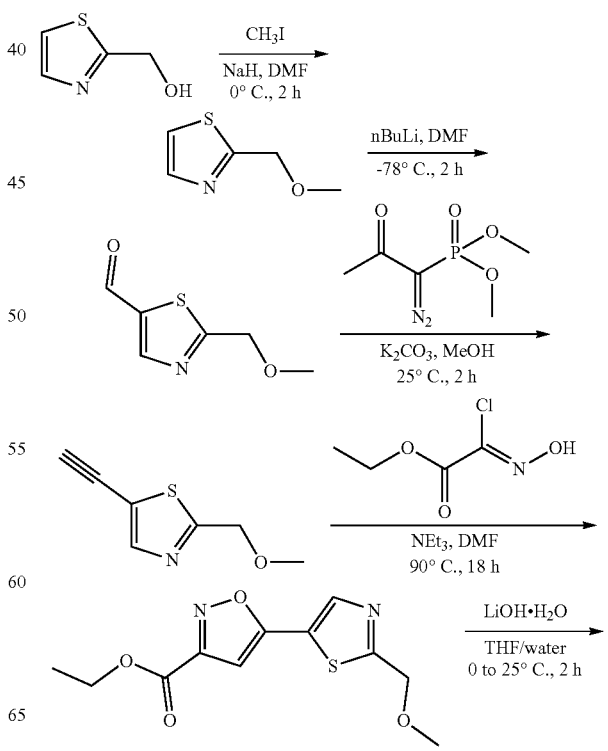

243

-continued

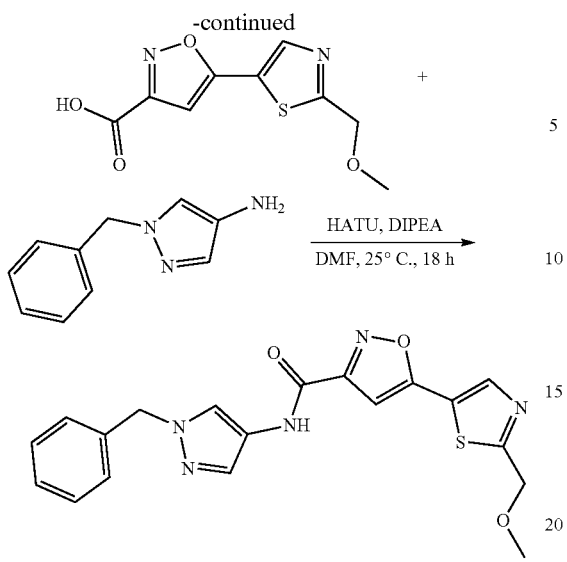

Step 1: Preparation of 2-(methoxymethyl)thiazole

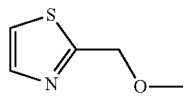

To a solution of thiazol-2-ylmethanol (1.15 g, 10 mmol) in anhydrous N,N-dimethylformamide (10 mL) at 0° C. was added sodium hydride (60% in mineral oil, 0.52 g, 13 mmol) in portions. After the addition, the mixture was stirred at 0° C. for 20 min before iodomethane (1.49 mL, 24 mmol) was added dropwise. The reaction mixture was stirred at 0° C. for 2 h. The reaction as quenched with ethyl acetate/water (30 mL/20 mL) and extracted with ethyl acetate (20 mL×2). The combined organic phases were washed with brine (40 mL), dried over sodium sulfate, filtered and concentrated in vacuo. The residue was purified by column chromatography (Biotage, 40 g silica, eluted with ethyl acetate in petroleum ether from 25% to 40%) to give 2-(methoxymethyl)thiazole (0.74 g, 5.74 mmol, 57%) as a colorless oil. LCMS (ESI) m/z: 130.1 [M+H]$^+$.

Step 2: Preparation of 2-(methoxymethyl)thiazole-5-carbaldehyde

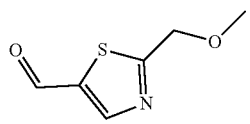

To a solution of 2-(methoxymethyl)thiazole (0.73 g, 5.66 mmol) in anhydrous tetrahydrofuran (20 mL) at −78° C. was added n-butyllithium (2.5 M solution in hexanes, 3.4 mL, 8.48 mmol) dropwise under nitrogen. After the addition, the reaction was stirred at −78° C. for 1 h then N,N-dimethylformamide (0.87 mL, 11.3 mmol) was added dropwise. The reaction mixture was stirred at −78° C. for 2 h. The reaction was quenched with aqueous ammonium chloride (30 mL) and extracted with ethyl acetate (30 mL×2). The combined organic phases were washed with brine (40 mL), dried over sodium sulfate, filtered and concentrated in vacuo. The residue was purified by column chromatography (Biotage, 40 g silica, eluted with ethyl acetate in petroleum ether from 30% to 40%) to give 2-(methoxymethyl)thiazole-5-carbaldehyde (0.48 g, 3.06 mmol, 53%) as a yellow oil. LCMS (ESI) m/z: 158.1 [M+H]$^+$.

Step 3: Preparation of 5-ethynyl-2-(methoxymethyl)thiazole

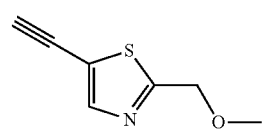

To a solution of 2-(methoxymethyl)thiazole-5-carbaldehyde (0.46 g, 2.93 mmol) in methanol (30 mL) at 25° C. was added dimethyl 1-diazo-2-oxopropylphosphonate (0.84 g, 4.39 mmol) and potassium carbonate (1.21 g, 8.79 mmol). The reaction mixture was stirred at 25° C. for 3 h. The volatiles were removed in vacuo. The crude residue was taken up in ethyl acetate (40 mL) and washed with water (30 mL×2) and brine (20 mL). The organic phases were dried over sodium sulfate, filtered and concentrated to give 5-ethynyl-2-(methoxymethyl)thiazole (0.46 g, 2.93 mmol, crude) as a yellow oil. LCMS (ESI) m/z: 154.1 [M+H]$^+$. The material was used directly in the next step without further purification Step 4: Preparation of 5-ethynyl-2-(methoxymethyl)thiazole

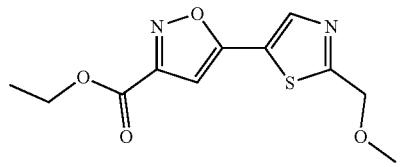 [SMILES: CCOC(=O)c1cc(-c2cnc(COC)s2)on1]

To a solution of 5-ethynyl-2-(methoxymethyl)thiazole (0.41 g, 2.68 mmol) in N,N-dimethylformamide (10 mL) at 25° C. was added ethyl 2-chloro-2-(hydroxyimino)acetate (0.27 g, 1.78 mmol) in N,N-dimethylformamide (3 mL) dropwise under nitrogen. After the addition, the reaction was stirred at 25° C. for 20 min and then heated to 90° C. A solution of triethylamine (0.54 g, 5.36 mmol) in dimethylformamide (6 mL) was added dropwise slowly. After the addition, the reaction was heated at 90° C. for 18 h. The reaction mixture was cooled, diluted with ethyl acetate/water (40 mL/40 mL) and extracted with ethyl acetate (30 mL×2) twice. The combined organic phases were washed with brine (40 mL), dried over sodium sulfate, filtered and concentrated in vacuo. The residue was purified by column chromatography (Biotage, 40 g silica, eluted with ethyl acetate in petroleum ether from 20% to 30%) to afford ethyl 5-(2-(methoxymethyl)thiazol-5-yl)isoxazole-3-carboxylate (0.17 g, 0.63 mmol, 20.7% over 2 steps) as a white solid. LCMS (ESI) m/z: 269.1 [M+H]$^+$.

Step 5: Preparation of 5-(2-(methoxymethyl)thiazol-5-yl)isoxazole-3-carboxylic Acid

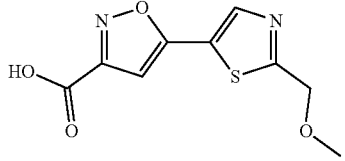 [SMILES: COCc1ncc(-c2cc(C(=O)O)no2)s1]

To a solution of ethyl 5-(2-(methoxymethyl)thiazol-5-yl)isoxazole-3-carboxylate (0.15 g, 0.56 mmol) in tetrahydrofuran/water (20 mL/5 mL at 0° C. was added lithium hydroxide monohydrate (35 mg, 0.84 mmol) in one portion. The reaction mixture was stirred for 1 h before the volatiles were removed. The crude residue was diluted with water (10 mL) and the aqueous layer was adjusted to pH=34 with aqueous 1N hydrogen chloride. The white precipitate was collected and dried to give 5-(2-(methoxymethyl)thiazol-5-yl)isoxazole-3-carboxylic acid (0.14 g, 0.58 mmol, 93%) as a white solid. LCMS (ESI) m/z: 241.1 [M+H]⁺.

Step 6: Preparation of (N-(1-benzyl-1H-pyrazol-4-yl)-5-(2-(methoxymethyl)thiazol-5-yl)isoxazole-3-carboxamide

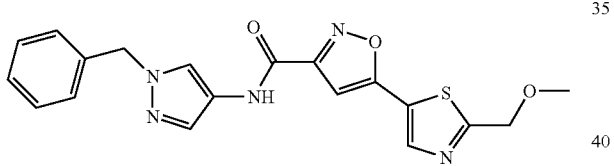

The mixture of 5-(2-(methoxymethyl)thiazol-5-yl)isoxazole-3-carboxylic acid (0.12 g, 0.5 mmol), 1-benzyl-1H-pyrazol-4-amine (0.125 g, 0.6 mmol), 2-(7-azabenzotriazol-1-yl)-N,N,N',N'-tetramethyluronium hexafluorophosphate (0.285, 0.75 mmol) in N,N-dimethylformamide (15 mL) at 25° C. was added N,N-diisopropylethylamine (0.19 g, 1.5 mmol) dropwise. The reaction mixture was stirred at 25° C. for 18 h. The reaction mixture was diluted with ethyl acetate/water (20 mL/20 mL) and extracted with ethyl acetate (20 mL×2). The combined organic phases were washed with brine (20 mL), dried over sodium sulfate, filtered and concentrated in vacuo. The residue was slurred in a mixture of ethyl acetate/petroleum ether (5 mL/50 mL), filtered and concentrated to give N-(1-benzyl-1H-pyrazol-4-yl)-5-(2-(methoxymethyl)thiazol-5-yl)isoxazole-3-carboxamide (130 mg, 0.33 mmol, 65.8%) as a brown solid. ¹H NMR (500 MHz, Dimethylsulfoxide-d₆) δ 11.06 (s, 1H), 8.49 (s, 1H), 8.17 (s, 1H), 7.68 (s, 1H), 7.40 (s, 1H), 7.22-7.37 (m, 5H), 5.34 (s, 2H), 4.81 (s, 2H), 3.46 (s, 3H); LCMS (ESI) m/z: 396.1 [M+H]⁺.

Example 17. Preparation of N-(1-benzyl-1H-pyrazol-4-yl)-5-(3-fluoropyridin-4-yl)isoxazole-3-carboxamide (147)

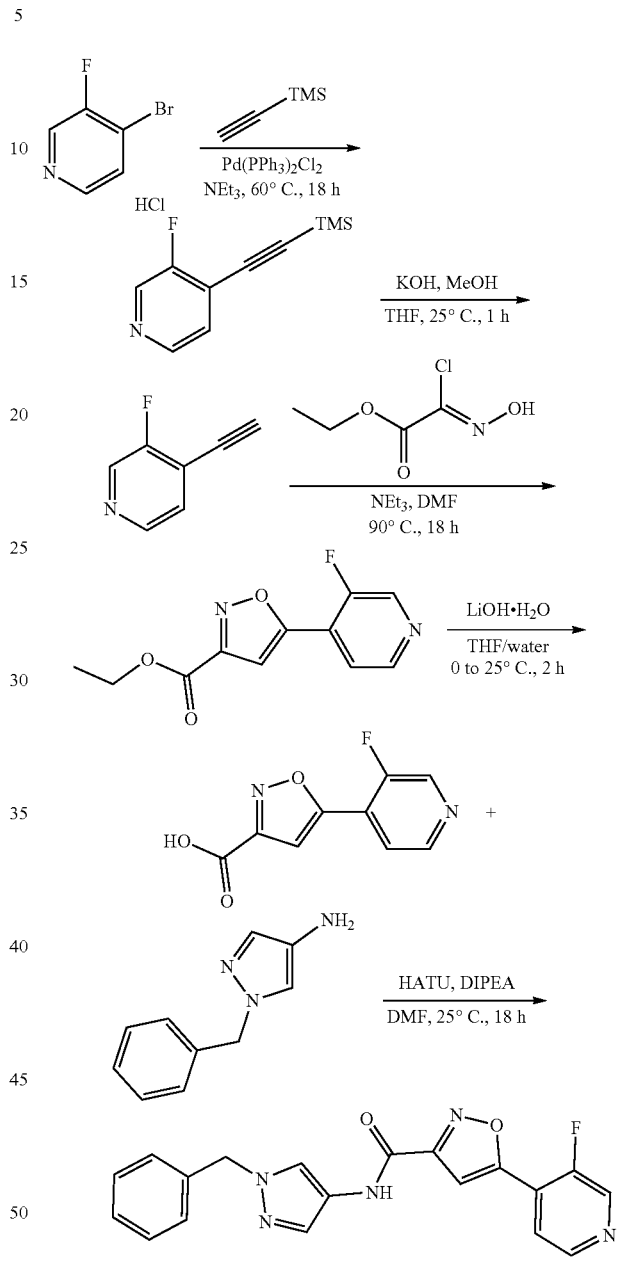

Step 1: Preparation of 3-fluoro-4-((trimethylsilyl)ethynyl)pyridine

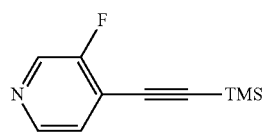

A mixture of 4-bromo-3-fluoropyridine hydrochloride (3 g, 14.2 mmol), bis(triphenylphosphine)palladium(II) chloride (0.5 g, 0.7 mmol), copper iodide (0.27 g, 1.41 mmol) in triethylamine (20 mL) was degassed and re-filled with nitrogen three times. Then ethynyltrimethylsilane (6 mL, 42.5 mmol) was added dropwise by a syringe. After the addition, the reaction was stirred at 60° C. for 18 h. The reaction mixture was diluted with water (100 mL) and extracted with ethyl acetate (100 mL×2). The combined organic phases were washed with brine (80 mL), dried over sodium sulfate, filtered and concentrated in vacuo. The residue was purified by column chromatography (Biotage, 40 g silica, eluted with ethyl acetate in petroleum ether from 10% to 15%) to give 3-fluoro-4-((trimethylsilyl)ethynyl) pyridine (2 g, 10.4 mmol, 73%) as a yellow oil. LCMS (ESI) m/z: 194.1 [M+H]$^+$.

Step 2: Preparation of 4-ethynyl-3-fluoropyridine

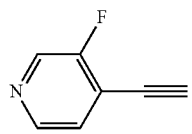

To a solution of 3-fluoro-4-((trimethylsilyl)ethynyl)pyridine (1.95 g, 10.1 mmol) in tetrahydrofuran (80 mL) at 0° C. was added potassium hydroxide (1.13 g, 20.2 mmol) in methanol (16 mL) dropwise. After the addition, the reaction was stirred at 25° C. for 1 h. The volatiles were removed in vacuo. The crude material was diluted with ethyl acetate/water (20 mL/20 mL) and extracted with ethyl acetate (20 mL×2). The combined organic phases were washed with brine (30 mL), dried over sodium sulfate, filtered and concentrated to give 4-ethynyl-3-fluoropyridine (0.6 g, 4.96 mmol, 49%) as pale yellow oil. The material was used directly in the next step without further purification.

Step 3: Preparation of ethyl 5-(3-fluoropyridin-4-yl)isoxazole-3-carboxylate

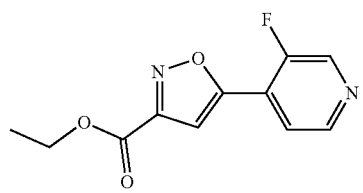 [SMILES: CCOC(=O)c1cc(-c2ccncc2F)on1]

To a solution of 4-ethynyl-3-fluoropyridine (0.6 g, 4.96 mmol) in N,N-dimethylformamide (6 mL) at 25° C. was added a solution of ethyl 2-chloro-2-(hydroxyimino)acetate (0.5 g, 3.30 mmol) in N,N-dimethylformamide (3 mL) dropwise under nitrogen. After the addition, the reaction was stirred at 25° C. for 20 min and then heated to 90° C. and added a solution of triethylamine (1.0 g, 9.93 mmol) in dimethylformamide (6 mL) dropwise. The reaction mixture was heated at 90° C. for 18 h. The reaction mixture was cooled, diluted with water (20 mL) and extracted with ethyl acetate (30 mL×2). The combined organic phases were washed with brine (30 mL), dried over sodium sulfate, filtered and concentrated in vacuo. The residue was purified by column chromatography (Biotage, 40 g silica, eluted with ethyl acetate in petroleum ether from 20% to 30%) to afford ethyl 5-(3-fluoropyridin-4-yl)isoxazole-3-carboxylate (0.2 g, 0.85 mmol, 25%) as a white solid. LCMS (ESI) m/z: 237.1 [M+H]$^+$.

Step 4: Preparation of 5-(3-fluoropyridin-4-yl)isoxazole-3-carboxylic Acid

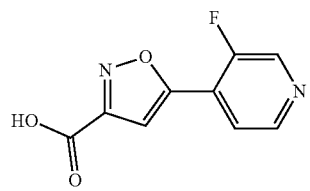 [SMILES: O=C(O)c1cc(-c2ccncc2F)on1]

To a solution of ethyl 5-(3-fluoropyridin-4-yl)isoxazole-3-carboxylate (0.18 g, 0.76 mmol) in tetrahydrofuran/water (20 mL/5 mL) was added lithium hydroxide monohydrate (48 mg, 1.14 mmol) in one portion at 0° C. The reaction mixture was stirred at 0° C. for 2 h. The volatiles were removed in vacuo. The crude residue was diluted with water (20 mL) and adjusted to pH=34 with aqueous 1N hydrogen chloride. The white precipitate was collected and dried to give 5-(3-fluoropyridin-4-yl)isoxazole-3-carboxylic acid (0.15 g, 0.72 mmol, 94%) as a white solid. LCMS (ESI) m/z: 209.1 [M+H]$^+$. The material was used directly in the next step without further purification.

Step 5: Preparation of N-(1-benzyl-1H-pyrazol-4-yl)-5-(3-fluoropyridin-4-yl)isoxazole-3-carboxamide

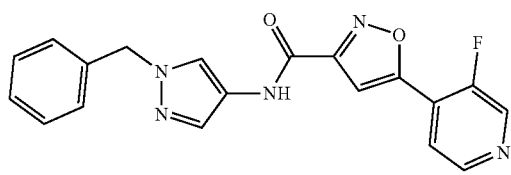 [SMILES: O=C(Nc1cnn(Cc2ccccc2)c1)c1cc(-c2ccncc2F)on1]

To a solution of 5-(3-fluoropyridin-4-yl)isoxazole-3-carboxylic acid (80 mg, 0.38 mmol), 1-benzyl-1H-pyrazol-4-amine (80 mg, 0.46 mmol) and 2-(7-azabenzotriazol-1-yl)-N,N,N',N'-tetramethyluronium hexafluorophosphate (0.22 g, 0.57 mmol) in N,N-dimethylformamide (15 mL) at 25° C. was added N,N-diisopropylethylamine (0.15 g, 1.15 mmol) slowly. The resulting reaction mixture was stirred at 25° C. for 18 h. The reaction mixture was diluted with ethyl acetate/water (20 mL/20 mL) and extracted with ethyl acetate (20 mL×2). The combined organic phases were washed with brine (20 mL), dried over sodium sulfate, filtered and concentrated in vacuo. The residue was triturated in a mixture of ethyl acetate/petroleum ether (5 mL/50 mL), filtered and concentrated to give N-(1-benzyl-1H-pyrazol-4-yl)-5-(3-fluoropyridin-4-yl)isoxazole-3-carboxamide (125 mg, 0.34 mmol, 75%) as a brown solid. $^1$H NMR (500 MHz, Dimethylsulfoxide-d$_6$) δ 11.12 (s, 1H), 8.88 (s, 1H), 8.64-8.68 (m, 1H), 8.19 (s, 1H), 8.02-8.07 (m, 1H), 7.68 (s, 1H), 7.52-7.54 (m, 1H), 7.23-7.38 (m, 5H), 5.34 (s, 2H); LCMS (ESI) m/z: 364.1 [M+H]$^+$.

Example 18. Preparation of N-(1-benzyl-1H-pyrazol-4-yl)-5-(3-chloropyridin-4-yl)isoxazole-3-carboxamide (134)

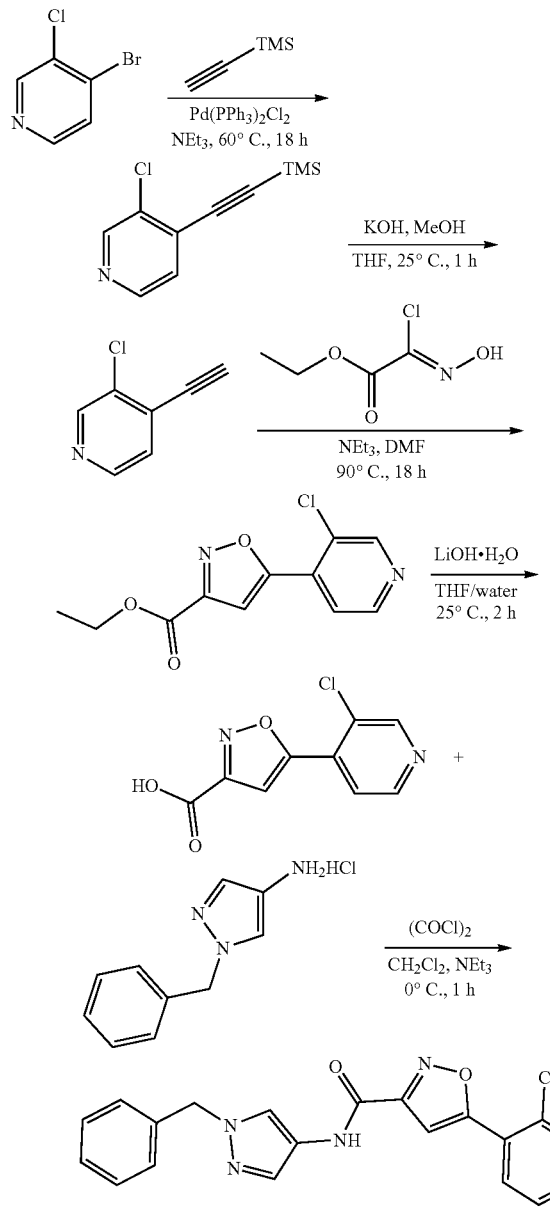

Step 1: Preparation of 3-chloro-4-((trimethylsilyl)ethynyl)pyridine

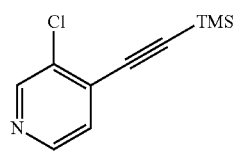 [SMILES: C[Si](C)(C)C#Cc1ccncc1Cl]

A mixture of 4-bromo-3-chloropyridine (2 g, 10.5 mmol), bis(triphenylphosphine)palladium(II) chloride (0.37 g, 0.52 mmol), copper iodide (0.2 g, 1.05 mmol) in triethylamine (20 mL) was degassed and re-filled with nitrogen (2×). Then ethynyltrimethylsilane (4.4 mL, 31.4 mmol) was added dropwise by a syringe. After the addition, the reaction mixture was stirred at 60° C. for 18 h. The reaction mixture was diluted with water (100 mL) and extracted with ethyl acetate (100 mL×2). The combined organic phases were washed with water (50 mL) and brine (50 mL), dried over sodium sulfate, filtered and concentrated in vacuo. The crude material was purified by column chromatography (Biotage, 40 g silica, eluted with ethyl acetate in petroleum ether from 10% to 15%) to give 3-chloro-4-((trimethylsilyl)ethynyl)pyridine (1.47 g, 7.03 mmol, 67%) as a yellow oil. LCMS (ESI) m/z: 210.1 [M+H]$^+$.

Step 2: Preparation of 3-chloro-4-ethynylpyridine

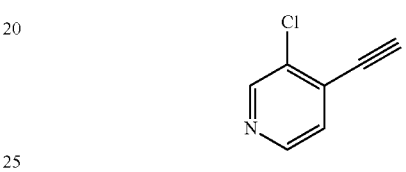

To a solution of 3-chloro-4-((trimethylsilyl)ethynyl)pyridine (1.27 g, 6.08 mmol) in tetrahydrofuran (60 mL) at 0° C. was added potassium hydroxide (0.68 g, 12.2 mmol) in methanol (12 mL) dropwise. After the addition, the reaction was stirred at 25° C. for 1 h. The volatiles were removed in vacuo. The residue was diluted with ethyl acetate (100 mL), washed with water (50 mL×2) and brine (50 mL), dried over sodium sulfate, filtered and concentrated to give 3-chloro-4-ethynylpyridine (0.77 g, 5.62 mmol, 92%) as a dark brown solid. This material was used directly in the next step without further purification.

Step 3: Preparation of ethyl 5-(3-chloropyridin-4-yl)isoxazole-3-carboxylate

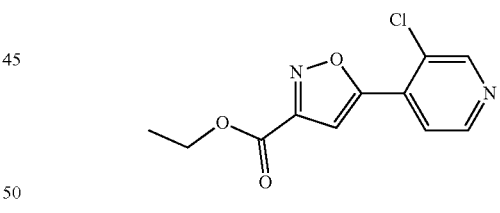

To a solution of 3-chloro-4-ethynylpyridine (0.67 g, 4.89 mmol) in N,N-dimethylformamide (6 mL) at 25° C. was added ethyl 2-chloro-2-(hydroxyimino)acetate (0.49 g, 3.26 mmol) in N,N-dimethylformamide (3 mL) dropwise under nitrogen. After the addition, the reaction was stirred at 25° C. for 20 min and heated to 90° C. Then a solution of triethylamine (0.98 g, 9.73 mmol) in N,N-dimethylformamide (6 mL) was added dropwise. The reaction mixture was heated at 90° C. for 18 h. The reaction mixture was cooled to room temperature, diluted with ethyl acetate/water (30 mL/30 mL) and extracted with ethyl acetate (50 mL×2). The combined organic phases were washed with water (40 mL) and brine (50 mL), dried over sodium sulfate, filtered and concentrated in vacuo. The residue was purified by column chromatography (Biotage, 40 g silica, eluted with ethyl acetate in petroleum ether from 30% to 40%) to afford ethyl 5-(3-chloropyridin-4-yl)isoxazole-3-carboxylate (0.21 g, 0.83 mmol, 17%) as an off-white solid. LCMS (ESI) m/z: 253.1 [M+H]⁺.

Step 4: Preparation of
5-(3-chloropyridin-4-yl)isoxazole-3-carboxylic Acid

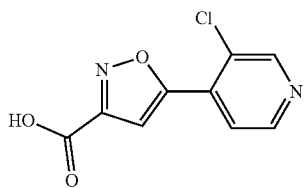 [SMILES: O=C(O)c1cc(-c2ccncc2Cl)on1]

To a solution of ethyl 5-(3-chloropyridin-4-yl)isoxazole-3-carboxylate (0.19 g, 0.75 mmol) in tetrahydrofuran/water (20 mL/5 mL) at 0° C. was added lithium hydroxide monohydrate (47.5 mg, 1.13 mmol) in one portion. The reaction mixture was stirred at 0° C. for 2 h. The volatiles were removed in vacuo. The residue was diluted with water (10 mL) and the aqueous layer was adjusted to pH=34 with aqueous 1N hydrogen chloride. The white precipitate was collected and dried to give 5-(3-chloropyridin-4-yl)isoxazole-3-carboxylic acid (0.16 g, 0.71 mmol, 86%) as a white solid. LCMS (ESI) m/z: 224.9 [M+H]⁺. This material was used directly in the next step without further purification.

Step 5: Preparation of
5-(3-chloropyridin-4-yl)isoxazole-3-carbonyl chloride

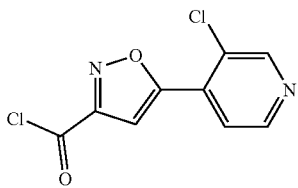 [SMILES: O=C(Cl)c1cc(-c2ccncc2Cl)on1]

To a suspension of 5-(3-chloropyridin-4-yl)isoxazole-3-carboxylic acid (50 mg, 0.22 mmol) in dichloromethane (20 mL) at 25° C. was added oxalyl chloride (2 mL) dropwise, followed by two drops of N,N-dimethylformamide. The reaction mixture was then stirred at 25° C. for 30 min. The reaction was concentrated and dried to give crude 5-(3-chloropyridin-4-yl)isoxazole-3-carbonyl chloride (55 mg, 0.22 mmol) as a yellow solid. This material was used directly in next step without further purification.

Step 6: Preparation of N-(1-benzyl-1H-pyrazol-4-yl)-5-(3-chloropyridin-4-yl)isoxazole-3-carboxamide

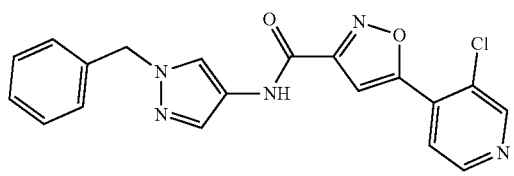 [SMILES: O=C(Nc1cnn(Cc2ccccc2)c1)c1cc(-c2ccncc2Cl)on1]

To a suspension of 1-benzyl-1H-pyrazol-4-amine hydrochloride (52 mg, 0.249 mmol) in dichloromethane (20 mL) at 0° C., was added triethylamine (68.6 mg, 0.679 mmol) slowly followed by a suspension of 5-(3-chloropyridin-4-yl)isoxazole-3-carbonyl chloride (55 mg, 0.226 mmol) in dichloromethane (10 mL). After the addition, the reaction was stirred at 0° C. for 1 h. The reaction mixture was diluted with water (30 mL) and extracted with dichloromethane (30 mL×2). The combined organic phases were washed with brine (30 mL), dried over sodium sulfate, filtered and concentrated in vacuo. The residue was slurred with a mixture of ethyl acetate/petroleum ether (1 mL/20 mL, containing two drops of methanol) with a supersonic instrument and filtered. The precipitate was filtered and concentrated to give N-(1-benzyl-1H-pyrazol-4-yl)-5-(3-chloropyridin-4-yl)isoxazole-3-carboxamide (60.4 mg, 0.159 mmol, 71% over 2 steps) as a gray solid. ¹H NMR (500 MHz, Dimethylsulfoxide-d₆) (11.14 (s, 1H), 8.91 (s, 1H), 8.74 (d, J=5.5 Hz, 1H), 8.18 (s, 1H), 8.02 (d, J=5 Hz, 1H), 7.69 (d, J=2.5 Hz, 2H), 7.23-7.38 (m, 5H), 5.35 (s, 2H); LCMS (ESI) m/z: 380.0 [M+H]⁺.

Example 19. Preparation of N-(1-benzyl-1H-pyrazol-4-yl)-5-(1,3,4-thiadiazol-2-yl)isoxazole-3-carboxamide (170)

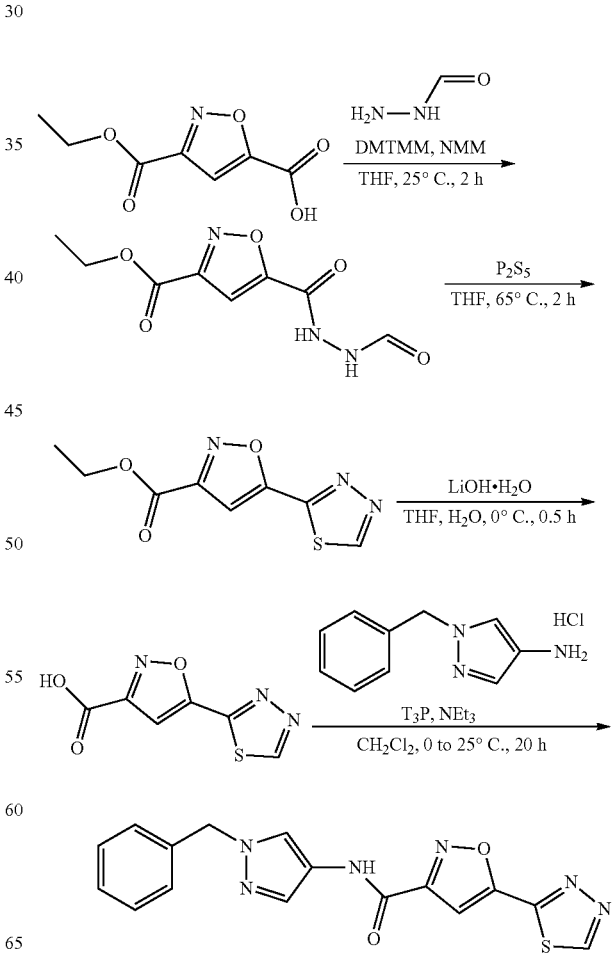

Step 1: Preparation of ethyl 5-(2-formylhydrazine-1-carbonyl)isoxazole-3-carboxylate

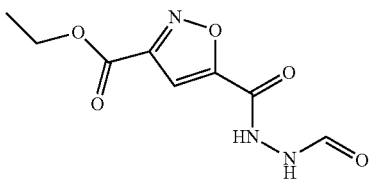 [SMILES: CCOC(=O)c1cc(C(=O)NNC=O)on1]

To a solution of 3-(ethoxycarbonyl)isoxazole-5-carboxylic acid (1.85 g, 10.0 mmol), formylhydrazide (1.2 g, 20.0 mmol) and 4-methylmorpholine (3.03 g, 30 mmol) in tetrahydrofuran (60 mL) at 25° C. was added 4-(4,6-dimethoxy-1,3,5-triazin-2-yl)-4-methyl morpholinium chloride (2.95 g, 10.0 mmol) under nitrogen. The mixture was stirred at 25° C. for 2 h. The volatiles were removed in vacuo. The crude residue was purified by column chromatography (silica, dichloromethane/methanol=30/1 to 20/1) to give ethyl 5-(2-formylhydrazine-1-carbonyl)isoxazole-3-carboxylate as a yellow oil (1.29 g, 5.68 mmol, 56%). LCMS (ESI) m/z: 227.9 [M+H]$^+$.

Step 2: Preparation of ethyl 5-(1,3,4-thiadiazol-2-yl)isoxazole-3-carboxylate

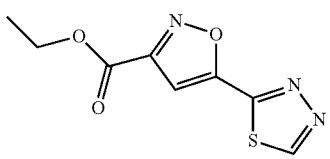

To a solution of ethyl 5-(2-formylhydrazine-1-carbonyl)isoxazole-3-carboxylate (0.682 g, 3.0 mmol) in tetrahydrofuran (50 mL) was added phosphorus pentasulfide (0.861 g, 4.5 mmol) at 25° C. under nitrogen. The mixture was stirred at 65° C. for 2 h. The volatiles were removed in vacuo. The crude residue was purified by column chromatography (silica, petroleum ether/ethyl acetate=4/1 to 3/1) to give ethyl 5-(1,3,4-thiadiazol-2-yl)isoxazole-3-carboxylate as a light yellow solid (0.263 g, 1.17 mmol, 38%). LCMS (ESI) m/z: 226.0 [M+H]$^+$.

Step 3: Preparation of 5-(1,3,4-thiadiazol-2-yl)isoxazole-3-carboxylic Acid

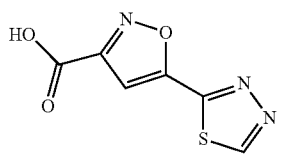 [SMILES: O=C(O)c1cc(-c2nncs2)on1]

To a solution of ethyl 5-(1,3,4-thiadiazol-2-yl)isoxazole-3-carboxylate (0.263 g, 1.17 mmol) in tetrahydrofuran (9 mL) and water (3 mL) at 0° C. was added lithium hydroxide hydrate (59 mg, 1.4 mmol) under nitrogen. The mixture was stirred 0° C. for 30 min. The aqueous phase was adjusted to pH=3 with aqueous 2N hydrochloric acid. The volatiles were removed in vacuo. The resulting precipitate was filtered and concentrated to give 5-(1,3,4-thiadiazol-2-yl)isoxazole-3-carboxylic acid (0.153 g, 0.78 mmol, 67%) as a yellow solid. LCMS (ESI) m/z: 198.0 [M+H]$^+$. This material was used directly in the next step without further purification.

Step 4: Preparation of N-(1-benzyl-1H-pyrazol-4-yl)-5-(1,3,4-thiadiazol-2-yl)isoxazole-3-carboxamide

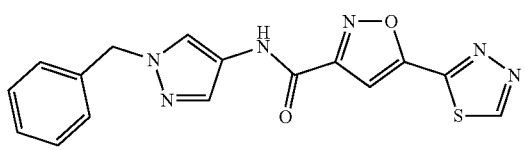 [SMILES: O=C(Nc1cnn(Cc2ccccc2)c1)c1cc(-c2nncs2)on1]

To a solution of 5-(1,3,4-thiadiazol-2-yl)isoxazole-3-carboxylic acid (75 mg, 0.38 mmol), 1-benzyl-1H-pyrazol-4-amine hydrochloride (80 mg, 0.38 mmol) and triethylamine (0.384 g, 3.8 mmol) in dichloromethane (30 mL) at 0° C. was added propylphosphonic anhydride (0.5 M in ethyl acetate, 1.2 g, 1.9 mmol) slowly under nitrogen. The mixture was stirred at room temperature for 20 h. The reaction mixture was quenched with water (30 mL) and the aqueous layer was extracted with dichloromethane (50 mL×3). The organic layer was dried over sodium sulfate, filtered and concentrated in vacuo. The crude residue was purified by Prep-TLC (dichloromethane/ammonia in methanol (7N)=25/1) to give N-(1-benzyl-1H-pyrazol-4-yl)-5-(1,3,4-thiadiazol-2-yl)isoxazole-3-carboxamide (0.102 g, 0.29 mmol, 76%) as a white solid. $^1$H NMR (400 MHz, Dimethylsulfoxide-d$_6$) δ 11.17 (s, 1H), 9.90 (s, 1H), 8.19 (s, 1H), 7.77 (s, 1H), 7.69 (s, 1H), 7.27-7.38 (m, 3H), 7.24-7.26 (m, 2H), 5.35 (s, 2H); LCMS (ESI) m/z: 353.1 [M+H]$^+$.

Example 20. Preparation of N-(1-benzyl-1H-pyrazol-4-yl)-5-(piperidin-1-yl)isoxazole-3-carboxamide (159)

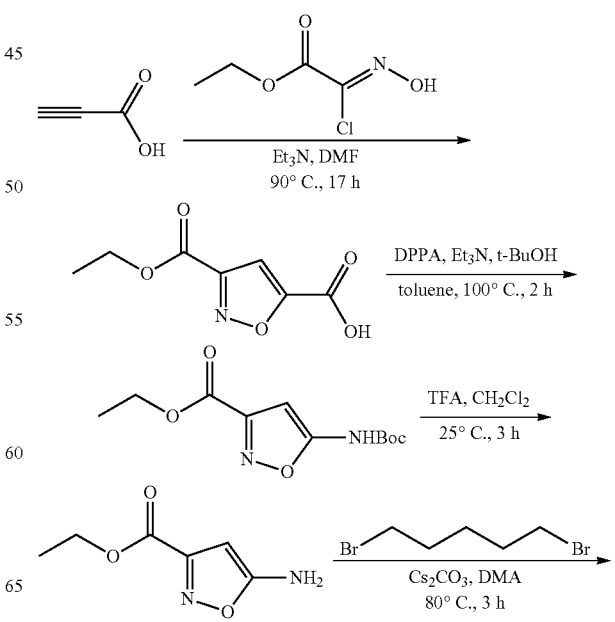

-continued

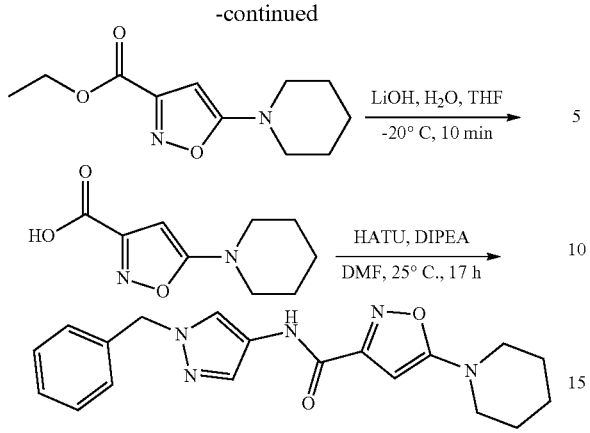

Step 1: Preparation of 3-(ethoxycarbonyl)isoxazole-5-carboxylic Acid

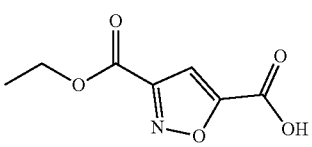

To a solution of propiolic acid (8.0 g, 114.2 mmol) in N,N-dimethylformamide (60 mL) was added (Z)-ethyl 2-chloro-2-(hydroxyimino)acetate (6.9 g, 45.7 mmol) in N,N-dimethylformamide (20 mL) dropwise over 40 min under nitrogen atmosphere. After addition, the reaction mixture was heated to 90° C. and a solution of triethylamine (13.8 g, 137 mmol) in N,N-dimethylformamide (20 mL) was added dropwise over 1 h. The reaction mixture was heated at 90° C. for 17 h and then cooled to room temperature. The reaction mixture was evaporated to dryness, diluted with water (30 mL) and adjusted to pH=2 with aqueous 1N hydrogen chloride. The aqueous layer was extracted with ethyl acetate (30 mL×2). The combined organic layers were washed with brine (30 mL×2), dried over anhydrous sodium sulfate, filtered and concentrated in vacuo to afford 3-(ethoxycarbonyl)isoxazole-5-carboxylic acid (3.2 g, 17.3 mmol, 38%) as a yellow oil. LCMS (ESI) m/z: 186.1 [M+H]$^+$.

Step 2: Preparation of ethyl 5-(tert-butoxycarbonylamino)isoxazole-3-carboxylate

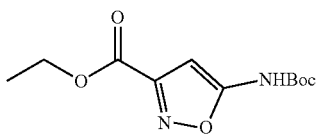 [SMILES: CCOC(=O)c1cc(NC(=O)OC(C)(C)C)on1]

To a solution of 3-(ethoxycarbonyl)isoxazole-5-carboxylic acid (2.7 g, 14.6 mmol) in toluene (40 mL) was added triethylamine (1.8 g, 17.5 mmol), tert-butanol (2.7 g, 36.5 mmol) and diphenylphosphoryl azide (4.8 g, 17.5 mmol). The reaction mixture was heated at 100° C. for 2 h and concentrated to dryness. The residue was purified by column chromatography (silica, petroleum ether/ethyl acetate=8/1) to give ethyl 5-(tert-butoxycarbonylamino)isoxazole-3-carboxylate (1.8 g, 7.0 mmol, 49%) as a white solid. LCMS (ESI) m/z: 257.2 [M+H]$^+$.

Step 3: Preparation of ethyl 5-aminoisoxazole-3-carboxylate

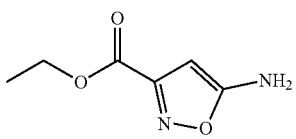

To a solution of ethyl 5-(tert-butoxycarbonylamino)isoxazole-3-carboxylate (1.8 g, 7.0 mmol) in dichloromethane (16.0 mL) was added trifluoroacetic acid (8.0 mL). The reaction mixture was stirred at 25° C. for 3 h and then it was concentrated in vacuo. The crude residue was purified by column chromatography (silica, petroleum ether/ethyl acetate=1/1) to yield ethyl 5-aminoisoxazole-3-carboxylate (0.620 g, 3.97 mmol, 57%) as a yellow solid. LCMS (ESI) m/z: 157.1 [M+H]$^+$.

Step 4: Preparation of ethyl 5-(piperidin-1-yl)isoxazole-3-carboxylate

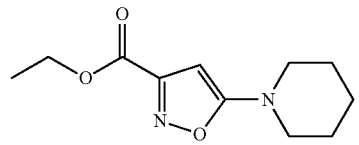 [SMILES: CCOC(=O)c1cc(N2CCCCC2)on1]

To a solution of ethyl 5-aminoisoxazole-3-carboxylate (0.310 g, 1.9 mmol) in dimethylacetamide (20 mL) was added cesium carbonate (1.8 g, 5.7 mmol) and 1,5-dibromopentane (1.1 g, 4.75 mmol). The reaction mixture was heated at 80° C. for 3 h and then cooled to room temperature. The volatiles were removed in vacuo. The crude material was purified by column chromatography (silica, dichloromethane/methanol=15/1) to give ethyl 5-(piperidin-1-yl)isoxazole-3-carboxylate (0.170 g, 0.76 mmol, 38%) as a white solid. LCMS (ESI) m/z: 225.2 [M+H]$^+$.

Step 5: Preparation of 5-(piperidin-1-yl)isoxazole-3-carboxylic Acid

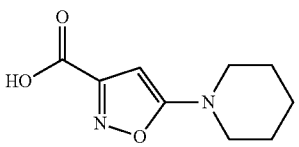 [SMILES: O=C(O)c1cc(N2CCCCC2)on1]

To a solution of ethyl 5-(piperidin-1-yl)isoxazole-3-carboxylate (170 mg, 0.76 mmol) in tetrahydrofuran/water (v/v=2/1, 9 mL) at −20° C. was added lithium hydroxide/water (95.8 mg, 2.28 mmol). The reaction mixture was stirred at −20° C. for 10 min. The volatiles were removed in vacuo to give 5-(piperidin-1-yl)isoxazole-3-carboxylic acid (120 mg, 0.61 mmol, 81%) as a yellow oil. LCMS (ESI) m/z: 197.1 [M+H]⁺. This material was used directly in the next step without further purification.

Step 6: Preparation of N-(1-benzyl-1H-pyrazol-4-yl)-5-(piperidin-1-yl)isoxazole-3-carboxamide

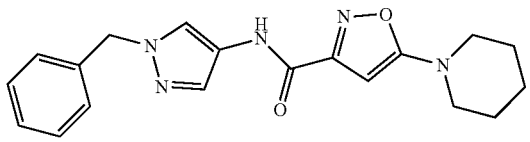 [SMILES: O=C(Nc1cnn(Cc2ccccc2)c1)c1cc(N2CCCCC2)on1]

To a solution of 5-(piperidin-1-yl)isoxazole-3-carboxylic acid (80 mg, 0.4 mmol) in N,N-dimethylformamide (15 mL) was added 1-benzyl-1H-pyrazol-4-amine (69 mg, 0.4 mmol), 1-[bis(dimethylamino)methylene]-1H-1,2,3-triazolo[4,5-b]pyridinium 3-oxide hexafluorophosphate (0.456 g, 1.2 mmol) and diisopropylethylamine (0.155 g, 1.2 mmol). The mixture was stirred at 25° C. for 17 h. The crude sample was dissolved in minimum amount of N,N-dimethylformamide and purified by prep-HPLC (Boston C18 21×250 mm 10 µm column; acetonitrile/0.01% aqueous trifluoroacetic acid) to give N-(1-benzyl-1H-pyrazol-4-yl)-5-(piperidin-1-yl)isoxazole-3-carboxamide (30.5 mg, 0.08 mmol, 23%) as a white solid. ¹H NMR (500 MHz, Dimethylsulfoxide-d₆) δ 10.64 (s, 1H), 8.10 (s, 1H), 7.63 (s, 1H), 7.40-7.11 (m, 5H), 5.62 (s, 1H), 5.31 (s, 2H), 3.33 (s, 4H), 1.58 (s, 6H); LCMS (ESI) m/z: 352.1 [M+H]⁺.

Example 21. Preparation of N-(1-benzyl-1H-pyrazol-4-yl)-4,5,6,7-tetrahydrobenzo[d]isoxazole-3-carboxamide (156)

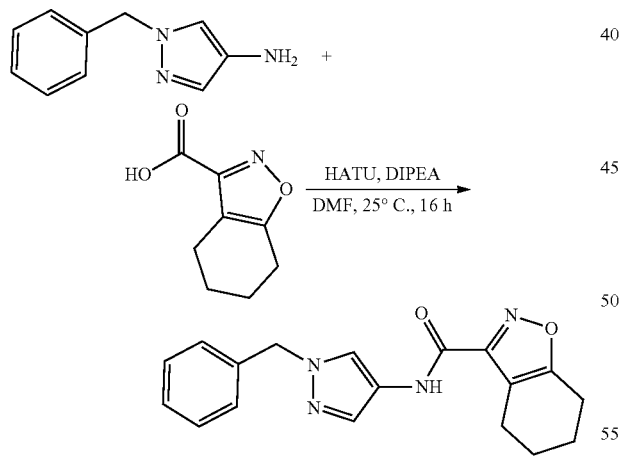

To a solution of 1-benzyl-1H-pyrazol-4-amine (0.050 g, 0.289 mmol), 4,5,6,7-tetrahydrobenzo[d]isoxazole-3-carboxylic acid (48.2 mg, 0.289 mmol) and 1-[bis(dimethylamino)methylene]-1H-1,2,3-triazolo[4,5-b]pyridinium 3-oxide hexafluorophosphate (109 mg, 0.289 mmol) in N,N'-dimethylformamide (1 mL) at 25° C. was added diisopropylethylamine (0.075 mL, 0.433 mmol). The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 60% ethyl acetate/hexanes for 20 min) to afford N-(1-benzyl-1H-pyrazol-4-yl)-4,5,6,7-tetrahydrobenzo[d]isoxazole-3-carboxamide (35.2 mg, 0.109 mmol, 38%) as a pale yellow solid. ¹H NMR (300 MHz, Dimethylsulfoxide-d₆) δ 11.35 (s, 1H), 8.55 (s, 1H), 8.06 (s, 1H), 7.82-7.59 (m, 5H), 5.72 (s, 2H), 3.16 (q, J=5.9 Hz, 4H), 2.13 (dt, J=12.9, 6.9 Hz, 4H); LCMS (ESI) m/z: 323.3 [M+H]⁺.

Example 22. Preparation of N-(1-benzyl-1H-pyrazol-4-yl)-5-(2-methyloxazol-5-yl)isoxazole-3-carboxamide (164)

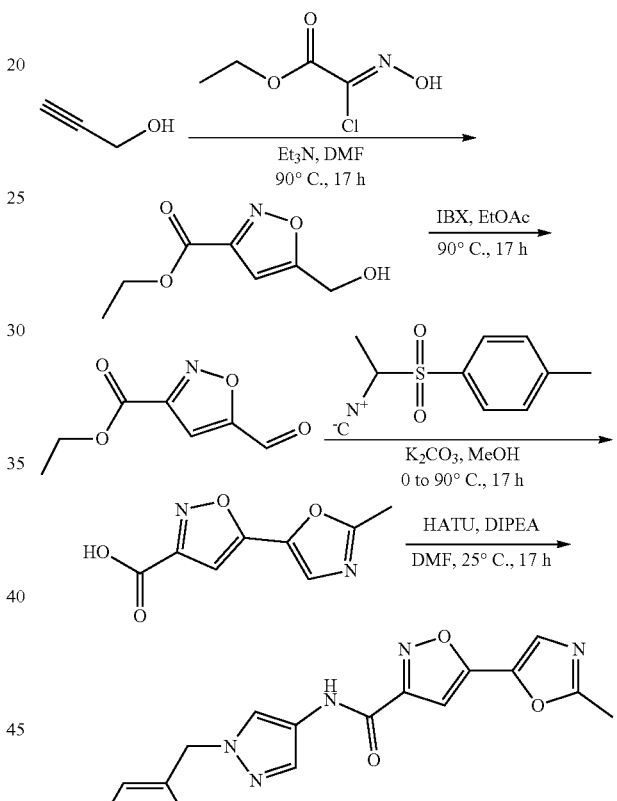

Step 1: Preparation of ethyl 5-(hydroxymethyl)isoxazole-3-carboxylate

To a solution of prop-2-yn-1-ol (8.4 g, 149 mmol) in N,N-dimethylformamide (25 mL) was added a solution of (Z)-ethyl 2-chloro-2-(hydroxyimino)acetate (7.5 g, 49.7 mmol) in N,N-dimethylformamide (50 mL) dropwise over 40 min under nitrogen atmosphere. After addition, the reaction mixture was heated to 90° C. and a solution of triethylamine (15.0 g, 149 mmol) in N,N-dimethylformamide (25 mL) was added dropwise over 1 h. The reaction mixture was heated at 90° C. for 17 h and then cooled to room temperature. The reaction mixture was diluted with ethyl acetate (50 mL), washed with water (60 mL×2) and brine (60 mL×2), dried over anhydrous sodium sulfate, filtered and concentrated in vacuo. The residue was purified by column chromatography (silica, petroleum ether/ethyl acetate=6/1) to give ethyl 5-(hydroxymethyl)isoxazole-3-carboxylate (4.5 g, 26.3 mmol, 53%) as a yellow oil. LCMS (ESI) m/z: 172.1 [M+H]$^+$.

Step 2: Preparation of ethyl 5-formylisoxazole-3-carboxylate

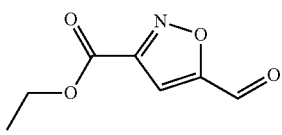

To a solution of ethyl 5-(hydroxymethyl)isoxazole-3-carboxylate (4.5 g, 26.3 mmol) in ethyl acetate (80.0 mL) was added 2-iodoxybenzoic acid (22.1 g, 78.9 mmol). After addition, the reaction mixture was heated to 90° C. and stirred for 17 h, then cooled to room temperature. The reaction mixture was filtered and concentrated in vacuo. The residue was purified by column chromatography (silica, petroleum ether/ethyl acetate=6/1) to give ethyl 5-formylisoxazole-3-carboxylate (3.5 g, 20.7 mmol, 80%) as a yellow oil.

Step 3: Preparation of 5-(2-methyloxazol-5-yl)isoxazole-3-carboxylic Acid

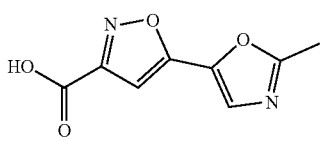

To a solution of 1-(1-isocyanoethylsulfonyl)-4-methylbenzene (1.85 g, 8.87 mmol) in acetonitrile (30 mL) was added potassium carbonate (2.4 g, 17.7 mmol). The reaction mixture was stirred at 25° C. for 1 h. The reaction mixture was cooled to 0° C. and ethyl 5-formylisoxazole-3-carboxylate (1.5 g, 8.87 mmol) was added. The reaction mixture was then heated to 90° C. for 17 h. The reaction was cooled to room temperature, diluted with water (20 mL) and adjusted to pH=3 with aqueous 1N hydrogen chloride solution. The aqueous layer was extracted with ethyl acetate (10 mL×3). The combined organic layers were washed with brine (10 mL×2), dried over anhydrous sodium sulfate, filtered and concentrated in vacuo to afford 5-(2-methyloxazol-5-yl)isoxazole-3-carboxylic acid (0.220 g, 1.13 mmol, 12%) as a white solid. LCMS (ESI) m/z: 195.1 [M+H]$^+$. This material was used directly in the next step without further purification.

Step 4: Preparation of N-(1-benzyl-1H-pyrazol-4-yl)-5-(2-methyloxazol-5-yl)isoxazole-3-carboxamide

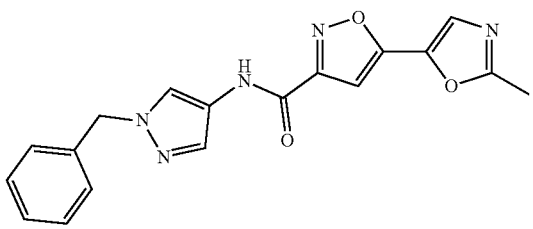 [SMILES: Cc1ncc(-c2cc(C(=O)Nc3cnn(Cc4ccccc4)c3)no2)o1]

To a solution of 5-(2-methyloxazol-5-yl)isoxazole-3-carboxylic acid (60 mg, 0.3 mmol) in N,N-dimethylformamide (15 mL) was added 1-benzyl-1H-pyrazol-4-amine (52 mg, 0.3 mmol), 1-[bis(dimethylamino)methylene]-1H-1,2,3-triazolo[4,5-b]pyridinium 3-oxide hexafluorophosphate (0.352 g, 0.9 mmol) and diisopropylethylamine (0.116 g, 0.9 mmol). The mixture was stirred at 25° C. for 17 h and purified via prep-HPLC (Boston C18 21×250 mm 10 μm column; acetonitrile/0.01% aqueous trifluoroacetic acid) to give N-(1-benzyl-1H-pyrazol-4-yl)-5-(2-methyloxazol-5-yl)isoxazole-3-carboxamide (25.8 mg, 0.07 mmol, 25%) as a white solid. $^1$H NMR (400 MHz, Dimethylsulfoxide-d$_6$) δ 11.04 (s, 1H), 8.60 (s, 1H), 8.16 (s, 1H), 7.67 (s, 1H), 7.40-7.19 (m, 6H), 5.34 (s, 2H), 2.44 (s, 3H); LCMS (ESI) m/z: 350.1 [M+H]$^+$.

Example 23. Preparation of N-(1-(3-fluorobenzyl)-1H-pyrazol-4-yl)-5-(prop-1-en-2-yl)isoxazole-3-carboxamide (58)

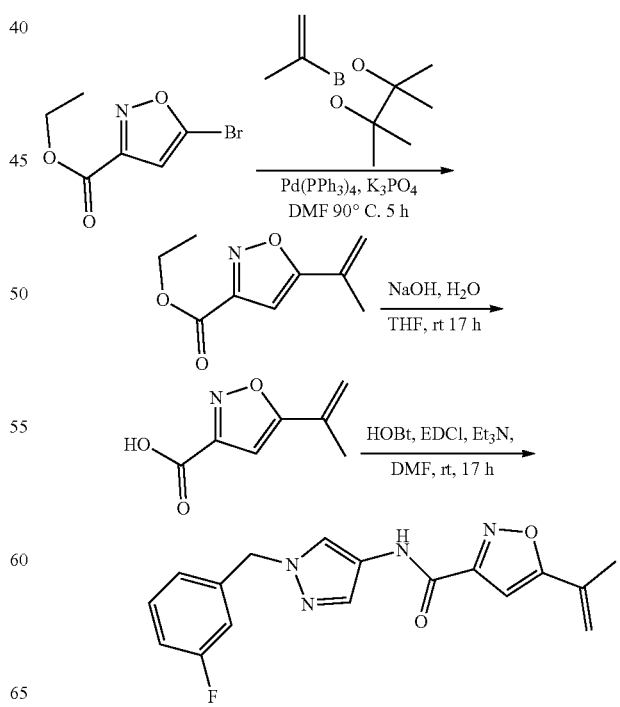

Step 1: Preparation of ethyl 5-(prop-1-en-2-yl)isoxazole-3-carboxylate

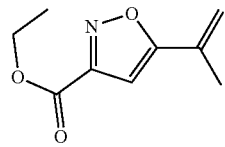

To a solution of ethyl 5-bromoisoxazole-3-carboxylate (0.960 g, 4.36 mmol) in N,N-dimethylformamide (20 mL) under nitrogen was added 4,4,5,5-tetramethyl-2-(prop-1-en-2-yl)-1,3,2-dioxaborolane (0.879 g, 5.23 mmol), tetrakis(triphenylphosphine)palladium(0) (0.504 g, 0.43 mmol) and potassium phosphate (1.8 g, 8.72 mmol). The mixture was heated at 90° C. for 5 h. The mixture was diluted with water (30 mL), extracted with ethyl acetate (20 mL×2). The combined organic layers were washed with water (20 mL×2) and brine (40 mL×2), then dried over anhydrous sodium sulfate, filtered and concentrated in vacuo. The residue was purified by column chromatography (silica, petroleum ether/ethyl acetate=20/1) to afford ethyl 5-(prop-1-en-2-yl)isoxazole-3-carboxylate (0.660 g, 3.64 mmol, 84%) as a yellow oil. LCMS (ESI) m/z: 182.2 [M+H]$^+$.

Step 2: Preparation of 5-(prop-1-en-2-yl)isoxazole-3-carboxylic Acid

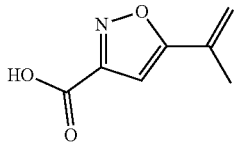

To a solution of ethyl 5-(prop-1-en-2-yl)isoxazole-3-carboxylate (0.660 g, 3.64 mmol) in tetrahydrofuran/water (v/v=4/1, 20 mL) at 15° C. was added sodium hydroxide (0.349 g, 8.73 mmol). The reaction mixture was stirred at room temperature for 17 h. The reaction mixture was evaporated to dryness, diluted with water (30 mL) and adjusted to pH=2 with aqueous 1N hydrogen chloride. The reaction mixture was then extracted with ethyl acetate (20 mL×2). The combined organic layers were washed with brine (20 mL×2), dried over anhydrous sodium sulfate, filtered and concentrated in vacuo to afford 5-(prop-1-en-2-yl)isoxazole-3-carboxylic acid (0.350 g, 2.28 mmol, 63%) as a yellow solid. LCMS (ESI) m/z 154.1 [M+H]$^+$. This material was used directly in the next step without further purification.

Step 3: Preparation of N-(1-(3-fluorobenzyl)-1H-pyrazol-4-yl)-5-(prop-1-en-2-yl)isoxazole-3-carboxamide

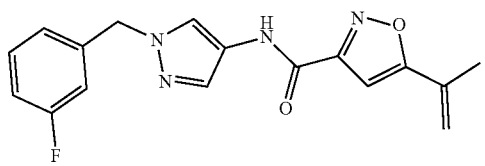 [SMILES: C=C(C)c1cc(C(=O)Nc2cnn(Cc3cccc(F)c3)c2)no1]

To a solution of 5-(prop-1-en-2-yl)isoxazole-3-carboxylic acid (0.350 g, 2.28 mmol) in N,N-dimethylformamide (20 mL) was added 1-(3-fluorobenzyl)-1H-pyrazol-4-amine (0.435 g, 2.28 mmol), triethylamine (0.691 g, 6.84 mmol), 1-hydroxybenzotriazole hydrate (0.462 g, 3.42 mmol) and N-(3-dimethylaminopropyl)-N-ethylcarbodiimide hydrochloride (1.22 g, 6.84 mmol). The mixture was stirred at room temperature for 17 h, then purified directly by Prep-HPLC (Boston C18 21×250 mm 10 μm column; acetonitrile/0.01% aqueous trifluoroacetic acid) to afford N-(1-(3-fluorobenzyl)-1H-pyrazol-4-yl)-5-(prop-1-en-2-yl)isoxazole-3-carboxamide (0.433 g, 1.32 mmol, 58%) as a white solid. $^1$H NMR (400 MHz, Dimethylsulfoxide-d$_6$) δ 10.97 (s, 1H), 8.20 (s, 1H), 7.68 (s, 1H), 7.40 (dt, J=14.1, 7.1 Hz, 1H), 7.21-7.10 (m, 1H), 7.09-6.96 (m, 3H), 5.86 (s, 1H), 5.48 (s, 1H), 5.36 (s, 2H), 2.11 (s, 3H); LCMS (ESI) m/z: 327.1 [M+H]$^+$.

Example 24. Preparation of 4-phenylpiperidin-1-yl)(5-(pyridin-4-yl)isoxazol-3-yl)methanone, trifluoroacetic Acid (313)

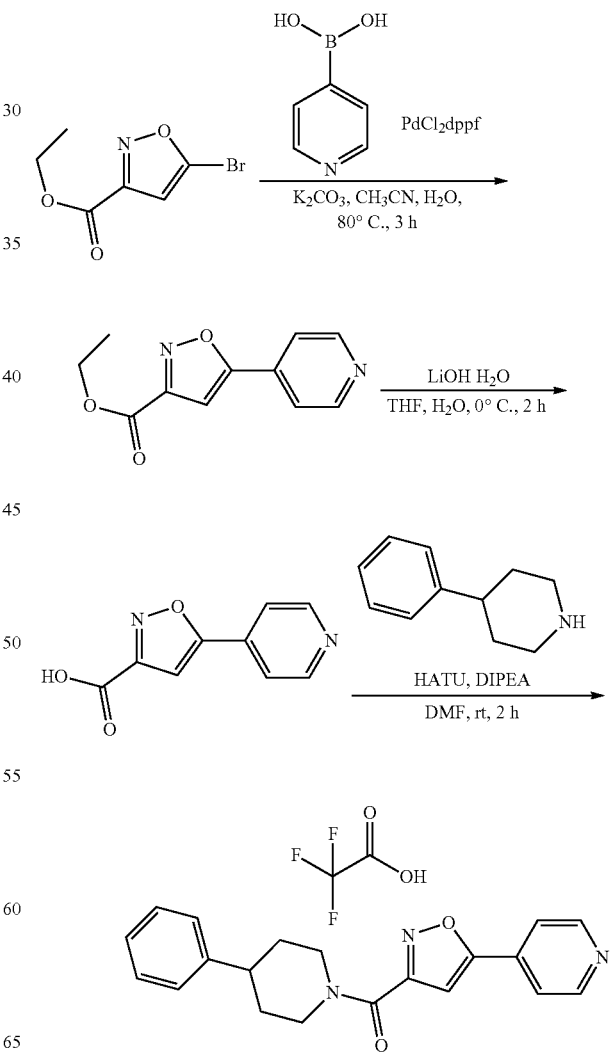

Step 1: Preparation of ethyl 5-(pyridin-4-yl)isoxazole-3-carboxylate

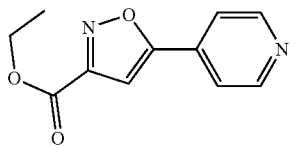 [SMILES: CCOC(=O)c1cc(-c2ccncc2)on1]

A mixture of ethyl 5-bromoisoxazole-3-carboxylate (0.850 g, 3.86 mmol), pyridin-4-ylboronic acid (0.522 g, 4.25 mmol), [1,1'-bis(diphenylphosphino)ferrocene]palladium(II) dichloride (0.285 g, 0.39 mmol) and potassium carbonate (1.07 g, 7.72 mmol) in acetonitrile (40 mL) and water (10 mL) under nitrogen was heated at 80° C. for 3 h. The mixture was concentrated under reduced pressure, and the residue was purified by column chromatography (silica, petroleum ether/ethyl acetate=4/1) to give ethyl 5-(pyridin-4-yl)isoxazole-3-carboxylate (0.280 g, 1.28 mmol, 33%) as a yellow solid. LCMS (ESI) m/z: 219.1 [M+H]$^+$.

Step 2: Preparation of 5-(pyridin-4-yl)isoxazole-3-carboxylic Acid

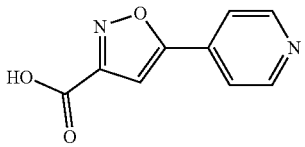 [SMILES: O=C(O)c1cc(-c2ccncc2)on1]

To a stirred solution of ethyl 5-(pyridin-4-yl)isoxazole-3-carboxylate (0.280 g, 1.28 mmol) in tetrahydrofuran (10 mL) and water (10 mL) at 0° C. was added lithium hydroxide monohydrate (0.107 g, 2.56 mmol). The mixture was stirred at this temperature for 2 h. The volatiles were removed under reduced pressure and the aqueous layer was adjusted to pH=5 with aqueous 1N hydrogen chloride. The resulting precipitate was collected by filtration and dried in vacuo to give 5-(pyridin-4-yl)isoxazole-3-carboxylic acid (0.120 g, 0.63 mmol, 49%) as a white solid. LCMS (ESI) m/z: 191.2 [M+H]$^+$.

Step 3: Preparation of (4-phenylpiperidin-1-yl)(5-(pyridin-4-yl)isoxazol-3-yl)methanone, trifluoroacetic Acid

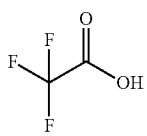

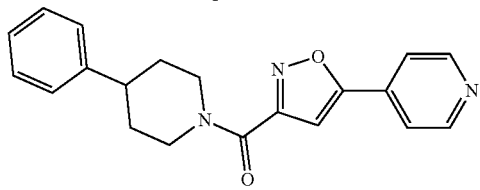

To a stirred solution of 5-(pyridin-4-yl)isoxazole-3-carboxylic acid (40.0 mg, 0.21 mmol), 4-phenylpiperidine (40.0 mg, 0.25 mmol) and 1-[bis(dimethylamino)methylene]-1H-1,2,3-triazolo[4,5-b]pyridinium 3-oxide hexafluorophosphate (0.122 g, 0.32 mmol) in N,N'-dimethylformamide (3 mL) was added diisopropylethylamine (54.0 mg, 0.42 mmol). After addition, the reaction mixture was stirred at room temperature for 2 h. The mixture was purified by prep-HPLC (column: Sunfire prep C18 10 μm OBD 19×250 mm; mobile phase: [water (0.05% trifluoroacetic acid)-acetonitrile]; B %: 60%-88%, 15 min gradient) to give (4-phenylpiperidin-1-yl)(5-(pyridin-4-yl)isoxazol-3-yl)methanone, trifluoroacetic acid (0.036 g, 0.08 mmol, 38%) as a white solid. $^1$H NMR (500 MHz, Dimethylsulfoxide-d$_6$) δ 8.88 (d, J=6.0 Hz, 2H), 8.07-8.06 (m, 2H), 7.72 (s, 1H), 7.33-7.19 (m, 5H), 4.67-4.64 (m, 1H), 4.11-4.08 (m, 1H), 3.33-3.27 (m, 1H), 2.99-2.86 (m, 2H), 1.94-1.91 (m, 1H), 1.85-1.82 (m, 1H), 1.69-1.58 (m, 2H); LCMS (ESI) m/z: 334.1 [M+H]$^+$.

Example 25. Preparation of N-(1-(3-fluorobenzyl)-1H-pyrazol-4-yl)-5-isopropylisoxazole-3-carboxamide (60)

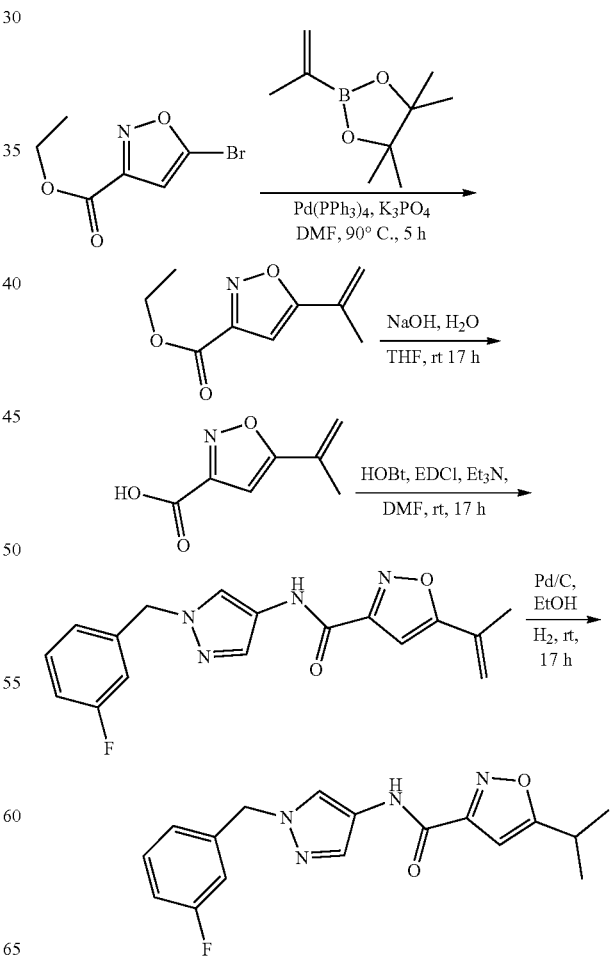

Step 1: Preparation of ethyl
5-(prop-1-en-2-yl)isoxazole-3-carboxylate

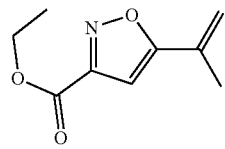

To a mixture of ethyl 5-bromoisoxazole-3-carboxylate (0.960 g, 4.36 mmol) in N,N-dimethylformamide (20 mL) under nitrogen was added 4,4,5,5-tetramethyl-2-(prop-1-en-2-yl)-1,3,2-dioxaborolane (0.879 g, 5.23 mmol), tetrakis(triphenylphosphine)palladium(0) (0.504 g, 0.43 mmol) and potassium phosphate (1.8 g, 8.72 mmol). The mixture was heated at 90° C. for 5 h. The mixture was cooled, diluted with water (30 mL) and then extracted with ethyl acetate (20 mL×2). The combined organic layers were washed with water (20 mL×2), brine (40 mL×2), dried over anhydrous sodium sulfate, filtered and concentrated in vacuo. The residue was purified by column chromatography (silica, petroleum ether/ethyl acetate=20/1) to give ethyl 5-(prop-1-en-2-yl)isoxazole-3-carboxylate (0.660 g, 3.64 mmol, 84%) as a yellow oil. LCMS (ESI) m/z: 182.2 [M+H]$^+$.

Step 2: Preparation of
5-(prop-1-en-2-yl)isoxazole-3-carboxylic Acid

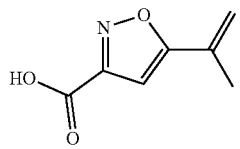

To a solution of ethyl 5-(prop-1-en-2-yl)isoxazole-3-carboxylate (0.660 g, 3.64 mmol) in tetrahydrofuran/water (v/v=4:1, 20 mL) at 15° C. was added sodium hydroxide (0.349 g, 8.73 mmol). The reaction mixture was stirred at room temperature for 17 h. The reaction mixture was evaporated to dryness, diluted with water (30 mL) and adjusted to pH=2 with aqueous 1N hydrogen chloride solution. The reaction mixture was then extracted with ethyl acetate (20 mL×2). The combined organic layers were washed with brine (20 mL×2), dried over anhydrous sodium sulfate, filtered and concentrated in vacuo to give 5-(prop-1-en-2-yl)isoxazole-3-carboxylic acid (0.350 g, 2.28 mmol, 63%) as a yellow solid. LCMS (ESI) m/z: 154.1 [M+H]$^+$. This material was used directly in the next step without further purification.

Step 3: Preparation of N-(1-(3-fluorobenzyl)-1H-pyrazol-4-yl)-5-(prop-1-en-2-yl)isoxazole-3-carboxamide

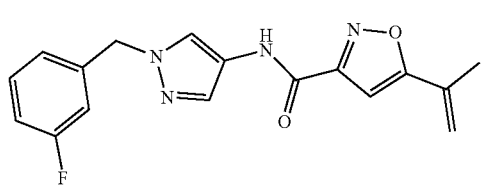 [SMILES: C=C(C)c1cc(C(=O)Nc2cnn(Cc3cccc(F)c3)c2)no1]

To a solution of 5-(prop-1-en-2-yl)isoxazole-3-carboxylic acid (0.350 g, 2.28 mmol) in N,N-dimethylformamide (20 mL) was added 1-(3-fluorobenzyl)-1H-pyrazol-4-amine (0.435 g, 2.28 mmol), triethylamine (0.691 g, 6.84 mmol), 1-hydroxybenzotriazole hydrate (0.462 g, 3.42 mmol) and N-(3-dimethylaminopropyl)-N'-ethylcarbodiimide hydrochloride (1.22 g, 6.84 mmol). The mixture was stirred at room temperature for 17 h and purified directly by Prep-HPLC (Boston C18 21×250 mm 10 μm column; acetonitrile/0.01% aqueous trifluoroacetic acid)) to give N-(1-(3-fluorobenzyl)-1H-pyrazol-4-yl)-5-(prop-1-en-2-yl)isoxazole-3-carboxamide (0.433 g, 1.32 mmol, 58%) as a white solid. $^1$H NMR (400 MHz, Dimethylsulfoxide-d$_6$) δ 10.97 (s, 1H), 8.20 (s, 1H), 7.68 (s, 1H), 7.40 (dt, J=14.1, 7.1 Hz, 1H), 7.21-7.10 (m, 1H), 7.09-6.96 (m, 3H), 5.86 (s, 1H), 5.48 (s, 1H), 5.36 (s, 2H), 2.11 (s, 3H); LCMS (ESI) m/z: 327.1 [M+H]$^+$.

Step 4: Preparation of N-(1-(3-fluorobenzyl)-1H-pyrazol-4-yl)-5-isopropylisoxazole-3-carboxamide

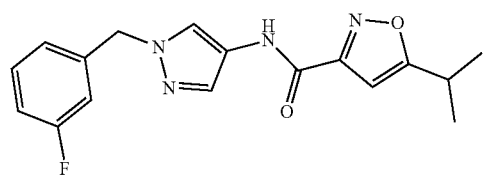 [SMILES: CC(C)c1cc(C(=O)Nc2cnn(Cc3cccc(F)c3)c2)no1]

To a stirred solution of N-(1-(3-fluorobenzyl)-1H-pyrazol-4-yl)-5-(prop-1-en-2-yl)isoxazole-3-carboxamide (0.380 g, 1.16 mmol) in ethanol (20 mL) was added palladium on activated carbon (0.200 g, 10% Pd by weight) at room temperature. The mixture was stirred at room temperature for 17 h under hydrogen. The mixture was filtered through Celite® then concentrated in vacuo. The crude product was dissolved in minimum amount of N,N-dimethylformamide and purified by prep-HPLC (Boston C18 21×250 mm 10 μm column; acetonitrile/0.01% aqueous trifluoroacetic acid) to give N-(1-(3-fluorobenzyl)-1H-pyrazol-4-yl)-5-isopropylisoxazole-3-carboxamide (0.105 g, 0.32 mmol, 27%) as a white solid. $^1$H NMR (400 MHz, Dimethylsulfoxide-d6) δ 10.90 (s, 1H), 8.18 (s, 1H), 7.66 (s, 1H), 7.40 (dt, J=14.0, 7.2 Hz, 1H), 7.20-6.93 (m, 3H), 6.64 (d, J=0.6 Hz, 1H), 5.35 (s, 2H), 3.17 (hept, J=6.9 Hz, 1H), 1.29 (d, J=6.9 Hz, 6H); LCMS (ESI) m/z: 329.1 [M+H]$^+$.

Example 26. Preparation of N-(1-(3-fluorobenzyl)-1H-pyrazol-4-yl)-5-(2-methyloxazol-5-yl)isoxazole-3-carboxamide (67)

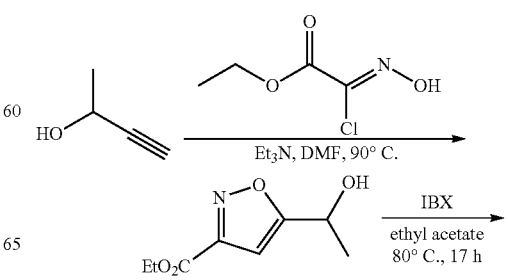

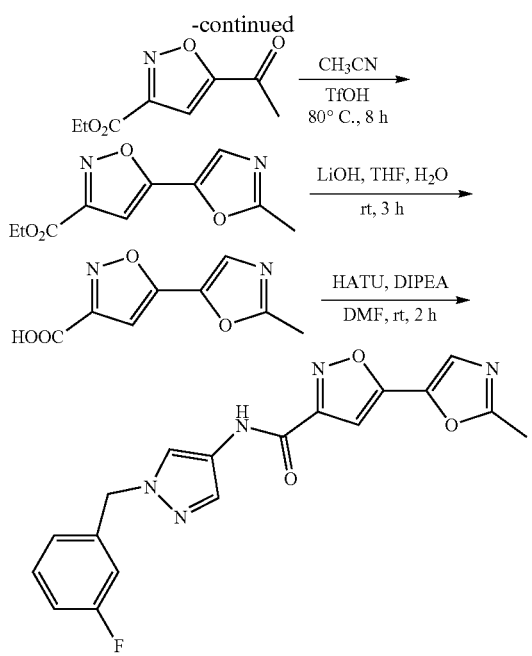

Step 1: Preparation of ethyl 5-(1-hydroxyethyl)isoxazole-3-carboxylate

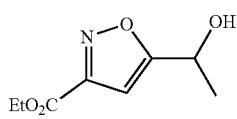

To a solution of but-3-yn-2-ol (5.0 g, 71.4 mmol) in N,N-dimethylformamide (50 mL) was added a solution of (Z)-ethyl 2-chloro-2-(hydroxyimino)acetate (4.33 g, 28.6 mmol) in N,N-dimethylformamide (10 mL) dropwise over 40 min under nitrogen. After addition, the reaction mixture was heated to 90° C. and a solution of triethylamine (8.7 g, 85.7 mmol) in N,N-dimethylformamide (10 mL) was added dropwise over 1 h. The reaction mixture was heated at 90° C. for 17 h, then cooled to room temperature. The reaction mixture was diluted with ethyl acetate (150 mL), washed with water (100 mL×2) and brine (100 mL×2), dried over anhydrous sodium sulfate, filtered and concentrated in vacuo. The residue was purified by column chromatography (silica, petroleum ether/ethyl acetate=4/1) to give ethyl 5-(1-hydroxyethyl)isoxazole-3-carboxylate (1.86 g, 10.1 mmol, 35%) as a yellow oil. LCMS (ESI) m/z: 186.1 [M+H]$^+$.

Step 2: Preparation of ethyl 5-acetylisoxazole-3-carboxylate

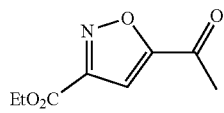

To a solution of ethyl 5-(1-hydroxyethyl)isoxazole-3-carboxylate (5.0 g, 27.0 mmol) in ethyl acetate (50 mL) was added 2-iodoxybenzoic acid (22.7 g, 81.1 mmol). After addition, the reaction mixture was heated to 80° C. and stirred for 17 h, then cooled to room temperature. The reaction mixture was filtered and concentrated in vacuo. The residue was purified by column chromatography (silica, petroleum ether/ethyl acetate=6/1) to give ethyl 5-acetyl-isoxazole-3-carboxylate (4.4 g, 24.0 mmol, 89%) as a yellow oil. LCMS (ESI) m/z: 184.1 [M+H]$^+$.

Step 3: Preparation of ethyl 5-(2-methyloxazol-5-yl)isoxazole-3-carboxylate

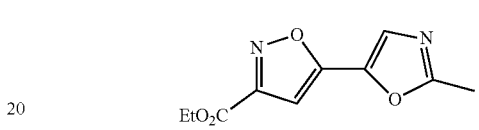

To a solution of iodobenzene diacetate (2.35 g, 5.46 mmol) in acetonitrile (20 mL) was added trifluoromethanesulfonic acid (1.64 g, 10.9 mmol) dropwise under nitrogen at room temperature. After 30 min, a solution of ethyl 5-acetylisoxazole-3-carboxylate (1.0 g, 5.46 mmol) in acetonitrile (10 mL) was added dropwise over 30 min. After addition, the reaction mixture was heated to 80° C. and stirred for 6 h, then cooled to room temperature. The reaction mixture was concentrated in vacuo. The residue was diluted with saturated aqueous sodium hydrogen carbonate (30 mL) and extracted with ethyl acetate (50 mL×2). The combined organic layers were washed with brine (50 mL×2), dried over anhydrous sodium sulfate, filtered and concentrated in vacuo. The residue was purified by column chromatography (silica, petroleum ether/ethyl acetate=4/1) to afford ethyl 5-(2-methyloxazol-5-yl)isoxazole-3-carboxylate (0.31 g, 1.40 mmol, 26%) as a yellow oil. LCMS (ESI) m/z: 223.1 [M+H]$^+$.

Step 4: Preparation of 5-(2-methyloxazol-5-yl)isoxazole-3-carboxylic Acid

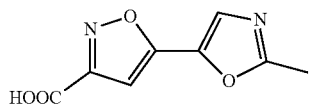

To a solution of ethyl 5-(2-methyloxazol-5-yl)isoxazole-3-carboxylate (0.32 g, 1.44 mmol) in tetrahydrofuran/water (v/v=4/1, 10 mL) at 0° C., was added lithium hydroxide (0.0908 g, 2.16 mmol). The reaction mixture was warmed to room temperature and stirred for 3 h. The reaction was concentrated to dryness, diluted with water (15 mL) and adjusted to pH=2 with aqueous 1N hydrogen chloride solution. The aqueous layer was extracted with dichloromethane (20 mL×2). The combined organic layers was washed with saturated solution of sodium bicarbonate (20 mL×2), brine (20 mL×2), dried over anhydrous sodium sulfate, filtered and concentrated in vacuo to give 5-(2-methyloxazol-5-yl)isoxazole-3-carboxylic acid (0.20 g, 1.03 mmol, 72%) as a white solid. LCMS (ESI) m/z: 195.1 [M+H]$^+$. This material was used directly in the next step without further purification.

Step 5: Preparation of N-(1-(3-fluorobenzyl)-1H-pyrazol-4-yl)-5-(2-methyloxazol-5-yl)isoxazole-3-carboxamide

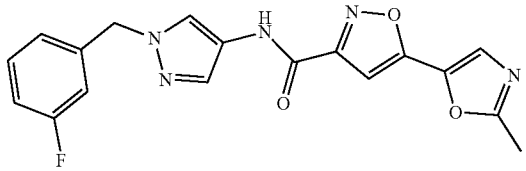 [SMILES: Cc1ncc(-c2cc(C(=O)Nc3cnn(Cc4cccc(F)c4)c3)no2)o1]

To a solution of 5-(2-methyloxazol-5-yl)isoxazole-3-carboxylic acid (0.20 g, 1.03 mmol), 1-(3-fluorobenzyl)-1H-pyrazol-4-amine (0.20 g, 1.24 mmol) and 1-[bis(dimethylamino)methylene]-1H-1,2,3-triazolo[4,5-b]pyridinium 3-oxide hexafluorophosphate (0.47 g, 1.24 mmol) in N,N-dimethylformamide (4 mL) was added triethylamine (0.31 g, 3.09 mmol). The mixture was stirred at room temperature for 2 h then purified directly by Prep-HPLC (Boston C18 21×250 mm 10 μm column; acetonitrile/0.01% aqueous trifluoroacetic acid)) to give N-(1-(3-fluorobenzyl)-1H-pyrazol-4-yl)-5-(2-methyloxazol-5-yl)isoxazole-3-carboxamide (0.0516 g, 0.14 mmol, 14%) as a white solid. $^1$H NMR (500 MHz, Dimethylsulfoxide-$d_6$) δ 11.08 (s, 1H), 8.21 (s, 1H), 7.86 (s, 1H), 7.69 (s, 1H), 7.42-7.37 (m, 1H), 7.24 (s, 1H), 7.17-7.00 (m, 3H), 5.34 (s, 2H), 2.53 (s, 3H); LCMS (ESI) m/z: 368.0 [M+H]$^+$.

Example 27. Preparation of N-(1-(3-fluorobenzyl)-1H-pyrazol-4-yl)-5-vinylisoxazole-3-carboxamide (106)

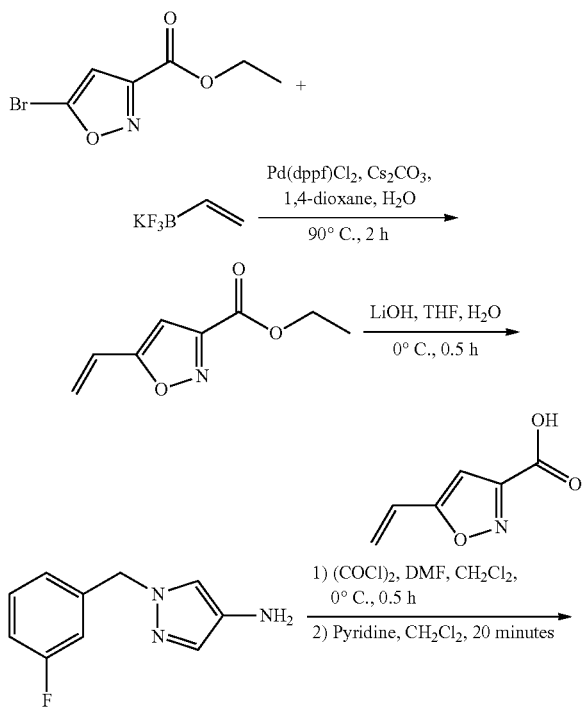

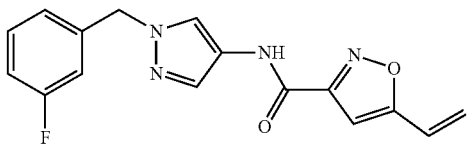

Step 1: Preparation of ethyl 5-vinylisoxazole-3-carboxylate

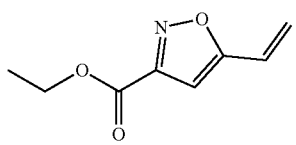

To a mixture of ethyl 5-bromoisoxazole-3-carboxylate (0.400 g, 1.83 mmol) and potassium vinyltrifluoroborate (0.295 g, 2.20 mmol) in 1,4-dioxane (8 mL) and water (2 mL) was added [1,1'-bis(diphenylphosphino)ferrocene]dichloropalladium(II) (0.067 g, 0.092 mmol) and cesium carbonate (1.19 g, 3.66 mmol). The reaction was heated at 90° C. for 2 h under nitrogen. The reaction mixture was cooled then diluted with water (50 mL), filtered through Celite®, and washed with ethyl acetate (20 mL). The filtrate was extracted with ethyl acetate (20 mL×3). The combined organic layers were washed with brine (30 mL), dried over sodium sulfate, filtered and concentrated in vacuo to give ethyl 5-vinylisoxazole-3-carboxylate (0.380 g, crude) as a brown oil that was used in the next step without further purification. LCMS (ESI) m/z: 168.1 [M+H]$^+$.

Step 2: Preparation of 5-vinylisoxazole-3-carboxylic Acid

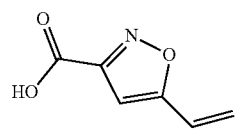

A mixture of ethyl 5-vinylisoxazole-3-carboxylate (0.300 g, 1.8 mmol) in tetrahydrofuran (8 mL) and water (2 mL) was cooled to 0° C. and lithium hydroxide monohydrate (0.151 g, 3.6 mmol) was added. The mixture was stirred at 0° C. for 0.5 h. The reaction was diluted with water (50 mL) and extracted with ethyl acetate (20 mL×2). The water layer was separated and acidified with aqueous 1N hydrogen chloride to pH=2-3 and extracted with ethyl acetate (20 mL×3). The combined extracts were dried over sodium sulfate, filtered and concentrated in vacuo to give 5-vinylisoxazole-3-carboxylic acid (0.380 g, crude) which was used in the next step directly. LCMS (ESI) m/z: 140.1 [M+H]$^+$.

Step 3: Preparation of N-(1-(3-fluorobenzyl)-1H-pyrazol-4-yl)-5-vinylisoxazole-3-carboxamide

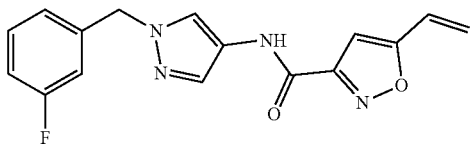 [SMILES: C=Cc1cc(C(=O)Nc2cnn(Cc3cccc(F)c3)c2)no1]

To a solution of 5-vinylisoxazole-3-carboxylic acid (0.100 g, 0.719 mmol) in dichloromethane (2 mL) was added N,N-dimethylformamide (1 drop) and oxalyl chloride (0.183 g, 1.44 mmol) at 0° C. The reaction mixture was stirred at 0° C. for 0.5 h and then concentrated in vacuo. The crude oil was dissolved in dichloromethane (2 mL) and added to a mixture of 1-(3-fluorobenzyl)-1H-pyrazol-4-amine hydrochloride (0.163 g, 0.719 mmol) and pyridine (0.228 g, 2.88 mmol) in dichloromethane (2 mL) at 0° C. The reaction mixture was stirred at 0° C. for 20 min and then concentrated in vacuo. The crude product was dissolved in minimum amount of N,N-dimethylformamide and purified by prep-HPLC (Boston C18 21×250 mm 10 μm column; acetonitrile/0.01% aqueous trifluoroacetic acid) to give N-(1-(3-fluorobenzyl)-1H-pyrazol-4-yl)-5-vinylisoxazole-3-carboxamide (0.106 g, 0.34 mmol, 47%) as a white solid. $^1$H NMR (400 MHz, Dimethylsulfoxide-d$_6$) δ 10.98 (s, 1H), 8.19 (s, 1H), 7.67 (s, 1H), 7.45-7.32 (m, 1H), 7.11 (tt, J=12.0, 6.0 Hz, 1H), 7.07-6.95 (m, 3H), 6.84 (dd, J=18.0, 11.6 Hz, 1H), 6.14 (d, J=18.0 Hz, 1H), 5.74 (d, J=11.6 Hz, 1H), 5.36 (s, 2H); LCMS (ESI) m/z: 313.1 [M+H]$^+$.

Example 28. Preparation of 5-ethyl-N-(1-(3-fluorobenzyl)-1H-pyrazol-4-yl)isoxazole-3-carboxamide (104)

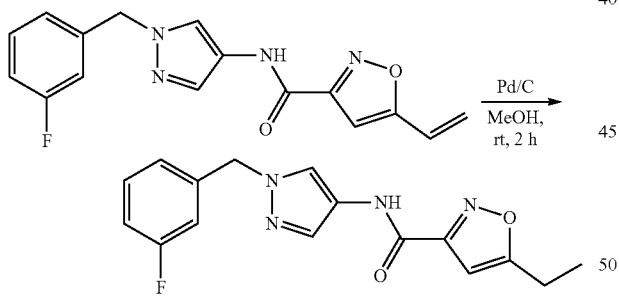

Step 1: Preparation of 5-ethyl-N-(1-(3-fluorobenzyl)-1H-pyrazol-4-yl)isoxazole-3-carboxamide

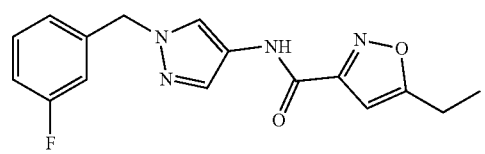 [SMILES: CCc1cc(C(=O)Nc2cnn(Cc3cccc(F)c3)c2)no1]

A mixture N-(1-(3-fluorobenzyl)-1H-pyrazol-4-yl)-5-vinylisoxazole-3-carboxamide (0.320 g, 1.03 mmol) and palladium 10% on activated carbon (0.030 g, 10% Pd by weight) in methanol (5 mL) under hydrogen (balloon) was stirred at room temperature for 2 h. The reaction mixture was filtered through Celite® and washed with methanol (20 mL). The filtrate was concentrated in vacuo, dissolved in minimal amount of N,N-dimethylformamide and purified by prep-HPLC (Boston C18 21×250 mm 10 μm column; acetonitrile/0.01% aqueous trifluoroacetic acid) to give 5-ethyl-N-(1-(3-fluorobenzyl)-1H-pyrazol-4-yl)isoxazole-3-carboxamide (0.167 g, 0.53 mmol, 52%) as a pink solid. $^1$H NMR (400 MHz, Dimethylsulfoxide-d$_6$) δ 10.90 (s, 1H), 8.17 (s, 1H), 7.66 (s, 1H), 7.40 (dt, J=14.0, 7.2 Hz, 1H), 7.18-7.09 (m, 1H), 7.05 (t, J=8.4 Hz, 2H), 6.64 (s, 1H), 5.34 (s, 2H), 2.84 (q, J=7.6 Hz, 2H), 1.26 (t, J=7.6 Hz, 3H); LCMS (ESI) m/z: 315.1 [M+H]$^+$.

Example 29. Preparation of 5-chloro-N-(1-(3-fluorobenzyl)-1H-pyrazol-4-yl)isoxazole-3-carboxamide (105)

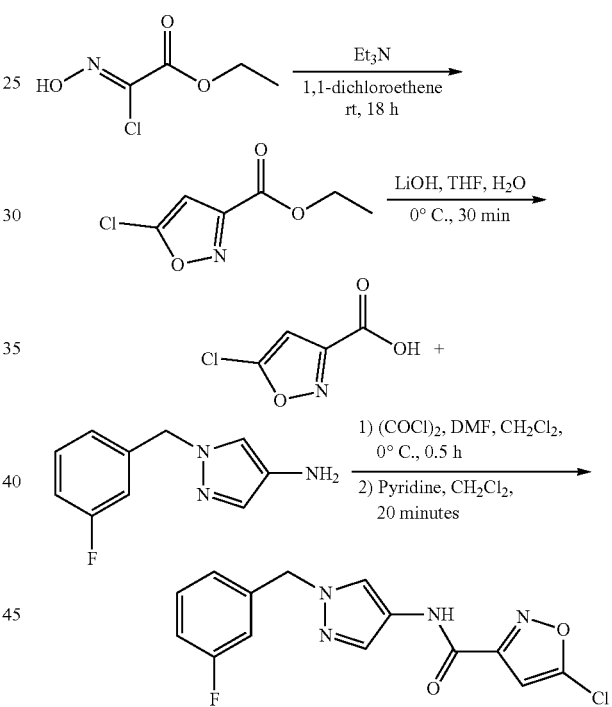

Step 1: Preparation of ethyl 5-chloroisoxazole-3-carboxylate

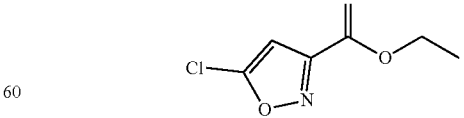

To a solution of (Z)-ethyl 2-chloro-2-(hydroxyimino)acetate (10.0 g, 66.2 mmol) in 1,1-dichloroethene (100 mL) was added a solution of triethylamine (16.8 g, 166 mmol) in 1,1-dichloroethene (100 mL) over a period of 2 h. The reaction mixture was stirred at room temperature for 16 h.

The reaction was poured into water (500 mL) and extracted with dichloromethane (200 mL×3). The combined organic layers were washed with brine (500 mL), dried over sodium sulfate, filtered and concentrated in vacuo. The crude product was purified by column chromatography (silica, ethyl acetate/petroleum ether=1/20) to give ethyl 5-chloroisoxazole-3-carboxylate (1.67 g, mmol, 14%) as a yellow oil. LCMS (ESI) m/z: 376.1 [M+H]+.

Step 2: Preparation of 5-chloroisoxazole-3-carboxylic Acid

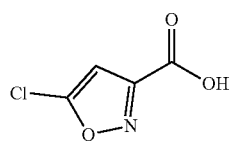

A mixture of ethyl 5-chloroisoxazole-3-carboxylate (0.200 g, 1.14 mmol) in tetrahydrofuran (1.6 mL) and water (0.4 mL) was cooled to 0° C. and lithium hydroxide hydrate (0.096 g, 2.28 mmol) was added. The mixture was stirred at 0° C. for 0.5 h then diluted with water (10 mL) and extracted with ethyl acetate (10 mL×2). The aqueous phase was separated and acidified to pH=2-3 with 1N aqueous hydrochloric acid solution and then extracted with ethyl acetate (10 mL×3). The combined extracts were dried over sodium sulfate, filtered and concentrated in vacuo to give 5-chloroisoxazole-3-carboxylic acid (140 mg, crude) as a white solid that was used directly in the next step. LCMS (ESI) m/z: 148.1 [M+H]+.

Step 3: Preparation of 5-chloro-N-(1-(3-fluorobenzyl)-1H-pyrazol-4-yl)isoxazole-3-carboxamide

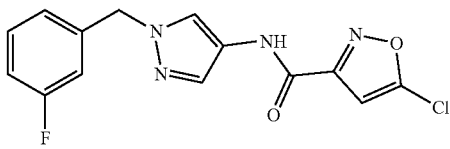 [SMILES: O=C(Nc1cnn(Cc2cccc(F)c2)c1)c1cc(Cl)on1]

To a solution of 5-chloroisoxazole-3-carboxylic acid (0.120 g, 0.816 mmol) in dichloromethane (2 mL) was added N,N-dimethylformamide (1 drop) and oxalyl chloride (0.207 g, 1.63 mmol) at 0° C. The reaction mixture was stirred at 0° C. for 0.5 h then concentrated in vacuo. The crude yellow oil was dissolved in dichloromethane (2 mL) and added to a mixture of 1-(3-fluorobenzyl)-1H-pyrazol-4-amine hydrochloride (0.185 g, 0.816 mmol) and pyridine (0.258 g, 3.26 mmol) in dichloromethane (2 mL) at 0° C. The reaction mixture was stirred at 0° C. for 20 min. The reaction mixture was concentrated in vacuo then dissolved in minimum amount of N,N-dimethylformamide and purified by prep-HPLC (Boston C18 21×250 mm 10 μm column; acetonitrile/0.01% aqueous trifluoroacetic acid) to give 5-chloro-N-(1-(3-fluorobenzyl)-1H-pyrazol-4-yl)isoxazole-3-carboxamide (0.111 g, 0.348 mmol, 36%) as a white solid. 1H NMR (500 MHz, Dimethylsulfoxide-d6) δ 11.07 (s, 1H), 8.19 (s, 1H), 7.67 (s, 1H), 7.44-7.36 (m, 1H), 7.17-7.09 (m, 2H), 7.05 (t, J=9.5 Hz, 2H), 5.36 (s, 2H); LCMS (ESI) m/z: 321.1 [M+H]+.

Example 30. Preparation of N-(1-(3-fluorobenzyl)-1H-pyrazol-4-yl)-5-morpholinoisoxazole-3-carboxamide (101)

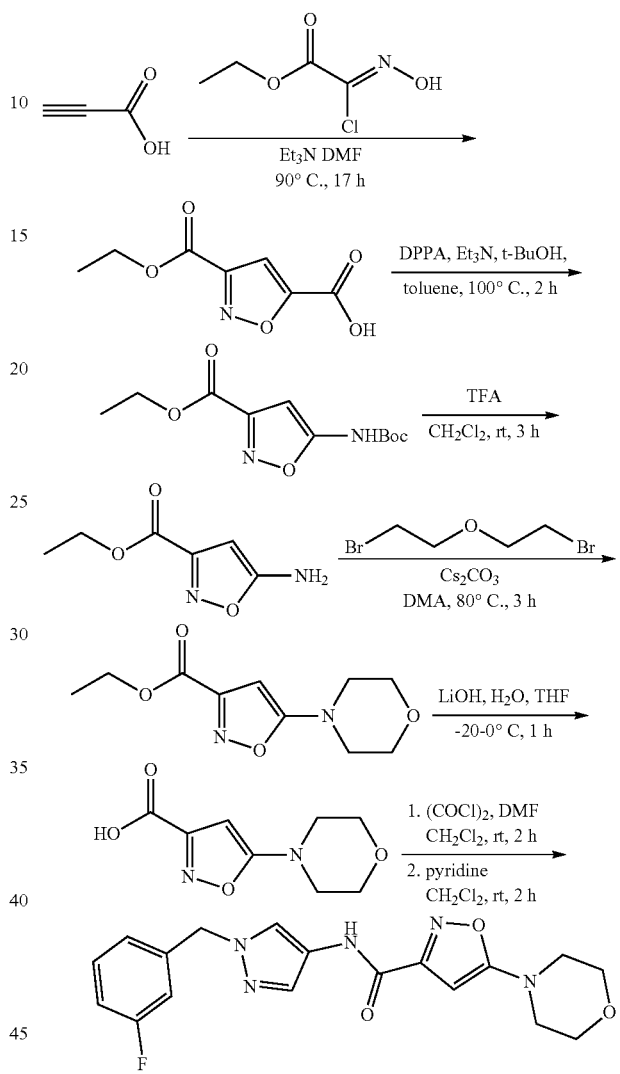

Step 1: Preparation of 3-(ethoxycarbonyl)isoxazole-5-carboxylic Acid

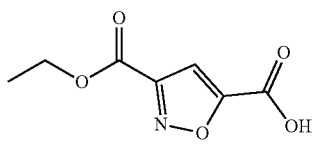

To a solution of propiolic acid (23.0 g, 328.5 mmol) in N,N-dimethylformamide (200 mL) at room temperature was added a solution of (Z)-ethyl 2-chloro-2-(hydroxyimino) acetate (20.0 g, 132 mmol) in N,N-dimethylformamide (100 mL) dropwise over 40 min under nitrogen. After addition, the reaction mixture was heated to 90° C. and a solution of triethylamine (40.1 g, 397 mmol) in N,N-dimethylformamide (100 mL) was added dropwise over 1 h. The reaction mixture was heated at 90° C. for 17 h then cooled to room temperature. The reaction mixture was concentrated to dryness, diluted with water (200 mL) and adjusted to pH=2 with aqueous 1N hydrogen chloride. The reaction mixture was then extracted with ethyl acetate (100 mL×2) and the combined organic layers were washed with brine (10 mL×2), dried over anhydrous sodium sulfate, filtered and concentrated in vacuo. The crude 3-(ethoxycarbonyl)isoxazole-5-carboxylic acid (10.3 g, 55.6 mmol, 16.9%) was obtained as a yellow oil and was used directly in the next step without further purification. LCMS (ESI) m/z: 186.0 [M+H]$^+$.

Step 2: Preparation of ethyl 5-(tert-butoxycarbonylamino)isoxazole-3-carboxylate

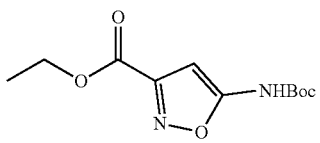 [SMILES: CCOC(=O)c1cc(NC(=O)OC(C)(C)C)on1]

To a solution of 3-(ethoxycarbonyl)isoxazole-5-carboxylic acid (10.3 g, 55.6 mmol) in toluene (30 mL) was added triethylamine (6.73 g, 66.7 mmol), tert-butanol (10.3 g, 139.0 mmol) and diphenyl phosphoryl azide (18.3 g, 66.7 mmol). The reaction mixture was heated at 100° C. for 2 h then cooled and concentrated under reduced pressure. The residue was purified by column chromatography (silica, petroleum ether/ethyl acetate=8/1) to give ethyl 5-(tert-butoxycarbonylamino)isoxazole-3-carboxylate (3.1 g, 12.1 mmol, 22%) as a white solid.

Step 3: Preparation of ethyl 5-aminoisoxazole-3-carboxylate

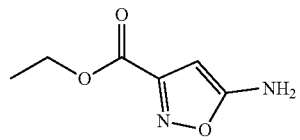

To a solution of ethyl 5-(tert-butoxycarbonylamino)isoxazole-3-carboxylate (3.1 g, 12.1 mmol) in dichloromethane (30 mL) was added trifluoroacetic acid (15 mL). The mixture was stirred at room temperature for 3 h then concentrated in vacuo. The residue was purified by column chromatography (silica, petroleum ether/ethyl acetate=1/1) to give ethyl 5-aminoisoxazole-3-carboxylate (0.740 g, 4.74 mmol, 41%) as a white solid. LCMS (ESI) m/z: 157.1 [M+H]$^+$.

Step 4: Preparation of ethyl 5-morpholinoisoxazole-3-carboxylate

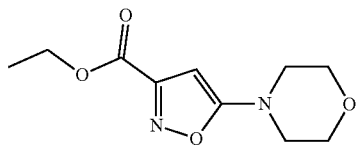 [SMILES: CCOC(=O)c1cc(N2CCOCC2)on1]

To a solution of ethyl 5-aminoisoxazole-3-carboxylate (0.320 g, 2.05 mmol) in dimethylacetamide (20 mL) was added cesium carbonate (1.99 g, 6.15 mmol) and 1-bromo-2-(2-bromoethoxy)ethane (1.18 g, 5.12 mmol). The reaction mixture was stirred at 80° C. for 3 h then cooled to room temperature. The mixture was diluted with water (30 mL), then extracted with ethyl acetate (10 mL×2). The combined organic layers were washed with brine (10 mL×2), dried over anhydrous sodium sulfate, filtered and concentrated in vacuo. The residue was purified by column chromatography (silica, petroleum ether/ethyl acetate=3:1) to give ethyl 5-morpholinoisoxazole-3-carboxylate (0.260 g, 1.15 mmol, 56%) as a white solid. LCMS (ESI) m/z: 227.2 [M+H]$^+$.

Step 5: Preparation of 5-morpholinoisoxazole-3-carboxylic Acid

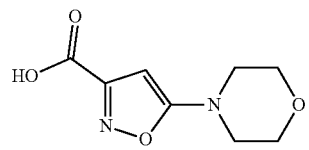 [SMILES: O=C(O)c1cc(N2CCOCC2)on1]

To a solution of ethyl 5-morpholinoisoxazole-3-carboxylate (0.260 g, 1.15 mmol) in tetrahydrofuran/water (v/v=4:1, 20 mL) at −20° C., was added lithium hydroxide hydrate (0.145 g, 3.45 mmol). The reaction mixture was stirred at 0° C. for 1 h then concentrated in vacuo, diluted with water (15 mL) and adjusted to pH=2 with aqueous 1N hydrogen chloride solution. The reaction mixture was then extracted with dichloromethane (10 mL×2). The combined organic layers were washed with brine (10 mL×2), dried over anhydrous sodium sulfate, filtered and concentrated in vacuo to give 5-morpholinoisoxazole-3-carboxylic acid (0.200 g, 1.01 mmol, 88%) as a white solid which was used directly without further purification. LCMS (ESI) m/z: 199.1 [M+H]$^+$.

Step 6: Preparation of N-(1-(3-fluorobenzyl)-1H-pyrazol-4-yl)-5-morpholinoisoxazole-3-carboxamide

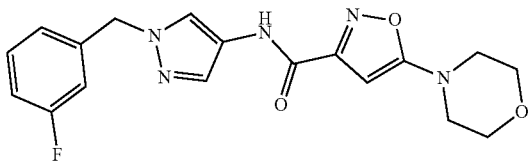 [SMILES: O=C(Nc1cnn(Cc2cccc(F)c2)c1)c1cc(N2CCOCC2)on1]

To a solution of 5-morpholinoisoxazole-3-carboxylic acid (0.200 g, 1.01 mmol) in dichloromethane (15 mL) at 0° C. was added oxalyl chloride (0.256 g, 2.02 mmol) and N,N-dimethylformamide (0.01 mL). The reaction mixture was warmed to room temperature for 1 h then concentrated in vacuo. The residue was diluted with dichloromethane (8 mL) and added to a solution of 1-(3-fluorobenzyl)-1H-pyrazol-4-amine (0.193 g, 1.01 mmol) and pyridine (0.359 g, 4.54 mmol) in dichloromethane (10 mL) at 0° C. The reaction mixture was stirred at room temperature for 2 h. The reaction mixture was evaporated to dryness. The crude product was dissolved in minimum amount of N,N-dimethylformamide and purified by prep-HPLC (Boston C18 21×250 mm 10 μm column; acetonitrile/0.01% aqueous trifluoroacetic acid) to give N-(1-(3-fluorobenzyl)-1H-pyrazol-4-yl)-5-morpholinoisoxazole-3-carboxamide (0.0812 g, 0.21 mmol, 22%) as a white solid. ¹H NMR (400 MHz, Dimethylsulfoxide-d₆) δ 10.72 (s, 1H), 8.16 (s, 1H), 7.66 (s, 1H), 7.39 (dt, J=14.0, 7.1 Hz, 1H), 7.18-6.95 (m, 3H), 5.72 (s, 1H), 5.34 (s, 2H), 3.76-3.61 (m, 4H), 3.36-3.30 (m, 4H); LCMS (ESI) m/z: 372.1 [M+H]⁺.

Example 31. Preparation of 5-cyclohexenyl-N-(1-(3-fluorobenzyl)-1H-pyrazol-4-yl)isoxazole-3-carboxamide (85)

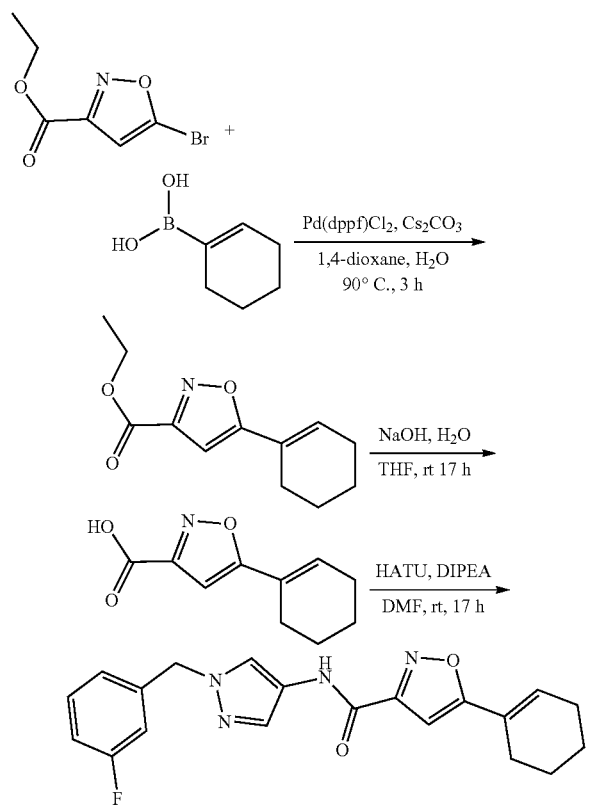

Step 1: Preparation of ethyl 5-cyclohexenylisoxazole-3-carboxylate

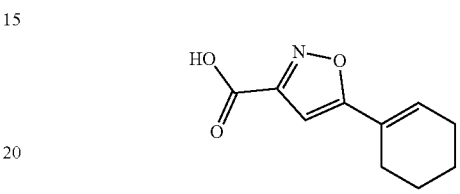

The mixture of ethyl 5-bromoisoxazole-3-carboxylate (1.5 g, 6.81 mmol) in 1,4-dioxane (30 mL) and water (10 mL) under nitrogen was added cyclohexenylboronic acid (1.02 g, 8.17 mmol), [1,1'-bis(diphenylphosphino)ferrocene] dichloropalladium(II) (0.497 g, 0.68 mmol) and cesium carbonate (6.63 g, 20.4 mmol). The mixture was heated at 90° C. for 3 h then cooled to room temperature. The reaction mixture was diluted with water (20 mL) and extracted with ethyl acetate (20 mL×2). The combined organic layers were washed with water (20 mL×2) and brine (20 mL×2), dried over anhydrous sodium sulfate, filtered and concentrated in vacuo. The residue was purified by column chromatography (silica, petroleum ether/ethyl acetate=20/1) to give ethyl 5-cyclohexenylisoxazole-3-carboxylate (1.1 g, 4.97 mmol, 73%) as a yellow oil. LCMS (ESI) m/z: 222.1 [M+H]⁺.

Step 2: Preparation of 5-cyclohexenylisoxazole-3-carboxylic Acid

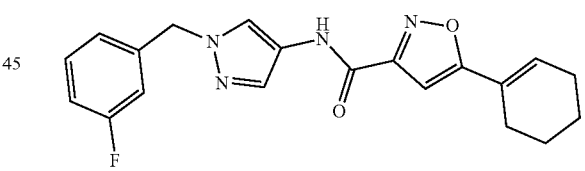

To a solution of ethyl 5-cyclohexenylisoxazole-3-carboxylate (1.1 g, 4.97 mmol) in tetrahydrofuran/water (v/v=4:1, 20 mL) at room temperature was added sodium hydroxide (0.476 g, 11.9 mmol). The reaction mixture was stirred at room temperature for 17 h. The reaction mixture was evaporated to dryness, diluted with water (20 mL) and adjusted to pH=2 with aqueous 1N hydrogen chloride. The aqueous layer was extracted with ethyl acetate (10 mL×2) and the combined organic layers were washed with brine (10 mL×2), dried over anhydrous sodium sulfate, filtered and concentrated in vacuo to give 5-cyclohexenylisoxazole-3-carboxylic acid (0.570 g, 2.95 mmol, 59%) as a white solid. LCMS (ESI) m/z: 194.2 [M+H]⁺. This material was used directly in the next step without additional purification.

Step 3: Preparation of 5-cyclohexenyl-N-(1-(3-fluorobenzyl)-1H-pyrazol-4-yl)isoxazole-3-carboxamide To a solution of 5-cyclohexenylisoxazole-3-carboxylic acid (0.410 g, 2.12 mmol), 1-(3-fluorobenzyl)-1H-pyrazol-4-amine (0.405 g, 2.12 mmol) and 1-[bis(dimethylamino)methylene]-1H-1,2,3-triazolo[4,5-b]pyridinium 3-oxide hexafluorophosphate (2.41 g, 6.36 mmol) in N,N-dimethylformamide (15 mL) was added diisopropylethylamine (0.820 g, 6.36 mmol). The mixture was stirred at room temperature for 17 h and then concentrated in vacuo. The crude product was dissolved in minimum amount of N,N-dimethylformamide and purified by prep-HPLC (Boston C18 21×250 mm 10 m column; acetonitrile/0.01% aqueous trifluoroacetic acid) to give 5-cyclohexenyl-N-(1-(3-fluorobenzyl)-1H-pyrazol-4-yl)isoxazole-3-carboxamide (0.300 g, 0.81 mmol, 27%) as a white solid. ¹H NMR (500 MHz, Dimethylsulfoxide-d₆) δ 10.92 (s, 1H), 8.18 (s, 1H), 7.67 (s, 1H), 7.39 (td, J=7.9, 6.3 Hz, 1H), 7.13 (td, J=8.6, 2.3 Hz, 1H), 7.05 (t, J=9.8 Hz, 2H), 6.83 (s, 1H), 6.68 (d, J=4.0 Hz, 1H), 5.35 (s, 2H), 2.29 (dd, J=60.1, 2.9 Hz, 4H), 1.77-1.54 (m, 4H); LCMS (ESI) m/z: 367.1 [M+H]⁺.

Example 32. Preparation of 5-cyclohexyl-N-(1-(3-fluorobenzyl)-1H-pyrazol-4-yl)isoxazole-3-carboxamide (83)

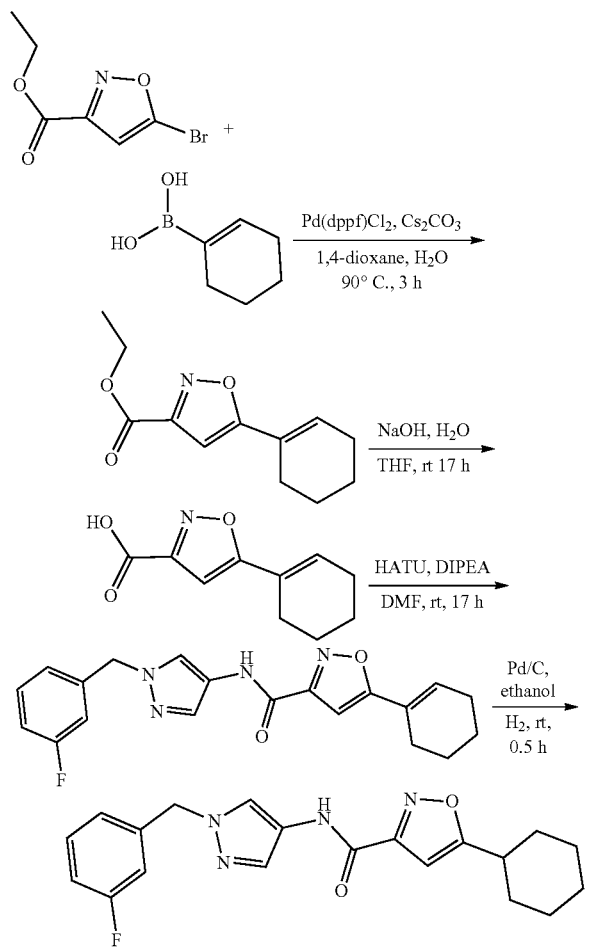

Step 1: Preparation of ethyl 5-cyclohexenylisoxazole-3-carboxylate

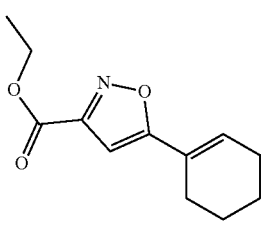 [SMILES: CCOC(=O)c1cc(C2=CCCCC2)on1]

To a solution of ethyl 5-bromoisoxazole-3-carboxylate (1.5 g, 6.81 mmol) in 1,4-dioxane (30 mL) and water (10 mL) under nitrogen was added cyclohexenylboronic acid (1.02 g, 8.17 mmol), [1,1'-bis(diphenylphosphino)ferrocene] dichloropalladium(II) (0.497 g, 0.68 mmol) and cesium carbonate (6.63 g, 20.4 mmol). The mixture was heated at 90° C. for 3 h then cooled, diluted with water (20 mL) and extracted with ethyl acetate (20 mL×2). The combined organic layers were washed with water (20 mL×2) and brine (20 mL×2), dried over anhydrous sodium sulfate, filtered and concentrated in vacuo. The residue was purified by column chromatography (silica, petroleum ether/ethyl acetate=20/1) to give ethyl 5-cyclohexenylisoxazole-3-carboxylate (1.1 g, 4.97 mmol, 73%) as a yellow oil. LCMS (ESI) m/z: 222.1 [M+H]⁺.

Step 2: Preparation of 5-cyclohexenylisoxazole-3-carboxylic Acid

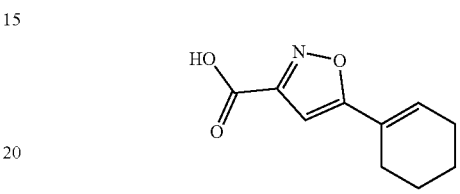

To a solution of ethyl 5-cyclohexenylisoxazole-3-carboxylate (1.1 g, 4.97 mmol) in tetrahydrofuran/water (v/v=4:1, 20 mL) at room temperature was added sodium hydroxide (0.476 g, 11.9 mmol). The reaction mixture was stirred at room temperature for 17 h. The reaction mixture was evaporated to dryness, diluted with water (20 mL) and adjusted to pH=2 with aqueous 1N hydrogen chloride. The aqueous layer was then extracted with ethyl acetate (10 mL×2), and the combined organic layers were washed with brine (10 mL×2), dried over anhydrous sodium sulfate, filtered and concentrated in vacuo to give 5-cyclohexenylisoxazole-3-carboxylic acid (0.570 g, 2.95 mmol, 59%) as a white solid. LCMS (ESI) m/z: 194.2 [M+H]⁺. This material was used directly in the next step without further purification.

Step 3: Preparation of 5-cyclohexenyl-N-(1-(3-fluorobenzyl)-1H-pyrazol-4-yl)isoxazole-3-carboxamide

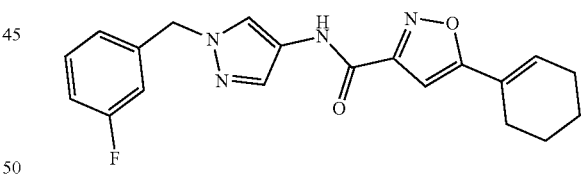

To a solution of 5-cyclohexenylisoxazole-3-carboxylic acid (0.410 g, 2.12 mmol), 1-(3-fluorobenzyl)-1H-pyrazol-4-amine (0.405 g, 2.12 mmol) and 1-[bis(dimethylamino)methylene]-1H-1,2,3-triazolo[4,5-b]pyridinium 3-oxide hexafluorophosphate (2.41 g, 6.36 mmol) in N,N-dimethylformamide (15 mL) was added diisopropylethylamine (0.820 g, 6.36 mmol). The mixture was stirred at room temperature for 17 h and then concentrated under reduced pressure. The crude product was dissolved in minimum amount of N,N-dimethylformamide and purified by prep-HPLC (Boston C18 21×250 mm 10 am column; acetonitrile/ 0.01% aqueous trifluoroacetic acid) to give 5-cyclohexenyl-N-(1-(3-fluorobenzyl)-1H-pyrazol-4-yl)isoxazole-3-carboxamide (0.300 g, 0.81 mmol, 27%) as a white solid. ¹H NMR (500 MHz, Dimethylsulfoxide-d₆) δ 10.92 (s, 1H), 8.18 (s, 1H), 7.67 (s, 1H), 7.39 (td, J=7.9, 6.3 Hz, 1H), 7.13

(td, J=8.6, 2.3 Hz, 1H), 7.05 (t, J=9.8 Hz, 2H), 6.83 (s, 1H), 6.68 (d, J=4.0 Hz, 1H), 5.35 (s, 2H), 2.29 (dd, J=60.1, 2.9 Hz, 4H), 1.77-1.54 (m, 4H); LCMS (ESI) m/z: 367.1 [M+H]⁺.

Step 4: Preparation of 5-cyclohexyl-N-(1-(3-fluorobenzyl)-1H-pyrazol-4-yl)isoxazole-3-carboxamide

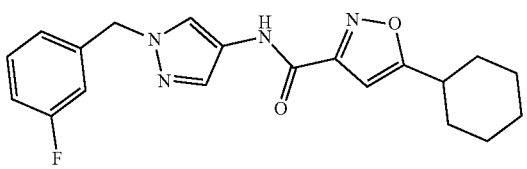 [SMILES: O=C(Nc1cnn(Cc2cccc(F)c2)c1)c1cc(C2CCCCC2)on1]

To a stirred solution of 5-cyclohexenyl-N-(1-(3-fluorobenzyl)-1H-pyrazol-4-yl)isoxazole-3-carboxamide (0.240 g, 0.65 mmol) in ethanol (10 mL) was added palladium on activated carbon (0.100 g, 10% Pd by weight) at room temperature. The mixture was stirred under and atmosphere of hydrogen (balloon) for 0.5 h. The mixture was filtered through Celite® and the filtrate was concentrated in vacuo. The crude product was dissolved in minimum amount of N,N-dimethylformamide and purified by prep-HPLC (Boston C18 21×250 mm 10 μm column; acetonitrile/0.01% aqueous trifluoroacetic acid) to give 5-cyclohexyl-N-(1-(3-fluorobenzyl)-1H-pyrazol-4-yl)isoxazole-3-carboxamide (0.139 g, 0.37 mmol, 58%) as a white solid. ¹H NMR (400 MHz, Dimethylsulfoxide-d₆) δ 10.90 (s, 1H), 8.18 (s, 1H), 7.66 (s, 1H), 7.39 (dt, J=14.0, 7.2 Hz, 1H), 7.18-6.92 (m, 3H), 6.62 (s, 1H), 5.35 (s, 2H), 2.89 (td, J=10.9, 3.4 Hz, 1H), 2.00 (d, J=11.4 Hz, 2H), 1.82-1.59 (m, 3H), 1.42 (tt, J=24.3, 7.3 Hz, 4H), 1.31-1.17 (m, 1H); LCMS (ESI) m/z: 369.2 [M+H]⁺.

Example 33. Preparation of N-(1-(3-fluorobenzyl)-1H-pyrazol-4-yl)-5-(piperidin-1-yl)isoxazole-3-carboxamide (102)

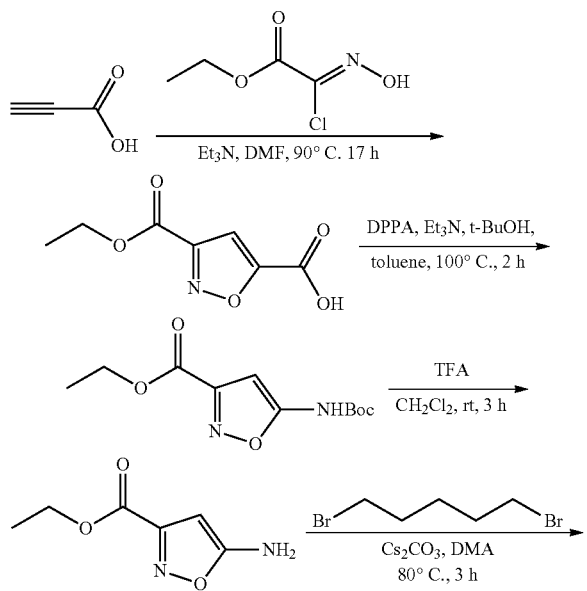

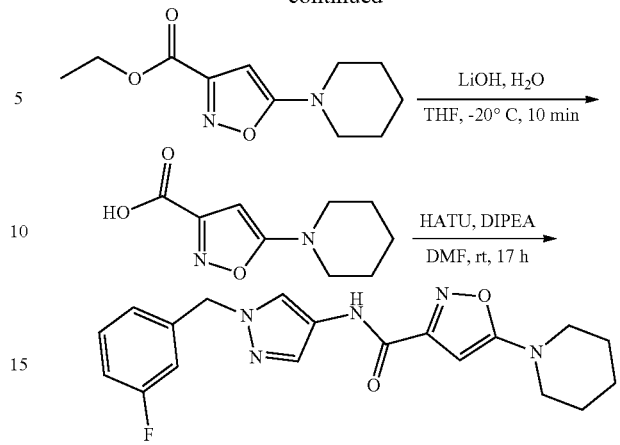

Step 1: Preparation of 3-(ethoxycarbonyl)isoxazole-5-carboxylic Acid

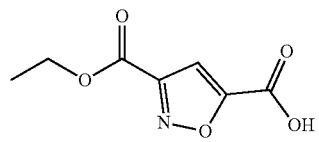

To a solution of propiolic acid (23.0 g, 3295 mmol) in N,N-dimethylformamide (200 mL) at room temperature was added a solution of (Z)-ethyl 2-chloro-2-(hydroxyimino) acetate (20.0 g, 132 mmol) in N,N-dimethylformamide (100 mL) dropwise over 40 min under nitrogen. After addition, the reaction mixture was heated to 90° C. and then a solution of triethylamine (40.1 g, 397 mmol) in N,N-dimethylformamide (100 mL) was added dropwise over 1 h. The reaction mixture was heated at 90° C. for 17 h then cooled to room temperature and evaporated to dryness. The residue was diluted with water (200 mL) and adjusted to pH=2 with aqueous 1N hydrogen chloride. The aqueous layer was extracted with ethyl acetate (100 mL×2) and the combined organic layers were washed with brine (10 mL×2), dried over anhydrous sodium sulfate, filtered and concentrated in vacuo to give 3-(ethoxycarbonyl)isoxazole-5-carboxylic acid (10.3 g, 55.6 mmol, 17%) as a yellow oil. LCMS (ESI) m/z: 186.1 [M+H]⁺. This material was used directly in the next step without further purification.

Step 2: Preparation of ethyl 5-(tert-butoxycarbonylamino)isoxazole-3-carboxylate

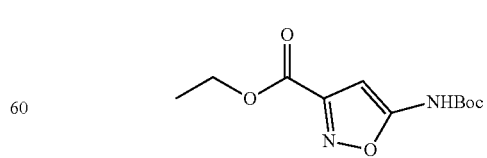

To a solution of 3-(ethoxycarbonyl)isoxazole-5-carboxylic acid (10.3 g, 55.6 mmol) in toluene (30 mL) was added triethylamine (6.73 g, 66.7 mmol), tert-butanol (10.3 g, 139.0 mmol) and diphenyl phosphoryl azide (18.3 g, 66.7 mmol). The reaction mixture was heated at 100° C. for 2 h then cooled and concentrated to dryness. The residue was purified by column chromatography (silica, petroleum ether/ ethyl acetate=8/1) to give ethyl 5-(tert-butoxycarbonylamino)isoxazole-3-carboxylate (3.1 g, 12.1 mmol, 22%) as a white solid. LCMS (ESI) m/z: 257.2 [M+H]+.

Step 3: Preparation of ethyl 5-aminoisoxazole-3-carboxylate

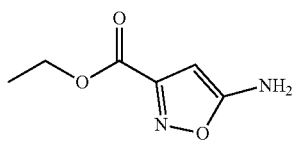

To a solution of ethyl 5-(tert-butoxycarbonylamino)isoxazole-3-carboxylate (3.1 g, 12.1 mmol) in dichloromethane (30 mL) was added trifluoroacetic acid (15 mL). After addition, the mixture was stirred at room temperature for 3 h then concentrated in vacuo. The residue was purified by column chromatography (silica, petroleum ether/ethyl acetate=1/1) to give ethyl 5-aminoisoxazole-3-carboxylate (0.740 g, 4.74 mmol, 41%) as a white solid. (LCMS (ESI) for m/z: 157.1 [M+H]+.

Step 4: Preparation of ethyl 5-(piperidin-1-yl)isoxazole-3-carboxylate

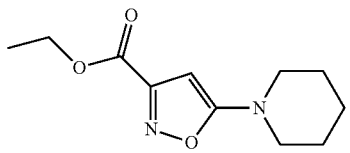 [SMILES: CCOC(=O)c1cc(N2CCCCC2)on1]

To a solution of ethyl 5-aminoisoxazole-3-carboxylate (0.280 g, 1.79 mmol) in N,N-dimethylacetamide (20 mL) at room temperature was added cesium carbonate (1.74 g, 5.37 mmol) and 1,5-dibromopentane (1.02 g, 4.47 mmol). The reaction mixture was heated at 80° C. for 3 h then cooled to room temperature and diluted with water (30 mL). The aqueous layer was extracted with ethyl acetate (10 mL×2) and the combined organic layers were washed with brine (10 mL×2), dried over anhydrous sodium sulfate, filtered and concentrated in vacuo. The residue was purified by column chromatography (silica, petroleum ether/ethyl acetate=3/1) to give ethyl 5-(piperidin-1-yl)isoxazole-3-carboxylate (0.300 g, 1.33 mmol, 75%) as a white solid. LCMS (ESI) m/z: 225.3 [M+H]+.

Step 5: Preparation of 5-(piperidin-1-yl)isoxazole-3-carboxylic Acid

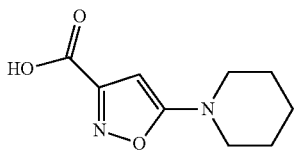 [SMILES: O=C(O)c1cc(N2CCCCC2)on1]

To a solution of ethyl 5-(piperidin-1-yl)isoxazole-3-carboxylate (0.300 mg, 1.33 mmol) in tetrahydrofuran/water (v/v=4:1, 20 mL) at −20° C. was added lithium hydroxide hydrate (0.894 g, 3.99 mmol). The reaction mixture was stirred at 20° C. for 10 min then evaporated to dryness to give 5-(piperidin-1-yl)isoxazole-3-carboxylic acid (0.220 g, 1.12 mmol, 84%) as a white solid. (LCMS (ESI) m/z: 197.1 [M+H]+. This material was used directly in the next step without further purification.

Step 6: Preparation of N-(1-(3-fluorobenzyl)-1H-pyrazol-4-yl)-5-(piperidin-1-yl)isoxazole-3-carboxamide

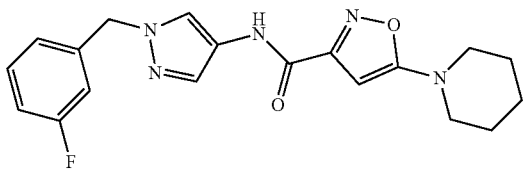 [SMILES: O=C(Nc1cnn(Cc2cccc(F)c2)c1)c1cc(N2CCCCC2)on1]

To a solution of 5-(piperidin-1-yl)isoxazole-3-carboxylic acid (0.220 g, 1.12 mmol) in N,N-dimethylformamide (15 mL) was added 1-(3-fluorobenzyl)-1H-pyrazol-4-amine (0.214 g, 1.12 mmol), 1-[bis(dimethylamino)methylene]-1H-1,2,3-triazolo[4,5-b]pyridinium 3-oxide hexafluorophosphate (1.27 g, 3.36 mmol) and diisopropylethylamine (0.433 g, 3.36 mmol). The mixture was stirred at room temperature for 17 h, and then concentrated in vacuo. The crude product was dissolved in minimum amount of N,N-dimethylformamide and purified by prep-HPLC (Boston C18 21×250 mm 10 m column; acetonitrile/0.01% aqueous trifluoroacetic acid) to give N-(1-(3-fluorobenzyl)-1H-pyrazol-4-yl)-5-(piperidin-1-yl)isoxazole-3-carboxamide (0.0317 g, 0.08 mmol, 8%) as a white solid. 1H NMR (500 MHz, Dimethylsulfoxide-d6) δ 10.66 (s, 1H), 8.15 (s, 1H), 7.65 (s, 1H), 7.39 (td, J=8.0, 6.3 Hz, 1H), 7.18-6.89 (m, 3H), 5.62 (s, 1H), 5.34 (s, 2H), 3.34 (s, 4H), 1.58 (s, 6H); LCMS (ESI) m/z: 370.1 [M+H]+.

Example 34. Preparation of N-(1-(3-fluorobenzyl)-1H-pyrazol-4-yl)-5-(oxazol-5-yl)isoxazole-3-carboxamide (86)

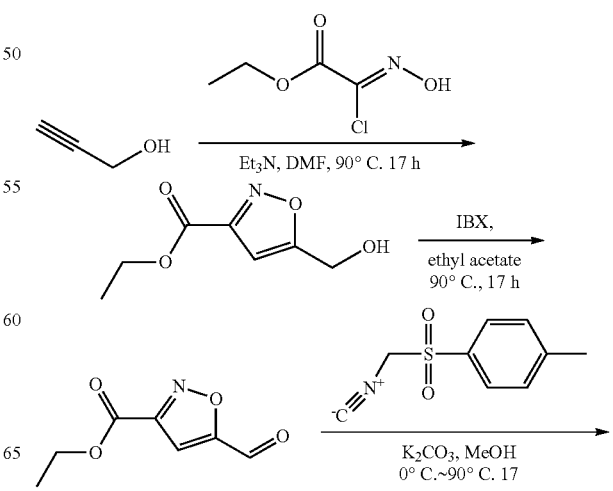

-continued

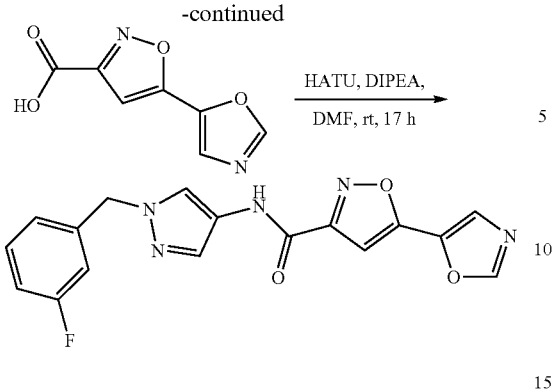

Step 1: Preparation of ethyl 5-(hydroxymethyl)isoxazole-3-carboxylate

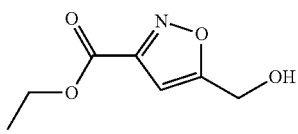

To a solution of prop-2-yn-1-ol (3.3 g, 59.4 mmol) in N,N-dimethylformamide (40 mL) was added a solution of (Z)-ethyl 2-chloro-2-(hydroxyimino)acetate (3.0 g, 19.8 mmol) in N,N-dimethylformamide (10 mL) dropwise over 40 min under nitrogen. After addition, the reaction mixture was heated to 90° C. then a solution of triethylamine (5.9 g, 59.4 mmol) in N,N-dimethylformamide (10 mL) was added dropwise over 1 h. The reaction mixture was heated at 90° C. for 17 h and then cooled to room temperature. The reaction mixture was diluted with ethyl acetate (50 mL), washed with water (60 mL×2) and brine (60 mL×2), dried over anhydrous sodium sulfate, filtered and concentrated in vacuo. The residue was purified by column chromatography (silica, petroleum ether/ethyl acetate=2/1) to give ethyl 5-(hydroxymethyl)isoxazole-3-carboxylate (1.6 g, 9.3 mmol, 49%) as a yellow oil. LCMS (ESI) m/z: 172.1 [M+H]$^+$.

Step 2: Preparation of ethyl 5-formylisoxazole-3-carboxylate

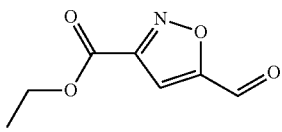

To a solution of ethyl 5-(hydroxymethyl)isoxazole-3-carboxylate (1.2 g, 7.0 mmol) in ethyl acetate (20 mL) was added 2-iodoxybenzoic acid (5.9 g, 21.0 mmol). After addition, the reaction mixture was heated to 90° C. and stirred for 17 h, then cooled to room temperature. The reaction mixture was filtered and concentrated in vacuo. The residue was purified by column chromatography (silica, petroleum ether/ethyl acetate=5/1) to give ethyl 5-formylisoxazole-3-carboxylate (0.540 g, 3.2 mmol, 46%) as a yellow oil.

Step 3: Preparation of 5-(oxazol-5-yl)isoxazole-3-carboxylic Acid

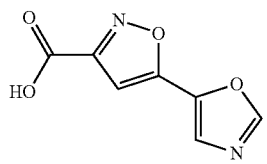 [SMILES: O=C(O)c1cc(-c2cnco2)on1]

To a solution of 1-(isocyanomethylsulfonyl)-4-methylbenzene (0.622 g, 3.19 mmol) in acetonitrile (20 mL) was added potassium carbonate (0.527 g, 3.82 mmol). The reaction mixture was stirred at room temperature for 1 h. The reaction mixture was cooled to 0° C. and 5-(oxazol-5-yl)isoxazole-3-carboxylic acid (0.540 g, 3.19 mmol) was added. The solution was heated to 90° C. and stirred for 17 h. The reaction mixture was cooled to room temperature, diluted with water (15 mL) and adjusted to pH=2 with aqueous 1N hydrogen chloride. The reaction mixture was then extracted with ethyl acetate (10 mL×2). The combined organic layers were washed with brine (10 mL×2), dried over anhydrous sodium sulfate, filtered and concentrated in vacuo to give 5-(oxazol-5-yl)isoxazole-3-carboxylic acid (0.140 mg, 0.77 mmol, 24%) as a white solid. LCMS (ESI) m/z: 181.1 [M+H]$^+$.

Step 4: Preparation of N-(1-(3-fluorobenzyl)-1H-pyrazol-4-yl)-5-(oxazol-5-yl)isoxazole-3-carboxamide

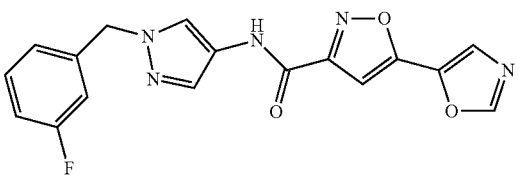 [SMILES: O=C(Nc1cnn(Cc2cccc(F)c2)c1)c1cc(-c2cnco2)on1]

To a solution of 5-(oxazol-5-yl)isoxazole-3-carboxylic acid (0.140 g, 0.77 mmol), 1-(3-fluorobenzyl)-1H-pyrazol-4-amine (0.147 g, 0.77 mmol) and 1-[bis(dimethylamino)methylene]-1H-1,2,3-triazolo[4,5-b]pyridinium 3-oxide hexafluorophosphate (0.877 g, 2.31 mmol) in N,N-dimethylformamide (6 mL) was added diisopropylethylamine (0.298 g, 2.31 mmol). The mixture was stirred at room temperature for 17 h. The crude reaction mixture was purified by prep-HPLC (Boston C18 21×250 mm 10 μm column; acetonitrile/0.01% aqueous trifluoroacetic acid) to give N-(1-(3-fluorobenzyl)-1H-pyrazol-4-yl)-5-(oxazol-5-yl)isoxazole-3-carboxamide (0.070 g, 0.19 mmol, 26%) as a white solid. $^1$H NMR (500 MHz, Dimethylsulfoxide-d$_6$) δ 11.11 (s, 1H), 8.74 (s, 1H), 8.20 (d, J=18.7 Hz, 1H), 8.02 (s, 1H), 7.69 (s, 1H), 7.45-7.28 (m, 2H), 7.20-6.95 (m, 3H), 5.37 (s, 2H); LCMS (ESI) m/z: 354.1 [M+H]$^+$.

Example 35. Preparation of N-(1-(3-fluorobenzyl)-1H-pyrazol-4-yl)-5-(isothiazol-5-yl)isoxazole-3-carboxamide (81)

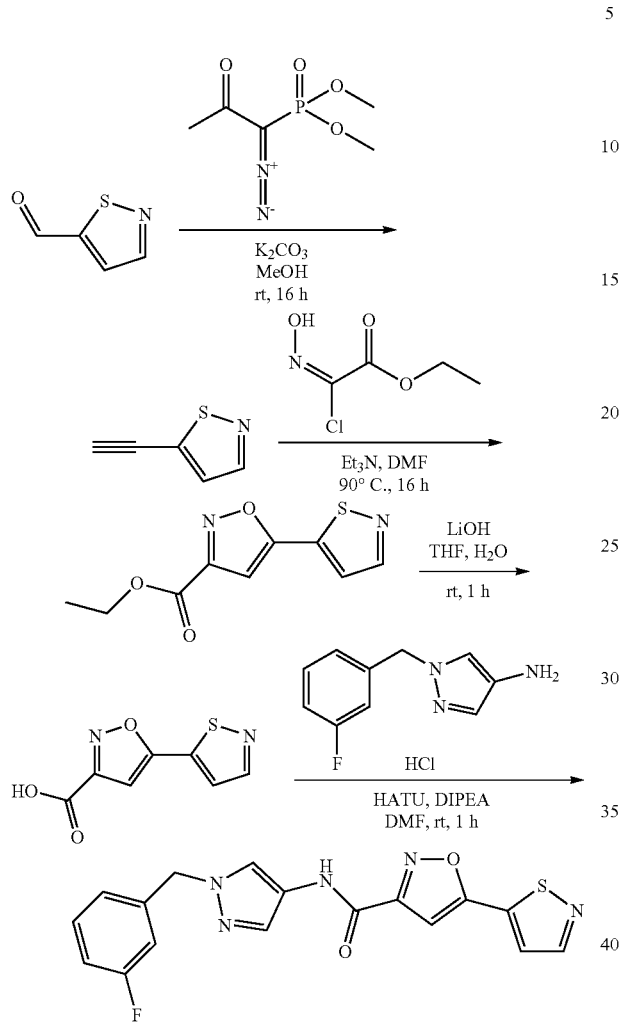

Step 1: Preparation of 5-ethynylisothiazole

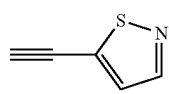

To a stirred mixture of dimethyl 1-diazo-2-oxopropylphosphonate (2.12 g, 11.0 mmol), potassium carbonate (2.76 g, 20.0 mmol) in methanol (100 mL) at 0° C. was added dropwise a solution of isothiazole-5-carbaldehyde (1.13 g, 10.0 mmol) in methanol (5 mL). The reaction mixture was stirred at room temperature for 16 h then poured into water (50 mL) and extracted with ethyl acetate (100 mL×2). The combined organic phases were dried over sodium sulfate, filtered and concentrated to give 5-ethynylisothiazole (0.250 g, 2.29 mmol, 23%) as a red-brown oil. $^1$H NMR (500 MHz, Chloroform-d) δ 8.44 (d, J=1.5 Hz, 1H), 7.36 (d, J=1.5 Hz, 1H), 3.80 (s, 1H).

Step 2: Preparation of ethyl 5-(isothiazol-5-yl)isoxazole-3-carboxylate

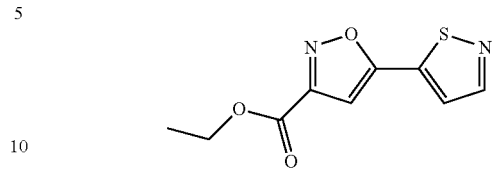

To a stirred solution of 5-ethynylisothiazole (0.250 g, 2.3 mmol) in N,N-dimethylformamide (2 mL) was added a solution of ethyl 2-chloro-2-(hydroxyimino)acetate (0.347 g, 2.3 mmol) in N,N-dimethylformamide (2 mL) dropwise. After the addition was complete, the mixture was stirred at room temperature for 1 h and was then heated to 90° C. Triethylamine (0.465 g, 4.6 mmol) was added dropwise and the reaction mixture was heated at 90° C. for 16 h. The reaction mixture was cooled to room temperature and quenched with water (20 mL) and extracted with ethyl acetate (40 mL×2). The combined organic phases were dried over sodium sulfate, filtered and concentrated in vacuo. The residue was purified by column chromatography (silica, petroleum ether/ethyl acetate=10/1) to afford ethyl 5-(isothiazol-5-yl)isoxazole-3-carboxylate (0.080 g, 0.357 mmol, 16%) as an off-white solid. LCMS (ESI) m/z: 225.1 [M+H]$^+$.

Step 3: Preparation of 5-(isothiazol-5-yl)isoxazole-3-carboxylic Acid

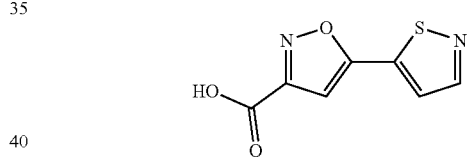

The synthesis of 5-(isothiazol-5-yl)isoxazole-3-carboxylic acid was carried out following the same procedure as in Example 24. Compound 5-(isothiazol-5-yl)isoxazole-3-carboxylic acid (40 mg, 0.94 mmol, 58%) was obtained as an off-white solid. LCMS (ESI) m/z: 197.1 [M+H]$^+$.

Step 4: Preparation of N-(1-(3-fluorobenzyl)-1H-pyrazol-4-yl)-5-(isothiazol-5-yl)isoxazole-3-carboxamide

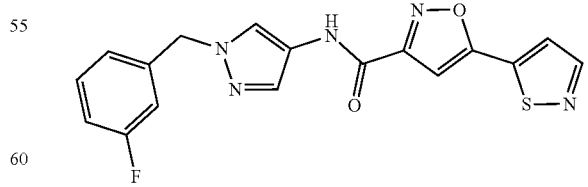

The synthesis of N-(1-(3-fluorobenzyl)-1H-pyrazol-4-yl)-5-(isothiazol-5-yl)isoxazole-3-carboxamide was carried out following the same procedure as in Example 24. Compound N-(1-(3-fluorobenzyl)-1H-pyrazol-4-yl)-5-(isothiazol-5-yl) isoxazole-3-carboxamide (0.0329 g, 0.089 mmol, 45%) was obtained as a white solid. $^1$H NMR (500 MHz, Dimethylsulfoxide-d$_6$). 11.11 (s, 1H), 8.76 (d, J=2.0 Hz, 1H), 8.22 (s, 1H), 8.10 (d, J=1.5 Hz, 1H), 7.69 (s, 1H), 7.61 (s, 1H), 7.40-7.37 (m, 1H), 7.13 (td, J=8.5, 2.0 Hz, 1H), 7.07-7.03 (m, 2H), 5.36 (s, 2H); LCMS (ESI) m/z: 370.0 [M+H]$^+$.

Example 36. Preparation of N-(1-(3-fluorobenzyl)-1H-pyrazol-4-yl)-5-(pyridin-4-yl)isoxazole-3-carboxamide, trifluoroacetic Acid Salt (56)

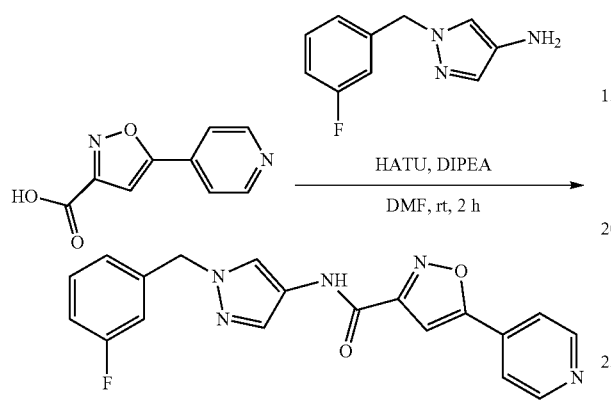

The synthesis of N-(1-(3-fluorobenzyl)-1H-pyrazol-4-yl)-5-(pyridin-4-yl)isoxazole-3-carboxamide, trifluoroacetic acid was carried out following the same procedure as in Example 24. N-(1-(3-fluorobenzyl)-1H-pyrazol-4-yl)-5-(pyridin-4-yl)isoxazole-3-carboxamide, trifluoroacetic acid (0.0509 g, 0.11 mmol, 52%) was obtained as a white solid. $^1$H NMR (500 MHz, Dimethylsulfoxide-d$_6$) δ 11.15 (s, 1H), 8.88-8.87 (m, 2H), 8.24 (s, 1H), 8.10-8.08 (m, 2H), 7.85 (s, 1H), 7.72 (s, 1H), 7.43-7.38 (m, 3H), 5.38 (s, 2H); LCMS (ESI) m/z: 364.1. [M+H]$^+$.

Example 37. Preparation of N-(1-(3-fluorobenzyl)-1H-pyrazol-4-yl)-5-(thiazol-5-yl)isoxazole-3-carboxamide (69)

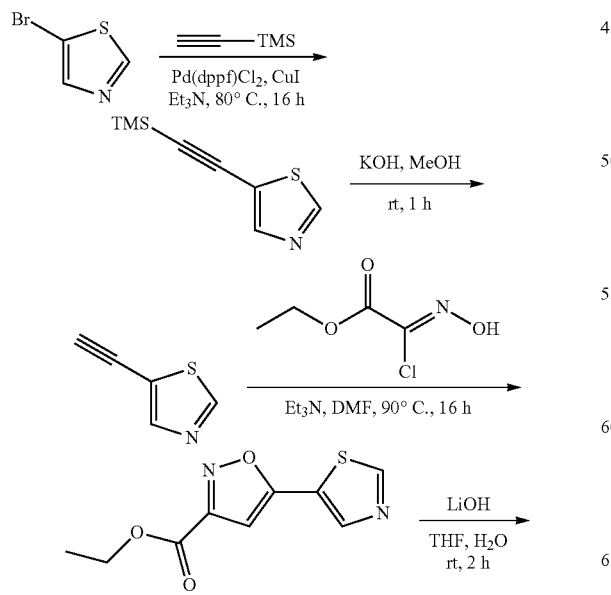

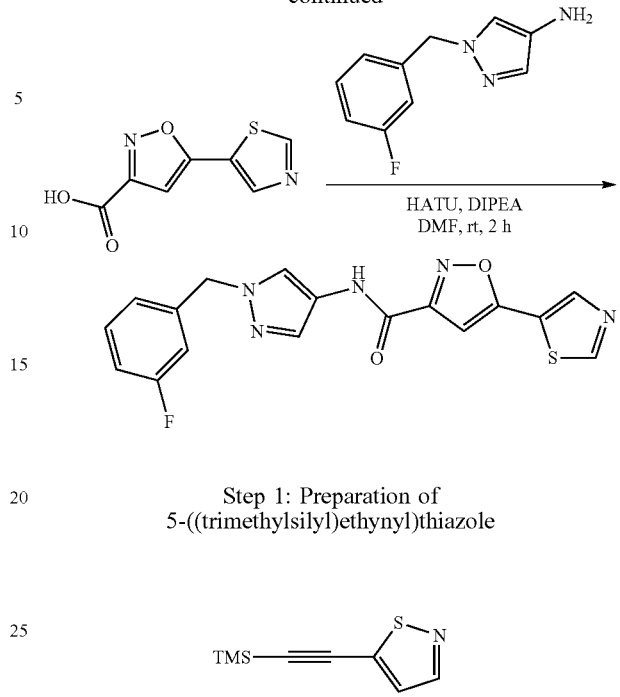

Step 1: Preparation of 5-((trimethylsilyl)ethynyl)thiazole

A mixture of 5-bromothiazole (4.0 g, 24.5 mmol), ethynyltrimethylsilane (4.8 g, 48.96 mmol), [1,1'-bis(diphenylphosphino)ferrocene]dichloropalladium(II) (1.96 g, 2.4 mmol) and copper iodide (475 mg, 2.4 mmol) in triethylamine (30 mL) was heated at 80° C. for 16 h. The mixture was concentrated and purified by column chromatography (silica, petroleum ether/ethyl acetate=10/1) to afford 5-((trimethylsilyl)ethynyl)thiazole (3.2 g, 17.7 mmol, 72%) as a light yellow oil. LCMS (ESI) m/z: 182.1 [M+H]$^+$.

Step 2: Preparation of 5-ethynylthiazole

A mixture of 5-((trimethylsilyl)ethynyl)thiazole (4.0 g, 22.0 mmol), KOH (1.24 g, 22.0 mmol) in methanol (30 mL) was stirred at room temperature for 1 h. The mixture was quenched with saturated aqueous ammonium chloride and extracted with ethyl acetate (150 mL×2). The combined organic phases were dried over sodium sulfate, filtered and concentrated to afford 5-ethynylthiazole (1.5 g, 13.8 mmol, 63%) as a brown oil. $^1$H NMR (500 MHz, Chloroform-d) δ 8.72 (s, 1H), 8.04 (s, 1H), 3.46 (s, 1H).

Step 3: Preparation of ethyl 5-(thiazol-5-yl)isoxazole-3-carboxylate

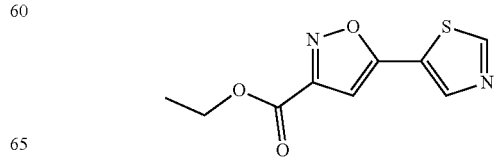

The synthesis of ethyl 5-(thiazol-5-yl)isoxazole-3-carboxylate was accomplished using the same procedure as Example 35 to give ethyl 5-(thiazol-5-yl)isoxazole-3-carboxylate (0.800 g, 3.57 mmol, 26%) as a light yellow solid. LCMS (ESI) m/z: 225.1 [M+H]$^+$.

Step 4: Preparation of 5-(thiazol-5-yl)isoxazole-3-carboxylic Acid

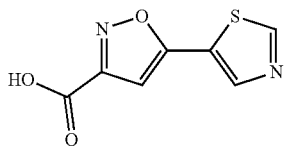 [SMILES: O=C(O)c1cc(-c2cncs2)on1]

The synthesis of 5-(thiazol-5-yl)isoxazole-3-carboxylic acid was carried out following the same procedure as for Example 24. Compound 5-(thiazol-5-yl)isoxazole-3-carboxylic acid (0.280 g, 1.42 mmol, 80%) was obtained as a grey-yellow solid. LCMS (ESI) m/z: 197.1 [M+H]$^+$.

Step 5: Preparation of N-(1-(3-fluorobenzyl)-1H-pyrazol-4-yl)-5-(thiazol-5-yl)isoxazole-3-carboxamide

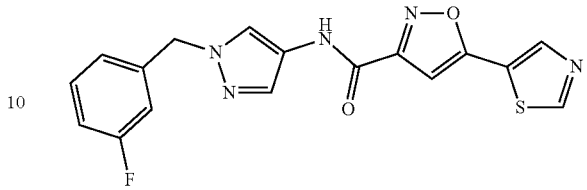

The synthesis of N-(1-(3-fluorobenzyl)-1H-pyrazol-4-yl)-5-(thiazol-5-yl)isoxazole-3-carboxamide was carried out following the same procedure as for Example 24. Compound N-(1-(3-fluorobenzyl)-1H-pyrazol-4-yl)-5-(thiazol-5-yl)isoxazole-3-carboxamide (0.0581 g, 0.157 mmol, 39%) was obtained as a white solid. $^1$H NMR (500 MHz, Dimethylsulfoxide-d$_6$) δ 11.08 (s, 1H), 9.36 (s, 1H), 8.64 (s, 1H), 8.22 (s, 1H), 7.69 (s, 1H), 7.44 (s, 1H), 7.42-7.37 (m, 1H), 7.13 (td, J=8.5, 2.0 Hz, 1H), 7.07-7.04 (m, 2H), 5.36 (s, 2H); LCMS (ESI) m/z: 370.0 [M+H]$^+$.

Example 38. Preparation of N-(1-(3-fluorobenzyl)-1H-pyrazol-4-yl)-5-(pyrimidin-4-yl)isoxazole-3-carboxamide (90) and 5-acetyl-N-(1-(3-fluorobenzyl)-1H-pyrazol-4-yl)isoxazole-3-carboxamide (91)

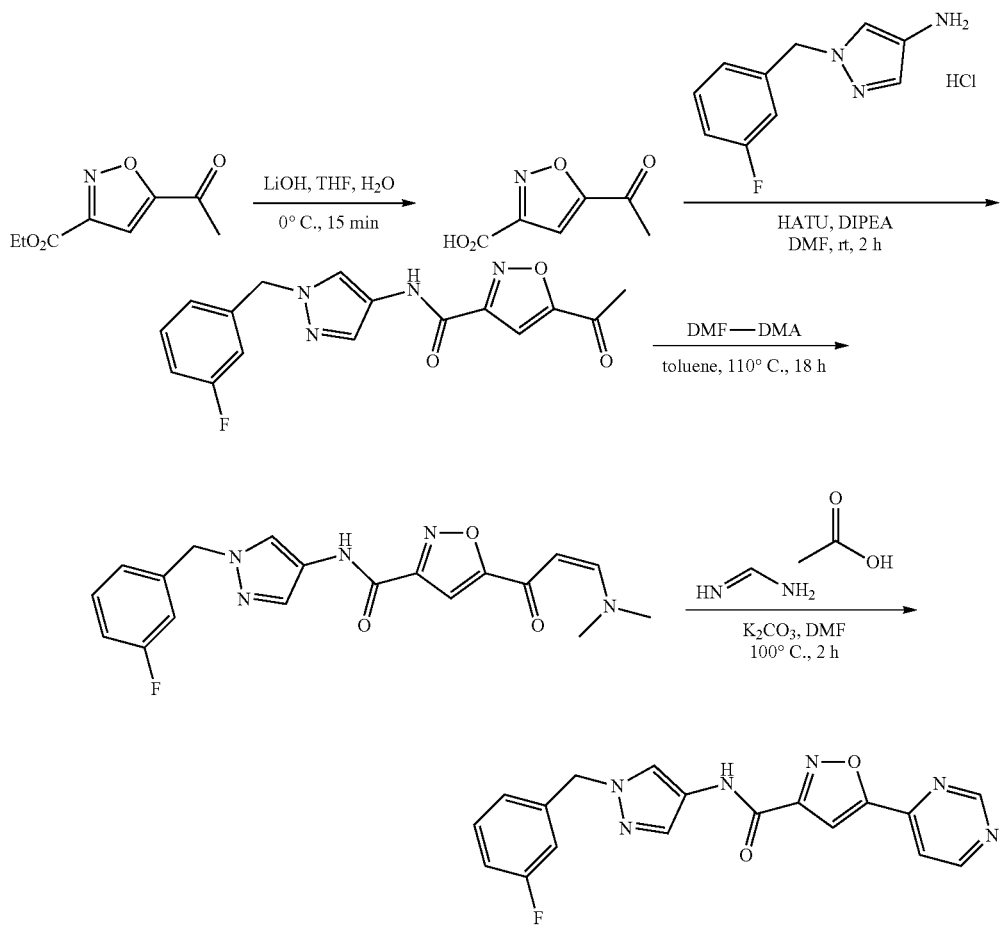

Step 1: Preparation of 5-acetylisoxazole-3-carboxylic Acid

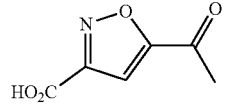

The synthesis of 5-acetylisoxazole-3-carboxylic acid was carried out following the same procedure as in Example 24 to give 5-acetylisoxazole-3-carboxylic acid (0.300 g, crude) as a yellow solid. LCMS (ESI) m/z: 156.1 [M+H]$^+$.

Step 2: Preparation of 5-acetyl-N-(1-(3-fluorobenzyl)-1H-pyrazol-4-yl)isoxazole-3-carboxamide

The synthesis of 5-acetyl-N-(1-(3-fluorobenzyl)-1H-pyrazol-4-yl)isoxazole-3-carboxamide was carried out following the same procedure as in Example 24 to give 5-acetyl-N-(1-(3-fluorobenzyl)-1H-pyrazol-4-yl)isoxazole-3-carboxamide (0.370 g, 1.13 mmol, 58%) as a white solid. $^1$H NMR (500 MHz, Dimethylsulfoxide-d$_6$) δ 11.17 (s, 1H), 8.22 (s, 1H), 7.70 (d, J=10.4 Hz, 2H), 7.40 (d, J=6.4 Hz, 1H), 7.08 (dd, J=27.9, 20.3 Hz, 3H), 5.37 (s, 2H), 2.62 (s, 3H); LCMS (ESI) m/z: 329.0 [M+H]$^+$.

Step 3: Preparation of (Z)-5-(3-(dimethylamino)acryloyl)-N-(1-(3-fluorobenzyl)-1H-pyrazol-4-yl)isoxazole-3-carboxamide

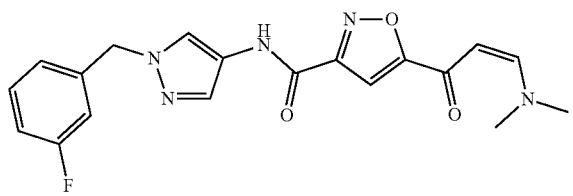 [SMILES: CN(C)/C=C\C(=O)c1cc(C(=O)Nc2cnn(Cc3cccc(F)c3)c2)no1]

A mixture of 5-acetyl-N-(1-(3-fluorobenzyl)-1H-pyrazol-4-yl)isoxazole-3-carboxamide (0.342 g, 0.891 mmol) and N,N-dimethylformamide dimethyl acetal (0.21 g, 1.78 mmol) in toluene (2.6 mL) was stirred at 110° C. for 18 h. The volatiles were removed and the residue was recrystallized from diethyl ether/petroleum ether to give (Z)-5-(3-(dimethylamino)acryloyl)-N-(1-(3-fluorobenzyl)-1H-pyrazol-4-yl)isoxazole-3-carboxamide (0.290 g, 0.76 mmol, 83%) as a yellow solid. LCMS (ESI) m/z: 384.1 [M+H]$^+$.

Step 4: N-(1-(3-fluorobenzyl)-1H-pyrazol-4-yl)-5-(pyrimidin-4-yl)isoxazole-3-carboxamide

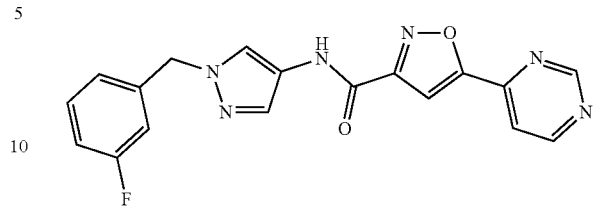

A mixture of (Z)-5-(3-(dimethylamino)acryloyl)-N-(1-(3-fluorobenzyl)-1H-pyrazol-4-yl)isoxazole-3-carboxamide (0.240 g, 0.62 mmol), formamidine acetate (0.196 g, 1.88 mmol) and potassium carbonate (0.259 g, 1.88 mmol) in N,N-dimethylformamide (6 mL) was heated at 100° C. for 2 h in a sealed tube. The reaction mixture was filtered and the filtrate was purified by prep-HPLC (Boston C18 21×250 mm 10 μm column; acetonitrile/0.01% aqueous trifluoroacetic acid) to give N-(1-(3-fluorobenzyl)-1H-pyrazol-4-yl)-5-(pyrimidin-4-yl)isoxazole-3-carboxamide (0.060 g, 0.16 mmol, 26%) as a white solid. $^1$H NMR (500 MHz, Dimethylsulfoxide-d$_6$) δ 11.16 (s, 1H), 9.39 (d, J=1.1 Hz, 1H), 9.08 (d, J=5.2 Hz, 1H), 8.38-8.09 (m, 2H), 7.75 (d, J=35.1 Hz, 2H), 7.54-7.26 (m, 1H), 7.11 (dt, J=18.8, 9.1 Hz, 3H), 5.38 (s, 2H); LCMS (ESI) m/z: 365.0 [M+H]$^+$.

Example 39. Preparation of N-(1-(3-fluorobenzyl)-1H-pyrazol-4-yl)-5-(1-methoxycyclobutyl)isoxazole-3-carboxamide (115)

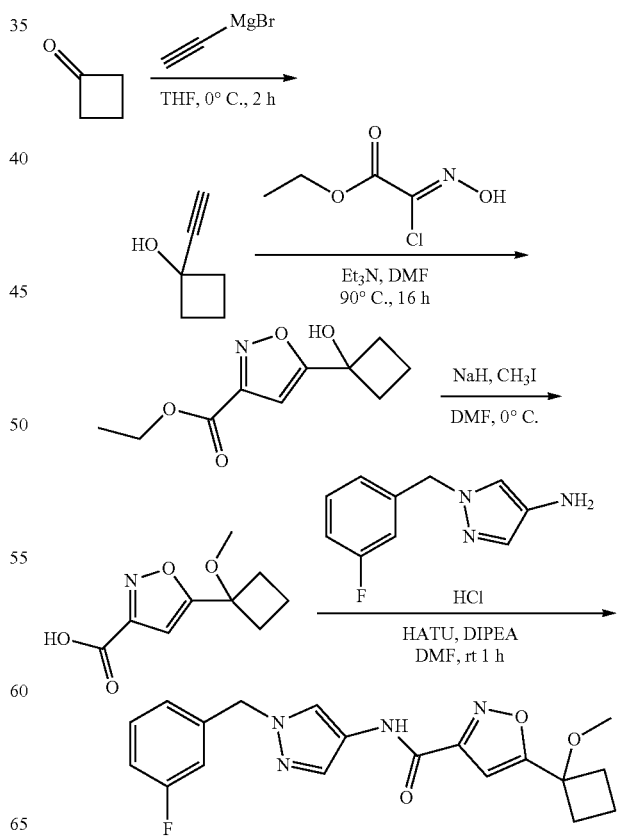

Step 1: Preparation of 1-ethynylcyclobutanol

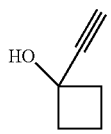

To a stirred solution of cyclobutanone (1.4 g, 20.0 mmol) in tetrahydrofuran (20 mL) at 0° C. was added dropwise ethynylmagnesium bromide (0.5 M in tetrahydrofuran, 40 mL). After the addition was complete, the reaction mixture was stirred at 0° C. for another 2 h then quenched with saturated aqueous ammonium chloride (40 mL) and extracted with ethyl acetate (100 mL×2). The combined organic phases were dried over sodium sulfate, filtered and concentrated to afford 1-ethynylcyclobutanol (1.4 g, 14.6 mmol, 73%) as a red oil. $^1$H NMR (500 MHz, Chloroform-d) δ 2.54 (s, 1H), 2.46-2.42 (m, 2H), 2.29-2.23 (m, 2H), 1.88-1.80 (m, 2H).

Step 2: Preparation of ethyl 5-(1-hydroxycyclobutyl)isoxazole-3-carboxylate

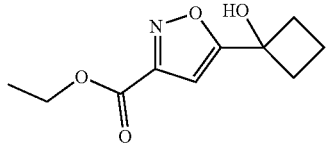

The synthesis of compound ethyl 5-(1-hydroxycyclobutyl)isoxazole-3-carboxylate was carried out following the same procedure as Example 35 to give ethyl 5-(1-hydroxycyclobutyl)isoxazole-3-carboxylate (3.0 g, 0.014 mmol, 24%) as a light yellow oil. LCMS (ESI) m/z: 212.1 [M+H]$^+$.

Step 3: 5-(1-methoxycyclobutyl)isoxazole-3-carboxylic Acid

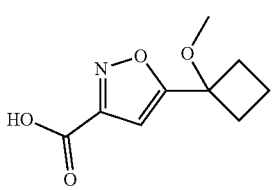

To a stirred solution of sodium hydride (0.208 g, 60% in petroleum ether, 5.2 mmol) in N,N-dimethylformamide (6 mL) was added dropwise a solution of ethyl 5-(1-hydroxycyclobutyl)isoxazole-3-carboxylate (1.0 g, 4.74 mmol) in N,N-dimethylformamide (2 mL) at room temperature. After the addition, the mixture was stirred for another 1 h then iodomethane (0.673 g, 4.74 mmol) was added dropwise. The reaction mixture was stirred at room temperature for another 2 h, quenched with water (20 mL), extracted with ethyl acetate (50 mL×2). The combined organic phases were dried over sodium sulfate, filtered and concentrated in vacuo. The crude residue was dissolved in minimum amount of N,N-dimethylformamide and purified by prep-HPLC (Boston C18 21×250 mm 10 μm column. The mobile phase was acetonitrile/0.01% aqueous trifluoroacetic acid) to afford 5-(1-methoxycyclobutyl)isoxazole-3-carboxylic acid (0.200 g, 1.01 mmol, 21%) as a light yellow solid. LCMS (ESI) m/z: 198.1 [M+H]$^+$.

Step 4: N-(1-(3-fluorobenzyl)-1H-pyrazol-4-yl)-5-(1-methoxycyclobutyl)isoxazole-3-carboxamide

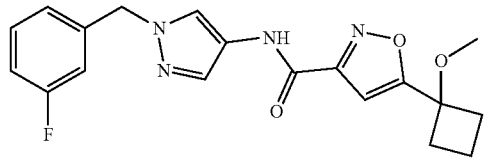 [SMILES: COC1(c2cc(C(=O)Nc3cnn(Cc4cccc(F)c4)c3)no2)CCC1]

The synthesis of N-(1-(3-fluorobenzyl)-1H-pyrazol-4-yl)-5-(1-methoxycyclobutyl) isoxazole-3-carboxamide was carried out following the same procedure as Example 24. The crude sample was dissolved in minimum amount of N,N-dimethylformamide and purified by prep-HPLC (Boston C18 21×250 mm 10 μm column. The mobile phase was acetonitrile/10 mM ammonium acetate aqueous solution) to give N-(1-(3-fluorobenzyl)-1H-pyrazol-4-yl)-5-(1-methoxycyclobutyl)isoxazole-3-carboxamide (72.7 mg, 0.196 mmol, 65%) as a colorless oil. $^1$H NMR (500 MHz, Dimethylsulfoxide-d$_6$) δ. 10.96 (s, 1H), 8.18 (s, 1H), 7.67 (s, 1H), 7.39 (dd, J=14.0, 7.5 Hz, 1H), 7.14-7.10 (m, 1H), 7.07-7.03 (m, 3H), 5.35 (s, 2H), 3.03 (s, 3H), 2.45-2.34 (m, 4H), 1.86-1.84 (m, 1H), 1.70-1.65 (m, 1H); LCMS (ESI) m/z: 371.1 [M+H]$^+$.

Example 40. Preparation of N-[1-[(3-fluorophenyl)methyl]pyrazol-4-yl]-5-(2-furyl)isoxazole-3-carboxamide (30)

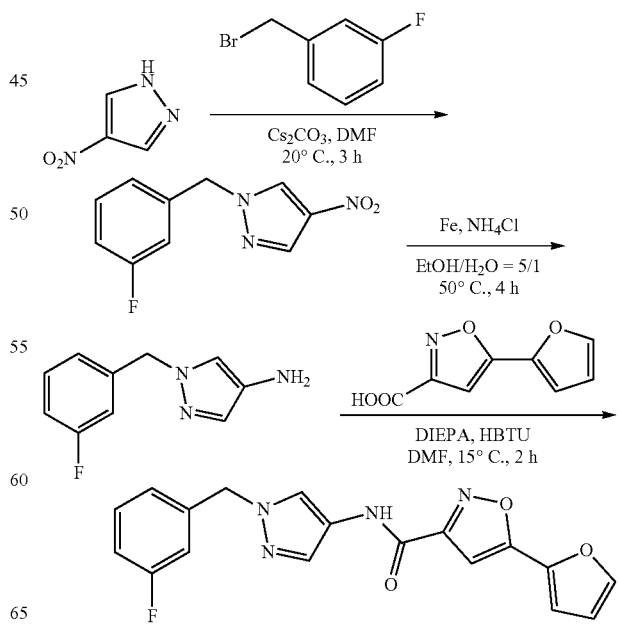

Step 1: Preparation of 1-[(3-fluorophenyl)methyl]-4-nitro-pyrazole

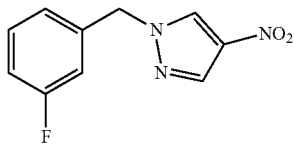 [SMILES: O=[N+]([O-])c1cnn(Cc2cccc(F)c2)c1]

To a solution of 4-nitro-1H-pyrazole (0.100 g, 0.884 mmol) in N,N-dimethylformamide (3 mL) was added cesium carbonate (0.864 g, 2.65 mmol) and 1-(bromomethyl)-3-fluoro-benzene (0.109 mL, 0.884 mmol). The mixture was stirred at 20° C. for 3 h. The reaction mixture was diluted with water (20 mL) and extracted with ethyl acetate (10 mL×3). The combined organic layers were washed with brine (20 mL), dried over sodium sulfate, filtered and concentrated under reduced pressure to give a colorless residue. The crude product 1-[(3-fluorophenyl)methyl]-4-nitro-pyrazole (0.196 g, 884 mmol) was used into the next step without further purification. LCMS (ESI) m/z: 222.1 [M+H]$^+$.

Step 2: Preparation of 1-[(3-fluorophenyl)methyl]pyrazol-4-amine

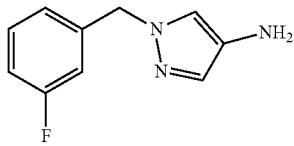 [SMILES: Nc1cnn(Cc2cccc(F)c2)c1]

To a solution of 1-[(3-fluorophenyl)methyl]-4-nitro-pyrazole (0.196 g, 0.884 mmol) in ethanol (10 mL) and water (2 mL) was added ammonium chloride (155 mL, 4.42 mmol) and iron powder (0.247 g, 4.42 mmol) under nitrogen. The mixture was heated at 50° C. for 4 h. The reaction mixture was concentrated under reduced pressure to remove ethanol (2 mL). The residue was diluted with water (20 mL) and extracted with ethyl acetate (10 mL×3). The combined organic layers were washed with brine (20 mL), dried over sodium sulfate, filtered and concentrated under reduced pressure to give a residue as a brown oil. The crude product 1-[(3-fluorophenyl)methyl]pyrazol-4-amine (0.169 g, 0.884 mmol) was used into the next step without further purification. LCMS (ESI) m/z: 192.1 [M+H]$^+$.

Step 3: Preparation of N-[1-[(3-fluorophenyl)methyl]pyrazol-4-yl]-5-(2-furyl)isoxazole-3-carboxamide

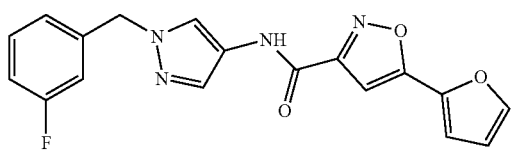 [SMILES: O=C(Nc1cnn(Cc2cccc(F)c2)c1)c1cc(-c2ccco2)on1]

To a solution of 5-(2-furyl)isoxazole-3-carboxylic acid (0.100 g, 0.558 mmol) in N,N-dimethylformamide (3 mL) was added N,N,N',N'-tetramethyl-O-(1H-benzotriazol-1-yl)uronium hexafluorophosphate (0.254 g, 0.670 mmol), 1-[(3-fluorophenyl)methyl]pyrazol-4-amine (0.117 g, 0.614 mmol) and diisopropylethylamine (292 mL, 1.67 mmol) at 15° C. The mixture was stirred at 15° C. for 2 h. The residue was purified by prep-HPLC (YMC-Actus Triart C18 100×30 mm×5 μm; mobile phase: [water (10 mM ammonium bicarbonate)-acetonitrile]; B %: 40%-60%, 12 min) to afford N-[1-[(3-fluorophenyl)methyl]pyrazol-4-yl]-5-(2-furyl)isoxazole-3-carboxamide (0.126 g, 0.36 mmol, 64%) as a pale yellow solid. $^1$H NMR (400 MHz, Chloroform-d) δ 8.60 (br. s, 1H), 8.08 (s, 1H), 7.61 (br. d, J=11.0 Hz, 2H), 7.38-7.28 (m, 1H), 7.12-6.81 (m, 5H), 6.58 (br. s, 1H), 5.30 (s, 2H); LCMS (ESI) m/z: 353.1 [M+H]$^+$.

Example 41. Preparation of N-(1-(3-fluorobenzyl)-1H-pyrazol-4-yl)-5-(3-fluoropyridin-2-yl)isoxazole-3-carboxamide (108)

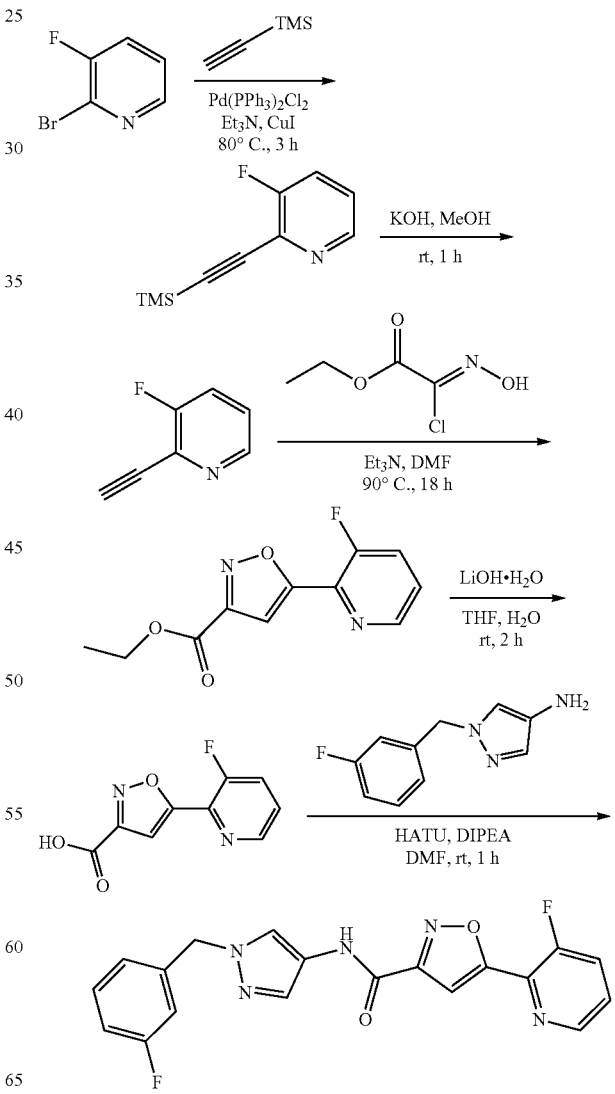

Step 1: Preparation of 3-fluoro-2-((trimethylsilyl)ethynyl)pyridine

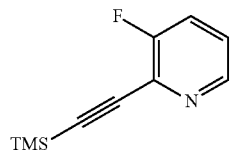 [SMILES: C[Si](C)(C)C#Cc1ncccc1F]

The synthesis of compound 3-fluoro-2-((trimethylsilyl)ethynyl)pyridine was carried out following the same procedure as Example 37. Compound 3-fluoro-2-((trimethylsilyl)ethynyl)pyridine (5.0 g, 25.9 mmol, 94%) was obtained as a red-brown oil. LCMS (ESI) m/z: 194.1 [M+H]$^+$.

Step 2: Preparation of 2-ethynyl-3-fluoropyridine

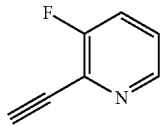

The synthesis of compound 2-ethynyl-3-fluoropyridine was carried out following the same procedure as Example 37. Compound 2-ethynyl-3-fluoropyridine (2.0 g, 16.5 mmol, 64%) was obtained as a dark brown oil.

Step 3: Preparation of ethyl 5-(3-fluoropyridin-2-yl)isoxazole-3-carboxylate

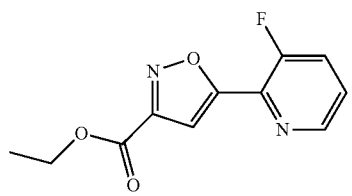 [SMILES: CCOC(=O)c1cc(-c2ncccc2F)on1]

The synthesis of compound ethyl 5-(3-fluoropyridin-2-yl)isoxazole-3-carboxylate was carried out following the same procedure as Example 35. Compound ethyl 5-(3-fluoropyridin-2-yl)isoxazole-3-carboxylate (1.2 g, 3.57 mmol, 39%) was obtained as a yellow green solid. LCMS (ESI) m/z: 237.1 [M+H]$^+$.

Step 4: Preparation of 5-(3-fluoropyridin-2-yl)isoxazole-3-carboxylic Acid

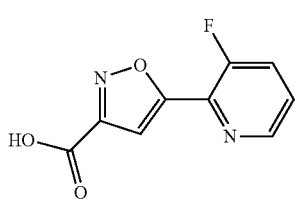 [SMILES: O=C(O)c1cc(-c2ncccc2F)on1]

The synthesis of 5-(3-fluoropyridin-2-yl)isoxazole-3-carboxylic acid was carried out following the same procedure as Example 24. Compound 5-(3-fluoropyridin-2-yl)isoxazole-3-carboxylic acid (0.400 g, 1.92 mmol, 76%) was obtained as a grey-solid. LCMS (ESI) m/z: 209.1 [M+H]$^+$.

Step 5: Preparation of N-(1-(3-fluorobenzyl)-1H-pyrazol-4-yl)-5-(3-fluoropyridin-2-yl)isoxazole-3-carboxamide

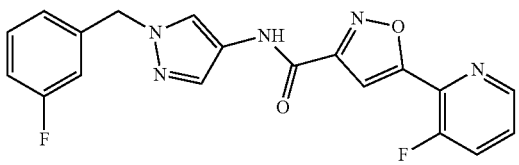 [SMILES: O=C(Nc1cnn(Cc2cccc(F)c2)c1)c1cc(-c2ncccc2F)on1]

The synthesis of N-(1-(3-fluorobenzyl)-1H-pyrazol-4-yl)-5-(3-fluoropyridin-2-yl)isoxazole-3-carboxamide was carried out following the same procedure as Example 24. Compound N-(1-(3-fluorobenzyl)-1H-pyrazol-4-yl)-5-(3-fluoropyridin-2-yl)isoxazole-3-carboxamide (0.151 g, 0.395 mmol, 82%) was obtained as a white solid. $^1$H NMR (500 MHz, Dimethylsulfoxide-d$_6$) δ. 11.12 (s, 1H), 8.65 (d, J=4.5 Hz, 1H), 8.23 (s, 1H), 8.03 (t, J=10.0 Hz, 1H), 7.73-7.69 (m, 2H), 7.40-7.38 (m, 2H), 7.13 (td, J=8.5, 2.0 Hz, 1H), 7.08-7.04 (m, 2H), 5.37 (s, 2H); LCMS (ESI) m/z: 382.0 [M+H]$^+$.

Example 42. Preparation of N-(1-(3-fluorobenzyl)-1H-pyrazol-4-yl)-5-(oxetan-3-yl)isoxazole-3-carboxamide (139)

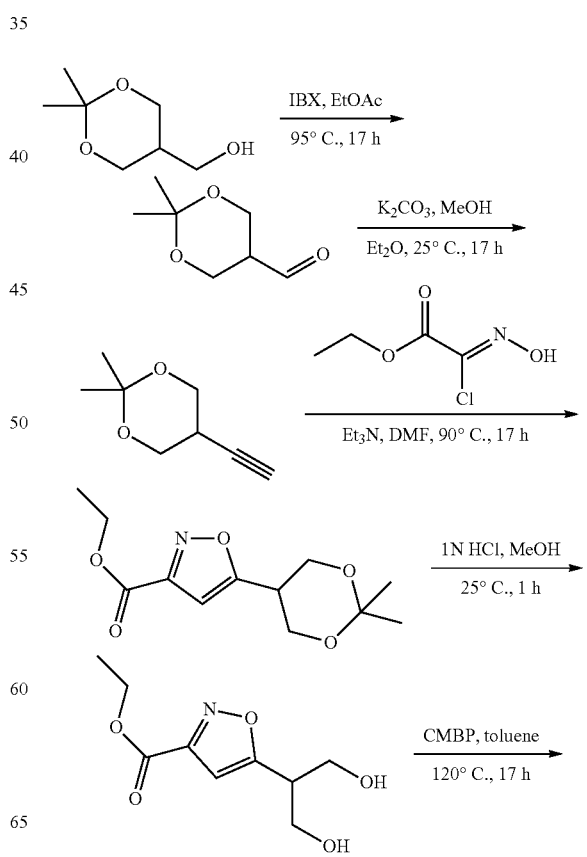

-continued

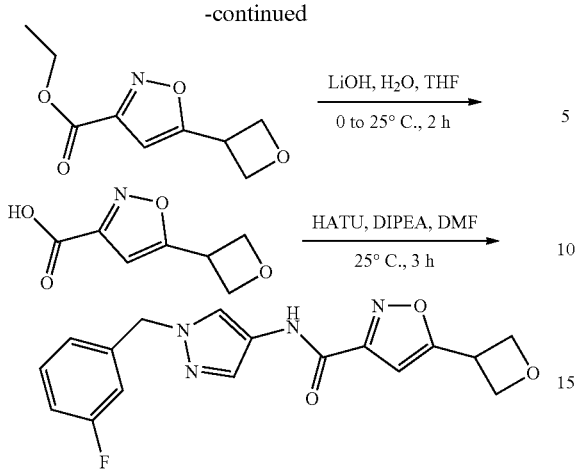

Step 1: Preparation of 2,2-dimethyl-1,3-dioxane-5-carbaldehyde

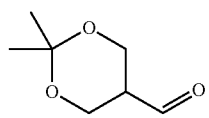

To a solution of (2,2-dimethyl-1,3-dioxan-5-yl)methanol (11 g, 75.3 mmol) in ethyl acetate (150 mL) under nitrogen was added 2-iodoxybenzoic acid (25.3 g, 90.3 mmol). The reaction mixture was heated to 95° C. and stirred for 17 h and then cooled to room temperature. The reaction mixture was filtered and concentrated in vacuo. The residue was purified by column chromatography (silica, petroleum ether/ethyl acetate=1/1) to yield 2,2-dimethyl-1,3-dioxane-5-carbaldehyde (2.8 g, 19.4 mmol, 26%) as a colorless oil. Three same batches (each from 2.8 g start material) were prepared and combined to give a total of 8.4 g of 2,2-dimethyl-1,3-dioxane-5-carbaldehyde.

Step 2: Preparation of 5-ethynyl-2,2-dimethyl-1,3-dioxane

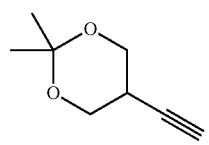

To a solution of 2,2-dimethyl-1,3-dioxane-5-carbaldehyde (6.1 g, 42.4 mmol) in methanol (60 mL) and ethyl ether (30 mL) was added (1-diazo-2-oxopropyl)phosphonic acid dimethyl ester (16.2 g, 84.7 mmol) and potassium carbonate (23.4 g, 169 mmol). The reaction mixture was stirred at 25° C. for 17 h. The reaction mixture was diluted with water (30 mL) and extracted with petroleum ether (20 mL×3). The combined organic layers were washed with brine (10 mL×2), dried over anhydrous sodium sulfate, filtered and concentrated in vacuo to give crude 5-ethynyl-2,2-dimethyl-1,3-dioxane (4.0 g, 28.6 mmol, 68%) as a colorless oil. LCMS (ESI) m/z: 141.1 [M+H]⁺.

Step 3: Preparation of ethyl 5-(2,2-dimethyl-1,3-dioxan-5-yl)isoxazole-3-carboxylate

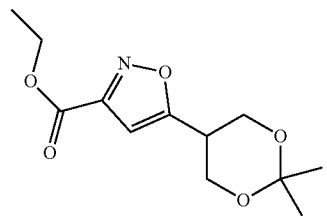 [SMILES: CCOC(=O)c1cc(C2COC(C)(C)OC2)on1]

To a solution of 5-ethynyl-2,2-dimethyl-1,3-dioxane (4.0 g, 28.5 mmol) in N,N-dimethylformamide (10 mL) was added a solution of (Z)-ethyl 2-chloro-2-(hydroxyimino) acetate (4.3 g, 28.5 mmol) in N,N-dimethylformamide (40 mL) dropwise over 40 min under nitrogen atmosphere. After addition, the reaction mixture was heated to 90° C. and a solution of triethylamine (8.6 g, 85.5 mmol) in N,N-dimethylformamide (10 mL) was added dropwise over 1 h. The reaction mixture was heated at 90° C. for 17 h and cooled to room temperature. The reaction mixture was diluted with ethyl acetate (20 mL), washed with water (10 mL×2) and brine (10 mL×2), dried over anhydrous sodium sulfate, filtered and concentrated in vacuo. The residue was purified by column chromatography (silica, petroleum ether/ethyl acetate=10/1) to give ethyl 5-(2,2-dimethyl-1,3-dioxan-5-yl)isoxazole-3-carboxylate (1.6 g, 6.27 mmol, 22%) as a yellow solid. LCMS (ESI) m/z: 256.1 [M+H]⁺.

Step 4: Preparation of ethyl 5-(1,3-dihydroxypropan-2-yl)isoxazole-3-carboxylate

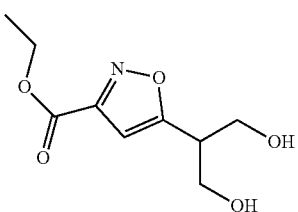

To a solution of ethyl 5-(2,2-dimethyl-1,3-dioxan-5-yl)isoxazole-3-carboxylate (1.5 g, 5.88 mmol) in methanol (20 mL) was added 1N hydrochloric acid (10 mL). The reaction mixture was stirred at 25° C. for 1 h. The pH of reaction mixture was adjusted to pH=8 with solid sodium bicarbonate and the aqueous layer was extracted with ethyl acetate (10 mL×2). The combined organic layers were washed with water (10 mL) and brine (10 mL), dried over anhydrous sodium sulfate, filtered and concentrated in vacuo to afford ethyl 5-(1,3-dihydroxypropan-2-yl)isoxazole-3-carboxylate (0.94 g, 4.37 mmol, 78%) as a yellow oil. LCMS (ESI) m/z: 216.1 [M+H]⁺.

Step 5: Preparation of ethyl 5-(oxetan-3-yl)isoxazole-3-carboxylate

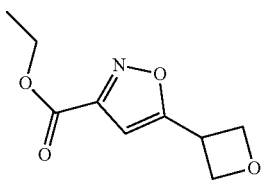

To a solution of ethyl 5-(1,3-dihydroxypropan-2-yl)isoxazole-3-carboxylate (0.6 g, 2.79 mmol) in toluene (20 mL) was added cyanomethylenetributylphosphorane (1.0 g, 4.18 mmol). The reaction mixture was stirred at 120° C. for 17 h. The reaction mixture was cooled to room temperature, filtered and concentrated in vacuo. The residue was purified by prep-TLC (silica, petroleum ether/ethyl acetate=1/1) to give ethyl 5-(oxetan-3-yl)isoxazole-3-carboxylate (0.120 g, 0.61 mmol, 22%) as a yellow oil. LCMS (ESI) m/z: 198.1 [M+H]$^+$.

Step 6: Preparation of 5-(oxetan-3-yl)isoxazole-3-carboxylic Acid

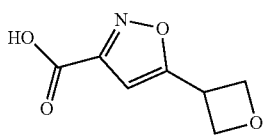 [SMILES: O=C(O)c1cc(C2COC2)on1]

To a solution of ethyl 5-(oxetan-3-yl)isoxazole-3-carboxylate (0.120 g, 0.61 mmol) in tetrahydrofuran/water (v/v=2/1, 12 mL) at 0° C. was added lithium hydroxide hydrate (77 mg, 1.83 mmol). The reaction mixture was stirred at 25° C. for 2 h. The reaction mixture was quenched with ice-water and then adjusted to pH=3 with aqueous 1N hydrogen chloride solution. The aqueous layer was extracted with ethyl acetate (10 mL×2). The combined organic layers were washed with brine (10 mL), dried over anhydrous sodium sulfate, filtered and concentrated in vacuo to give 5-(oxetan-3-yl)isoxazole-3-carboxylic acid (0.085 g, 0.5 mmol, 83%) as a white solid. LCMS (ESI) m/z: 170.1 [M+H]$^+$.

Step 7: Preparation of N-(1-(3-fluorobenzyl)-1H-pyrazol-4-yl)-5-(oxetan-3-yl)isoxazole-3-carboxamide

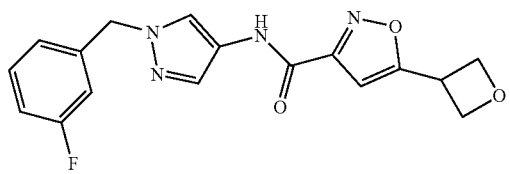 [SMILES: O=C(Nc1cnn(Cc2cccc(F)c2)c1)c1cc(C2COC2)on1]

To a solution of 5-(oxetan-3-yl)isoxazole-3-carboxylic acid (80 mg, 0.47 mmol) in N,N-dimethylformamide (15 mL) was added 1-(3-fluorobenzyl)-1H-pyrazol-4-amine (90 mg, 0.47 mmol), 1-[bis(dimethylamino)methylene]-1H-1,2,3-triazolo[4,5-b]pyridinium 3-oxide hexafluorophosphate (536 mg, 1.41 mmol) and diisopropylethylamine (0.182 g, 1.41 mmol). The mixture was stirred at 25° C. for 3 h. The crude sample was dissolved in minimum amount of N,N-dimethylformamide and purified via prep-HPLC (Boston C18 21×250 mm 10 µm column; acetonitrile/0.01% aqueous trifluoroacetic acid) to give N-(1-(3-fluorobenzyl)-1H-pyrazol-4-yl)-5-(oxetan-3-yl)isoxazole-3-carboxamide (57.8 mg, 0.17 mmol, 36%) as a white solid. $^1$H NMR (500 MHz, Dimethylsulfoxide-d$_6$) δ 10.98 (s, 1H), 8.20 (s, 1H), 7.68 (s, 1H), 7.39 (dd, J=14.0, 7.9 Hz, 1H), 7.21-6.93 (m, 4H), 5.95 (s, 1H), 5.67 (s, 1H), 5.36 (s, 2H), 4.31 (s, 2H); LCMS (ESI) m/z: 343.1 [M+H]$^+$.

Example 43. Preparation of N-{1-[(3-fluorophenyl)methyl]-1H-pyrazol-4-yl}-4,5,6,7-tetrahydro-1,2-benzoxazole-3-carboxamide (193)

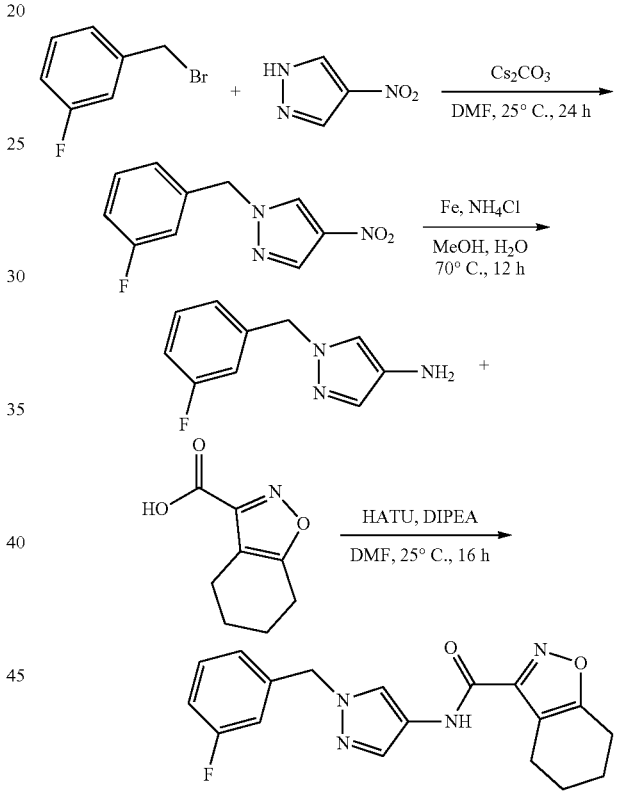

Step 1: Preparation of 1-[(3-fluorophenyl)methyl]-4-nitro-1H-pyrazole

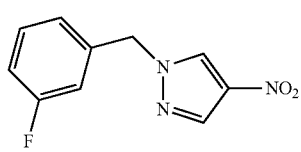 [SMILES: O=[N+]([O-])c1cnn(Cc2cccc(F)c2)c1]

To a solution of 4-nitro-1H-pyrazole (0.500 g, 4.42 mmol) and 1-(bromomethyl)-3-fluorobenzene (918 mg, 4.86 mmol) in N,N'-dimethylformamide (11 mL) at 25° C. was added cesium carbonate (2.16 g, 6.63 mmol) and reaction was stirred at 25° C. for 24 h then quenched by addition of water (10 mL) and extracted with ethyl acetate (20 mL×3). The combined organic layers were dried over magnesium sulfate, filtered and concentrated in vacuo. The crude residue was purified by column chromatography (ISCO, 40 g silica, 0-30% ethyl acetate in hexanes, gradient over 20 min) to give 1-[(3-fluorophenyl)methyl]-4-nitro-1H-pyrazole (0.98 g, 4.40 mmol, 99%) as a yellow oil. ¹H NMR (300 MHz, Chloroform-d) δ 8.12 (d, J=3.8 Hz, 2H), 7.49-7.32 (m, 1H), 7.17-6.89 (m, 3H), 5.33 (s, 2H); LCMS (ESI) m/z: 222.1 [M+H]⁺.

Step 2: Preparation of 1-[(3-fluorophenyl)methyl]-1H-pyrazol-4-amine

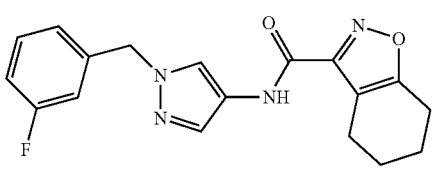 [SMILES: O=C(Nc1cnn(Cc2cccc(F)c2)c1)c1noc2c1CCCC2]

To a solution of 1-[(3-fluorophenyl)methyl]-4-nitro-1H-pyrazole (1.90 g, 8.58 mmol) and ammonium chloride (1.83 g, 34.3 mmol) in methanol (40 mL) and water (8.2 mL) at 70° C. was added iron (1.91 g, 34.3 mmol) in one portion. The reaction mixture was stirred at 70° C. for 16 h, after which the reaction was cooled to room temperature and diluted with saturated aqueous sodium bicarbonate (40 mL). The reaction mixture was diluted with ethyl acetate (50 mL) and filtered through a pad of Celite®. The filter pad was washed with ethyl acetate (20 mL×2). The filtrate was concentrated and the aqueous layer was extracted with ethyl acetate (50 mL×2). The combined organic layers were dried over magnesium sulfate, filtered and concentrated to give 1-[(3-fluorophenyl)methyl]-1H-pyrazol-4-amine (1.40 g, 7.32 mmol, 85%) as a crude red solid. The crude material is used without further purification. ¹H NMR (300 MHz, Dimethylsulfoxide-d₆) δ 7.42-7.22 (m, 1H), 7.18-6.87 (m, 5H), 5.15 (s, 2H); LCMS (ESI) m/z: 192.2 [M+H]⁺.

Step 3: Preparation of N-{1-[(3-fluorophenyl)methyl]-1H-pyrazol-4-yl}-4,5,6,7-tetrahydro-1,2-benzoxazole-3-carboxamide To a solution of 1-[(3-fluorophenyl)methyl]-1H-pyrazol-4-amine (57.1 mg, 0.299 mmol), 4,5,6,7-tetrahydro-1,2-benzoxazole-3-carboxylic acid (50.0 mg, 0.299 mmol) and 1-[bis(dimethylamino)methylene]-1H-1,2,3-triazolo[4,5-b]pyridinium 3-oxide hexafluorophosphate (113 mg, 0.299 mmol) in N,N'-dimethylformamide (1 mL) at 25° C. was added diisopropylethylamine (130 μL, 0.748 mmol). The reaction mixture was stirred at 25° C. for 16 h then quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 60% ethyl acetate/hexanes for 20 min) to afford N-{1-[(3-fluorophenyl)methyl]-1H-pyrazol-4-yl}-4,5,6,7-tetrahydro-1,2-benzoxazole-3-carboxamide (60.3 mg, 0.177 mmol, 60%) as a yellow solid. ¹H NMR (300 MHz, Dimethylsulfoxide-d₆) δ 10.95 (s, 1H), 8.18 (d, J=0.7 Hz, 1H), 7.66 (d, J=0.7 Hz, 1H), 7.39 (td, J=8.0, 6.1 Hz, 1H), 7.21-6.94 (m, 3H), 5.33 (s, 2H), 2.74 (q, J=5.9 Hz, 4H), 1.81-1.56 (m, 4H); LCMS (ESI) m/z: 341.2 [M+H]⁺.

Example 44. Preparation of 5-ethynyl-N-(1-(3-fluorobenzyl)-1H-pyrazol-4-yl)isoxazole-3-carboxamide (154)

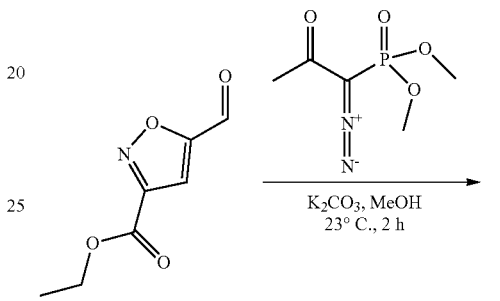

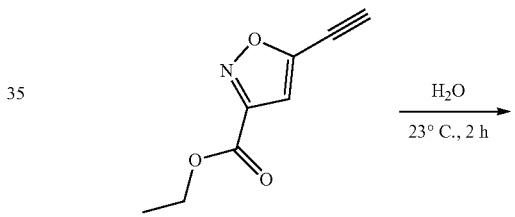

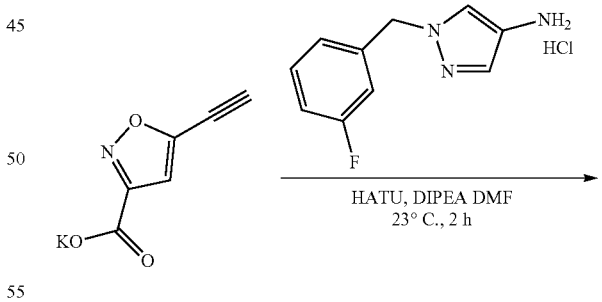

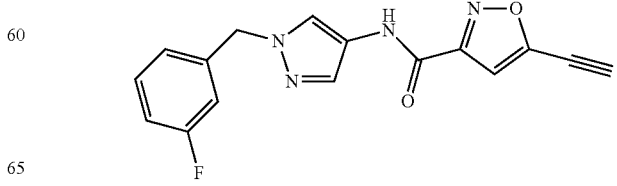

Step 1: Preparation of potassium 5-ethynylisoxazole-3-carboxylate

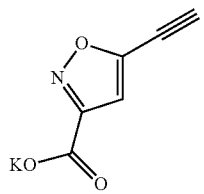

To an ice-cooled solution of ethyl 5-formylisoxazole-3-carboxylate (2.0 g, 11.8 mmol) in methanol (40 mL) was added potassium carbonate (3.27 g, 23.7 mmol) and dimethyl 1-diazo-2-oxopropylphosphonate (2.5 g, 13.0 mmol). The mixture was warmed to 23° C. and stirred at for 2 h. Water (4 mL) was added to the mixture and stirred for 2 h. The reaction mixture was concentrated and dried in vacuo to offer potassium 5-ethynylisoxazole-3-carboxylate (4.0 g, crude) as a yellow solid. LCMS (ESI) m/z: 138.1 [M+H]$^+$. This material was used in the next step without further purification.

Step 2: Preparation of 5-ethynyl-N-(1-(3-fluorobenzyl)-1H-pyrazol-4-yl)isoxazole-3-carboxamide

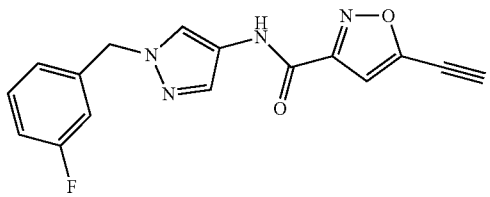 [SMILES: C#Cc1cc(C(=O)Nc2cnn(Cc3cccc(F)c3)c2)no1]

To an ice-cooled solution of potassium 5-ethynylisoxazole-3-carboxylate (4.00 g, 11.8 mmol), 1-(3-fluorobenzyl)-1H-pyrazol-4-amine hydrochloride (2.69 g, 11.8 mmol) and 2-(7-aza-1H-benzotriazole-1-yl)-1,1,3,3-tetramethyluronium hexafluorophosphate (4.5 g, 11.8 mmol) in N,N-dimethylformamide (15 mL) was added N,N-diisopropylethylamine (6.3 mL, 35.5 mmol). The mixture was stirred at 23° C. for 2 h. The reaction mixture was diluted with ethyl acetate (300 mL) and washed with hydrochloric acid (0.5N, 100 mL), water (100 mL) and brine (100 mL). The organic layer was dried over sodium sulfate, filtered and concentrated in vacuo. The residue was purified by column chromatography (silica, petroleum ether/ethyl acetate=2/1) to afford 5-ethynyl-N-(1-(3-fluorobenzyl)-1H-pyrazol-4-yl)isoxazole-3-carboxamide (313 mg, 1.01 mmol, 9%) as a white yellow solid. $^1$H NMR (500 MHz, Dimethylsulfoxide-d$_6$) δ 11.08 (s, 1H), 8.19 (s, 1H), 7.68 (s, 1H), 7.39 (d, J=6.2 Hz, 1H), 7.33 (s, 1H), 7.13 (d, J=1.9 Hz, 1H), 7.05 (t, J=9.4 Hz, 2H), 5.37 (d, J=14.7 Hz, 3H); LCMS (ESI) m/z: 311.0 [M+H]$^+$.

Example 45. Preparation of N-(1-(2-methoxybenzyl)-1H-pyrazol-4-yl)-5-phenylisoxazole-3-carboxamide (125)

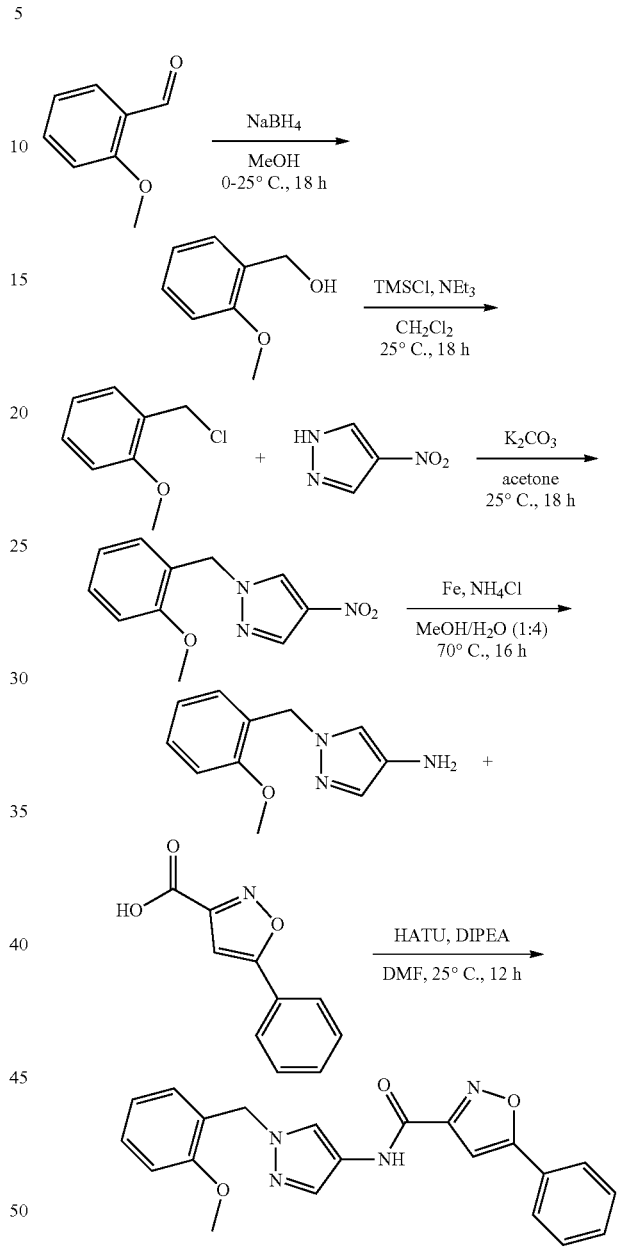

Step 1: Preparation of (2-methoxyphenyl)methanol

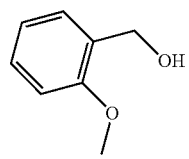

To a cooled solution of 2-methoxybenzaldehyde (1.55 g, 11.3 mmol) in methanol (8 mL) at 0° C. was added dropwise a solution of sodium borohydride (0.854 g, 22.6 mmol) in water. The reaction mixture was stirred in the cooling bath for an additional 1 h, after which the cooling bath was removed. The reaction mixture was stirred at room temperature for 18 h. The reaction mixture was cooled to 0° C. and carefully adjusted to pH=3 with aqueous 1 M hydrogen chloride. The mixture was stirred in the cooling bath for an additional 30 min. The acidic mixture was neutralized to pH=6-7 with aqueous 1 M sodium hydroxide and stirred for 1 h. The organics were concentrated and the remaining aqueous layer was extracted with ethyl acetate (25 mL×5). The combined organics were dried over sodium sulfate, filtered and concentrated in vacuo. The crude material was purified by column chromatography (ISCO, 12 g silica, eluting with 0% to 25% ethyl acetate in hexanes) to afford (2-methoxyphenyl)methanol (1.16 g, 8.25 mmol, 73%) as a colorless oil. $^1$H NMR (300 MHz, Dimethylsulfoxide-$d_6$) δ 7.36 (ddt, J=7.5, 1.8, 0.9 Hz, 1H), 7.27-7.15 (m, 1H), 6.98-6.87 (m, 2H), 4.96 (t, J=5.7 Hz, 1H), 4.48 (d, J=5.6 Hz, 2H), 3.76 (s, 3H).

Step 2: Preparation of
1-(chloromethyl)-2-methoxybenzene

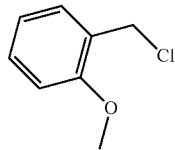

To a solution of (2-methoxyphenyl)methanol (1.15 g, 8.32 mmol) and triethylamine (1.24 g, 12.3 mmol, 1.7 mL) in methylene chloride (16 mL) at 0° C. was added dropwise chlorotrimethylsilane (0.939 g, 8.65 mmol). The reaction mixture was stirred in the cooling bath for an additional 30 min after which the cooling bath was removed and stirred at room temperature for 18 h. The reaction mixture was washed with water (10 mL×2), dried over sodium sulfate, filtered and concentrated to give crude 1-(chloromethyl)-2-methoxybenzene (1.36 g, crude) as an orange oil. The material was used directly in the next step without further purification.

Step 3: Preparation of
1-(2-methoxybenzyl)-4-nitro-1H-pyrazole

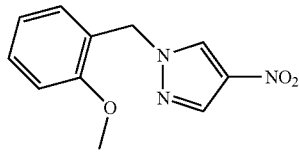 [SMILES: COc1ccccc1Cn1cc([N+](=O)[O-])cn1]

To a suspension of 4-nitro-1H-pyrazole (1.19 g, 10.6 mmol) and freshly crushed anhydrous potassium carbonate (4.40 g, 31.9 mmol) in anhydrous acetone (13 mL) was added crude 1-(chloromethyl)-2-methoxybenzene (1.84 g, 11.7 mmol). The reaction mixture was stirred at room temperature for 18 h followed by heating at 50° C. for 30 min. The reaction mixture was filtered and the filtrate was concentrated in vacuo. The crude product was purified by column chromatography (ISCO, 24 g silica, 0-25% ethyl acetate in hexanes) to afford 1-(2-methoxybenzyl)-4-nitro-1H-pyrazole (0.97 g, 4.15 mmol, 39%). $^1$H NMR (300 MHz, Dimethylsulfoxide-$d_6$) δ 8.86 (d, J=0.7 Hz, 1H), 8.25 (d, J=0.8 Hz, 1H), 7.34 (td, J=7.9, 1.8 Hz, 1H), 7.10 (dd, J=7.5, 1.8 Hz, 1H), 7.04 (d, J=8.0 Hz, 1H), 6.93 (td, J=7.4, 1.1 Hz, 1H), 5.35 (s, 2H), 3.81 (s, 3H).

Step 4: Preparation of
1-(2-methoxybenzyl)-1H-pyrazol-4-amine

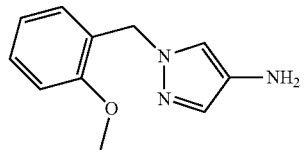

To a solution of 1-(2-methoxybenzyl)-4-nitro-1H-pyrazole (0.97 g, 4.15 mmol) and ammonium chloride (1.10 g, 20.7 mmol) in methanol (8 mL) and water (2 mL) at 70° C. was added iron (1.15 g, 20.7 mmol) in one portion. The reaction mixture was heated to 70° C. for 16 h. The reaction mixture was cooled to room temperature and diluted with saturated aqueous sodium bicarbonate (40 mL) and ethyl acetate (50 mL). The mixture was filtered through a pad of Celite® and the filter cake was washed with ethyl acetate (20 mL×3). The aqueous layer was extracted with ethyl acetate (50 mL×2). The combined organic layers were dried over magnesium sulfate, filtered and concentrated to give 1-(2-methoxybenzyl)-1H-pyrazol-4-amine (0.595 g, 2.92 mmol, 70%) as a crude red oil. The material was used directly in the next step without further purification. $^1$H NMR (300 MHz, dimethylsulfoxide-$d_6$) δ 7.35-7.17 (m, 1H), 7.01 (td, J=4.0, 1.0 Hz, 2H), 6.92 (d, J=0.9 Hz, 1H), 6.87 (td, J=7.4, 1.1 Hz, 1H), 6.77 (dd, J=7.4, 1.8 Hz, 1H), 5.08 (s, 2H), 3.81 (s, 3H).

Step 5: Preparation of N-(1-(2-methoxybenzyl)-1H-pyrazol-4-yl)-5-phenylisoxazole-3-carboxamide

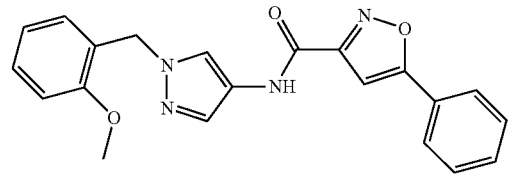 [SMILES: COc1ccccc1Cn1cc(NC(=O)c2cc(-c3ccccc3)on2)cn1]

To a solution of 5-phenylisoxazole-3-carboxylic acid (0.075, 0.396 mmol), 1-(2-methoxybenzyl)-1H-pyrazol-4-amine (0.088 g, 0.435 mmol) and 1-[bis(dimethylamino)methylene]-1H-1,2,3-triazolo[4,5-b]pyridinium 3-oxide hexafluorophosphate (0.190 g, 0.593 mmol) in N,N-dimethylformamide (1 mL) was added diisopropylethylamine (0.152 g, 1.18 mmol). The reaction mixture was stirred at room temperature for 12 h and then concentrated in vacuo. The residue was dissolved with ethyl acetate (5 mL), washed with saturated sodium bicarbonate (2 mL×2), and concentrated in vacuo. The crude product was purified by column chromatography (ISCO, 24 g silica, 0-40% ethyl acetate in hexanes) to afford N-(1-(2-methoxybenzyl)-1H-pyrazol-4-yl)-5-phenylisoxazole-3-carboxamide (29.8 mg, 0.0792 mmol, 20%) as an off white solid. $^1$H NMR (300 MHz, Dimethylsulfoxide-$d_6$) δ 11.00 (s, 1H), 8.06 (d, J=0.7 Hz, 1H), 8.01-7.92 (m, 2H), 7.67 (d, J=0.7 Hz, 1H), 7.62-7.53 (m, 3H), 7.45 (s, 1H), 7.31 (ddd, J=8.2, 5.1, 4.0 Hz, 1H), 7.05 (d, J=8.2 Hz, 1H), 6.91 (dd, J=4.3, 0.8 Hz, 2H), 5.27 (s, 2H), 3.84 (s, 3H); LCMS (ESI) m/z: 375.3 [M+H]+.

Example 46. Preparation of N-(1-benzylpyrazol-4-yl)-5-thiazol-5-yl-isoxazole-3-carboxamide (37)

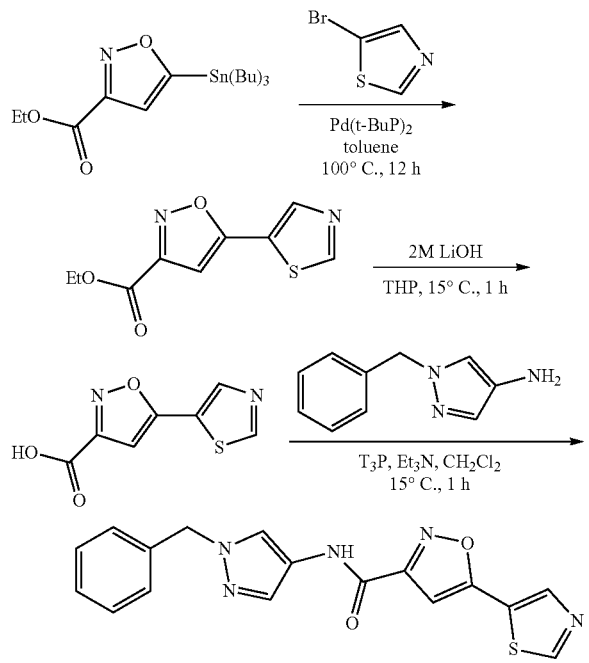

Step 1: Preparation of ethyl 5-thiazol-5-ylisoxazole-3-carboxylate

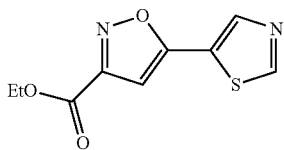 [SMILES: CCOC(=O)c1cc(-c2cncs2)on1]

A mixture of ethyl 5-tributylstannylisoxazole-3-carboxylate (1.00 g, 2.32 mmol), 5-bromothiazole (0.763 g, 4.65 mmol), and bis(tri-tert-butylphosphine)palladium(0) (0.059 g, 0.116 mmol) in toluene (10 mL) was purged with nitrogen (3×), and then the mixture was heated at 100° C. for 12 h under nitrogen. The mixture was cooled to 15° C. and then poured into ice-water (10 mL). The aqueous phase was extracted with ethyl acetate (15 mL×3). The combined organic phase was washed with brine (10 mL), dried with anhydrous sodium sulfate, filtered and concentrated in vacuo to afford crude product. The crude product was purified by column chromatography (silica, petroleum ether/ethyl acetate=100/1 to 5/1) to give ethyl 5-thiazol-5-ylisoxazole-3-carboxylate (0.060 mg, 0.268 mmol, 12%) as a yellow solid. LCMS (ESI) m/z: 225.0 [M+H]+.

Step 2: Preparation of 5-thiazol-5-ylisoxazole-3-carboxylic Acid

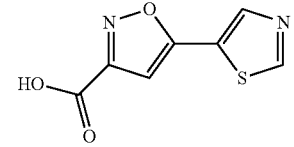 [SMILES: O=C(O)c1cc(-c2cncs2)on1]

To a stirred solution of ethyl 5-thiazol-5-ylisoxazole-3-carboxylate (0.06 g, 0.268 mmol) in tetrahydrofuran (1 mL) was added lithium hydroxide (2 M, 0.268 mL). The mixture was stirred at 15° C. for 1 h. The mixture was diluted with water (1 mL) and adjusted to pH=5 with hydrogen chloride solution (2 M, 1 mL). The aqueous phase was extracted with ethyl acetate (5 mL×3). The combined organic phases were washed with brine (5 mL), dried with anhydrous sodium sulfate, filtered and concentrated in vacuo to afford crude 5-thiazol-5-ylisoxazole-3-carboxylic acid (0.05 g, 0.255 mmol) as a yellow solid that was used without additional purification.

Step 3: Preparation of N-(1-benzylpyrazol-4-yl)-5-thiazol-5-yl-isoxazole-3-carboxamide

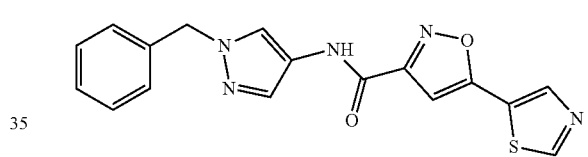

To a stirred solution of 5-thiazol-5-ylisoxazole-3-carboxylic acid (0.05 g, 0.255 mmol) in dichloromethane (0.5 mL) was added propylphosphonic anhydride (0.227 mL, 0.382 mmol, 50% wt), triethylamine (0.071 mL, 0.510 mmol) and 1-benzylpyrazol-4-amine (0.044 g, 0.255 mmol). The mixture was stirred at 15° C. for 1 h. The reaction mixture was concentrated under reduced pressure to give a residue. The crude residue was purified by prep-HPLC (YMC-Actus Triart C18 150×30 5 um column; 24-54% acetonitrile in a 10 mM ammonium acetate solution in water, 10 min gradient) to give N-(1-benzylpyrazol-4-yl)-5-thiazol-5-yl-isoxazole-3-carboxamide (0.024 g, 0.068 mmol, 27%) as a pale yellow solid. 1H NMR (400 MHz, Dimethylsulfoxide-d6) δ 11.05 (s, 1H), 9.36 (s, 1H), 8.64 (s, 1H), 8.17 (s, 1H), 7.67 (s, 1H), 7.43 (s, 1H), 7.38-7.21 (m, 5H), 5.33 (s, 2H); LCMS (ESI) m/z: 352.1 [M+H]+.

Example 47. Preparation of 5-(2-fluorophenyl)-N-(1-((4-(trifluoromethyl)pyridin-3-yl)methyl)-1H-pyrazol-4-yl)isoxazole-3-carboxamide (114)

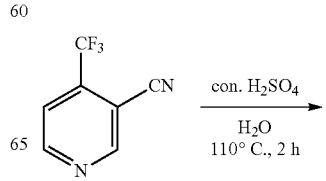

-continued

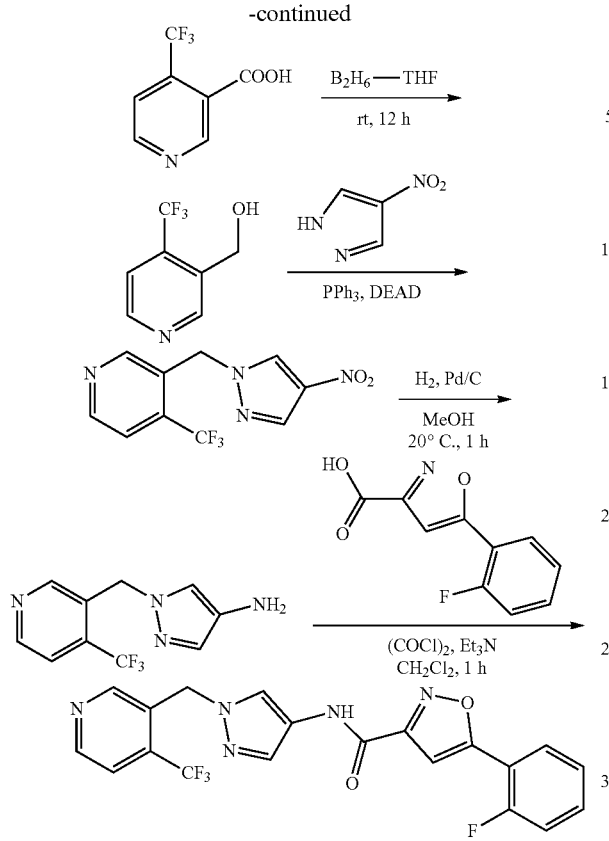

Step 1: Preparation of 4-(trifluoromethyl)nicotinic Acid

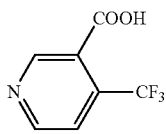 [SMILES: O=C(O)c1cnccc1C(F)(F)F]

To a solution of 4-(trifluoromethyl)nicotinonitrile (5.0 g, 29.0 mmol) in water (30 mL) was added concentrated sulfuric acid (30 mL) slowly. The reaction mixture was heated to 110° C. and stirred for 12 h. The mixture was cooled then aqueous sodium carbonate was added to adjust the pH to 35. The aqueous phase was extracted with dichloromethane (200 mL×2). The combined organic layers were dried over sodium sulfate, filtered and concentrated to give 4-(trifluoromethyl)nicotinic acid as a white solid (2.0 g, crude, 36%). This material was used in the step without additional purification.

Step 2: Preparation of (4-(trifluoromethyl)pyridin-3-yl)methanol

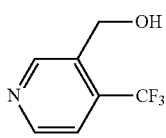

To a solution of 4-(trifluoromethyl)nicotinic acid (2.0 g, 10.5 mmol) in tetrahydrofuran (20 mL) was added borane-tetrahydrofuran (31 mL, 31.4 mmol, 1 M). The reaction mixture was stirred at 20° C. for 12 h then was quenched with aqueous 1N hydrogen chloride solution. The crude mixture was heated to 90° C. and stirred for 1 h. The solid was filtered and aqueous sodium hydroxide was added to adjust the pH value to 8-10. The aqueous phase was extracted with dichloromethane (100 mL×2), dried over magnesium sulfate, filtered and concentrated under reduced pressure to offer 4-(trifluoromethyl)pyridin-3-yl)methanol (0.87 g, 47%) as a yellow solid. LCMS (ESI) m/z: 178.1 [M+H]$^+$.

Step 3: Preparation of 3-((4-nitro-1H-pyrazol-1-yl)methyl)-4-(trifluoromethyl)pyridine

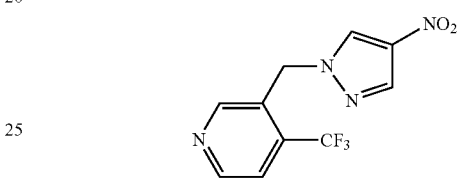

A mixture of (4-(trifluoromethyl)pyridin-3-yl)methanol (0.72 g, 4.07 mmol), 4-nitro-1H-pyrazole (0.46 g, 4.07 mmol), triphenylphosphine (4.3 g, 16.3 mmol) and tetrahydrofuran (30 mL) was stirred at 20° C. for 20 min. Diisopropyl azodicarboxylate (3.3 g, 16.3 mmol) was slowly added to the reaction and the reaction was then stirred at 20° C. for 2 h. The reaction mixture was diluted with ethyl acetate (100 mL) and washed with water (100 mL), brine (100 mL), dried over sodium sulfate, filtered and concentrated in vacuo. The crude residue was purified by column chromatography (silica, petroleum ether/ethyl acetate=5/1 to 2/1) to offer 3-((4-nitro-1H-pyrazol-1-yl)methyl)-4-(trifluoromethyl)pyridine (0.700 g, 2.6 mmol, 64%) as a yellow oil. LCMS (ESI) m/z: 273.1 [M+H]$^+$.

Step 4: Preparation of 1-((4-(trifluoromethyl)pyridin-3-yl)methyl)-1H-pyrazol-4-amine

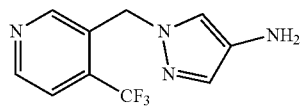

To a solution of 3-((4-nitro-1H-pyrazol-1-yl)methyl)-4-(trifluoromethyl)pyridine (0.300 g, 1.10 mmol) in methanol (10 mL) under nitrogen was added palladium on carbon (10% by weight, 0.030 g). The reaction mixture was purged with hydrogen and stirred at 20° C. for 30 min. The reaction mixture was filtered and the filtrate was concentrated in vacuo to afford 1-((4-(trifluoromethyl)pyridin-3-yl)methyl)-1H-pyrazol-4-amine (0.228 g, 9.35 mmol, 85%) as a red oil (which was used in the next step without further purification); LCMS (ESI) m/z: 243.2 [M+H]$^+$.

Step 5: Preparation of ethyl 5-(2-fluorophenyl)isoxazole-3-carboxylate

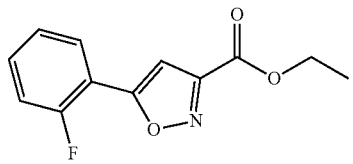 [SMILES: CCOC(=O)c1cc(-c2ccccc2F)on1]

A mixture of (Z)-ethyl 2-chloro-2-(hydroxyimino)acetate (2.0 g, 13.2 mmol) in N,N-dimethylformamide (5 mL) was slowly added to a solution of 1-ethynyl-2-fluorobenzene (3.97 g, 33.1 mmol) in N,N-dimethylformamide (10 mL) under nitrogen. The mixture was heated to 90° C. before a solution of triethylamine (4.02 g, 39.7 mmol) in N,N-dimethylformamide (5 mL) was slowly added. The reaction mixture was heated at 90° C. for 16 h then concentrated under reduced pressure. The residue was purified by column chromatography (silica, petroleum ether/ethyl acetate=2/1) to give ethyl 5-(2-fluorophenyl)isoxazole-3-carboxylate (2.0 g, 8.45 mmol, 64%) as a red solid. (LCMS (ESI) m/z: 236.1 [M+H]$^+$.

Step 6: Preparation of 5-(2-fluorophenyl)isoxazole-3-carboxylic Acid

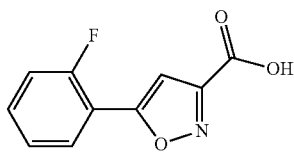 [SMILES: O=C(O)c1cc(-c2ccccc2F)on1]

To a solution of ethyl 5-(2-fluorophenyl)isoxazole-3-carboxylate (0.500 g, 2.13 mmol) in tetrahydrofuran (5 mL) at 0° C. was added lithium hydroxide hydrate (0.0894 g, 2.13 mmol) in water (4 mL) slowly. Then the reaction was stirred at 10° C. for 20 min before aqueous 1N hydrogen chloride solution was added to adjust pH to 23. Volatiles were removed under reduced pressure to give crude 5-(2-fluorophenyl)isoxazole-3-carboxylic acid (0.280 g, 1.36 mmol, 64%) as a yellow solid (which was used in the next step without further purification); LCMS (ESI) m/z: 208.1 [M+H]$^+$.

Step 7: Preparation of 5-(2-fluorophenyl)-N-(1-((4-(trifluoromethyl)pyridin-3-yl)methyl)-1H-pyrazol-4-yl)isoxazole-3-carboxamide

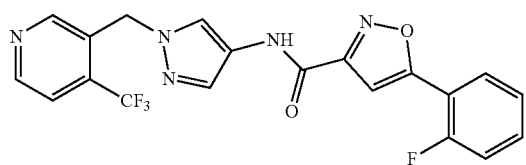 [SMILES: O=C(Nc1cnn(Cc2cnccc2C(F)(F)F)c1)c1cc(-c2ccccc2F)on1]

To a solution of 5-(2-fluorophenyl)isoxazole-3-carboxylic acid (0.150 g, 0.724 mmol) in dichloromethane (2 mL) at 20° C. was added oxalyl chloride (2 mL). The mixture was stirred at room temperature for 0.5 h before solvent was removed under reduced pressure. The resulting solid was dissolved in dichloromethane (2 mL) and added to a mixture of 1-((4-(trifluoromethyl)pyridin-3-yl)methyl)-1H-pyrazol-4-amine (0.228 g, 0.942 mmol) and triethylamine (220 mg, 2.172 mmol) in dichloromethane (5 mL) dropwise. The reaction mixture was stirred for another 0.5 h then purified by prep-TLC (silica, petroleum ether/ethyl acetate=1/1) to give 5-(2-fluorophenyl)-N-(1-((4-(trifluoromethyl)pyridin-3-yl)methyl)-1H-pyrazol-4-yl)isoxazole-3-carboxamide (0.0630 g, 0.145 mmol, 20%) as a white solid. ($^1$H NMR (400 MHz, Dimethylsulfoxide-d$_6$) δ 11.10 (s, 1H), 8.81 (s, 1H), 8.29-8.35 (m, 2H), 8.02-8.04 (m, 1H), 7.75-7.80 (m, 2H), 7.64-7.65 (m, 1H), 7.42-7.52 (m, 2H), 7.27 (s, 1H), 5.61 (s, 2H); LCMS (ESI) m/z: 432.0 [M+H]$^+$.

Example 48. Preparation of N-(1-{[4-(trifluoromethyl)pyridin-3-yl]methyl}-1H-pyrazol-4-yl)-4,5,6,7-tetrahydro-1,2-benzoxazole-3-carboxamide (194)

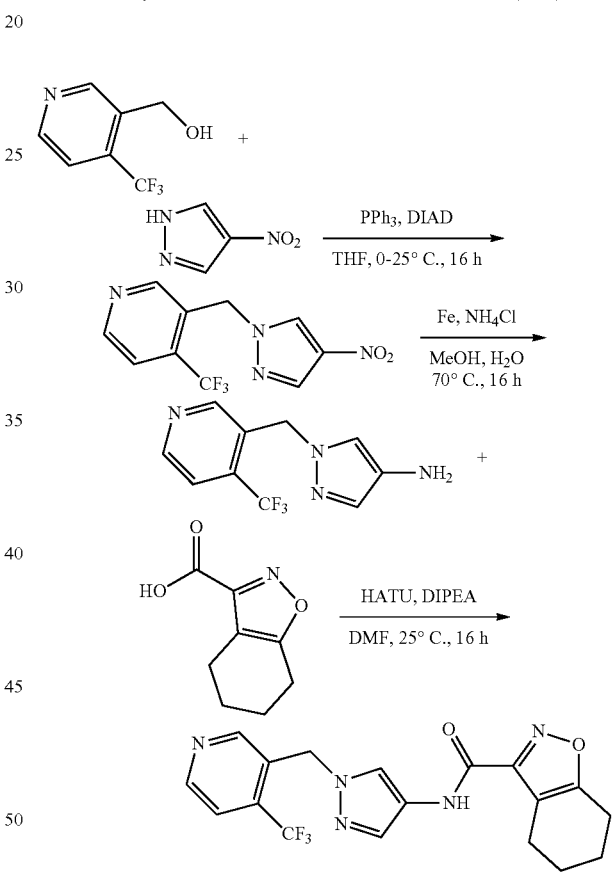

Step 1: Preparation of 3-((4-nitro-1H-pyrazol-1-yl)methyl)-4-(trifluoromethyl)pyridine

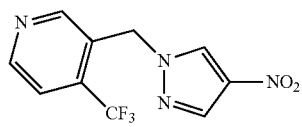

To a solution of [4-(trifluoromethyl)pyridin-3-yl]methanol (0.870 g, 4.91 mmol), 4-nitro-1H-pyrazole (0.555 g, 4.91 mmol) and triphenylphosphine (1.93 g, 7.36 mmol) in tetrahydrofuran (12.2 mL) at 0° C. was added diisopropyl azodicarboxylate (1.4 mL, 7.36 mmol). The reaction mixture was warmed to room temperature over 16 h. The volatiles were concentrated under reduced pressure. The crude residue was purified by column chromatography (ISCO, 24 g silica, eluting with 70% ethyl acetate/hexanes for 20 min) to afford 3-((4-nitro-1H-pyrazol-1-yl)methyl)-4-(trifluoromethyl)pyridine (0.90 g, 3.3 mmol, 67%) as a yellow solid. $^1$H NMR (300 MHz, Chloroform-d) δ 8.86 (d, J=5.1 Hz, 1H), 8.71 (s, 1H), 8.23-8.11 (m, 2H), 7.64 (d, J=5.1 Hz, 1H), 5.56 (s, 2H), 4.98 (h, J=6.3 Hz, 1H), 1.28 (d, J=6.2 Hz, 4H); LCMS (ESI) m/z: 273.1 [M+H]$^+$.

Step 2: Preparation of 1-{[4-(trifluoromethyl)pyridin-3-yl]methyl}-1H-pyrazol-4-amine

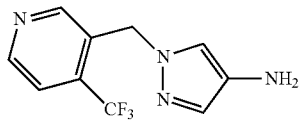

To a solution of 3-[(4-nitro-1H-pyrazol-1-yl)methyl]-4-(trifluoromethyl)pyridine (1.80 g, 6.61 mmol) and ammonium chloride (1.41 g, 26.4 mmol) in methanol (26 mL) and water (6.6 mL) at 70° C. was added iron (1.47 g, 26.4 mmol) in one portion. The reaction mixture was heated to 70° C. for 16 h. The reaction mixture was cooled to room temperature and diluted with saturated aqueous sodium bicarbonate (40 mL) and ethyl acetate (50 mL). The mixture was filtered through a pad of Celite® and the filter cake was washed with ethyl acetate (20 mL×3). The aqueous layer was extracted with ethyl acetate (50 mL×2). The combined organic layers were dried over magnesium sulfate, filtered and concentrated to give the 1-{[4-(trifluoromethyl)pyridin-3-yl]methyl}-1H-pyrazol-4-amine (1.50 g, 6.19 mmol, 94%) as a crude red solid. The material was used directly in the next step without further purification. $^1$H NMR (300 MHz, Dimethylsulfoxide-d$_6$) δ 8.91 (s, 1H), 8.78 (d, J=5.0 Hz, 1H), 8.16 (s, 1H), 7.78 (d, J=5.1 Hz, 1H), 7.20 (s, 1H), 7.03 (d, J=3.7 Hz, 1H), 5.41 (s, 2H), 4.03 (d, J=19.7 Hz, 2H).

Step 3: Preparation of N-(1-{[4-(trifluoromethyl)pyridin-3-yl]methyl}-1H-pyrazol-4-yl)-4,5,6,7-tetrahydro-1,2-benzoxazole-3-carboxamide

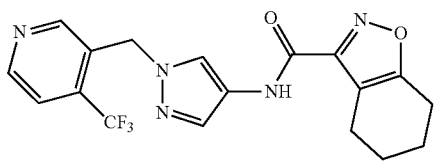 [SMILES: O=C(Nc1cnn(Cc2cnccc2C(F)(F)F)c1)c1noc2c1CCCC2]

To a solution of 1-{[4-(trifluoromethyl)pyridin-3-yl]methyl}-1H-pyrazol-4-amine (72.4 mg, 0.299 mmol), 4,5,6,7-tetrahydro-1,2-benzoxazole-3-carboxylic acid (50.0 mg, 0.299 mmol) and 1-[bis(dimethylamino)methylene]-1H-1,2,3-triazolo[4,5-b]pyridinium 3-oxide hexafluorophosphate (113 mg, 0.299 mmol) in N,N-dimethylformamide (1 mL) at 25° C. was added diisopropylethylamine (130 µL, 0.748 mmol). The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 60% ethyl acetate/hexanes for 20 min) to afford N-(1-{[4-(trifluoromethyl)pyridin-3-yl]methyl}-1H-pyrazol-4-yl)-4,5,6,7-tetrahydro-1,2-benzoxazole-3-carboxamide (55.4 mg, 0.142 mmol, 47%) as a yellow solid. $^1$H NMR (300 MHz, dimethylsulfoxide-d$_6$) δ 11.00 (s, 1H), 8.84-8.73 (m, 1H), 8.34 (s, 1H), 8.24 (s, 1H), 7.79 (d, J=5.1 Hz, 1H), 7.71 (d, J=0.7 Hz, 1H), 5.58 (s, 2H), 2.75 (q, J=6.1 Hz, 4H), 1.72 (dd, J=12.7, 7.6 Hz, 4H); LCMS (ESI) m/z: 392.3 [M+H]$^+$.

Example 49. Preparation of 5-(pyridin-2-yl)-N-(1-{[4-(trifluoromethyl)pyridin-3-yl]methyl}-1H-pyrazol-4-yl)-1,2-oxazole-3-carboxamide (197)

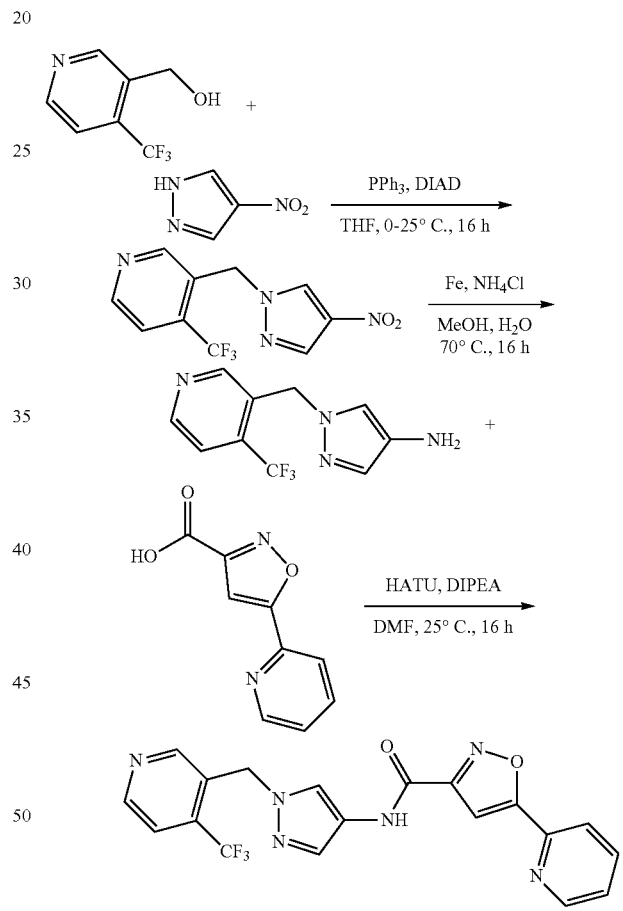

Step 1: Preparation of 3-((4-nitro-1H-pyrazol-1-yl)methyl)-4-(trifluoromethyl)pyridine

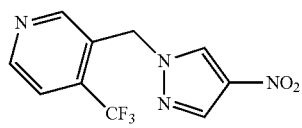 [SMILES: O=[N+]([O-])c1cnn(Cc2cnccc2C(F)(F)F)c1]

To a solution of [4-(trifluoromethyl)pyridin-3-yl]methanol (0.870 g, 4.91 mmol), 4-nitro-1H-pyrazole (0.555 g, 4.91 mmol) and triphenylphosphine (1.93 g, 7.36 mmol) in tetrahydrofuran (12.2 mL) at 0° C. was added diisopropyl azodicarboxylate (1.4 mL, 7.36 mmol). The reaction mixture was warmed to room temperature over 16 h. The volatiles were concentrated under reduced pressure. The crude residue was purified by column chromatography (ISCO, 24 g silica, eluting with 70% ethyl acetate/hexanes for 20 min) to afford 3-((4-nitro-1H-pyrazol-1-yl)methyl)-4-(trifluoromethyl)pyridine (0.90 g, 3.3 mmol, 67%) as a yellow solid. $^1$H NMR (300 MHz, Chloroform-d) δ 8.86 (d, J=5.1 Hz, 1H), 8.71 (s, 1H), 8.23-8.11 (m, 2H), 7.64 (d, J=5.1 Hz, 1H), 5.56 (s, 2H), 4.98 (h, J=6.3 Hz, 1H), 1.28 (d, J=6.2 Hz, 4H); LCMS (ESI) m/z: 273.1 [M+H]$^+$.

Step 2: Preparation of 1-{[4-(trifluoromethyl)pyridin-3-yl]methyl}-1H-pyrazol-4-amine

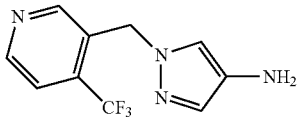

To a solution of 3-[(4-nitro-1H-pyrazol-1-yl)methyl]-4-(trifluoromethyl)pyridine (1.80 g, 6.61 mmol) and ammonium chloride (1.41 g, 26.4 mmol) in methanol (26 mL) and water (6.6 mL) at 70° C. was added iron (1.47 g, 26.4 mmol) in one portion. The reaction mixture was heated to 70° C. for 16 h. The reaction mixture was cooled to room temperature and diluted with saturated aqueous sodium bicarbonate (40 mL) and ethyl acetate (50 mL). The mixture was filtered through a pad of Celite® and the filter cake was washed with ethyl acetate (20 mL×3). The aqueous layer was extracted with ethyl acetate (50 mL×2). The combined organic layers were dried over magnesium sulfate, filtered and concentrated to give the 1-{[4-(trifluoromethyl)pyridin-3-yl]methyl}-1H-pyrazol-4-amine (1.50 g, 6.19 mmol, 94%) as a crude red solid. The material was used directly in the next step without further purification. $^1$H NMR (300 MHz, Dimethylsulfoxide-d$_6$) δ 8.91 (s, 1H), 8.78 (d, J=5.0 Hz, 1H), 8.16 (s, 1H), 7.78 (d, J=5.1 Hz, 1H), 7.20 (s, 1H), 7.03 (d, J=3.7 Hz, 1H), 5.41 (s, 2H), 4.03 (d, J=19.7 Hz, 2H).

Step 3: Preparation of 5-(pyridin-2-yl)-N-(1-{[4-(trifluoromethyl)pyridin-3-yl]methyl}-1H-pyrazol-4-yl)-1,2-oxazole-3-carboxamide

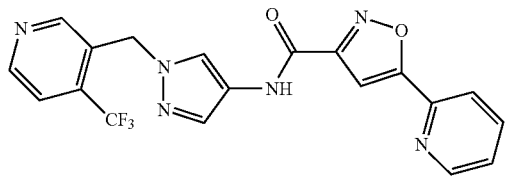 [SMILES: O=C(Nc1cnn(Cc2cnccc2C(F)(F)F)c1)c1cc(-c2ccccn2)on1]

To a solution of 5-(pyridin-2-yl)-1,2-oxazole-3-carboxylic acid (50 mg, 0.263 mmol), 1-{[4-(trifluoromethyl)pyridin-3-yl]methyl}-1H-pyrazol-4-amine (63.6 mg, 0.263 mmol) and 1-[bis(dimethylamino)methylene]-1H-1,2,3-triazolo[4,5-b]pyridinium 3-oxide hexafluorophosphate (99.9 mg, 0.263 mmol) in N,N'-dimethylformamide (1.1 mL) at 25° C. was added diisopropylethylamine (91.5 μL, 0.526 mmol) dropwise. The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 0-80% ethyl acetate/hexanes for 20 min) to afford 5-(pyridin-2-yl)-N-(1-{[4-(trifluoromethyl)pyridin-3-yl]methyl}-1H-pyrazol-4-yl)-1,2-oxazole-3-carboxamide (53.0 mg, 0.128 mmol, 49%) as a pale yellow solid. $^1$H NMR (300 MHz, Chloroform-d) δ 8.85-8.73 (m, 2H), 8.60 (s, 1H), 8.40 (s, 1H), 8.18 (s, 1H), 7.91 (dtd, J=17.1, 8.0, 1.5 Hz, 2H), 7.69 (s, 1H), 7.58 (d, J=5.1 Hz, 1H), 7.50-7.36 (m, 2H), 5.57 (s, 2H); LCMS (ESI) m/z: 415.3 [M+H]$^+$.

Example 50. Preparation of 5-(furan-2-yl)-N-(1-{[4-(trifluoromethyl)pyridin-3-yl]methyl}-1H-pyrazol-4-yl)-1,2-oxazole-3-carboxamide (198)

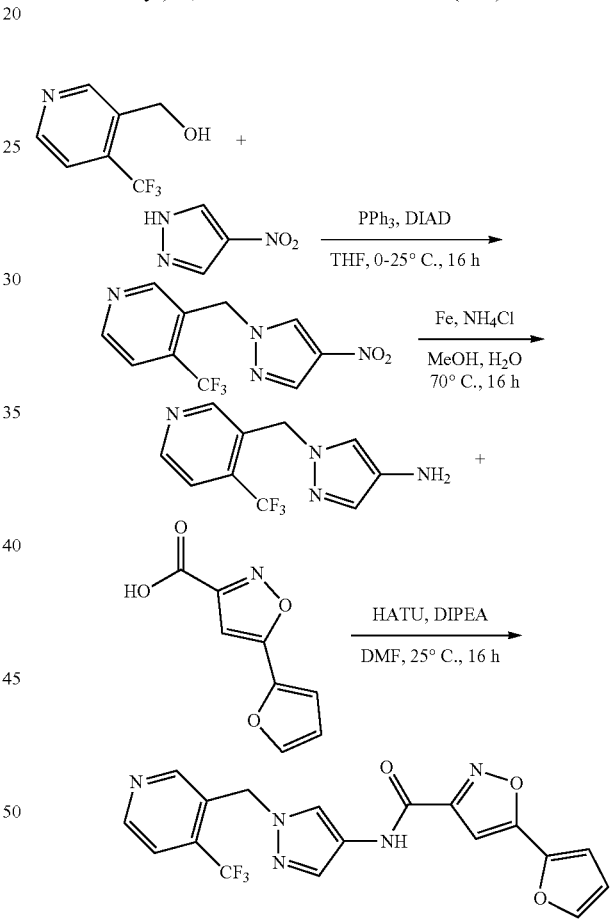

Step 1: Preparation of 3-((4-nitro-1H-pyrazol-1-yl)methyl)-4-(trifluoromethyl)pyridine

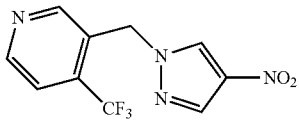 [SMILES: O=[N+]([O-])c1cnn(Cc2cnccc2C(F)(F)F)c1]

To a solution of [4-(trifluoromethyl)pyridin-3-yl]methanol (0.870 g, 4.91 mmol), 4-nitro-1H-pyrazole (0.555 g, 4.91 mmol) and triphenylphosphine (1.93 g, 7.36 mmol) in tetrahydrofuran (12.2 mL) at 0° C. was added diisopropyl azodicarboxylate (1.4 mL, 7.36 mmol). The reaction mixture was warmed to room temperature over 16 h. The volatiles were concentrated under reduced pressure. The crude residue was purified by column chromatography (ISCO, 24 g silica, eluting with 70% ethyl acetate/hexanes for 20 min) to afford 3-((4-nitro-1H-pyrazol-1-yl)methyl)-4-(trifluoromethyl)pyridine (0.90 g, 3.3 mmol, 67%) as a yellow solid. $^1$H NMR (300 MHz, Chloroform-d) δ 8.86 (d, J=5.1 Hz, 1H), 8.71 (s, 1H), 8.23-8.11 (m, 2H), 7.64 (d, J=5.1 Hz, 1H), 5.56 (s, 2H), 4.98 (h, J=6.3 Hz, 1H), 1.28 (d, J=6.2 Hz, 4H); LCMS (ESI) m/z: 273.1 [M+H]$^+$.

Step 2: Preparation of 1-{[4-(trifluoromethyl)pyridin-3-yl]methyl}-1H-pyrazol-4-amine

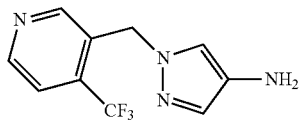

To a solution of 3-[(4-nitro-1H-pyrazol-1-yl)methyl]-4-(trifluoromethyl)pyridine (1.80 g, 6.61 mmol) and ammonium chloride (1.41 g, 26.4 mmol) in methanol (26.0 mL) and water (6.61 mL) at 70° C. was added iron (1.47 g, 26.4 mmol) in one portion. The reaction mixture was heated to 70° C. for 16 h. The reaction mixture was cooled to room temperature and diluted with saturated aqueous sodium bicarbonate (40 mL) and ethyl acetate (50 mL). The mixture was filtered through a pad of Celite® and the filter cake was washed with ethyl acetate (20 mL×3). The aqueous layer was extracted with ethyl acetate (50 mL×2). The combined organic layers were dried over magnesium sulfate, filtered and concentrated to give the 1-{[4-(trifluoromethyl)pyridin-3-yl]methyl}-1H-pyrazol-4-amine (1.50 g, 6.19 mmol, 94%) as a crude red solid. The material was used directly in the next step without further purification. $^1$H NMR (300 MHz, dimethylsulfoxide-d$_6$) δ 8.91 (s, 1H), 8.78 (d, J=5.0 Hz, 1H), 8.16 (s, 1H), 7.78 (d, J=5.1 Hz, 1H), 7.20 (s, 1H), 7.03 (d, J=3.7 Hz, 1H), 5.41 (s, 2H), 4.03 (d, J=19.7 Hz, 2H).

Step 3: Preparation of 5-(furan-2-yl)-N-(1-{[4-(trifluoromethyl)pyridin-3-yl]methyl}-1H-pyrazol-4-yl)-1,2-oxazole-3-carboxamide

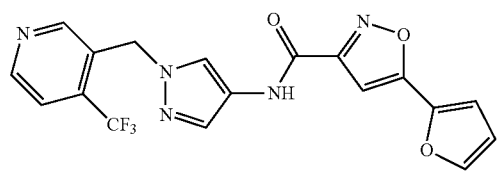 [SMILES: O=C(Nc1cnn(Cc2cnccc2C(F)(F)F)c1)c1cc(-c2ccco2)on1]

To a solution of 5-(furan-2-yl)-1,2-oxazole-3-carboxylic acid (0.05 g, 0.279 mmol), 1-{[4-(trifluoromethyl)pyridin-3-yl]methyl}-1H-pyrazol-4-amine (67.5 mg, 0.279 mmol) and 1-[bis(dimethylamino)methylene]-1H-1,2,3-triazolo[4,5-b]pyridinium 3-oxide hexafluorophosphate (106 mg, 0.279 mmol) in N,N'-dimethylformamide (1.1 mL) at 25° C. was added diisopropylethylamine (97.1 µL, 0.558 mmol) dropwise. The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 0-80% ethyl acetate/hexanes for 20 min) to afford 5-(furan-2-yl)-N-(1-{[4-(trifluoromethyl)pyridin-3-yl]methyl}-1H-pyrazol-4-yl)-1,2-oxazole-3-carboxamide (48.5 mg, 0.120 mmol, 50%) as a yellow solid. $^1$H NMR (300 MHz, Chloroform-d) δ 8.77 (d, J=5.1 Hz, 1H), 8.55 (s, 1H), 8.40 (s, 1H), 8.15 (s, 1H), 7.68 (d, J=0.7 Hz, 1H), 7.63-7.46 (m, 2H), 7.01 (dd, J=3.5, 0.7 Hz, 1H), 6.93 (s, 1H), 6.59 (dd, J=3.5, 1.8 Hz, 1H), 5.56 (s, 2H); LCMS (ESI) m/z: 404.2 [M+H]$^+$.

Example 51. Preparation of 5-(2H-1,3-benzodioxol-5-yl)-N-(1-{[4-(trifluoromethyl)pyridin-3-yl]methyl}-1H-pyrazol-4-yl)-1,2-oxazole-3-carboxamide (199)

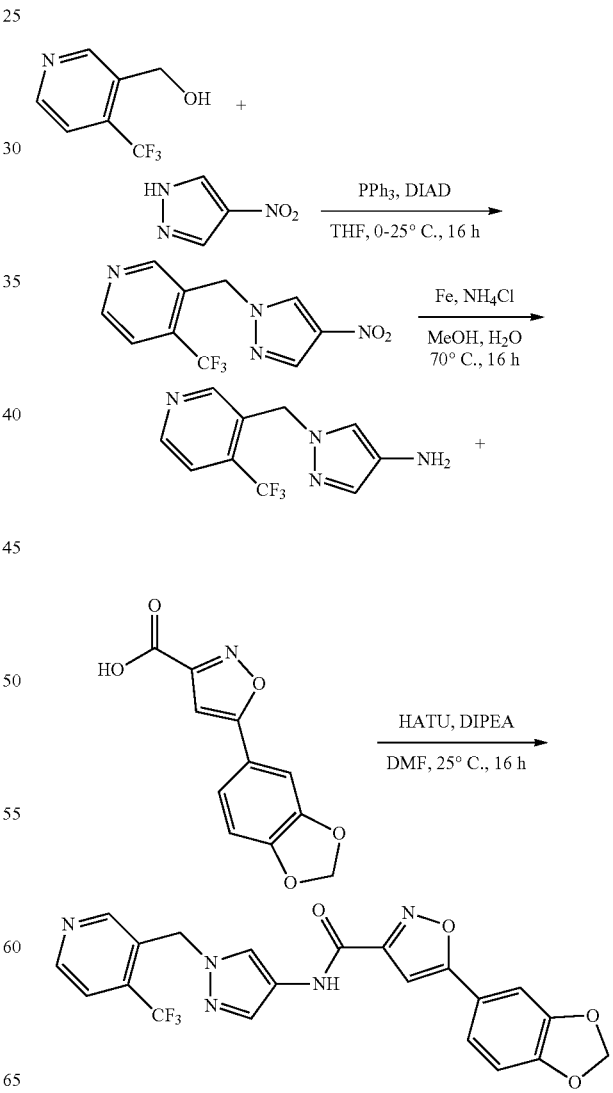

Step 1: Preparation of 3-((4-nitro-1H-pyrazol-1-yl)methyl)-4-(trifluoromethyl)pyridine

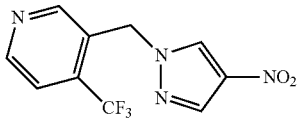

To a solution of [4-(trifluoromethyl)pyridin-3-yl]methanol (0.870 g, 4.91 mmol), 4-nitro-1H-pyrazole (0.555 g, 4.91 mmol) and triphenylphosphine (1.93 g, 7.36 mmol) in tetrahydrofuran (12.2 mL) at 0° C. was added diisopropyl azodicarboxylate (1.4 mL, 7.36 mmol). The reaction mixture was warmed to room temperature over 16 h. The volatiles were concentrated under reduced pressure. The crude residue was purified by column chromatography (ISCO, 24 g silica, eluting with 70% ethyl acetate/hexanes for 20 min) to afford 3-((4-nitro-1H-pyrazol-1-yl)methyl)-4-(trifluoromethyl)pyridine (0.90 g, 3.3 mmol, 67%) as a yellow solid. $^1$H NMR (300 MHz, Chloroform-d) δ 8.86 (d, J=5.1 Hz, 1H), 8.71 (s, 1H), 8.23-8.11 (m, 2H), 7.64 (d, J=5.1 Hz, 1H), 5.56 (s, 2H), 4.98 (h, J=6.3 Hz, 1H), 1.28 (d, J=6.2 Hz, 4H); LCMS (ESI) m/z: 273.1 [M+H]$^+$.

Step 2: Preparation of 1-{[4-(trifluoromethyl)pyridin-3-yl]methyl}-1H-pyrazol-4-amine

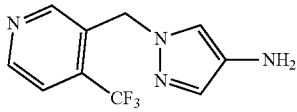

To a hot solution of 3-[(4-nitro-1H-pyrazol-1-yl)methyl]-4-(trifluoromethyl)pyridine (1.80 g, 6.61 mmol) and ammonium chloride (1.41 g, 26.4 mmol) in methanol (26.0 mL) and water (6.61 mL) at 70° C. was added iron (1.47 g, 26.4 mmol) in one portion. The reaction mixture was heated to 70° C. for 16 h. The reaction mixture was cooled to room temperature and diluted with saturated aqueous solution of sodium bicarbonate (40 mL) and ethyl acetate (50 mL). The mixture was filtered through a pad of Celite® and the filter cake was washed with ethyl acetate (20 mL×3). The aqueous layer was extracted with ethyl acetate (50 mL×2). The combined organic layers were dried over magnesium sulfate, filtered and concentrated to give the 1-{[4-(trifluoromethyl)pyridin-3-yl]methyl}-1H-pyrazol-4-amine (1.50 g, 6.19 mmol, 94%) as a crude red solid. The material was used directly in the next step without further purification. $^1$H NMR (300 MHz, Dimethylsulfoxide-d$_6$) δ 8.91 (s, 1H), 8.78 (d, J=5.0 Hz, 1H), 8.16 (s, 1H), 7.78 (d, J=5.1 Hz, 1H), 7.20 (s, 1H), 7.03 (d, J=3.7 Hz, 1H), 5.41 (s, 2H), 4.03 (d, J=19.7 Hz, 2H).

Step 3: Preparation of 5-(2H-1,3-benzodioxol-5-yl)-N-(1-{[4-(trifluoromethyl)pyridin-3-yl]methyl}-1H-pyrazol-4-yl)-1,2-oxazole-3-carboxamide

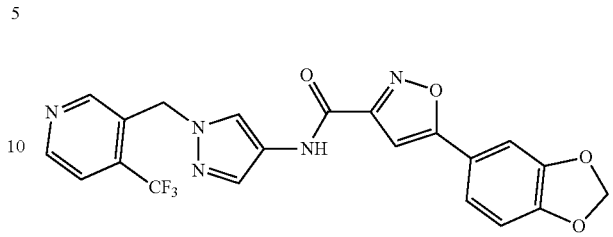

To a solution of 5-(2H-1,3-benzodioxol-5-yl)-1,2-oxazole-3-carboxylic acid (0.05 g, 0.214 mmol), 1-{[4-(trifluoromethyl)pyridin-3-yl]methyl}-1H-pyrazol-4-amine (51.9 mg, 0.214 mmol) and 1-[bis(dimethylamino)methylene]-1H-1,2,3-triazolo[4,5-b]pyridinium 3-oxide hexafluorophosphate (81.5 mg, 0.214 mmol) in N,N'-dimethylformamide (0.9 mL) at 25° C. was added diisopropylethylamine (74.6 µL, 0.429 mmol) dropwise. The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 0-80% ethyl acetate/hexanes for 20 min) to afford 5-(2H-1,3-benzodioxol-5-yl)-N-(1-{[4-(trifluoromethyl)pyridin-3-yl]methyl}-1H-pyrazol-4-yl)-1,2-oxazole-3-carboxamide (48.5 mg, 0.106 mmol, 55%) as a white solid. $^1$H NMR (300 MHz, Chloroform-d) δ 8.77 (d, J=5.1 Hz, 1H), 8.56 (s, 1H), 8.40 (s, 1H), 8.15 (s, 1H), 7.68 (d, J=0.7 Hz, 1H), 7.58 (d, J=5.1 Hz, 1H), 7.37 (dd, J=8.1, 1.7 Hz, 1H), 7.28 (s, 1H), 6.99-6.85 (m, 2H), 6.08 (s, 2H), 5.56 (s, 2H). LCMS (ESI) m/z: 458.3 [M+H]$^+$.

Example 52. Preparation of 5-(pyrimidin-4-yl)-N-(1-((4-(trifluoromethyl)pyridin-3-yl)methyl)-1H-pyrazol-4-yl)isoxazole-3-carboxamide (200)

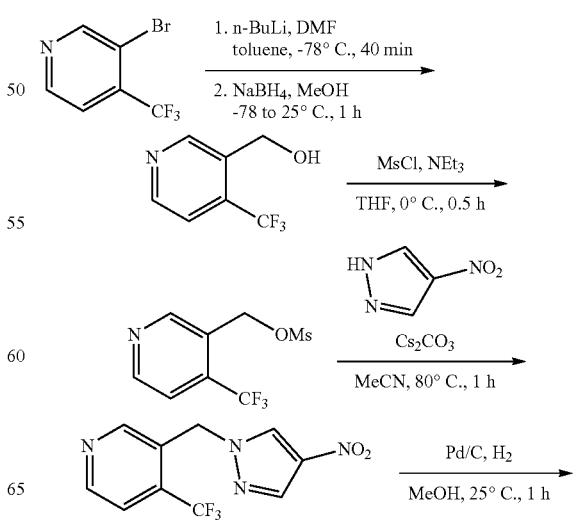

-continued

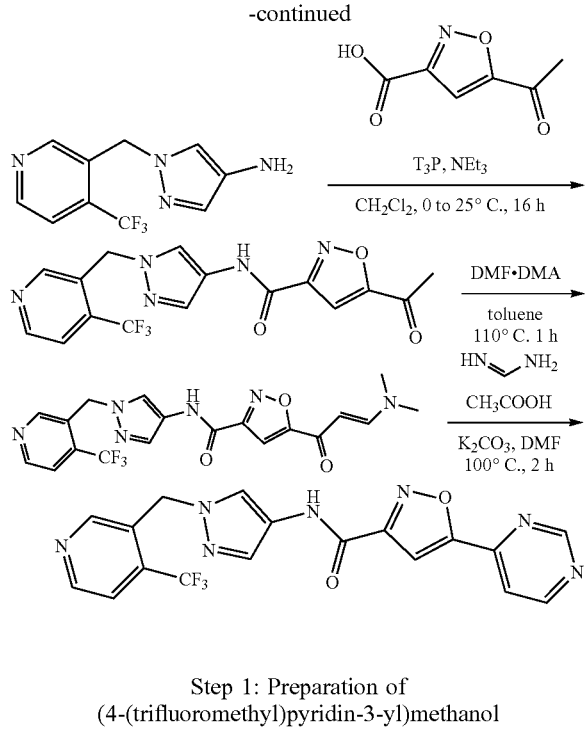

Step 1: Preparation of (4-(trifluoromethyl)pyridin-3-yl)methanol

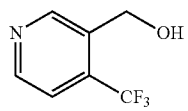

To a solution of 3-bromo-4-(trifluoromethyl)pyridine (2.26 g, 10.0 mmol) in toluene (50 mL) at −78° C. was added n-butyllithium (4.8 mL, 12 mmol) under nitrogen. The mixture was stirred at −78° C. for 30 min before N,N-dimethylformamide (1.1 g, 15 mmol) was added. The reaction mixture was stirred at −78° C. for 10 min then sodium borohydride (0.756 g, 20 mmol) and methanol (5 mL) was added sequentially at −78° C. and the reaction was warmed to 25° C. and stirred for 1 h. After completion, aqueous ammonium chloride was added to quench the reaction and the mixture was extracted with ethyl acetate (80 mL×3). The organic layer was dried over sodium sulfate, filtered and concentrated in vacuo. The crude residue was purified by column chromatography (silica, petroleum ether/ethyl acetate=2/1 to 1/1) to give (4-(trifluoromethyl)pyridin-3-yl)methanol (1.23 g, 6.95 mmol, 69%) as a colorless oil. LCMS (ESI) m/z: 178.1 [M+H]$^+$.

Step 2: Preparation of ethyl (4-(trifluoromethyl)pyridin-3-yl)methyl methanesulfonate

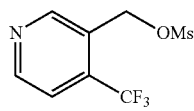

To a solution of ethyl (4-(trifluoromethyl)pyridin-3-yl) methanol (1.23 g, 6.9 mmol) and triethylamine (2.1 g, 20.8 mmol) in tetrahydrofuran (50 mL) at 0° C. was added methanesulfonyl chloride (1.59 g, 13.9 mmol) under nitrogen. The mixture was stirred at 0° C. for 30 min. The reaction mixture was used in next step directly. LCMS (ESI) m/z: 256.0 [M+H]$^+$.

Step 3: Preparation of 3-((4-nitro-1H-pyrazol-1-yl) methyl)-4-(trifluoromethyl)pyridine

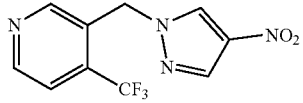

To a solution of 4-nitro-1H-pyrazole (1.57 g, 13.9 mmol) and cesium carbonate (6.78 g, 20.8 mmol) in acetonitrile (50 mL) at 25° C. was added ethyl (4-(trifluoromethyl)pyridin-3-yl)methyl methanesulfonate (crude solution in tetrahydrofuran, 6.9 mmol) under nitrogen. The mixture was heated at 80° C. for 1 h. After completion, ethyl acetate (100 mL) was added to dilute the mixture, the mixture was then washed with water (50 mL×2). The organic layer was dried over sodium sulfate, filtered and concentrated in vacuo. The crude residue was purified by column chromatography (silica, petroleum ether/ethyl acetate=3/1) to give 3-((4-nitro-1H-pyrazol-1-yl)methyl)-4-(trifluoromethyl)pyridine (0.870 g, 3.2 mmol, 46%) as a white solid. LCMS (ESI) m/z: 273.1 [M+H]$^+$.

Step 4: Preparation of 1-((4-(trifluoromethyl)pyridin-3-yl)methyl)-1H-pyrazol-4-amine

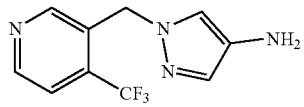 [SMILES: Nc1cnn(Cc2cnccc2C(F)(F)F)c1]

To a solution of 3-((4-nitro-1H-pyrazol-1-yl)methyl)-4-(trifluoromethyl)pyridine (436 mg, 1.6 mmol) in methanol (50 mL) was added 10% palladium on activated carbon (0.170 g, 1.6 mmol) at 25° C. under hydrogen balloon. The mixture was stirred 25° C. for 1 h. After completion, the reaction mixture was filtered through Celite® and washed with methanol. The filtrate was concentrated to give 1-((4-(trifluoromethyl)pyridin-3-yl)methyl)-1H-pyrazol-4-amine as a red oil (384 mg, 1.6 mmol, 100%). LCMS (ESI) m/z: 243.1 [M+H]$^+$.

Step 5: Preparation of N-(1-benzyl-1H-pyrazol-4-yl)-5-(1,3,4-thiadiazol-2-yl)isoxazole-3-carboxamide

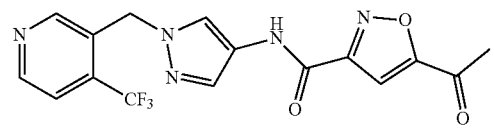 [SMILES: CC(=O)c1cc(C(=O)Nc2cnn(Cc3cnccc3C(F)(F)F)c2)no1]

To a solution of 1-((4-(trifluoromethyl)pyridin-3-yl) methyl)-1H-pyrazol-4-amine (384 mg, 1.6 mmol), 5-acetyl-isoxazole-3-carboxylic acid (272 mg, 1.75 mmol) and triethylamine (1.62 g, 16 mmol) in dichloromethane (50 mL) was added propylphosphonic anhydride (0.5 Min ethyl acetate, 5.1 g, 8.0 mmol) slowly at 0° C. under nitrogen. The mixture was stirred at room temperature for 16 h. After completion, water (30 mL) was added and the mixture was extracted with dichloromethane (100 mL×3). The organic layer was dried over sodium sulfate, filtered and concentrated in vacuo. The crude residue was purified by Prep-TLC (dichloromethane/ammonia in methanol (7N)=40/1) to give N-(1-benzyl-1H-pyrazol-4-yl)-5-(1,3,4-thiadiazol-2-yl)isoxazole-3-carboxamide (180 mg, 0.47 mmol, 30%) as a white solid. LCMS (ESI) m/z: 380.1 [M+H]$^+$.

Step 6: Preparation of (E)-5-(3-(dimethylamino)acryloyl)-N-(1-((4-(trifluoromethyl)pyridin-3-yl)methyl)-1H-pyrazol-4-yl)isoxazole-3-carboxamide

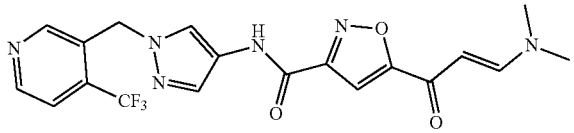 [SMILES: CN(C)/C=C/C(=O)c1cc(C(=O)Nc2cnn(Cc3cnccc3C(F)(F)F)c2)no1]

To a solution of N-(1-benzyl-1H-pyrazol-4-yl)-5-(1,3,4-thiadiazol-2-yl)isoxazole-3-carboxamide (0.180 g, 0.47 mmol) in toluene (15 mL) was added N,N-dimethylformamide dimethyl acetal (0.283 g, 2.37 mmol) under nitrogen. The mixture was stirred at 110° C. for 1 h and then cooled and concentrated in vacuo. The crude residue was triturated with diethyl ether (10 mL×2) and dried in vacuo to give (E)-5-(3-(dimethylamino)acryloyl)-N-(1-((4-(trifluoromethyl)pyridin-3-yl)methyl)-1H-pyrazol-4-yl)isoxazole-3-carboxamide (0.170 g, 0.39 mmol, 83%) as an orange solid. LCMS (ESI) m/z: 435.1 [M+H]$^+$.

Step 7: Preparation of 5-(pyrimidin-4-yl)-N-(1-((4-(trifluoromethyl)pyridin-3-yl)methyl)-1H-pyrazol-4-yl)isoxazole-3-carboxamide

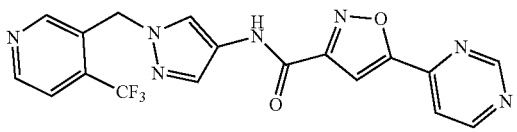 [SMILES: O=C(Nc1cnn(Cc2cnccc2C(F)(F)F)c1)c1cc(-c2ccncn2)on1]

A mixture of (E)-5-(3-(dimethylamino)acryloyl)-N-(1-((4-(trifluoromethyl)pyridin-3-yl)methyl)-1H-pyrazol-4-yl)isoxazole-3-carboxamide (136 mg, 0.31 mmol), formamide acetate (65 mg, 0.62 mmol) and potassium carbonate (87 mg, 0.62 mmol) in N,N-dimethylformamide (6 mL) was heated at 100° C. for 2 h in a sealed tube. The mixture was cooled then diluted with ethyl acetate (50 mL) and washed with brine (30 mL×3). The organic layer was dried over sodium sulfate, filtered and concentrated in vacuo. The crude residue was purified by Prep-HPLC (dissolved in minimal amount of N,N-dimethylformamide and loaded on Boston C18 21×250 mm 10 μm column. The mobile phases were acetonitrile/10 mM ammonium acetate aqueous solution) to give 5-(pyrimidin-4-yl)-N-(1-((4-(trifluoromethyl)pyridin-3-yl)methyl)-1H-pyrazol-4-yl)isoxazole-3-carboxamide (49 mg, 0.12 mmol, 38%) as a white solid. $^1$H NMR (400 MHz, Dimethylsulfoxide-d$_6$) δ 11.18 (s, 1H), 9.38 (d, J=1.2 Hz, 1H), 9.07 (d, J=5.2 Hz, 1H), 8.80 (d, J=4.8 Hz, 1H), 8.34 (s, 1H), 8.28 (s, 1H), 8.16 (dd, J$_1$=1.2 Hz, J$_2$=4.8 Hz, 1H), 7.77-7.79 (m, 2H), 7.74 (s, 1H), 5.60 (s, 2H); LCMS (ESI) m/z: 379.0 [M+H]$^+$.

Example 53. Preparation of 5-(piperidin-1-yl)-N-(1-((4-(trifluoromethyl)pyridin-3-yl)methyl)-1H-pyrazol-4-yl)isoxazole-3-carboxamide (182)

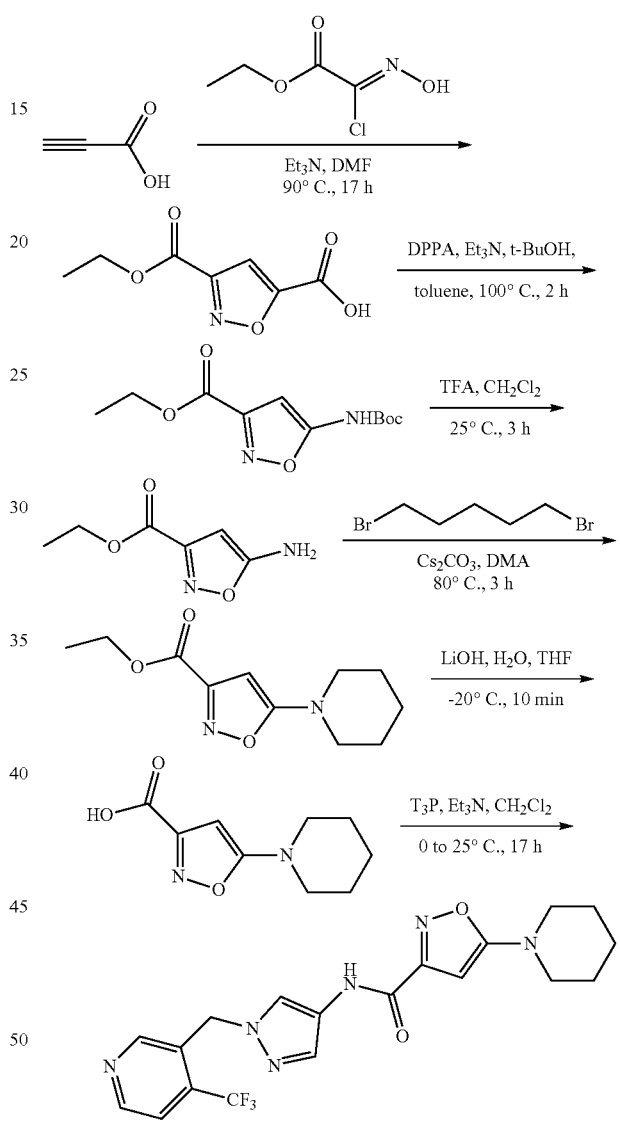

Step 1: Preparation of 3-(ethoxycarbonyl)isoxazole-5-carboxylic Acid

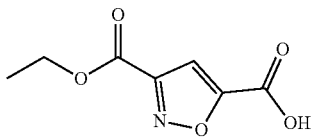

To a solution of propiolic acid (8.0 g, 114.2 mmol) in N,N-dimethylformamide (60 mL) was added a solution of (Z)-ethyl 2-chloro-2-(hydroxyimino)acetate (6.9 g, 45.7 mmol) in N,N-dimethylformamide (20 mL) dropwise over 40 min under nitrogen atmosphere. After the addition, the reaction mixture was heated to 90° C. and a solution of triethylamine (13.8 g, 137 mmol in N,N-dimethylformamide (20 mL) was added dropwise over 1 h. The reaction mixture was heated at 90° C. for 17 h and then cooled to room temperature. The reaction mixture was evaporated to dryness, diluted with water (30 mL) and adjusted to pH=2 with aqueous 1N hydrogen chloride. The aqueous layer was extracted with ethyl acetate (30 mL×2). The combined organic layers were washed with brine (30 mL×2), dried over anhydrous sodium sulfate, filtered and concentrated in vacuo to yield 3-(ethoxycarbonyl)isoxazole-5-carboxylic acid (3.2 g, 17.3 mmol, 38%) as a yellow oil. LCMS (ESI) m/z: 186.1 [M+H]⁺.

Step 2: Preparation of ethyl 5-(tert-butoxycarbonylamino)isoxazole-3-carboxylate

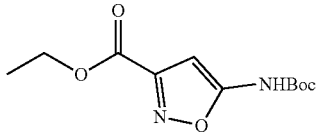 [SMILES: CCOC(=O)c1cc(NC(=O)OC(C)(C)C)on1]

To a solution of 3-(ethoxycarbonyl)isoxazole-5-carboxylic acid (2.7 g, 14.6 mmol) in toluene (40 mL) was added triethylamine (1.8 g, 17.5 mmol), tert-butanol (2.7 g, 36.5 mmol) and diphenylphosphoryl azide (4.8 g, 17.5 mmol). The reaction mixture was heated at 100° C. for 2 h and concentrated to dryness. The residue was purified by column chromatography (silica, petroleum ether/ethyl acetate=8/1) to afford ethyl 5-(tert-butoxycarbonylamino)isoxazole-3-carboxylate (1.8 g, 7.0 mmol, 49%) as a white solid. LCMS (ESI) m/z: 257.2 [M+H]⁺.

Step 3: Preparation of ethyl 5-aminoisoxazole-3-carboxylate

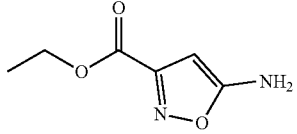

To a solution of ethyl 5-(tert-butoxycarbonylamino)isoxazole-3-carboxylate (0.5 g, 1.95 mmol) in dichloromethane (12 mL) was added trifluoroacetic acid (6 mL). The reaction mixture was stirred at 25° C. for 3 h and then concentrated in vacuo. The residue was purified by column chromatography (silica, petroleum ether/ethyl acetate=1/1) to yield ethyl 5-aminoisoxazole-3-carboxylate (0.170 g, 1.08 mmol, 57%) as a yellow solid. LCMS (ESI) m/z: 157.1 [M+H]⁺.

Step 4: Preparation of ethyl 5-(piperidin-1-yl)isoxazole-3-carboxylate

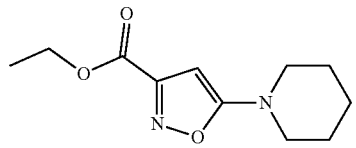 [SMILES: CCOC(=O)c1cc(N2CCCCC2)on1]

To a solution of ethyl 5-aminoisoxazole-3-carboxylate (0.170 g, 1.1 mmol) in dimethylacetamide (20 mL) was added cesium carbonate (1.07 g, 3.3 mmol) and 1,5-dibromopentane (0.630 g, 2.75 mmol). The reaction mixture was heated at 80° C. for 3 h and then cooled to room temperature and concentrated in vacuo. The residue was purified by column chromatography (silica, dichloromethane/methanol=15/1) to afford ethyl 5-(piperidin-1-yl)isoxazole-3-carboxylate (0.100 g, 0.44 mmol, 38%) as a white solid. LCMS (ESI) m/z: 225.2 [M+H]⁺.

Step 5: Preparation of 5-(piperidin-1-yl)isoxazole-3-carboxylic Acid

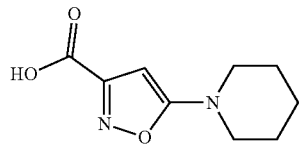

To a solution of ethyl 5-(piperidin-1-yl)isoxazole-3-carboxylate (0.100 g, 0.44 mmol) in tetrahydrofuran/water (v/v=2/1, 9 mL) at −20° C. was added lithium hydroxide hydrate (56 mg, 1.32 mmol). The reaction mixture was stirred at −20° C. for 10 min then evaporated to dryness to give 5-(piperidin-1-yl)isoxazole-3-carboxylic acid (75 mg, 0.38 mmol, 86%) as a yellow solid. LCMS (ESI) m/z: 197.1 [M+H]⁺.

Step 6: Preparation of 5-(piperidin-1-yl)-N-(1-((4-(trifluoromethyl)pyridin-3-yl)methyl)-1H-pyrazol-4-yl)isoxazole-3-carboxamide

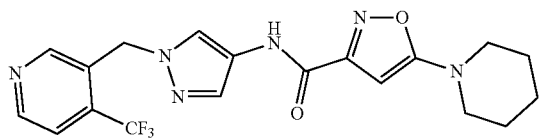 [SMILES: O=C(Nc1cnn(Cc2cnccc2C(F)(F)F)c1)c1cc(N2CCCCC2)on1]

To a solution of 5-(piperidin-1-yl)isoxazole-3-carboxylic acid (55 mg, 0.28 mmol) in dichloromethane (15 mL) at 0° C. was added 1-((4-(trifluoromethyl)pyridin-3-yl)methyl)-1H-pyrazol-4-amine (68 mg, 0.28 mmol) and triethylamine (0.283 g, 2.8 mmol) and propylphosphonic anhydride (0.445 g, 1.4 mmol). The mixture was stirred at 25° C. for 17 h. The crude sample was dissolved in minimum amount of N,N-dimethylformamide and purified via prep-HPLC (Boston C18 21×250 mm 10 μm column; acetonitrile/0.01% aqueous trifluoroacetic acid) to give (piperidin-1-yl)-N-(1-((4-(trifluoromethyl)pyridin-3-yl)methyl)-1H-pyrazol-4-yl)isoxazole-3-carboxamide (7.5 mg, 0.02 mmol, 6%) as a white solid. ¹H NMR (500 MHz, Dimethylsulfoxide-d₆) δ 10.72 (s, 1H), 8.80 (d, J=5.0 Hz, 1H), 8.32 (d, J=12.9 Hz, 1H), 8.22 (s, 1H), 7.79 (d, J=5.1 Hz, 1H), 7.70 (d, J=4.6 Hz, 1H), 5.63 (d, J=6.5 Hz, 1H), 5.58 (s, 2H), 3.35-3.31 (m, 4H), 1.58 (s, 6H); LCMS (ESI) m/z: 421.0 [M+H]⁺.

Example 54. Preparation of 5-(prop-1-en-2-yl)-N-(1-((4-(trifluoromethyl)pyridin-3-yl)methyl)-1H-pyrazol-4-yl)isoxazole-3-carboxamide (166)

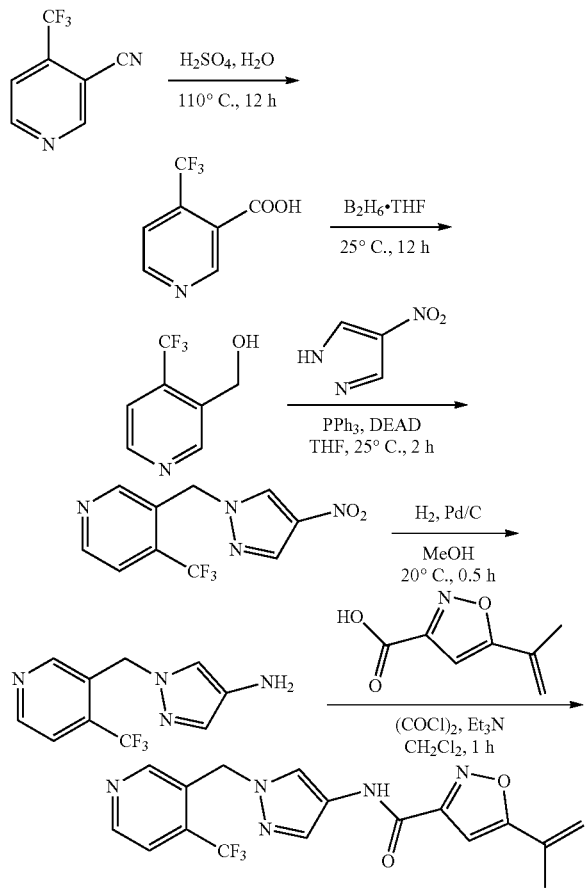

Step 1: Preparation of 4-(trifluoromethyl)nicotinic Acid

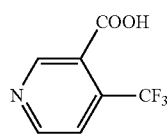 [SMILES: O=C(O)c1cnccc1C(F)(F)F]

The mixture of 4-(trifluoromethyl)nicotinonitrile (5.0 g, 29.1 mmol) in water (15 mL) was added concentrated sulfuric acid (15 mL) slowly. The reaction mixture was heated at 110° C. for 12 h, then cooled and extracted with tetrahydrofuran (50 mL×2). The organic layer was dried over sodium sulfate, filtered and concentrated under reduced pressure to offer 4-(trifluoromethyl)nicotinic acid (5.2 g, crude) as a white solid. LCMS (ESI) m/z: 192.1 [M+H]⁺. The material was used in the next step without further purification.

Step 2: Preparation of (4-(trifluoromethyl)pyridin-3-yl)methanol

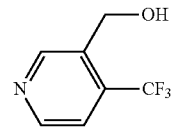

To a solution of 4-(trifluoromethyl)nicotinic acid (5.2 g, 27.2 mmol) in tetrahydrofuran (150 mL) was added borane tetrahydrofuran solution (82 mL, 1 M, 82 mmol). The reaction mixture was stirred for 16 h before 3N sodium hydroxide was added. The mixture was heated to 60° C. and stirred for 1 h. The bi-phasic mixture was separated and the organic layer was concentrated to offer crude (4-(trifluoromethyl)pyridin-3-yl)methanol (3.3 g, crude) as a yellow oil. LCMS (ESI) m/z: 178.1 [M+H]⁺. The material was used in the next step without further purification.

Step 3: Preparation of 3-((4-nitro-1H-pyrazol-1-yl)methyl)-4-(trifluoromethyl)pyridine

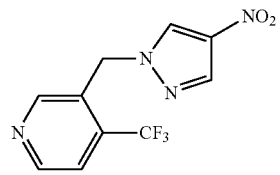 [SMILES: O=[N+]([O-])c1cnn(Cc2cnccc2C(F)(F)F)c1]

A mixture of (4-(trifluoromethyl)pyridin-3-yl)methanol (3.2 g, 18.1 mmol), 4-nitro-1H-pyrazole (2.05 g, 18.1 mmol) and triphenylphosphine (10.4 g, 39.8 mmol) in tetrahydrofuran (20 mL) was stirred at 20° C. for 0.5 h. Diisopropyl azodicarboxylate (8.04 g, 39.8 mmol) was added slowly and the reaction mixture was stirred at 20° C. for 4 h. The volatiles were removed under reduced pressure and the crude material was purified by column chromatography (silica, petroleum ether/ethyl acetate=1/1) to yield 3-((4-nitro-1H-pyrazol-1-yl)methyl)-4-(trifluoromethyl)pyridine (1.24 g, 4.56 mmol, 25%) as a yellow solid. LCMS (ESI) m/z: 273.1 [M+H]⁺.

Step 4: Preparation of 1-((4-(trifluoromethyl)pyridin-3-yl)methyl)-1H-pyrazol-4-amine

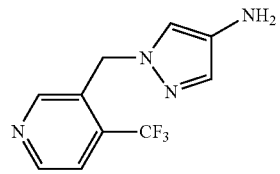

To a solution of 3-((4-nitro-1H-pyrazol-1-yl)methyl)-4-(trifluoromethyl)pyridine (1.24 g, 4.56 mmol) in methanol (15 mL) under nitrogen was added palladium on carbon (0.248 g, 10% Pd by weight). The reaction mixture was stirred at 20° C. for 0.5 h under hydrogen balloon. The mixture was filtered and the filtrate was concentrated in vacuo to give 1-((4-(trifluoromethyl)pyridin-3-yl)methyl)-1H-pyrazol-4-amine (1.1 g, crude) as a red solid. LCMS (ESI) m/z: 243.1 [M+H]$^+$.

Step 5: Preparation of 5-(prop-1-en-2-yl)-N-(1-((4-(trifluoromethyl)pyridin-3-yl)methyl)-1H-pyrazol-4-yl)isoxazole-3-carboxamide

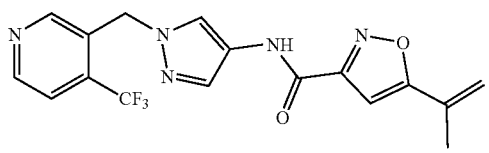 [SMILES: C=C(C)c1cc(C(=O)Nc2cnn(Cc3cnccc3C(F)(F)F)c2)no1]

To a solution of 5-(prop-1-en-2-yl)isoxazole-3-carboxylic acid (100 mg, 0.653 mmol) in dichloromethane (2 mL) at 20° C. was added oxalyl chloride (1 mL). The reaction mixture was stirred at room temperature for 0.5 h. The volatiles were removed in vacuo and the residue was dissolved in dichloromethane (2 mL). and added to a mixture of 1-((4-(trifluoromethyl)pyridin-3-yl)methyl)-1H-pyrazol-4-amine (158 mg, 0.653 mmol) and triethylamine (198 mg, 1.96 mmol) in dichloromethane (5 mL) dropwise. The reaction mixture was stirred for 0.5 h and dissolved in minimum amount of N,N-dimethylformamide and purified by Prep-HPLC (Boston C18 21×250 mm 10 μm column. The mobile phases were acetonitrile/0.01% aqueous trifluoroacetic acid) to offer 5-(prop-1-en-2-yl)-N-(1-((4-(trifluoromethyl)pyridin-3-yl)methyl)-1H-pyrazol-4-yl)isoxazole-3-carboxamide (8.8 mg, 0.023 mmol, 4%) as a white solid. $^1$H NMR (500 MHz, Dimethylsulfoxide-d$_6$) δ 11.02 (s, 1H), 8.81 (d, J=5.5 Hz, 1H), 8.33 (s, 1H), 8.27 (s, 1H), 7.79 (d, J=5.0 Hz, 1H), 7.72 (s, 1H), 7.02 (s, 1H), 5.87 (s, 1H), 5.60 (s, 2H), 5.48 (s, 1H), 2.12 (s, 3H); LCMS (ESI) m/z: 378.1 [M+H]$^+$.

Example 55. Preparation of 5-phenyl-N-(1-((4-(trifluoromethyl)pyridin-3-yl)methyl)-1H-pyrazol-4-yl)isoxazole-3-carboxamide (160)

Step 1: Preparation of 1-((4-(trifluoromethyl)pyridin-3-yl)methyl)-1H-pyrazol-4-amine

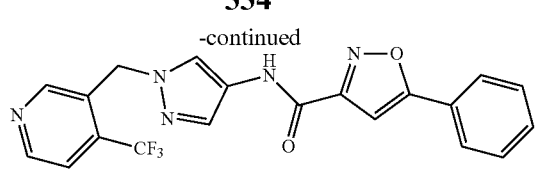

To a solution of 3-((4-nitro-1H-pyrazol-1-yl)methyl)-4-(trifluoromethyl)pyridine (300 mg, 1.03 mmol) in methanol (10 mL) under nitrogen was added palladium on carbon (90 mg, 10% Pd by weight). The reaction mixture was stirred at 20° C. for 0.5 h under hydrogen balloon. The mixture was filtered and the filtrate was concentrated in vacuo to give 1-((4-(trifluoromethyl)pyridin-3-yl)methyl)-1H-pyrazol-4-amine (250 mg, crude) as a red oil. LCMS (ESI) m/z: 243.1 [M+H]$^+$.

Step 2: Preparation of 5-phenyl-N-(1-((4-(trifluoromethyl)pyridin-3-yl)methyl)-1H-pyrazol-4-yl)isoxazole-3-carboxamide

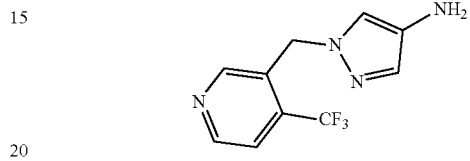

To a solution of 5-phenylisoxazole-3-carboxylic acid (117 mg, 0.620 mmol) in dichloromethane (2 mL) at 20° C. was added oxalyl chloride (1 mL). The reaction mixture was stirred at room temperature for 0.5 h. The volatiles were removed in vacuo. The crude residue was dissolved in dichloromethane (2 mL) and added to a mixture of 1-((4-(trifluoromethyl)pyridin-3-yl)methyl)-1H-pyrazol-4-amine (0.150 g, 0.620 mmol) and triethylamine (0.188 g, 1.86 mmol) in dichloromethane (5 mL) dropwise. The reaction mixture was stirred for 0.5 h and purified by prep-HPLC (the crude sample was dissolved in N,N-dimethylformamide and loaded onto Boston C18 21×250 mm 10 μm column. The mobile phases were acetonitrile/0.01% aqueous trifluoroacetic acid) to offer 5-phenyl-N-(1-((4-(trifluoromethyl)pyridin-3-yl)methyl)-1H-pyrazol-4-yl)isoxazole-3-carboxamide (65.5 mg, 0.158 mmol, 25%) as a white solid. $^1$H NMR (500 MHz, Dimethylsulfoxide-d$_6$) δ 11.09 (s, 1H), 8.81 (d, J=5.0 Hz, 1H), 8.34 (s, 1H), 8.29 (s, 1H), 7.98 (dd, J=7.6, 1.6 Hz, 2H), 7.80 (d, J=5.0 Hz, 1H), 7.75 (s, 1H), 7.59-7.56 (m, 3H), 7.47 (s, 1H), 5.61 (s, 2H); LCMS (ESI) m/z: 414.1 [M+H]$^+$.

Example 56. Preparation of 5-isopropyl-N-(1-((4-(trifluoromethyl)pyridin-3-yl)methyl)-1H-pyrazol-4-yl)isoxazole-3-carboxamide (161)

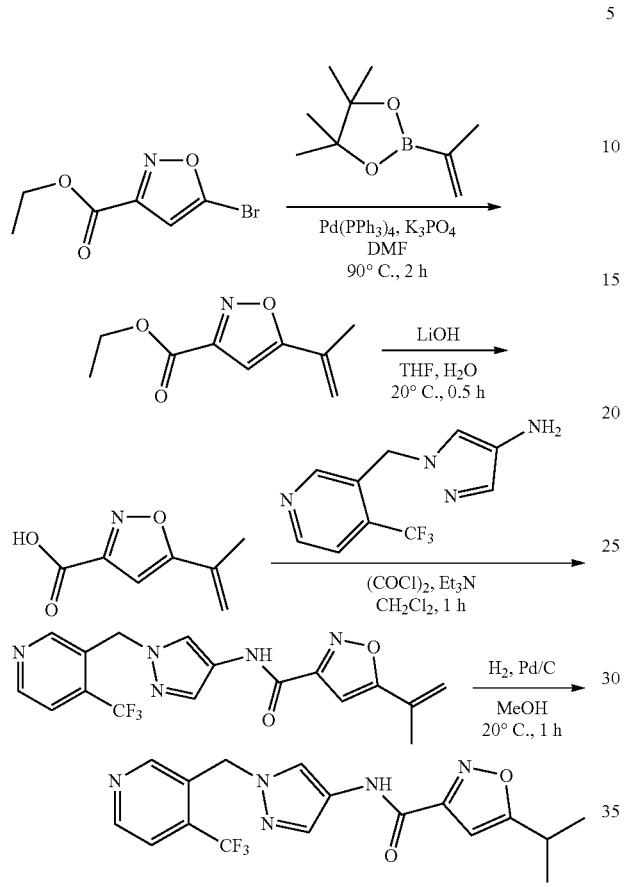

Step 1: Preparation of ethyl 5-(prop-1-en-2-yl)isoxazole-3-carboxylate

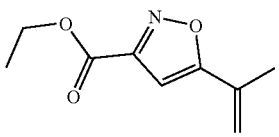

To a solution of ethyl 5-bromoisoxazole-3-carboxylate (0.5 g, 2.28 mmol), 4,4,5,5-tetramethyl-2-(prop-1-en-2-yl)-1,3,2-dioxaborolane (461 mg, 2.74 mmol) and potassium phosphate (968 mg, 4.568 mmol) in N,N-dimethylformamide (5 mL) under nitrogen was added palladium tetraphosphate (257 mg, 0.223 mmol). The reaction mixture was heated to 90° C. and stirred for 2 h. The organic layer was diluted with ethyl acetate (50 mL) and washed with water (100 mL). The organic layer was concentrated in vacuo. The crude material was purified by prep-TLC (silica, petroleum ether/ethyl acetate=4/1) to yield ethyl 5-(prop-1-en-2-yl)isoxazole-3-carboxylate as a yellow oil (350 mg, 1.93 mmol, 85%). LCMS (ESI) m/z: 182.1 [M+H]$^+$.

Step 2: Preparation of 5-(prop-1-en-2-yl)isoxazole-3-carboxylic Acid

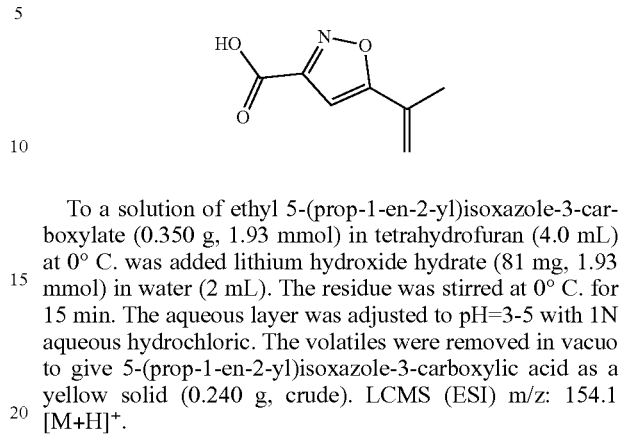

To a solution of ethyl 5-(prop-1-en-2-yl)isoxazole-3-carboxylate (0.350 g, 1.93 mmol) in tetrahydrofuran (4.0 mL) at 0° C. was added lithium hydroxide hydrate (81 mg, 1.93 mmol) in water (2 mL). The residue was stirred at 0° C. for 15 min. The aqueous layer was adjusted to pH=3-5 with 1N aqueous hydrochloric. The volatiles were removed in vacuo to give 5-(prop-1-en-2-yl)isoxazole-3-carboxylic acid as a yellow solid (0.240 g, crude). LCMS (ESI) m/z: 154.1 [M+H]$^+$.

Step 3: Preparation of 5-(prop-1-en-2-yl)-N-(1-((4-(trifluoromethyl)pyridin-3-yl)methyl)-1H-pyrazol-4-yl)isoxazole-3-carboxamide

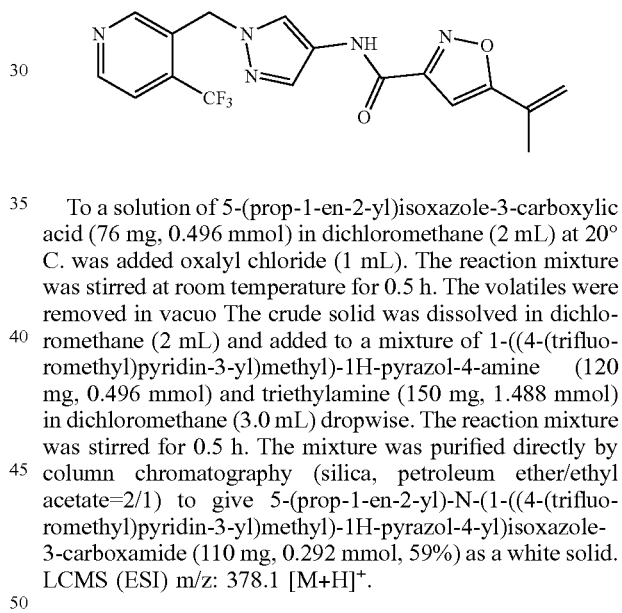

To a solution of 5-(prop-1-en-2-yl)isoxazole-3-carboxylic acid (76 mg, 0.496 mmol) in dichloromethane (2 mL) at 20° C. was added oxalyl chloride (1 mL). The reaction mixture was stirred at room temperature for 0.5 h. The volatiles were removed in vacuo The crude solid was dissolved in dichloromethane (2 mL) and added to a mixture of 1-((4-(trifluoromethyl)pyridin-3-yl)methyl)-1H-pyrazol-4-amine (120 mg, 0.496 mmol) and triethylamine (150 mg, 1.488 mmol) in dichloromethane (3.0 mL) dropwise. The reaction mixture was stirred for 0.5 h. The mixture was purified directly by column chromatography (silica, petroleum ether/ethyl acetate=2/1) to give 5-(prop-1-en-2-yl)-N-(1-((4-(trifluoromethyl)pyridin-3-yl)methyl)-1H-pyrazol-4-yl)isoxazole-3-carboxamide (110 mg, 0.292 mmol, 59%) as a white solid. LCMS (ESI) m/z: 378.1 [M+H]$^+$.

Step 4: Preparation of 5-isopropyl-N-(1-((4-(trifluoromethyl)pyridin-3-yl)methyl)-1H-pyrazol-4-yl)isoxazole-3-carboxamide

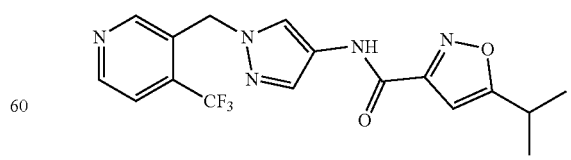

To a solution of 5-(prop-1-en-2-yl)-N-(1-((4-(trifluoromethyl)pyridin-3-yl)methyl)-1H-pyrazol-4-yl)isoxazole-3-carboxamide (110 mg, 0.292 mmol) in methanol (5 mL) under nitrogen was added 10% palladium on carbon (33 mg, 10%). The reaction mixture was stirred at 20° C. for 25 min under hydrogen balloon. The volatiles were removed in vacuo and the residue was purified by prep-HPLC (the crude sample was dissolved in N,N-dimethylformamide and loaded onto Boston C18 21×250 mm 10 μm column. The mobile phases were acetonitrile/0.01% aqueous trifluoroacetic acid) to give 5-isopropyl-N-(1-((4-(trifluoromethyl)pyridin-3-yl)methyl)-1H-pyrazol-4-yl)isoxazole-3-carboxamide (51.2 mg, 0.135 mmol, 46%) as a white solid. $^1$H NMR (500 MHz, Dimethylsulfoxide-$d_6$) δ 10.95 (s, 1H), 8.81 (d, J=5.0 Hz, 1H), 8.33 (s, 1H), 8.25 (s, 1H), 7.79 (d, J=5.0 Hz, 1H), 7.71 (s, 1H), 6.65 (d, J=1.0 Hz, 1H), 5.60 (s, 2H), 3.20-3.15 (m, 1H), 1.29 (d, J=7.0 Hz, 6H); LCMS (ESI) m/z: 380.1 [M+H]$^+$.

Example 57. Preparation of N-(1-(3,4-dichlorobenzyl)-3-methyl-1H-pyrazol-4-yl)-5-(furan-2-yl)isoxazole-3-carboxamide (17)

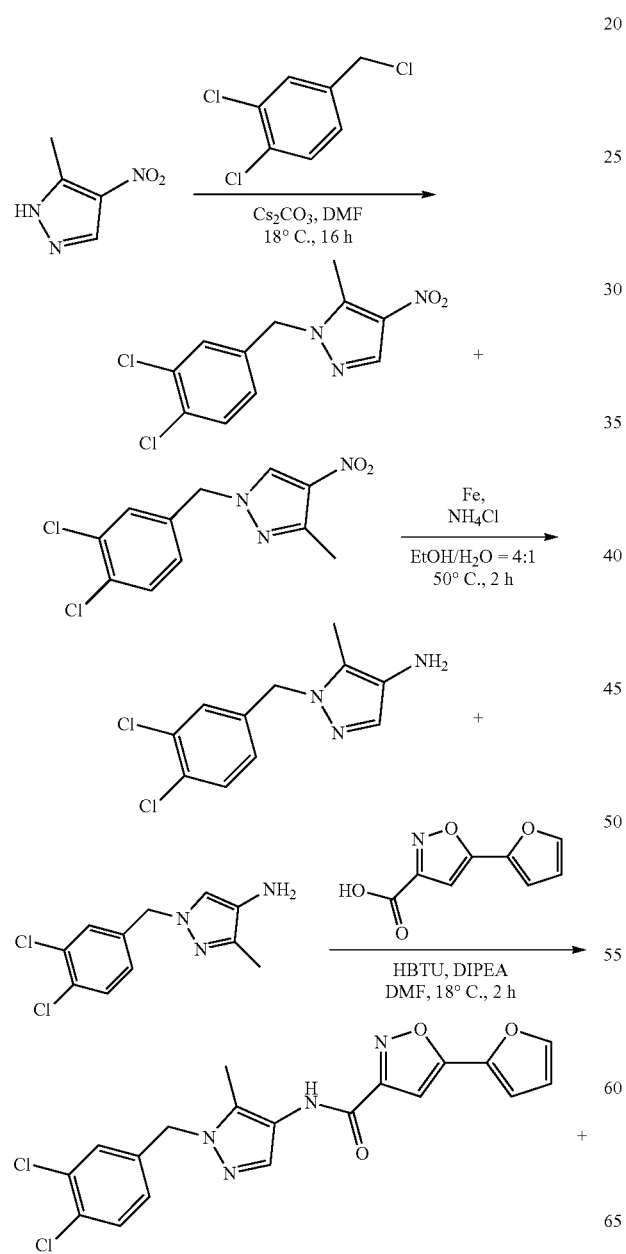

Step 1: Preparation of 1-[(3,4-dichlorophenyl)methyl]-5-methyl-4-nitro-pyrazole and 1-[(3,4-dichlorophenyl)methy]-3-methyl-4-nitro-pyrazole

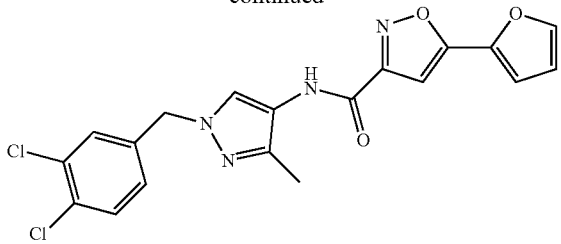

A mixture of 5-methyl-4-nitro-1H-pyrazole (1.00 g, 7.87 mmol), 1,2-dichloro-4-(chloromethyl)benzene (1.6 mL, 11.8 mmol) and cesium carbonate (2.56 g, 7.87 mmol) in N,N-dimethylformamide (10 mL) was purged with nitrogen (3×), and then the mixture was stirred at 18° C. for 16 h under nitrogen. The reaction mixture was washed with water (20 mL) and then extracted with ethyl acetate (10 mL×2). The combined organic layers were dried over sodium sulfate, filtered and concentrated under reduced pressure to give a residue. The residue was purified by column chromatography (silica, petroleum ether/ethyl acetate=40/1) to afford 1-[(3,4-dichlorophenyl)methyl]-5-methyl-4-nitro-pyrazole (1.6 g, crude) and 1-[(3,4-dichlorophenyl)methyl]-3-methyl-4-nitro-pyrazole (0.8 g, crude) as light yellow solids. LCMS (ESI) m/z: 285.9 [M+H]$^+$.

Step 2: Preparation of 1-[(3,4-dichlorophenyl)methyl]-3-methyl-pyrazol-4-amine and 1-[(3,4-dichlorophenyl)methyl]-5-methyl-pyrazol-4-amine

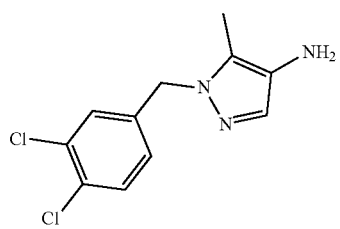

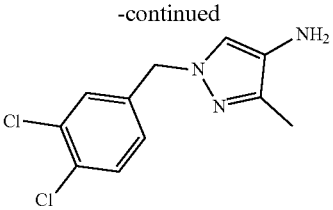

A mixture of 1-[(3,4-dichlorophenyl)methyl]-5-methyl-4-nitro-pyrazole (0.800 g, 2.80 mmol), 1-[(3,4-dichlorophenyl)methyl]-3-methyl-4-nitro-pyrazole (0.400 g, 1.40 mmol), iron powder (0.781 g, 14.0 mmol) and ammonium chloride (0.489 mL, 14.0 mmol) in ethanol (8 mL) and water (2 mL) was purged with nitrogen (3×) and then the mixture was heated at 50° C. for 2 h under nitrogen. The reaction mixture was filtered and the filtrate was extracted with dichloromethane (10 mL×2). The combined organic layers were washed with brine (5 mL×2), dried over sodium sulfate, filtered and concentrated under reduced pressure to give a mixture of 1-[(3,4-dichlorophenyl)methyl]-3-methyl-pyrazol-4-amine (0.5 g, crude) and 1-[(3,4-dichlorophenyl)methyl]-5-methyl-pyrazol-4-amine (1 g, crude) as yellow oils. LCMS (ESI) m/z: 256.0 [M+H]$^+$.

Step 3: Preparation of N-(1-(3,4-dichlorobenzyl)-5-methyl-1H-pyrazol-4-yl)-5-(furan-2-yl) isoxazole-3-carboxamide and N-(1-(3,4-dichlorobenzyl)-3-methyl-1H-pyrazol-4-yl)-5-(furan-2-yl)isoxazole-3-carboxamide

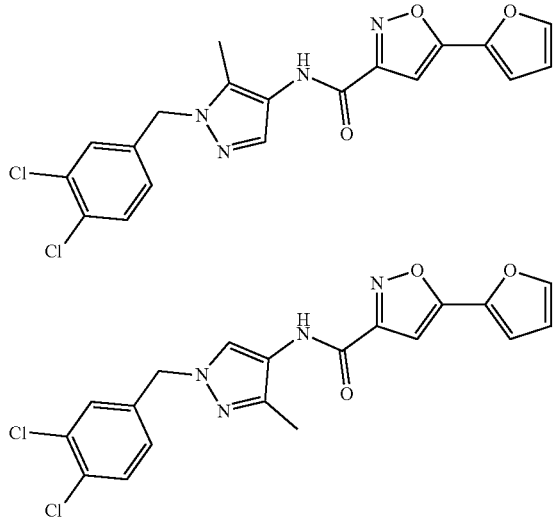

A mixture of 1-[(3,4-dichlorophenyl)methyl]-3-methyl-pyrazol-4-amine (0.107 g, 0.419 mmol), 1-[(3,4-dichlorophenyl)methyl]-5-methyl-pyrazol-4-amine (0.214 g, 0.837 mmol), 5-(2-furyl)isoxazole-3-carboxylic acid (0.150 g, 838 mmol), diisopropylethylamine (438 mL, 2.51 mmol) and N,N,N',N'-tetramethyl-O-(1H-benzotriazol-1-yl)uronium hexafluorophosphate (0.381 g, 1.00 mmol) in N,N-dimethylformamide (3 mL) was purged with nitrogen (3×) and then the mixture was stirred at 18° C. for 2 hour under nitrogen. The reaction mixture was washed with water (10 mL) and then extracted with ethyl acetate (5 mL×2). The combined organic layers were washed with brine (5 mL×2), dried over sodium sulfate, filtered and concentrated under reduced pressure to give a residue. The residue was purified by column chromatography (silica, petroleum ether/ethyl acetate=7/3, then by prep-HPLC (column: Agela Durashell C18 150×25 5 u; mobile phase: [water (0.04% ammonia)-acetonitrile]; B %: 35%-85%, 12 min) to produce firstly N-[1-[(3,4-dichlorophenyl)methyl]-3-methyl-pyrazol-4-yl]-5-(2-furyl)isoxazole-3-carboxamide (0.177 g, 0.409 mmol, 49%) as a brown solid. $^1$H NMR (400 MHz, Chloroform-d) δ=8.22 (s, 1H), 8.07 (s, 1H), 7.61 (d, J=1.2 Hz, 1H), 7.42 (d, J=8.4 Hz, 1H), 7.33 (d, J=2.0 Hz, 1H), 7.07 (dd, J=2.0, 8.4 Hz, 1H), 7.00 (d, J=3.6 Hz, 1H), 6.92 (s, 1H), 6.59 (dd, J=1.6, 3.5 Hz, 1H), 5.19 (s, 2H), 2.33 (s, 3H); LCMS (ESI) m/z: 417.2 [M+H]$^+$. and secondly N-[1-[(3,4-dichlorophenyl)methyl]-5-methyl-pyrazol-4-yl]-5-(2-furyl)isoxazole-3-carboxamide (0.040 g, 0.0957 mmol, 11%) as a white solid. $^1$H NMR (400 MHz, Chloroform-d) δ=8.07 (s, 1H), 7.83 (s, 1H), 7.61 (d, J=1.6 Hz, 1H), 7.41 (d, J=8.4 Hz, 1H), 7.24 (d, J=2.0 Hz, 1H), 7.00 (d, J=3.2 Hz, 1H), 6.96 (dd, J=1.6, 8.3 Hz, 1H), 6.94 (s, 1H), 6.59 (dd, J=2.0, 3.3 Hz, 1H), 5.26 (s, 2H), 2.21 (s, 3H); LCMS (ESI) m/z: 417.0 [M+H]$^+$.

Example 58. Preparation of N-[1-[[5-fluoro-2-(trifluoromethyl)phenyl]methyl]pyrazol-4-yl]-5-(2-furyl)isoxazole-3-carboxamide (36)

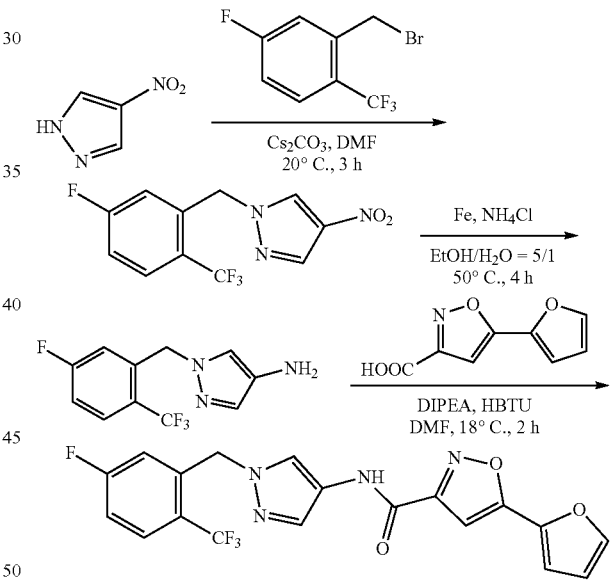

Step 1: Preparation of 1-[[5-fluoro-2-(trifluoromethyl)phenyl]methyl]-4-nitro-pyrazole

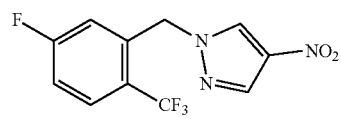 [SMILES: O=[N+]([O-])c1cnn(Cc2cc(F)ccc2C(F)(F)F)c1]

To a solution of 4-nitro-1H-pyrazole (0.150 g, 1.33 mmol) in N,N-dimethylformamide (4 mL) was added cesium carbonate (0.864 g, 2.65 mmol) and 2-(bromomethyl)-4-fluoro-1-(trifluoromethyl)benzene (0.358 g, 1.39 mmol). The mixture was stirred at 20° C. for 3 h. The reaction mixture was diluted with water (20 mL) and extracted with ethyl acetate (10 mL×3). The combined organic layers were washed with brine (20 mL), dried over sodium sulfate, filtered and concentrated under reduced pressure to give 1-[[5-fluoro-2-(trifluoromethyl)phenyl]methyl]-4-nitro-pyrazole (0.380 g, crude) as a red solid which was used in the next step without further purification. LCMS (ESI) mz: 290.0 [M+H]+.

Step 2: Preparation of 1-[[5-fluoro-2-(trifluoromethyl)phenyl]methyl]pyrazol-4-amine

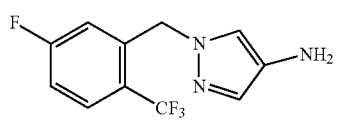 [SMILES: Nc1cnn(Cc2cc(F)ccc2C(F)(F)F)c1]

A mixture of 1-[[5-fluoro-2-(trifluoromethyl)phenyl]methyl]-4-nitro-pyrazole (0.380 g, 1.31 mmol), iron powder (0.367 g, 6.57 mmol), ammonium chloride (0.230 mL g, 6.57 mmol) in ethanol (20 mL) and water (5 mL) was purged with nitrogen (3×). The reaction mixture was warmed at 50° C. for 4 h under nitrogen atmosphere then concentrated under reduced pressure and diluted with water (20 mL). The aqueous layer was extracted with ethyl acetate (10 mL×3). The combined organic layers were washed with brine (20 mL), dried over sodium sulfate, filtered and concentrated under reduced pressure to give 1-[[5-fluoro-2-(trifluoromethyl)phenyl]methyl]pyrazol-4-amine (0.300 g, 1.16 mmol, 88%) as a red residue that was used in the next step without further purification. LCMS (ESI) m/z: 260.1 [M+H]+.

Step 3: Preparation of N-[1-[[5-fluoro-2-(trifluoromethyl)phenyl]methyl]pyrazol-4-yl]-5-(2-furyl)isoxazole-3-carboxamide

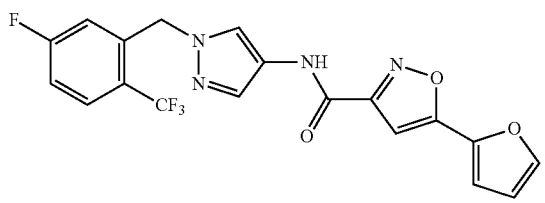 [SMILES: O=C(Nc1cnn(Cc2cc(F)ccc2C(F)(F)F)c1)c1cc(-c2ccco2)on1]

To a solution of 5-(2-furyl)isoxazole-3-carboxylic acid (0.150 g, 0.837 mmol) in N,N-dimethylformamide (3 mL) was added N,N,N',N'-tetramethyl-O-(1H-benzotriazol-1-yl)uronium hexafluorophosphate (0.381 g, 1.00 mmol), diisopropylethylamine (0.438 mL, 2.51 mmol), and 1-[[5-fluoro-2-(trifluoromethyl)phenyl]methyl]pyrazol-4-amine (0.239 g, 0.921 mmol) at 15° C. The mixture was stirred at 15° C. for 2 h. The residue was purified by prep-HPLC (YMC-Actus Triart C18 150×30 5 u; mobile phase: [water (10 mM ammonium bicarbonate)-acetonitrile]; B %: 50%-70%, 10 min) to give N-[1-[[5-fluoro-2-(trifluoromethyl)phenyl]methyl]pyrazol-4-yl]-5-(2-furyl)isoxazole-3-carboxamide (0.083 g, 0.20 mmol, 24%) as a pale yellow solid. $^1$H NMR (400 MHz, Chloroform-d) δ 8.61 (s, 1H), 8.12 (s, 1H), 7.74-7.67 (m, 2H), 7.60 (d, J=1.1 Hz, 1H), 7.11-7.04 (m, 1H), 6.99 (d, J=3.5 Hz, 1H), 6.93 (s, 1H), 6.65 (dd, J=1.9, 9.4 Hz, 1H), 6.58 (dd, J=1.8, 3.5 Hz, 1H), 5.53 (s, 2H); LCMS (ESI) m/z: 421.1 [M+H]+.

Example 59. Preparation of N-(1-(2-chloro-5-fluorobenzyl)-1H-pyrazol-4-yl)-5-(furan-2-yl)isoxazole-3-carboxamide (28)

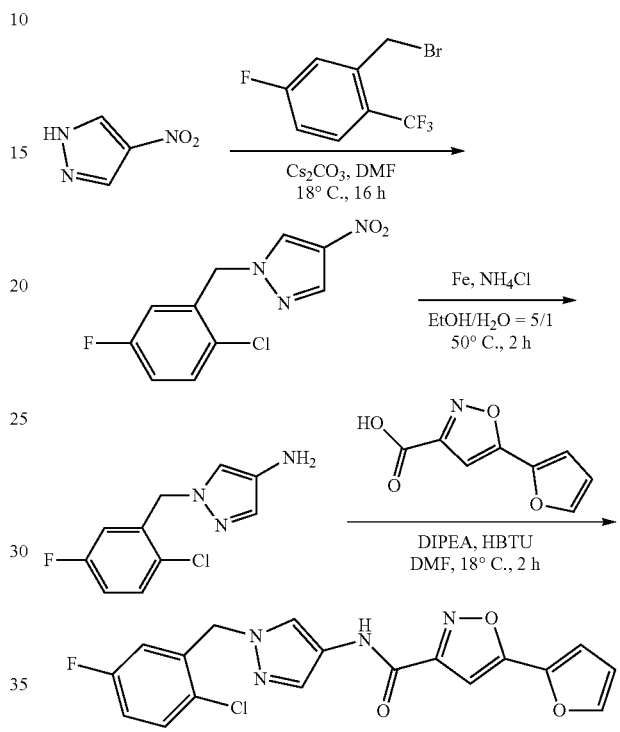

Step 1: Preparation of 1-[(2-chloro-5-fluoro-phenyl)methyl]-4-nitro-pyrazole

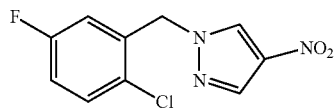 [SMILES: O=[N+]([O-])c1cnn(Cc2cc(F)ccc2Cl)c1]

A mixture of 4-nitro-1H-pyrazole (0.2 g, 1.77 mmol), 2-(bromomethyl)-1-chloro-4-fluoro-benzene (0.395 g, 1.77 mmol) and cesium carbonate (1.73 g, 5.31 mmol) in N,N-dimethylformamide (2 mL) was purged with nitrogen (3×) and then the mixture was stirred at 18° C. for 16 h under nitrogen. The reaction mixture was diluted with water (5 mL) and extracted with ethyl acetate (5 mL×2). The combined organic layers were washed with brine (5 mL×2), dried over sodium sulfate, filtered and concentrated under reduced pressure to give 1-[(2-chloro-5-fluoro-phenyl)methyl]-4-nitro-pyrazole (0.407 g, 1.59 mmol, 90%) as a yellow solid. The material was used directly in the next step without additional purification. $^1$H NMR (400 MHz, Chloroform-d) δ 8.20 (s, 1H), 8.142 (s, 1H), 7.44-7.41 (m, 1H), 7.09-7.07 (m, 1H), 6.98-6.95 (m, 1H), 5.42 (s, 2H); LCMS (ESI) m/z: 256.0 [M+H]+.

Step 2: Preparation of 1-[(2-chloro-5-fluoro-phenyl)methyl]pyrazol-4-amine

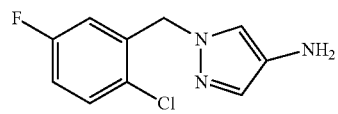 [SMILES: Nc1cnn(Cc2cc(F)ccc2Cl)c1]

A mixture of 1-[(2-chloro-5-fluoro-phenyl)methyl]-4-nitro-pyrazole (0.407 g, 1.59 mmol), iron powder (0.444 g, 7.96 mmol) and ammonium chloride (0.278 mL, 7.96 mmol) in ethanol (4 mL) and water (1 mL) was purged with nitrogen (3×) and then the mixture was heated at 50° C. for 2 h under nitrogen. The reaction mixture was filtered and the filtrate was extracted with dichloromethane (10 mL×2). The combined organic layers were washed with brine (5 mL×2), dried over sodium sulfate, filtered and concentrated under reduced pressure to give 1-[(2-chloro-5-fluoro-phenyl)methyl]pyrazol-4-amine (0.279 g, 1.24 mmol, 78%) as dark brown oil. $^1$H NMR (400 MHz, Chloroform-d) δ 7.35-7.31 (m, 1H), 7.25 (s, 1H), 7.09 (s, 1H), 6.95-6.93 (m, 1H), 6.58-6.55 (m, 1H), 5.27 (s, 2H); LCMS (ESI) m/z: 226.4 [M+H]$^+$.

Step 3: Preparation of N-[1-[(2-chloro-5-fluoro-phenyl)methyl]pyrazol-4-yl]-5-(2-furyl)isoxazole-3-carboxamide

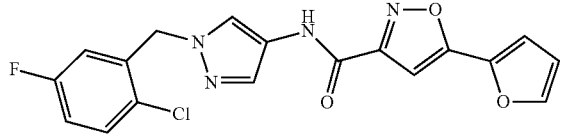 [SMILES: O=C(Nc1cnn(Cc2cc(F)ccc2Cl)c1)c1cc(-c2ccco2)on1]

A mixture of 1-[(2-chloro-5-fluoro-phenyl)methyl]pyrazol-4-amine (0.101 g, 0.447 mmol), 5-(2-furyl)isoxazole-3-carboxylic acid (0.080 g, 447 mmol), N,N,N',N'-tetramethyl-O-(1H-benzotriazol-1-yl)uronium hexafluorophosphate (0.203 g, 0.536 mmol) and diisopropylethylamine (0.233 mL, 1.34 mmol) in N,N-dimethylformamide (2 mL) was purged with nitrogen (3×) and then the mixture was stirred at 18° C. for 2 h under nitrogen. The residue was purified by prep-HPLC (Waters Xbridge C18 150×25 mm×5 um column; 37-67% acetonitrile in a 10 mM ammonium acetate solution in water, 11 min gradient) to give N-[1-[(2-chloro-5-fluoro-phenyl)methyl]pyrazol-4-yl]-5-(2-furyl)isoxazole-3-carboxamide (0.075 g, 0.192 mmol, 43%) as a pale yellow solid. $^1$H NMR (400 MHz, Chloroform-d) δ=8.58 (s, 1H), 8.14 (s, 1H), 7.67 (s, 1H), 7.60 (s, 1H), 7.37 (dd, J=5.2, 8.8 Hz, 1H), 7.05-6.95 (m, 2H), 6.93 (s, 1H), 6.69 (dd, J=3.2, 8.9 Hz, 1H), 6.58 (dd, J=1.6, 3.2 Hz, 1H), 5.41 (s, 2H); LCMS (ESI) m/z: 387.0 [M+H]$^+$.

Example 60. Preparation of 5-(2-furyl)-N-[1-[[3-(trifluoromethyl)phenyl]methyl]pyrazol-4-yl]isoxazole-3-carboxamide (20)

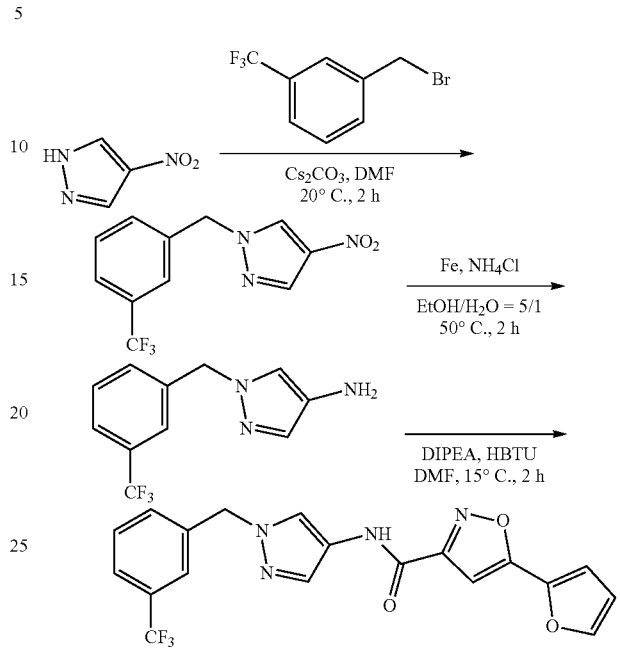

Step 1: Preparation of 4-nitro-1-[[3-(trifluoromethyl)phenyl]methyl]pyrazole

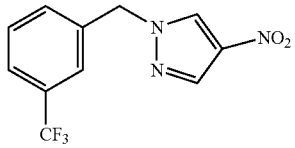 [SMILES: O=[N+]([O-])c1cnn(Cc2cccc(C(F)(F)F)c2)c1]

To a stirred solution of 4-nitro-1H-pyrazole (0.3 g, 2.65 mmol), 1-(bromomethyl)-3-(trifluoromethyl)benzene (0.404 mL, 2.65 mmol) in N,N-dimethylformamide (3 mL) was added cesium carbonate (2.59 g, 7.96 mmol) and then the mixture was stirred at 20° C. for 12 h. The mixture was poured into water (20 mL), extracted with ethyl acetate (20 mL×3) and the combined organic layers were concentrated under reduced pressure to afford 4-nitro-1-[[3-(trifluoromethyl)phenyl]methyl]pyrazole (0.5 g, 1.84 mmol, 69%) as a yellow oil. LCMS (ESI) m/z: 272.3 [M+H]$^+$. This material was used in the next step without further purification.

Step 2: Preparation of 1-[[3-(trifluoromethyl)phenyl]methyl]pyrazol-4-amine

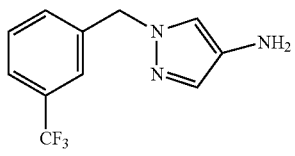 [SMILES: Nc1cnn(Cc2cccc(C(F)(F)F)c2)c1]

To a stirred solution of 4-nitro-1-[[3-(trifluoromethyl)phenyl]methyl]pyrazole (0.5 g, 1.84 mmol) in ethanol (20 mL) and water (5 mL) was added iron powder (0.515 g, 9.22 mmol) and ammonium chloride (0.129 mL, 3.69 mmol) and the mixture was heated at 50° C. for 2 h. The mixture was filtered and the filtrate was extracted with dichloromethane (20 mL×3) and the combined organic layers was concentrated under reduced pressure to give 1-[[3-(trifluoromethyl)phenyl]methyl]pyrazol-4-amine (0.3 g, crude) as a yellow oil. LCMS (ESI) m/z: 242.4 [M+H]$^+$. This material was used in the next step without further purification.

Step 3: Preparation of 5-(2-furyl)-N-[1-[[3-(trifluoromethyl)phenyl]methyl]pyrazol-4-yl]isoxazole-3-carboxamide

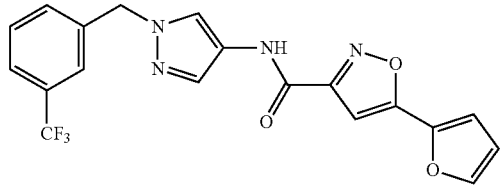 [SMILES: O=C(Nc1cnn(Cc2cccc(C(F)(F)F)c2)c1)c1cc(-c2ccco2)on1]

To a solution of 5-(2-furyl)isoxazole-3-carboxylic acid (0.090 g, 0.502 mol) in N,N-dimethylformamide (2 mL) was added N,N,N',N'-tetramethyl-O-(1H-benzotriazol-1-yl)uronium hexafluorophosphate (0.286 g, 0.754 mmol), diisopropylethylamine (0.263 mL, 1.51 mmol), and 1-[[3-(trifluoromethyl)phenyl]methyl]pyrazol-4-amine (0.133 g, 0.553 mmol). The reaction mixture was stirred at 15° C. for 2 h. The crude residue was purified by prep-HPLC (YMC-Actus Triart C18 100×30 mm×5 um; 40-60% acetonitrile in a 10 mM ammonium acetate solution in water, 12 min gradient) to give 5-(2-furyl)-N-[1-[[3-(trifluoromethyl)phenyl]methyl]pyrazol-4-yl]isoxazole-3-carboxamide (0.030 g, 0.073 mmol, 14%) as a pale yellow solid. $^1$H NMR (400 MHz, Chloroform-d) δ 8.50 (br. s, 1H), 8.07 (s, 1H), 7.62 (s, 1H), 7.59-7.55 (m, 2H), 7.52-7.43 (m, 2H), 7.42-7.38 (m, 1H), 6.98 (d, J=3.3 Hz, 1H), 6.90 (s, 1H), 6.57 (dd, J=1.5, 3.3 Hz, 1H), 5.35 (s, 2H); LCMS (ESI) m/z: 403.0 [M+H]$^+$.

Example 61. Preparation of 5-(furan-2-yl)-N-(1-(2-(trifluoromethyl)benzyl)-1H-pyrazol-4-yl)isoxazole-3-carboxamide (14)

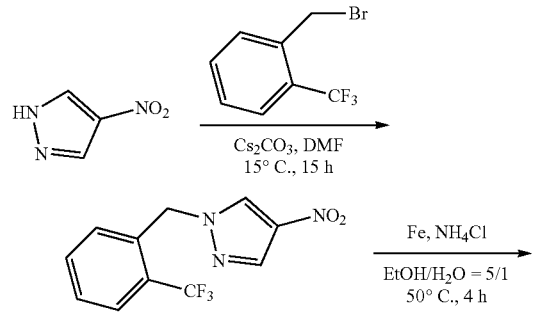

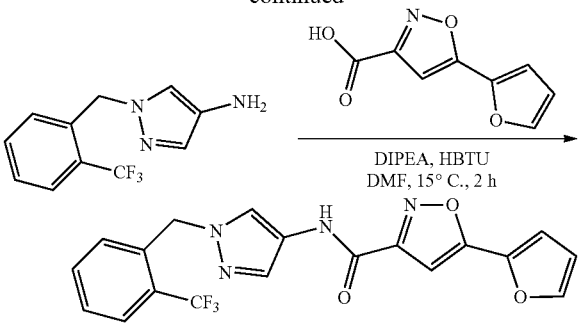

Step 1: Preparation of 4-nitro-1-[[2-(trifluoromethyl)phenyl]methyl]pyrazole

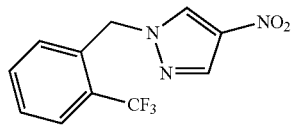 [SMILES: O=[N+]([O-])c1cnn(Cc2ccccc2C(F)(F)F)c1]

A mixture of 4-nitro-1H-pyrazole (0.3 g, 2.65 mmol), 1-(bromomethyl)-2-(trifluoromethyl)benzene (0.403 mL, 2.65 mmol) and cesium carbonate (2.59 g, 7.95 mmol) in N,N-dimethylformamide (8 mL) was purged with nitrogen (3×) and then the mixture was stirred at 18° C. for 16 h under nitrogen. The reaction mixture was diluted with water (5 mL) and extracted with ethyl acetate (5 mL×2). The combined organic layers were washed with brine (5 mL×2), dried over sodium sulfate, filtered and concentrated under reduced pressure to give 4-nitro-1-[[2-(trifluoromethyl)phenyl]methyl]pyrazole (0.748 g, 2.43 mmol, 92%) as a yellow solid. This material was used in the next step without further purification. $^1$H NMR (400 MHz, Chloroform-d) δ 8.13 (s, 1H), 8.09 (s, 1H), 7.77-7.75 (d, J=8.0 Hz, 1H), 7.62-7.58 (t, J=7.6, 1H), 7.54-7.50 (t, J=7.6, 1H), 7.31-7.29 (t, J=7.6, 1H), 5.54 (s, 2H); LCMS (ESI) m/z: 272.1 [M+H]$^+$.

Step 2: Preparation of 1-[[2-(trifluoromethyl)phenyl]methyl]pyrazol-4-amine

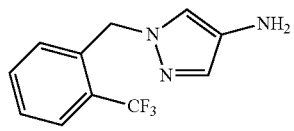 [SMILES: Nc1cnn(Cc2ccccc2C(F)(F)F)c1]

A mixture of 4-nitro-1-[[2-(trifluoromethyl)phenyl]methyl]pyrazole (0.374 g, 1.38 mmol), iron powder (0.385 g, 6.90 mmol) and ammonium chloride (241 mL, 6.90 mmol) in ethanol (4 mL) and water (1 mL) was purged with nitrogen (3×) and then the mixture was heated at 50° C. for 2 h under nitrogen. The reaction mixture was filtered and the filtrate was extracted with dichloromethane (10 mL×2). The combined organic layers were washed with brine (5 mL×2), dried over sodium sulfate, filtered and concentrated under reduced pressure to give 1-[[2-(trifluoromethyl)phenyl]methyl]pyrazol-4-amine (0.192 g, 0.798 mmol, 56%) as a yellow oil. This material was used in the next step without further purification. ¹H NMR (400 MHz, Chloroform-d) δ 7.67-7.65 (t, J=7.6, 1H), 7.48-7.44 (t, J=7.6, 1H), 7.39-7.35 (t, J=7.6, 1H), 7.28 (s, 1H), 7.03 (s, 1H), 6.95-6.93 (d, J=8.0 Hz, 1H), 5.54 (s, 2H); LCMS (ESI) m/z: 242.3 [M+H]⁺.

Step 3: Preparation of 5-(2-furyl)-N-[1-[[2-(trifluoromethyl)phenyl]methyl]pyrazol-4-yl]isoxazole-3-carboxamide

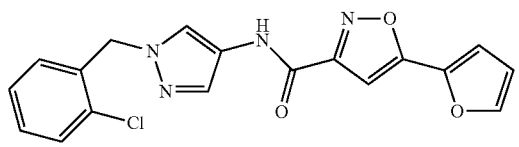 [SMILES: O=C(Nc1cnn(Cc2ccccc2Cl)c1)c1cc(-c2ccco2)on1]

A mixture of 1-[[2-(trifluoromethyl)phenyl]methyl]pyrazol-4-amine (0.108 g, 0.447 mmol), 5-(2-furyl)isoxazole-3-carboxylic acid (0.080 g, 447 mmol), N,N,N',N'-tetramethyl-O-(1H-benzotriazol-1-yl)uronium hexafluorophosphate (0.203 g, 0.536 mmol) and diisopropylethylamine (0.233 mL, 1.34 mmol) in N,N-dimethylformamide (2 mL) was purged with nitrogen (3x). The reaction mixture was stirred at 18° C. for 1 h under nitrogen. The residue was purified by prep-HPLC (Agela Durashell C18 150×25 5 um column; 45-95% acetonitrile in an a 0.04% ammonium hydroxide, 12 min gradient) to afford 5-(2-furyl)-N-[1-[[2-(trifluoromethyl)phenyl]methyl]pyrazol-4-yl]isoxazole-3-carboxamide (0.088 g, 0.217 mmol, 49%) as a pale yellow solid. ¹H NMR (400 MHz, Chloroform-d) δ 8.55 (br. s, 1H), 8.07 (s, 1H), 7.72-7.66 (m, 2H), 7.60 (s, 1H), 7.53-7.45 (m, 1H), 7.44-7.36 (m, 1H), 7.05-6.96 (m, 2H), 6.92 (s, 1H), 6.58 (dd, J=2.0, 3.4 Hz, 1H), 5.54 (s, 2H); LCMS (ESI) m/z: 403.1 [M+H]⁺.

Example 62. Preparation of N-[1-[(4-fluorophenyl)methyl]pyrazol-4-yl]-5-(2-furyl)isoxazole-3-carboxamide (18)

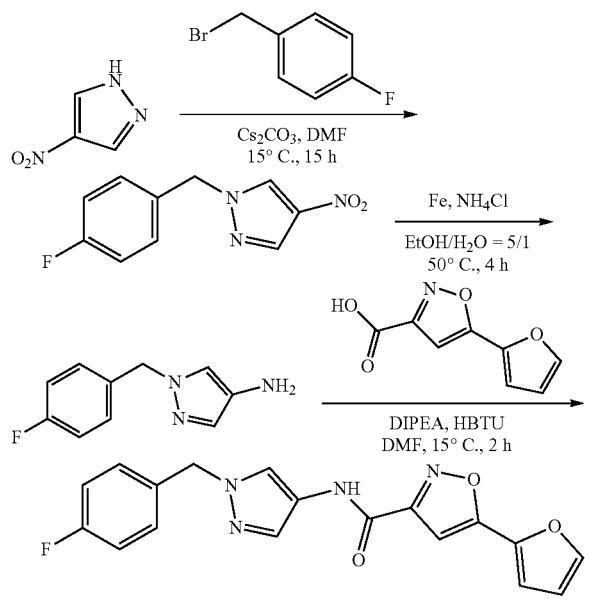

Step 1: Preparation of 1-[(4-fluorophenyl)methyl]-4-nitro-pyrazole

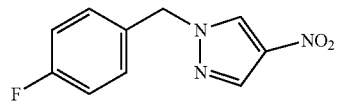

To a solution of 4-nitro-1H-pyrazole (0.300 g, 2.65 mmol) in N,N-dimethylformamide (5 mL) was added cesium carbonate (2.59 g, 7.95 mmol) and 1-(chloromethyl)-4-fluorobenzene (317 mL, 2.65 mmol). The mixture was stirred at 15° C. for 15 h. The reaction mixture was partitioned between ethyl acetate (40 mL) and water (40 mL). The organic phase was separated, washed with brine (20 mL), dried over sodium sulfate, filtered and concentrated under reduced pressure to give 1-[(4-fluorophenyl)methyl]-4-nitro-pyrazole (0.586 g, 2.65 mmol) as a brown oil which was used directly in the next step. LCMS (ESI) m/z: 222.0 [M+H]⁺.

Step 2: Preparation of 1-[(4-fluorophenyl)methyl]pyrazol-4-amine

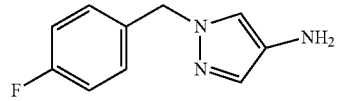 [SMILES: O=[N+]([O-])c1cnn(Cc2ccc(F)cc2)c1]

To a solution of 1-[(4-fluorophenyl)methyl]-4-nitro-pyrazole (0.586 g, 2.65 mmol) in ethanol (20 mL) and water (5 mL) was added ammonium chloride (463 mg, 13.3 mmol) and iron powder (0.740 g, 13.3 mmol) under nitrogen. The mixture was heated at 50° C. for 4 h. The reaction mixture was concentrated under reduced pressure to remove ethanol. The residue was diluted with water (20 mL) and extracted with ethyl acetate (10 mL×3). The combined organic layers were washed with brine (20 mL), dried over sodium sulfate, filtered and concentrated under reduced pressure to give 1-[(4-fluorophenyl)methyl]pyrazol-4-amine (0.390 g, crude) as a red oil which was used into the next step without further purification. LCMS (ESI) m/z: 192.3 [M+H]⁺.

Step 3: Preparation of N-[1-[(4-fluorophenyl)methyl]pyrazol-4-yl]-5-(2-furyl)isoxazole-3-carboxamide

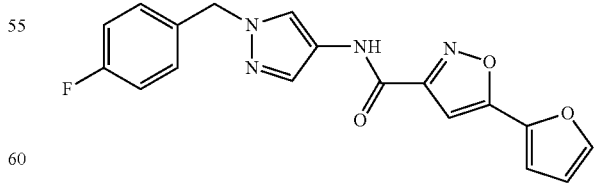

To a solution of 5-(2-furyl)isoxazole-3-carboxylic acid (0.090 g, 0.50 mmol) in N,N-dimethylformamide (3 mL) was added N,N,N',N'-tetramethyl-O-(1H-benzotriazol-1-yl)uronium hexafluorophosphate (0.229 g, 0.60 mmol), 1-[(4-fluorophenyl)methyl]pyrazol-4-amine (0.106 g, 0.55 mmol), diisopropylethylamine (263 mL, 1.51 mmol) at 15° C. The mixture was stirred at 15° C. for 2 h. The mixture was purified by prep-HPLC (Waters X bridge 150×25 5 μm column; 30-65% acetonitrile in a 10 mM ammonium acetate solution in water, 10 min gradient) to give N-[1-[(4-fluorophenyl)methyl]pyrazol-4-yl]-5-(2-furyl)isoxazole-3-carboxamide (0.077 g, 0.21 mmol, 43%) as a pale yellow solid. $^1$H NMR (400 MHz, Chloroform-d) δ 8.51 (s, 1H), 8.04 (s, 1H), 7.60 (s, 2H), 7.27-7.23 (m, 2H), 7.04 (t, J=8.6 Hz, 2H), 6.99 (d, J=3.5 Hz, 1H), 6.91 (s, 1H), 6.58 (dd, J=1.8, 3.5 Hz, 1H), 5.27 (s, 2H); LCMS (ESI) m/z: 353.1 [M+H]$^+$.

Example 63. Preparation of N-[1-[(2-fluorophenyl)methyl]pyrazol-4-yl]-5-(2-furyl)isoxazole-3-carboxamide (19)

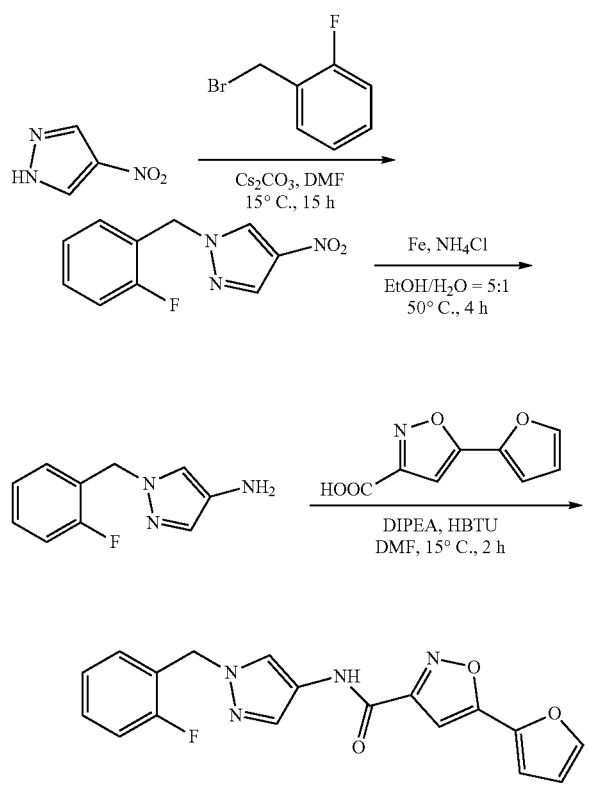

Step 1: Preparation of 1-[(2-fluorophenyl)methyl]-4-nitro-pyrazole

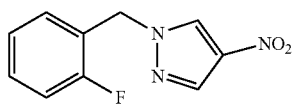 [SMILES: O=[N+]([O-])c1cnn(Cc2ccccc2F)c1]

To a solution of 4-nitro-1H-pyrazole (0.30 g, 2.65 mmol) in N,N-dimethylformamide (5 mL) was added cesium carbonate (2.59 g, 7.96 mmol) and 1-(bromomethyl)-2-fluorobenzene (0.319 mL, 2.65 mmol). The mixture was stirred at 15° C. for 15 h. The reaction mixture was diluted with water (20 mL) and extracted with ethyl acetate (10 mL×3). The combined organic layers were washed with brine (20 mL), dried over sodium sulfate, filtered and concentrated under reduced pressure to give 1-[(2-fluorophenyl)methyl]-4-nitro-pyrazole (0.586 g, 2.65 mmol) as a brown oil. LCMS (ESI) m/z: 222.0 [M+H]$^+$. This material was used in the next step without further purification Step 2: Preparation of 1-[(2-fluorophenyl)methyl]pyrazol-4-amine

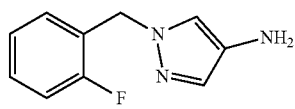 [SMILES: Nc1cnn(Cc2ccccc2F)c1]

To a solution of 1-[(2-fluorophenyl)methyl]-4-nitro-pyrazole (0.586 g, 2.65 mmol) in water (5 mL) and ethanol (20 mL) was added ammonium chloride (0.463 mL, 13.3 mmol) and iron powder (0.740 g, 13.25 mmol) under nitrogen. The mixture was heated at 50° C. for 4 h. The reaction mixture was concentrated under reduced pressure to remove ethanol. The residue was diluted with water 20 mL and extracted with ethyl acetate (10 mL×3). The combined organic layers were washed with brine 20 mL, dried over sodium sulfate, filtered and concentrated under reduced pressure to give 1-[(2-fluorophenyl)methyl]pyrazol-4-amine (0.400 g, crude) as a brown oil. LCMS (ESI) m/z: 192.4 [M+H]$^+$. This material was used in the next step without further purification.

Step 3: Preparation of N-[1-[(2-fluorophenyl)methyl]pyrazol-4-yl]-5-(2-furyl)isoxazole-3-carboxamide

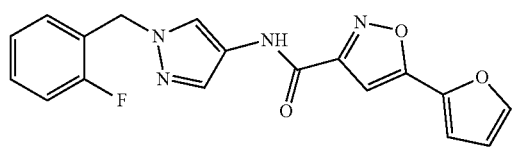 [SMILES: O=C(Nc1cnn(Cc2ccccc2F)c1)c1cc(-c2ccco2)on1]

To a solution of 5-(2-furyl)isoxazole-3-carboxylic acid (0.090 g, 0.50 mmol) in N,N-dimethylformamide (3 mL) was added N,N,N',N'-tetramethyl-O-(1H-benzotriazol-1-yl)uronium hexafluorophosphate (0.229 g, 0.60 mmol), 1-[(2-fluorophenyl)methyl]pyrazol-4-amine (0.106 g, 0.56 mmol) and diisopropylethylamine (0.263 mL, 1.51 mmol) at 15° C. The mixture was stirred at 15° C. for 2 h. The mixture was purified by prep-HPLC (Waters X bridge 150×25 5 μm column; 35-65% acetonitrile in a 10 mM ammonium acetate solution in water, 10 min gradient) to give N-[1-[(2-fluorophenyl)methyl]pyrazol-4-yl]-5-(2-furyl)isoxazole-3-carboxamide (0.075 g, 0.21 mmol, 43%) as a pale yellow solid. $^1$H NMR (400 MHz, Chloroform-d) δ 8.51 (s, 1H), 8.08 (s, 1H), 7.64-7.58 (m, 2H), 7.36-7.28 (m, 1H), 7.23-7.17 (m, 1H), 7.15-7.07 (m, 2H), 6.99 (d, J=3.5 Hz, 1H), 6.92 (s, 1H), 6.58 (dd, J=1.8, 3.3 Hz, 1H), 5.37 (s, 2H); LCMS (ESI) m/z: 353.1 M+H]$^+$.

Example 64. Preparation of N-[1-[(3-chlorophenyl)methyl]pyrazol-4-yl]-5-(2-furyl)isoxazole-3-carboxamide (22)

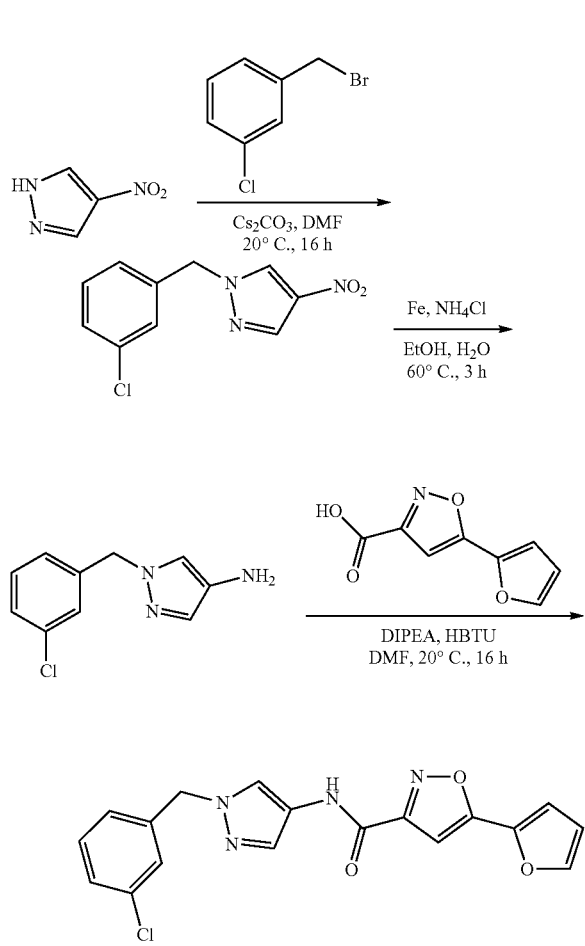

Step 1: Preparation of 1-[(3-chlorophenyl)methyl]-4-nitro-pyrazole

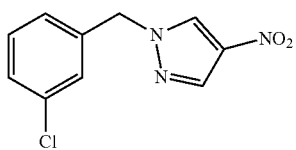

To a stirred solution of 4-nitro-1H-pyrazole (0.300 g, 2.65 mmol) in N,N-dimethylformamide (4 mL) was added cesium carbonate (2.59 g, 7.96 mmol) and 1-(bromomethyl)-3-chloro-benzene (0.347 mL, 2.65 mmol). Then the mixture was stirred at 20° C. for 16 h and then added to water (5 mL) and extracted with ethyl acetate (10 mL×3). The combined organic layers were washed with brine (10 mL×2), dried over sodium sulfate, filtered and concentrated under reduced pressure to give 1-[(3-chlorophenyl)methyl]-4-nitro-pyrazole (0.700 g, 2.94 mmol, crude) as a yellow oil. This material was used in the next step without further purification. $^1$H NMR (400 MHz, Chloroform-d) δ 8.10 (s, 1H), 8.01 (s, 1H), 7.37-7.16 (m, 4H), 5.28 (s, 2H).

Step 2: Preparation of to give 1-[(3-chlorophenyl)methyl]pyrazol-4-amine

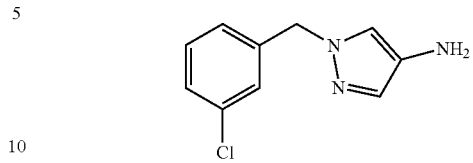

To a stirred solution of 1-[(3-chlorophenyl)methyl]-4-nitro-pyrazole (0.350 g, 1.47 mmol) in ethanol (4 mL) and water (1 mL) was added iron powder (0.411 g, 7.36 mmol) and ammonium chloride (0.26 mL, 7.36 mmol). The reaction mixture was stirred at 60° C. for 3 h then filtered and extracted with ethyl acetate (10 mL×3). The combined organic layers were washed with brine (10 mL×2), dried over sodium sulfate, filtered and concentrated under reduced pressure to give 1-[(3-chlorophenyl)methyl]pyrazol-4-amine (0.300 g, crude) as a red oil. LCMS (ESI) m/z: 208.1 [M+H]$^+$.

Step 3: Preparation of N-[1-[(3-chlorophenyl)methyl]pyrazol-4-yl]-5-(2-furyl)isoxazole-3-carboxamide

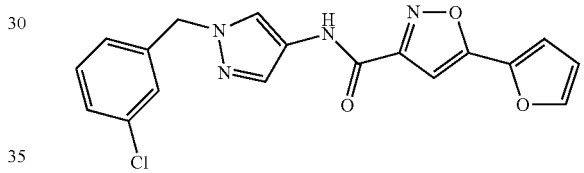

To a solution of 1-[(3-chlorophenyl)methyl]pyrazol-4-amine (0.115 g, 0.554 mmol) in N,N-dimethylformamide (3 mL) was added diisopropylethylamine (0.276 mL, 1.58 mmol) and N,N,N',N'-tetramethyl-O-(1H-benzotriazol-1-yl)uronium hexafluorophosphate (0.200 g, 0.527 mmol) and 5-(2-furyl)isoxazole-3-carboxylic acid (0.094 g, 0.527 mmol). The mixture was stirred at 20° C. for 16 h. The reaction mixture was filtered and purified by prep-HPLC (column: Agela Durashell C18 150×25 5 µm; mobile phase: [water (10 mM ammonium bicarbonate)-acetonitrile]; B %: 40%-75%, 12 min gradient) to afford N-[1-[(3-chlorophenyl)methyl]pyrazol-4-yl]-5-(2-furyl)isoxazole-3-carboxamide (0.0450 g, 0.122 mmol, 23%) as a white solid. $^1$H NMR (400 MHz, Chloroform-d) δ 8.55 (s, 1H), 8.06 (s, 1H), 7.65-7.55 (m, 2H), 7.31-7.26 (m, 2H), 7.22 (s, 1H), 7.16-7.08 (m, 1H), 6.98 (d, J=3.5 Hz, 1H), 6.91 (s, 1H), 6.57 (m, 1H), 5.27 (s, 2H); LCMS (ESI) m/z: 369.1 [M+H]$^+$.

Example 65. Preparation of N-[1-[(2-chlorophenyl)methyl]pyrazol-4-yl]-5-(2-furyl)isoxazole-3-carboxamide (23)

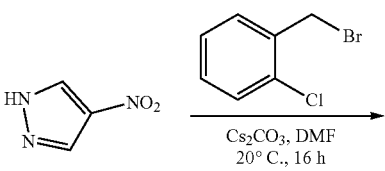

353

-continued

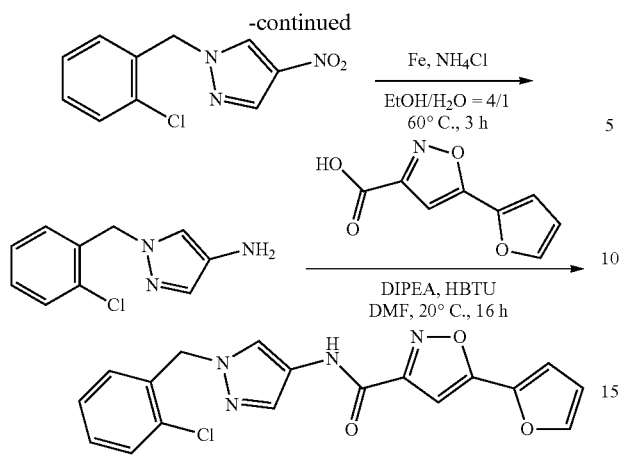

Step 1: Preparation of 1-[(2-chlorophenyl)methyl]-4-nitro-pyrazole

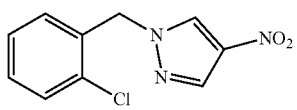 [SMILES: O=[N+]([O-])c1cnn(Cc2ccccc2Cl)c1]

To a stirred solution of 4-nitro-1H-pyrazole (0.300 g, 2.65 mmol) in N,N-dimethylformamide (4 mL) was added cesium carbonate (2.59 g, 7.95 mmol) and 1-chloro-2-(chloromethyl)benzene (0.336 mL, 2.65 mmol). Then the mixture was stirred at 20° C. for 16 h then added to water (5 mL) and extracted with ethyl acetate (10 mL×3). The combined organic layers were washed with brine (10 mL×2), dried over sodium sulfate, filtered and concentrated under reduced pressure to give 1-[(2-chlorophenyl)methyl]-4-nitro-pyrazole (0.700 g, 2.94 mmol) as a yellow oil. $^1$H NMR (400 MHz, Chloroform-d) δ 8.15 (s, 1H), 8.11 (s, 1H), 7.49-7.28 (m, 4H), 5.46 (s, 2H). This material was used in the next step without further purification.

Step 2: Preparation of 1-[(2-chlorophenyl)methyl]pyrazol-4-amine

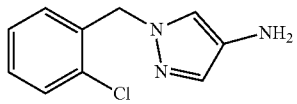 [SMILES: Nc1cnn(Cc2ccccc2Cl)c1]

To a stirred solution of 1-[(2-chlorophenyl)methyl]-4-nitro-pyrazole (0.700 g, 2.94 mmol) in ethanol (4 mL) and water (1 mL) was added iron powder (0.411 g, 7.36 mmol) and ammonium chloride (0.257 mL, 7.36 mmol). The reaction mixture was stirred at 60° C. for 3 h then filtered and extracted with ethyl acetate (10 mL×3). The combined organic layers were washed with brine (10 mL×2), dried over sodium sulfate, filtered and concentrated under reduced pressure to give 1-[(2-chlorophenyl)methyl]pyrazol-4-amine (0.270 g, crude) as a red oil. LCMS (ESI) m/z: 208.1 [M+H]$^+$. This material was used in the next step without additional purification.

354

Step 3: Preparation of -[1-[(2-chlorophenyl)methyl]pyrazol-4-yl]-5-(2-furyl)isoxazole-3-carboxamide

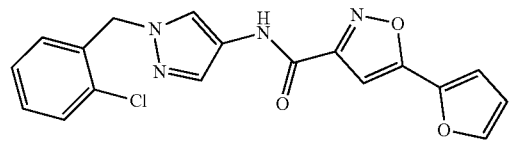 [SMILES: O=C(Nc1cnn(Cc2ccccc2Cl)c1)c1cc(-c2ccco2)on1]

To a solution of 1-[(2-chlorophenyl)methyl]pyrazol-4-amine (0.150 g, 0.722 mmol) in N,N-dimethylformamide (3 mL) was added diisopropylethylamine (359 mL, 2.06 mmol), N,N,N',N'-tetramethyl-O-(1H-benzotriazol-1-yl)uronium hexafluorophosphate (0.261 g, 0.688 mmol) and 5-(2-furyl)isoxazole-3-carboxylic acid (0.123 g, 0.688 mmol). The mixture was stirred at 20° C. for 16 h. The reaction mixture was filtered. The crude residue was purified by prep-HPLC (Agela Durashell 150×25 5 μm column; 40-70% acetonitrile in a 10 mM ammonium bicarbonate solution in water, 12 min gradient) to afford N-[1-[(2-chlorophenyl)methyl]pyrazol-4-yl]-5-(2-furyl)isoxazole-3-carboxamide (0.066 mg, 0.180 mmol, 26%) as a white solid. $^1$H NMR (400 MHz, Chloroform-d) (8.53 (s, 1H), 8.08 (s, 1H), 7.64 (s, 1H), 7.59 (d, J=1.1 Hz, 1H), 7.40 (dd, J=1.7, 7.6 Hz, 1H), 7.28-7.22 (m, 2H), 7.06 (dd, J=1.8, 7.3 Hz, 1H), 6.98 (d, J=3.5 Hz, 1H), 6.91 (s, 1H), 6.58 (m, 1H), 5.43 (s, 2H); LCMS (ESI) m/z: 369.0 [M+H]$^+$.

Example 66. 5-(2-furyl)-N-[1-(4,4,4-trifluorobutyl)pyrazol-4-yl]isoxazole-3-carboxamide (34)

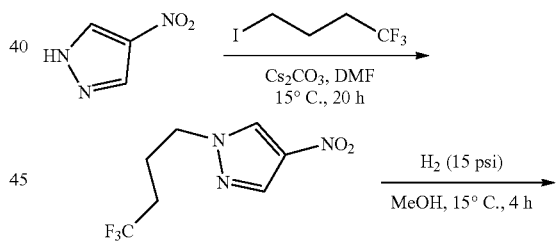

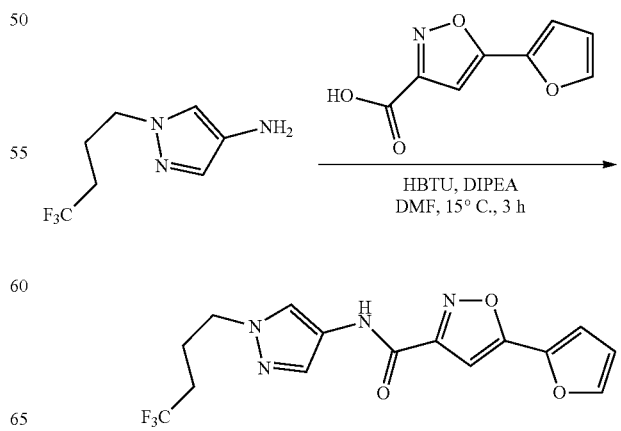

Step 1: Preparation of 4-nitro-1-(4,4,4-trifluorobutyl)pyrazole

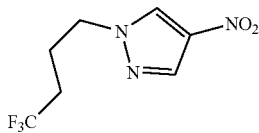 [SMILES: O=[N+]([O-])c1cnn(CCCC(F)(F)F)c1]

To a stirred solution of 4-nitro-1H-pyrazole (0.100 g, 0.884 mmol) and 1,1,1-trifluoro-4-iodo-butane (0.232 g, 0.973 mol) in N,N-dimethylformamide (2 mL) was added potassium carbonate (0.134 g, 0.973 mmol) at 15° C. and then stirred at 15° C. for 20 h. The reaction mixture was quenched with ice water (2 mL) and extracted with ethyl acetate (10 mL×3). The combined organic layers were washed with water (3 mL×3) and brine (3 mL), dried over sodium sulfate, filtered and concentrated under reduced pressure to give a crude residue. The residue was purified by column chromatography (ISCO, 10 g silica, 0-25% ethyl acetate in petroleum ether, gradient over 20 min) to afford 4-nitro-1-(4,4,4-trifluorobutyl)pyrazole (0.150 g, 0.672 mmol, 76%) as a colorless oil. LCMS (ESI) m/z: 224.0 [M+H]$^+$.

Step 2: Preparation of 1-(4,4,4-trifluorobutyl)pyrazol-4-amine

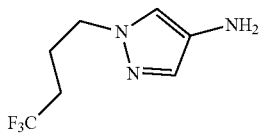 [SMILES: Nc1cnn(CCCC(F)(F)F)c1]

To a solution of 4-nitro-1-(4,4,4-trifluorobutyl)pyrazole (0.130 g, 0.583 mmol) in methanol (5 mL) was added palladium on activated carbon (0.020 g, 0.058 mmol, 10% Pd by weight) under nitrogen. The suspension was purged with hydrogen (3×). The mixture was stirred under hydrogen (15 psi) at 15° C. for 4 h. The mixture was filtered and the filtrate was concentrated in vacuo to give 1-(4,4,4-trifluorobutyl)pyrazol-4-amine (0.100 g, 0.466 mmol, 80%) as a pink solid. This material was used in the next step without further purification. LCMS (ESI) m/z: 194.1 [M+H]$^+$.

Step 3: Preparation of 5-(2-furyl)-N-[1-(4,4,4-trifluorobutyl)pyrazol-4-yl]isoxazole-3-carboxamide

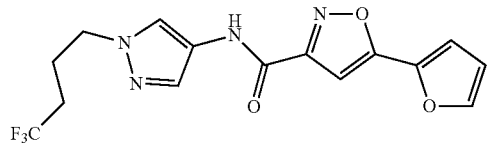 [SMILES: O=C(Nc1cnn(CCCC(F)(F)F)c1)c1cc(-c2ccco2)on1]

To a stirred solution of 1-(4,4,4-trifluorobutyl)pyrazol-4-amine (0.090 g, 0.466 mmol) and 5-(2-furyl)isoxazole-3-carboxylic acid (0.092 g, 0.513 mmol) in N,N-dimethylformamide (1 mL) was added N,N,N',N'-tetramethyl-O-(1H-benzotriazol-1-yl)uronium hexafluorophosphate (0.194 g, 0.513 mmol) and diisopropylethylamine (0.162 mL, 0.932 mmol) at 15° C. The reaction mixture was stirred at 15° C. for 3 h then purified by prep-HPLC (Agela Durashell C18 150×25 5 μm column; 20%-70% acetonitrile in an a 0.04% ammonium hydroxide, 12 min gradient). Then purified by prep-HPLC (YMC-Actus ODS-AQ 100×30 5 um column; 38%-68% acetonitrile in a 0.225% formic acid solution in water, 12 min gradient) to give 5-(2-furyl)-N-[1-(4,4,4-trifluorobutyl)pyrazol-4-yl]isoxazole-3-carboxamide (0.035 g, 0.099 mmol, 21%) as a white solid. $^1$H NMR (400 MHz, Chloroform-d) δ 8.55 (s, 1H), 8.06 (s, 1H), 7.62-7.56 (m, 2H), 6.99 (d, J=3.4 Hz, 1H), 6.93 (s, 1H), 6.58 (dd, J=1.8, 3.5 Hz, 1H), 4.20 (t, J=6.4 Hz, 2H), 2.22-2.03 (m, 4H); LCMS (ESI) m/z: 355.1[M+H]$^+$.

Example 67: Preparation of N-[1-(cyclohexylmethyl)pyrazol-4-yl]-5-(2-furyl)isoxazole-3-carboxamide (26)

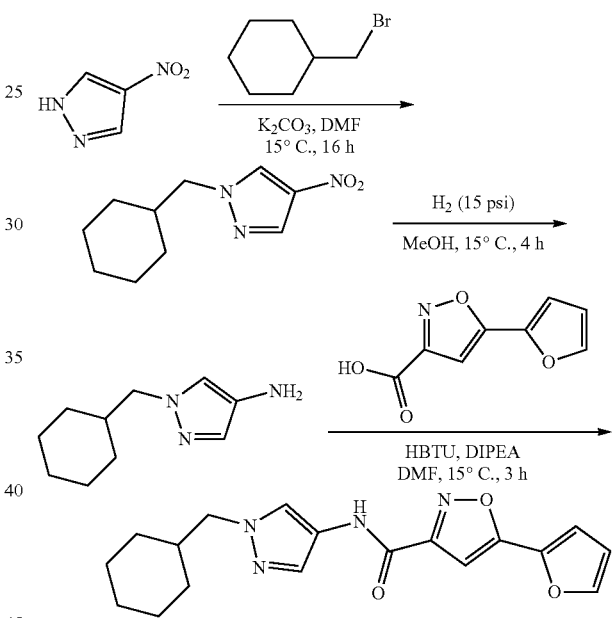

Step 1: Preparation of 1-(cyclohexylmethyl)-4-nitro-pyrazole

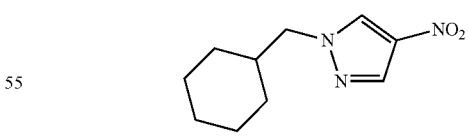

To a stirred solution of 4-nitro-1H-pyrazole (0.300 g, 2.65 mmol) and bromomethylcyclohexane (0.564 g, 3.18 mmol, 0.444 mL) in N,N-dimethylformamide (5 mL) was added potassium carbonate (0.440 g, 3.18 mmol) at 15° C., then stirred at 15° C. for 16 h. The reaction mixture was added to ice water (2 mL) and extracted with ethyl acetate (10 mL×3). The combined organic layers were washed with water (3 mL×3), and brine (3 mL), dried over sodium sulfate, filtered and concentrated under reduced pressure to give a residue.

The residue was purified by column chromatography (ISCO 10 g silica, 0-25% ethyl acetate in petroleum ether, gradient over 20 min) to yield 1-(cyclohexylmethyl)-4-nitro-pyrazole (420 mg, 1.97 mmol, 74%) as a white solid. $^1$H NMR (400 MHz, Chloroform-d) δ 8.07 (d, J=6.1 Hz, 2H), 3.96 (d, J=7.5 Hz, 2H), 1.97-1.84 (m, 1H), 1.79-1.57 (m, 5H), 1.31-1.10 (m, 3H), 1.04-0.91 (m, 2H); LCMS (ESI) m/z: 210.1 [M+H]$^+$.

Step 2: Preparation of 1-(cyclohexylmethyl)pyrazol-4-amine

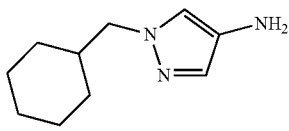 [SMILES: Nc1cnn(CC2CCCCC2)c1]

To a solution of 1-(cyclohexylmethyl)-4-nitro-pyrazole (0.200 g, 0.956 mmol) in methanol (5 mL) was added palladium on carbon (0.020 g, 0.096 mmol, 10% Pd by weight) under nitrogen. The suspension was purged with hydrogen (3×). The mixture was stirred under hydrogen (15 psi) at 15° C. for 4 h. The reaction mixture was filtered and the filtrate was concentrated in vacuo to afford 1-(cyclohexylmethyl)pyrazol-4-amine (0.160 g, 0.803 mmol, 84%) as a pink solid. LCMS (ESI) m/z: 180.2 [M+H]$^+$. This material was used in the next step without further purification.

Step 3: Preparation of N-[1-(cyclohexylmethyl)pyrazol-4-yl]-5-(2-furyl)isoxazole-3-carboxamide

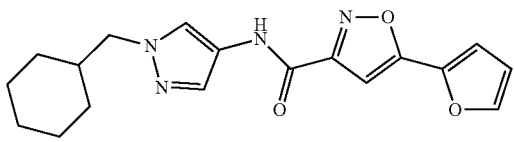 [SMILES: O=C(Nc1cnn(CC2CCCCC2)c1)c1cc(-c2ccco2)on1]

To a stirred solution of 1-(cyclohexylmethyl)pyrazol-4-amine (0.090 g, 0.502 mmol) and 5-(2-furyl)isoxazole-3-carboxylic acid (0.090 g, 0.502 mmol) in N,N-dimethylformamide (1 mL) was added N,N,N',N'-tetramethyl-O-(1H-benzotriazol-1-yl)uronium hexafluorophosphate (0.190 g, 0.502 mmol) and diisopropylethylamine (0.175 mL, 1.00 mmol) at 15° C., and then stirred at 15° C. for 3 h. The reaction mixture was purified directly by prep-HPLC (Agela Durashell C18 150×25 5 μm column; 40%-90% acetonitrile in an a 0.04% ammonium hydroxide, 12 min gradient) to give N-[1-(cyclohexylmethyl)pyrazol-4-yl]-5-(2-furyl)isoxazole-3-carboxamide (0.055 g, 0.160 mmol, 32%) as a white solid. $^1$H NMR (400 MHz, Chloroform-d) δ 8.50 (br. s, 1H), 7.99 (s, 1H), 7.62-7.53 (m, 2H), 6.99 (d, J=3.4 Hz, 1H), 6.92 (s, 1H), 6.57 (dd, J=1.7, 3.4 Hz, 1H), 3.93 (d, J=7.2 Hz, 2H), 1.89 (ttd, J=3.8, 7.4, 14.8 Hz, 1H), 1.76-1.61 (m, 5H), 1.30-1.10 (m, 3H), 1.05-0.91 (m, 2H); LCMS (ESI) m/z: 341.2 [M+H]$^+$.

Example 68. Preparation of N-(1-(3,4-dichlorobenzyl)-3,5-dimethyl-1H-pyrazol-4-yl)-5-(furan-2-yl)isoxazole-3-carboxamide (3)

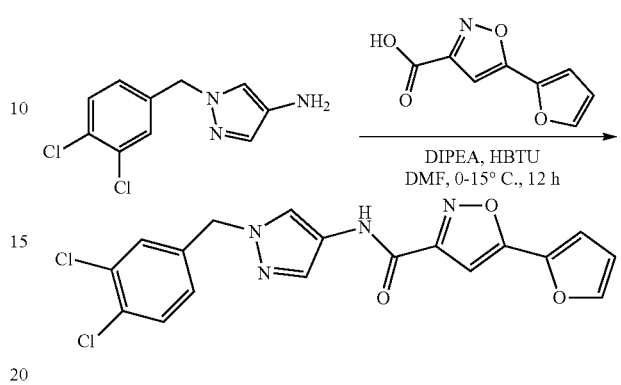

Step 1: Preparation of N-(1-(3,4-dichlorobenzyl)-3,5-dimethyl-1H-pyrazol-4-yl)-5-(furan-2-yl)isoxazole-3-carboxamide

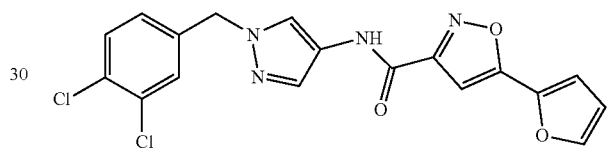

The mixture of 5-(furan-2-yl)isoxazole-3-carboxylic acid (0.120 g, 0.669 mmol), N,N,N',N'-tetramethyl-O-(1H-benzotriazol-1-yl)uronium hexafluorophosphate (0.254 g, 0.670 mmol) and diisopropylethylamine (0.234 g, 1.34 mmol) in N,N-dimethylformamide (1 mL) at 0° C. was added 1-(3,4-dichlorobenzyl)-3,5-dimethyl-1H-pyrazol-4-amine (0.199 g, 0.737 mmol). The reaction mixture was stirred at 15° C. for 12 h. The residue was purified by prep-HPLC (column: Luna C8 100×30 5p; mobile phase: [water (10 mM ammonium bicarbonate)-acetonitrile]; B %: 40%-65%, 12 min gradient) to give N-(1-(3,4-dichlorobenzyl)-3,5-dimethyl-1H-pyrazol-4-yl)-5-(furan-2-yl)isoxazole-3-carboxamide (0.0963 g, 0.222 mmol, 33%) as a yellow solid. $^1$H NMR (400 MHz, Chloroform-d) δ 7.90 (s, 1H), 7.61 (s, 1H), 7.41 (d, J=7.9 Hz, 1H), 7.24 (s, 1H), 7.00 (d, J=3.5 Hz, 1H), 6.96 (d, J=8.4 Hz, 1H), 6.93 (s, 1H), 6.59 (dd, J=1.8, 3.5 Hz, 1H), 5.18 (s, 2H), 2.24 (s, 3H), 2.15 (s, 3H); LCMS (ESI) m/z: 431.1 [M+H]$^+$.

Example 69. Preparation of 5-(oxazol-5-yl)-N-(1-((4-(trifluoromethyl)pyridin-3-yl)methyl)-1H-pyrazol-4-yl)isoxazole-3-carboxamide (171)

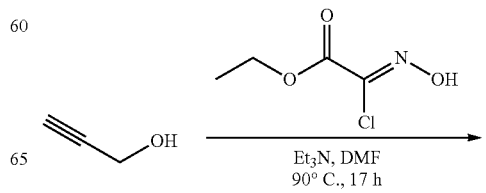

-continued

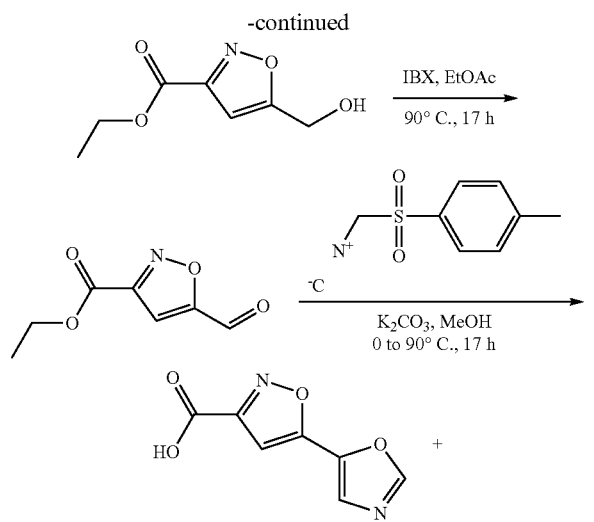

Step 1: Preparation of ethyl 5-(hydroxymethyl)isoxazole-3-carboxylate

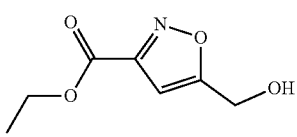

To a solution of prop-2-yn-1-ol (8.4 g, 149.1 mmol) in N,N-dimethylformamide (50 mL) was added a solution of (Z)-ethyl 2-chloro-2-(hydroxyimino)acetate (7.5 g, 49.7 mmol) in N,N-dimethylformamide (50 mL) dropwise over 40 min under nitrogen atmosphere. After addition, the reaction mixture was heated to 90° C. and a solution of triethylamine (15.0 g, 149.1 mmol) in N,N-dimethylformamide (50 mL) was added dropwise over 1 h. The reaction mixture was heated at 90° C. for 17 h and cooled to room temperature. The reaction mixture was diluted with ethyl acetate (50 mL), washed with water (60 mL×2) and brine (60 mL×2), dried over anhydrous sodium sulfate, filtered and concentrated in vacuo. The residue was purified by column chromatography (silica, petroleum ether/ethyl acetate=6/1) to give ethyl 5-(hydroxymethyl)isoxazole-3-carboxylate (3.35 g, 19.6 mmol, 39%) as a yellow oil. LCMS (ESI) m/z: 172.1 [M+H]$^+$.

Step 2: Preparation of ethyl 5-formylisoxazole-3-carboxylate

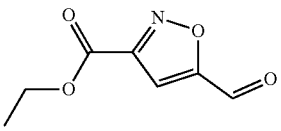

To a solution of ethyl 5-(hydroxymethyl)isoxazole-3-carboxylate (1.2 g, 7.0 mmol) in ethyl acetate (20 mL) was added 2-iodoxybenzoic acid (5.9 g, 21.0 mmol). The reaction mixture was heated at 90° C. for 17 h, and then cooled to room temperature. The reaction mixture was filtered and the filtrate was concentrated in vacuo. The residue was purified by column chromatography (silica, petroleum ether/ethyl acetate=5/1) to give ethyl 5-formylisoxazole-3-carboxylate (780 mg, 4.6 mmol, 71%) as a yellow oil.

Step 3: Preparation of 5-(oxazol-5-yl)isoxazole-3-carboxylic Acid

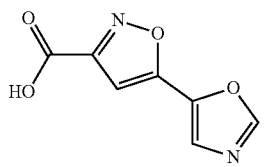 [SMILES: O=C(O)c1cc(-c2cnco2)on1]

To a solution of 1-(isocyanomethylsulfonyl)-4-methylbenzene (0.460 g, 2.36 mmol) in acetonitrile (15 mL) was added potassium carbonate (0.391 g, 2.83 mmol). The reaction mixture was stirred at 25° C. for 1 h before ethyl 5-formylisoxazole-3-carboxylate (0.400 g, 2.36 mmol) was added at 0° C. The reaction mixture was heated at 90° C. for 17 h and then cooled to room temperature. The reaction mixture was diluted with water (15 mL) and the aqueous layer was adjusted to pH=2 with aqueous 1N hydrogen chloride. The aqueous layer was extracted with ethyl acetate (10 mL×2). The combined organic layers were washed with brine (10 mL×2), dried over anhydrous sodium sulfate, filtered and concentrated in vacuo to yield 5-(oxazol-5-yl)isoxazole-3-carboxylic acid (140 mg, 0.77 mmol, 33%) as a white solid. This material was used in the next step without further purification.

Step 4: Preparation of 5-(oxazol-5-yl)-N-(1-((4-(trifluoromethyl)pyridin-3-yl)methyl)-1H-pyrazol-4-yl)isoxazole-3-carboxamide

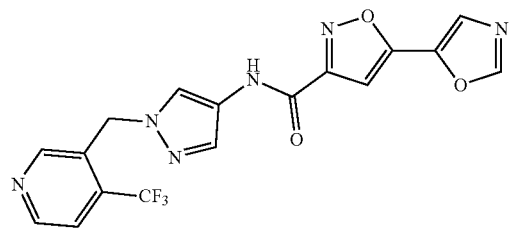 [SMILES: O=C(Nc1cnn(Cc2cnccc2C(F)(F)F)c1)c1cc(-c2cnco2)on1]

To a solution of 5-(oxazol-5-yl)isoxazole-3-carboxylic acid (0.100 mg, 0.55 mmol), 1-((4-(trifluoromethyl)pyridin-3-yl)methyl)-1H-pyrazol-4-amine (133 mg, 0.55 mmol) and 4-(4,6-dimethoxy-1,3,5-triazin-2-yl)-4-methylmorpholinium chloride (0.182 g, 0.66 mmol) in tetrahydrofuran (15 mL) was added N-methylmorpholine (167 mg, 1.65 mmol). The mixture was stirred at 25° C. for 4 h. The reaction mixture was diluted with water (15 mL) and extracted with ethyl acetate (10 mL×2). The combined organic layers were washed with brine (10 mL), dried over sodium sulfate, filtered and concentrated in vacuo. The crude sample was dissolved in minimum amount of N,N-dimethylformamide and purified via prep-HPLC (Boston C18 21×250 mm 10 µm column; acetonitrile/0.01% aqueous trifluoroacetic acid) to give 5-(oxazol-5-yl)-N-(1-((4-(trifluoromethyl)pyridin-3-yl)methyl)-1H-pyrazol-4-yl)isoxazole-3-carboxamide (35.3 mg, 0.08 mmol, 16%) as a white solid. $^1$H NMR (400 MHz, Dimethylsulfoxide-d$_6$) δ 11.19 (d, J=31.8 Hz, 1H), 8.81 (d, J=5.0 Hz, 1H), 8.73 (s, 1H), 8.31 (d, J=23.9 Hz, 2H), 8.02 (s, 1H), 7.80 (d, J=5.1 Hz, 1H), 7.74 (s, 1H), 7.35 (s, 1H), 5.61 (s, 2H); LCMS (ESI) m/z: 405.1 [M+H]$^+$.

Example 70. Preparation of N-(1-benzyl-1H-pyrazol-4-yl)-5-(3-methylpyridin-4-yl)isoxazole-3-carboxamide (201)

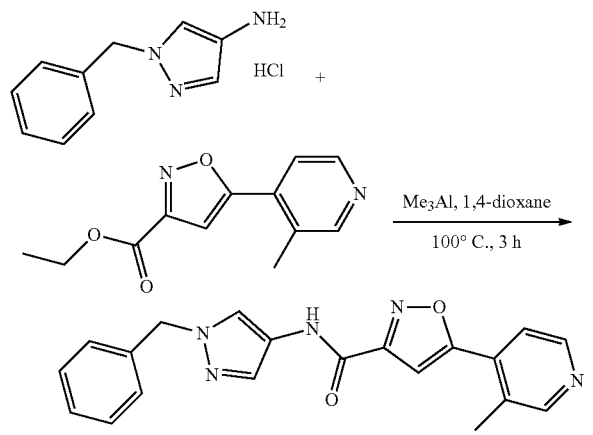

To a solution of 1-benzyl-1H-pyrazol-4-amine hydrochloride (257 mg, 1.23 mmol) in 1,4-dioxane (6 mL) at 23° C. was added triethylaluminium (2.0 M in toluene, 0.60 mL, 1.20 mmol) slowly under argon. The mixture was stirred at 23° C. for 30 min before ethyl 5-(3-methylpyridin-4-yl)isoxazole-3-carboxylate (65 mg, 0.30 mmol) in 1,4-dioxane (2 mL) was added. The resulting reaction mixture was heated to 100° C. and stirred for 3 h. After being cooled to room temperature, the mixture was quenched with aqueous 1N hydrochloric acid (25 mL) and extracted with ethyl acetate (50 mL). The organic layer was washed with aqueous 0.5N hydrochloric acid (25 mL×2), and brine (25 mL), dried over sodium sulfate, filtered and concentrated in vacuo. The crude material was purified by prep-HPLC (column: Sunfire prep C18 10 am OBD 19*250 mm; mobile phase: [water (0.05% trifluoroacetic acid)-acetonitrile]; B %: 60%-88%, 15 min) to offer N-(1-benzyl-1H-pyrazol-4-yl)-5-(3-methylpyridin-4-yl)isoxazole-3-carboxamide (12 mg, 0.03 mmol, 11%) as a white solid. $^1$H NMR (500 MHz, Methanol-d4) δ 8.94 (d, 1H), 8.55 (dd, 11.2 Hz, 3H), 7.98 (d, 1H), 7.63 (d, 1H), 7.33-7.04 (m, 5H), 5.21 (d, 2H), 2.62 (s, 2H), 2.30 (s, 1H); LCMS (ESI) m/z: 360.1 [M+H]$^+$.

Example 71. Preparation of (S)—N-(1-benzyl-1H-pyrazol-4-yl)-5-(3-methoxypyrrolidin-1-yl)isoxazole-3-carboxamide (189)

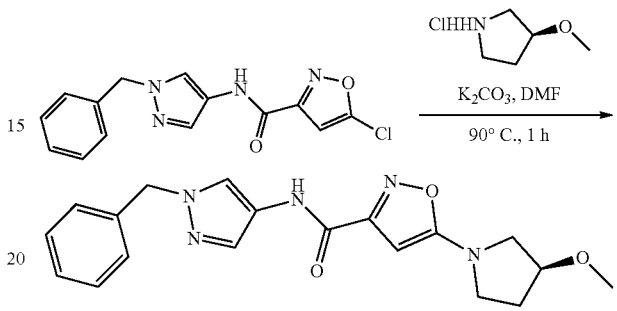

To a solution of N-(1-benzyl-1H-pyrazol-4-yl)-5-chloroisoxazole-3-carboxamide (0.1 g, 0.331 mmol), (R)-3-methoxypyrrolidine hydrochloride (0.136 g, 0.993 mmol) in N,N-dimethylformamide (3.0 mL) was added potassium carbonate (0.068 g, 0.497 mmol). The reaction mixture was heated at 90° C. for 1 h, cooled to room temperature and concentrated in vacuo. The crude sample was dissolved in minimum amount of N,N-dimethylformamide and purified by prep-HPLC (Boston C18 21×250 mm 10 µm column. The mobile phase was acetonitrile/10 mM ammonium acetate aqueous solution) to give (R)—N-(1-benzyl-1H-pyrazol-4-yl)-5-(3-methoxypyrrolidin-1-yl)isoxazole-3-carboxamide (19.0 mg, 0.052 mmol, 15%) as a light yellow solid. $^1$H NMR (500 MHz, Dimethylsulfoxide-d$_6$) δ 10.64 (s, 1H), 8.11 (s, 1H), 7.63 (s, 1H), 7.35-7.22 (m, 5H), 5.41 (s, 1H), 5.31 (s, 2H), 4.09-4.08 (m, 1H), 3.52-3.36 (m, 4H), 3.26 (s, 3H), 2.09-2.03 (m, 2H); LCMS (ESI) m/z: 368.2 [M+H]$^+$.

Example 72. Preparation of tert-butyl 4-(3-(1-benzyl-1H-pyrazol-4-ylcarbamoyl)isoxazol-5-yl)piperazine-1-carboxylate (185)

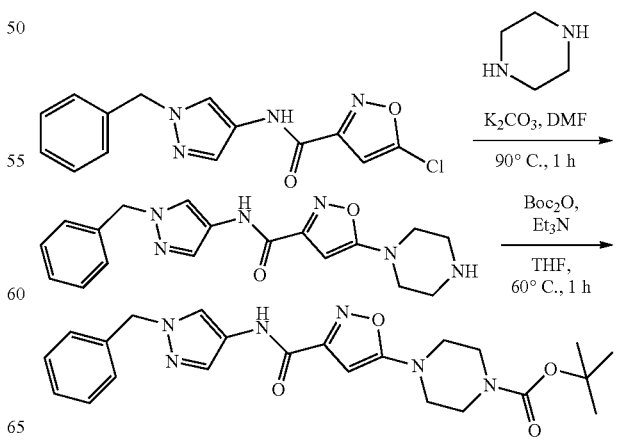

Step 1: Preparation of N-(1-benzyl-1H-pyrazol-4-yl)-5-(piperazin-1-yl)isoxazole-3-carboxamide

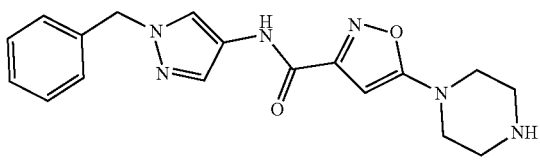 [SMILES: O=C(Nc1cnn(Cc2ccccc2)c1)c1cc(N2CCNCC2)on1]

To a solution of N-(1-benzyl-1H-pyrazol-4-yl)-5-chloroisoxazole-3-carboxamide (0.3 g, 0.993 mmol) and piperazine (256 mg, 2.98 mmol) in N,N-dimethylformamide (5 mL) was added potassium carbonate (0.205 g, 1.44 mmol). The reaction mixture was heated to 90° C. and stirred for 1 h. The crude sample was dissolved in minimum amount of N,N-dimethylformamide and purified by prep-HPLC (Boston C18 21×250 mm 10 μm column. The mobile phase was acetonitrile/10 mM ammonium acetate aqueous solution) to give N-(1-benzyl-1H-pyrazol-4-yl)-5-(piperazin-1-yl)isoxazole-3-carboxamide (130 mg, 0.369 mmol, 37%) as a white solid. LCMS (ESI) m/z: 353.1 [M+H]$^+$.

Step 2: Preparation of tert-butyl 4-(3-(1-benzyl-1H-pyrazol-4-ylcarbamoyl)isoxazol-5-yl)piperazine-1-carboxylate

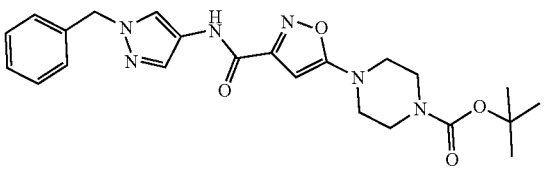 [SMILES: CC(C)(C)OC(=O)N1CCN(c2cc(C(=O)Nc3cnn(Cc4ccccc4)c3)no2)CC1]

To a solution of N-(1-benzyl-1H-pyrazol-4-yl)-5-(piperazin-1-yl)isoxazole-3-carboxamide (60 mg, 0.17 mmol) and triethylamine (34 mg, 0.34 mmol) in tetrahydrofuran (5 mL) was added di-tert-butyl dicarbonate (37 mg, 0.17 mmol). The reaction mixture was heated to 60° C. and stirred for 1 h. The volatiles were removed in vacuo. The crude sample was dissolved in minimum amount of N,N-dimethylformamide and purified by prep-HPLC (Boston C18 21×250 mm 10 μm column. The mobile phase was acetonitrile/10 mM ammonium acetate aqueous solution) to give tert-butyl 4-(3-(1-benzyl-1H-pyrazol-4-ylcarbamoyl)isoxazol-5-yl)piperazine-1-carboxylate (51.5 mg, 0.114 mmol, 66%) as a white solid. $^1$H NMR (500 MHz, Dimethylsulfoxide-d$_6$) δ 10.69 (s, 1H), 8.10 (s, 1H), 7.63 (s, 1H), 7.35-7.22 (m, 5H), 5.71 (s, 1H), 5.31 (s, 2H), 3.44 (d, J=5.5 Hz, 4H), 3.35 (d, J=5.5 Hz, 4H), 1.42 (s, 9H); LCMS (ESI) m/z: 453.3 [M+H]$^+$.

Example 73. Preparation of (R)—N-(1-benzyl-1H-pyrazol-4-yl)-5-(3-methoxypyrrolidin-1-yl)isoxazole-3-carboxamide (188)

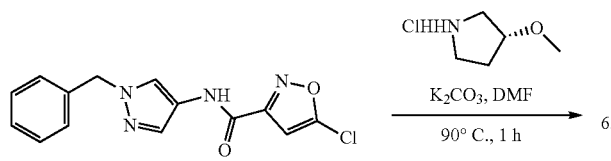

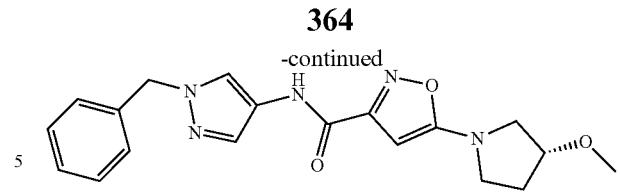

To a solution of N-(1-benzyl-1H-pyrazol-4-yl)-5-chloroisoxazole-3-carboxamide (0.1 g, 0.331 mmol) and (R)-3-methoxypyrrolidine hydrochloride (113 mg, 0.828 mmol) in N,N-dimethylformamide (3.0 mL) was added potassium carbonate (68 mg, 0.497 mmol). The reaction mixture was heated to 90° C. and stirred for 1 h. The crude sample was dissolved in minimum amount of N,N-dimethylformamide and purified by prep-HPLC (Boston C18 21×250 mm 10 μm column. The mobile phase was acetonitrile/10 mM ammonium acetate aqueous solution) to give (R)—N-(1-benzyl-1H-pyrazol-4-yl)-5-(3-methoxypyrrolidin-1-yl)isoxazole-3-carboxamide (21.1 mg, 0.057 mmol, 17%) as a light yellow solid. $^1$H NMR (500 MHz, Dimethylsulfoxide-d$_6$) δ 10.64 (s, 1H), 8.11 (s, 1H), 7.63 (s, 1H), 7.35-7.22 (m, 5H), 5.41 (s, 1H), 5.31 (s, 2H), 4.09-4.08 (m, 1H), 3.52-3.36 (m, 4H), 3.26 (s, 3H), 2.08-2.03 (m, 2H); LCMS (ESI) m/z: 368.0 [M+H]$^+$.

Example 74. Preparation of 1-benzyl-N-[5-(2-furyl)isoxazol-3-yl]pyrazole-4-carboxamide (49)

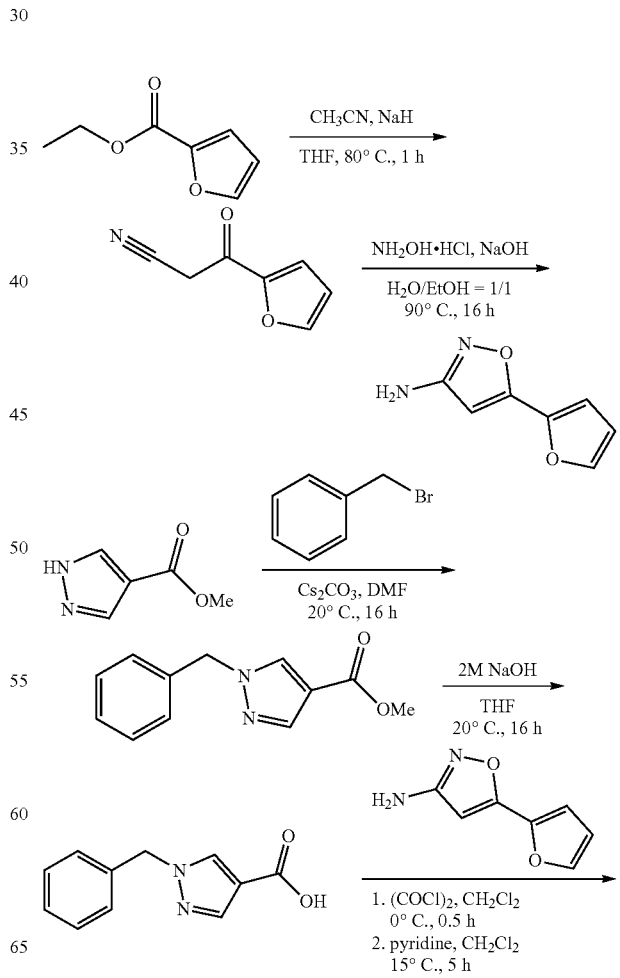

-continued

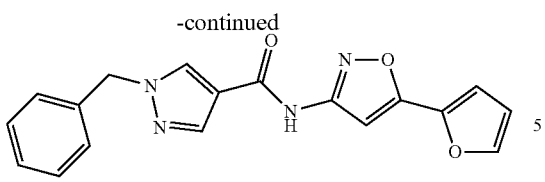

Step 1: Preparation of 3-(2-furyl)-3-oxo-propanenitrile

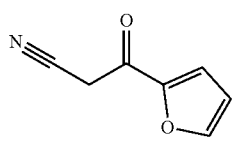

To a stirred solution of acetonitrile (7.51 mL, 1423 mmol) and sodium hydride (8.56 g, 214 mmol, 60% in mineral oil) in tetrahydrofuran (100 mL) at 20° C. was added ethyl furan-2-carboxylate (10.0 g, 71.4 mmol) dropwise. The reaction mixture was heated to 80° C. for 1 h. The mixture was cooled to 0° C. and water (40 mL) was added until no bubbles were being generated and then neutralized to pH=7 with aqueous 4 M hydrogen chloride. The aqueous layer was extracted with ethyl acetate (100 mL×3). The combined organic layers were washed with brine (20 mL), dried over sodium sulfate, filtered and concentrated in vacuo. The residue was purified by column chromatography (ISCO, 40 g silica, 0-30% ethyl acetate in petroleum ether, gradient over 20 min) to give 3-(2-furyl)-3-oxo-propanenitrile (7.5 g, 55.5 mmol, 78%) as a yellow solid. $^1$H NMR (400 MHz, Chloroform-d) δ 7.68 (d, J=1.1 Hz, 1H), 7.40 (d, J=3.5 Hz, 1H), 6.66 (dd, J=1.7, 3.7 Hz, 1H), 3.99 (s, 2H).

Step 2: Preparation of 5-(2-furyl)isoxazol-3-amine

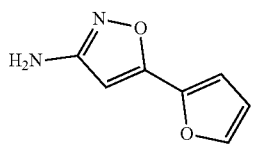 [SMILES: Nc1cc(-c2ccco2)on1]

To a solution of 3-(2-furyl)-3-oxo-propanenitrile (4.00 g, 29.6 mmol) in ethanol (60 mL) and water (40 mL) was added ammonia hydroxide (2.26 g, 32.6 mmol) and sodium hydroxide (1.42 g, 35.5 mmol). The reaction mixture was heated at 90° C. for 16 h. The mixture was cooled to 20° C. and concentrated hydrogen chloride (4 mL) was added to the above solution and the mixture was heated at 90° C. for 2 h. The mixture was basified to pH=8 with 1 M lithium hydroxide hydrate, extracted with dichloromethane (20 mL×4). The organic layers were washed with brine (10 mL×2), dried over sodium sulfate, filtered and concentrated in vacuo. The crude residue was purified by column chromatography (ISCO, 40 g silica, 40-55% ethyl acetate in petroleum ether, gradient over 20 min) to give 5-(2-furyl)isoxazol-3-amine (1 g, 6.10 mmol, 21%) as a yellow solid. $^1$H NMR (400 MHz, Acetone-d$_6$) δ 7.75-7.67 (m, 1H), 6.87 (d, J=3.4 Hz, 1H), 6.61 (dd, J=1.8, 3.4 Hz, 1H), 6.13 (s, 1H), 5.32-4.90 (m, 2H).

Step 3. Preparation of methyl 1-benzylpyrazole-4-carboxylate

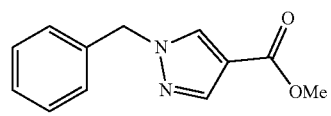 [SMILES: COC(=O)c1cnn(Cc2ccccc2)c1]

A mixture of methyl 1H-pyrazole-4-carboxylate (1.10 g, 8.72 mmol), benzyl bromide (1.55 mL, 13.1 mmol) and cesium carbonate (8.53 g, 26.2 mmol) in N,N-dimethylformamide (20 mL) was stirred at 20° C. for 16 h. The reaction mixture was diluted with water (30 mL) and extracted with dichloromethane (15 mL×2). The combined organic layers were washed with brine (20 mL×2), dried over sodium sulfate, filtered and concentrated under reduced pressure. The crude residue was purified by column chromatography (ISCO, 12 g silica, 0-30% ethyl acetate in petroleum ether, gradient over 15 min) to give methyl 1-benzylpyrazole-4-carboxylate (1.0 g, 4.62 mmol, 53%) as a white solid. $^1$H NMR (400 MHz, Acetone-d$_6$) δ 7.86 (s, 1H), 7.77 (s, 1H), 7.31-7.25 (m, 2H), 7.18-7.16 (m, 2H), 5.22 (s, 2H), 3.72 (ds, 1H), 6.13 (s, 3H).

Step 4. Preparation of methyl 1-benzylpyrazole-4-carboxylic Acid

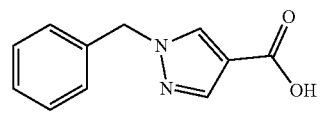 [SMILES: O=C(O)c1cnn(Cc2ccccc2)c1]

To a solution of methyl 1-benzylpyrazole-4-carboxylate (1.00 g, 4.62 mmol) in tetrahydrofuran (20 mL) was added sodium hydroxide (2 M, 4.6 mL). The reaction mixture was stirred at 20° C. for 16 h. The reaction mixture was adjusted to pH=3 with aqueous 2 M hydrogen chloride and the aqueous phase was extracted with ethyl acetate (10 mL×2). The combined organic layers were washed with brine (10 mL×2), dried over sodium sulfate, filtered and concentrated under reduced pressure to give 1-benzylpyrazole-4-carboxylic acid (0.600 g, 2.97 mmol, 64%) as a white solid. This material was used in the next step without further purification.

Step 5: Preparation of 1-benzyl-N-[5-(2-furyl)isoxazol-3-yl]pyrazole-4-carboxamide

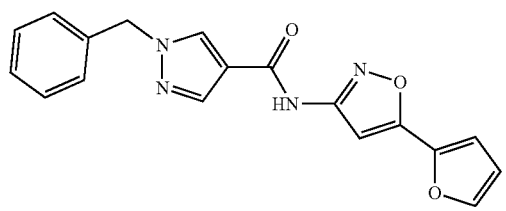 [SMILES: O=C(Nc1cc(-c2ccco2)on1)c1cnn(Cc2ccccc2)c1]

To a solution 1-benzylpyrazole-4-carboxylic acid (0.242 g, 1.20 mmol) in dichloromethane (3 mL) at 0° C. was added dropwise oxalyl chloride (0.26 mL, 3.00 mmol) followed by 1 drop of dry N,N-dimethylformamide. The reaction mixture was stirred at 20° C. for 30 min. The reaction mixture was concentrated in vacuo, dissolved in dichloromethane (1 mL) and added slowly to a solution of 5-(2-furyl)isoxazol-3-amine (150 mg, 0.999 mmol) and pyridine (158 mg, 2.00 mmol) in dichloromethane (3 mL). The reaction mixture was stirred at 15° C. for 5 h then filtered and purified by column chromatography (ISCO, 12 g silica, 40-60% ethyl acetate in petroleum ether, gradient over 20 min) to afford 1-benzyl-N-[5-(2-furyl)isoxazol-3-yl]pyrazole-4-carboxamide (0.100 g, 0.298 mmol, 30%) as a white solid. $^1$H NMR (400 MHz, Dimethylsulfoxide-d$_6$) δ 11.22 (s, 1H), 8.56 (s, 1H), 8.16 (s, 1H), 7.96 (d, J=1.2 Hz, 1H), 7.45-7.26 (m, 5H), 7.23-7.15 (m, 2H), 6.74 (dd, J=1.8, 3.5 Hz, 1H), 5.40 (s, 2H); LCMS (ESI) m/z: 335.1 [M+H]$^+$.

Example 75. Preparation of N-(1-benzyl-1H-pyrazol-4-yl)-3-isopropylisoxazole-5-carboxamide (158)

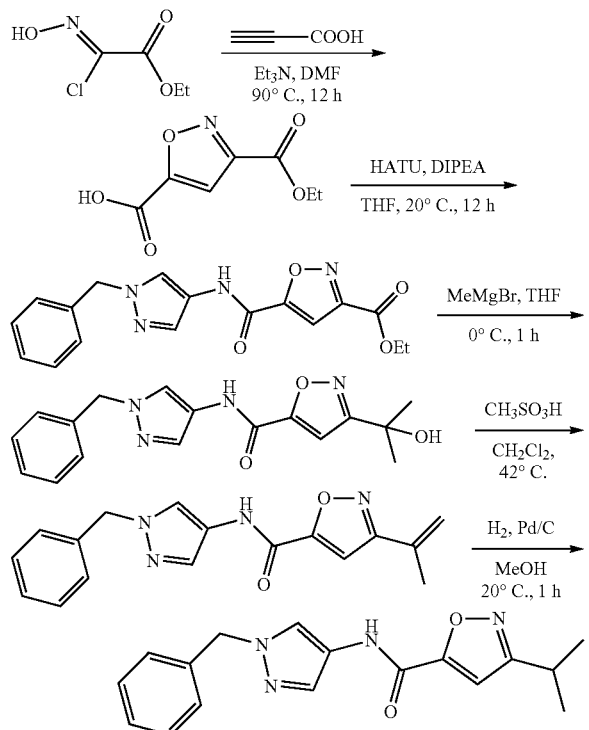

Step 1: Preparation of 3-(ethoxycarbonyl)isoxazole-5-carboxylic Acid

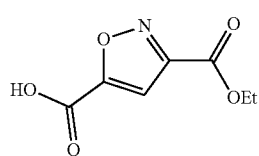 [SMILES: CCOC(=O)c1cc(C(=O)O)on1]

A solution of (Z)-ethyl 2-chloro-2-(hydroxyimino)acetate (3.36 g, 22.3 mmol) in N,N-dimethylformamide (10 mL) was slowly added to a solution of propiolic acid (3.9 g, 55.7 mmol) in N,N-dimethylformamide (10 mL) under nitrogen. The reaction mixture was heated to 90° C. and triethylamine (6.76 g, 66.9 mmol) was slowly added to the mixture. Then the solution was heated at 90° C. for 12 h. The volatiles were removed under the reduced pressure and the crude residue was extracted with ethyl acetate (40 mL). The aqueous layer was adjusted to pH=3-5 with aqueous 1N hydrochloric acid and then extracted with dichloromethane (50 mL×2). The dichloromethane layer was dried over sodium sulfate, filtered and concentrated in vacuo to give 3-(ethoxycarbonyl)isoxazole-5-carboxylic acid (4.5 g, crude) as a brown oil. LCMS (ESI) m/z: 186.1 [M+H]$^+$. This material was used in the next step without further purification.

Step 2: Preparation of ethyl 5-(1-benzyl-1H-pyrazol-4-ylcarbamoyl)isoxazole-3-carboxylate

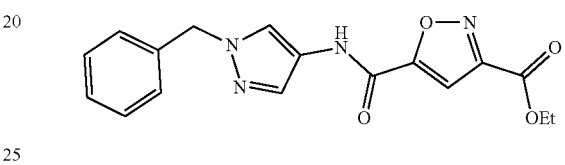

To a solution of 3-(ethoxycarbonyl)isoxazole-5-carboxylic acid (0.6 g, 3.24 mmol) in diisopropylethylamine (1.26 g, 9.72 mmol) in tetrahydrofuran (20 mL) at 20° C. was added 1-[bis(dimethylamino)methylene]-1H-1,2,3-triazolo[4,5-b]pyridinium 3-oxide hexafluorophosphate (1.86 g, 4.91 mmol). The reaction mixture was stirred at 20° C. for 30 min before 1-benzyl-1H-pyrazol-4-amine (0.561 g, 3.24 mmol) was added. The reaction mixture was stirred at 20° C. for 12 h. The volatiles were removed in vacuo. The crude product was purified by column chromatography (silica, petroleum ether/ethyl acetate=1/1) to yield ethyl 5-(1-benzyl-1H-pyrazol-4-ylcarbamoyl)isoxazole-3-carboxylate (0.300 g, 0.882 mmol, 27%) as a white solid. LCMS (ESI) m/z: 341.1 [M+H]$^+$.

Step 3: Preparation of ethyl 5-(1-benzyl-1H-pyrazol-4-ylcarbamoyl)isoxazole-3-carboxylate

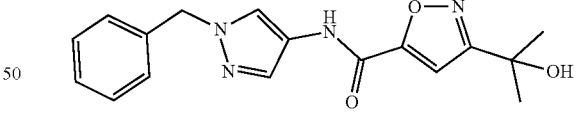

To a solution of ethyl 5-(1-benzyl-1H-pyrazol-4-ylcarbamoyl)isoxazole-3-carboxylate (0.200 g, 0.588 mmol) in tetrahydrofuran (10 mL) at 0° C. was added methyl magnesium bromide (1 mL, 2.94 mmol) under nitrogen. The reaction mixture was quenched with aqueous ammonium chloride (10 mL) and extracted with dichloromethane (100 mL). The organic layer was dried over sodium sulfate, filtered and concentrated in vacuo. The crude sample was dissolved in minimum amount of N,N-dimethylformamide and purified via prep-HPLC (Boston C18 21×250 mm 10 μm column; acetonitrile/0.01% aqueous trifluoroacetic acid) to give ethyl 5-(1-benzyl-1H-pyrazol-4-ylcarbamoyl)isoxazole-3-carboxylate (72.7 mg, 0.223 mmol, 25%) as a white solid. LCMS (ESI) m/z: 327.2 [M+H]$^+$.

Step 4: Preparation of N-(1-benzyl-1H-pyrazol-4-yl)-3-(prop-1-en-2-yl)isoxazole-5-carboxamide

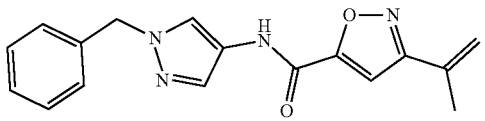 [SMILES: C=C(C)c1cc(C(=O)Nc2cnn(Cc3ccccc3)c2)on1]

To a solution of (Z)-ethyl 2-chloro-2-(hydroxyimino)acetate (40 mg, 0.123 mmol) in dichloromethane (10 mL) was added methyl sulfonic acid (0.5 mL). The reaction mixture was refluxed for 2 h. The volatiles were removed in vacuo. The crude sample was dissolved in minimum amount of N,N-dimethylformamide and purified via prep-HPLC (Boston C18 21×250 mm 10 μm column; acetonitrile/0.01% aqueous trifluoroacetic acid) to give N-(1-benzyl-1H-pyrazol-4-yl)-3-(prop-1-en-2-yl)isoxazole-5-carboxamide (22.2 mg, 0.072 mmol, 58%) as a white solid. $^1$H NMR (500 MHz, Dimethylsulfoxide-d$_6$) δ 11.07 (s, 1H), 8.16 (s, 1H), 7.65 (s, 1H), 7.50 (s, 1H), 7.36-7.23 (m, 5H), 5.88 (s, 1H), 5.52 (s, 1H), 5.33 (s, 2H), 2.11 (s, 3H); LCMS (ESI) m/z: 309.1 [M+H]$^+$.

Step 5: Preparation of N-(1-benzyl-1H-pyrazol-4-yl)-3-(prop-1-en-2-yl)isoxazole-5-carboxamide

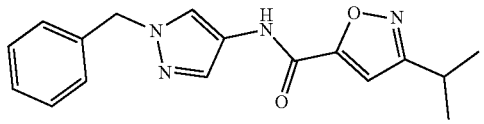 [SMILES: CC(C)c1cc(C(=O)Nc2cnn(Cc3ccccc3)c2)on1]

To a solution of N-(1-benzyl-1H-pyrazol-4-yl)-3-(prop-1-en-2-yl)isoxazole-5-carboxamide (80 mg, 0.26 mmol) in methanol (10 mL) under nitrogen was added palladium on carbon (8 mg, 10% Pd by weight). The reaction mixture was stirred at 20 C for 1 h under hydrogen balloon. The volatiles were removed in vacuo. The crude sample was dissolved in minimum amount of N,N-dimethylformamide and purified via prep-HPLC (Boston C18 21×250 mm 10 μm column; acetonitrile/0.01% aqueous trifluoroacetic acid) to give N-(1-benzyl-1H-pyrazol-4-yl)-3-(prop-1-en-2-yl)isoxazole-5-carboxamide (14.5 mg, 0.047 mmol, 18%) as a white solid. $^1$H NMR (500 MHz, Dimethylsulfoxide-d$_6$) δ 11.00 (s, 1H), 8.15 (s, 1H), 7.64 (s, 1H), 7.36-7.23 (m, 5H), 7.14 (s, 1H), 5.33 (s, 2H), 3.11-3.06 (m, 1H), 1.26 (d, J=7.0 Hz, 6H); LCMS (ESI) m/z: 311.2 [M+H]$^+$.

Example 76: Preparation of N-(1-benzylpyrazol-4-yl)-3-(2-furyl)isoxazole-5-carboxamide (11)

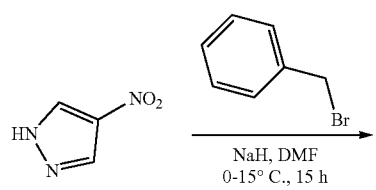

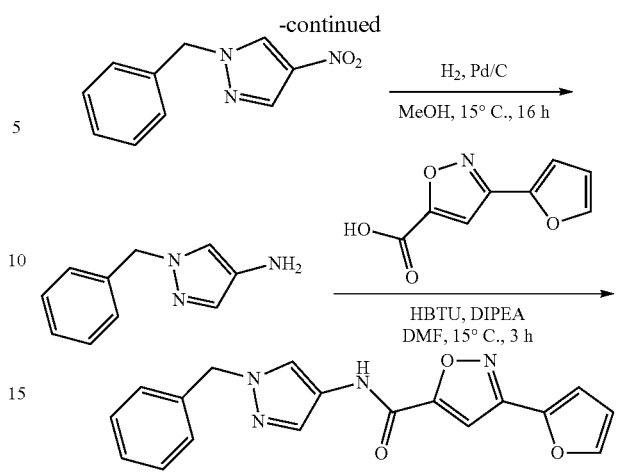

Step 1: Preparation of 1-benzyl-4-nitro-pyrazole

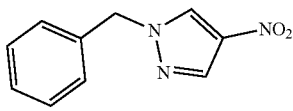 [SMILES: O=[N+]([O-])c1cnn(Cc2ccccc2)c1]

To a stirred solution of 4-nitro-1H-pyrazole (2.00 g, 17.7 mmol) in N,N-dimethylformamide (15 mL) at 0° C. was added sodium hydride (0.778 g, 19.0 mmol, 60% purity by weight in mineral oil). The reaction mixture was stirred at 15° C. for 1 h, then cooled to 0° C. and benzyl bromide (3.03 g, 17.7 mmol, 2.1 mL) was added. The reaction mixture was warmed to 15° C. and stirred for 15 h. The reaction mixture was added to ice water (5 mL) and extracted with ethyl acetate (15 mL×3). The combined organic layers were washed with water (10 mL×2), then brine (5 mL), dried over sodium sulfate, filtered and concentrated under reduced pressure. The crude residue was purified by column chromatography (ISCO, 20 g silica, 0-30% ethyl acetate in petroleum ether, gradient over 20 min) to give 1-benzyl-4-nitro-pyrazole (2.80 g, 13.8 mmol, 78%) as a white solid. $^1$H NMR (400 MHz, Chloroform-d) δ 8.10 (s, 1H), 8.04 (s, 1H), 7.45-7.39 (m, 3H), 7.32-7.28 (m, 2H), 5.31 (s, 2H), LCMS (ESI) m/z: 204.1 [M+H]$^+$.

Step 2: Preparation of 1-benzylpyrazol-4-amine

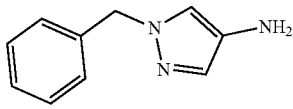 [SMILES: Nc1cnn(Cc2ccccc2)c1]

To a solution of 1-benzyl-4-nitro-pyrazole (1.50 g, 7.38 mmol) in methanol (10 mL) was added palladium on activated carbon (10% Pd by weight, 0.500 g) under nitrogen. The suspension was evacuated and purged with hydrogen several times. The mixture was stirred under hydrogen at 15° C. for 16 h. The reaction mixture was filtered and the filtrate was concentrated in vacuo to give 1-benzylpyrazol-4-amine (1.10 g, 6.35 mmol, 86%) as a pink solid. LCMS (ESI) m/z: 174.1 [M+H]$^+$. This material was used in the next step without further purification.

Step 3: Preparation of N-(1-benzylpyrazol-4-yl)-3-(2-furyl)isoxazole-5-carboxamide

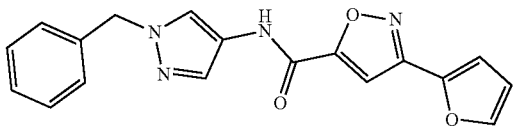 [SMILES: O=C(Nc1cnn(Cc2ccccc2)c1)c1cc(-c2ccco2)no1]

To a stirred solution of 1-benzylpyrazol-4-amine (0.120 g, 0.693 mmol) and 3-(furan-2-yl)isoxazole-5-carboxylic acid (0.157 g, 0.831 mmol) in N,N-dimethylformamide (1 mL) at 15° C. was added N,N,N',N'-tetramethyl-O-(1H-benzotriazol-1-yl)uronium hexafluorophosphate (0.315 g, 0.831 mmol) and diisopropylethylamine (0.179 mg, 1.39 mmol). The reaction mixture was stirred at 15° C. for 3 h. Upon completion of reaction, the reaction mixture was purified by prep-HPLC (Agela Venusil XBP C18 150×25 5 um column; 50-75% acetonitrile in a 10 mM 0.04% ammonium hydroxide, 10 min gradient) to give N-(1-benzylpyrazol-4-yl)-3-(2-furyl)isoxazole-5-carboxamide (0.070 g, 0.209 mmol, 36%) as a white solid. $^1$H NMR (400 MHz, Chloroform-d) δ 8.55 (br. s, 1H), 8.04 (s, 1H), 7.65-7.59 (m, 2H), 7.40-7.32 (m, 3H), 7.30-7.26 (m, 2H), 7.00 (d, J=3.4 Hz, 1H), 6.92 (s, 1H), 6.59 (dd, J=1.8, 3.5 Hz, 1H), 5.32 (s, 2H); LCMS (ESI) m/z: 335.1 [M+H]$^+$.

Example 77. Preparation of (5-(5-fluoropyridin-2-yl)isoxazol-3-yl)(3-phenylazetidin-1-yl)methanone (243)

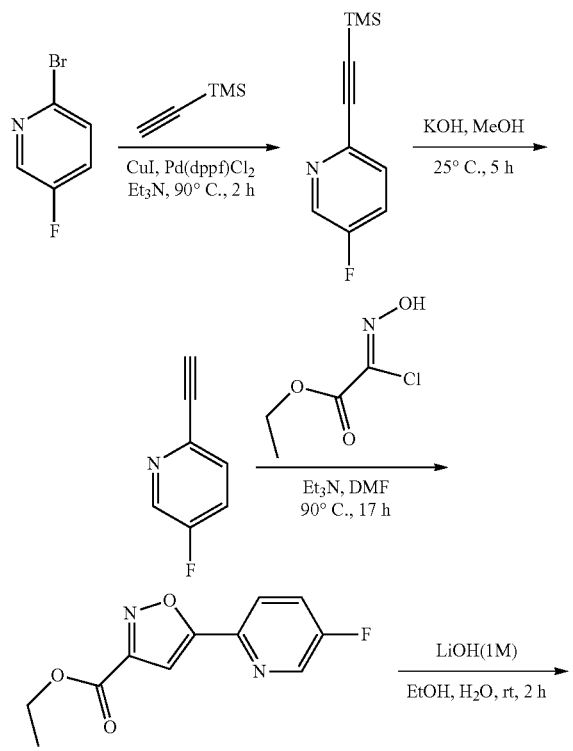

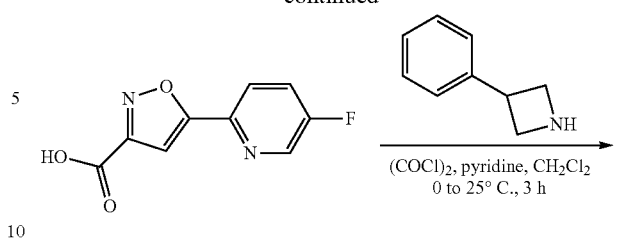

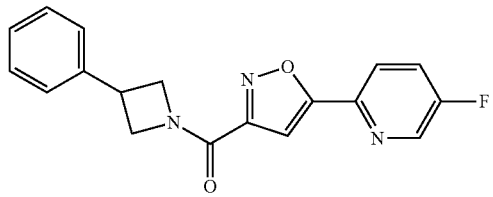

Step 1: Preparation of 5-fluoro-2-((trimethylsilyl)ethynyl)pyridine

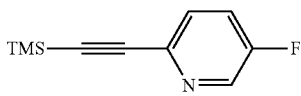

A mixture of 2-bromo-5-fluoropyridine (4.9 g, 27.8 mmol), ethynyltrimethylsilane (3.27 g, 33.4 mmol), [1,1'-bis(diphenylphosphino)ferrocene]dichloropalladium(II) (2.03 g, 2.78 mmol) and copper iodide (1.06 g, 5.57 mmol) in triethylamine (100 mL) was heated at 90° C. for 2 h. The mixture was diluted with brine (100 mL), extracted with ethyl acetate (100 mL×2) and purified by column chromatography (silica, petroleum ether/ethyl acetate=20/1) yield 5-fluoro-2-((trimethylsilyl)ethynyl)pyridine (1.5 g, 7.7 mmol, 28%) as a yellow oil. LCMS (ESI) m/z: 194.2 [M+Na]$^+$.

Step 2: Preparation of 2-ethynyl-5-fluoropyridine

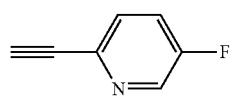

A mixture of 5-fluoro-2-((trimethylsilyl)ethynyl)pyridine (3.5 g, 18.1 mmol) and potassium hydroxide (1.02 g, 18.1 mmol) in methanol (100 mL) was stirred at 20° C. for 5 h. The mixture was diluted with brine (100 mL), extracted with ethyl acetate (100 mL×2) and purified by column chromatography (silica, petroleum ether/ethyl acetate=20/1) to yield 2-ethynyl-5-fluoropyridine (1.75 g, 14.5 mmol, 80%) as a yellow oil. LCMS (ESI) m/z: 122.0 [M+H]$^+$.

Step 3: Preparation of ethyl 5-(5-fluoropyridin-2-yl)isoxazole-3-carboxylate

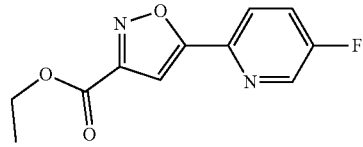 [SMILES: CCOC(=O)c1cc(-c2ccc(F)cn2)on1]

To a solution of 2-ethynyl-5-fluoropyridine (1.5 g, 12.4 mmol) in N,N-dimethylformamide (20 mL) at 23° C. was added (Z)-Ethyl 2-chloro-2-(hydroxyimino)acetate (2.81 g, 18.6 mmol). The reaction mixture stirred for 1 h before triethylamine (1.88 g, 18.6 mmol) was added. The mixture was heated at 90° C. for 16 h. The mixture was diluted with brine (100 mL), extracted with ethyl acetate (100 mL×2) and purified by column chromatography (silica, petroleum ether/ethyl acetate=20/1) to give ethyl 5-(5-fluoropyridin-2-yl)isoxazole-3-carboxylate (300 mg, 1.27 mmol, 10%) as a gray oil. LCMS (ESI) m/z: 237.1 [M+H]$^+$.

Step 4: Preparation of 5-(5-fluoropyridin-2-yl)isoxazole-3-carboxylic Acid

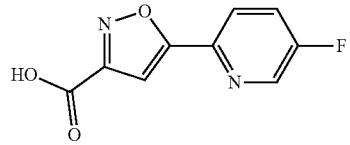 [SMILES: O=C(O)c1cc(-c2ccc(F)cn2)on1]

A mixture of ethyl 5-(5-fluoropyridin-2-yl)isoxazole-3-carboxylate (0.2 g, 0.85 mmol) and lithium hydroxide (1.7 mL, 3.39 mmol, aqueous 2 M) in ethanol (1.7 mL) was stirred at 20° C. for 2 h. The mixture was extracted with ethyl acetate and concentrated in vacuo to afford crude 5-(5-fluoropyridin-2-yl)isoxazole-3-carboxylic acid (1.3 g, 0.63 mmol, 73%) as a gray solid. LCMS (ESI) m/z: 209.1 [M+H]$^+$. This material was used in the next step without further purification.

Step 5: Preparation of (5-(5-fluoropyridin-2-yl)isoxazol-3-yl)(3-phenylazetidin-1-yl)methanone

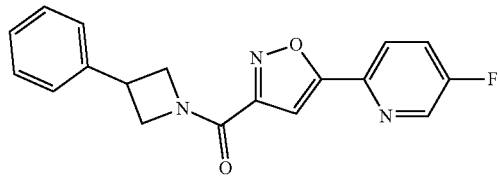 [SMILES: O=C(c1cc(-c2ccc(F)cn2)on1)N1CC(c2ccccc2)C1]

To a solution of 5-(5-fluoropyridin-2-yl)isoxazole-3-carboxylic acid (0.1 g, 0.48 mmol) and N,N-dimethylformamide (0.001 g, 0.01 mmol) in dichloromethane (5 mL) at 0° C. was added oxalyl chloride (0.106 g, 1.44 mmol). The reaction mixture was stirred at 23° C. for 1 h. The reaction mixture was concentrated in vacuo. The crude residue was diluted with dichloromethane (5 mL) and pyridine (0.19 g, 2.4 mmol) followed by 3-phenylazetidine (0.122 g, 0.72 mmol) was added. The reaction mixture was stirred for 2 h. The reaction mixture was extracted with ethyl acetate (20 mL×2) and washed with water (30 mL) and brine (30 mL). The combined organic phases were dried over anhydrous sodium sulfate, filtered, concentrated in vacuo. The crude sample was dissolved in minimum amount of N,N-dimethylformamide and purified via prep-HPLC (Boston C18 21×250 mm 10 μm column; acetonitrile/0.01% aqueous trifluoroacetic acid) to give (5-(5-fluoropyridin-2-yl)isoxazol-3-yl)(3-phenylazetidin-1-yl)methanone (0.033 g, 0.1 mmol, 21%) as a white solid. $^1$H NMR (500 MHz, Dimethylsulfoxide-d$_6$) δ 8.77 (d, J=2.8 Hz, 1H), 8.17 (dd, J=8.8, 4.4 Hz, 1H), 7.97 (td, J=8.7, 2.9 Hz, 1H), 7.43 (m, 2H), 7.41-7.35 (m, 3H), 7.28 (t, J=7.2 Hz, 1H), 4.92 (t, J=9.2 Hz, 1H), 4.57-4.46 (m, 2H), 4.10 (dd, J=10.0, 6.5 Hz, 1H), 4.06-3.98 (m, 1H). LCMS (ESI) m/z: 324.1 [M+H]$^+$.

Example 78. Preparation of (5-(6-methoxypyridazin-3-yl)isoxazol-3-yl)(3-phenylazetidin-1-yl)methanone (255)

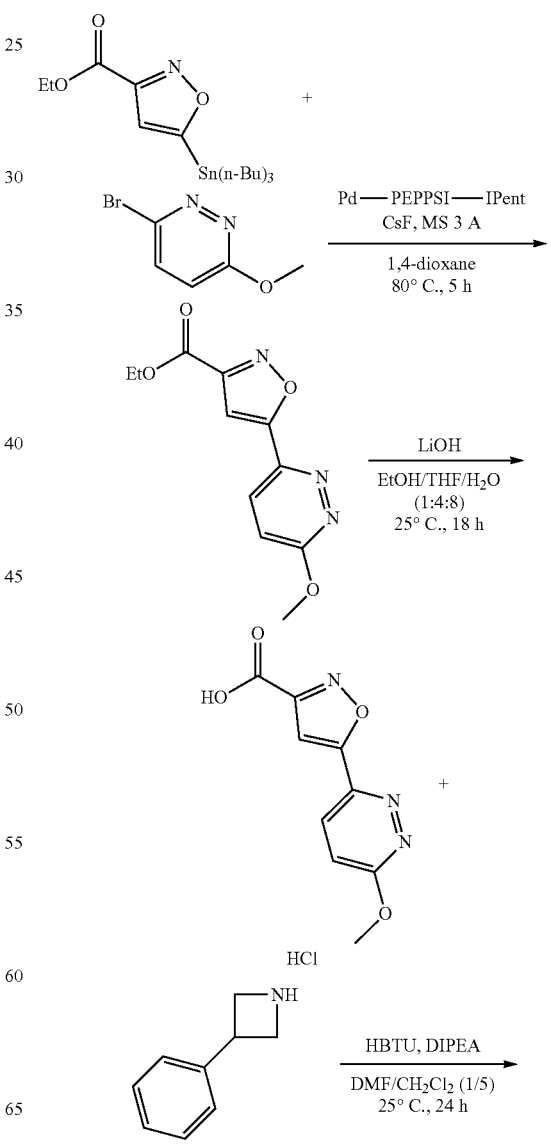

-continued

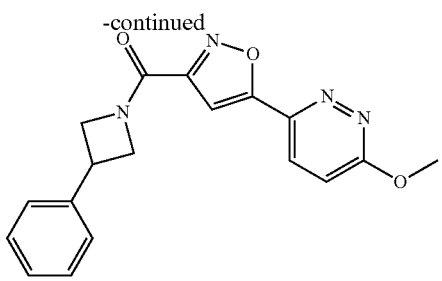

Step 1: Preparation of ethyl 5-(6-methoxypyridazin-3-yl)isoxazole-3-carboxylate

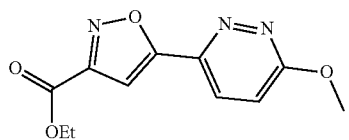

A reaction vial was charged with 3-bromo-6-methoxypyridazine (58.7 mg, 0.311 mmol), cesium fluoride (85.9 mg, 0.566 mmol), Pd-PEPPSI-IPent catalyst (17.8 mg, 0.023 mmol), crushed 3 A molecular sieves (100 mg) and ethyl 5-(tributylstannyl)-1,2-oxazole-3-carboxylate (0.122 g, 0.283 mmol). The vial was sealed, purged, and placed under an argon atmosphere then, 1,4-dioxane (1.5 mL) was added. The reaction mixture heated to 80° C. and stirred for 5 h. The reaction mixture was cooled to room temperature, filtered, and concentrated in vacuo. The crude material was purified by column chromatography (ISCO, 4 g silica, eluting with 0% to 30% ethyl acetate in hexanes with 2% triethylamine) to give ethyl 5-(6-methoxypyridazin-3-yl)isoxazole-3-carboxylate as a yellow solid (46.9 mg, 0.190 mmol, 67%). $^1$H NMR (300 MHz, Dimethylsulfoxide-d$_6$) δ 8.29 (d, J=9.3 Hz, 1H), 7.63 (s, 1H), 7.47 (d, J=9.2 Hz, 1H), 4.42 (q, J=7.1 Hz, 2H), 4.13 (s, 3H), 1.35 (t, J=7.1 Hz, 3H).

Step 2: Preparation of 5-(6-methoxypyridazin-3-yl)isoxazole-3-carboxylic Acid

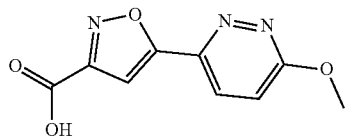 [SMILES: CCOC(=O)c1cc(-c2ccc(OC)nn2)on1]

To a solution of ethyl 5-(6-methoxypyridazin-3-yl)-1,2-oxazole-3-carboxylate (66.5 mg, 0.266 mmol) in ethanol/THF/water (1:4:8, 3.25 mL) at 25° C. was added in one portion lithium hydroxide monohydrate (55.8 mg, 1.33 mmol). The reaction mixture was stirred at 25° C. for 18 h. The reaction was cooled in an ice bath and quenched with aqueous 1N hydrogen chloride solution (1.5 mL). The volume of reaction mixture was doubled with water and the volatiles were concentrated in vacuo. The remaining aqueous layer was extracted with ethyl acetate (20 mL×3). The combined organics were washed with brine (5 mL) and concentrated in vacuo. The crude 5-(6-methoxypyridazin-3-yl)isoxazole-3-carboxylic acid was obtained as a light yellow solid (53.0 mg, 0.239 mmol, 90%). This material was used in the next step without further purification. $^1$H NMR (300 MHz, Dimethylsulfoxide-d$_6$) δ 8.26 (d, J=9.2 Hz, 1H), 7.54 (s, 1H), 7.46 (d, J=9.3 Hz, 1H), 4.12 (s, 3H); LCMS (ESI) m/z: 222.1[M+H]$^+$.

Step 3: Preparation of (5-(6-methoxypyridazin-3-yl)isoxazol-3-yl)(3-phenylazetidin-1-yl)methanone

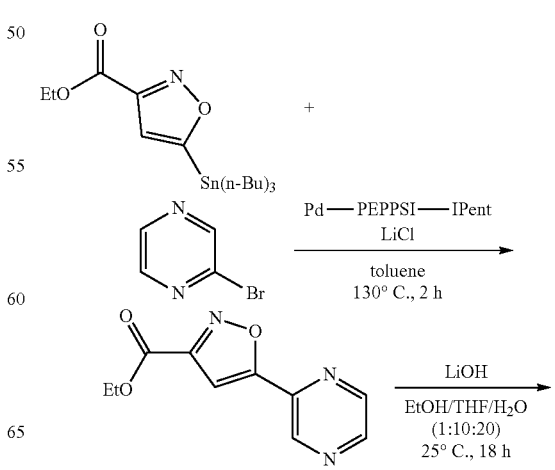

To a suspension of 5-(6-methoxypyridazin-3-yl)-1,2-oxazole-3-carboxylic acid (25 mg, 0.113 mmol), N,N,N',N'-tetramethyl-O-(1H-benzotriazol-1-yl)uronium hexafluorophosphate (0.192 g, 0.508 mmol), and diisopropylethylamine (58.4 mg, 0.452 mmol) in N,N-dimethylformamide/dichloromethane (1/5, 1.2 mL) at 25° C. was added 3-phenylazetidine hydrochloride (28.6 mg, 0.169 mmol). The reaction mixture was stirred at room temperature for 24 h. The reaction was poured into ethyl acetate (20 mL) and water (2 mL). The aqueous phase was removed and the organic layer was concentrated in vacuo. The crude oil was purified by column chromatography (ISCO, 4 g silica, eluting with 0% to 50% ethyl acetates in hexanes) to yield (5-(6-methoxypyridazin-3-yl)isoxazol-3-yl)(3-phenylazetidin-1-yl)methanone as a white solid (12.1 mg, 0.036 mmol, 32%). $^1$H NMR (300 MHz, Dimethylsulfoxide-d$_6$) δ 8.27 (dd, J=9.3, 1.0 Hz, 1H), 7.53 (d, J=0.9 Hz, 1H), 7.51-7.35 (m, 5H), 7.35-7.21 (m, 1H), 4.93 (t, J=9.2 Hz, 1H), 4.52 (td, J=11.2, 9.9, 7.5 Hz, 2H), 4.12 (s, 3H), 4.10-3.93 (m, 3H); LCMS (ESI) m/z: 337.2 [M+H]$^+$.

Example 79. Preparation of (3-phenylazetidin-1-yl)(5-(pyrazin-2-yl)isoxazol-3-yl)methanone (259)

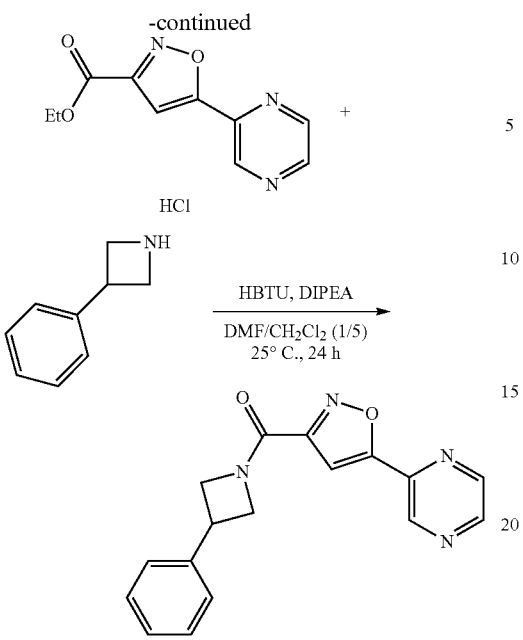

Step 1: Preparation of ethyl 5-(pyrazin-2-yl)isoxazole-3-carboxylate

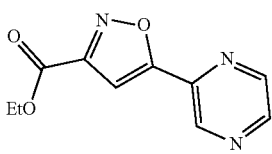 [SMILES: CCOC(=O)c1cc(-c2cnccn2)on1]

A reaction vial was charged with 2-bromopyrazine (50 mg, 0.314 mmol), lithium chloride (13 mg, 0.314 mmol), Pd-PEPPSI-IPent catalyst (19.8 mg, 0.025 mmol) and toluene (2 mL). The vial was sealed, purged, and placed under an argon atmosphere and ethyl 5-(tributylstannyl)-1,2-oxazole-3-carboxylate (148 mg, 0.345 mmol) was added. The reaction mixture was heated in the microwave reactor at 130° C. for 2 h. The reaction mixture was cooled to room temperature, filtered, and concentrated in vacuo. The crude material was purified by column chromatography (ISCO, 4 g silica, eluting with 0% to 40% ethyl acetate in hexanes) to give ethyl 5-(pyrazin-2-yl)isoxazole-3-carboxylate (0.035 g, 0.126 mmol, 40%).

Step 2: Preparation of 5-(pyrazin-2-yl)isoxazole-3-carboxylic Acid

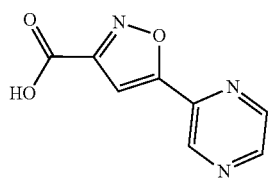 [SMILES: O=C(O)c1cc(-c2cnccn2)on1]

To a solution of ethyl 5-(pyrazin-2-yl)-1,2-oxazole-3-carboxylate (35.9 mg, 0.126 mmol) in ethanol (0.050 mL) and THF (0.50 mL) was added in one portion lithium hydroxide monohydrate (34.1 mg, 0.815 mmol) followed by water (1 mL). The reaction mixture was stirred at room temperature for 18 h. The reaction was cooled in an ice bath, diluted with water (2 mL), and quenched with aqueous 1 M hydrogen chloride (0.90 mL). All volatiles were removed in vacuo, the remaining aqueous layer was extracted with ethyl acetate 5× (2 mL), and the combined organics were concentrated in vacuo to afford 5-(pyrazin-2-yl)-1,2-oxazole-3-carboxylic acid (26.1 mg, 0.130 mmol, 84%) as a yellow solid. This material was used in the next step without further purification. $^1$H NMR (300 MHz, Dimethylsulfoxide-d$_6$) δ 9.33 (d, J=1.5 Hz, 1H), 8.83 (dd, J=2.5, 1.5 Hz, 1H), 8.80 (d, J=2.5 Hz, 1H), 7.62 (s, 1H); LCMS (ESI) m/z: 192.1 [M+H]$^+$.

Step 3: Preparation of (3-phenylazetidin-1-yl)(5-(pyrazin-2-yl)isoxazol-3-yl)methanone

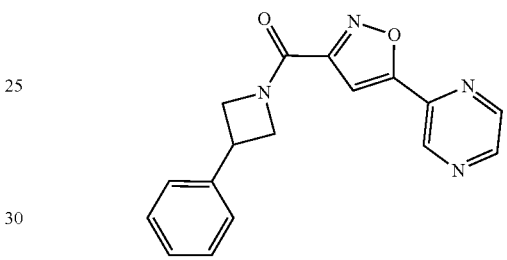

To a suspension of 5-(pyrazin-2-yl)-1,2-oxazole-3-carboxylic acid (25.0 mg, 0.130 mmol), N,N,N',N'-tetramethyl-O-(1H-benzotriazol-1-yl)uronium hexafluorophosphate (73.5 mg, 0.194 mmol) and diisopropylethylamine (50.2 mg, 0.389 mmol) in N,N-dimethylformamide/methylene chloride (1/5, 1.2 mL) was added 3-phenylazetidine hydrochloride (24.2 mg, 0.143 mmol). The reaction mixture was stirred at room temperature for 8 h. The reaction was poured into ethyl acetate (20 mL), washed with water (2 mL), aqueous 1 M sodium hydroxide (2 mL×2), brine (2 mL) and concentrated in vacuo. The crude product was purified by column chromatography (ISCO, 4 g silica, eluting with 0% to 50% ethyl acetates in hexanes) to afford (3-phenylazetidin-1-yl)(5-(pyrazin-2-yl)isoxazol-3-yl)methanone as an off-white solid (9.0 mg, 0.0299 mmol, 23%). $^1$H NMR (300 MHz, Dimethylsulfoxide-d$_6$) δ 9.34 (d, J=1.5 Hz, 1H), 8.84 (dd, J=2.5, 1.5 Hz, 1H), 8.80 (d, J=2.5 Hz, 1H), 7.61 (s, 1H), 7.49-7.24 (m, 5H), 4.93 (t, J=9.2 Hz, 1H), 4.60-4.46 (m, 2H), 4.14-3.95 (m, 2H); LCMS (ESI) m/z: 307.1 [M+H]$^+$.

Example 80. Preparation of (3-phenylazetidin-1-yl)(5-(pyrimidin-4-yl)isoxazol-3-yl)methanone (257)

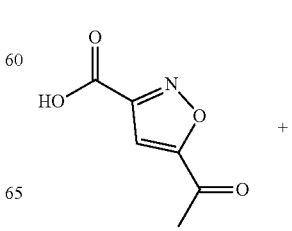

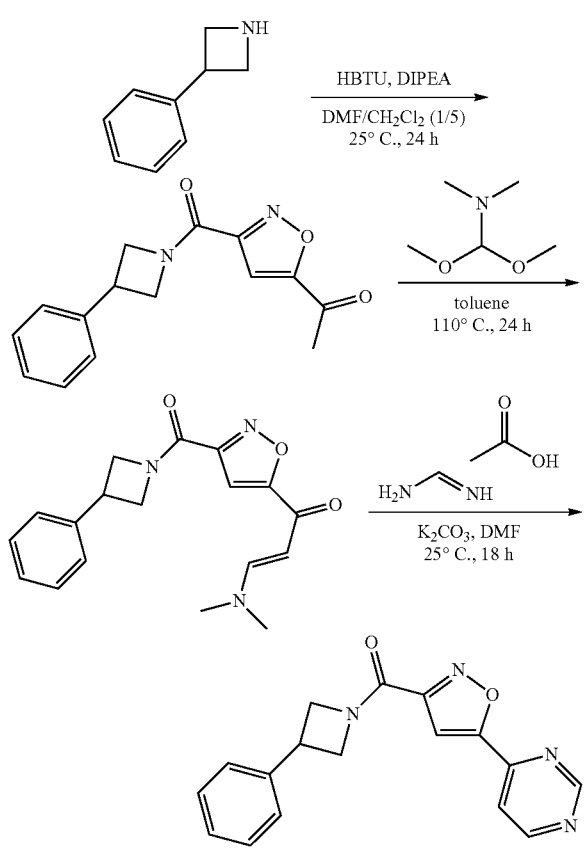

Step 1: Preparation of 1-(3-(3-phenylazetidine-1-carbonyl)isoxazol-5-yl)ethan-1-one

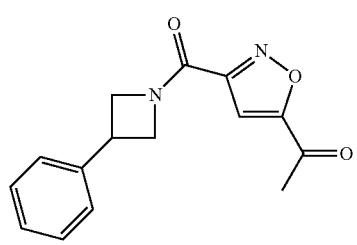 [SMILES: CC(=O)c1cc(C(=O)N2CC(c3ccccc3)C2)no1]

To a suspension of 5-acetyl-1,2-oxazole-3-carboxylic acid (50 mg, 0.322 mmol), N,N,N',N'-tetramethyl-O-(1H-benzotriazol-1-yl)uronium hexafluorophosphate (170 mg, 0.448 mmol) and diisopropylethylamine (124 mg, 0.965 mmol) in N,N-dimethylformamide/methylene chloride (1/5, 1.2 mL) was added 3-phenylazetidine hydrochloride salt (65.4 mg, 0.386 mmol) in one portion. The reaction mixture was stirred at room temperature for 24 h. The reaction was poured into ethyl acetate (20 mL) and water (2 mL). The aqueous phase was removed and the organic layer was concentrated in vacuo. The crude material was purified by column chromatography (ISCO, 4 g silica, eluting with 0% to 50% ethyl acetates in hexanes) to afford 1-(3-(3-phenylazetidine-1-carbonyl)isoxazol-5-yl)ethan-1-one (20 mg, 0.0739 mmol, 23%). $^1$H NMR (300 MHz, Dimethylsulfoxide-$d_6$) δ 7.65 (s, 1H), 7.45-7.34 (m, 4H), 7.32-7.25 (m, 1H), 4.95-4.82 (m, 1H), 4.56-4.43 (m, 2H), 4.17-3.93 (m, 2H), 2.60 (s, 3H); LCMS (ESI) m/z: 271.0 [M+H]$^+$.

Step 2: Preparation of (E)-3-(dimethylamino)-1-(3-(3-phenylazetidine-1-carbonyl)isoxazol-5-yl)prop-2-en-1-one

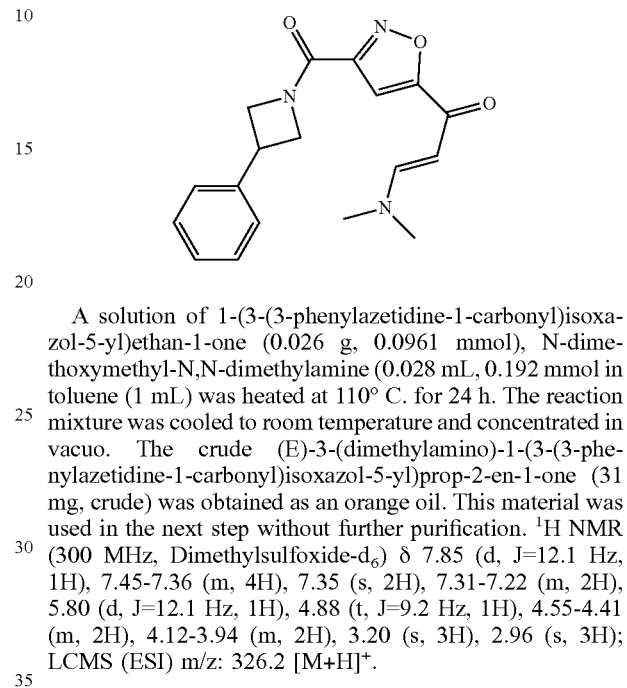

A solution of 1-(3-(3-phenylazetidine-1-carbonyl)isoxazol-5-yl)ethan-1-one (0.026 g, 0.0961 mmol), N-dimethoxymethyl-N,N-dimethylamine (0.028 mL, 0.192 mmol in toluene (1 mL) was heated at 110° C. for 24 h. The reaction mixture was cooled to room temperature and concentrated in vacuo. The crude (E)-3-(dimethylamino)-1-(3-(3-phenylazetidine-1-carbonyl)isoxazol-5-yl)prop-2-en-1-one (31 mg, crude) was obtained as an orange oil. This material was used in the next step without further purification. $^1$H NMR (300 MHz, Dimethylsulfoxide-$d_6$) δ 7.85 (d, J=12.1 Hz, 1H), 7.45-7.36 (m, 4H), 7.35 (s, 2H), 7.31-7.22 (m, 2H), 5.80 (d, J=12.1 Hz, 1H), 4.88 (t, J=9.2 Hz, 1H), 4.55-4.41 (m, 2H), 4.12-3.94 (m, 2H), 3.20 (s, 3H), 2.96 (s, 3H); LCMS (ESI) m/z: 326.2 [M+H]$^+$.

Step 3: Preparation of (3-phenylazetidin-1-yl)(5-(pyrimidin-4-yl)isoxazol-3-yl)methanone

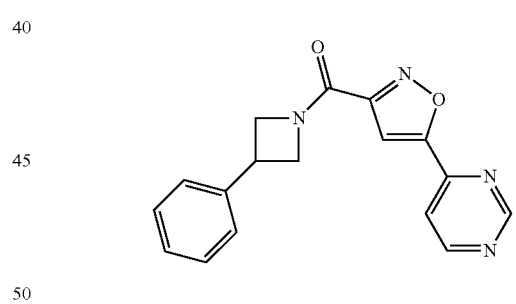

A mixture of (E)-3-(dimethylamino)-1-(3-(3-phenylazetidine-1-carbonyl)isoxazol-5-yl)prop-2-en-1-one (30.5 mg, 0.0952 mmol), formamidine acetate (30 mg, 0.285 mmol), potassium carbonate (39 mg, 0.285 mmol) in N,N-dimethylformamide (0.5 mL) was heated at 100° C. for 8 h. The reaction mixture was cooled to room temperature, diluted with ethyl acetate (10 mL), filtered and concentrated in vacuo. The crude residue was suspended in hot heptanes/ethyl acetate (1/1, 2-3 mL) and let stand at room temperature for 24 h. Yellow crystals were filtered to give (3-phenylazetidin-1-yl)(5-(pyrimidin-4-yl)isoxazol-3-yl)methanone (10 mg, 0.031 mmol, 33%). $^1$H NMR (300 MHz, Dimethylsulfoxide-$d_6$) δ 9.38 (d, J=1.4 Hz, 1H), 9.07 (d, J=5.3 Hz, 1H), 8.16 (dd, J=5.2, 1.5 Hz, 1H), 7.69 (s, 1H), 7.50-7.32 (m, 4H), 7.32-7.21 (m, 1H), 4.92 (t, J=9.2 Hz, 1H), 4.59-4.46 (m, 2H), 4.15-3.93 (m, 2H); LCMS (ESI) m/z: 307.2 [M+H]$^+$.

Example 81. Preparation of (3-benzylazetidin-1-yl)(5-(pyrimidin-4-yl)isoxazol-3-yl)methanone (258)

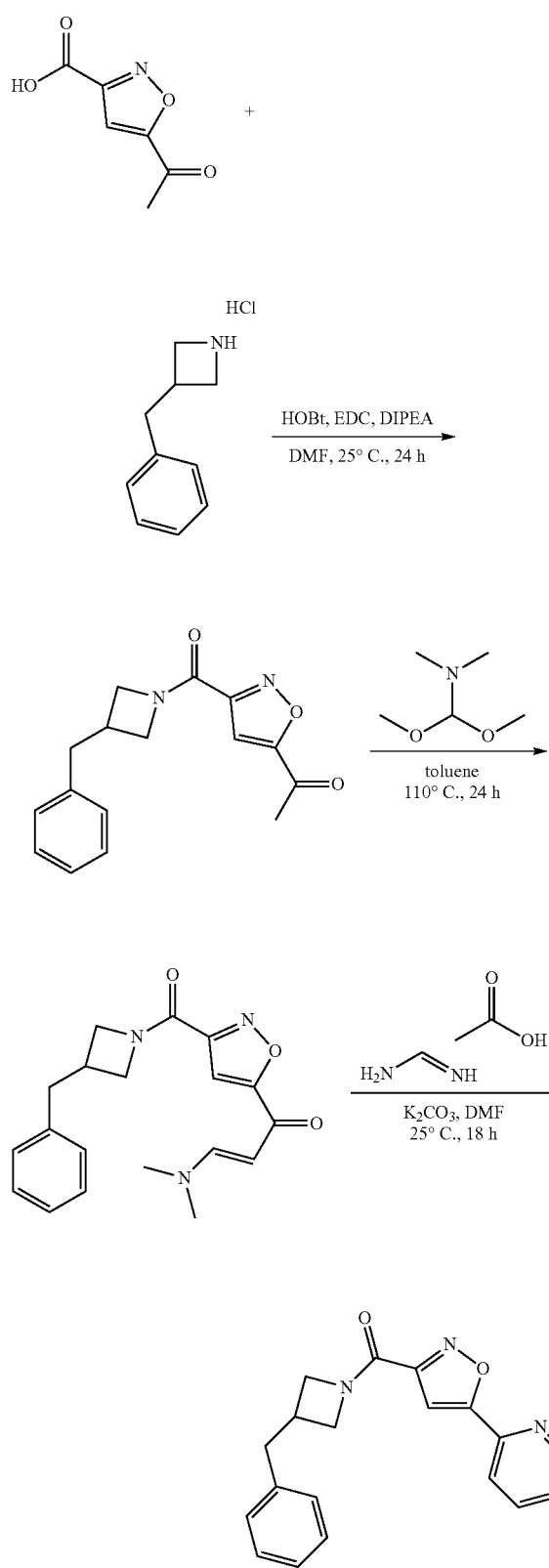

Step 1: Preparation of 1-[3-(3-benzylazetidine-1-carbonyl)-1,2-oxazol-5-yl]ethan-1-one

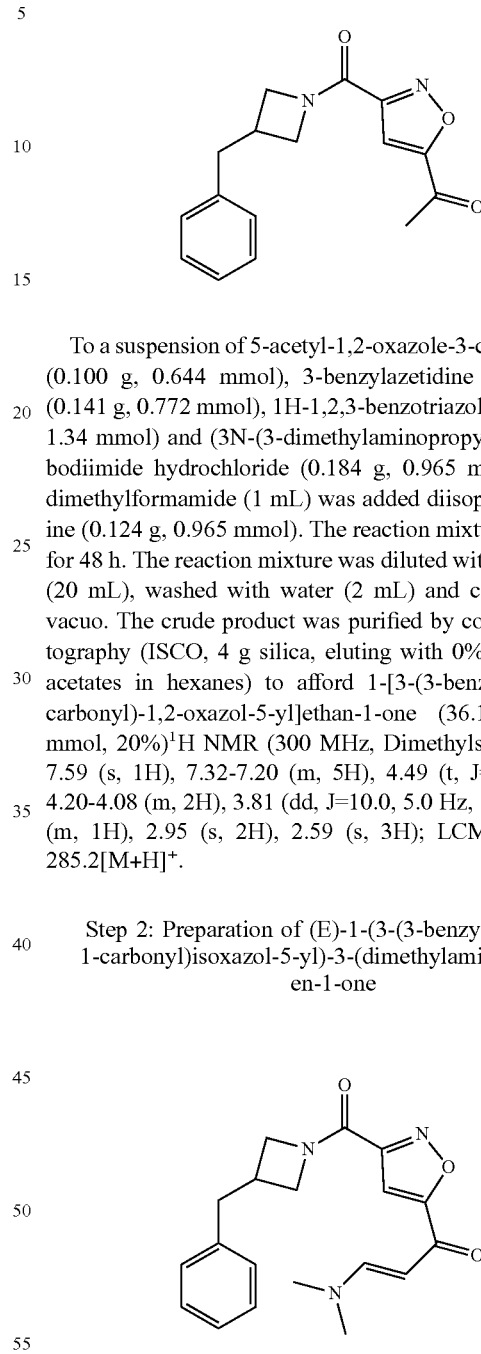

To a suspension of 5-acetyl-1,2-oxazole-3-carboxylic acid (0.100 g, 0.644 mmol), 3-benzylazetidine hydrochloride (0.141 g, 0.772 mmol), 1H-1,2,3-benzotriazol-1-ol (0.182 g, 1.34 mmol) and (3N-(3-dimethylaminopropyl)-N'-ethylcarbodiimide hydrochloride (0.184 g, 0.965 mmol) in N,N-dimethylformamide (1 mL) was added diisopropylethylamine (0.124 g, 0.965 mmol). The reaction mixture was stirred for 48 h. The reaction mixture was diluted with ethyl acetate (20 mL), washed with water (2 mL) and concentrated in vacuo. The crude product was purified by column chromatography (ISCO, 4 g silica, eluting with 0% to 50% ethyl acetates in hexanes) to afford 1-[3-(3-benzylazetidine-1-carbonyl)-1,2-oxazol-5-yl]ethan-1-one (36.1 mg, 0.126 mmol, 20%) $^1$H NMR (300 MHz, Dimethylsulfoxide-d$_6$) δ 7.59 (s, 1H), 7.32-7.20 (m, 5H), 4.49 (t, J=8.6 Hz, 1H), 4.20-4.08 (m, 2H), 3.81 (dd, J=10.0, 5.0 Hz, 1H), 3.01-2.91 (m, 1H), 2.95 (s, 2H), 2.59 (s, 3H); LCMS (ESI) m/z: 285.2[M+H]$^+$.

Step 2: Preparation of (E)-1-(3-(3-benzylazetidine-1-carbonyl)isoxazol-5-yl)-3-(dimethylamino)prop-2-en-1-one A solution of 1-[3-(3-benzylazetidine-1-carbonyl)-1,2-oxazol-5-yl]ethan-1-one (0.032 g, 0.112 mmol), N-dimethoxymethyl-N,N-dimethylamine (0.030 mL, 0.224 mmol) in toluene (1 mL) was heated at 110° C. for 24 h. The reaction mixture was cooled to room temperature and concentrated in vacuo. The crude (E)-1-(3-(3-benzylazetidine-1-carbonyl)isoxazol-5-yl)-3-(dimethylamino)prop-2-en-1-one (30 mg, 0.0886 mmol) was obtained as a red oil. This material was used in the next step without further purification.

Step 3: Preparation of (3-benzylazetidin-1-yl)(5-(pyrimidin-4-yl)isoxazol-3-yl)methanone

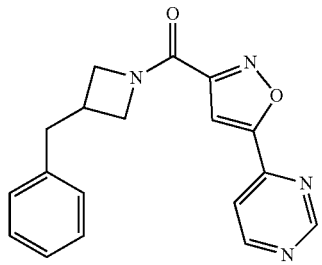 [SMILES: O=C(c1cc(-c2ccncn2)on1)N1CC(Cc2ccccc2)C1]

A mixture of (E)-1-(3-(3-benzylazetidine-1-carbonyl)isoxazol-5-yl)-3-(dimethylamino)prop-2-en-1-one (29 mg, 0.0854 mmol), formamidine acetate (26.6 mg, 0.256 mmol), potassium carbonate (35.3 mg, 0.256 mmol) in N,N-dimethylformamide (0.5 mL) was heated at 100° C. for 8 h. The reaction mixture was cooled to room temperature, diluted with ethyl acetate (10 mL), filtered and concentrated in vacuo. The crude residue was purified by column chromatography (ISCO, 4 g silica, eluting with 0% to 50% ethyl acetates in hexanes) to afford (3-benzylazetidin-1-yl)(5-(pyrimidin-4-yl)isoxazol-3-yl)methanone (15 mg, 0.0468 mmol, 55%) as a off white solid. $^1$H NMR (300 MHz, Dimethylsulfoxide-d$_6$) δ 9.37 (d, J=1.4 Hz, 1H), 9.06 (d, J=5.2 Hz, 1H), 8.14 (dd, J=5.2, 1.5 Hz, 1H), 7.64 (s, 1H), 7.39-7.15 (m, 5H), 4.52 (t, J=8.6 Hz, 1H), 4.27-4.09 (m, 2H), 3.83 (dd, J=10.2, 4.9 Hz, 1H), 3.03-2.93 (m, 2H), 2.96 (s, 2H); LCMS (ESI) m/z: 321.1 [M+H]$^+$.

Example 82. Preparation of N-methyl-4-(3-(3-phenylazetidine-1-carbonyl)isoxazol-5-yl)benzamide (231)

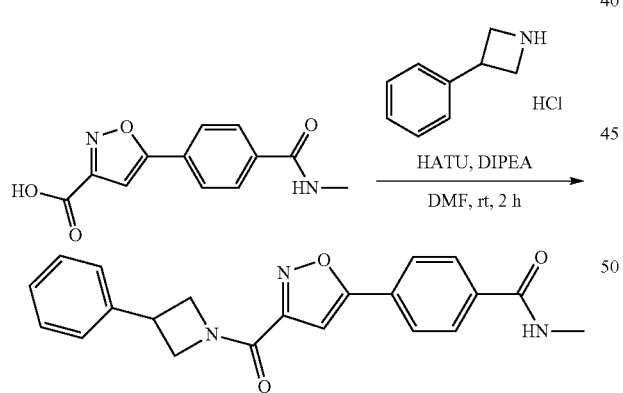

The synthesis of N-methyl-4-(3-(3-phenylazetidine-1-carbonyl)isoxazol-5-yl)benzamide was carried out following the same procedure as in Example 24. Compound N-methyl-4-(3-(3-phenylazetidine-1-carbonyl)isoxazol-5-yl)benzamide (25.9 mg, 0.07 mmol, 22%) was obtained as a white solid. $^1$H NMR (500 MHz, Dimethylsulfoxide-d6) δ 8.61 (d, J=9.0 Hz, 4.0 Hz, 1H), 8.05 (d, J=8.5 Hz, 2H), 7.99 (d, J=8.5 Hz, 2H), 7.52 (s, 1H), 7.44-7.27 (m, 5H), 4.92 (t, J=9.0 Hz, 1H), 4.55-4.48 (m, 2H), 4.12-4.08 (m, 1H), 4.04-3.98 (m, 1H), 2.81 (d, J=4.5 Hz, 3H); LCMS (ESI) m/z: 362.2 [M+H]$^+$.

Example 83. Preparation of 5-(3,4-dimethoxyphenyl)isoxazol-3-yl)(3-(3-fluorophenyl)azetidin-1-yl)methanone (236)

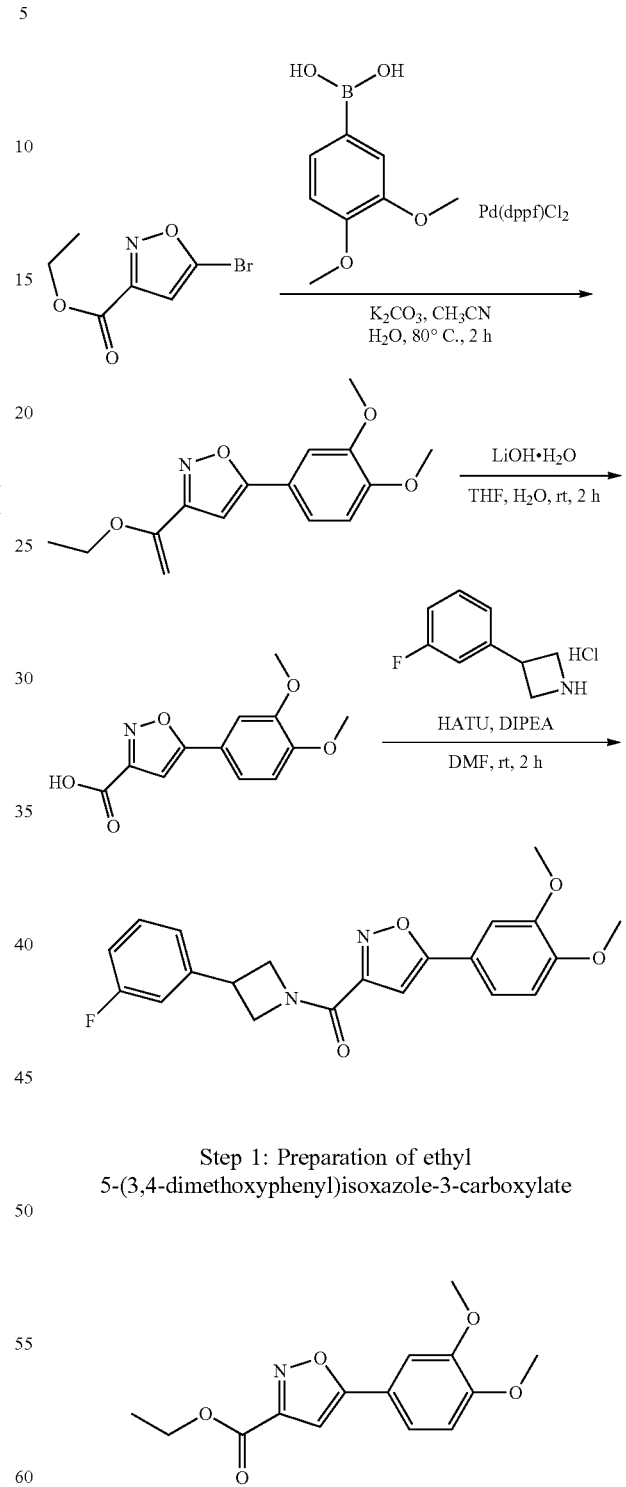

Step 1: Preparation of ethyl 5-(3,4-dimethoxyphenyl)isoxazole-3-carboxylate

The synthesis of ethyl 5-(3,4-dimethoxyphenyl)isoxazole-3-carboxylate was carried out following the same procedure as Example 24. Compound ethyl 5-(3,4-dimethoxyphenyl)isoxazole-3-carboxylate (230 mg, 0.83 mmol, 46%) as a yellow solid. LCMS (ESI) m/z: 277/1 [M+H]$^+$.

Step 2: Preparation of 5-(3,4-dimethoxyphenyl)isoxazole-3-carboxylic Acid

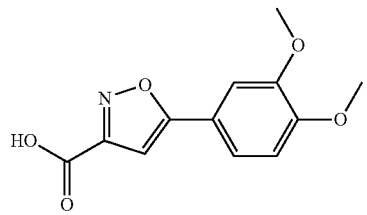 [SMILES: COc1ccc(-c2cc(C(=O)O)no2)cc1OC]

The synthesis of 5-(3,4-dimethoxyphenyl)isoxazole-3-carboxylic acid was carried out following the same procedure as Example 24. Compound 5-(3,4-dimethoxyphenyl)isoxazole-3-carboxylic acid (90 mg, 0.36 mmol, 43%) as a white solid. LCMS (ESI) m/z: 250.2 [M+H]$^+$.

Step 3: Preparation of (5-(3,4-dimethoxyphenyl)isoxazol-3-yl)(3-(3-fluorophenyl)azetidin-1-yl)methanone

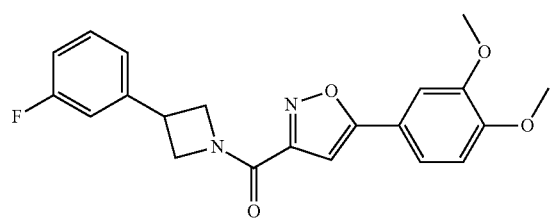 [SMILES: COc1ccc(-c2cc(C(=O)N3CC(c4cccc(F)c4)C3)no2)cc1OC]

The synthesis of (5-(3,4-dimethoxyphenyl)isoxazol-3-yl)(3-(3-fluorophenyl)azetidin-1-yl)methanone was carried out following the same procedure as Example 24. Compound (5-(3,4-dimethoxyphenyl)isoxazol-3-yl)(3-(3-fluorophenyl)azetidin-1-yl)methanone (60.6 mg, 0.16 mmol, 44%) as a white solid. $^1$H NMR (500 MHz, Dimethylsulfoxide-d$_6$) δ 7.53-7.50 (m, 2H), 7.44-7.40 (m, 1H), 7.34-7.26 (m, 3H), 7.13-7.09 (m, 2H), 4.90 (t, J=9.0 Hz, 1H), 4.52-4.47 (m, 2H), 4.12-4.03 (m, 2H), 3.85 (s, 3H), 3.83 (s, 3H); LCMS (ESI) m/z: 383.0 [M+H]$^+$.

Example 84. Preparation of (5-(2-methyl-2H-indazol-6-yl)isoxazol-3-yl)(3-phenylazetidin-1-yl)methanone (235)

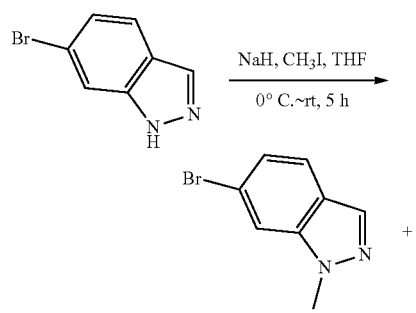

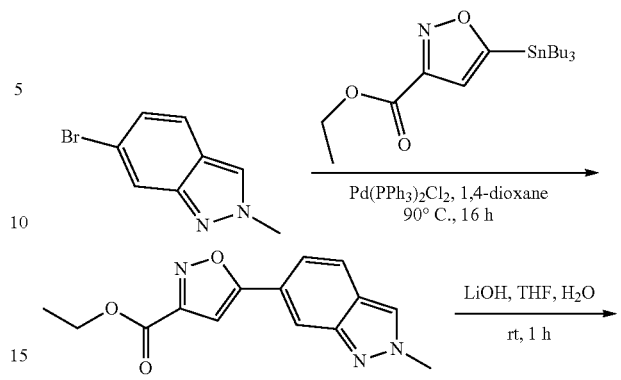

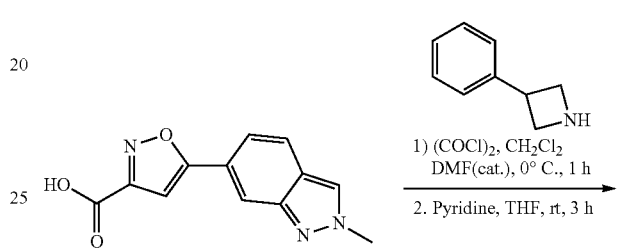

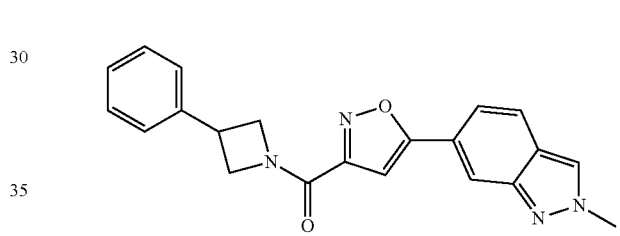

Step 1: Preparation of 6-bromo-2-methyl-2H-indazole

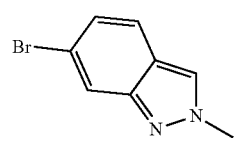

To a solution of 6-bromo-1H-indazole (6.48 g, 32.9 mmol) in anhydrous tetrahydrofuran (80 mL) at 0° C. was added sodium hydride (60% in mineral oil, 1.39 g, 34.5 mmol). The reaction mixture was warmed to room temperature for 2 h before iodomethane (18.68 g, 131.6 mmol) was added. The reaction mixture was stirred at room temperature for 3 h. The reaction mixture was diluted with water (300 mL) and extracted with ethyl acetate (100 mL×3). The combined organic layers were washed with brine, dried over sodium sulfate, filtered, and concentrated in vacuo. The crude residue was purified by column chromatography (silica, petroleum ether/ethyl acetate=4/1) to give 6-bromo-2-methyl-2H-indazole (3.4 g, 16.11 mmol, 49%) as a yellow oil. LCMS (ESI) m/z: 211.1 [M+H]$^+$.

Step 2: Preparation of ethyl 5-(2-methyl-2H-indazol-6-yl)isoxazole-3-carboxylate

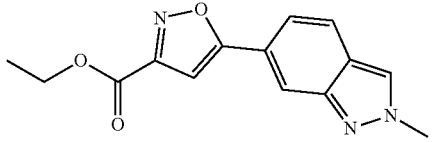 [SMILES: CCOC(=O)c1cc(-c2ccc3cn(C)nc3c2)on1]

To a solution of 6-bromo-2-methyl-2H-indazole (0.600 g, 2.84 mmol) in 1,4-dioxane (10 mL) at room temperature was added ethyl 5-(tributylstannyl)isoxazole-3-carboxylate (1.35 g, 3.13 mmol) and bis(triphenylphosphine)palladium (II) dichloride (0.199 g, 0.29 mmol) under nitrogen. The reaction mixture was heated at 90° C. for 16 h. The reaction mixture was cooled to room temperature and diluted with water (100 mL) and extracted with ethyl acetate (50 mL×3). The combined organic layers were washed with brine, dried over sodium sulfate, filtered and concentrated in vacuo. The crude residue was purified by column chromatography (silica, petroleum ether/ethyl acetate=5/1) to afford ethyl 5-(2-methyl-2H-indazol-6-yl)isoxazole-3-carboxylate (620 mg, 2.29 mmol, 81%) as a yellow solid. LCMS (ESI) m/z: 272.1 [M+H]$^+$.

Step 3: Preparation of ethyl 5-(2-methyl-2H-indazol-6-yl)isoxazole-3-carboxylic Acid

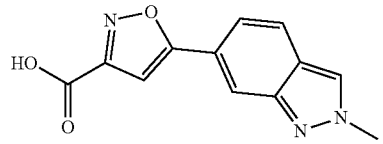 [SMILES: Cn1cc2ccc(-c3cc(C(=O)O)no3)cc2n1]

To a solution of 5-(2-methyl-2H-indazol-6-yl)isoxazole-3-carboxylate (0.570 g, 2.10 mmol) in tetrahydrofuran (5 mL) at room temperature, was added lithium hydroxide hydrate (0.441 g, 10.5 mmol) in water (5 mL). The reaction mixture was stirred at room temperature for 1 h then the aqueous layer was adjusted to pH=3-4 with aqueous 2N hydrogen chloride. The aqueous layer was extracted with ethyl acetate (50 mL×3). The combined organic layers were washed with brine, dried over sodium sulfate, filtered and concentrated to afford 5-(2-methyl-2H-indazol-6-yl)isoxazole-3-carboxylic acid (0.220 g, 0.91 mmol, 43%) yellow solid. LCMS (ESI) m/z: 244.1 [M+H]$^+$.

Step 4: Preparation of 5(5-(2-methyl-2H-indazol-6-yl)isoxazol-3-yl)(3-phenylazetidin-1-yl)methanone

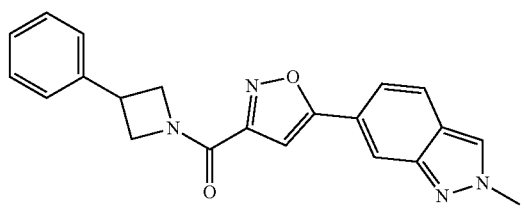 [SMILES: Cn1cc2ccc(-c3cc(C(=O)N4CC(c5ccccc5)C4)no3)cc2n1]

To a solution of 5-(2-methyl-2H-indazol-6-yl)isoxazole-3-carboxylic acid (0.120 g, 0.90 mmol) in anhydrous dichloromethane (15 mL) at 0° C. was added N,N'-dimethylformamide (7 mg, 0.09 mmol) and oxalyl chloride (0.229 g, 1.80 mmol). The mixture was stirred at room temperature for 1 h, before the volatiles were removed in vacuo. The residue was dissolved in anhydrous tetrahydrofuran (6 mL) and added to a solution of 3-phenylazetidine hydrochloride (263 mg, 1.08 mmol) in anhydrous tetrahydrofuran (6 mL). The reaction mixture was stirred at room temperature for 3 h. The reaction mixture was diluted with water (100 mL) and extracted with dichloromethane (50 mL×3). The combined organic layers were washed with brine, dried over sodium sulfate, filtered and concentrated in vacuo. The crude sample was dissolved in minimum amount of N,N-dimethylformamide and purified via prep-HPLC (Boston C18 21×250 mm 10 μm column; acetonitrile/0.01% aqueous trifluoroacetic acid) to give 5(5-(2-methyl-2H-indazol-6-yl)isoxazol-3-yl) (3-phenylazetidin-1-yl)methanone (60 mg, 0.17 mmol, 19%) as yellow solid. $^1$H NMR (500 MHz, Dimethylsulfoxide-d$_6$) δ 8.34 (s, 1H), 8.15 (s, 1H), 7.92 (d, J=8.4 Hz, 1H), 7.70 (d, J=8.4 Hz, 1H), 7.51 (s, 1H), 7.44 (d, J=7.4 Hz, 2H), 7.39 (t, J=7.6 Hz, 2H), 7.29 (t, J=7.2 Hz, 1H), 4.94 (t, J=9.2 Hz, 1H), 4.52 (dt, J=9.6, 7.9 Hz, 2H), 4.16-4.09 (m, 4H), 4.07-3.97 (m, 1H); LCMS (ESI) m/z: 359.2 [M+H]$^+$.

Example 85. (5-(1-methyl-1H-indazol-6-yl)isoxazol-3-yl)(3-phenylazetidin-1-yl)methanone (232)

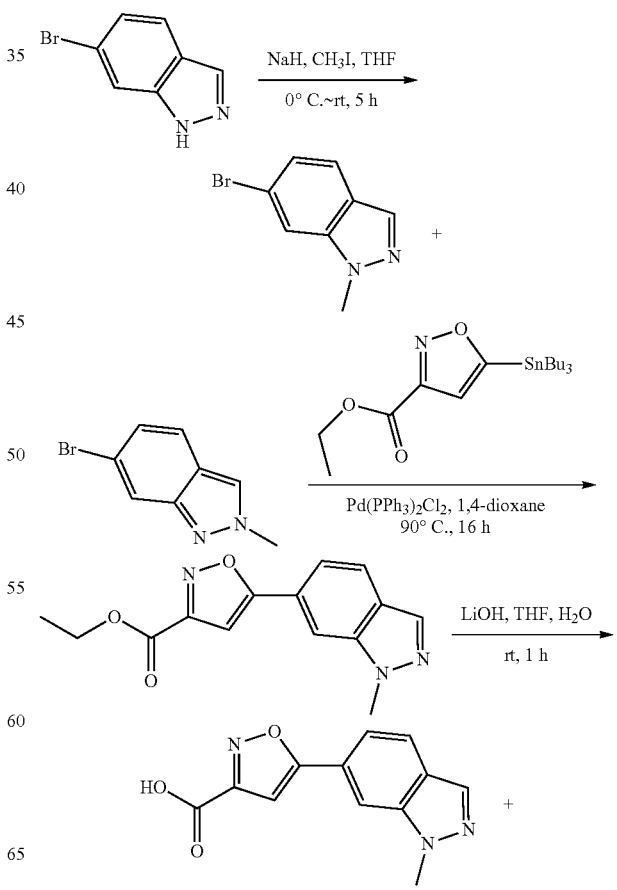

-continued

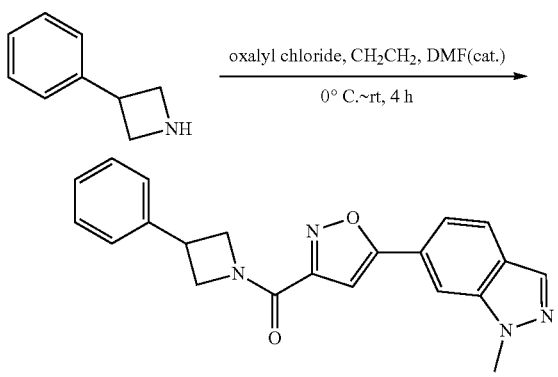

Step 1: Preparation of 6-Bromo-1-methyl-1H-indazole

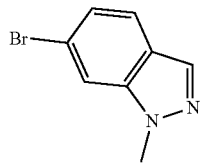

To a solution of 6-bromo-1H-indazole (6.48 g, 32.9 mmol) in anhydrous tetrahydrofuran (80 mL) at 0° C. was added sodium hydride (60% in mineral oil, 1.39 g, 34.5 mmol). The reaction mixture was warmed to room temperature for 2 h, then iodomethane (18.68 g, 132 mmol) was added and reaction mixture stirred at room temperature for 3 h. The reaction mixture was diluted with water (300 mL) and extracted with ethyl acetate (100 mL×3). The combined organic layers were washed with brine, dried over sodium sulfate, filtered, concentrated in vacuo. The crude residue was purified by column chromatography (silica, petroleum ether/ethyl acetate=4/1) to afford 6-bromo-1-methyl-1H-indazole (3.2 g, 15.2 mmol, 46%) as a yellow oil. LCMS (ESI) m/z: 211.1 [M+H]$^+$.

Step 2: Preparation of ethyl 5-(1-methyl-1H-indazol-6-yl)isoxazole-3-carboxylate

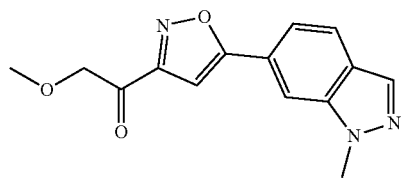 [SMILES: COCC(=O)c1cc(-c2ccc3cnn(C)c3c2)on1]

The synthesis of ethyl 5-(1-methyl-1H-indazol-6-yl)isoxazole-3-carboxylate was carried out following the same procedure as Example 84. Compound 5-(1-methyl-1H-indazol-6-yl)isoxazole-3-carboxylate (0.680 g, 2.51 mmol, 88% yield) was obtained as product. LCMS (ESI) m/z: 272.1 [M+H]$^+$.

Step 3: Preparation of 5-(1-methyl-1H-indazol-6-yl)isoxazole-3-carboxylic Acid

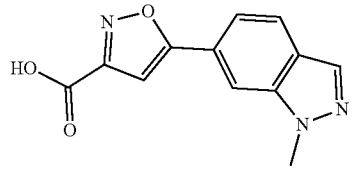 [SMILES: Cn1ncc2ccc(-c3cc(C(=O)O)no3)cc21]

The synthesis of 5-(1-methyl-1H-indazol-6-yl)isoxazole-3-carboxylic acid was carried out following the same procedure as Example 84. Compound 5-(1-methyl-1H-indazol-6-yl)isoxazole-3-carboxylic acid (0.300 g, 1.23 mmol, 49%) as a yellow solid. LCMS (ESI) m/z: 244.1 [M+H]$^+$.

Step 4: Preparation of ethyl (5-(1-methyl-1H-indazol-6-yl)isoxazol-3-yl)(3-phenylazetidin-1-yl)methanone

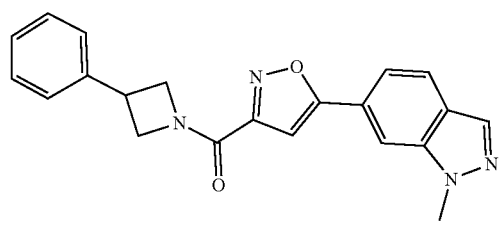 [SMILES: Cn1ncc2ccc(-c3cc(C(=O)N4CC(c5ccccc5)C4)no3)cc21]

The synthesis of ethyl (5-(1-methyl-1H-indazol-6-yl)isoxazol-3-yl)(3-phenylazetidin-1-yl)methanone was carried out following the same procedure as Example 84. Compound ethyl (5-(1-methyl-1H-indazol-6-yl)isoxazol-3-yl)(3-phenylazetidin-1-yl)methanone (0.100 g, 0.28 mmol, 45%) as yellow solid. $^1$H NMR (500 MHz, Dimethylsulfoxide-d$_6$) δ 8.44 (s, 1H), 8.24 (s, 1H), 7.87 (d, J=8.7 Hz, 1H), 7.73-7.47 (m, 1H), 7.44 (d, J=7.1 Hz, 3H), 7.39 (t, J=7.6 Hz, 2H), 7.29 (t, J=7.2 Hz, 1H), 4.93 (t, J=9.2 Hz, 1H), 4.52 (dt, J=9.7, 7.8 Hz, 2H), 4.22 (s, 3H), 4.10 (dd, J=9.9, 6.4 Hz, 1H), 4.05-3.97 (m, 1H); LCMS (ESI) m/z: 359.2 [M+H]$^+$.

Example 86. Preparation of (3-phenylazetidin-1-yl)(5-(pyridin-2-yl)isoxazol-3-yl)methanone (233)

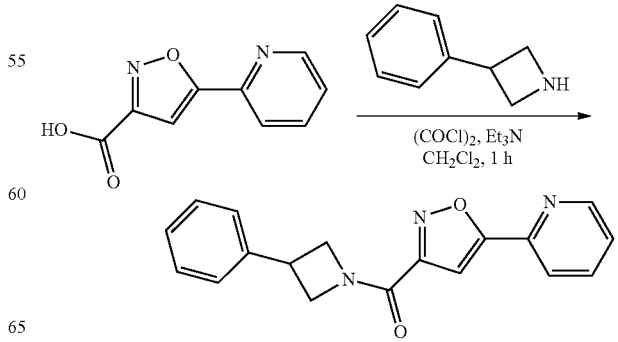

To a solution of 5-(pyridin-2-yl)isoxazole-3-carboxylic acid (0.150 g, 0.79 mmol) in dichloromethane (2 mL) at 20° C. was added oxalyl chloride (2 mL). The reaction mixture was stirred at room temperature for 0.5 h before volatiles were removed in vacuo. The residue was dissolved in dichloromethane (2 mL) and added to a mixture of 3-phenylazetidine hydrochloride (0.137 g, 1.03 mmol) and triethylamine (0.239 g, 2.37 mmol) in dichloromethane (5 mL) dropwise. The reaction mixture was stirred for another 0.5 h and concentrated in vacuo. The crude sample was dissolved in minimum amount of N,N-dimethylformamide and purified via prep-HPLC (Boston C18 21×250 mm 10 am column; acetonitrile/0.01% aqueous trifluoroacetic acid) to give (3-phenylazetidin-1-yl)(5-(pyridin-2-yl)isoxazol-3-yl)methanone as a white solid (72.8 mg, 0.237 mmol, 30%). $^1$H NMR (400 MHz, Dimethylsulfoxide-$d_6$) δ 8.76 (s, 1H), 8.03-8.08 (m, 2H), 7.55-7.57 (m, 1H), 7.37-7.44 (m, 5H), 7.28-7.30 (m, 1H), 4.90-4.92 (m, 1H), 4.48-4.54 (m, 2H), 4.09-4.12 (m, 1H), 4.02 (m, 1H); LCMS (ESI) m/z: 306.1 [M+H]$^+$.

Example 87. Preparation of 3-phenylazetidin-1-yl) (5-(pyridin-3-yl)isoxazol-3-yl)methanone, trifluoroacetic Acid (234)

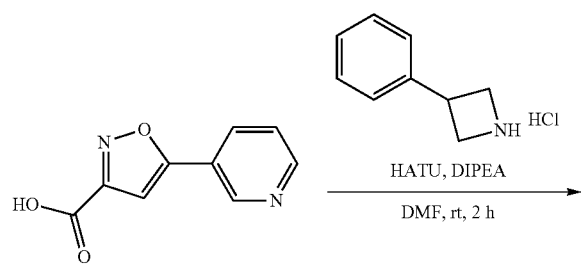

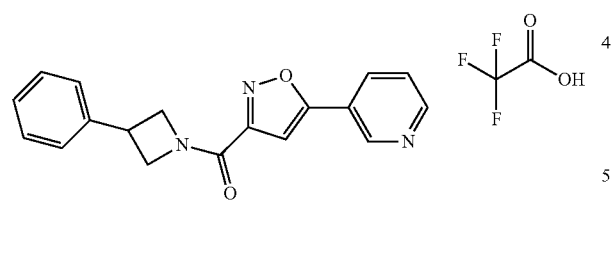

The synthesis of (3-phenylazetidin-1-yl)(5-(pyridin-3-yl) isoxazol-3-yl)methanone, trifluoroacetic acid was carried out following the same procedure as Example 24. Compound (3-phenylazetidin-1-yl)(5-(pyridin-3-yl)isoxazol-3-yl)methanone, trifluoroacetic acid (29.4 mg, 0.07 mmol, 33%) as a white solid. $^1$H NMR (500 MHz, Dimethylsulfoxide-$d_6$) δ 9.20 (d, J=2.0 Hz, 1H), 8.75-8.73 (m, 1H), 8.39 (d, J=8.5 Hz, 1H), 7.66-7.63 (m, 1H), 7.60 (s, 1H), 7.44-7.40 (m, 2H), 7.38-7.37 (m, 2H), 7.30-7.27 (m, 1H), 4.92 (d, J=9.0 Hz, 1H), 4.55-4.48 (m, 2H), 4.12-4.03 (m, 1H), 4.02-3.99 (m, 1H); LCMS (ESI) m/z: 306.1 [M+H]$^+$.

Example 88. Preparation of (3-phenylazetidin-1-yl) (5-(pyridin-4-yl)isoxazol-3-yl)methanone, trifluoroacetic Acid (229)

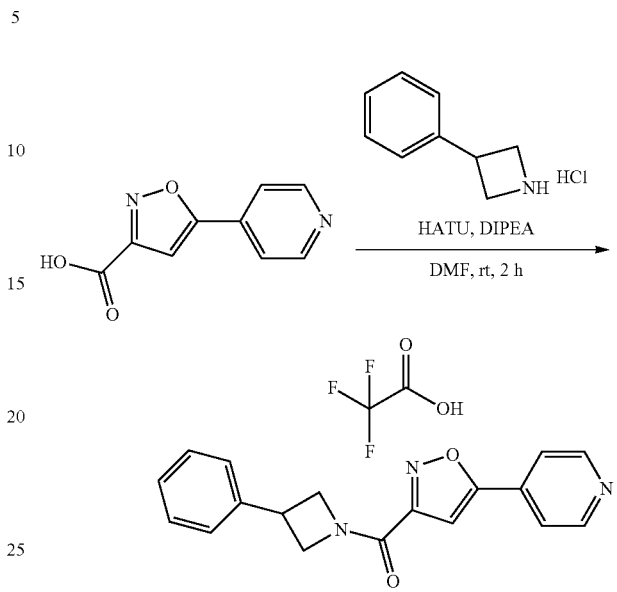

The synthesis of (3-phenylazetidin-1-yl)(5-(pyridin-4-yl) isoxazol-3-yl)methanone, trifluoroacetic acid was carried out following the same procedure as Example 24. Compound (3-phenylazetidin-1-yl)(5-(pyridin-4-yl)isoxazol-3-yl)methanone, trifluoroacetic acid (8.0 mg, 0.02 mmol, 10%) as a white solid. $^1$H NMR (500 MHz, Dimethylsulfoxide-$d_6$) δ 8.82-8.80 (m, 2H), 7.98-7.97 (m, 2H), 7.75 (s, 1H), 7.44-7.37 (m, 4H), 7.28 (t, J=7.5 Hz, 1H), 4.92 (t, J=9.0 Hz, 1H), 4.56-4.48 (m, 2H), 4.12-4.05 (m, 1H), 4.04-4.00 (m, 1H); LCMS (ESI) m/z: 306.1 [M+H]$^+$.

Example 89. Preparation of (5-(5-chloropyridin-2-yl)isoxazol-3-yl)(3-phenylazetidin-1-yl)methanone (241)

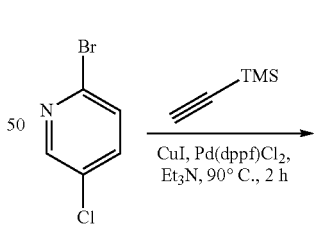

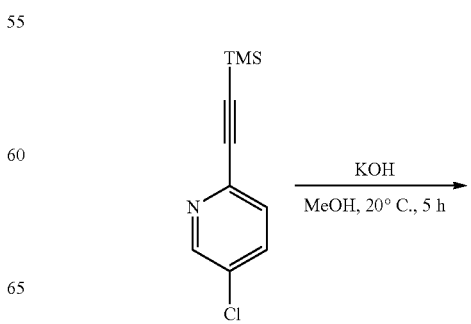

393
-continued

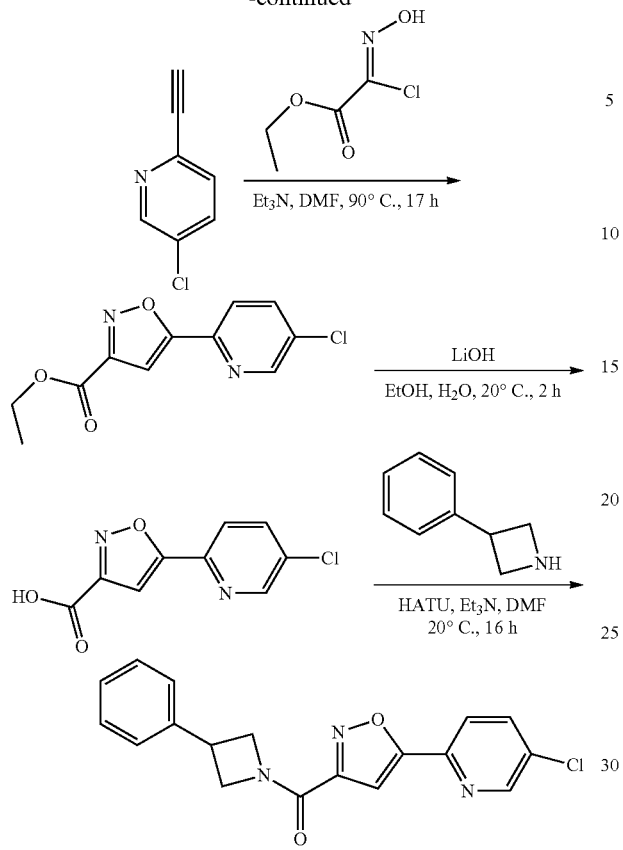

Step 1: Preparation of
5-chloro-2-((trimethylsilyl)ethynyl)pyridine

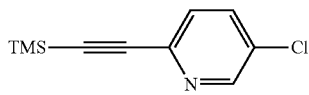

A mixture of 2-bromo-5-chloropyridine (3.5 g, 18.2 mmol), ethynyltrimethylsilane (2.14 g, 21.9 mmol), [1,1'-bis(diphenylphosphino)ferrocene]dichloropalladium(II) (1.33 g, 1.82 mmol) and copper(I) iodide (0.68 g, 3.65 mmol) in triethylamine (50 mL) was heated at 90° C. for 2 h. The mixture was diluted with brine (100 mL) and extracted with ethyl acetate (100 mL×2). The combined organic layers were dried over sodium sulfate, filtered and concentrated in vacuo. The crude residue was purified by column chromatography (silica, petroleum ether/ethyl acetate=20/1) to give 5-chloro-2-((trimethylsilyl)ethynyl) pyridine (1.4 g, 6.7 mmol, 37%) as a yellow oil. LCMS (ESI) m/z: 210.1 [M+H]$^+$.

Step 2: Preparation of 5-chloro-2-ethynylpyridine

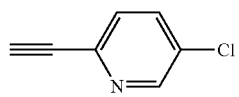

394

A mixture of 5-chloro-2-((trimethylsilyl)ethynyl)pyridine (1.4 g, 6.7 mmol) and potassium hydroxide (0.38 g, 6.7 mmol) in methanol (50 mL) was stirred at 20° C. for 5 h. The reaction mixture was diluted with brine (100 mL) and extracted with ethyl acetate (100 mL×2). The combined organic layers were dried over sodium sulfate, filtered and concentrated in vacuo. The crude residue was purified by column chromatography (silica, petroleum ether/ethyl acetate=20/1) to give 5-chloro-2-ethynylpyridine (0.75 g, 5.5 mmol, 82%) as a yellow oil. LCMS (ESI) m/z: 138.0 [M+H]$^+$.

Step 3: Preparation of ethyl
5-(5-chloropyridin-2-yl)isoxazole-3-carboxylate

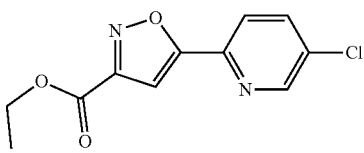 [SMILES: CCOC(=O)c1cc(-c2ccc(Cl)cn2)on1]

Synthesis of ethyl 5-(5-chloropyridin-2-yl)isoxazole-3-carboxylate was carried out following the same procedure as Example 89. Compound ethyl 5-(5-chloropyridin-2-yl) isoxazole-3-carboxylate (290 mg, 1.15 mmol, 21%) was obtained as a gray oil. LCMS (ESI) m/z: 253.1 [M+H]$^+$.

Step 4: Preparation of
5-(5-chloropyridin-2-yl)isoxazole-3-carboxylic Acid

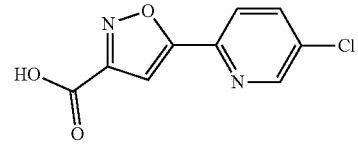 [SMILES: O=C(O)c1cc(-c2ccc(Cl)cn2)on1]

A mixture of ethyl 5-(5-chloropyridin-2-yl)isoxazole-3-carboxylate (0.29 g, 1.15 mmol) and aqueous lithium hydroxide (2.3 mL, 4.6 mmol, 2 M) in ethanol (2.3 mL) was stirred at 20° C. for 2 h. The reaction mixture was extracted with ethyl acetate (20 mL) and concentrated in vacuo to give 1-(5-fluoro-2-(trifluoromethyl)benzyl)-1H-pyrazole-4-carboxylic acid (0.200 g, 0.89 mmol, 78%) as a gray solid. LCMS (ESI) m/z: 225.1 [M+H]$^+$.

Step 5: Preparation of (5-(5-chloropyridin-2-yl)
isoxazol-3-yl)(3-phenylazetidin-1-yl)methanone

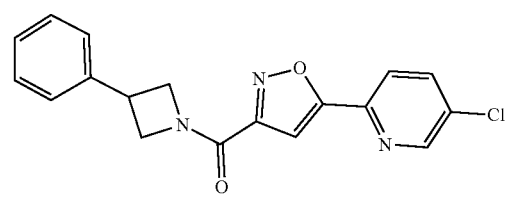 [SMILES: O=C(c1cc(-c2ccc(Cl)cn2)on1)N1CC(c2ccccc2)C1]

A mixture of 3-phenylazetidine hydrochloride (143 mg, 1.07 mmol), 5-(5-chloropyridin-2-yl)isoxazole-3-carboxylic acid (200 mg, 0.89 mmol), 1-[bis(dimethylamino)methylene]-1H-1,2,3-triazolo[4,5-b]pyridinium 3-oxide hexafluorophosphate (407 mg, 1.07 mmol) and triethylamine (270 mg, 2.67 mmol) in anhydrous N,N'-dimethylformamide (5.0 mL) was stirred at 20° C. for 16 h. The reaction mixture was extracted with ethyl acetate (20 mL×2) and washed with water (30 mL) and brine (30 mL). The combined organic phases were dried over anhydrous sodium sulfate, filtered, and concentrated in vacuo. The crude sample was dissolved in minimum amount of N,N-dimethylformamide and purified via prep-HPLC (Boston C18 21×250 mm 10 µm column; acetonitrile/0.01% aqueous trifluoroacetic acid) to give (5-(5-chloropyridin-2-yl)isoxazol-3-yl)(3-phenylazetidin-1-yl)methanone (28 mg, 0.08 mmol, 9%) as a gray solid. $^{1}$H NMR (500 MHz, Dimethylsulfoxide-d$_{6}$) δ 8.82 (d, J=2.4 Hz, 1H), 8.19 (dd, J=8.5, 2.4 Hz, 1H), 8.12 (d, J=8.5 Hz, 1H), 7.44 (d, J=8.2 Hz, 3H), 7.38 (t, J=7.6 Hz, 2H), 7.28 (t, J=7.2 Hz, 1H), 4.91 (t, J=9.1 Hz, 1H), 4.51 (dt, J=9.6, 7.8 Hz, 2H), 4.10 (dd, J=9.9, 6.5 Hz, 1H), 4.01 (dt, J=15.2, 7.6 Hz, 1H); LCMS (ESI) m/z: 340.0 [M+H]$^{+}$.

Example 90. Preparation of (5-(5-methoxypyridin-2-yl)isoxazol-3-yl)(3-phenylazetidin-1-yl)methanone (242)

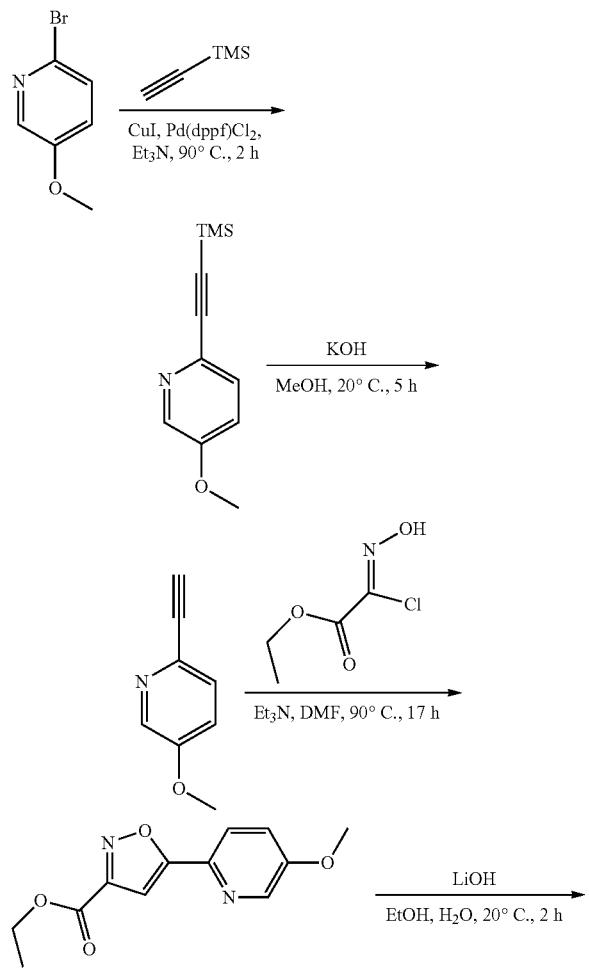

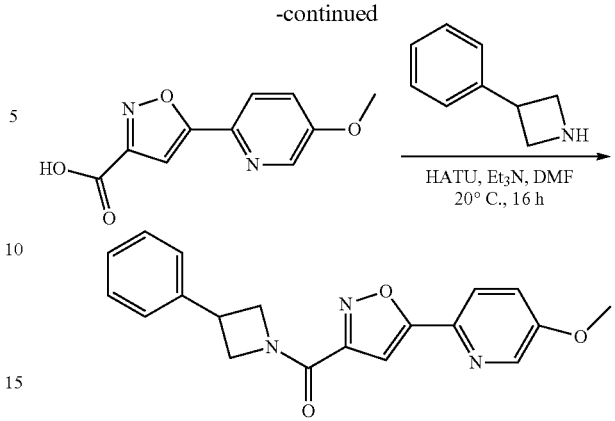

Step 1: Preparation of 5-methoxy-2-((trimethylsilyl)ethynyl)pyridine

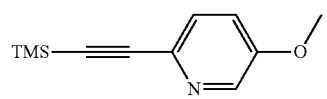

The synthesis of 5-methoxy-2-((trimethylsilyl)ethynyl)pyridine was carried out following the same procedure as Example 89. Compound 5-methoxy-2-((trimethylsilyl)ethynyl)pyridine (1.6 g, 7.8 mmol, 30%) was obtained as a colorless oil. LCMS (ESI) m/z: 206.2 [M+H]$^{+}$.

Step 2: Preparation of 2-ethynyl-5-methoxypyridine

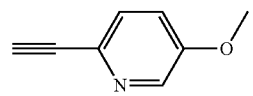

The synthesis of 2-ethynyl-5-methoxypyridine was carried out following the same procedure as Example 89. Compound 2-ethynyl-5-methoxypyridine (0.8 g, 6.0 mmol, 77%) was obtained as colorless oil. LCMS (ESI) m/z: 134.2 [M+H]$^{+}$.

Step 3: Preparation of ethyl 5-(5-methoxypyridin-2-yl)isoxazole-3-carboxylate

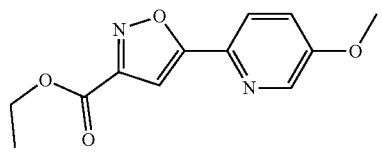 [SMILES: CCOC(=O)c1cc(-c2ccc(OC)cn2)on1]

The synthesis of ethyl 5-(5-methoxypyridin-2-yl)isoxazole-3-carboxylate was carried out following the same procedure as for Example 89. Compound ethyl 5-(5-methoxypyridin-2-yl)isoxazole-3-carboxylate (0.330 g, 1.33 mmol, 22%) was obtained as a gray solid. LCMS (ESI) m/z: 249.1 [M+H]$^{+}$.

Step 4: Preparation of 5-(5-methoxypyridin-2-yl)isoxazole-3-carboxylic Acid

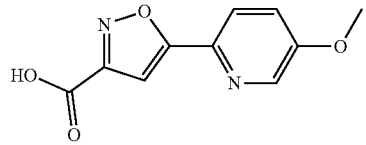 [SMILES: COc1ccc(-c2cc(C(=O)O)no2)nc1]

The synthesis of 5-(5-methoxypyridin-2-yl)isoxazole-3-carboxylic acid was carried out following the same procedure as for Example 89. Compound (5-(5-methoxypyridin-2-yl)isoxazol-3-yl)(3-phenylazetidin-1-yl)methanone (0.200 g, 0.90 mmol, 68%) was obtained as a gray solid. LCMS (ESI) m/z: 221.1 [M+H]$^+$.

Step 5: Preparation of ((5-(5-methoxypyridin-2-yl)isoxazol-3-yl)(3-phenylazetidin-1-yl)methanone

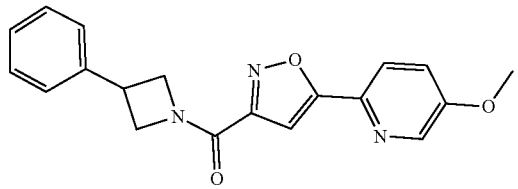 [SMILES: COc1ccc(-c2cc(C(=O)N3CC(c4ccccc4)C3)no2)nc1]

The synthesis of ((5-(5-methoxypyridin-2-yl)isoxazol-3-yl)(3-phenylazetidin-1-yl)methanone was carried out following the same procedure as Example 89. Compound (5-(5-methoxypyridin-2-yl)isoxazol-3-yl)(3-phenylazetidin-1-yl)methanone (32.8 mg, 0.1 mmol, 8%) was obtained as a gray solid. $^1$H NMR (500 MHz, Dimethylsulfoxide-d$_6$) δ 8.46 (d, J=2.9 Hz, 1H), 8.04 (d, J=8.8 Hz, 1H), 7.59 (dd, J=8.8, 2.9 Hz, 1H), 7.47-7.35 (m, 4H), 7.28 (t, J=7.3 Hz, 1H), 7.23 (s, 1H), 4.91 (t, J=9.2 Hz, 1H), 4.59-4.44 (m, 2H), 4.17-4.05 (m, 1H), 4.00 (td, J=8.7, 4.3 Hz, 1H), 3.91 (d, J=11.6 Hz, 3H); LCMS (ESI) m/z: 336.1 [M+H]$^+$.

Example 91. Preparation of (5-(benzo[d][1,3]dioxol-5-yl)isoxazol-3-yl)(3-(3-fluorophenyl)azetidin-1-yl)methanone (239)

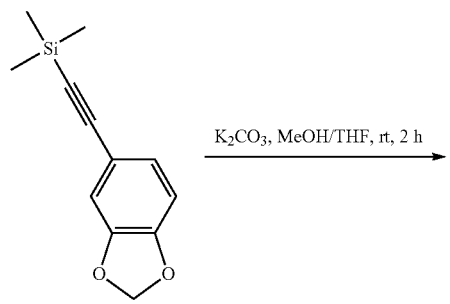

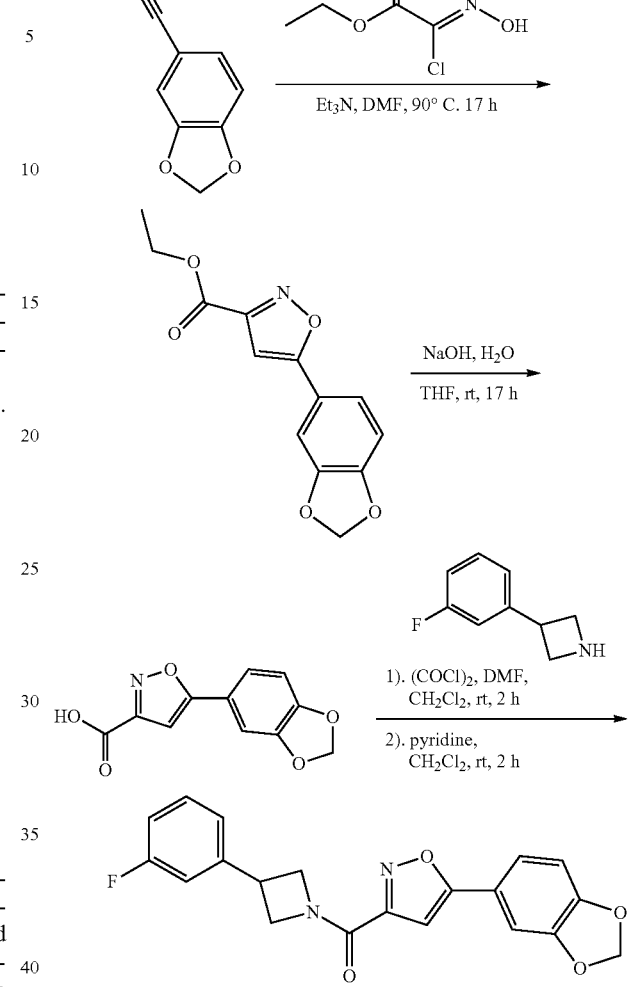

Step 1: Preparation of 5-ethynylbenzo[d][1,3]dioxole

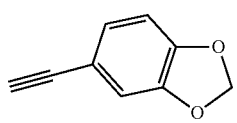

To a solution of (benzo[d][1,3]dioxol-5-ylethynyl)trimethylsilane (10.0 g, 45.8 mmol) in methanol (80 mL) and tetrahydrofuran (80 mL) was added potassium carbonate (12.6 g, 91.6 mmol). The mixture was stirred at room temperature for 2 h. The mixture was diluted with water (100 mL) and extracted with ethyl acetate (80 mL×2). The combined organic layers were washed with brine (60 mL×2), dried over anhydrous sodium sulfate, filtered and concentrated in vacuo to give 5-ethynylbenzo[d][1,3]dioxole (5.8 g, 39.7 mmol, 88%) as a yellow oil. This material was used in the next step without further purification.

Step 2: Preparation of ethyl 5-(benzo[d][1,3]dioxol-5-yl)isoxazole-3-carboxylate

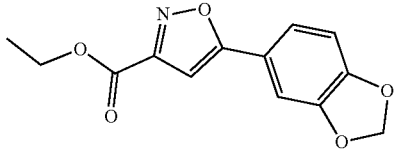 [SMILES: CCOC(=O)c1cc(-c2ccc3c(c2)OCO3)on1]

To a solution of 5-ethynylbenzo[d][1,3]dioxole (5.8 g, 39.7 mmol) in N,N'-dimethylformamide (60.0 mL) was added a solution of (Z)-ethyl 2-chloro-2-(hydroxyimino)acetate (5.9 g, 39.7 mmol) in N,N'-dimethylformamide (20 mL) dropwise over 40 min under nitrogen. After addition, the reaction mixture was heated to 90° C. and a solution of triethylamine (12.0 g, 119 mmol) in N,N'-dimethylformamide (20 mL) was added dropwise over 1 h. The reaction mixture was stirred at this temperature for 17 h and cooled to room temperature. The reaction mixture was diluted with ethyl acetate (50 mL), washed with water (60 mL×2) and brine (60 mL×2), dried over anhydrous sodium sulfate, filtered and concentrated in vacuo. The residue was purified by column chromatography (silica, petroleum ether/ethyl acetate=20/1) to yield ethyl 5-(benzo[d][1,3]dioxol-5-yl)isoxazole-3-carboxylate (3.7 g, 14.1 mmol, 36%) as a yellow solid. LCMS (ESI) m/z: 262.1 [M+H]$^+$.

Step 3: Preparation of 5-(benzo[d][1,3]dioxol-5-yl)isoxazole-3-carboxylic Acid

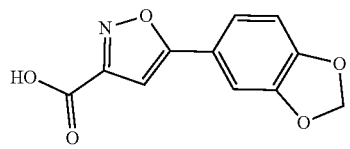 [SMILES: O=C(O)c1cc(-c2ccc3c(c2)OCO3)on1]

To a solution of ethyl 5-(benzo[d][1,3]dioxol-5-yl)isoxazole-3-carboxylate (220.0 mg, 0.84 mmol) in tetrahydrofuran/water (v/v=4/1, 20 mL) at room temperature was added sodium hydroxide (80.6 mg, 2.01 mmol). The reaction mixture was stirred at room temperature for 17 h before the volatiles were removed in vacuo. The residue was diluted with water (10 mL) and adjusted to pH=2 with aqueous 1N hydrogen chloride. The aqueous layer was extracted with ethyl acetate (10 mL×2). The combined organic layers were washed with brine (10 mL×2), dried over anhydrous sodium sulfate and concentrated in vacuo to give 5-(benzo[d][1,3]dioxol-5-yl)isoxazole-3-carboxylic acid (120 mg, 0.51 mmol, 67%) as a yellow solid. LCMS (ESI) m/z: 234.1 [M+H]$^+$. This material was used in the next step without further purification.

Step 4: Preparation of (5-(benzo[d][1,3]dioxol-5-yl)isoxazol-3-yl)(3-(3-fluorophenyl)azetidin-1-yl)methanone

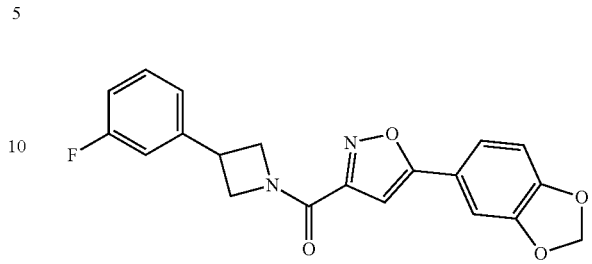

To a solution of 5-(benzo[d][1,3]dioxol-5-yl)isoxazole-3-carboxylic acid (0.120 g, 0.51 mmol) in dichloromethane (6 mL) at 0° C. was added oxalyl chloride (0.129 g, 1.02 mmol) and N,N'-dimethylformamide (0.01 mL). The reaction mixture was stirred at room temperature for 1 h then evaporated to dryness. The residue was dissolved in dichloromethane (8 mL) and added to 3-(3-fluorophenyl)azetidine (92.1 mg, 0.61 mmol) and pyridine (0.181 g, 2.29 mmol) in dichloromethane (10 mL) at 0° C. The reaction mixture was stirred at room temperature for 2 h. The reaction mixture was concentrated in vacuo. The crude sample was dissolved in minimum amount of N,N-dimethylformamide and purified via prep-HPLC (Boston C18 21×250 mm 10 μm column; acetonitrile/0.01% aqueous trifluoroacetic acid) to give (5-(benzo[d][1,3]dioxol-5-yl)isoxazol-3-yl)(3-(3-fluorophenyl)azetidin-1-yl)methanone (33.8 mg, 0.09 mmol, 18%) as a white solid. $^1$H NMR (500 MHz, Dimethylsulfoxide-d$_6$) δ 7.60-7.46 (m, 2H), 7.45-7.37 (m, 1H), 7.35-7.24 (m, 3H), 7.15-7.04 (m, 2H), 6.13 (s, 2H), 4.94-4.80 (m, 1H), 4.49 (dd, J=17.3, 9.1 Hz, 2H), 4.14-3.98 (m, 2H); LCMS (ESI) m/z: 367.0 [M+H]$^+$.

Example 92. Preparation of (5-(benzo[d][1,3]dioxol-5-yl)isoxazol-3-yl)(2-phenylazetidin-1-yl)methanone (204)

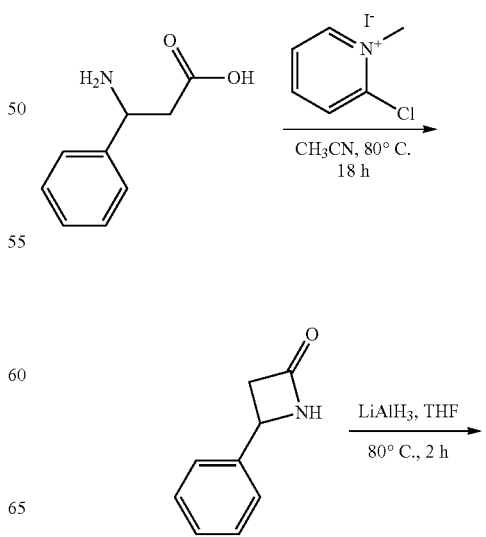

-continued

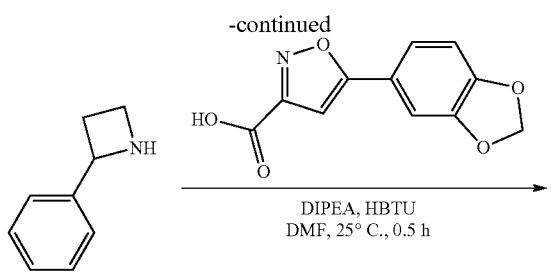

Step 1: Preparation of 4-phenylazetidin-2-one

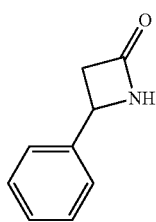 [SMILES: O=C1CC(c2ccccc2)N1]

To a solution of 3-amino-3-phenyl-propanoic acid (2.00 g, 12.1 mmol) in acetonitrile (20 mL) was added 2-chloro-1-methyl-pyridin-1-ium iodide (3.40 g, 13.3 mmol) and triethylamine (2.70 g, 26.6 mmol). The reaction mixture was heated to 80° C. and stirred for 18 h. The mixture was cooled to 25° C. and filtered. The filtrate was concentrated in vacuo. The crude product was purified by column chromatography (silica, petroleum ether/ethyl acetate=10/1 to 1/2) to give 4-phenylazetidin-2-one (0.900 g, 6.12 mmol, 50%) as a white solid. $^1$H NMR (400 MHz, Chloroform-d) δ 7.47-7.33 (m, 5H), 6.12 (br. s, 1H), 4.76 (dd, J=2.6, 5.3 Hz, 1H), 3.48 (ddd, J=2.4, 5.3, 14.8 Hz, 1H), 2.92 (dd, J=1.6, 14.9 Hz, 1H)

Step 2: Preparation of 2-phenylazetidine

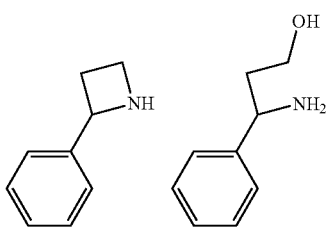 [SMILES: c1ccc(C2CCN2)cc1 ; NC(CCO)c1ccccc1]

To a solution of lithium aluminum hydride (0.361 g, 9.52 mmol) in tetrahydrofuran (10 mL) was added 4-phenylazetidin-2-one (0.400 g, 2.72 mmol). The reaction mixture was heated to 80° C. and stirred for 2 h. The reaction mixture was cooled to 0° C. and quenched with saturated aqueous ammonium chloride (1 mL). Then the mixture was filtered. The cake was washed with dichloromethane/methanol=10/1, 10 mL) and the filtrate was concentrated in vacuo. A mixture of compounds 2-phenylazetidine (190 mg, crude) and 3-amino-3-phenyl-propan-1-ol (190 mg, 1.26 mmol, 46%) were obtained as colorless oils.

Step 3: Preparation of (5-(benzo[d][1,3]dioxol-5-yl)isoxazol-3-yl)(2-phenylazetidin-1-yl)methanone, 5-(benzo[d][1,3]dioxol-5-yl)-N-(3-hydroxy-1-phenylpropyl)isoxazole-3-carboxamide

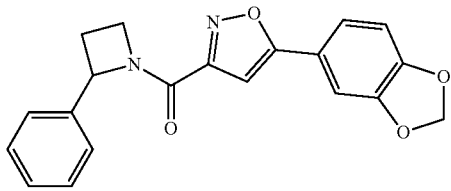 [SMILES: O=C(c1cc(-c2ccc3c(c2)OCO3)on1)N1CCC1c1ccccc1]

To a solution of 5-(benzo[d][1,3]dioxol-5-yl)isoxazole-3-carboxylic acid (0.231 g, 0.992 mmol) in N,N'-dimethylformamide (3 mL) was added N,N,N',N'-tetramethyl-O-(1H-benzotriazol-1-yl)uronium hexafluorophosphate (0.376 g, 0.992 mmol), diisopropylethylamine (0.256 g, 1.98 mmol) and 3-amino-3-phenyl-propan-1-ol (0.150 g, 0.992 mmol). The reaction mixture was stirred at 25° C. for 0.5 h. The reaction mixture was directly purified by Prep-HPLC (Waters Xbridge 150×25 5 μm column; 37-67% acetonitrile in a 10 mM ammonium bicarbonate solution in water, 12 min gradient) to give (5-(benzo[d][1,3]dioxol-5-yl)isoxazol-3-yl)(2-phenylazetidin-1-yl)methanone (53 mg, 0.141 mmol, 14%) as a yellow solid. $^1$H NMR (400 MHz, Chloroform-d) δ 7.31-7.34 (m, 3H), 7.24-7.27 (m, 2.6vH), 7.16-7.24 (m, 2H), 6.82-6.84 (m, 1H), 6.71 (s 1H), 6.5 (s, 1H), 5.96 (d, J=1.2, 2H), 5.86-5.88 (m, 1H), 5.3-5.5 (m, 1H), 4.59-4.68 (m, 1H), 4.25-4.32 (m, 1H), 2.78-2.85 (m, 1H), 2.10-2.28 (m, 1H); LCMS (ESI m/z: 349.1 [M+H]$^+$.

Example 93. Preparation of [5-(1,3-benzodioxol-5-yl)isoxazol-3-yl]-[2-(3-fluorophenyl)azetidin-1-yl]methanone (220)

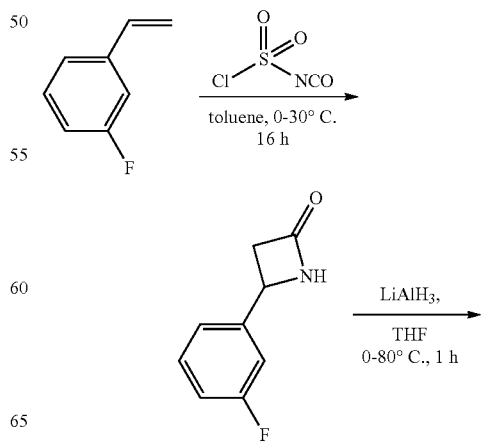

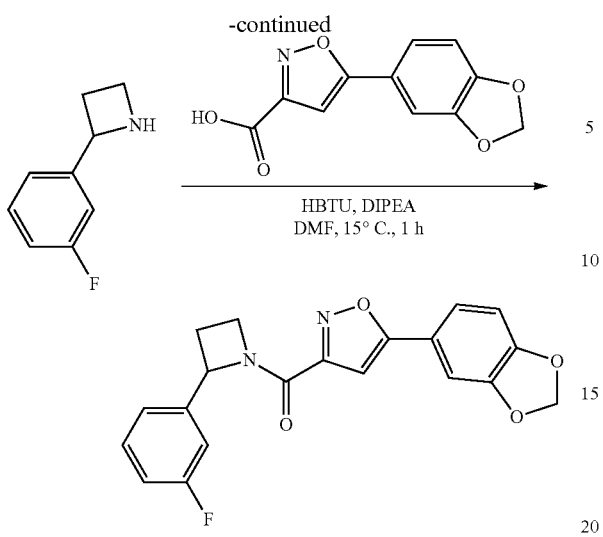

Step 1: Preparation of 4-(3-fluorophenyl)azetidin-2-one

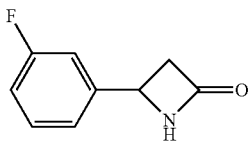 [SMILES: O=C1CC(c2cccc(F)c2)N1]

To a stirred solution of N-(oxomethylene)sulfamoyl chloride (1.16 g, 8.19 mmol) in toluene (5 mL) was added dropwise 1-fluoro-3-vinylbenzene (1.00 g, 8.19 mmol) in toluene (5 mL) at 0° C. Then the mixture was stirred at 30° C. for 16 h. The reaction mixture was poured into a solution of sodium sulfate (0.4 g) and sodium carbonate (1.6 g) in water (15 mL) and then stirred at 15° C. for 30 min. The aqueous layer was extracted with ethyl acetate (20 mL×3). The combined organic layers were washed with brine (5 mL), dried over sodium sulfate, filtered and concentrated in vacuo. The crude product was purified by column (ISCO, 20 g silica, 30-60% ethyl acetate in petroleum ether, gradient over 20 min) to yield 4-(3-fluorophenyl)azetidin-2-one (0.300 g, 1.82 mmol, 22%) as a pale yellow solid.

Step 2: Preparation of 2-(3-fluorophenyl)azetidine

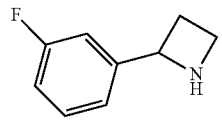 [SMILES: Fc1cccc(C2CCN2)c1]

To a solution of lithium aluminum hydride (0.207 g, 5.45 mmol) in tetrahydrofuran (5 mL) was added 4-(3-fluorophenyl)azetidin-2-one (0.300 g, 1.82 mmol) in portions at 0° C. Then the mixture was heated at 80° C. for 1 h. Then the reaction mixture was quenched sequentially with water, 10% sodium hydroxide and water (1:2:1, total 0.4 mL). The reaction mixture was dried over anhydrous sodium sulfated and filtered. The filtrate was concentrated in vacuo to afford 2-(2-fluorophenyl)azetidine (0.070 g, 0.463 mmol, 25%) as a colorless oil.

Step 3: Preparation of [5-(1,3-benzodioxol-5-yl)isoxazol-3-yl]-[2-(3-fluorophenyl)azetidin-1-yl]methanone

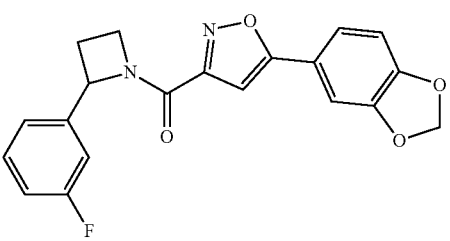 [SMILES: O=C(c1cc(-c2ccc3c(c2)OCO3)on1)N1CCC1c1cccc(F)c1]

To a stirred solution of 5-(1,3-benzodioxol-5-yl)isoxazole-3-carboxylic acid (0.090 g, 0.386 mmol) in N,N'-dimethylformamide (0.5 mL) was added N,N,N',N'-tetramethyl-O-(1H-benzotriazol-1-yl)uronium hexafluorophosphate (0.176 g, 0.463 mmol), diisopropylethylamine (150 mg, 1.16 mmol) and 2-(3-fluorophenyl)azetidine (0.070 g, 0.463 mmol). Then the mixture was stirred at 15° C. for 1 h and purified directly by prep-HPLC: (Waters X bridge 150×25 5 μm column; 35-60% acetonitrile in a 10 mM ammonium bicarbonate solution in water, 11 min gradient) to give [5-(1,3-benzodioxol-5-yl)isoxazol-3-yl]-[2-(3-fluorophenyl)azetidin-1-yl]methanone (49 mg, 0.133 mmol, 31%) as brown solid. $^1$H NMR (400 MHz, Chloroform-d) δ 7.44-7.30 (m, 1.8H), 7.26-6.95 (m, 4.2H), 6.95-6.85 (m, 1H), 6.83-6.67 (m, 1H), 6.12-6.02 (m, 2H), 5.98 (dd, J=5.6, 9.2 Hz, 0.4H), 5.59 (dd, J=6.0, 8.8 Hz, 0.6H), 4.81-4.64 (m, 1.4H), 4.44-4.29 (m, 0.6H), 3.03-2.84 (m, 1H), 2.37-2.15 (m, 1H); LCMS (ESI) m/z: 367.0 [M+H]$^+$.

Example 94. Preparation of [5-(1,3-benzodioxol-5-yl)isoxazol-3-yl]-[2-(4-fluorophenyl)azetidin-1-yl]methanone (223)

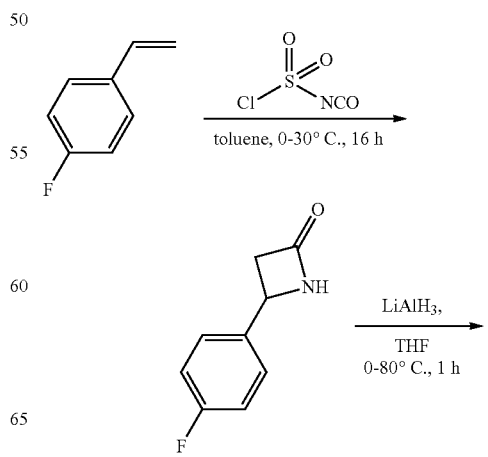

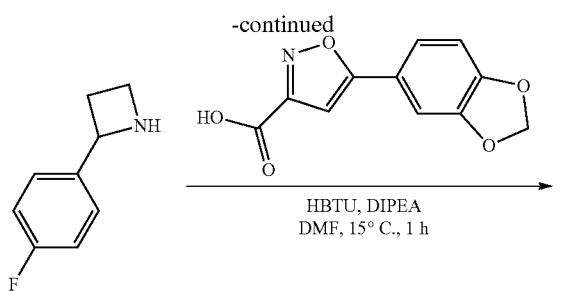

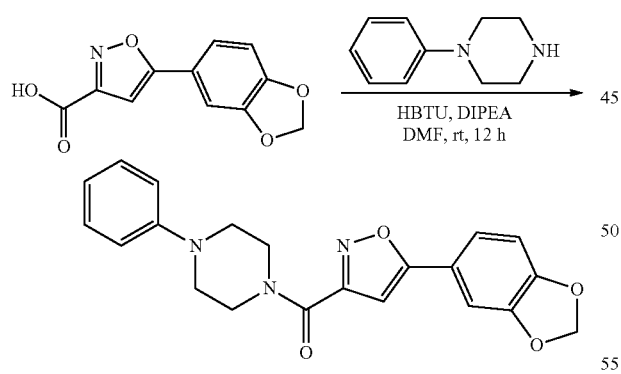

The synthesis of [5-(1,3-benzodioxol-5-yl)isoxazol-3-yl]-[2-(4-fluorophenyl)azetidin-1-yl]methanone was carried out following the procedure for Example 93. Compound [5-(1,3-benzodioxol-5-yl)isoxazol-3-yl]-[2-(4-fluorophenyl)azetidin-1-yl]methanone (39 mg, 0.104 mmol, 24%) was obtained as a white solid. $^1$H NMR (400 MHz, Chloroform-d) 7.41 (dd, J=5.6, 8.4 Hz, 1H), 7.37-7.30 (m, 1H), 7.26-7.20 (m, 1H), 7.07 (t, J=8.4 Hz, 1H), 7.00 (t, J=8.8 Hz, 1H), 6.90 (t, J=1H), 6.85 (d, J=8.0 Hz, 1H), 6.78 (s, 1H), 6.61 (s, 1H), 6.05 (s, 1H), 6.02 (s, 1H), 5.94 (dd, J=4.8, 8.8 Hz, 1H), 5.56 (dd, J=6.0, 8.8 Hz, 1), 4.84-4.55 (m, 1H), 4.45-4.26 (m, 1H), 3.00-2.77 (m, 1H), 2.38-2.14 (m, 1H); LCMS (ESI) m/z: 367.1 [M+H]$^+$.

Example 95. Preparation of 5-(benzo[d][1,3]dioxol-5-yl)isoxazol-3-yl)(4-phenylpiperazin-1-yl)methanone (265)

To a stirred mixture of 5-(benzo[d][1,3]dioxol-5-yl)isoxazole-3-carboxylic acid (0.050 g, 0.214 mmol) and 1-phenylpiperazine (42 mg, 0.257 mmol) in N,N'-dimethylformamide (1 mL) was added N,N,N',N'-tetramethyl-O-(1H-benzotriazol-1-yl)uronium hexafluorophosphate (81 mg, 0.214 mmol) and diisopropylethylamine (0.055 g, 0.429 mmol) in one portion at 25° C. The mixture was stirred at 25° C. for 15 h. The solvent was removed under vacuum. The residue was purified by prep-HPLC (Luna C18 100×30 5 μm column; mobile phase: 45-65% acetonitrile in an a 0.1% trifluoro acetic acid solution in water, 12 min gradient) to give (5-(benzo[d][1,3]dioxol-5-yl)isoxazol-3-yl)(4-phenylpiperazin-1-yl)methanone (64 mg, 0.262 mmol, 79%) as a white solid. $^1$H NMR (400 MHz, Acetonitrile-d$_3$) δ 7.43 (dd, J=1.7, 8.0 Hz, 1H), 7.35 (d, J=1.5 Hz, 1H), 7.29-7.24 (m, 2H), 7.00-6.95 (m, 3H), 6.86 (t, J=7.3 Hz, 1H), 6.78 (s, 1H), 6.06 (s, 2H), 3.88-3.83 (m, 4H), 3.28-3.17 (m, 4H); LCMS (ESI) m/z: 378.2[M+H]$^+$.

Example 96. Preparation of (3-phenylazetidin-1-yl)-(5-phenylisoxazol-3-yl)methanone (212)

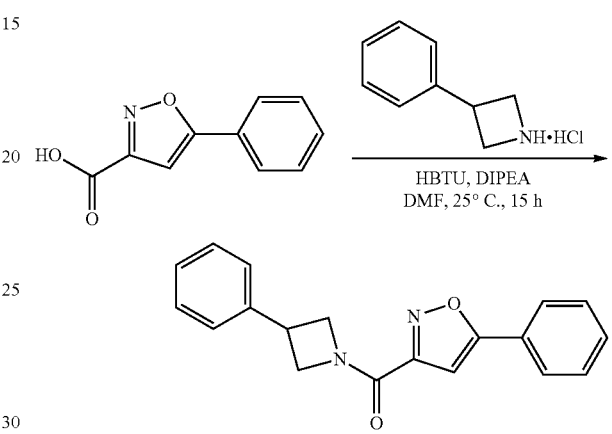

The synthesis of (3-phenylazetidin-1-yl)-(5-phenylisoxazol-3-yl)methanone was carried out following the procedure for Example 95. Compound (3-phenylazetidin-1-yl)-(5-phenylisoxazol-3-yl)methanone (51 mg, 0.168 mmol, 40%) was obtained as a pale yellow solid. $^1$H NMR (400 MHz, Chloroform-d) δ 7.82 (dd, J=1.8, 7.5 Hz, 2H), 7.55-7.45 (m, 3H), 7.43-7.35 (m, 4H), 7.33-7.28 (m, 1H), 6.99 (s, 1H), 5.04 (t, J=9.9 Hz, 1H), 4.77-4.58 (m, 2H), 4.30 (dd, J=6.1, 10.1 Hz, 1H), 4.06-3.86 (m, 1H); LCMS (ESI) m/z: 305.1 [M+H]$^+$.

Example 97. Preparation of [5-(1,3-benzodioxol-5-yl)isoxazol-3-yl]-(3-phenylazetidin-1-yl)methanone (217)

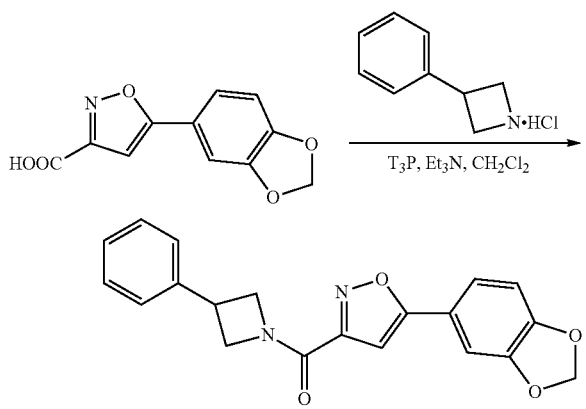

Step 1: Preparation of [5-(1,3-benzodioxol-5-yl)isoxazol-3-yl]-(3-phenylazetidin-1-yl)methanone

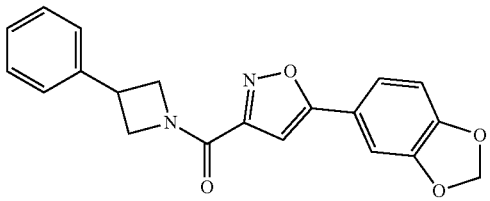 [SMILES: O=C(c1cc(-c2ccc3c(c2)OCO3)on1)N1CC(c2ccccc2)C1]

To a stirred solution of 5-(1,3-benzodioxol-5-yl)isoxazole-3-carboxylic acid (0.100 g, 0.429 mmol) and 3-phenylazetidine hydrochloride (87 mg, 0.515 mmol) in dichloromethane (2 mL) was added propylphosphonic anhydride (0.409 g, 0.643 mmol, 50% by weight in ethyl acetate) and triethylamine (0.130 g, 1.29 mmol). The mixture was stirred at 20° C. for 15 h. The reaction mixture was quenched with water (5 mL) and extracted with dichloromethane (5 mL×3). The combined organic layers were washed with brine (10 mL), dried over sodium sulfate, filtered and concentrated under reduced pressure. The residue was purified by prep-HPLC (YMC-Actus Triart C18 100×30 mm×5 μm column; 60-80% acetonitrile in a 10 mM ammonium bicarbonate solution in water, 12 min gradient) to give [5-(1,3-benzodioxol-5-yl)isoxazol-3-yl]-(3-phenylazetidin-1-yl)methanone (19 mg, 0.053 mmol, 12%) as a white solid. $^1$H NMR (400 MHz, Dimethylsulfoxide-$d_6$) δ 7.53 (d, J=1.3 Hz, 1H), 7.49 (dd, J=1.5, 8.1 Hz, 1H), 7.45-7.35 (m, 4H), 7.31-7.25 (m, 2H), 7.09 (d, J=8.1 Hz, 1H), 6.13 (s, 2H), 4.89 (t, J=9.2 Hz, 1H), 4.55-4.43 (m, 2H), 4.12-3.94 (m, 2H); LCMS (ESI) m/z: 349.1 [M+H]$^+$.

Example 98. Preparation of [5-(2-furyl)isoxazol-3-yl]-(3-phenylazetidin-1-yl)methanone (207)

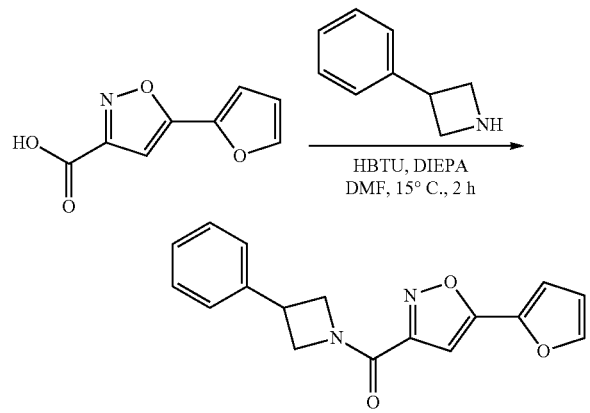

To a solution of 5-(2-furyl)isoxazole-3-carboxylic acid (140 mg, 0.78 mmol) and N,N,N',N'-tetramethyl-O-(1H-benzotriazol-1-yl)uronium hexafluorophosphate (356 mg, 0.94 mmol) in N,N'-dimethylformamide (3 mL) was added diisopropylethylamine (303 mg, 2.34 mmol) and 3-phenylazetidine hydrochloride (146 mg, 0.86 mmol). The mixture was stirred at 15° C. for 2 h. The mixture was purified by prep-HPLC (Waters X bridge 150×25 5 μM column; 35-70% acetonitrile in a 10 mM ammonium acetate solution in water, 10 min gradient) to afford [5-(2-furyl)isoxazol-3-yl]-(3-phenylazetidin-1-yl)methanone (0.086 g, 0.29 mmol, 37%) as a brown solid. $^1$H NMR (400 MHz, Chloroform-d) δ 7.59 (s, 1H), 7.41-7.35 (m, 4H), 7.31 (br. d, J=7.0 Hz, 1H), 6.95 (d, J=3.5 Hz, 1H), 6.89 (s, 1H), 6.56 (dd, J=1.8, 3.5 Hz, 1H), 5.02 (t, J=9.6 Hz, 1H), 4.68-4.61 (m, 2H), 4.32-4.26 (m, 1H), 4.01-3.92 (m, 1H); LCMS (ESI) m/z: 295.0 [M+H]$^+$.

Example 99. Preparation of 3-(3-phenylazetidine-1-carbonyl)-4,5,6,7-tetrahydro-1,2-benzoxazole (252)

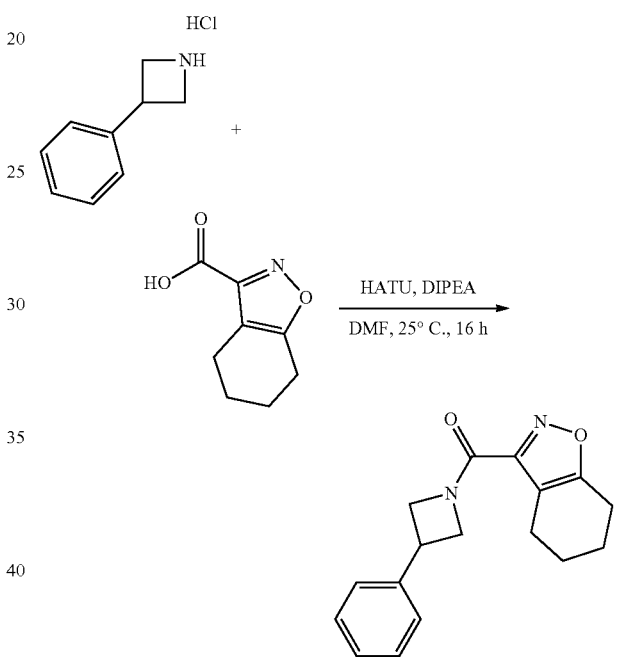

To a solution of 3-phenylazetidine hydrochloride (50.7 mg, 0.299 mmol), 4,5,6,7-tetrahydro-1,2-benzoxazole-3-carboxylic acid (50.0 mg, 0.299 mmol) and 1-[bis(dimethylamino)methylene]-1H-1,2,3-triazolo[4,5-b]pyridinium 3-oxide hexafluorophosphate (0.113 g, 0.299 mmol) in N,N'-dimethylformamide (1 mL) at 25° C. was added diisopropylethylamine (130 μL, 0.748 mmol). The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 60% ethyl acetate/hexanes for 20 min) to afford 3-(3-phenylazetidine-1-carbonyl)-4,5,6,7-tetrahydro-1,2-benzoxazole (34.3 mg, 0.121 mmol, 40%) as a clear oil. $^1$H NMR (300 MHz, Dimethylsulfoxide-$d_6$) δ 7.45-7.20 (m, 5H), 4.91 (t, J=8.7 Hz, 1H), 4.53-4.41 (m, 2H), 4.07-3.91 (m, 2H), 2.71 (t, J=6.1 Hz, 4H), 1.71 (tt, J=12.7, 5.5 Hz, 4H); LCMS (ESI) m/z: 283.3 [M+H]$^+$.

409

Example 100. Preparation of 3-(3-benzylazetidine-1-carbonyl)-4,5,6,7-tetrahydro-1,2-benzoxazole (253)

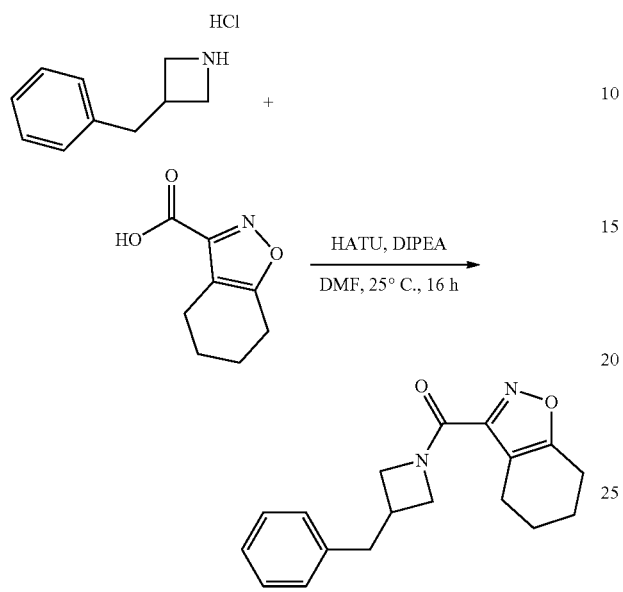

To a solution of 3-benzylazetidine hydrochloride salt (54.9 mg, 0.299 mmol), 4,5,6,7-tetrahydro-1,2-benzoxazole-3-carboxylic acid (50.0 mg, 0.299 mmol) and 1-[bis(dimethylamino)methylene]-1H-1,2,3-triazolo[4,5-b]pyridinium 3-oxide hexafluorophosphate (113 mg, 0.299 mmol) in N,N'-dimethylformamide (1 mL) at 25° C. was added diisopropylethylamine (130 μL, 0.748 mmol). The reaction mixture was stirred at 25° C. for 16 h. The reaction mixture was quenched with water (1 mL). The aqueous layer was extracted with ethyl acetate (5 mL×3). The combined organic layers were washed with brine, dried over magnesium sulfate, filtered and concentrated in vacuo. The crude residue was purified by column chromatography (ISCO, 12 g silica, eluting with 60% ethyl acetate/hexanes for 20 min) to afford 3-(3-benzylazetidine-1-carbonyl)-4,5,6,7-tetrahydro-1,2-benzoxazole (33.3 mg, 0.112 mmol, 37%) as a white solid. $^1$H NMR (300 MHz, Dimethylsulfoxide-d$_6$) δ 7.36-7.15 (m, 5H), 4.51 (t, J=8.4 Hz, 1H), 4.23-4.02 (m, 2H), 3.75 (dd, J=9.9, 4.9 Hz, 1H), 3.05-2.87 (m, 3H), 2.68 (q, J=6.3 Hz, 4H), 1.69 (dt, J=14.1, 4.8 Hz, 4H). LCMS (ESI) m/z: 297.2[M+H]$^+$.

Example 101. Preparation of 5-(1,3-benzodioxol-5-yl)isoxazol-3-yl]-(3-benzylazetidin-1-yl)methanone (216)

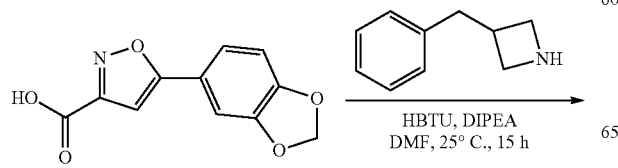

410

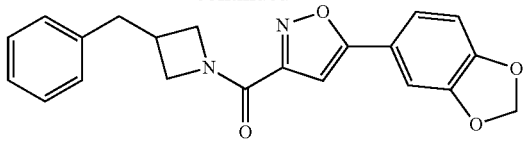

The synthesis of 5-(1,3-benzodioxol-5-yl)isoxazol-3-yl]-(3-benzylazetidin-1-yl)methanone was carried out following the procedure reported for Example 95. Compound [5-(1,3-benzodioxol-5-yl)isoxazol-3-yl]-(3-benzylazetidin-1-yl)methanone (32 mg, 0.085 mmol, 20%) was obtained as a yellow solid. $^1$H NMR (400 MHz, Chloroform-d) δ 7.36-7.29 (m, 3H), 7.26-7.21 (m, 2H), 7.18 (d, J=7.1 Hz, 2H), 6.91 (d, J=7.9 Hz, 1H), 6.81 (s, 1H), 6.05 (s, 2H), 4.71-4.61 (m, 1H), 4.39-4.23 (m, 2H), 3.96 (dd, J=4.4, 10.8 Hz, 1H), 3.11-3.07 (m, 1H), 3.05-2.92 (m, 2H); LCMS (ESI) m/z: 363.1 [M+H]$^+$.

Example 102. Preparation of 3-benzylazetidin-1-yl)-(5-phenylisoxazol-3-yl)methanone (211)

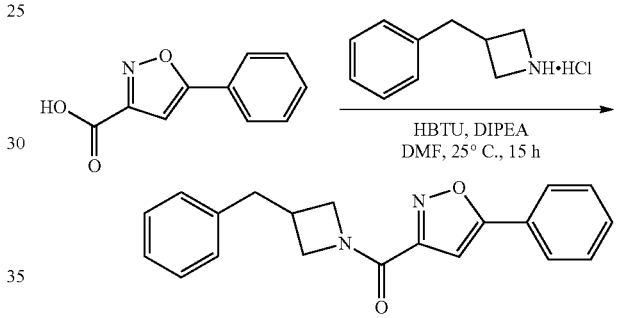

The synthesis of 3-benzylazetidin-1-yl)-(5-phenylisoxazol-3-yl)methanone was carried out following the procedure reported for Example 95. Compound (3-benzylazetidin-1-yl)-(5-phenylisoxazol-3-yl)methanone (77 mg, 0.241 mmol, 46%) was obtained as a pale yellow solid. $^1$H NMR (400 MHz, Chloroform-d) δ 7.79 (dd, J=2.0, 7.7 Hz, 2H), 7.52-7.42 (m, 3H), 7.36-7.28 (m, 2H), 7.27-7.15 (m, 3H), 6.95 (s, 1H), 4.73-4.62 (m, 1H), 4.38-4.23 (m, 2H), 3.96 (dd, J=4.8, 10.5 Hz, 1H), 3.11-2.92 (m, 3H); LCMS (ESI) m/z: 319.1 [M+H]$^+$.

Example 103. Preparation of (3-benzylazetidin-1-yl)-[5-(2-furyl)isoxazol-3-yl]methanone (205)

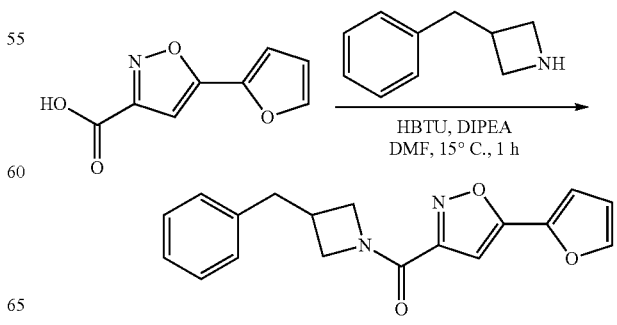

To a solution of 5-(2-furyl)isoxazole-3-carboxylic acid (0.100 g, 0.56 mmol) and N,N,N',N'-tetramethyl-O-(1H-benzotriazol-1-yl)uronium hexafluorophosphate (0.254 g, 0.67 mmol) in N,N'-dimethylformamide (3 mL) was added diisopropylethylamine (0.216 g, 1.67 mmol) and 3-benzylazetidine hydrochloride (0.113 g, 0.61 mmol). The mixture was stirred at 15° C. for 1 h and then directly purified by prep-HPLC (Waters X bridge 150×25 5 µM column; 35-75% acetonitrile in a 10 mM ammonium acetate solution in water, 10 min gradient) to give (3-benzylazetidin-1-yl)-[5-(2-furyl)isoxazol-3-yl]methanone (0.062 g, 0.20 mmol, 36%) as a yellow solid. $^1$H NMR (400 MHz, Chloroform-d) δ 7.57 (s, 1H), 7.31 (d, J=7.6 Hz, 2H), 7.26-7.22 (m, 1H), 7.18 (d, J=7.2 Hz, 2H), 6.94 (d, J=3.4 Hz, 1H), 6.85 (s, 1H), 6.56 (dd, J=1.7, 3.3 Hz, 1H), 4.68-4.62 (m, 1H), 4.33-4.26 (m, 2H), 3.95 (dd, J=4.7, 10.8 Hz, 1H), 3.05-2.97 (m, 3H); LCMS (ESI) m/z: 309.0 [M+H]$^+$.

Example 104. Preparation of [5-(2-furyl)isoxazol-3-yl]-(3-phenoxyazetidin-1-yl)methanone (206)

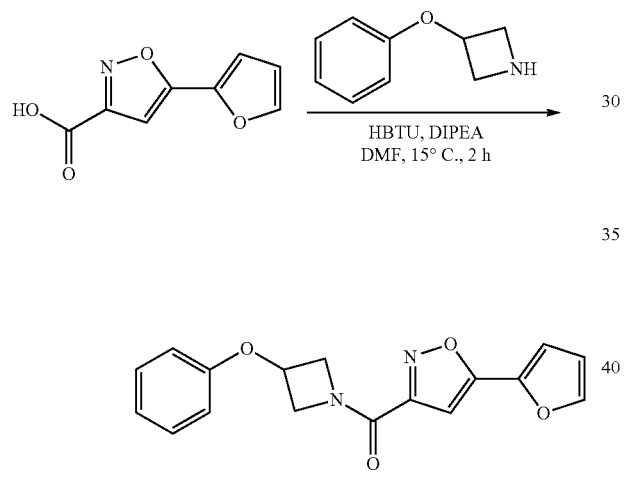

To a solution of 5-(2-furyl)isoxazole-3-carboxylic acid (0.120 g, 0.67 mmol) and N,N,N',N'-tetramethyl-O-(1H-benzotriazol-1-yl)uronium hexafluorophosphate (0.305 g, 0.80 mmol) in N,N'-dimethylformamide (3 mL) was added diisopropylethylamine (260 mg, 2.01 mmol) and 3-phenoxyazetidine hydrochloride salt (137 mg, 0.74 mmol). The mixture was stirred at 15° C. for 2 h. The mixture was purified by prep-HPLC (Waters X bridge 150×25 5 uM column; 35-65% acetonitrile in a 10 mM ammonium acetate solution in water, 11 min gradient) to afford [5-(2-furyl)isoxazol-3-yl]-(3-phenoxyazetidin-1-yl)methanone (52 mg, 0.17 mmol, 25%) as a pale yellow solid. $^1$H NMR (400 MHz, Chloroform-d) δ 7.58 (s, 1H), 7.32 (t, J=7.9 Hz, 2H), 7.05-7.00 (m, 1H), 6.95 (d, J=3.5 Hz, 1H), 6.87 (s, 1H), 6.79 (d, J=7.9 Hz, 2H), 6.56 (dd, J=1.8, 3.5 Hz, 1H), 5.08-4.97 (m, 2H), 4.66-4.58 (m, 2H), 4.30 (dd, J=4.2, 11.2 Hz, 1H); LCMS (ESI) m/z: 311.1 [M+H]$^+$.

Example 105. Preparation of 6-hydroxy-6-phenyl-2-azaspiro[3.3]heptan-2-yl)-(5-phenylisoxazol-3-yl) methanone (226) and [5-(1,3-benzodioxol-5-yl) isoxazol-3-yl]-(6-hydroxy-6-phenyl-2-azaspiro[3.3] heptan-2-yl)methanone (YUMAX-3015) and (6-phenyl-2-azaspiro[3.3]hept-6-en-2-yl)-(5-phenylisoxazol-3-yl)methanone (225)

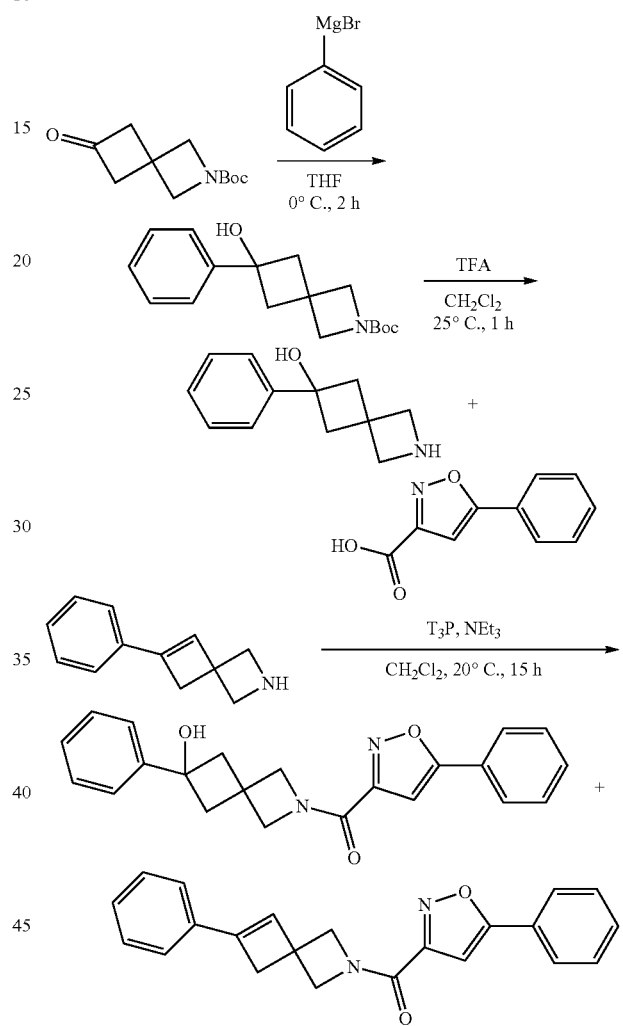

Step 1: Preparation of tert-butyl 6-hydroxy-6-phenyl-2-azaspiro[3.3]heptane-2-carboxylate

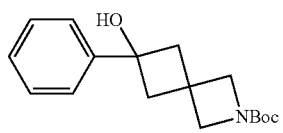 [SMILES: CC(C)(C)OC(=O)N1CC2(C1)CC(O)(c1ccccc1)C2]

To a stirred solution of tert-butyl 6-oxo-2-azaspiro[3.3]heptane-2-carboxylate (0.43 g, 2.04 mmol) in tetrahydrofuran (20 mL) was added phenyl magnesium bromide (3 M, 0.746 mL) dropwise at 0° C. under nitrogen. The mixture was stirred at 0° C. for 2 h. The reaction mixture was quenched by addition of water (30 mL) and was extracted with ethyl acetate (50 mL×2). The combined organic layers were dried over sodium sulfate, filtered and concentrated under reduced pressure to give crude tert-butyl 6-hydroxy-6-phenyl-2-azaspiro[3.3]heptane-2-carboxylate (0.500 g, 1.73 mmol, 85%) as a white solid. The material was used directly in the next step. ¹H NMR (400 MHz, Chloroform-d) δ 7.45-7.33 (m, 4H), 7.32-7.24 (m, 1H), 4.07 (s, 2H), 3.80 (s, 2H), 2.79-2.72 (m, 2H), 2.55 (m, 2H), 2.18-2.00 (m, 1H), 1.42 (s, 9H); LCMS (ESI) m/z: 234.1 [M−56+H]⁺.

Step 2: Preparation of 6-phenyl-2-azaspiro[3.3]heptan-6-ol and 6-phenyl-2-azaspiro[3.3]hept-6-ene

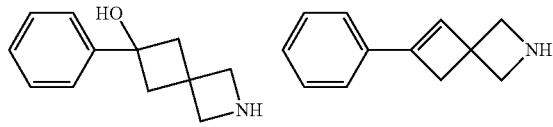

A solution of tert-butyl 6-hydroxy-6-phenyl-2-azaspiro[3.3]heptane-2-carboxylate (0.400 g, 1.38 mmol) in dichloromethane (8 mL) was treated at 0° C. with trifluoroacetic acid (6.15 g, 53.9 mmol) dropwise. The reaction mixture was then stirred at 25° C. for 1 h. The reaction mixture was concentrated under reduced pressure and the crude residue was directly purified by prep-HPLC (Phenomenex Gemini C18 250×50 10 μm column; 12-40% acetonitrile in a 10 mM ammonium bicarbonate solution in water, 20 min gradient) to yield (6-phenyl-2-azaspiro[3.3]heptan-6-ol (0.120 g, crude) as a white solid. The material was used directly in the next step. ¹H NMR (400 MHz, Chloroform-d) δ 7.41-7.31 (m, 4H), 7.28 (m, 1H), 5.47 (br. s, 1H), 3.84 (br. s, 2H), 3.56 (br. s, 2H), 3.35 (br. s, 1H), 2.73 (br. d, J=12.8 Hz, 2H), 2.59-2.48 (br. d, J=12.8 Hz, 2H); LCMS (ESI) m/z: 190.1 [M+H]⁺. and 6-phenyl-2-azaspiro[3.3]hept-6-ene (0.200 g, crude) as a white solid: ¹H NMR (400 MHz, Chloroform-d) δ 7.43-7.20 (m, 5H), 6.41 (s, 1H), 5.35-5.07 (m, 1H), 4.14 (br. s, 1H), 3.94 (br. d, J=16.5 Hz, 3H), 2.98 (br. s, 2H); LCMS (ESI) m/z: 172.1 [M+H]⁺.

Step 3: Preparation of (6-hydroxy-6-phenyl-2-azaspiro[3.3]heptan-2-yl)-(5-phenylisoxazol-3-yl)methanone

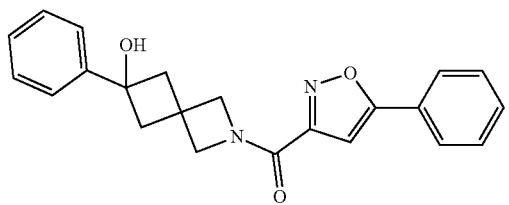 [SMILES: O=C(c1cc(-c2ccccc2)on1)N1CC2(C1)CC(O)(c1ccccc1)C2]

To a stirred solution of 5-phenylisoxazole-3-carboxylic acid (60 mg, 0.317 mmol), 6-phenyl-2-azaspiro[3.3]heptan-6-ol (60 mg, 0.317 mmol) and triethylamine (96 mg, 0.951 mmol) in dichloromethane (3 mL) at 0° C. was added propylphosphonic anhydride in ethyl acetate (0.303 g, 0.476 mmol, 50% in ethyl acetate) dropwise. The reaction mixture was stirred at 20° C. for 15 h. The reaction mixture was quenched with water (10 mL) and then extracted with dichloromethane (10 mL×3). The combined organic layers were dried over sodium sulfate, filtered and concentrated in vacuo. The crude product was purified by Prep-HPLC (Waters Xbridge 150×25 5 μm column; 30-70% acetonitrile in a 10 mM ammonium bicarbonate solution in water, 11 min gradient) to give (6-hydroxy-6-phenyl-2-azaspiro[3.3]heptan-2-yl)-(5-phenylisoxazol-3-yl)methanone (29 mg, 0.080 mmol, 25%) as a pale yellow solid. ¹H NMR (400 MHz, Chloroform-d) δ 7.79 (dt, J=2.1, 8.0 Hz, 2H), 7.54-7.38 (m, 7H), 7.36-7.29 (m, 1H), 6.94 (d, J=1.1 Hz, 1H), 4.78 (s, 1H), 4.50 (s, 1H), 4.39 (s, 1H), 4.11 (s, 1H), 2.94-2.82 (m, 2H), 2.74-2.60 (m, 2H), 2.00 (d, J=4.0 Hz, 1H); LCMS (ESI) m/z: 361.1 [M+H]⁺.

Step 4: Preparation of (6-phenyl-2-azaspiro[3.3]hept-6-en-2-yl)-(5-phenylisoxazol-3-yl)methanone

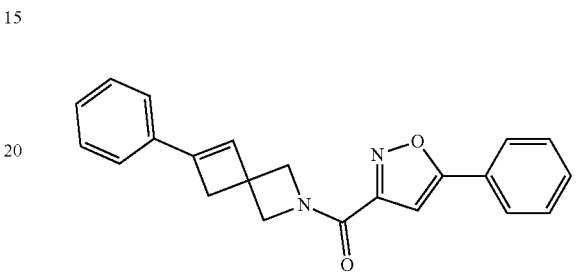

To a stirred solution of 5-phenylisoxazole-3-carboxylic acid (0.062 g, 0.330 mmol), 6-phenyl-2-azaspiro[3.3]heptan-6-ol trifluoroacetic acid (20 mg, 0.066 mmol), 6-phenyl-2-azaspiro[3.3]hept-6-ene trifluoroacetic acid (80 mg, 0.280 mmol) and triethylamine (0.100 g, 0.989 mmol) in dichloromethane (3 mL) at 0° C. was added propylphosphonic anhydride (0.504 g, 0.791 mmol, 50% in ethyl acetate) dropwise. The reaction mixture was stirred at 15° C. for 15 h. The reaction mixture was quenched with water (10 mL) and then extracted with dichloromethane (10 mL×3). The combined organic layers were dried over sodium sulfate, concentrated in vacuo. The crude product was purified by Prep-HPLC (YMC-Actus Triart C18 150×30 5 μm column; 65-90% acetonitrile in a 10 mM ammonium bicarbonate solution in water, 10 min gradient) to give (6-phenyl-2-azaspiro[3.3]hept-6-en-2-yl)-(5-phenylisoxazol-3-yl)methanone (10 mg, 0.026 mmol, 40%) as a brown solid. ¹H NMR (400 MHz, Chloroform-d) δ 7.82-7.77 (m, 2H), 7.51-7.44 (m, 3H), 7.39-7.26 (m, 5H), 6.96 (s, 1H), 6.42 (s, 1H), 4.86-4.71 (m, 2H), 4.49-4.35 (m, 2H), 3.04 (s, 2H); LCMS (ESI) m/z: 343.1 [M+H]⁺.

Example 106. Preparation of (6-phenyl-2-azaspiro[3.3]heptan-2-yl)-(5-phenylisoxazol-3-yl)methanone (227)

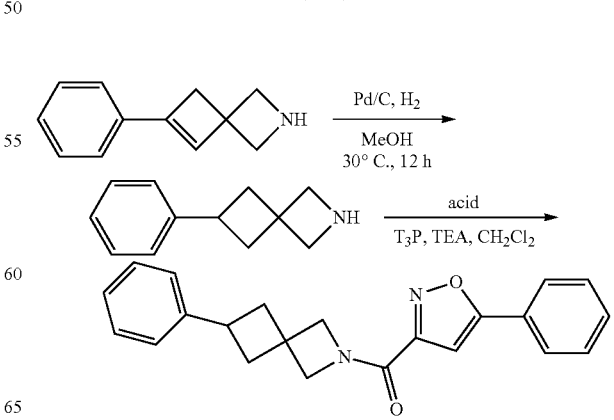

Step 1: Preparation of
6-phenyl-2-azaspiro[3.3]heptane

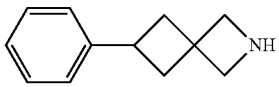

A solution of 6-phenyl-2-azaspiro[3.3]hept-6-ene (540 mg, 1.68 mmol) and palladium on carbon (50 mg, 10% Pd by weight) in methanol (20 mL) at 30° C. under hydrogen (15 psi) was stirred for 12 h. The reaction mixture was filtered and concentrated under reduced pressure to give 6-phenyl-2-azaspiro[3.3]heptane (0.520 g, 1.61 mmol, 96%) as a yellow solid. LCMS (ESI) m/z: 174.3 [M+H]$^+$. The material was used directly in the next step without further purification.

Step 2: Preparation of (6-phenyl-2-azaspiro[3.3]
heptan-2-yl)-(5-phenylisoxazol-3-yl)methanone

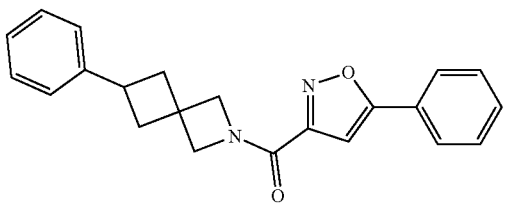 [SMILES: O=C(c1cc(-c2ccccc2)on1)N1CC2(CC(c3ccccc3)C2)C1]

The synthesis of (6-phenyl-2-azaspiro[3.3]heptan-2-yl)-(5-phenylisoxazol-3-yl)methanone was carried out following the procedure reported for the preparation of Example 105. Compound (6-phenyl-2-azaspiro[3.3]heptan-2-yl)-(5-phenylisoxazol-3-yl)methanone (10 mg, 0.028 mmol, 4%) was obtained as a brown solid. $^1$H NMR (400 MHz, Chloroform-d) δ 7.77-7.64 (m, 2H), 7.47-7.32 (m, 3H), 7.24 (m, 1H), 7.19 (s, 1H), 7.17-7.09 (m, 3H), 6.88 (d, J=3.8 Hz, 1H), 4.68 (s, 1H), 4.46 (s, 1H), 4.29 (s, 1H), 4.07 (s, 1H), 3.51-3.29 (m, 1H), 2.70-2.50 (m, 2H), 2.40-2.14 (m, 2H); LCMS (ESI) m/z: 345.0 [M+H]$^+$.

Example 107. Preparation of 4-phenylpiperidin-1-yl)(5-(pyridin-2-yl)isoxazol-3-yl)methanone (318)

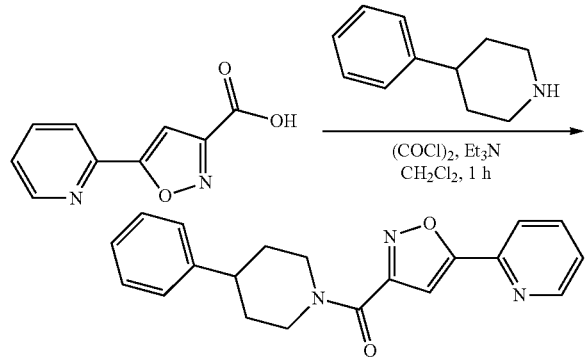

To a solution of 5-(pyridin-2-yl)isoxazole-3-carboxylic acid (150 mg, 0.79 mmol) in dichloromethane (2 mL) at 20° C. was added oxalyl chloride (2 mL). The mixture was stirred at room temperature for 0.5 h. The solvent was removed in vacuo and the solid was dissolved in dichloromethane (2 mL) and added to a mixture of 4-phenylpiperidine (166 mg, 1.03 mmol), triethylamine (239 mg, 2.37 mmol) in dichloromethane (5 mL) dropwise. The reaction mixture was stirred for 0.5 h. The mixture was purified by Prep-HPLC to offer 4-phenylpiperidin-1-yl)(5-(pyridin-2-yl)isoxazol-3-yl)methanone as a white solid (0.104 g, 0.316 mmol, 40%). $^1$H NMR (400 MHz, Dimethylsulfoxide-d$_6$) δ 8.76 (s, 1H), 8.02-8.04 (m, 2H), 7.55-7.57 (m, 1H), 7.20-7.36 (m, 6H), 4.65-4.67 (m, 1H), 4.04-4.06 (m, 1H), 3.26-3.31 (m, 1H), 2.85-2.97 (m, 2H), 1.90-1.92 (m, 1H), 1.81-1.83 (m, 1H), 1.62-1.68 (m, 2H); LCMS (ESI) m/z: 334.1 [M+H]$^+$.

Example 108. Preparation of (4-phenylpiperidin-1-yl)(5-(pyridin-3-yl)isoxazol-3-yl)methanone, trifluoroacetic Acid (315)

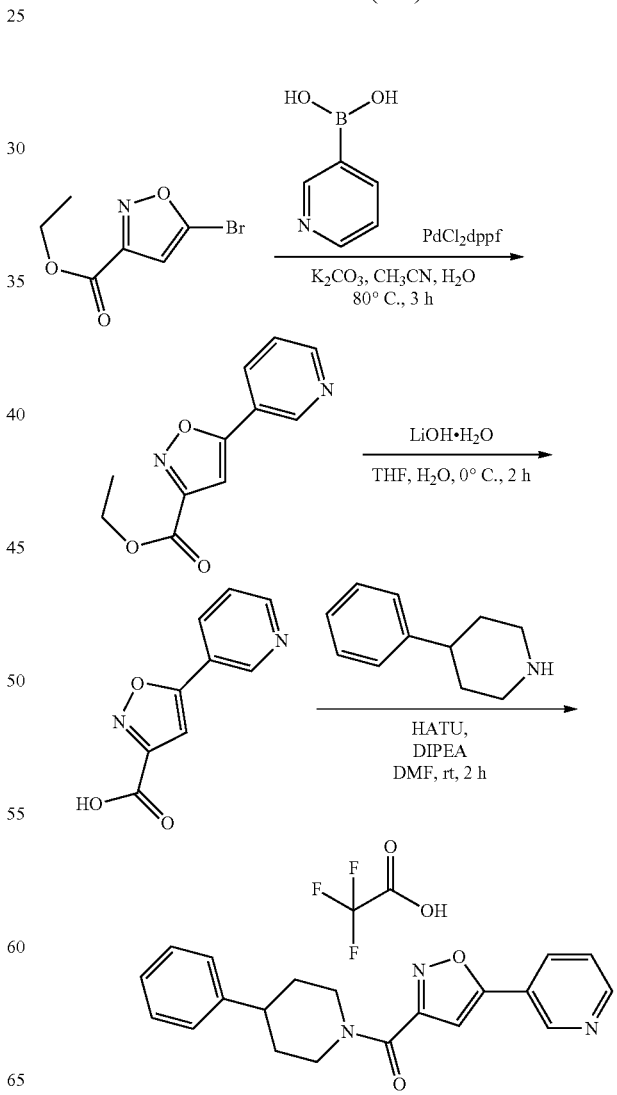

Step 1: Preparation of ethyl 5-(pyridin-3-yl)isoxazole-3-carboxylate

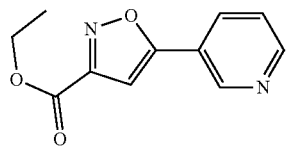 [SMILES: CCOC(=O)c1cc(-c2cccnc2)on1]

The synthesis of ethyl 5-(pyridin-3-yl)isoxazole-3-carboxylate was carried out following the same procedure as Example 24. Compound ethyl 5-(pyridin-3-yl)isoxazole-3-carboxylate (0.360 g, 1.65 mmol, 43%) was obtained as a yellow solid. LCMS (ESI) m/z: 219.1 [M+H]$^+$.

Step 2: Preparation of 5-(pyridin-3-yl)isoxazole-3-carboxylic Acid

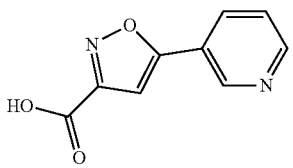 [SMILES: O=C(O)c1cc(-c2cccnc2)on1]

The synthesis of 5-(pyridin-3-yl)isoxazole-3-carboxylic acid was carried out following the same procedure as Example 24. Compound 5-(pyridin-3-yl)isoxazole-3-carboxylic acid (0.180 g, 0.94 mmol, 57%) was obtained as a white solid. LCMS (ESI) m/z: 191.2 [M+H]$^+$.

Step 3: Preparation of (4-phenylpiperidin-1-yl)(5-(pyridin-3-yl)isoxazol-3-yl)methanone, trifluoroacetic Acid Salt

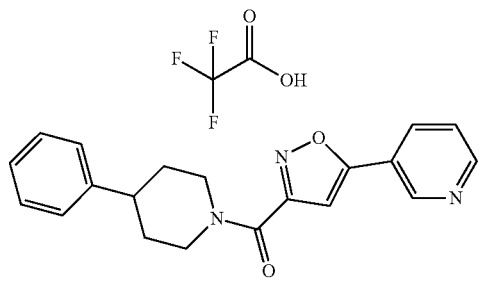

The synthesis of (4-phenylpiperidin-1-yl)(5-(pyridin-3-yl)isoxazol-3-yl)methanone, trifluoroacetic acid salt was carried out following the same procedure as Example 24. Compound (4-phenylpiperidin-1-yl)(5-(pyridin-3-yl)isoxazol-3-yl)methanone, trifluoroacetic acid salt (0.080 g, 0.18 mmol, 58%) was obtained as a white solid. $^1$H NMR (500 MHz, Dimethylsulfoxide-d$_6$) δ 9.19 (d, J=2.0 Hz, 1H), 8.76-8.74 (m, 1H), 8.39-8.37 (m, 1H), 7.67-7.65 (m, 1H), 7.50 (s, 1H), 7.33-7.20 (m, 5H), 4.68-4.65 (m, 1H), 4.12-4.10 (m, 1H), 3.32-3.27 (m, 1H), 2.98-2.85 (m, 2H), 1.93-1.82 (m, 2H), 1.69-1.59 (m, 2H); LCMS (ESI) m/z: 334.1 [M+H]$^+$.

Example 109. Preparation of 4-(3-(4-phenylpiperidine-1-carbonyl)isoxazol-5-yl)benzonitrile (316)

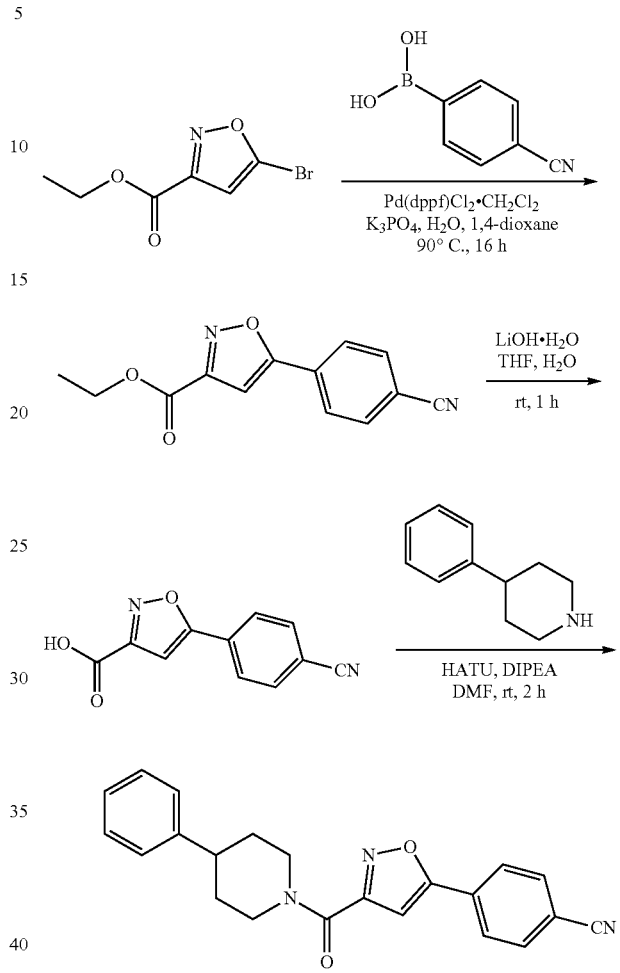

Step 1: Preparation of ethyl 5-(4-cyanophenyl)isoxazole-3-carboxylate

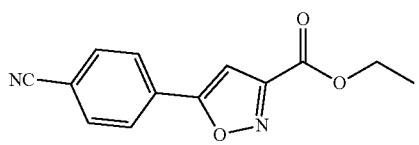 [SMILES: CCOC(=O)c1cc(-c2ccc(C#N)cc2)on1]

The mixture of ethyl 5-bromoisoxazole-3-carboxylate (0.300 g, 1.37 mmol), 4-cyanophenylboronic acid (201 mg, 1.37 mmol), 1,1'-bis(diphenylphosphino)ferrocene]palladium(II) dichloride (224 mg, 0.27 mmol) and potassium phosphate (580 mg, 2.74 mmol) in 1,4-dioxane (15 mL) and water (4 mL) under nitrogen was heated to 80° C. for 16 h. The mixture was concentrated under reduced pressure, and the residue was purified by column chromatography (silica, petroleum ether/ethyl acetate=4/1) to afford ethyl 5-(4-cyanophenyl)isoxazole-3-carboxylate (240 mg, 0.99 mmol, 67%) as a grey solid. LCMS (ESI) m/z: 243.1 [M+H]$^+$.

Step 2: Preparation of 5-(4-cyanophenyl)isoxazole-3-carboxylic Acid

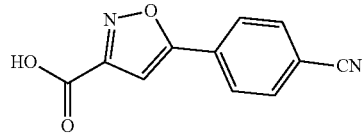 [SMILES: N#Cc1ccc(-c2cc(C(=O)O)no2)cc1]

The synthesis of 5-(4-cyanophenyl)isoxazole-3-carboxylic acid was carried out following the same procedure as Example 24. Compound 5-(4-cyanophenyl)isoxazole-3-carboxylic acid (0.120 g, 0.56 mmol, 56%) was obtained as a grey solid. LCMS (ESI) m/z: 215.1 [M+H]+.

Step 3: Preparation of 4-(3-(4-phenylpiperidine-1-carbonyl)isoxazol-5-yl)benzonitrile

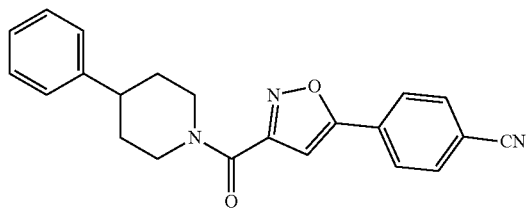 [SMILES: N#Cc1ccc(-c2cc(C(=O)N3CCC(c4ccccc4)CC3)no2)cc1]

The synthesis of 4-(3-(4-phenylpiperidine-1-carbonyl)isoxazol-5-yl)benzonitrile was carried out following the same procedure as Example 24. Compound 4-(3-(4-phenylpiperidine-1-carbonyl)isoxazol-5-yl)benzonitrile (0.051 g, 0.14 mmol, 51%) was obtained as a white solid. $^1$H NMR (500 MHz, Dimethylsulfoxide-d$_6$) δ 8.13 (d, J=8.0 Hz, 2H), 8.05 (d, J=8.0 Hz, 2H), 7.55 (s, 1H), 7.32-7.28 (m, 4H), 7.22-7.19 (m, 1H), 4.65 (d, J=13.0 Hz, 1H), 4.08 (d, J=13.0 Hz, 1H), 3.32-3.26 (m, 1H), 2.97-2.88 (m, 2H), 1.92 (d, J=8.0 Hz, 1H), 1.83 (d, J=8.0 Hz, 1H), 1.65-1.60 (m, 2H); LCMS (ESI) m/z: 358.2 [M+H]+.

Example 110. Preparation of 2-(3-(4-phenylpiperidine-1-carbonyl)isoxazol-5-yl)benzonitrile (326)

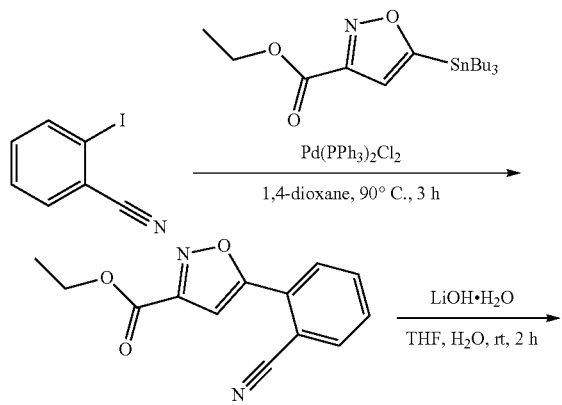

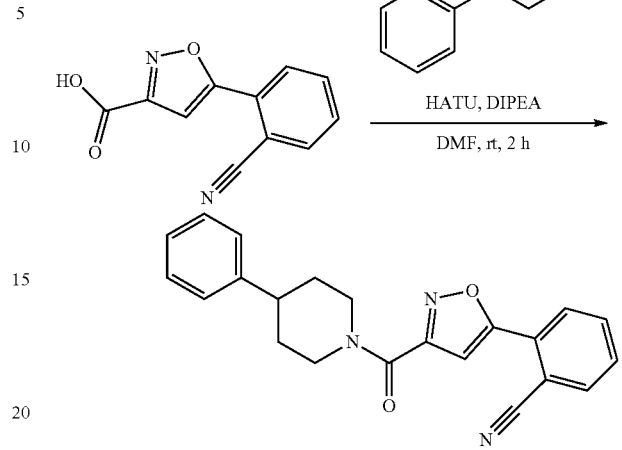

Step 1: Preparation of ethyl 5-(2-cyanophenyl)isoxazole-3-carboxylate

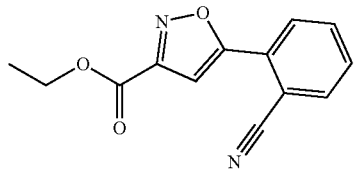 [SMILES: CCOC(=O)c1cc(-c2ccccc2C#N)on1]

The mixture of 2-iodobenzonitrile (0.600 g, 2.62 mmol), ethyl 5-(tributylstannyl)isoxazole-3-carboxylate (1.69 g, 3.93 mmol) and bis(triphenylphosphine)palladium(II) dichloride (0.184 g, 0.26 mmol) in 1,4-dioxane (40 mL) under nitrogen was heated 90° C. for 3 h. The mixture was concentrated under reduced pressure, and the residue was purified by column chromatography (silica, petroleum ether/ethyl acetate=5/1) to give ethyl 5-(2-cyanophenyl)isoxazole-3-carboxylate (0.191 g, 0.79 mmol, 30%) as a yellow oil. LCMS (ESI) m/z: 243.1 [M+H]+.

Step 2: Preparation of 5-(2-cyanophenyl)isoxazole-3-carboxylic Acid)

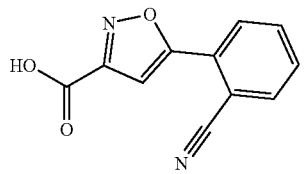 [SMILES: N#Cc1ccccc1-c1cc(C(=O)O)no1]

The synthesis of 5-(2-cyanophenyl)isoxazole-3-carboxylic acid was carried out following the same procedure as Example 24. Compound 5-(2-cyanophenyl)isoxazole-3-carboxylic acid (0.123 g, 0.57 mmol, 72%) was obtained as a yellow solid. LCMS (ESI) m/z: 215.1 [M+H]+.

Step 3: Preparation of 2-(3-(4-phenylpiperidine-1-carbonyl)isoxazol-5-yl)benzonitrile

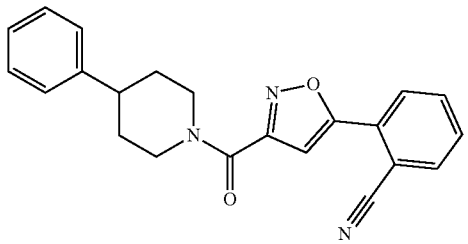 [SMILES: N#Cc1ccccc1-c1cc(C(=O)N2CCC(c3ccccc3)CC2)no1]

The synthesis of 2-(3-(4-phenylpiperidine-1-carbonyl)isoxazol-5-yl)benzonitrile was carried out following the same procedure as Example 24. Compound 2-(3-(4-phenylpiperidine-1-carbonyl)isoxazol-5-yl)benzonitrile (0.019 g, 0.05 mmol, 18%) was obtained as a white solid. $^1$H NMR (500 MHz, Dimethylsulfoxide-$d_6$) δ 8.14-8.09 (m, 2H), 7.92 (t, J=7.5 Hz, 1H), 7.76 (t, J=7.5 Hz, 1H), 7.44 (s, 1H), 7.33-7.27 (m, 4H), 7.22-7.19 (m, 1H), 4.68-4.65 (m, 1H), 4.14-4.11 (m, 1H), 3.33-3.28 (m, 1H), 2.99-2.86 (m, 2H), 1.93-1.82 (m, 2H), 1.71-1.62 (m, 2H); LCMS (ESI) m/z: 358.1 [M+H]$^+$.

Example 111. Preparation of 5-phenylisoxazol-3-yl)(4-phenylpiperidin-1-yl)methanone (314)

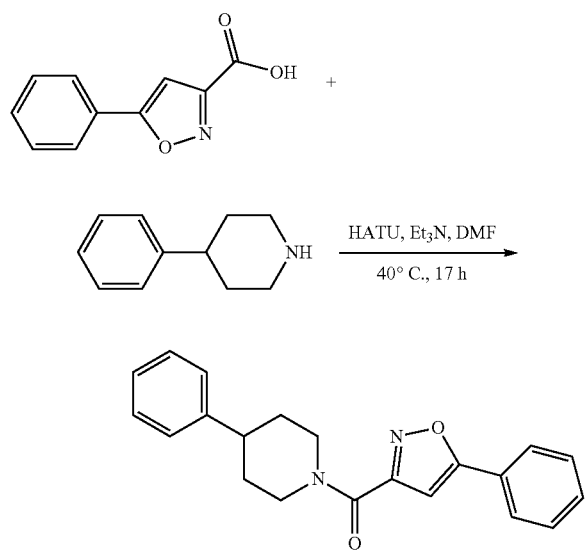

The synthesis of (5-phenylisoxazol-3-yl)(4-phenylpiperidin-1-yl)methanone was carried out following the same procedure as Example 24. Compound (5-phenylisoxazol-3-yl)(4-phenylpiperidin-1-yl)methanone (67.5 mg, 0.20 mmol, 26%) was obtained as a white solid. $^1$H NMR (500 MHz, Dimethylsulfoxide-$d_6$) δ 7.94 (dd, J=8.0, 1.5 Hz, 2H), 7.63-7.44 (m, 3H), 7.36-7.25 (m, 5H), 7.21 (t, J=7.0 Hz, 1H), 4.66 (d, J=13.0 Hz, 1H), 4.10 (d, J=13.5 Hz, 1H), 3.27 (dd, J=18.5, 7.5 Hz, 1H), 3.00-2.79 (m, 2H), 1.91 (d, J=13.0 Hz, 1H), 1.83 (d, J=12.5 Hz, 1H), 1.73-1.50 (m, 2H); LCMS (ESI) m/z: 333.1 [M+H]$^+$.

Example 112. Preparation of 3-fluoro-4-(3-(4-phenylpiperidine-1-carbonyl)isoxazol-5-yl)benzonitrile (325)

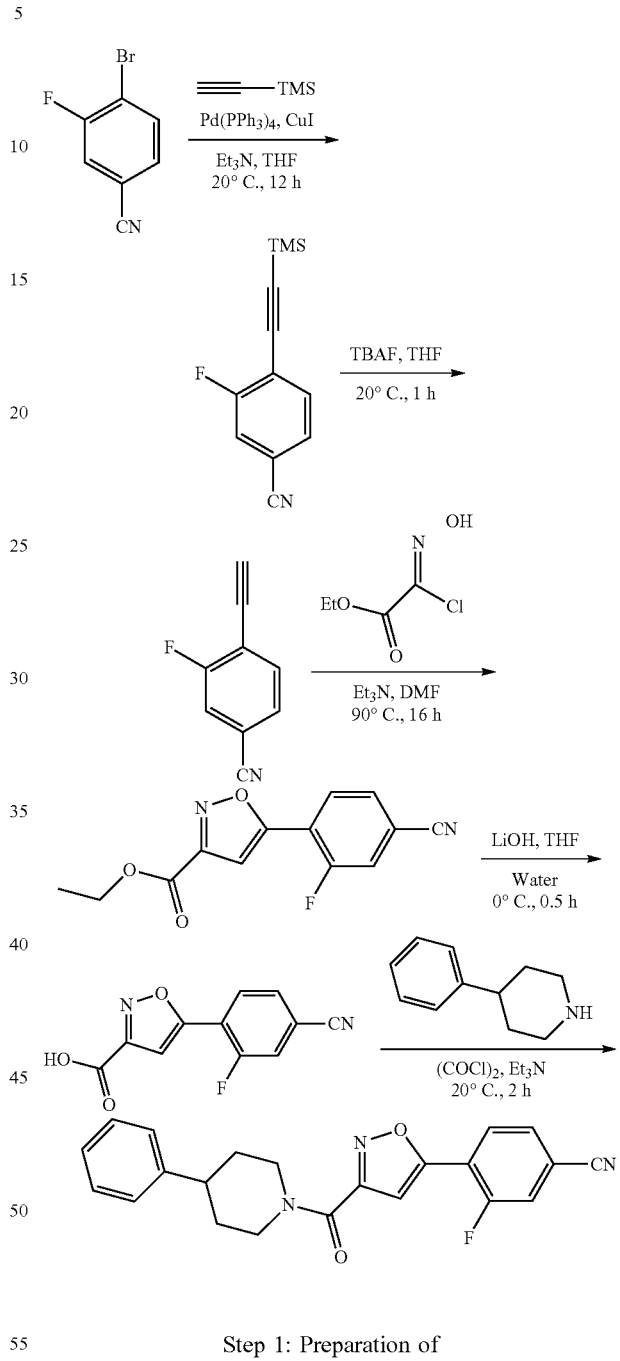

Step 1: Preparation of 3-fluoro-4-((trimethylsilyl)ethynyl)benzonitrile

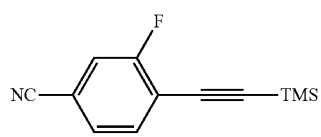 [SMILES: C[Si](C)(C)C#Cc1ccc(C#N)cc1F]

To a solution of 4-bromo-3-fluorobenzonitrile (4.0 g, 20.1 mmol) and triethylamine (5 mL) in tetrahydrofuran (5 mL)

under nitrogen was added ethynyltrimethylsilane (2.17 g, 22.1 mmol), tetrakis(triphenylphosphine)palladium(0) (0.460 g, 0.40 mmol) and copper(I) iodide (84 mg, 0.44 mmol). Then the mixture was stirred at 20° C. for 3 h. The solvent was removed under reduced pressure. The residue was dissolved in dichloromethane (100 mL) and then washed with water (100 mL) and brine (100 mL), dried over sodium sulfate, filtered and concentrated in vacuo. The crude product was purified by column chromatography (silica, petroleum ether/ethyl acetate=6/1) to give 3-fluoro-4-((trimethylsilyl)ethynyl)benzonitrile (3.0 g, 13.9 mmol, 69%) as a white solid; LCMS (ESI) m/z: 218.1 [M+H]$^+$.

Step 2: Preparation of 4-ethynyl-3-fluorobenzonitrile

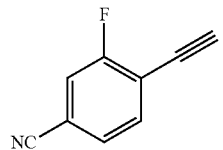

To a solution of 3-fluoro-4-((trimethylsilyl)ethynyl)benzonitrile (3.0 g, 13.8 mmol) in tetrahydrofuran (25 mL) at 20° C. was added tetrabutylammonium fluoride in tetrahydrofuran (27 mL, 1 M). The solution mixture was stirred at 20° C. for 0.5 h. The volatiles were removed under reduced pressure. The residue was dissolved in dichloromethane (100 mL) and then washed with water (100 mL) and brine (100 mL) dried over sodium sulfate, filtered and concentrated in vacuo. The crude product was purified by column chromatography (petroleum ether/ethyl acetate=6/1) to give 4-ethynyl-3-fluorobenzonitrile as a yellow solid (0.88 g, 6.07 mmol, 44%).

Step 3: Preparation of ethyl 5-(4-cyano-2-fluorophenyl)isoxazole-3-carboxylate

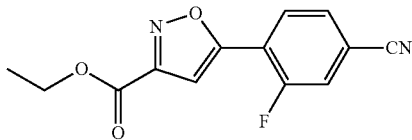 [SMILES: CCOC(=O)c1cc(-c2ccc(C#N)cc2F)on1]

To a solution of (Z)-ethyl 2-chloro-2-(hydroxyimino) acetate (0.366 g, 2.43 mmol) in N,N'-dimethylformamide (2 mL) at 20° C. was slowly added a solution of 4-ethynyl-3-fluorobenzonitrile (0.88 g, 6.07 mmol) in N,N'-dimethylformamide (10 mL) under nitrogen. The solution mixture was heated to 90° C. before triethylamine (0.737 g, 7.29 mmol) in N,N'-dimethylformamide (2 mL) was slowly added. The reaction mixture was heated at 90° C. for 2 h. The reaction was diluted with dichloromethane (100 mL) and then washed with water (100 mL) and brine (100 mL), dried over sodium sulfate, filtered and concentrated in vacuo. The crude product was purified by column chromatography (silica, petroleum ether/ethyl acetate=4/1) to give ethyl 5-(4-cyano-2-fluorophenyl)isoxazole-3-carboxylate as a yellow oil (0.36 g, 1.39 mmol, 57%). LCMS (ESI) m/z: 261.1 [M+H]$^+$.

Step 4: Preparation of 5-(4-cyano-2-fluorophenyl)isoxazole-3-carboxylic Acid

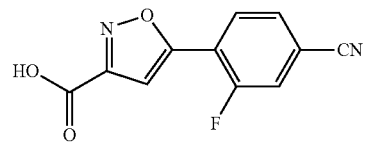 [SMILES: N#Cc1ccc(-c2cc(C(=O)O)no2)c(F)c1]

To the solution of ethyl 5-(4-cyano-2-fluorophenyl)isoxazole-3-carboxylate (0.2 g, 0.769 mmol) in a 1/1 mixture of tetrahydrofuran/water (3 mL) was added lithium hydroxide hydrate (32 mg, 0.769 mmol). The reaction mixture was stirred at 10° C. for 0.5 h. The volatiles were removed in vacuo and the aqueous layer was adjusted to pH=3'5 with aqueous 1N hydrogen chloride. Then water was removed to give 5-(4-cyano-2-fluorophenyl)isoxazole-3-carboxylic acid as a white solid (0.130 g, 0.561 mmol, 73%). This material was used in the next step without further purification. LCMS (ESI) m/z: 233.1 [M+H]$^+$.

Step 5: Preparation of 3-fluoro-4-(3-(4-phenylpiperidine-1-carbonyl)isoxazol-5-yl)benzonitrile

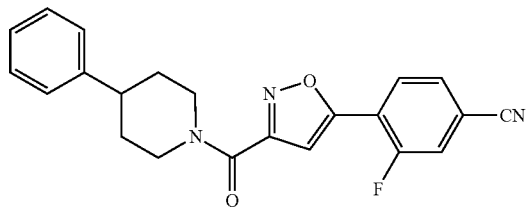 [SMILES: N#Cc1ccc(-c2cc(C(=O)N3CCC(c4ccccc4)CC3)no2)c(F)c1]

To a solution of 5-(4-cyano-2-fluorophenyl)isoxazole-3-carboxylic acid (0.120 g, 0.577 mmol) in dichloromethane (3 mL) was added at 20° C. oxalyl chloride (1 mL). The reaction mixture was stirred at room temperature for 0.5 h. The solvent was removed in vacuo and the resulting solid was dissolved in dichloromethane (5 mL) and added to a mixture of 4-phenylpiperidine (0.108 g, 0.672 mmol) and triethylamine (0.157 g, 1.55 mmol) in dichloromethane (3 mL) dropwise. Then the mixture was stirred for another 0.5 h. The reaction was purified by column chromatography (silica, petroleum ether/ethyl acetate=1/1) to offer 3-fluoro-4-(3-(4-phenylpiperidine-1-carbonyl)isoxazol-5-yl)benzonitrile as a light yellow solid (0.128 g, 0.340 mmol, 59%). $^1$H NMR (400 MHz, Dimethylsulfoxide-d$_6$) δ 8.16-8.21 (m, 2H), 7.91-7.93 (m, 1H), 7.27-7.35 (m, 5H), 7.19-7.22 (m, 1H), 4.64-4.67 (m, 1H), 4.02-4.05 (m, 1H), 3.27-3.29 (m, 1H), 2.87-2.97 (m, 2H), 1.90-1.92 (m, 1H), 1.80-1.83 (m, 1H), 1.62-1.68 (m, 2H); LCMS (ESI) m/z: 376.1 [M+H]$^+$.

Example 113. Preparation of 5-(1,3-benzodioxol-5-yl)isoxazol-3-yl]-(4-phenyl-1-piperidyl)methanone (275)

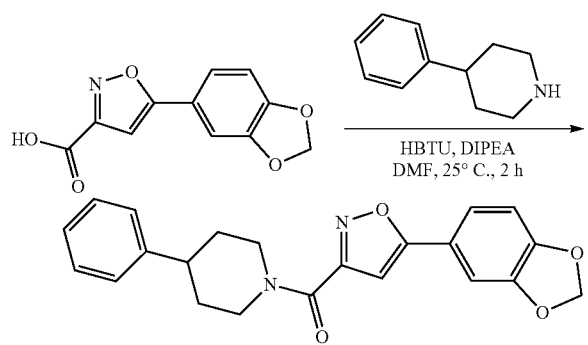

To a stirred solution of 5-(1,3-benzodioxol-5-yl)isoxazole-3-carboxylic acid (0.080 g, 0.343 mmol) and N,N,N',N'-tetramethyl-O-(1H-benzotriazol-1-yl)uronium hexafluorophosphate (0.130 g, 0.343 mmol) in N,N'-dimethylformamide (2 mL) was added diisopropylethylamine (0.089 g, 0.686 mmol) and 4-phenylpiperidine (0.055 g, 0.343 mmol). The mixture was stirred at 25° C. for 2 h and purified directly by prep-HPLC (Luna C18 150×25 5 μm; 47-77% acetonitrile in a 10 mM ammonium bicarbonate solution in water, 12 min gradient) to give [5-(1,3-benzodioxol-5-yl)isoxazol-3-yl]-(4-phenyl-1-piperidyl)methanone (64 mg, 0.171 mmol, 50%) as a yellow solid. $^1$H NMR (400 MHz, Chloroform-d) δ 7.35 (br. t, J=8.3 Hz, 3H), 7.29 (s, 1H), 7.27-7.22 (m, 3H), 6.93 (d, J=8.2 Hz, 1H), 6.71 (s, 1H), 6.08 (s, 2H), 4.93 (br. d, J=13.2 Hz, 1H), 4.66 (br. d, J=13.7 Hz, 1H), 3.35-3.22 (m, 1H), 2.98-2.81 (m, 2H), 2.09-1.93 (m, 2H), 1.89-1.75 (m, 2H); LCMS (ESI) m/z: 377.1 [M+H]$^+$.

Example 114. Preparation of 5-phenylisoxazol-3-yl)-[4-[2-(trifluoromethyl)phenyl]-1-piperidyl]methanone (289)

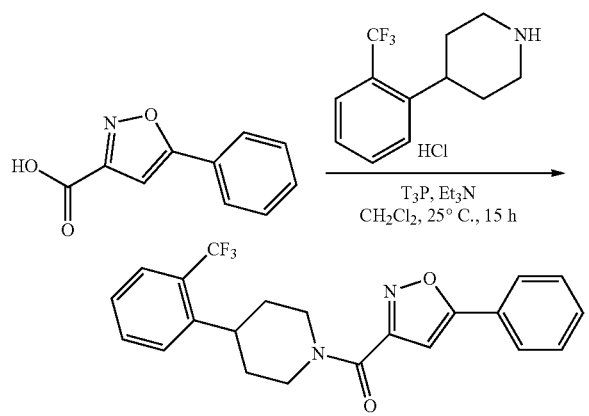

To a stirred solution of 5-phenylisoxazole-3-carboxylic acid (0.100 g, 0.529 mmol) in dichloromethane (3 mL) was added 4-[2-(trifluoromethyl)phenyl]piperidine (0.155 g, 0.582 mmol), triethylamine (0.160 g, 1.59 mmol) and propylphosphonic anhydride (0.505 g, 0.793 mmol, 50% in ethyl acetate). The mixture was stirred at 25° C. for 15 h. The reaction mixture was quenched with water (10 mL) and extracted with dichloromethane (10 mL×3). The combined organic layers were washed with brine (30 mL), dried over sodium sulfate, filtered and concentrated under reduced pressure. The residue was purified by prep-HPLC (YMC-Actus Triart C18 100×30 mm×5 μm column; 60-90% acetonitrile in a 10 mM ammonium bicarbonate solution in water, 12 min gradient) to offer (5-phenylisoxazol-3-yl)-[4-[2-(trifluoromethyl)phenyl]-1-piperidyl]methanone (0.135 g, 0.336 mmol, 64%) as a pale yellow solid. $^1$H NMR (400 MHz, Chloroform-d) δ 7.82 (dd, J=1.8, 7.5 Hz, 2H), 7.66 (d, J=7.9 Hz, 1H), 7.57-7.43 (m, 5H), 7.33 (t, J=7.7 Hz, 1H), 6.85 (s, 1H), 4.95 (br. d, J=13.6 Hz, 1H), 4.69 (br. d, J=13.6 Hz, 1H), 3.35-3.21 (m, 2H), 2.92 (dt, J=2.9, 13.0 Hz, 1H), 2.02-1.75 (m, 4H); LCMS (ESI) m/z: 401.1 [M+H]$^+$.

Example 115. Preparation of [5-(1,3-benzodioxol-5-yl)isoxazol-3-yl]-[4-[2-(trifluoromethyl)phenyl]-1-piperidyl]methanone (302)

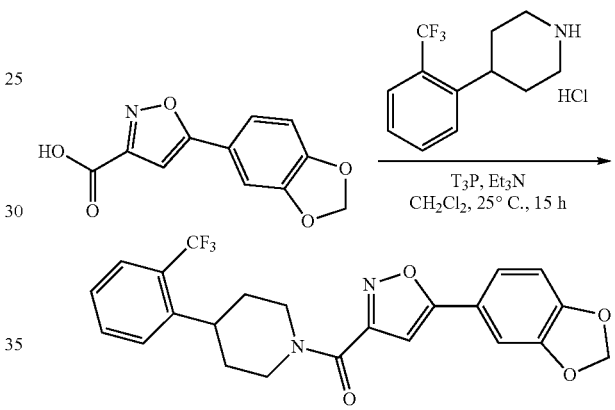

The synthesis of 5-(1,3-benzodioxol-5-yl)isoxazol-3-yl]-[4-[2-(trifluoromethyl)phenyl]-1-piperidyl]methanone was carried out following the same procedure as Example 114. Compound [5-(1,3-benzodioxol-5-yl)isoxazol-3-yl]-[4-[2-(trifluoromethyl)phenyl]-1-piperidyl]methanone (0.072 g, 0.162 mmol, 38%) was obtained as a white solid. $^1$H NMR (400 MHz, Dimethylsulfoxide-d$_6$) δ 7.72-7.60 (m, 3H), 7.51-7.45 (m, 2H), 7.45-7.39 (m, 1H), 7.18 (s, 1H), 7.10 (d, J=8.1 Hz, 1H), 6.14 (s, 2H), 4.67 (br. d, J=13.1 Hz, 1H), 4.16 (br. d, J=13.6 Hz, 1H), 3.32-3.24 (m, 1H), 3.17 (br. t, J=10.9 Hz, 1H), 2.94 (dt, J=2.9, 12.6 Hz, 1H), 1.89-1.66 (m, 4H); LCMS (ESI) m/z: 445.1 [M+H]$^+$.

Example 116. Preparation of 5-(1,3-benzodioxol-5-yl)isoxazol-3-yl]-[4-(2-chloro-5-fluoro-phenyl)-1-piperidyl]methanone (308)

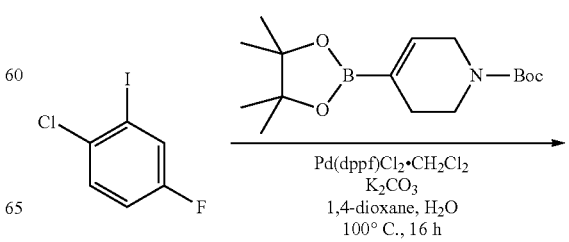

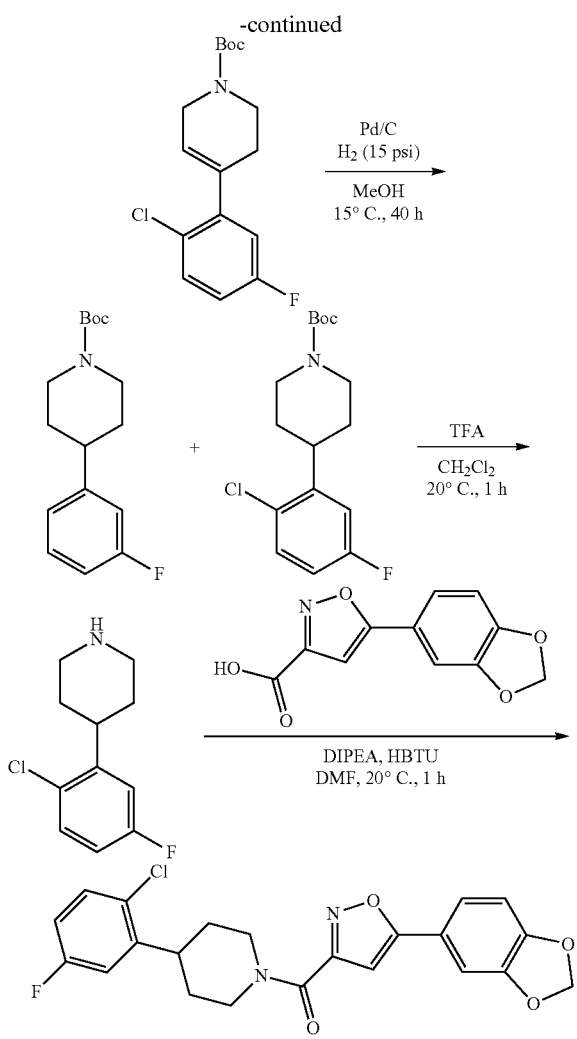

Step 1: Preparation of tert-butyl 4-(2-chloro-5-fluoro-phenyl)-3,6-dihydro-2H-pyridine-1-carboxylate

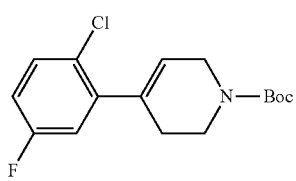

To a sealed tube was added sequentially 1-chloro-4-fluoro-2-iodo-benzene (1 g, 3.90 mmol), tert-butyl 4-(4,4,5,5-tetramethyl-1,3,2-dioxaborolan-2-yl)-3,6-dihydro-2H-pyridine-1-carboxylate (1.21 g, 3.90 mmol), potassium carbonate (1.62 g, 11.7 mmol), [1,1'-bis(diphenylphosphino)ferrocene]palladium(II) dichloride (0.318 g, 0.390 mmol) and 1,4-dioxane (10 mL) and water (1 mL). Then the mixture was degassed with nitrogen for 30 seconds and heated to 100° C. 16 h. The reaction mixture was cooled to room temperature and purified by column chromatography (ISCO, 20 g silica, 0-5% ethyl acetate in petroleum ether, gradient over 20 min) to afford tert-butyl 4-(2-chloro-5-fluoro-phenyl)-3,6-dihydro-2H-pyridine-1-carboxylate (0.860 g, 2.76 mmol, 71%) as a colorless gum. LCMS (ESI) m/z: 256.3 [M+H-56]⁺.

Step 2: Preparation of tert-butyl 4-(2-chloro-5-fluoro-phenyl)piperidine-1-carboxylate and tert-butyl 4-(3-fluorophenyl)piperidine-1-carboxylate

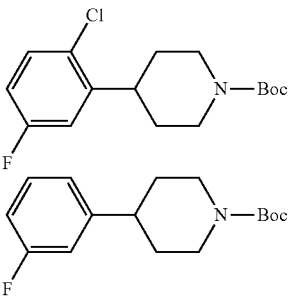

To a solution of tert-butyl 4-(2-chloro-5-fluoro-phenyl)-3,6-dihydro-2H-pyridine-1-carboxylate (0.700 g, 2.25 mmol) in methanol (5 mL) was added palladium on carbon (10% Pd by weight, 0.05 g) under nitrogen. The suspension was degassed under vacuum and purged with hydrogen (3×). Then the mixture was stirred at 15° C. for 40 h under hydrogen (15 psi). The mixture was filtered and the filtrate was concentrated in vacuo. The crude product was purified by prep-HPLC (Waters X bridge 150×25 5 μm column; 51-71% acetonitrile in a 10 mM ammonium bicarbonate solution in water, 11 min gradient) to afford firstly tert-butyl 4-(2-chloro-5-fluoro-phenyl)piperidine-1-carboxylate (0.050 g, 0.159 mmol, 7%) as a white solid. LCMS (ESI) m/z: 257.9 [M+H-56]⁺ and secondly tert-butyl 4-(3-fluorophenyl)piperidine-1-carboxylate (0.160 g, 0.573 mmol, 25%) as a white solid.

Step 3: Preparation of 4-(2-chloro-5-fluoro-phenyl)piperidine

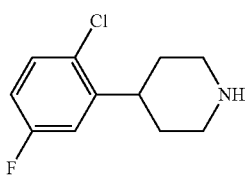 [SMILES: Fc1ccc(Cl)c(C2CCNCC2)c1]

To a stirred solution of tert-butyl 4-(2-chloro-5-fluoro-phenyl)piperidine-1-carboxylate (0.044 g, 0.140 mmol) in dichloromethane (3 mL) was added trifluoroacetic acid (1 mL). The reaction mixture was stirred at 20° C. for 1 h then concentrated to afford 4-(2-chloro-5-fluoro-phenyl)piperidine (0.050 g, crude, trifluoroacetic acid salt) as a yellow gum. LCMS (ESI) m/z: 214.4 [M+H]⁺. This material was used in the next step without further purification.

Step 4: Preparation of [5-(1,3-benzodioxol-5-yl)isoxazol-3-yl]-[4-(2-chloro-5-fluoro-phenyl)-1-piperidyl]methanone

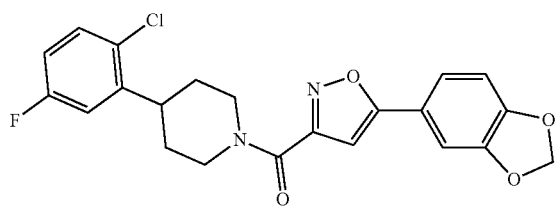 [SMILES: O=C(c1cc(-c2ccc3c(c2)OCO3)on1)N1CCC(c2cc(F)ccc2Cl)CC1]

To a stirred solution of 5-(1,3-benzodioxol-5-yl)isoxazole-3-carboxylic acid (32 mg, 0.137 mmol) in N,N'-dimethylformamide (2 mL) was added N,N,N',N'-tetramethyl-O-(1H-benzotriazol-1-yl)uronium hexafluorophosphate (62 mg, 0.165 mmol), diisopropylethylamine (89 mg, 0.687 mmol) and 4-(2-chloro-5-fluoro-phenyl)piperidine trifluoroacetic acid salt (45 mg, 0.137 mmol). Then the mixture was stirred at 20° C. for 1 h. The mixture was purified directly by prep-HPLC (Waters X bridge 150×25 5 μm column; 46-66% acetonitrile in a 10 mM ammonium bicarbonate solution in water, 11 min gradient) to give [5-(1,3-benzodioxol-5-yl)isoxazol-3-yl]-[4-(2-chloro-5-fluoro-phenyl)-1-piperidyl]methanone (31 mg, 0.071 mmol, 52%) as a yellow solid. $^{1}$H NMR (400 MHz, Chloroform-d) δ 7.37-7.30 (m, 2H), 7.25 (s, 1H), 6.97 (dd, J=2.0, 9.6 Hz, 1H), 6.94-6.85 (m, 2H), 6.70 (s, 1H), 6.06 (s, 2H), 4.94 (br. d, J=13.2 Hz, 1H), 4.70 (d, J=13.4 Hz, 1H), 3.41-3.22 (m, 2H), 2.94 (t, J=11.2 Hz, 1H), 2.11-1.91 (m, 2H), 1.78-1.59 (m, 2H); LCMS (ESI m/z: 429.0 [M+H]$^{+}$.

Example 117. Preparation of 4-(2-chloro-5-fluoro-phenyl)-1-piperidyl]-(5-phenylisoxazol-3-yl)methanone (310)

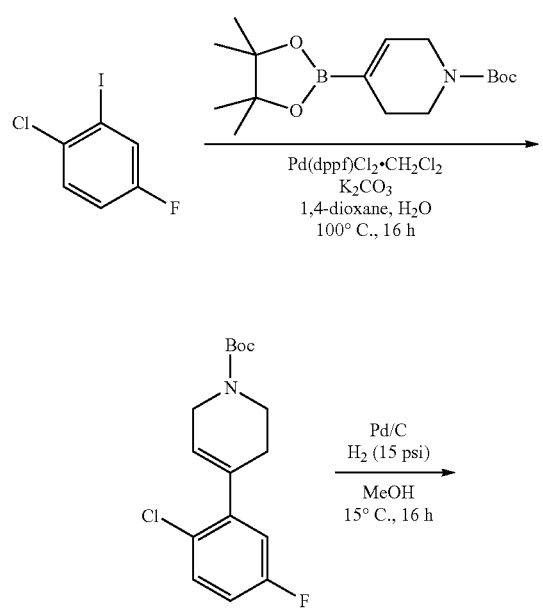

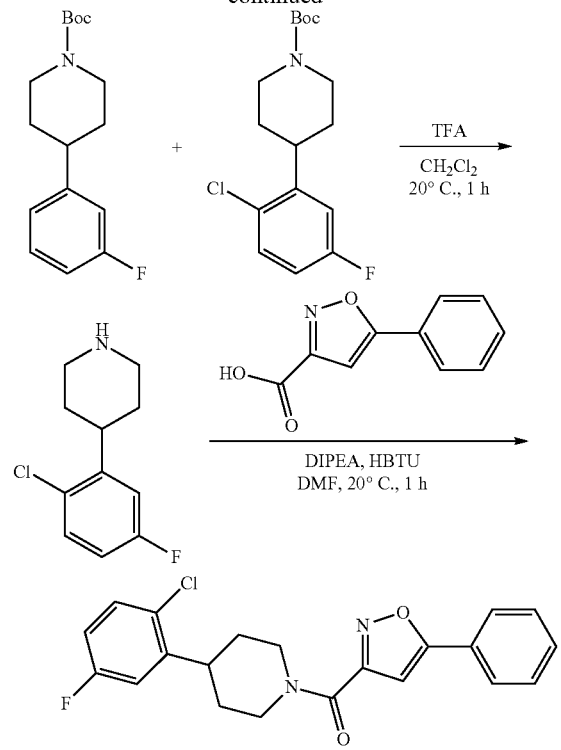

Step 1: Preparation of tert-butyl 4-(2-chloro-5-fluoro-phenyl)-3,6-dihydro-2H-pyridine-1-carboxylate

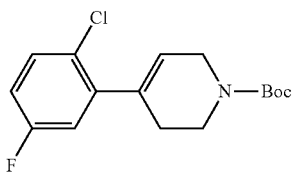

To a sealed tube was added sequentially 1-chloro-4-fluoro-2-iodo-benzene (1.0 g, 3.90 mmol), tert-butyl 4-(4,4,5,5-tetramethyl-1,3,2-dioxaborolan-2-yl)-3,6-dihydro-2H-pyridine-1-carboxylate (1.21 g, 3.90 mmol), potassium carbonate (1.62 g, 11.7 mmol), [1,1'-bis(diphenylphosphino)ferrocene]palladium(II) dichloride (0.318 g, 0.390 mmol) and 1,4-dioxane (10 mL) and water (1 mL). Then the mixture was degassed with nitrogen for 30 seconds and heated to 100° C. for 16 h. The reaction mixture was concentrated in vacuo. The crude product was purified by column chromatography (ISCO, 20 g silica, 0-5% ethyl acetate in petroleum ether, gradient over 20 min) to afford tert-butyl 4-(2-chloro-5-fluoro-phenyl)-3,6-dihydro-2H-pyridine-1-carboxylate (0.860 g, 2.76 mmol, 71%) as a colorless gum. LCMS (ESI) m/z: 256.3 [M+H-56]$^{+}$.

Step 2: Preparation of tert-butyl 4-(2-chloro-5-fluoro-phenyl)piperidine-1-carboxylate and tert-butyl 4-(3-fluorophenyl)piperidine-1-carboxylate

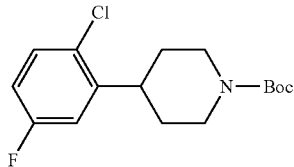

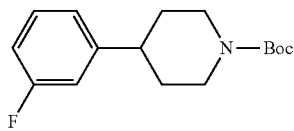

To a solution of tert-butyl 4-(2-chloro-5-fluoro-phenyl)-3,6-dihydro-2H-pyridine-1-carboxylate (0.300 g, 0.962 mmol) in methanol (5 mL) was added palladium on carbon (0.05 g, 0.962 mmol, 10% Pd by weight) under nitrogen. The suspension was degassed under vacuum and purged with hydrogen (3×). The reaction mixture was stirred at 15° C. for 16 h under hydrogen (15 psi). The mixture was filtered and the filtrate was concentrated in vacuo. A mixture of tert-butyl 4-(2-chloro-5-fluoro-phenyl)piperidine-1-carboxylate and tert-butyl 4-(3-fluorophenyl)piperidine-1-carboxylate (0.280 g, crude, 1:1) was obtained as a yellow gum. This material was used in the next step without further purification.

Step 3: Preparation of 4-(2-chloro-5-fluoro-phenyl)piperidine and 4-(3-fluorophenyl)piperidine

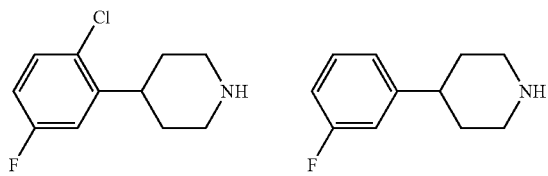 [SMILES: Fc1ccc(Cl)c(C2CCNCC2)c1 ; Fc1cccc(C2CCNCC2)c1]

To a mixture of tert-butyl 4-(2-chloro-5-fluoro-phenyl)piperidine-1-carboxylate and tert-butyl 4-(3-fluorophenyl)piperidine-1-carboxylate (0.280 g, 0.892 mmol) in dichloromethane (4 mL) was added trifluoroacetic acid (1 mL). Then the mixture was stirred at 20° C. for 2 h. The mixture was concentrated in vacuo to give a mixture of 4-(2-chloro-5-fluoro-phenyl)piperidine (trifluoroacetic acid) and 4-(3-fluorophenyl)piperidine (total 300 mg, crude, trifluoroacetic acid, 1:1) as a yellow gum. This material was used in the next step without further purification.

Step 4: Preparation of [5-(1,3-benzodioxol-5-yl)isoxazol-3-yl]-[4-(2-chloro-5-fluoro-phenyl)-1-piperidyl]methanone

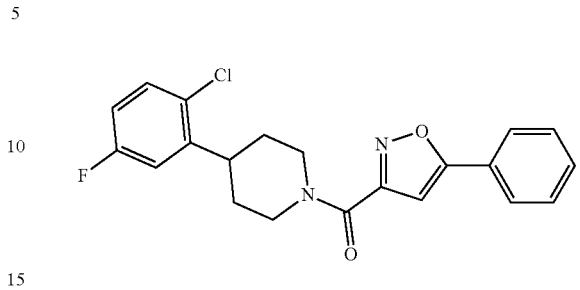

To a stirred solution of 5-phenylisoxazole-3-carboxylic acid (0.120 g, 0.634 mmol) in N,N'-dimethylformamide (4 mL) was added [4-(2-chloro-5-fluoro-phenyl)piperidine and 4-(3-fluorophenyl)piperidine (0.250 mg, 0.763 mmol, trifluoroacetic acid salt, mixture, 1:1)], followed by N,N,N',N'-tetramethyl-O-(1H-benzotriazol-1-yl)uronium hexafluorophosphate (0.289 g, 0.761 mmol) and diisopropylethylamine (0.410 g, 3.17 mmol). The mixture was stirred at 20° C. for 2 h and purified directly by prep-HPLC: (Waters X bridge 150×25 5 μm column; 46-70% acetonitrile in a 10 mM ammonium bicarbonate solution in water, 11 min gradient) to give [4-(2-chloro-5-fluoro-phenyl)-1-piperidyl]-(5-phenylisoxazol-3-yl)methanone (49 mg, 0.125 mmol, 20%) as a brown solid. $^1$H NMR (400 MHz, Chloroform-d) δ 7.88-7.76 (m, 2H), 7.55-7.44 (m, 3H), 7.39-7.31 (m, 1H), 6.98 (dd, J=2.4, 9.6 Hz, 1H), 6.93-6.86 (m, 1H), 6.85 (d, J=1.2 Hz, 1H), 4.95 (br. d, J=13.2 Hz, 1H), 6.70 (d, J=13.6 Hz, 1H), 3.42-3.22 (m, 2H), 2.94 (td, J=2.4, 13.2 Hz, 1H), 2.10-1.93 (m, 2H), 1.81-1.63 (m, 2H); LCMS (ESI) m/z: 385.0 [M+H]$^+$.

Example 118. Preparation of N-methyl-2-[3-(4-phenylpiperidine-1-carbonyl)isoxazol-5-yl]benzamide (301)

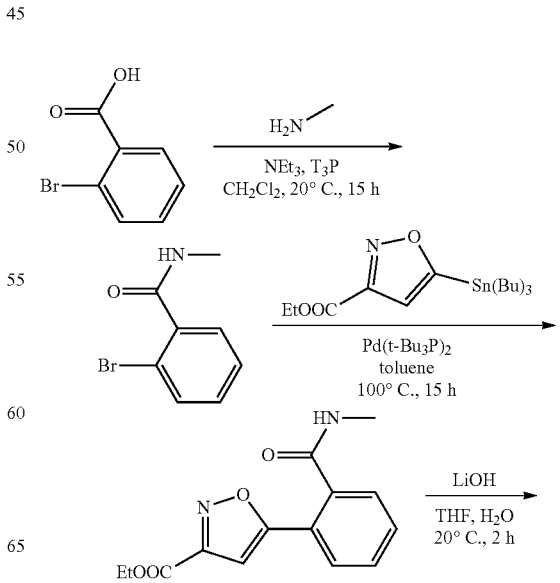

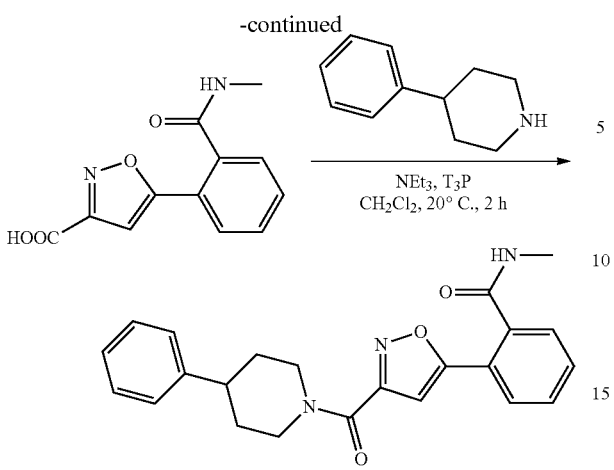

Step 1: Preparation of
2-bromo-N-methyl-benzamide

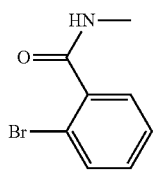

To a stirred solution of 2-bromobenzoic acid (2.00 g, 9.95 mmol) and methylamine (2 M, 25 mL) in dichloromethane (50 mL) was added propylphosphonic anhydride (9.50 g, 14.9 mmol, 50% in ethyl acetate) and triethylamine (3.02 g, 29.9 mmol). The reaction mixture was stirred at 20° C. for 15 h. The reaction mixture was quenched with water (80 mL) and extracted with dichloromethane (80 mL×3). The combined organic layers were washed with brine (150 mL), dried over sodium sulfate, filtered and concentrated under reduced pressure. The crude 2-bromo-N-methyl-benzamide (1.20 g, 5.61 mmol, 56%) was obtained as a brown solid. $^1$H NMR (400 MHz, Chloroform-d) δ 7.50 (d, J=7.9 Hz, 1H), 7.43 (dd, J=1.3, 7.6 Hz, 1H), 7.26 (t, J=7.5 Hz, 1H), 7.21-7.15 (m, 1H), 6.07 (br. s, 1H), 2.93 (d, J=4.9 Hz, 3H); LCMS (ESI) m/z: 214.0 [M+H]$^+$. The material was used directly in the next step without additional purification.

Step 2: Preparation of ethyl 5-[2-(methylcarbamoyl)phenyl]isoxazole-3-carboxylate

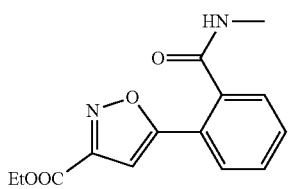 [SMILES: CNC(=O)c1ccccc1-c1cc(C(=O)O)no1]

A solution of ethyl 5-tributylstannylisoxazole-3-carboxylate (0.60 g, 1.39 mmol), 2-bromo-N-methyl-benzamide (0.358 g, 1.67 mmol) and bis(tri-tert-butylphosphine)palladium(0) (0.036 g, 0.070 mmol) in toluene (5 mL) was degassed and then heated to 100° C. for 15 h under nitrogen. The reaction mixture was concentrated in vacuo. The crude product was purified by column chromatography (silica, petroleum ether/ethyl acetate=10/1-1/1) to give ethyl 5-[2-(methylcarbamoyl)phenyl]isoxazole-3-carboxylate (0.090 g, 0.328 mmol, 24%) as a dark brown oil. $^1$H NMR (400 MHz, Chloroform-d) δ 7.81 (d, J=7.3 Hz, 1H), 7.65-7.41 (m, 3H), 6.94 (s, 1H), 5.94-5.74 (m, 1H), 4.46 (q, J=7.2 Hz, 2H), 2.99 (d, J=4.9 Hz, 3H), 1.43 (t, J=7.1 Hz, 3H); LCMS (ESI) m/z: 275.0 [M+H]$^+$.

Step 3: Preparation of 5-[2-(methylcarbamoyl)phenyl]isoxazole-3-carboxylic Acid

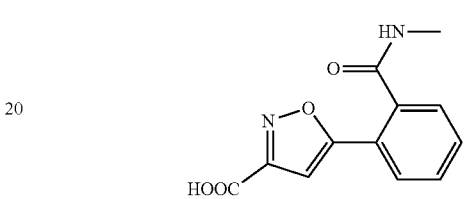

To a stirred solution of ethyl 5-[2-(methylcarbamoyl)phenyl]isoxazole-3-carboxylate (90 mg, 0.328 mmol) in tetrahydrofuran (2 mL) and water (2 mL) was added lithium hydroxide (24 mg, 0.984 mmol). The reaction mixture was stirred at 20° C. for 2 h. The reaction mixture was concentrated and the residue was dissolved in water (3 mL). The aqueous phase was extracted with methyl tert-butyl ether (3 mL×4) and the aqueous phase was adjusted to pH=3 with aqueous 1N hydrogen chloride. The aqueous phase was extracted with dichloromethane (3 mL×4). The combined organic phases were dried over anhydrous sodium sulfate, filtered and concentrated in vacuo. Compound 5-[2-(methylcarbamoyl)phenyl]isoxazole-3-carboxylic acid (0.080 g, 0.325 mmol, 99%) was obtained as a yellow oil. This material was used in next step directly. LCMS (ESI) m/z: 246.9 [M+H]$^+$.

Step 4: Preparation of N-methyl-2-[3-(4-phenylpiperidine-1-carbonyl)isoxazol-5-yl]benzamide

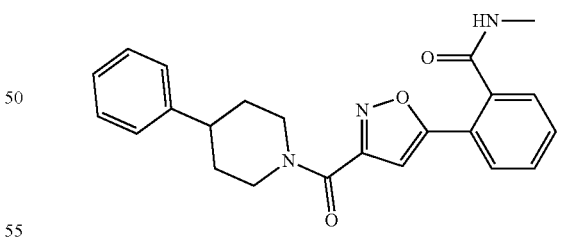

To a stirred solution of 5-[2-(methylcarbamoyl)phenyl]isoxazole-3-carboxylic acid (40 mg, 0.163 mmol) and 4-phenylpiperidine (26 mg, 0.163 mmol) in dichloromethane (1 mL) was added triethylamine (49 mg, 0.487 mmol) and propylphosphonic anhydride (124 mg, 0.195 mmol, 50% in ethyl acetate). The reaction mixture was stirred at 20° C. for 2 h. The reaction mixture was concentrated and the residue was purified by prep-HPLC (Waters Xbridge 150×25 5 μm column; 25-60% acetonitrile in a 10 mM ammonium bicarbonate solution in water, 11 min gradient) to give N-methyl-2-[3-(4-phenylpiperidine-1-carbonyl)

isoxazol-5-yl]benzamide (46 mg, 0.118 mmol, 73%) as a brown solid. ¹H NMR (400 MHz, Chloroform-d) δ 7.84 (d, J=7.5 Hz, 1H), 7.60-7.48 (m, 3H), 7.37-7.29 (m, 2H), 7.26-7.19 (m, 3H), 6.82 (s, 1H), 5.89 (br. d, J=4.4 Hz, 1H), 4.89 (td, J=1.8, 13.1 Hz, 1H), 4.57-4.49 (m, 1H), 3.30-3.20 (m, 1H), 3.00 (d, J=4.9 Hz, 3H), 2.95-2.79 (m, 2H), 2.05-1.90 (m, 2H), 1.86-1.72 (m, 2H); LCMS (ESI) m/z: 390.2 [M+H]⁺.

Example 119. Preparation of N-methyl-4-[3-(4-phenylpiperidine-1-carbonyl)isoxazol-5-yl]benzamide (304)

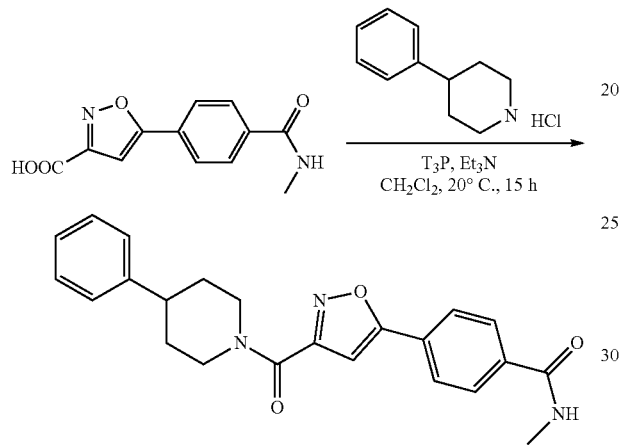

The synthesis of N-methyl-4-[3-(4-phenylpiperidine-1-carbonyl)isoxazol-5-yl]benzamide was carried out following the same procedure as Example 97. Compound N-methyl-4-[3-(4-phenylpiperidine-1-carbonyl)isoxazol-5-yl]benzamide (0.075 g, 0.193 mmol, 53%) was obtained as a white solid. ¹H NMR (400 MHz, Chloroform-d) δ 7.97-7.83 (m, 4H), 7.38-7.32 (m, 2H), 7.28-7.22 (m, 3H), 6.90 (s, 1H), 6.36 (br. d, J=4.5 Hz, 1H), 4.93 (td, J=1.9, 13.3 Hz, 1H), 4.72-4.58 (m, 1H), 3.37-3.24 (m, 1H), 3.07 (d, J=4.9 Hz, 3H), 2.99-2.90 (m, 1H), 2.90-2.82 (m, 1H), 2.15-1.94 (m, 2H), 1.88-1.78 (m, 2H); LCMS (ESI) m/z: 390.2 [M+H]⁺.

Example 120. Preparation of 5-(1,3-benzodioxol-5-yl)isoxazol-3-yl]-[4-(3-fluorophenyl)-1-piperidyl]methanone (309)

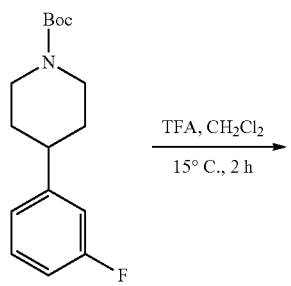

Step 1: Preparation of tert-butyl 4-(2-chloro-5-fluoro-phenyl)piperidine-1-carboxylate and tert-butyl 4-(3-fluorophenyl)piperidine-1-carboxylate

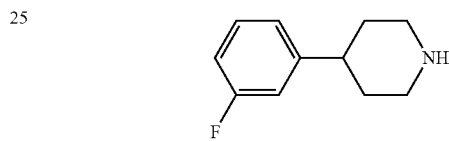

To a stirred solution of tert-butyl 4-(3-fluorophenyl)piperidine-1-carboxylate (0.160 g, 0.573 mmol) in dichloromethane (4 mL) was added trifluoroacetic acid (1 mL). The mixture was stirred at 15° C. for 2 h. The reaction mixture was concentrated to afford 4-(3-fluorophenyl)piperidine trifluoroacetic acid salt (0.240 g, crude) as a yellow gum. LCMS (ESI) m/z: 179.9 [M+H]⁺.

Step 2: Preparation of [5-(1,3-benzodioxol-5-yl)isoxazol-3-yl]-[4-(2-chloro-5-fluoro-phenyl)-1-piperidyl]methanone

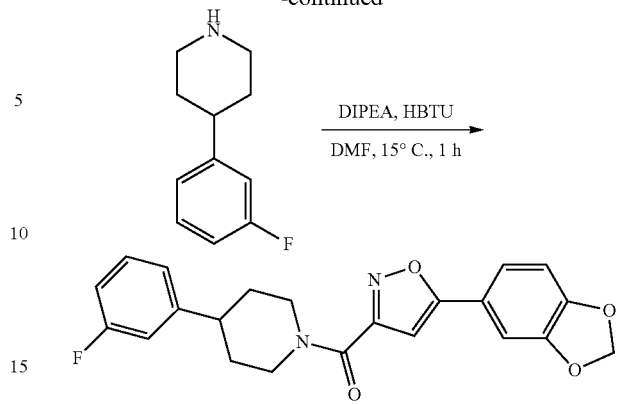

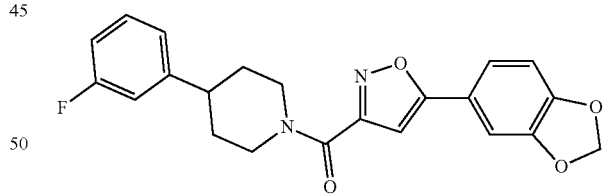

To a solution of 5-(1,3-benzodioxol-5-yl)isoxazole-3-carboxylic acid (0.065 g, 0.279 mmol) in N,N'-dimethylformamide (3 mL) was added N,N,N',N'-tetramethyl-O-(1H-benzotriazol-1-yl)uronium hexafluorophosphate (0.127 g, 0.334 mmol), diisopropylethylamine (0.180 g, 1.39 mmol) and 4-(3-fluorophenyl)piperidine (0.050 g, 0.279 mmol). The mixture was stirred at 15° C. for 1 h and then purified directly by prep-HPLC: (Waters X bridge 150×25 5 μM column; 41-76% acetonitrile in a 10 mM ammonium bicarbonate solution in water, 11 min gradient) to give [5-(1,3-benzodioxol-5-yl)isoxazol-3-yl]-[4-(3-fluorophenyl)-1-piperidyl]methanone (0.075 g, 0.191 mmol, 69%) as a pale yellow solid. ¹H NMR (400 MHz, Chloroform-d) δ 7.35 (dd, J=1.6, 8.0 Hz, 1H), 7.32-7.28 (m, 1H), 7.25 (d, J=2.0 Hz, 1H), 7.01 (d, J=7.6 Hz, 1H), 6.97-6.88 (m, 3H), 6.69 (s, 1H), 6.06 (s, 2H), 4.97-4.86 (m, 1H), 4.70-4.61 (m, 1H), 3.26 (td, J=2.4, 13.2 Hz, 1H), 2.97-2.80 (m, 2H), 2.06-1.90 (m, 2H), 1.84-1.67 (m, 2H); LCMS (ESI) m/z: 395.1 [M+H]$^+$.

Example 121. Preparation of [4-(3-fluorophenyl)-1-piperidyl]-(5-phenylisoxazol-3-yl)methanone (307)

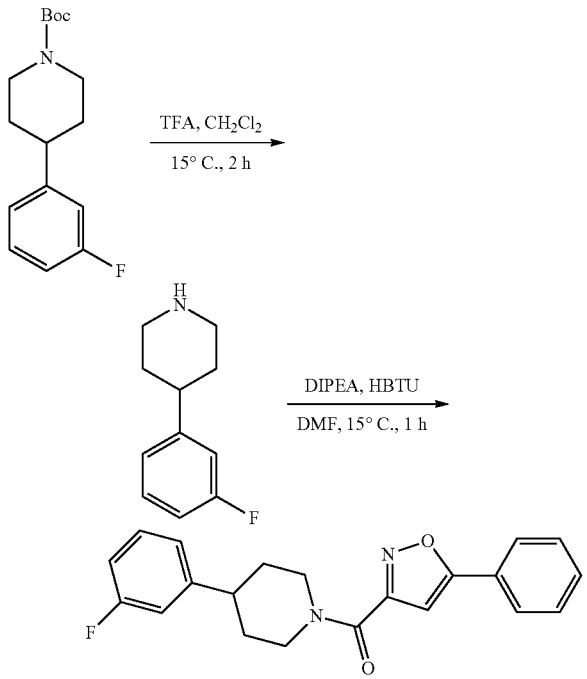

[4-(3-fluorophenyl)-1-piperidyl]-(5-phenylisoxazol-3-yl)methanone was synthesized according to the synthetic procedure reported for the preparation of Example 120. Compound [4-(3-fluorophenyl)-1-piperidyl]-(5-phenylisoxazol-3-yl)methanone (66 mg, 0.186 mmol, 64%) was obtained as a yellow solid. $^1$H NMR (400 MHz, Chloroform-d) δ 7.85-7.65 (m, 2H), 7.52-7.36 (m, 3H), 7.32-7.18 (m, 1H), 6.97 (br. d, J=7.6 Hz, 1H), 6.92-6.82 (m, 2H), 6.80 (s, 1H), 4.87 (br. d, J=13.2 Hz, 1H), 4.63 (br. d, J=13.6 Hz, 1H), 3.22 (td, J=2.4, 13.2 Hz, 1H), 2.94-2.68 (m, 2H), 2.06-1.84 (m, 2H), 1.82-1.64 (m, 2H); LCMS (ESI) m/z: 351.2 [M+H]$^+$.

Example 122. Preparation of 4-{1-[5-(2H-1,3-benzodioxol-5-yl)-1,3-oxazole-2-carbonyl]piperidin-4-yl}benzonitrile (291)

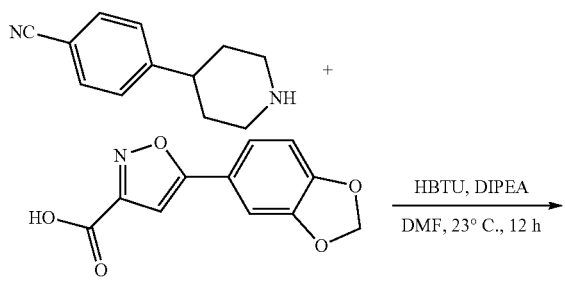

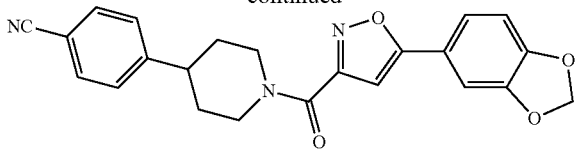

To a stirred solution 4-(piperidin-4-yl)benzonitrile, (0.06 g, 0.4 mmol), 5-(benzo[d][1,3]dioxol-5-yl)isoxazole-3-carboxylic acid (0.1 g, 0.4 mmol) in N,N-dimethylformamide (2 mL) at 23° C. was added N,N,N',N'-tetramethyl-O-(1H-benzotriazol-1-yl)uronium hexafluorophosphate (0.06 g, 0.4 mmol) and diisopropylethylamine (0.05 g, 0.5 mmol). The reaction mixture was stirred at 23° C. for 12 h and then purified by column chromatography (ISCO, silica, 0-100% ethyl acetate) to give 4-{1-[5-(2H-1,3-benzodioxol-5-yl)-1,3-oxazole-2-carbonyl]piperidin-4-yl}benzonitrile (0.096 g, 0.24 mmol, 60%) as an orange solid. $^1$H NMR (300 MHz, Chloroform-d) δ 7.35 (dd, J=8.2, 1.7 Hz, 1H), 7.31-7.14 (m, 4H), 7.08-6.88 (m, 3H), 6.70 (s, 1H), 6.38 (s, OH), 6.07 (s, 2H), 4.92 (d, J=13.1 Hz, 1H), 4.65 (d, J=13.6 Hz, 1H), 3.26 (t, J=11.7 Hz, 1H), 2.97-2.77 (m, 1H), 1.95 (d, J=16.4 Hz, 2H), 1.78 (t, J=12.6 Hz, 1H); LCMS (ESI) m/z: 402.1 [M+H]$^+$.

Example 123. Preparation of 1-[5-(2H-1,3-benzodioxol-5-yl)-1,3-oxazole-2-carbonyl]-4-(3,4-difluorophenyl)piperidine (292)

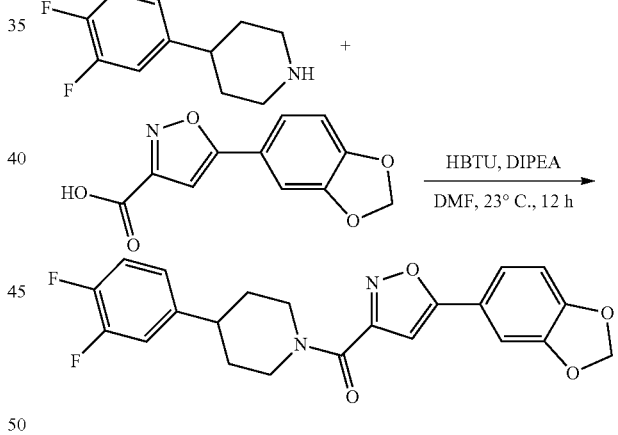

To a stirred solution 4-(3,4-difluorophenyl)piperidine hydrochloride, (0.02 g, 0.09 mmol), 5-(benzo[d][1,3]dioxol-5-yl)isoxazole-3-carboxylic acid (0.02 g, 0.09 mmol) in N,N-dimethylformamide (3 mL) at 23° C. was added N,N,N',N'-tetramethyl-O-(1H-benzotriazol-1-yl)uronium hexafluorophosphate (0.1 g, 0.09 mmol) and diisopropylethylamine (0.1 g, 0.09 mmol). The reaction mixture was stirred at 23° C. for 12 h and then purified by column chromatography (ISCO, 4 g silica, 0-100% ethyl acetate) to give 1-[5-(2H-1,3-benzodioxol-5-yl)-1,3-oxazole-2-carbonyl]-4-(3,4-difluorophenyl)piperidine (0.02 g, 0. mmol, 53%) as a white solid. $^1$H NMR (300 MHz, Chloroform-d) δ 8.57 (d, J=5.1 Hz, 2H), 7.40-7.22 (m, 2H), 7.18 (d, J=5.7 Hz, 2H), 6.93 (d, J=8.2 Hz, 1H), 6.71 (s, 1H), 6.07 (d, J=0.7 Hz, 2H), 5.32 (s, OH), 4.94 (d, J=13.5 Hz, 1H), 4.72 (d, J=14.0 Hz, 1H), 4.14 (d, J=7.1 Hz, 1H), 3.28 (t, J=12.0 Hz, 1H), 2.90 (q, J=13.0 Hz, 2H), 2.09-1.92 (m, 2H), 1.81 (td, J=12.4, 5.9 Hz, 2H), 1.27 (t, J=7.1 Hz, 1H); LCMS (ESI) m/z: 413.4 [M+H]+.

Example 124. Preparation of 4-[5-(1,3-benzodioxol-5-yl)isoxazole-3-carbonyl]-1-phenyl-piperazin-2-one (280)

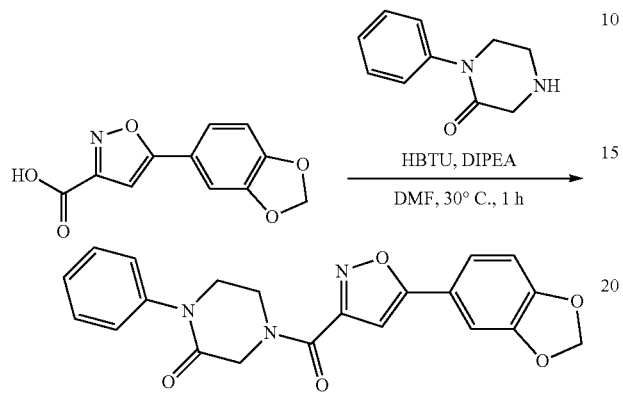

To a stirred solution of 5-(1,3-benzodioxol-5-yl)isoxazole-3-carboxylic acid (40 mg, 0.172 mmol) in N,N'-dimethylformamide (2 mL) at 30° C. was added N,N,N',N'-tetramethyl-O-(1H-benzotriazol-1-yl)uronium hexafluorophosphate (0.078 g, 0.206 mmol), diisopropylethylamine (0.067 g, 0.515 mmol) and 1-phenylpiperazin-2-one (0.033 g, 0.189 mmol). Then the mixture was stirred at 30° C. for 1 h. The mixture was purified by Prep-HPLC (Waters X bridge 150×25 5 μm column; 25-55% acetonitrile in a 10 mM ammonium bicarbonate solution in water, 12 min gradient) to afford 4-[5-(1,3-benzodioxol-5-yl)isoxazole-3-carbonyl]-1-phenyl-piperazin-2-one (26 mg, 0.067 mmol, 39%) as a brown solid. 1H NMR (400 MHz, Chloroform-d) δ 7.44 (t, J=7.2 Hz, 2H), 7.38-7.28 (m, 4H), 7.26 (t, J=1.6 Hz, 1H), 6.93 (d, J=8.0 Hz, 1H), 6.79 (d, J=18.0 Hz, 1H), 6.07 (s, 2H), 4.85 (s, 1H), 4.61 (s, 1H), 4.43 (t, J=4.2 Hz, 1H), 4.17 (t, J=4.2 Hz, 1H), 3.91-3.66 (m, 2H); LCMS (ESI) m/z: 392.1 [M+H]+.

Example 125. Preparation of 1-[5-(2H-1,3-benzodioxol-5-yl)-1,2-oxazole-3-carbonyl]-4-methyl-4-phenylpiperidine (290)

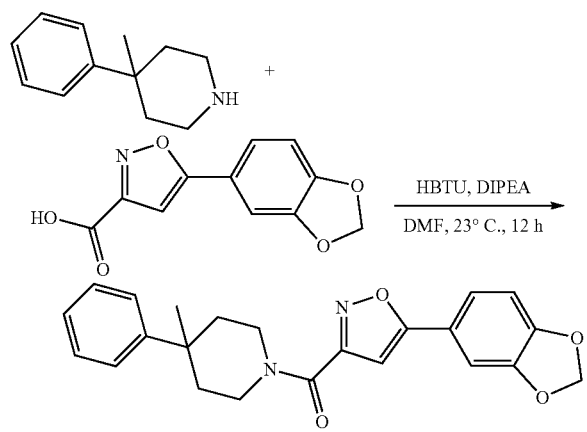

To a stirred solution 4-methyl-4-phenylpiperidine hydrochloride (0.25 g, 1.2 mmol), 5-(benzo[d][1,3]dioxol-5-yl)isoxazole-3-carboxylic acid (0.17 g, 1.1 mmol) in N,N-dimethylformamide (2 mL) at 23° C. was added N,N,N',N'-tetramethyl-O-(1H-benzotriazol-1-yl)uronium hexafluorophosphate (0.37 g, 0.98 mmol) and diisopropylethylamine (0.29 g, 2.26 mmol). The reaction mixture was stirred at 23° C. for 12 h and purified directly by column chromatography (ISCO, silica 12 g, 0-100% ethyl acetate) to give 1-[5-(2H-1,3-benzodioxol-5-yl)-1,2-oxazole-3-carbonyl]-4-methyl-4-phenylpiperidine (0.047 g, 0.12 mmol, 11%) as a yellow solid. 1H NMR (300 MHz, Chloroform-d) δ 7.42-7.21 (m, 6H), 6.91 (d, J=8.1 Hz, 1H), 6.65 (d, J=1.9 Hz, 1H), 6.06 (s, 1H), 6.06 (d, J=3.1 Hz, 0H), 3.97 (d, J=13.3 Hz, 2H), 3.73-3.59 (m, 1H), 2.25 (s, 2H), 1.84 (s, 3H), 1.33 (s, 2H); LCMS (ESI) m/z: 391.2 [M+H]+.

Example 126. Preparation of 5-(1,3-benzodioxol-5-yl)isoxazol-3-yl]-[4-(2-chloro-5-fluoro-phenyl)-3,6-dihydro-2H-pyridin-1-yl]methanone (306)

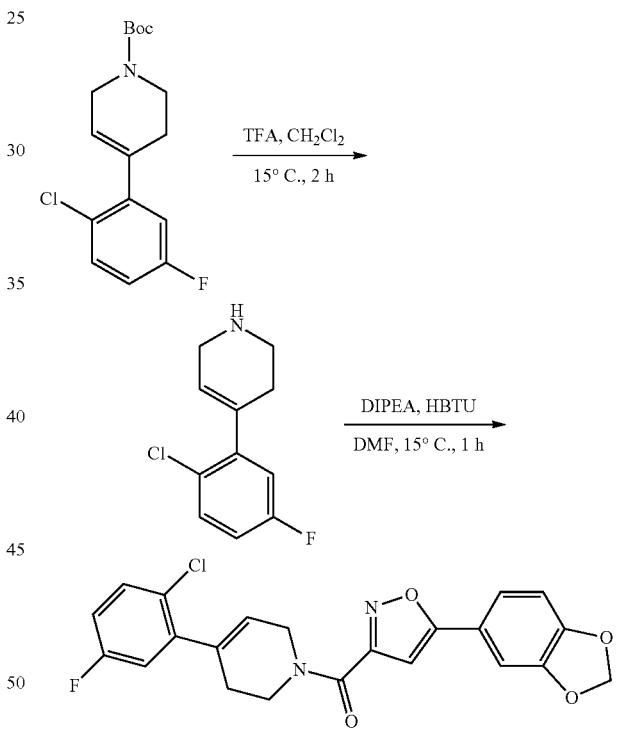

The synthesis of [5-(1,3-benzodioxol-5-yl)isoxazol-3-yl]-[4-(2-chloro-5-fluoro-phenyl)-3,6-dihydro-2H-pyridin-1-yl]methanone was carried out following the same procedure as Example 120. Compound [5-(1,3-benzodioxol-5-yl)isoxazol-3-yl]-[4-(2-chloro-5-fluoro-phenyl)-3,6-dihydro-2H-pyridin-1-yl]methanone (0.095 g, 0.222 mmol, 57%) was obtained as a yellow solid. 1H NMR (400 MHz, Chloroform-d) δ 7.42-7.31 (m, 2H), 7.28-7.26 (m, 1H), 7.07-6.85 (m, 3H), 6.74 (d, J=12.8 Hz, 1H), 6.06 (s, 2H), 5.87-5.65 (m, 1H), 4.70-4.35 (m, 2H), 4.10 (t, J=5.4 Hz, 1H), 4.03 (t, J=5.2 Hz, 1H), 2.73-2.47 (m, 2H); LCMS (ESI) m/z: 427.1 [M+H]+.

Example 127. Preparation of 4-(2-chloro-5-fluorophenyl)-3,6-dihydro-2H-pyridin-1-yl]-(5-phenylisoxazol-3-yl)methanone (305)

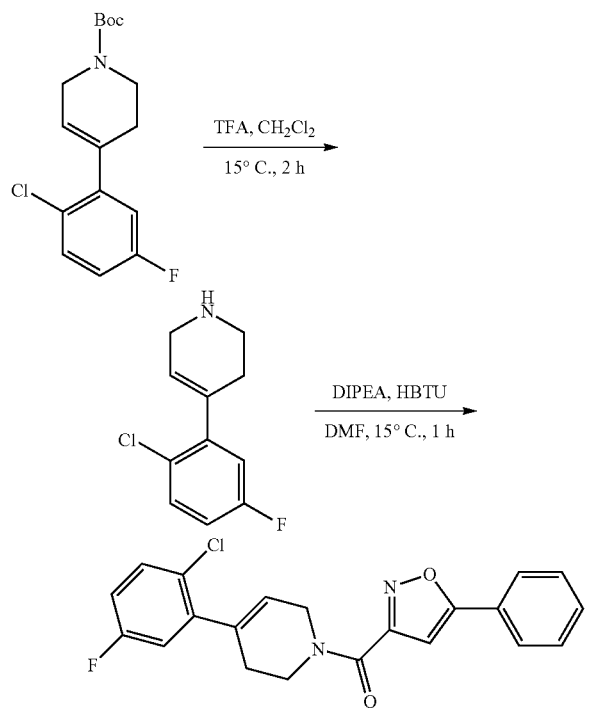

The synthesis of 4-(2-chloro-5-fluoro-phenyl)-3,6-dihydro-2H-pyridin-1-yl]-(5-phenylisoxazol-3-yl)methanone was carried out using the same procedure as Example 120. Compound 4-(2-chloro-5-fluoro-phenyl)-3,6-dihydro-2H-pyridin-1-yl]-(5-phenylisoxazol-3-yl)methanone (0.084 g, 0.219 mmol, 41%) was obtained as a yellow solid. $^1$H NMR (400 MHz, Chloroform-d) δ 7.98-7.70 (m, 2H), 7.62-7.38 (m, 3H), 7.36-7.30 (m, 1H), 7.05-6.80 (m, 3H), 5.95-5.60 (m, 1H), 4.60 (d, J=2.8 Hz, 1H), 4.43 (d, J=2.8 Hz, 1H), 4.11 (t, J=5.6 Hz, 1H), 4.04 (t, J=5.6 Hz, 1H), 2.75-2.46 (m, 2H); LCMS (ESI) m/z: 383.1 [M+H]$^+$.

Example 128. Preparation of [5-(1,3-benzodioxol-5-yl)isoxazol-3-yl]-(4-phenoxy-1-piperidyl)methanone (298)

[5-(1,3-benzodioxol-5-yl)isoxazol-3-yl]-(4-phenoxy-1-piperidyl)methanone was synthesized according to the synthetic procedure reported for the preparation of Example 95. Compound [5-(1,3-benzodioxol-5-yl)isoxazol-3-yl]-(4-phenoxy-1-piperidyl)methanone (0.059 g, 0.150 mmol, 35%) was obtained as a brown solid. $^1$H NMR (400 MHz, Methanol-d$_4$) δ 7.42 (dd, J=1.7, 8.0 Hz, 1H), 7.33 (d, J=1.5 Hz, 1H), 7.26 (t, J=8.0 Hz, 2H), 7.01-6.90 (m, 4H), 6.85 (s, 1H), 6.04 (s, 2H), 4.75-4.65 (m, 1H), 4.02-3.89 (m, 2H), 3.86-3.77 (m, 1H), 3.71 (ddd, J=3.9, 7.2, 13.7 Hz, 1H), 2.05 (tdd, J=4.4, 8.5, 12.9 Hz, 2H), 1.92-1.78 (m, 2H); LCMS (ESI) m/z: 393.1 [M+H]$^+$.

Example 129. Preparation of (4-phenoxy-1-piperidyl)-(5-phenylisoxazol-3-yl)methanone (288)

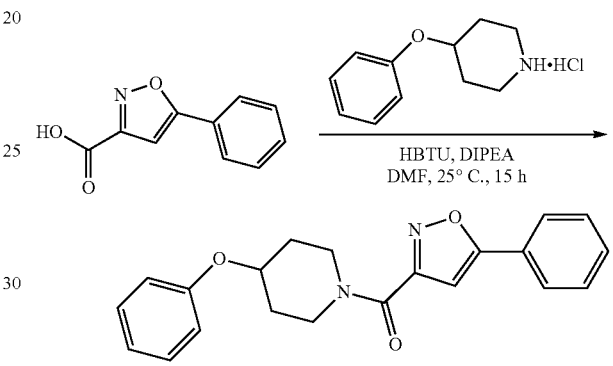

The synthesis of (4-phenoxy-1-piperidyl)-(5-phenylisoxazol-3-yl)methanone was carried following the same procedure as Example 95. Compound (4-phenoxy-1-piperidyl)-(5-phenylisoxazol-3-yl)methanone (0.100 g, 0.287 mmol, 54%) was obtained as a pale yellow solid. $^1$H NMR (400 MHz, Chloroform-d) δ 7.88-7.75 (m, 2H), 7.54-7.45 (m, 3H), 7.35-7.28 (m, 2H), 7.02-6.92 (m, 3H), 6.83 (s, 1H), 4.65 (br. s, 1H), 4.10-3.81 (m, 4H), 2.11-1.89 (m, 4H); LCMS (ESI) m/z: 349.1 [M+H]$^+$.

Example 130. Preparation of (5-(benzo[d][1,3]dioxol-5-yl)isoxazol-3-yl)(4-(3-methoxyphenyl)piperazin-1-yl)methanone (271)

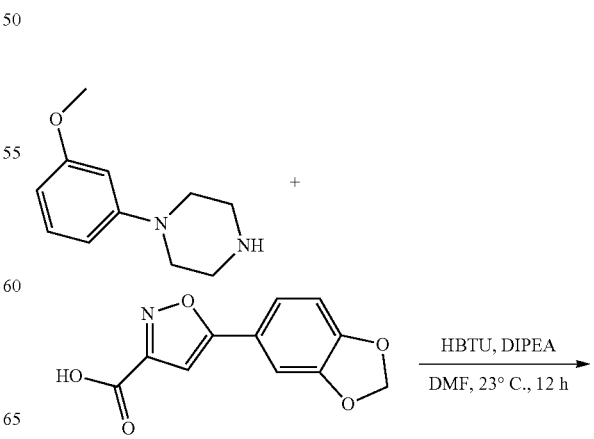

-continued

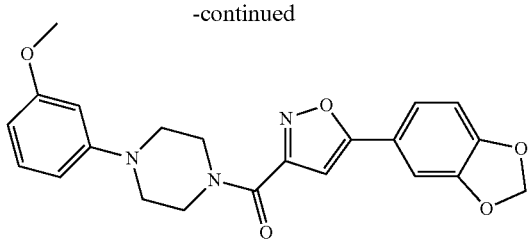

To a stirred solution 1-(3-methoxyphenyl)piperazine (0.20 g, 0.75 mmol) 5-(benzo[d][1,3]dioxol-5-yl)isoxazole-3-carboxylic acid (0.157 g, 0.831 mmol) in N,N-dimethylformamide (2.7 mL) at 23° C. was added N,N,N',N'-tetramethyl-O-(1H-benzotriazol-1-yl)uronium hexafluorophosphate (0.37 g, 0.98 mmol) and diisopropylethylamine (0.29 g, 2.26 mmol). The reaction mixture was stirred at 23° C. for 12 h and purified by column chromatography (ISCO, 12 g silica, 0-100% ethyl acetate) to give (5-(benzo[d][1,3]dioxol-5-yl)isoxazol-3-yl)(4-(3-methoxyphenyl)piperazin-1-yl)methanone (0.268 g, 0.658 mmol, 87%) as a white solid. $^1$H NMR (300 MHz, Dimethylsulfoxide-$d_6$) δ 7.54-7.42 (m, 2H), 7.23-7.05 (m, 3H), 6.61-6.36 (m, 3H), 6.14 (s, 2H), 3.85-3.68 (m, 7H), 3.34-3.13 (m, 4H). 3.30 (s, 3H); LCMS (ESI) m/z: 408.4 [M+H]$^+$.

Example 131. Preparation of (4-(2-chloro-5-fluorophenyl)piperazin-1-yl)(5-phenylisoxazol-3-yl)methanone (297)

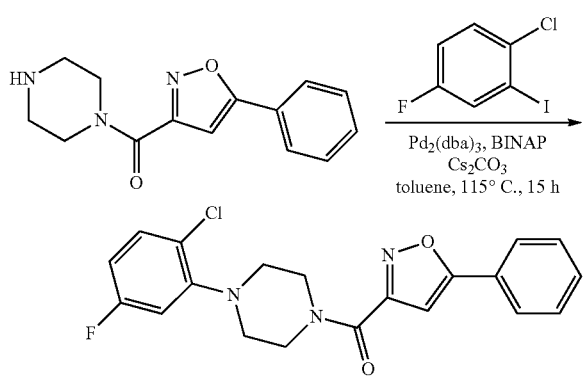

To a solution of (5-phenylisoxazol-3-yl)(piperazin-1-yl)methanone (0.25 g, 0.851 mmol) and 1-chloro-4-fluoro-2-iodobenzene (0.327 g, 1.28 mmol) in toluene (5 mL) was added cesium carbonate (0.832 g, 2.55 mmol), tris(dibenzylideneacetone)dipalladium(0) (0.078 g, 0.085 mmol) and BINAP (0.053 g, 0.085 mmol). The reaction mixture was purged with nitrogen for 3 min and stirred at 115° C. in a sealed tube for 15 h. The mixture was quenched with water (10 mL) and extracted with ethyl acetate (15 mL×3). The combined organic layers were washed with brine (5 mL), dried over sodium sulfate, filtered and concentrated in vacuo. The crude product was purified by column chromatography (ISCO, 10 g silica, 8-10% ethyl acetate in petroleum ether, gradient over 15 min) and then by prep-HPLC (YMC-Actus ODS-AQ 100×30 5 μm column; 45-85% acetonitrile in an a 0.05% hydrochloric acid solution in water, 12 min gradient) to give (4-(2-chloro-5-fluorophenyl)piperazin-1-yl)(5-phenylisoxazol-3-yl)methanone hydrochloride salt (0.172 g, 0.404 mmol, 47%) as a white solid.

$^1$H NMR (400 MHz, Chloroform-d) δ 7.89-7.80 (m, 2H), 7.57-7.46 (m, 3H), 7.40-7.31 (m, 1H), 6.89 (s, 1H), 6.82-6.71 (m, 2H), 4.20-4.10 (m, 2H), 4.08-3.97 (m, 2H), 3.18-3.13 (m, 4H); LCMS (ESI) m/z: 386.0 [M+H]$^+$.

Example 132. Preparation of 5-(1,3-benzodioxol-5-yl)isoxazol-3-yl]-[4-(2-chloro-5-fluoro-phenyl)piperazin-1-yl]methanone (299)

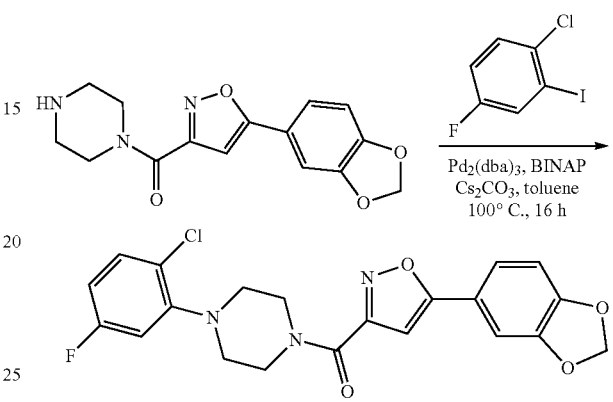

The synthesis of [5-(1,3-benzodioxol-5-yl)isoxazol-3-yl]-[4-(2-chloro-5-fluoro-phenyl)piperazin-1-yl]methanone was carried out following the same procedure as Example 131. Compound [5-(1,3-benzodioxol-5-yl)isoxazol-3-yl]-[4-(2-chloro-5-fluoro-phenyl)piperazin-1-yl]methanone (0.065 g, 0.147 mmol, 33%) was obtained as a pale yellow solid. $^1$H NMR (400 MHz, Chloroform-d) δ 7.39-7.30 (m, 2H), 7.25 (d, J=1.5 Hz, 1H), 6.92 (d, J=8.2 Hz, 1H), 6.81-6.68 (m, 3H), 6.06 (s, 2H), 4.18-4.06 (m, 2H), 4.05-3.97 (m, 2H), 3.14 (td, J=5.0, 10.4 Hz, 4H); LCMS (ESI) m/z: 430.0 [M+H]$^+$.

Example 133. Preparation of 5-phenylisoxazol-3-yl)(4-phenylpiperazin-1-yl)methanone (266)

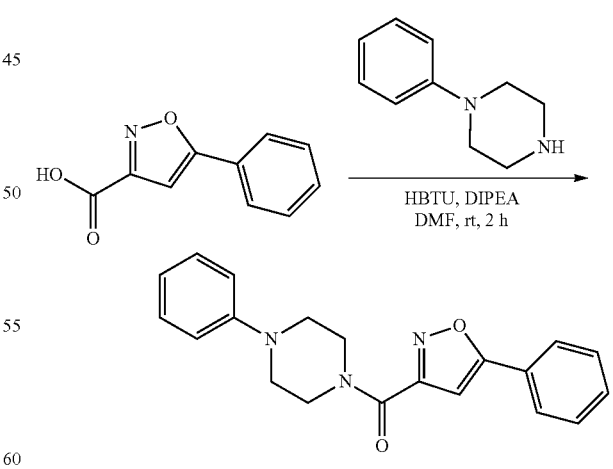

To a stirred solution of 5-phenylisoxazole-3-carboxylic acid (0.150 g, 0.793 mmol) and N,N,N',N'-tetramethyl-O-(1H-benzotriazol-1-yl)uronium hexafluorophosphate (0.301 g, 0.793 mmol) in N,N'-dimethylformamide (2 mL) was added diisopropylethylamine (0.205 g, 1.59 mmol) and 1-phenylpiperazine (0.129 g, 0.793 mmol). The mixture was stirred at 25° C. for 2 h then purified directly by prep-HPLC (Luna C18 100×30 5 μm column; 53-83% acetonitrile in a 10 mM ammonium bicarbonate solution in water, 10 min gradient) to give ((5-phenylisoxazol-3-yl) (4-phenylpiperazin-1-yl)methanone (0.198 g, 0.589 mmol, 74%) as a white solid. $^1$H NMR (400 MHz, Dimethylsulfoxide-d$_6$) δ 7.94 (dd, J=1.5, 7.7 Hz, 2H), 7.60-7.52 (m, 3H), 7.33 (s, 1H), 7.27-7.20 (m, 2H), 6.97 (d, J=7.9 Hz, 2H), 6.82 (t, J=7.2 Hz, 1H), 3.81 (td, J=4.9, 15.1 Hz, 4H), 3.26-3.15 (m, 4H); LCMS (ESI) m/z: 334.2 [M+H]$^+$.

Example 134. Preparation of (5-(benzo[d][1,3]dioxol-5-yl)isoxazol-3-yl)(2-methyl-4-phenylpiperazin-1-yl)methanone (270)

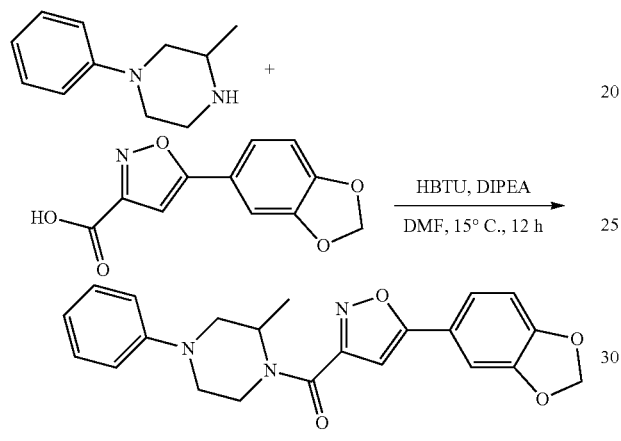

To a stirred solution 3-methyl-1-phenylpiperazine (0.050 g, 0.280 mmol) 5-(benzo[d][1,3]dioxol-5-yl)isoxazole-3-carboxylic acid (0.157 g, 0.831 mmol) in N,N-dimethylformamide (1 mL) at 15° C. was added N,N,N',N'-tetramethyl-O-(1H-benzotriazol-1-yl)uronium hexafluorophosphate (0.315 g, 0.831 mmol) and diisopropylethylamine (0.242 g, 1.39 mmol). The reaction mixture was stirred at 15° C. for 12 h and purified by column chromatography (ISCO, 12 g silica, 0-100% ethyl acetate) to give (5-(benzo[d][1,3]dioxol-5-yl)isoxazol-3-yl)(2-methyl-4-phenylpiperazin-1-yl)methanone (0.105 g, 0.268 mmol, 95%) as a yellow oil. $^1$H NMR (300 MHz, Dimethylsulfoxide-d$_6$) δ 7.55-7.43 (m, 2H), 7.29-7.05 (m, 2H), 6.97-6.88 (m, 2H), 6.78 (t, J=6.7 Hz, 1H), 6.14 (d, J=1.4 Hz, 2H), 5.76 (s, 1H), 4.41 (d, J=12.7 Hz, 1H), 4.25 (d, J=12.7 Hz, 1H), 4.18-3.87 (m, 2H), 3.42 (d, J=14.7 Hz, 1H), 3.04 (d, J=11.6 Hz, 1H), 2.40 (d, J=18.9 Hz, 1H), 0.91 (dd, J=10.9, 6.4 Hz, 2H); LCMS (ESI) m/z: 392.4 [M+H]$^+$.

Example 135. Preparation of N-(1-benzyl-1H-pyrazol-4-yl)-5-(oxazol-5-yl)isoxazole-3-carboxamide (149)

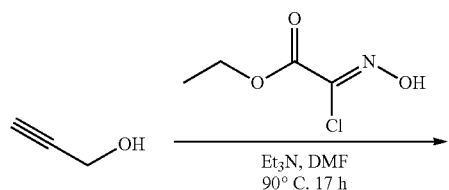

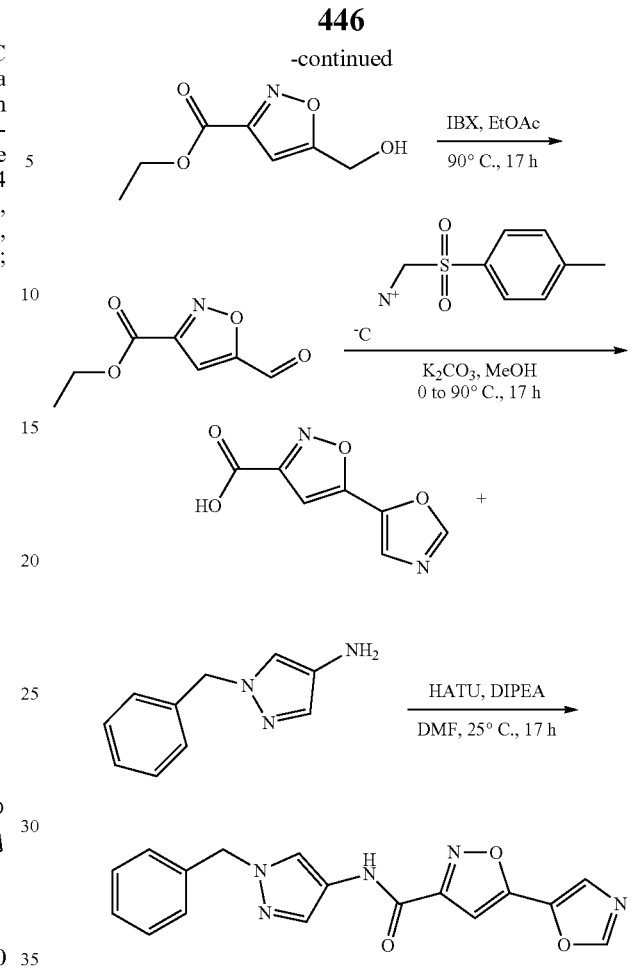

Step 1: Preparation of ethyl 5-(hydroxymethyl)isoxazole-3-carboxylate

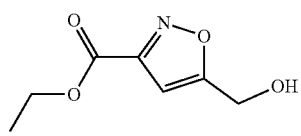

To a solution of prop-2-yn-1-ol (3.3 g, 59.4 mmol) in N,N-dimethylformamide (20 mL) was added (Z)-ethyl 2-chloro-2-(hydroxyimino)acetate (3.0 g, 19.8 mmol) in N,N-dimethylformamide (20 mL) dropwise over 40 min under nitrogen atmosphere. After addition, the reaction mixture was heated to 90° C. and a solution of triethylamine (6.0 g, 59.4 mmol) in N,N-dimethylformamide (20 mL) was added dropwise over 1 h. The reaction mixture was stirred at this temperature for 17 h and then cooled to room temperature. The reaction mixture was diluted with ethyl acetate (30 mL), washed with water (20 mL×3) and brine (20 mL), dried over anhydrous sodium sulfate, filtered and concentrated in vacuo. The residue was purified by column chromatography (silica, petroleum ether/ethyl acetate=6/1) to give ethyl 5-(hydroxymethyl)isoxazole-3-carboxylate (1.4 g, 8.19 mmol, 41%) as a yellow oil. LCMS (ESI) m/z: 172.1 [M+H]$^+$.

Step 2: Preparation of ethyl 5-formylisoxazole-3-carboxylate

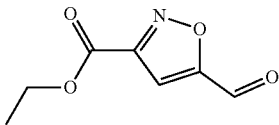

To a solution of ethyl 5-(hydroxymethyl)isoxazole-3-carboxylate (1.4 g, 8.18 mmol) in ethyl acetate (30 mL) was added 2-iodoxybenzoic acid (6.9 g, 24.5 mmol). The reaction mixture was heated at 90° C. for 17 h and then cooled to room temperature. The reaction mixture was filtered and the filtrate was concentrated in vacuo. The residue was purified by column chromatography (silica, petroleum ether/ethyl acetate=6/1) to give ethyl 5-formylisoxazole-3-carboxylate (1.1 g, 6.5 mmol, 80%) as a yellow oil.

Step 3: Preparation of 5-(oxazol-5-yl)isoxazole-3-carboxylic Acid

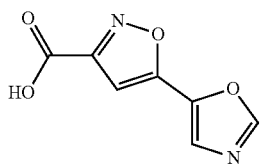 [SMILES: O=C(O)c1cc(-c2cnco2)on1]

To a solution of 1-(isocyanomethylsulfonyl)-4-methylbenzene (0.460 g, 2.36 mmol) in acetonitrile (15 mL) was added potassium carbonate (0.391 g, 2.83 mmol). The reaction mixture was stirred at 25° C. for 1 h before ethyl 5-formylisoxazole-3-carboxylate (0.400 g, 2.36 mmol) was added at 0° C. The reaction mixture was heated to 90° C. and stirred for 17 h. The reaction mixture was cooled to room temperature, diluted with water (20 mL) and the aqueous layer was adjusted to pH=3 with aqueous 1N hydrogen chloride. The reaction mixture was then extracted with ethyl acetate (10 mL×3). The combined organic layers were washed with brine (10 mL×2), dried over anhydrous sodium sulfate, filtered and concentrated in vacuo. The crude 5-(oxazol-5-yl)isoxazole-3-carboxylic acid (0.160 g, 0.89 mmol, 38%) was obtained as a white solid. This material was used directly in the next step without further purification.

Step 4: Preparation of N-(1-benzyl-1H-pyrazol-4-yl)-5-(oxazol-5-yl)isoxazole-3-carboxamide

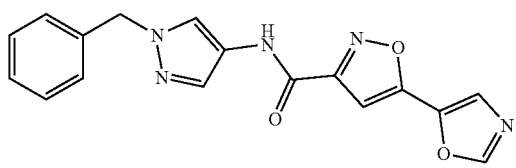 [SMILES: O=C(Nc1cnn(Cc2ccccc2)c1)c1cc(-c2cnco2)on1]

To a solution of 5-(oxazol-5-yl)isoxazole-3-carboxylic acid (0.140 g, 0.77 mmol) in N,N-dimethylformamide (16 mL) was added 1-benzyl-1H-pyrazol-4-amine (0.133 g, 0.77 mmol), 1-[bis(dimethylamino)methylene]-1H-1,2,3-triazolo[4,5-b]pyridinium 3-oxide hexafluorophosphate (0.878 g, 2.31 mmol) and diisopropylethylamine (0.298 g, 2.31 mmol). The mixture was stirred at 25° C. for 17 h. The crude sample was dissolved in minimum amount of N,N-dimethylformamide and purified via prep-HPLC (Boston C18 21×250 mm 10 µm column; acetonitrile/0.01% aqueous trifluoroacetic acid) to give N-(1-benzyl-1H-pyrazol-4-yl)-5-(oxazol-5-yl)isoxazole-3-carboxamide (20.4 mg, 0.06 mmol, 8%) as a white solid. $^1$H NMR (500 MHz, Dimethylsulfoxide-$d_6$) δ 11.09 (s, 1H), 8.73 (s, 1H), 8.17 (s, 1H), 8.02 (s, 1H), 7.67 (s, 1H), 7.30 (ddd, J=29.6, 18.3, 7.0 Hz, 6H), 5.34 (s, 2H); LCMS (ESI) m/z: 336.1 [M+H]$^+$.

Example 136. Characterization Data of Compounds of the Invention

The following compounds were synthesized by methods similar to those described above.

Compound 1: $^1$H NMR (400 MHz, CDCl3) δ 7.87 (br. s., 1H), 7.61 (s, 1H), 7.00 (d, J=3.1 Hz, 1H), 6.94 (s, 1H), 6.63-6.55 (m, 1H), 3.75 (s, 3H), 2.20 (d, J=5.3 Hz, 6H); LCMS (ESI) m/z: 287.1 [M+H]$^+$.

Compound 2: $^1$H NMR (400 MHz, CDCl3) δ 7.61 (d, J=1.1 Hz, 1H), 7.37-7.29 (m, 3H), 7.13 (d, J=6.9 Hz, 2H), 7.00 (d, J=3.5 Hz, 1H), 6.93 (s, 1H), 6.59 (dd, J=1.8, 3.5 Hz, 1H), 5.25 (s, 2H), 2.24 (s, 3H), 2.14 (s, 3H); LCMS (ESI) m/z: 363.2 [M+H]$^+$.

Compound 9: $^1$H NMR (400 MHz, DMSO-d6) δ 7.98-7.88 (m, 2H), 7.63-7.51 (m, 3H), 7.48-7.33 (m, 2H), 7.23-7.08 (m, 3H), 4.77 (s, 1H), 4.74 (s, 1H), 3.11 (s, 1.5H), 2.96 (s, 1.5H); LCMS (ESI) m/z: 311.0 [M+H]$^+$.

Compound 10: $^1$H NMR (400 MHz, CHLOROFORM-d) δ=8.54 (br s, 1H), 8.02 (s, 1H), 7.63-7.54 (m, 2H), 7.00 (d, J=3.5 Hz, 1H), 6.94 (s, 1H), 6.59 (dd, J=1.7, 3.3 Hz, 1H), 3.93 (s, 3H); LCMS (ESI) m/z: 259.0 [M+H]$^+$.

Compound 12: $^1$H NMR (400 MHz, CHLOROFORM-d) δ 8.69-8.53 (m, 2H), 7.87 (s, 1H), 7.60 (s, 1H), 6.99 (d, J=3.4 Hz, 1H), 6.93 (s, 1H), 6.63-6.53 (m, 1H), 1.66 (s, 9H); LCMS (ESI) m/z: 345.1 [M+H]$^+$.

Compound 13: $^1$H NMR (400 MHz, DMSO-d6) δ 12.72 (br s, 1H), 10.96 (s, 1H), 7.99 (d, J=1.1 Hz, 2H), 7.70 (br s, 1H), 7.27 (d, J=3.5 Hz, 1H), 7.14 (s, 1H), 6.76 (dd, J=1.8, 3.5 Hz, 1H); LCMS (ESI) m/z: 245.0 [M+H]$^+$.

Compound 15: $^1$H NMR (400 MHz, CHLOROFORM-d) δ 8.53 (br.s, 1H), 8.05 (s, 1H), 7.70-7.53 (m, 2H), 7.33 (d, J=8.4 Hz, 2H), 7.19 (d, J=8.4 Hz, 2H), 6.99 (d, J=3.6 Hz, 1H), 6.91 (s, 1H), 6.64-6.60 (m, 1H), 5.27 (s, 2H); LCMS (ESI) m/z: 369.0 [M+H]$^+$.

Compound 16: $^1$H NMR (400 MHz, CHLOROFORM-d) δ=8.55 (br s, 1H), 8.10 (s, 1H), 7.62 (br d, J=9.2 Hz, 3H), 7.35 (br d, J=8.0 Hz, 2H), 7.00 (d, J=3.2 Hz, 1H), 6.92 (s, 1H), 6.58 (br d, J=1.2 Hz, 1H), 5.37 (s, 2H); LCMS (ESI) m/z: 403.1 [M+H]$^+$.

Compound 21: $^1$H NMR (400 MHz, CHLOROFORM-d) δ=8.07 (s, 1H), 7.83 (s, 1H), 7.61 (d, J=1.6 Hz, 1H), 7.41 (d, J=8.4 Hz, 1H), 7.24 (d, J=2.0 Hz, 1H), 7.00 (d, J=3.2 Hz, 1H), 6.96 (dd, J=1.6, 8.3 Hz, 1H), 6.94 (s, 1H), 6.59 (dd, J=2.0, 3.3 Hz, 1H), 5.26 (s, 2H), 2.21 (s, 3H); LCMS (ESI) m/z: 417.0 [M+H]$^+$.

Compound 24: $^1$H NMR (400 MHz, CHLOROFORM-d) δ 8.48 (s, 1H), 7.86 (s, 1H), 7.61-7.57 (m, 2H), 7.32-7.20 (m, 3H), 7.13 (d, J=7.1 Hz, 2H), 6.98 (d, J=3.5 Hz, 1H), 6.91 (s, 1H), 6.57 (dd, J=1.9, 3.4 Hz, 1H), 4.33 (t, J=7.5 Hz, 2H), 3.18 (t, J=7.5 Hz, 2H); LCMS (ESI) m/z: 349.1 [M+H]$^+$.

Compound 25: ¹H NMR (400 MHz, CHLOROFORM-d) δ 8.47 (s, 2H), 7.95-7.87 (m, 2H), 7.59-7.49 (m, 3H), 7.23 (s, 1H); LCMS (ESI) m/z: 255.1 [M+H]⁺.

Compound 27: ¹H NMR (400 MHz, DMSO-d6) δ 10.82 (s, 1H), 8.01 (s, 1H), 7.60-7.50 (m, 2H), 7.33-7.24 (m, 2H), 7.20 (s, 1H), 6.77 (br d, J=1.3 Hz, 1H), 6.13 (s, 1H), 3.86 (s, 2H), 3.66 (s, 3H); LCMS (ESI) m/z: 417.0 [M+H]⁺.

Compound 29: ¹H NMR (400 MHz, DMSO-d6) δ 11.03 (s, 1H), 8.23 (s, 1H), 8.00 (d, J=1.2 Hz, 1H), 7.69 (s, 1H), 7.62 (d, J=8.3 Hz, 1H), 7.51 (d, J=1.8 Hz, 1H), 7.28 (d, J=3.5 Hz, 1H), 7.21 (dd, J=2.0, 8.3 Hz, 1H), 7.15 (s, 1H), 6.77 (dd, J=1.7, 3.4 Hz, 1H), 5.36 (s, 2H); LCMS (ESI) m/z: 403.0 [M+H]⁺.

Compound 31: ¹H NMR (400 MHz, CHLOROFORM-d) δ 8.57 (s, 1H), 8.04 (s, 1H), 7.63-7.55 (m, 2H), 6.99 (d, J=3.3 Hz, 1H), 6.93 (s, 1H), 6.58 (dd, J=1.7, 3.4 Hz, 1H), 4.01-3.95 (m, 4H), 3.37 (dt, J=1.8, 11.7 Hz, 2H), 2.18 (ttt, J=3.8, 7.5, 11.4 Hz, 1H), 1.55-1.49 (m, 2H), 1.44-1.33 (m, 2H); LCMS (ESI) m/z: 343.1 [M+H]⁺.

Compound 32: ¹H NMR (400 MHz, DMSO-d6) δ 8.24 (s, 0.1H), 7.97 (s, 0.9H), 7.72 (s, 0.75H), 7.62 (s, 0.25H), 7.46-7.25 (m, 5.4H), 7.24-7.04 (m, 3.6H), 6.85-6.70 (m, 3H), 5.32-5.13 (m, 2H), 5.12-4.90 (m, 2H); LCMS (ESI) m/z: 493.1 [M+H]⁺.

Compound 33: ¹H NMR (400 MHz, CHLOROFORM-d) δ=8.65 (s, 1H), 8.59 (s, 1H), 7.80 (s, 1H), 7.71 (d, J=7.9 Hz, 2H), 7.60 (s, 1H), 7.46 (t, J=7.9 Hz, 2H), 7.32-7.27 (m, 1H), 6.99 (d, J=3.5 Hz, 1H), 6.95 (s, 1H), 6.58 (dd, J=1.7, 3.4 Hz, 1H); LCMS (ESI) m/z: 321.0 [M+H]⁺.

Compound 35: ¹H NMR (400 MHz, CHLOROFORM-d) δ 8.63 (s, 1H), 8.61 (s, 1H), 7.89 (s, 1H), 7.86-7.80 (m, 2H), 7.56-7.47 (m, 3H), 7.05 (s, 1H), 1.68 (s, 9H); LCMS (ESI) m/z: 255.1 [M+H]⁺.

Compound 39: 1H NMR (400 MHz, DMSO-d6) δ 11.10 (s, 1H), 8.73 (s, 2H), 8.33 (s, 1H), 8.05 (d, J=8.0 Hz, 1H), 7.99-7.96 (m, 2H), 7.77-7.73 (m, 2H), 7.61-7.54 (m, 3H), 7.47 (s, 1H), 5.52 (s, 2H); LCMS (ESI) m/z: 346.1 [M+H]⁺.

Compound 40: 1H NMR (400 MHz, DMSO-d6) δ 11.08 (s, 1H), 8.58 (s, 1H), 8.25 (s, 1H), 7.99-7.97 (m, 2H), 7.85 (t, J=7.6 Hz, 1H), 7.72 (s, 1H), 7.58-7.57 (m, 3H), 7.48-7.37 (m, 2H), 7.10 (d, J=8.4 Hz, 1H), 7.47 (s, 1H), 5.48 (s, 2H); LCMS (ESI) m/z: 346.1 [M+H]⁺.

Compound 41: 1H NMR (400 MHz, DMSO-d6) δ 10.99 (s, 1H), 8.12 (s, 1H), 7.98 (dd, J=7.6, 2.0 Hz, 2H), 7.65 (s, 1H), 7.61-7.52 (m, 3H), 7.46 (s, 1H), 3.97 (d, J=7.0 Hz, 2H), 1.28-1.16 (m, 1H), 0.57-0.44 (m, 2H), 0.40-0.29 (m, 2H); LCMS (ESI) m/z: 309.1 [M+H]⁺.

Compound 42: 1H NMR (500 MHz, DMSO-d6) δ 11.07 (s, 1H), 8.26 (s, 1H), 7.97 (dd, J=7.5 Hz, J=2.0 Hz, 2H), 7.83 (d, J=8.5 Hz, 2H), 7.72 (s, 1H), 7.61-7.52 (m, 3H), 7.46 (s, 1H), 7.36 (d, J=8.5 Hz, 2H), 5.47 (s, 2H); LCMS (ESI) m/z: 370.1 [M+H]⁺.

Compound 43: 1H NMR (500 MHz, DMSO-d6) δ 11.08 (s, 1H), 8.27 (s, 1H), 7.97 (d, J=6.0 Hz, 2H), 7.86 (d, J=3.0 Hz, 1H), 7.73 (s, 1H), 7.58-7.57 (m, 3H), 7.47 (s, 1H), 7.25 (d, J=3.5 Hz, 1H), 5.66 (s, 2H); LCMS (ESI) m/z: 376.1 [M+H]⁺.

Compound 44: LCMS (ESI) m/z: 346.1 [M+H]⁺.

Compound 45: 1H NMR (500 MHz, DMSO-d6) δ 11.13 (s, 1H), 9.35 (d, J=1.5 Hz, 1H), 8.84 (dd, J=2.5, 1.5 Hz, 1H), 8.81 (d, J=1.5 Hz, 1H), 8.23 (s, 1H), 7.70 (s, 1H), 7.69 (s, 1H), 7.41-7.37 (m, 1H), 7.13 (td, J=8.5, 2.0 Hz, 1H), 7.08-7.04 (m, 2H), 5.37 (s, 2H); LCMS (ESI) m/z: 365.1 [M+H]⁺.

Compound 46: 1H NMR (500 MHz, DMSO-d6) δ 11.13 (s, 1H), 9.04 (d, J=4.0 Hz, 2H), 8.23 (s, 1H), 7.70 (s, 1H), 7.68-7.65 (m, 1H), 7.55 (s, 1H), 7.40-7.38 (m, 1H), 7.15-7.12 (m, 1H), 7.07-7.04 (m, 2H), 5.37 (s, 2H); LCMS (ESI) m/z: 365.1 [M+H]⁺.

Compound 47: LCMS (ESI) m/z: 485.1 [M+H]⁺.

Compound 48: ¹H NMR (400 MHz, DMSO-d6) δ 11.07 (br s, 1H), 8.45 (s, 1H), 8.15 (s, 1H), 8.08 (s, 1H), 7.66 (s, 1H), 7.41 (s, 1H), 7.38-7.26 (m, 3H), 7.23 (d, J=7.1 Hz, 2H), 5.33 (s, 2H); LCMS (ESI) m/z: 312.0 [M+H]⁺.

Compound 50: 1H NMR (500 MHz, DMSO-d6) δ 11.08 (s, 1H), 8.12 (s, 1H), 7.99-7.97 (m, 2H), 7.66 (s, 1H), 7.60-7.56 (m, 3H), 7.47 (s, 1H), 4.14-4.07 (m, 2H), 3.78-3.74 (m, 1H), 3.66-3.61 (m, 2H), 3.47-3.44 (m, 1H), 2.74-2.67 (m, 1H), 1.94-1.87 (m, 1H), 1.63-1.58 (m, 1H); LCMS (ESI) m/z: 339.1 [M+H]⁺.

Compound 51: 1H NMR (500 MHz, DMSO-d6) δ 11.01 (s, 1H), 8.14 (s, 1H), 7.98-7.96 (m, 2H), 7.71 (s, 1H), 7.60-7.53 (m, 3H), 7.45 (s, 1H), 7.36-7.26 (m, 5H), 5.64 (q, J=7.1 Hz, 1H), 1.81 (d, J=7.1 Hz, 3H); LCMS (ESI) m/z: 359.2 [M+H]⁺.

Compound 52: LCMS (ESI) m/z: 346.1 [M+H]⁺.

Compound 53: 1H NMR (500 MHz, DMSO-d6) δ 11.05 (s, 1H), 8.23 (s, 1H), 7.97 (dd, J=7.5, 2.0 Hz, 2H), 7.71 (s, 1H), 7.62-7.52 (m, 3H), 7.46 (s, 1H), 7.43-7.34 (m, 1H), 7.20-7.09 (m, 1H), 7.06 (t, J=9.0 Hz, 2H), 5.37 (s, 2H); LCMS (ESI) m/z: 363.0 [M+H]⁺.

Compound 54: 1H NMR (400 MHz, DMSO-d6) δ 11.10 (s, 1H), 8.77 (s, 1H), 8.23 (s, 1H), 8.02-8.10 (m, 2H), 7.72 (s, 1H), 7.56-7.58 (m, 1H), 7.51 (s, 1H), 7.38-7.41 (m, 1H), 7.05-7.14 (m, 3H), 5.37 (s, 2H); LCMS (ESI) m/z: 364.1 [M+H]⁺.

Compound 55: 1H NMR (500 MHz, DMSO-d6) δ 11.15 (s, 1H), 9.21 (s, 1H), 8.75-8.74 (m, 1H), 8.41-8.39 (m, 1H), 8.23 (s, 1H), 7.71 (s, 1H), 7.66-7.63 (m, 2H), 7.42-7.38 (m, 1H), 7.16-7.04 (m, 3H), 5.37 (s, 2H); LCMS (ESI) m/z: 364.1 [M+H]⁺.

Compound 57: 1H NMR (400 MHz, DMSO-d6) δ 11.09 (s, 1H), 8.77 (s, 1H), 8.25 (s, 1H), 8.04-8.10 (m, 2H), 7.72 (s, 1H), 7.56-7.57 (m, 1H), 7.50 (s, 1H), 7.38-7.40 (m, 2H), 7.31 (s, 1H), 7.21-7.22 (m, 1H), 5.37 (s, 2H); LCMS (ESI) m/z: 364.1 [M+H]⁺.

Compound 59: ¹H NMR (400 MHz, DMSO-d6) δ 11.25 (s, 1H), 8.59 (s, 1H), 8.18 (s, 1H), 7.96 (d, J=1.3 Hz, 1H), 7.66 (d, J=8.3 Hz, 1H), 7.61 (d, J=1.8 Hz, 1H), 7.29 (dd, J=2.0, 8.3 Hz, 1H), 7.22-7.18 (m, 2H), 6.74 (dd, J=1.7, 3.4 Hz, 1H), 5.43 (s, 2H); LCMS (ESI) m/z: 403.0 [M+H]⁺.

Compound 61: 1H NMR (500 MHz, DMSO-d6) δ 11.08 (s, 1H), 8.77 (d, J=4.5 Hz, 1H), 8.24 (s, 1H), 8.16-7.95 (m, 2H), 7.70 (s, 1H), 7.57 (ddd, J=7.5, 4.8, 1.1 Hz, 1H), 7.49 (s, 1H), 7.43 (dd, J=8.5, 2.3 Hz, 1H), 7.34 (d, J=1.3 Hz, 1H), 7.17-6.99 (m, 1H), 5.34 (s, 2H); LCMS (ESI) m/z: 382.1 [M+H]⁺.

Compound 63: 1H NMR (500 MHz, DMSO-d6) δ 11.08 (s, 1H), 9.00 (d, J=1.5 Hz, 1H), 8.34-8.18 (m, 2H), 7.97 (dd, J=7.7, 1.7 Hz, 2H), 7.74 (s, 1H), 7.58 (q, J=5.3 Hz, 3H), 7.47 (s, 1H), 7.17 (d, J=8.2 Hz, 1H), 5.58 (s, 2H); LCMS (ESI) m/z: 371.1 [M+H]⁺.

Compound 64: 1H NMR (500 MHz, DMSO-d6) δ 11.01 (s, 1H), 8.07 (s, 1H), 7.98-7.95 (m, 2H), 7.75 (s, 1H), 7.60-7.55 (m, 3H), 7.43 (s, 1H), 7.33-7.23 (m, 3H), 7.02 (d, J=7.6 Hz, 2H), 1.92 (s, 6H); LCMS (ESI) m/z: 373.1 [M+H]⁺.

Compound 65: 1H NMR (500 MHz, CDCl3) δ 8.96 (s, 1H), 8.07 (s, 1H), 7.78-7.77 (m, 3H), 7.47-7.46 (m, 3H), 7.31-7.26 (m, 3H), 7.22-7.21 (m, 2H), 7.04 (s, 1H), 5.62 (s, 1H), 5.54 (s, 1H), 3.25 (s, 1H), 2.99 (s, 2H), 2.91 (s, 6H), 2.60 (s, 1H); LCMS (ESI) m/z: 416.1 [M+H]⁺.

Compound 66: 1H NMR (500 MHz, DMSO-d6) δ 10.21 (s, 1H), 8.05 (s, 1H), 7.97-7.95 (m, 2H), 7.58-7.55 (m, 3H), 7.44 (s, 1H), 7.37-7.26 (m, 5H), 5.24 (s, 2H), 2.16 (s, 3H); LCMS (ESI) m/z: 359.2 [M+H]+.

Compound 68: 1H NMR (500 MHz, DMSO-d6) δ 11.19 (s, 1H), 8.40 (s, 1H), 7.98 (dd, J=7.6, 1.9 Hz, 2H), 7.63-7.55 (m, 3H), 7.52 (s, 1H), 7.42-7.32 (m, 5H), 5.47 (s, 2H); LCMS (ESI) m/z: 370.1 [M+H]+.

Compound 70: 1H NMR (500 MHz, DMSO-d6) δ. 11.02 (s, 1H), 8.19 (s, 1H), 7.97-7.97 (m, 2H), 7.73 (s, 1H), 7.59-7.55 (m, 3H), 7.44 (s, 1H), 7.38-7.33 (m, 4H), 7.30-7.27 (m, 1H), 5.59-5.57 (m, 1H), 2.67-2.65 (m, 1H), 2.36-2.29 (m, 3H), 2.05 (s, 3H); LCMS (ESI) m/z: 419.1 [M+H]+.

Compound 71: 1H NMR (500 MHz, DMSO-d6) δ. 11.03 (s, 1H), 8.20 (d, J=1.5 Hz, 1H), 7.97-7.95 (m, 2H), 7.74 (s, 1H), 7.59-7.55 (m, 3H), 7.44 (s, 1H), 7.39-7.34 (m, 4H), 7.32-7.29 (m, 1H), 5.63-5.60 (m, 1H), 7.75-2.43 (m, 7H); LCMS (ESI) m/z: 435.1 [M+H]+.

Compound 72: 1H NMR (400 MHz, DMSO-d6) δ 11.16 (s, 1H), 8.90 (d, J=2.0 Hz, 1H), 8.23 (s, 1H), 7.66 (d, J=34.9 Hz, 2H), 7.38 (dd, J=12.2, 4.1 Hz, 2H), 7.22-6.86 (m, 3H), 5.37 (s, 2H); LCMS (ESI) m/z: 354.1 [M+H]+.

Compound 73: 1H NMR (500 MHz, CDCl3) δ 8.55 (s, 1H), 8.13 (s, 1H), 7.82 (dd, J=7.4, 2.2 Hz, 2H), 7.68 (s, 1H), 7.54-7.46 (m, 3H), 7.36 (d, J=4.4 Hz, 4H), 7.33 (dd, J=8.5, 4.3 Hz, 1H), 7.01 (s, 1H), 5.41 (dd, J=9.0, 5.9 Hz, 1H), 3.60 (dd, J=13.9, 9.0 Hz, 1H), 3.24 (dd, J=13.9, 5.9 Hz, 1H), 2.03 (s, 3H); LCMS (ESI) m/z: 405.0 [M+H]+.

Compound 74: LCMS (ESI) m/z: 431.0 [M+H]+.

Compound 75: 1H NMR (500 MHz, DMSO-d6) δ 11.06 (s, 1H), 8.20 (s, 1H), 7.97 (dd, J=2.0 Hz, 2H), 7.77 (s, 1H), 7.59-7.55 (m, 3H), 7.45 (s, 1H), 7.38-7.37 (m, 4H), 7.34-7.31 (m, 1H), 5.64-5.61 (m, 1H), 3.13-3.07 (m, 1H), 3.02 (s, 3H), 2.91-2.78 (m, 2H), 2.55-2.52 (m, 1H); LCMS (ESI) m/z: 451.1 [M+H]+.

Compound 76: 1H NMR (400 MHz, DMSO-d6) δ 8.45 (s, 1H), 7.10-7.99 (m, 9H), 6.43-6.73 (m, 1H), 5.47-5.60 (m, 2H), 3.34-3.50 (m, 3H); LCMS (ESI) m/z: 445.0 [M+H]+.

Compound 77: 1H NMR (400 MHz, DMSO-d6) δ 11.17 (s, 1H), 8.78 (s, 1H), 8.29 (s, 1H), 8.03-8.09 (m, 2H), 7.79-7.89 (m, 2H), 7.38-7.56 (m, 3H), 6.65 (s, 1H), 5.58 (s, 2H); LCMS (ESI) m/z: 432.1 [M+H]+.

Compound 78: 1H NMR (500 MHz, DMSO-d6) δ 11.02 (d, J=9.1 Hz, 1H), 8.29 (d, J=25.1 Hz, 1H), 8.01-7.93 (m, 2H), 7.76 (d, J=11.6 Hz, 1H), 7.56 (m, 3H), 7.50-7.30 (m, 6H), 6.01-5.84 (m, 1H), 4.13-3.77 (m, H), 3.54 (m, 1H), 2.61 (d, J=21.4 Hz, 3H); LCMS (ESI) m/z: 421.1 [M+H]+.

Compound 79: 1H NMR (500 MHz, CDCl3) δ 9.13 (s, 1H), 7.82 (dd, J=6.5, 3.0 Hz, 2H), 7.57-7.44 (m, 3H), 7.42-7.28 (m, 5H), 7.09 (s, 1H), 4.24 (s, 2H); LCMS (ESI) m/z: 347.1 [M+H]+.

Compound 80: 1H NMR (500 MHz, DMSO-d6) δ 11.03 (s, 1H), 8.35 (s, 1H), 7.96 (dd, J=7.7, 1.8 Hz, 2H), 7.76 (s, 1H), 7.60-7.54 (m, 3H), 7.47-7.43 (m, 3H), 7.34 (dt, J=24.8, 7.1 Hz, 3H), 6.10 (dd, J=9.8, 3.8 Hz, 1H), 4.53 (dd, J=14.8, 9.9 Hz, 1H), 3.94 (dd, J=14.9, 3.7 Hz, 1H), 2.73 (s, 3H); LCMS (ESI) m/z: 437.0 [M+H]+.

Compound 82: 1H NMR (500 MHz, DMSO-d6) δ 10.33 (s, 1H), 8.32 (s, 1H), 8.02-7.90 (m, 2H), 7.61-7.53 (m, 3H), 7.47 (s, 1H), 7.43-7.30 (m, 5H), 5.44 (s, 2H); LCMS (ESI) m/z: 413.0 [M+H]+.

Compound 84: 1H NMR (400 MHz, DMSO-d6) δ 11.05 (s, 1H), 8.27 (s, 1H), 7.86-7.89 (m, 1H), 7.76 (s, 1H), 7.37-7.41 (m, 1H), 7.03 (s, 1H), 6.62-6.64 (m, 1H), 5.87 (s, 1H), 5.57 (s, 1H), 5.48 (s, 1H), 2.12 (s, 3H); LCMS (ESI) m/z: 395.0 [M+H]+.

Compound 87: 1H NMR (400 MHz, DMSO-d6) δ 11.08 (s, 1H), 9.04 (d, J=4.6 Hz, 1H), 8.22 (s, 1H), 7.69 (s, 1H), 7.47-7.30 (m, 2H), 7.19-6.93 (m, 3H), 5.37 (s, 2H), 2.81 (d, J=4.6 Hz, 3H); LCMS (ESI) m/z: 344.1 [M+H]+

Compound 88: 1H NMR (500 MHz, DMSO-d6) δ 11.09 (s, 1H), 8.32 (s, 1H), 8.03-7.97 (m, 3H), 7.75 (s, 1H), 7.60-7.54 (m, 3H), 7.47 (s, 1H), 7.45-7.41 (m, 1H), 7.11-7.08 (m, 1H), 5.57 (s, 2H); LCMS (ESI) m/z: 388.1 [M+H]+.

Compound 89: 1H NMR (500 MHz, DMSO-d6) δ 10.99 (s, 1H), 8.22-8.19 (m, 2H), 8.02 (dd, J=6.6, 1.9 Hz, 1H), 7.69 (s, 1H), 7.47 (s, 1H), 7.42-7.37 (m, 1H), 7.17-6.97 (m, 3H), 6.48 (t, J=6.9 Hz, 1H), 5.36 (s, 2H), 3.59 (s, 3H); LCMS (ESI) m/z: 394.1 [M+H]+.

Compound 92: 1H NMR (500 MHz, DMSO-d6) δ 11.14 (s, 1H), 8.80 (s, 1H), 8.20 (s, 1H), 8.04-7.95 (m, 2H), 7.75 (d, J=14.5 Hz, 2H), 7.51 (dd, J=7.6, 1.6 Hz, 1H), 7.36 (pd, J=7.4, 1.7 Hz, 2H), 7.28 (dd, J=8.3, 7.2 Hz, 1H), 7.03 (dd, J=7.3, 2.0 Hz, 1H), 6.07-5.96 (m, 1H), 5.46 (s, 2H), 5.11 (dt, J=14.5, 6.9 Hz, 4H); LCMS (ESI) m/z: 475.1 [M+H]+.

Compound 93: 1H NMR (500 MHz, DMSO-d6) δ 11.18 (s, 1H), 8.46 (s, 1H), 8.22 (s, 1H), 8.08 (dd, J=8.0, 0.8 Hz, 1H), 7.76 (s, 1H), 7.67 (dd, J=7.2, 0.8 Hz, 1H), 7.51 (dd, J=7.6, 1.6 Hz, 1H), 7.41-7.28 (m, 4H), 7.02 (dd, J=7.3, 1.9 Hz, 1H), 5.47 (s, 2H), 5.45-5.37 (m, 1H), 5.05 (t, J=6.3 Hz, 2H), 4.78 (t, J=7.0 Hz, 2H); LCMS (ESI) m/z: 475.1 [M+H]+.

Compound 94: 1H NMR (500 MHz, DMSO-d6) δ 11.13 (s, 1H), 8.70 (s, 1H), 8.21 (s, 1H), 7.95 (d, J=8.5 Hz, 1H), 7.87 (d, J=7.0 Hz, 1H), 7.74 (s, 1H), 7.67 (s, 1H), 7.61-7.59 (m, 1H), 7.52-7.50 (m, 1H), 7.38-7.32 (m, 2H), 7.02-7.00 (m, 1H), 6.20-6.17 (m, 1H), 5.46 (s, 2H), 5.09-5.03 (m, 4H); LCMS (ESI) m/: 475.0 [M+H]+.

Compound 95: 1H NMR (500 MHz, DMSO-d6) δ 11.10 (s, 1H), 8.80 (s, 1H), 8.18 (s, 1H), 8.00 (t, J=7.8 Hz, 2H), 7.72 (d, J=2.0 Hz, 2H), 7.36 (t, J=7.3 Hz, 2H), 7.32-7.19 (m, 4H), 6.05-5.97 (m, 1H), 5.35 (s, 2H), 5.11 (dt, J=14.6, 7.0 Hz, 4H); LCMS (ESI) m/z: 441.1 [M+H]+.

Compound 96: 1H NMR (500 MHz, DMSO-d6) δ 11.15 (s, 1H), 8.46 (s, 1H), 8.21 (s, 1H), 8.08 (dd, J=8.0, 0.8 Hz, 1H), 8.08 (dd, J=8.0, 0.8 Hz, 1H), 7.72 (s, 1H), 7.67 (dd, J=7.1, 0.8 Hz, 1H), 7.39-7.28 (m, 5H), 7.26 (d, J=7.0 Hz, 2H), 5.45-5.38 (m, 1H), 5.36 (s, 2H), 5.05 (t, J=6.3 Hz, 2H), 4.78 (t, J=7.1 Hz, 2H); LCMS (ESI) m/z: 441.1 [M+H]+.

Compound 97: 1H NMR (500 MHz, DMSO-d6) δ 11.09 (s, 1H), 8.69 (s, 1H), 8.19 (s, 1H), 7.94 (d, J=8.5 Hz, 1H), 7.87 (d, J=7.5 Hz, 1H), 7.70-7.59 (m, 3H), 7.38-7.25 (m, 5H), 6.21-6.15 (m, 1H), 5.35 (s, 2H), 5.09-5.03 (m, 4H); LCMS (ESI) m/z: 441.1 [M+H]+.

Compound 98: 1H NMR (500 MHz, DMSO-d6) δ 11.07 (s, 1H), 8.30 (s, 1H), 7.98 (dd, J=8.5 2.0 Hz, 2H), 7.84-7.82 (m, 1H), 7.73 (s, 1H), 7.60-7.55 (m, 4H), 7.47-7.44 (m, 2H), 5.44 (s, 2H); LCMS (ESI) m/z: 388.1 [M+H]+.

Compound 99: 1H NMR (400 MHz, DMSO-d6) δ 11.21 (s, 1H), 9.21 (s, 1H), 8.56-8.58 (d, J=8 Hz, 1H), 8.30-8.31 (d, J=4 Hz, 2H), 7.87-7.90 (m, 1H), 7.72-7.79 (m, 2H), 7.39-7.42 (m, 1H), 6.64-6.66 (d, J=8 Hz, 1H), 5.58 (s, 2H); LCMS (ESI) m/z: 457.0 [M+H]+.

Compound 100: 1H NMR (500 MHz, DMSO-d6) δ. 10.93 (s, 1H), 8.19 (s, 1H), 7.67 (s, 1H), 7.39 (dd, J=14.0, 3.5 Hz, 1H), 7.14-7.11 (m, 1H), 7.07-7.03 (m, 2H), 6.78 (s, 1H), 6.25 (s, 1H), 5.35 (s, 2H), 2.50-2.45 (m, 2H), 2.35-2.29 (m, 2H), 1.88-1.85 (m, 1H), 1.74-1.70 (m, 1H; LCMS (ESI) m/z: 357.1 [M+H]+.

Compound 103: 1H NMR (500 MHz, DMSO-d6) δ 11.16 (s, 1H), 8.23 (s, 1H), 8.17-8.10 (m, 2H), 7.95-7.93 (m, 1H), 7.92-7.55 (m, 4H), 7.43-7.38 (m, 1H), 7.16-7.05 (m, 3H), 5.38 (s, 2H); LCMS (ESI) m/z: 388.0 [M+H]+.

Compound 107: 1H NMR (500 MHz, DMSO-d6) δ. 11.18 (s, 1H), 8.66-8.65 (m, 1H), 8.30 (s, 1H), 8.04 (td, J=10.0, 1.0 Hz, 1H), 7.88 (dd, J=8.5, 5.5 Hz, 1H), 7.78 (s, 1H), 7.73-7.70 (m, 1H), 7.42 (d, J=2.5 Hz, 1H), 7.38 (dd, J=8.5, 2.0 Hz, 1H), 6.66 (dd, J=10.0, 2.0 Hz, 1H), 5.58 (s, 2H);

Compound 109: $^1$H NMR (300 MHz, DMF-d7) δ 11.02 (s, 1H), 8.18 (s, 1H), 8.00-7.93 (m, 2H), 7.67 (d, J=0.7 Hz, 1H), 7.61-7.54 (m, 3H), 7.45 (s, 1H), 7.38-7.25 (m, 2H), 7.23-7.13 (m, 2H), 5.32 (s, 2H); LCMS (ESI) m/z: 375.3 [M+H]$^+$.

Compound 111: $^1$H NMR (300 MHz, DMSO-d6) δ 11.03 (s, 1H), 8.17 (s, 1H), 8.00-7.93 (m, 2H), 7.68 (d, J=0.7 Hz, 1H), 7.57 (dd, J=5.2, 2.0 Hz, 3H), 7.45 (s, 1H), 7.43-7.32 (m, 1H), 7.27-7.15 (m, 3H), 5.40 (s, 2H); LCMS (ESI) m/z: 363.3 [M+H]$^+$.

Compound 112: $^1$H NMR (300 MHz, DMF-d7) δ 11.02 (s, 1H), 8.18 (s, 1H), 8.00-7.93 (m, 2H), 7.67 (d, J=0.7 Hz, 1H), 7.61-7.54 (m, 3H), 7.45 (s, 1H), 7.38-7.25 (m, 2H), 7.23-7.13 (m, 2H), 5.32 (s, 2H); LCMS (ESI) m/z: 363.2 [M+H]$^+$.

Compound 116: 1H NMR (500 MHz, DMSO-d6) δ. 10.96 (s, 1H), 8.20 (s, 1H), 7.67 (s, 1H), 7.39 (dd, J=14.0, 7.5 Hz, 1H), 7.13 (td, J=8.5, 2.0 Hz, 1H), 7.07-7.04 (m, 2H), 6.91 (s, 1H), 5.35 (s, 2H), 4.84 (d, J=6.0 Hz, 2H), 4.55 (d, J=6.0 Hz, 2H), 1.72 (s, 3H); LCMS (ESI) m/z: 357.2 [M+H]+.

Compound 120: 1H NMR (500 MHz, DMSO-d6) δ. 10.96 (s, 1H), 8.14 (s, 1H), 7.65 (s, 1H), 7.36-7.23 (m, 5H), 7.03 (s, 1H), 5.32 (s, 2H), 3.02 (s, 3H), 2.45-2.35 (m, 4H), 1.88-1.82 (m, 1H), 1.70-1.64 (m, 1H); LCMS (ESI) m/z: 353.2 [M+H]$^+$.

Compound 121: 1H NMR (500 MHz, DMSO-d6) δ. 10.09 (s, 1H), 8.14 (s, 1H), 7.64 (s, 1H), 7.36-7.23 (m, 5H), 6.90 (s, 1H), 5.32 (s, 2H), 4.83 (d, J=6.0 Hz, 2H), 4.54 (d, J=6.0 Hz, 2H), 1.72 (s, 3H); LCMS (ESI) m/z: 339.1 [M+H]$^+$.

Compound 122: 1H NMR (500 MHz, DMSO-d6) δ. 11.09 (s, 1H), 8.65 (d, J=4.5 Hz, 1H), 8.18 (s, 1H), 8.03 (td, J=10.0, 1.0 Hz, 1H), 7.72-7.69 (m, 1H), 7.68 (s, 1H), 7.39 (d, J=2.5 Hz, 1H), 7.36-7.24 (m, 5H), 5.34 (s, 2H); LCMS (ESI) m/z: 364.1 [M+H]$^+$.

Compound 123: 1H NMR (400 MHz, DMSO-d6) δ 11.16 (s, 1H), 8.20 (s, 1H), 7.96-7.97 (m, 1H), 7.69-7.73 (m, 2H), 7.55-7.56 (m, 3H), 7.25-7.37 (m, 5H), 5.35 (s, 2H); LCMS (ESI) m/z: 345.1 [M+H]+.

Compound 126: 1H NMR (500 MHz, DMSO-d6) δ. 11.10 (s, 1H), 8.76 (d, J=1.5 Hz, 1H), 8.17 (s, 1H), 8.09 (d, J=1.5 Hz, 1H), 7.67 (s, 1H), 7.61 (s, 1H), 7.36-7.23 (m, 5H), 5.33 (s, 2H); LCMS (ESI) m/z: 352.0 [M+H]+.

Compound 128: 1H NMR (500 MHz, DMSO-d6) δ. 11.07 (s, 1H), 8.17-8.16 (m, 3H), 8.05 (d, J=8.5 Hz, 2H), 7.68 (d, J=1.0 Hz, 2H), 7.36-7.23 (m, 5H), 5.33 (s, 2H); LCMS (ESI) m/z: 370.1 [M+H]+.

Compound 129: 1H NMR (400 MHz, DMSO-d6) δ 11.15 (s, 1H), 8.76-8.77 (m, 1H), 8.20 (s, 1H), 8.10-8.12 (m, 1H), 7.99-8.03 (m, 1H), 7.68-7.69 (m, 2H), 7.56-7.59 (m, 1H), 7.25-7.37 (m, 5H), 5.35 (s, 2H); LCMS (ESI) m/z: 346.1 [M+H]+.

Compound 130: 1H NMR (400 MHz, DMSO-d6) δ 11.16 (s, 1H), 8.19 (s, 1H), 7.98-7.99 (m, 1H), 7.58-7.68 (m, 3H), 7.46-7.48 (m, 2H), 7.25-7.42 (m, 5H), 5.35 (s, 2H); LCMS (ESI) m/z: 363.1 [M+H]+.

Compound 131: 1H NMR (400 MHz, DMSO-d6) δ 11.22 (s, 1H), 9.32 (s, 1H), 8.67 (s, 1H), 8.19 (s, 1H), 7.80 (s, 1H), 7.68 (s, 1H), 7.24-7.37 (m, 5H), 5.34 (s, 2H); LCMS (ESI) m/z: 352.0 [M+H]+.

Compound 132: 1H NMR (300 MHz, DMSO-d6) δ 11.05 (s, 1H), 8.26 (s, 1H), 8.06-7.90 (m, 2H), 7.79 (dt, J=6.5, 2.1 Hz, 1H), 7.71 (s, 2H), 7.61-7.52 (m, 5H), 7.46 (s, 1H), 5.42 (s, 2H); LCMS (ESI) m/z: 370.3 [M+H]+.

Compound 144: 1H NMR (300 MHz, DMSO-d6) δ 11.05 (s, 1H), 8.17 (d, J=0.7 Hz, 1H), 7.92-7.84 (m, 1H), 7.84-7.79 (m, 1H), 7.68 (d, J=0.7 Hz, 1H), 7.63 (td, J=8.0, 5.9 Hz, 1H), 7.56 (s, 1H), 7.45-7.21 (m, 6H), 5.34 (s, 2H); LCMS (ESI) m/z: 363.2 [M+H]+.

Compound 145: 1H NMR (400 MHz, CDCl3) δ 8.23 (dd, J=2.2, 15.8 Hz, 1H), 7.32-7.23 (m, 1H), 7.19 (s, 1H), 7.17-7.09 (m, 1H), 7.06-6.97 (m, 1H), 6.92-6.82 (m, 1H), 6.75 (s, 0.6H), 6.53 (s, 0.3H), 6.05-5.97 (m, 2H), 5.77 (m, 0.4H), 4.25-4.07 (m, 0.6H), 3.98-3.86 (m, 1H), 3.83-3.74 (m, 3H), 2.44-2.30 (m, 1H), 2.24-2.13 (m, 2H), 2.06-1.89 (m, 1H); LCMS (ESI) m/z [M+H]+: 394.1

Compound 148: $^1$H NMR (500 MHz, DMSO-d6) δ 11.13 (s, 1H), 9.39 (d, J=1.0 Hz, 1H), 9.08 (d, J=5.0 Hz, 1H), 8.18-8.16 (m, 2H), 7.77 (s, 1H), 7.69 (s, 1H), 7.37-7.34 (m, 2H), 7.31-7.28 (m, 1H), 7.25 (d, J=7.0 Hz, 2H), 5.34 (s, 2H); LCMS (ESI) m/z: 347.1 [M+H]$^+$.

Compound 153: $^1$H NMR (500 MHz, DMSO-d6) δ 11.07 (s, 1H), 8.16 (s, 1H), 7.65 (s, 1H), 7.50 (s, 1H), 7.36-7.23 (m, 5H), 5.88 (s, 1H), 5.52 (s, 1H), 5.33 (s, 2H), 2.11 (s, 3H); LCMS (ESI) m/z: 309.1 [M+H]$^+$.

Compound 167: $^1$H NMR (300 MHz, DMSO-d6) δ 10.82 (s, 1H), 7.91 (s, 1H), 7.57 (s, 1H), 6.63 (d, J=0.9 Hz, 1H), 3.77 (s, 2H), 3.17 (p, J=7.1 Hz, 1H), 1.57-1.41 (m, 6H), 1.30 (dd, J=10.9, 7.2 Hz, 13H); LCMS (ESI) m/z: 343.3 [M+H]$^+$.

Compound 176: $^1$H NMR (300 MHz, DMSO-d6) δ 11.35 (s, 1H), 8.64-8.49 (m, 1H), 7.64 (dt, J=8.9, 1.3 Hz, 1H), 7.22 (ddd, J=8.9, 6.7, 1.1 Hz, 1H), 6.96 (d, J=0.9 Hz, 1H), 6.91-6.68 (m, 2H), 3.26-3.06 (m, 1H), 1.29 (dd, J=6.9, 1.3 Hz, 6H); LCMS (ESI) m/z: 271.1 [M+H]$^+$.

Compound 202: $^1$H NMR (300 MHz, Chloroform-d) δ 8.86-8.70 (m, 3H), 8.56 (s, 1H), 8.41 (s, 1H), 8.16 (s, 1H), 7.77-7.65 (m, 3H), 7.59 (d, J=5.0 Hz, 1H), 7.23 (s, 1H), 5.57 (s, 2H); LCMS (ESI) m/z: 415.5[M+H]+.

Compound 208: $^1$H NMR (400 MHz, CHLOROFORM-d) δ 7.39-7.30 (m, 3H), 7.26 (s, 1H), 7.04 (t, J=7.3 Hz, 1H), 6.93 (d, J=8.2 Hz, 1H), 6.86-6.77 (m, 3H), 6.07 (s, 2H), 5.12-4.97 (m, 2H), 4.70-4.58 (m, 2H), 4.31 (dd, J=3.7, 11.2 Hz, 1H); LCMS (ESI) m/z: 365.1 [M+H]$^+$.

Compound 209: $^1$H NMR (400 MHz, CHLOROFORM-d) δ 7.85 (dd, J=2.0, 7.5 Hz, 2H), 7.60-7.47 (m, 3H), 7.32-7.28 (m, 2H), 7.00 (s, 1H), 6.85 (t, J=7.3 Hz, 1H), 6.54 (d, J=7.8 Hz, 2H), 4.83 (s, 2H), 4.44 (s, 2H), 4.19-4.04 (m, 4H); LCMS (ESI) m/z: 346.1 [M+H]$^+$.

Compound 210: $^1$H NMR (400 MHz, CHLOROFORM-d) δ 7.57 (d, J=0.9 Hz, 1H), 7.20 (m, 2H), 6.94 (d, J=3.5 Hz, 1H), 6.87-6.77 (m, 2H), 6.60-6.51 (m, 3H), 5.01-4.90 (m, 1H), 4.60 (m, 1H), 4.45-4.33 (m, 2H), 4.09 (br s, 1H), 4.05-3.96 (m, 1H); LCMS (ESI) m/z: 310.1 [M+H]$^+$.

Compound 213: $^1$H NMR (400 MHz, CDCl3) δ 7.81 (dd, J=2.0, 7.7 Hz, 2H), 7.54-7.44 (m, 3H), 7.32 (t, J=8.1 Hz, 2H), 7.03 (t, J=7.5 Hz, 1H), 6.97 (s, 1H), 6.80 (d, J=7.9 Hz, 2H), 5.12-4.99 (m, 2H), 4.70-4.58 (m, 2H), 4.31 (dd, J=3.7, 11.6 Hz, 1H); LCMS (ESI) m/z: 321.1 [M+H]$^+$.

Compound 214: $^1$H NMR (400 MHz, CDCl3) δ 7.80 (dd, J=2.1, 7.4 Hz, 2H), 7.57-7.46 (m, 3H), 7.26-7.20 (m, 2H), 6.97 (s, 1H), 6.82 (t, J=7.4 Hz, 1H), 6.58 (d, J=7.7 Hz, 2H), 5.06-4.94 (m, 1H), 4.62 (dd, J=6.3, 10.7 Hz, 1H), 4.47-4.37 (m, 2H), 4.12 (br s, 1H), 4.03 (dd, J=4.6, 11.7 Hz, 1H); LCMS (ESI) m/z: 320.2 [M+H]$^+$.

Compound 215: $^1$H NMR (400 MHz, DMSO-d6) δ 7.95 (dd, J=2.0, 7.3 Hz, 2H), 7.61-7.48 (m, 3H), 7.38 (s, 1H), 7.09 (t, J=7.8 Hz, 2H), 6.67 (d, J=7.9 Hz, 2H), 6.55 (t, J=7.3 Hz, 1H), 5.80 (br t, J=6.2 Hz, 1H), 4.41-4.24 (m, 2H), 4.05 (s, 2H), 3.99-3.85 (m, 2H), 3.40 (br d, J=6.2 Hz, 2H); LCMS (ESI) m/z: 382.1 [M+H]⁺.

Compound 218: $^1$H NMR (400 MHz, DMSO-d6) δ 7.53 (d, J=1.6 Hz, 0.7H), 7.52-7.46 (m, 1.2H), 7.46-7.40 (m, 0.8H), 7.39-7.33 (m, 1H), 7.31-7.24 (m, 0.3H), 7.26-7.24 (m, 1H) 7.24-7.19 (m, 1H), 7.19-7.11 (m, 1H), 7.09 (d, J=8.4 Hz, 0.7H), 7.02 (d, J=8.0 Hz, 0.3H), 6.13-6.10 (m, 2H), 6.05 (dd, J=5.2, 9.2 Hz, 0.3H), 5.66 (dd, J=6.0, 8.8 Hz, 0.7H), 4.64-4.50 (m, 1.5H), 4.30-4.14 (m, 0.5H), 3.00-2.92 (m, 0.3H), 2.90-2.78 (m, 0.7H), 2.23-2.05 (m, 1H); LCMS (ESI) m/z: 367.1 [M+H]⁺.

Compound 219: $^1$H NMR (400 MHz, CHLOROFORM-d) δ 7.46-7.28 (m, 4H), 7.26-7.16 (m, 2H), 6.92 (d, J=8.0 Hz, 0.7H), 6.87-6.87 (m, 1H), 6.75 (s, 0.2H), 6.28 (dd, J=4.8, 8.8 Hz, 0.2H), 6.06 (s, 1.4H), 6.01 (s, 0.6H), 5.85 (dd, J=6.0, 8.8 Hz, 0.7H), 4.67 (t, J=7.6 Hz, 1.4H), 4.42-4.20 (m, 0.6H), 3.11-2.90 (m, 1H), 2.27-2.07 (m, 1H); LCMS (ESI) m/z: 383.0 [M+H]⁺.

Compound 221: $^1$H NMR (400 MHz, CDCl3) δ 7.33 (dd, J=1.5, 8.2 Hz, 1H), 7.26-7.18 (m, 3H), 6.91 (d, J=8.2 Hz, 1H), 6.85-6.78 (m, 2H), 6.57 (d, J=7.7 Hz, 2H), 6.05 (s, 2H), 5.04-4.94 (m, 1H), 4.61 (dd, J=6.4, 10.8 Hz, 1H), 4.47-4.36 (m, 2H), 4.02 (dd, J=4.4, 12.1 Hz, 2H); LCMS (ESI) m/z: 364.1 [M+H]⁺.

Compound 222: $^1$H NMR (400 MHz, DMSO-d6) δ 7.52 (d, J=1.8 Hz, 1H), 7.48 (dd, J=1.8, 8.2 Hz, 1H), 7.25 (s, 1H), 7.17 (t, J=7.9 Hz, 2H), 7.08 (d, J=8.2 Hz, 1H), 6.69 (t, J=7.4 Hz, 1H), 6.44 (d, J=7.7 Hz, 2H), 6.13 (s, 2H), 4.65 (s, 2H), 4.29 (s, 2H), 3.98 (s, 4H); LCMS (ESI) m/z: 390.2 [M+H]⁺.

Compound 224: $^1$H NMR (400 MHz, CDCl3) δ 7.47-7.36 (m, 4H), 7.34-7.28 (m, 2H), 7.22 (dd, J=1.5, 7.3 Hz, 1H), 6.90 (dd, J=3.5, 8.2 Hz, 1H), 6.78 (d, J=1.1 Hz, 1H), 6.05 (d, J=2.6 Hz, 2H), 4.76 (s, 1H), 4.48 (s, 1H), 4.37 (s, 1H), 4.09 (s, 1H), 2.92-2.81 (m, 2H), 2.75-2.61 (m, 2H), 2.19 (br s, 1H); LCMS (ESI) m/z: 405.1 [M+H]⁺.

Compound 228: $^1$H NMR (400 MHz, MeOD) δ 7.47-7.40 (m, 1H), 7.34 (br d, J=3.4 Hz, 1H), 7.32-7.26 (m, 2H), 7.25-7.20 (m, 2H), 7.19-7.13 (m, 1H), 6.96 (dd, J=3.2, 8.1 Hz, 1H), 6.92 (d, J=3.5 Hz, 1H), 6.05 (d, J=2.0 Hz, 2H), 4.74 (s, 1H), 4.50 (s, 1H), 4.34 (s, 1H), 4.11 (s, 1H), 3.52-3.42 (m, 1H), 2.67 (br t, J=8.9 Hz, 2H), 2.49-2.28 (m, 1H), 2.49-2.28 (m, 1H); LCMS (ESI) m/z: 389.0 [M+H]⁺.

Compound 230: LCMS (ESI) m/z: 376.1 [M+H]+.
Compound 237: LCMS (ESI) m/z: 348.1 [M+H]+.
Compound 238: LCMS (ESI) m/z: 362.0 [M+H]+.
Compound 240: LCMS (ESI) m/z: 348.1 [M+H]+.

Compound 244: 1H NMR (300 MHz, DMSO-d6) δ 7.99 (d, J=1.8 Hz, 1H), 7.26 (d, J=3.5 Hz, 1H), 7.08 (s, 1H), 6.76 (dd, J=3.5, 1.8 Hz, 1H), 5.57 (tt, J=6.2, 3.2 Hz, 1H), 5.38 (tt, J=6.1, 3.1 Hz, 1H), 4.79 (dddd, J=21.5, 11.5, 5.9, 1.9 Hz, 1H), 4.61-4.34 (m, 2H), 4.23-4.02 (m, 1H); LCMS (ESI) m/z: 237.2 [M+H]+.

Compound 245: 1H NMR (300 MHz, DMSO-d6) δ 8.03-7.95 (m, 1H), 7.24 (d, J=3.5 Hz, 1H), 7.04 (s, 1H), 6.78-6.70 (m, 1H), 4.28 (s, 2H), 3.92 (s, 2H), 1.87-1.69 (m, 5H), 1.69-1.48 (m, 5H); LCMS (ESI) m/z: 273.2 [M+H]+.

Compound 246: 1H NMR (300 MHz, DMSO-d6) δ 7.98 (d, J=1.8 Hz, 1H), 7.24 (d, J=3.5 Hz, 1H), 7.02 (d, J=0.9 Hz, 1H), 6.81-6.66 (m, 1H), 4.41 (s, 2H), 4.04 (s, 2H), 2.17 (t, J=7.6 Hz, 5H), 1.78 (p, J=7.7 Hz, 2H); LCMS (ESI) m/z: 259.2 [M+H]+.

Compound 247: 1H NMR (300 MHz, DMSO-d6) δ 7.99 (d, J=1.8 Hz, 1H), 7.25 (d, J=3.5 Hz, 1H), 7.03 (s, 1H), 6.76 (dd, J=3.6, 1.8 Hz, 1H), 4.70 (d, J=1.1 Hz, 4H), 4.62 (s, 2H), 4.25 (s, 2H); LCMS (ESI) m/z: 261.2 [M+H]+.

Compound 248: $^1$H NMR (300 MHz, DMSO-d6) δ 7.43-7.20 (m, 5H), 5.66 (s, 1H), 4.80 (dd, J=9.8, 8.2 Hz, 1H), 4.45 (t, J=8.9 Hz, 1H), 4.35 (dd, J=9.7, 6.1 Hz, 1H), 4.07-3.87 (m, 2H), 3.69 (dd, J=5.9, 3.8 Hz, 4H), 3.29-3.35 (4H, under water peak); LCMS (ESI) m/z: 336.2 [M+Na]+.

Compound 249: $^1$H NMR (300 MHz, DMSO-d6) δ 7.47-7.33 (m, 5H), 7.32-7.23 (m, 1H), 5.61 (s, 1H), 4.79 (dd, J=9.9, 8.1 Hz, 1H), 4.44 (t, J=8.8 Hz, 1H), 4.35 (dd, J=9.4, 6.2 Hz, 1H), 4.07-3.88 (m, 2H), 3.60-3.48 (m, 2H), 3.40 (ddd, J=11.5, 7.8, 3.3 Hz, 9H), 3.16 (ddd, J=12.9, 8.9, 3.5 Hz, 2H), 1.97-1.78 (m, 2H), 1.49 (dtd, J=12.9, 8.7, 4.0 Hz, 2H); LCMS (ESI) m/z: 364.3 [M+Na]+.

Compound 250: 1H NMR (300 MHz, DMSO-d6) δ 7.42-7.32 (m, 4H), 7.32-7.23 (m, 1H), 6.56 (d, J=0.9 Hz, 1H), 4.89-4.76 (m, 1H), 4.53-4.33 (m, 2H), 4.08-3.89 (m, 2H), 3.22-3.06 (m, 1H), 1.27 (d, J=6.9 Hz, 6H); LCMS (ESI) m/z: 271.2 [M+H]+.

Compound 251: $^1$H NMR (300 MHz, DMSO-d6) δ 7.37-7.10 (m, 5H), 6.51 (d, J=0.9 Hz, 1H), 4.51-4.36 (m, 1H), 4.16-4.01 (m, 2H), 3.76 (dd, J=10.1, 4.8 Hz, 1H), 3.12 (pd, J=7.0, 0.9 Hz, 1H), 2.93 (s, 3H), 1.25 (d, J=6.9 Hz, 6H); LCMS (ESI) m/z: 285.2 [M+H]+.

Compound 254: $^1$H NMR (300 MHz, DMSO-d6) δ 8.81 (d, J=2.3 Hz, 1H), 8.24-8.01 (m, 2H), 7.39 (d, J=1.2 Hz, 1H), 7.37-7.11 (m, 6H), 4.51 (t, J=8.4 Hz, 1H), 4.25-4.06 (m, 2H), 3.81 (dd, J=9.9, 4.9 Hz, 1H), 2.95 (d, J=6.2 Hz, 3H); LCMS (ESI) m/z: 354.3 [M+H]+.

Compound 256: $^1$H NMR (300 MHz, DMSO-d6) δ 8.25 (d, J=9.3 Hz, 1H), 7.56-7.39 (m, 2H), 7.37-7.11 (m, 5H), 4.53 (t, J=8.6 Hz, 1H), 4.12 (s, 5H), 3.83 (dd, J=9.8, 5.0 Hz, 1H), 2.95 (d, J=6.1 Hz, 3H); LCMS (ESI) m/z: 351.2 [M+H]+.

Compound 260: $^1$H NMR (400 MHz, DMSO-d6) δ 7.48 (s, 1H), 7.48-7.46 (d, J=8.8 Hz, 1H), 7.18-7.15 (m, 4H), 7.12 (s, 1H), 7.08-7.06 (d, J=8.8 Hz, 1H), 6.11 (s, 2H), 4.80-4.79 (m, 2H), 3.87-3.80 (m, 2H), 2.89-2.83 (m, 2H); LCMS (ESI) m/z: 349.1 [M+H]+.

Compound 261: H NMR (400 MHz, CDCl3) δ 7.50-7.15 (m, 2H), 7.115-7.06 (m, 2H), 7.05-6.90 (m, 2H), 6.82-6.80 (d, J=8.0 Hz, 1H), 6.60-6.20 (m, 1H), 5.96 (s, 2H), 3.96-3.93 (t, J=6.4 Hz, 2H), 2.81-2.78 (t, J=6.4 Hz, 2H), 2.04-1.93 (m, 2H); LCMS (ESI) m/z: 349.1 [M+H]+.

Compound 262: 1H NMR (400 MHz, DMSO-d6) δ 8.04 (brs, 1H), 7.50-7.46 (m, 2H), 7.24 (s, 1H), 7.15-7.04 (m, 2H), 6.95 (dd, J1=8.4 Hz, J2=2.0 Hz, 1H), 6.89 (brs, 1H), 6.14 (s, 2H), 4.40-4.25 (m, 2H), 4.03 (t, J=5.2 Hz, 2H); LCMS (ESI) m/z: 351.1 [M+H]+.

Compound 263: $^1$H NMR (400 MHz, DMSO-d6) δ 7.49-7.40 (m, 2H), 7.14 (m, 3H), 7.08 (d, J=7.9 Hz, 1H), 7.02-6.95 (m, 1H), 6.12 (s, 2H), 3.87-3.80 (m, 2H), 2.79 (t, J=6.6 Hz, 2H), 2.02-1.94 (m, 2H); LCMS (ESI) m/z: 367.1 [M+H]+.

Compound 264: $^1$H NMR (400 MHz, DMSO-d6) δ7.41-7.39 (m, 2H), 7.18-7.14 (m, 1H), 7.09-7.07 (m, 1H), 7.04-7.01 (m, 2H), 6.98-6.93 (m, 1H), 6.09 (s, 2H), 3.90-3.65 (m, 2H), 2.84-2.80 (t, J=6.8 Hz, 2H), 2.00-1.97 (m, 2H); LCMS (ESI) m/z: 367.0 [M+H]+.

Compound 267: $^1$H NMR (300 MHz, DMSO-d6) δ 7.55-7.43 (m, 2H), 7.29-7.05 (m, 2H), 6.97-6.88 (m, 2H), 6.78 (t, J=6.7 Hz, 1H), 6.14 (d, J=1.4 Hz, 2H), 5.76 (s, 1H), 4.41 (d, J=12.7 Hz, 0H), 4.25 (d, J=12.7 Hz, 1H), 4.18-3.87 (m, 1H), 3.42 (d, J=14.7 Hz, 1H), 3.04 (d, J=11.6 Hz, 1H), 2.40 (d, J=18.9 Hz, 1H), 0.91 (dd, J=10.9, 6.4 Hz, 2H); LCMS (ESI) m/z: 402.4 [M+H]+.

Compound 268: $^1$H NMR (400 MHz, CDCl3-d) δ 7.82 (br d, J=3.5 Hz, 2H), 7.51 (br s, 3H), 7.08 (d, J=14.8 Hz, 1H), 6.97-6.85 (m, 2H), 5.29 (s, 1H), 5.05 (s, 1H), 4.44 (br t, J=5.2 Hz, 1H), 4.29-4.11 (m, 3H); LCMS (ESI) m/z: 295.1 [M+H]+.

Compound 269: $^1$H NMR (400 MHz, CDCl3-d) δ 7.34 (br d, J=8.4 Hz, 1H), 7.25 (s, 1H), 7.07 (d, J=13.9 Hz, 1H), 6.95-6.88 (m, 2H), 6.79 (s, 0.5H), 6.71 (s, 0.5H), 6.06 (d, J=2.4 Hz, 2H), 5.26 (s, 1H), 5.04 (s, 1H), 4.42 (t, J=5.2 Hz, 1H), 4.28-4.10 (m, 3H); LCMS (ESI) m/z: 339.1 [M+H]+.

Compound 272: 1H NMR (400 MHz, CDCl3) δ 8.41-8.29 (m, 1H), 7.37-7.26 (m, 2H), 7.22-7.15 (m, 1H), 7.12-7.07 (m, 1H), 6.90-6.79 (m, 0.6H), 6.75-6.70 (m, 0.6H), 6.61-6.53 (m, 0.3H), 6.05-5.97 (m, 2H), 5.84 (br d, J=7.3 Hz, 0.3H), 5.37 (dd, J=3.3, 8.4 Hz, 0.5H), 4.27-4.10 (m, 1H), 3.90 (br dd, J=6.7, 15.8 Hz, 1H), 2.44-2.30 (m, 1H), 2.22-1.88 (m, 3H); LCMS (ESI) m/z [M+H]+: 382.1.

Compound 273: 1H NMR (400 MHz, CDCl3-d) δ 7.78 (s, 1H), 7.72 (d, J=8.4 Hz, 1H), 7.51-7.39 (m, 4H), 7.36 (br d, J=6.6 Hz, 2H), 6.65 (s, 1H), 4.87-4.74 (m, 2H), 4.67 (t, J=8.9 Hz, 1H), 4.23 (t, J=8.0 Hz, 1H), 4.07 (s, 3H), 3.99 (d, J=15.4 Hz, 1H), 2.60 (s, 3H); LCMS (ESI) m/z [M+H]+=389.1.

Compound 274: $^1$H NMR (400 MHz, DMSO-d6) δ 7.54-7.44 (m, 2H), 7.28-7.20 (m, 3H), 7.13 (d, J=8.4 Hz, 1H), 6.98 (d, J=8.2 Hz, 2H), 6.83 (t, J=7.3 Hz, 1H), 3.87-3.77 (m, 1 OH), 3.22 (br d, J=19.8 Hz, 4H); LCMS (ESI) m/z: 394.2 [M+H]+.

Compound 276: $^1$H NMR (400 MHz, CDCl3-d) δ 8.75 (br s, 2H), 7.33 (br d, J=4.0 Hz, 3H), 7.24 (br s, 1H), 6.92 (br d, J=7.7 Hz, 1H), 6.73 (s, 1H), 6.06 (s, 2H), 4.16-3.73 (m, 6H), 3.51 (br s, 2H); LCMS (ESI) m/z: 407.0 [M+H]+.

Compound 277: $^1$H NMR (400 MHz, DMSO-d6) δ7.50 (d, J=1.76 Hz, 1H) 7.47 (dd, J=8.16, 1.76 Hz, 1H) 7.18 (s, 1H) 7.04-7.16 (m, 4H) 6.97-7.03 (m, 1H) 6.13 (s, 2H) 3.81 (dt, J=17.03, 4.82 Hz, 4H) 3.07 (dt, J=18.41, 5.02 Hz, 4H); LCMS (ESI) m/z: 396.2 [M+H]+.

Compound 278: $^1$H NMR (400 MHz, CDCl3) δ 7.84 (s, 1H), 7.76-7.74 (d, J=8.4 Hz, 1H), 7.52-7.50 (d, J=8.4 Hz, 1H), 7.33-7.27 (m, 2H), 6.99-6.94 (m, 4H), 4.16-4.13 (m, 2H), 4.05 (s, 3H), 4.02-3.99 (m, 2H), 3.33-3.27 (m, 4H), 2.61 (s, 3H); LCMS (ESI) m/z: 402.1 [M+H]+.

Compound 279: $^1$H NMR (400 MHz, CDCl3) δ 7.37 (dd, J=1.6, 8.0 Hz, 1H), 7.28 (d, J=6.4 Hz, 1H), 7.06-6.98 (m, 2H), 6.97-6.89 (m, 3H), 6.74 (s, 1H), 6.08 (s, 2H), 4.12 (t, J=4.8 Hz, 2H), 4.00 (t, J=4.2 Hz, 2H), 3.21 (td, J=5.2, 14.8 Hz, 4H); LCMS (ESI) m/z: 396.2 [M+H]+.

Compound 281: $^1$H NMR (400 MHz, CDCl3) δ 7.53-7.42 (m, 5H), 7.36-7.30 (m, 1H), 7.24 (s, 1H), 6.91 (d, J=8.0 Hz, 1H), 6.72 (s, 1H), 6.06 (s, 2H), 4.04-3.51 (m, 8H); LCMS (ESI) m/z: 406.2 [M+H]+.

Compound 282: 1HNMR (400 MHz, CDCl3) δ 7.35 (d, J=8.0 Hz, 1H), 7.29-7.19 (m, 2H), 6.92 (d, J=8.0 Hz, 1H), 6.76-6.67 (m, 2H), 6.66-6.55 (m, 2H), 6.06 (s, 2H), 4.11 (t, J=5.2 Hz, 2H), 3.97 (t, J=5.2 Hz, 2H), 3.29 (td, J=5.2, 15.2 Hz, 4H); LCMS (ESI) m/z: 396.1 [M+H]+.

Compound 283: $^1$H NMR (400 MHz, CDCl3) δ 7.89-7.77 (m, 2H), 7.56-7.46 (m, 3H), 7.04-6.97 (m, 2H), 6.96-6.90 (m, 2H), 6.87 (s, 1H), 4.20-4.07 (m, 2H), 4.04-3.94 (m, 2H), 3.20 (td, J=5.1, 13.3 Hz, 4H); LCMS (ESI) m/z: 352.1 [M+H]+.

Compound 284: $^1$H NMR (400 MHz, CDCl3) δ 7.86-7.79 (m, 2H), 7.55-7.45 (m, 3H), 7.12-7.04 (m, 2H), 7.03-6.94 (m, 2H), 6.87 (s, 1H), 4.19-4.09 (m, 2H), 4.06-3.97 (m, 2H), 3.19 (td, J=5.2, 10.6 Hz, 4H); LCMS (ESI) m/z: 352.1 [M+H]+.

Compound 285: $^1$H NMR (400 MHz, CHLOROFORM-d) δ=7.58 (d, J=0.8 Hz, 1H), 7.38-7.29 (m, 4H), 7.29-7.25 (m, 1H), 6.96 (s, 1H), 6.86 (s, 1H), 6.71 (br d, J=7.6 Hz, 1H), 6.61-6.50 (m, 1H), 4.06-3.93 (m, 1H), 3.53 (s, 2H), 2.86 (br d, J=12 Hz, 2H), 2.19 (br t, J=11.2 Hz, 2H), 2.05-1.97 (m, 2H), 1.68-1.56 (m, 2H); LCMS (ESI) m/z: 352.1 [M+H]+.

Compound 286: $^1$H NMR (400 MHz, CHLOROFORM-d) δ=7.56 (d, J=0.8 Hz, 1H), 7.26-7.20 (m, 2H), 6.97-6.91 (m, 3H), 6.88-6.81 (m, 1H), 6.73 (br d, J=8.0 Hz, 1H), 6.54 (dd, J=2.0, 2.9 Hz, 1H), 4.21-4.03 (m, 1H), 3.66 (br d, J=12.8 Hz, 2H), 3.00-2.82 (m, 2H), 2.13 (br d, J=10.0 Hz, 2H), 1.71 (dq, J=4.0, 11.6 Hz, 2H); LCMS (ESI) m/z: 338.1 [M+H]+.

Compound 287: $^1$H NMR (400 MHz, CHLOROFORM-d) δ=7.59 (d, J=1.1 Hz, 1H), 6.97 (d, J=3.3 Hz, 1H), 6.87 (s, 1H), 6.71 (br d, J=7.5 Hz, 1H), 6.57 (dd, J=1.8, 3.5 Hz, 1H), 4.23-3.97 (m, 4H), 2.92 (br t, J=11.8 Hz, 2H), 2.03 (br d, J=12.8 Hz, 3H), 1.48 (s, 9H); LCMS (ESI) m/z: 306.1 [M−55]+.

Compound 293: 1H NMR (300 MHz, Chloroform-d) δ 8.57 (s, 2H), 7.35 (dd, J=8.1, 1.7 Hz, 1H), 7.31-7.16 (m, 3H), 6.92 (d, J=8.2 Hz, 1H), 6.71 (s, 1H), 6.07 (s, 2H), 4.94 (d, J=13.3 Hz, 1H), 4.72 (d, J=13.3 Hz, 1H), 3.36-3.20 (m, 1H), 3.01-2.81 (m, 2H), 2.01 (s, 2H), 1.91-1.68 (m, 2H); LCMS (ESI) m/z: 378.1 [M+H]+.

Compound 294: $^1$H NMR (400 MHz, CDCl3) δ 7.86-7.79 (m, 2H), 7.55-7.46 (m, 3H), 7.27-7.18 (m, 1H), 6.88 (s, 1H), 6.71 (dd, J=2.0, 8.2 Hz, 1H), 6.67-6.56 (m, 2H), 4.24-4.07 (m, 2H), 4.07-3.85 (m, 2H), 3.31 (td, J=5.2, 14.2 Hz, 4H); LCMS (ESI) m/z: 352.1 [M+H]+.

Compound 295: $^1$H NMR (400 MHz, CDCl3) δ 7.85-7.76 (m, 2H), 7.54-7.42 (m, 3H), 6.97 (s, 1H), 4.19-4.01 (m, 1H), 3.98-3.87 (m, 1H), 3.86-3.75 (m, 1H), 3.74-3.59 (m, 1H), 3.55-3.26 (m, 4H), 2.10-1.83 (m, 4H), 1.47 (d, J=6.2 Hz, 9H); LCMS (ESI) m/z: 342.1 [M−55]+.

Compound 296: $^1$H NMR (400 MHz, CDCl3) δ 7.82 (dd, J=2.2, 7.5 Hz, 2H), 7.56-7.46 (m, 5H), 7.40 (t, J=7.7 Hz, 2H), 7.34-7.28 (m, 1H), 6.84 (s, 1H), 4.79-4.68 (m, 1H), 4.48 (br d, J=13.6 Hz, 1H), 3.72 (dt, J=2.6, 13.2 Hz, 1H), 3.47-3.32 (m, 1H), 2.25-2.12 (m, 2H), 1.98-1.84 (m, 2H), 1.67 (br s, 1H); LCMS (ESI) m/z: 347.1 [M−H]−.

Compound 300: $^1$H NMR (400 MHz, CHLOROFORM-d) δ 7.51 (d, J=7.3 Hz, 2H), 7.40 (t, J=7.5 Hz, 2H), 7.36-7.28 (m, 2H), 7.25 (d, J=1.5 Hz, 1H), 6.92 (d, J=8.2 Hz, 1H), 6.69 (s, 1H), 6.06 (s, 2H), 4.72 (td, J=2.1, 13.1 Hz, 1H), 4.46 (td, J=2.0, 13.6 Hz, 1H), 3.71 (dt, J=2.5, 13.1 Hz, 1H), 3.38 (dt, J=2.8, 13.0 Hz, 1H), 2.24-2.10 (m, 2H), 1.97-1.84 (m, 2H), 1.66 (br s, 1H); LCMS (ESI) m/z: 391.0 [M−H]−.

Compound 303: $^1$H NMR (400 MHz, CDCl3) δ 8.19 (s, 1H), 7.90 (br d, J=7.7 Hz, 1H), 7.86 (d, J=7.7 Hz, 1H), 7.55 (t, J=7.7 Hz, 1H), 7.38-7.29 (m, 2H), 7.27-7.20 (m, 3H), 6.86 (s, 1H), 6.52 (br s, 1H), 4.91 (br d, J=13.2 Hz, 1H), 4.58 (br d, J=13.7 Hz, 1H), 3.34-3.21 (m, 1H), 3.06 (d, J=4.9 Hz, 3H), 2.97-2.80 (m, 2H), 2.08-1.92 (m, 2H), 1.87-1.74 (m, 2H); LCMS (ESI) m/z: 390.2 [M+H]+.

Compound 311: 1H NMR (500 MHz, DMSO-d6) δ 11.61 (s, 1H), 9.38 (d, J=2.0 Hz, 1H), 8.00 (dd, J=7.5, 2.0 Hz, 2H), 7.84 (d, J=2.0 Hz, 1H), 7.66-7.53 (m, 4H), 7.52-7.45 (m, 2H), 7.35-7.21 (m, 3H); LCMS (ESI) m/z: 359.0 [M+H]+.

Compound 312: 1H NMR (500 MHz, DMSO-d6) δ 11.28 (s, 1H), 8.11 (d, J=5.6 Hz, 1H), 7.99-7.97 (m, 2H), 7.63-7.53 (m, 5H), 7.50 (d, J=1.5 Hz, 1H), 7.45-7.42 (m, 2H), 7.23 (t, J=7.4 Hz, 1H), 7.18-7.12 (m, 2H); LCMS (ESI) m/z: 358.1 [M+H]+.

Compound 317: 1H NMR (500 MHz, DMSO-d6) δ. 8.46 (s, 1H), 8.25 (d, J=8.5 Hz, 1H), 8.01 (d, J=7.5 Hz, 1H), 7.78 (t, J=8.0 Hz, 1H), 7.48 (s, 1H), 7.33-7.27 (m, 4H), 7.22-7.19 (m, 1H), 4.65 (d, J=13.0 Hz, 1H), 4.09 (d, J=14.0 Hz, 1H), 3.32-3.28 (m, 1H), 2.95-2.88 (m, 2H), 1.92 (d, J=13.5 Hz, 1H), 1.83 (d, J=12.5 Hz, 1H), 1.65-1.61 (m, 2H); LCMS (ESI) m/z: 358.2 [M+H]+.

Compound 319: 1H NMR (500 MHz, DMSO-d6) δ 8.61 (t, J=4.0 Hz, 1H), 8.05-7.99 (m, 4H), 7.48-7.43 (m, 3H), 7.38-7.35 (m, 2H), 7.30-7.27 (m, 2H), 6.26-6.16 (m, 1H), 4.35-4.34 (m, 2H), 3.93-3.82 (m, 2H), 2.82-2.81 (m, 2H), 2.62 (m, 2H); LCMS (ESI) m/z: 388.1 [M+H]+.

Compound 320: 1H NMR (500 MHz, DMSO-d6) δ 7.91 (dd, J=7.5 Hz, 1.5 Hz, 1H), 7.56-7.52 (m, 1H), 7.33-7.12 (m, 7H), 7.07 (s, 1H), 4.67-4.64 (m, 1H), 4.11-4.08 (m, 1H), 3.97 (s, 3H), 3.34-3.25 (m, 1H), 2.96-2.84 (m, 2H), 1.92-1.81 (m, 2H), 1.68-1.58 (m, 2H); LCMS (ESI) m/z: 363.1 [M+H]+.

Compound 322: 1H NMR (500 MHz, DMSO-d6) δ 8.82 (s, 1H), 8.73 (s, 1H), 8.33 (s, 1H), 7.95 (dd, J=8.0, 1.5 Hz, 2H), 7.89-7.80 (m, 1H), 7.62-7.52 (m, 3H), 7.32 (s, 1H), 4.70 (d, J=13.0 Hz, 1H), 4.19 (d, J=13.5 Hz, 1H), 3.38-3.25 (m, 1H), 3.14 (t, J=12.0 Hz, 1H), 2.97 (td, J=13.0, 2.5 Hz, 1H), 1.95 (dd, J=39.0, 12.5 Hz, 2H), 1.75 (qt, J=12.5, 4.0 Hz, 2H); LCMS (ESI) m/z: 334.1 [M+H]+.

Compound 323: ¹H NMR (400 MHz, DMSO-d6) δ 7.92-7.94 (m, 2H), 7.56-7.57 (m, 3H), 7.40-7.42 (m, 4H), 7.32 (s, 2H), 4.43-4.46 (m, 1H), 3.90-3.93 (m, 1H), 3.48-3.51 (m, 1H), 3.14-3.20 (m, 1H), 2.93 (s, 3H), 1.86-2.15 (m, 4H); LCMS (ESI) m/z: 385.2 [M+Na]+.

Compound 324: ¹H NMR (400 MHz, DMSO-d6) δ 7.11-7.13 (m, 1H), 6.86 (s, 1H), 6.68-6.71 (m, 1H), 5.82 (s, 1H), 5.45 (s, 1H), 4.23-4.26 (m, 1H), 3.79-3.82 (m, 1H), 3.47-3.48 (m, 1H), 3.24-3.25 (m, 1H), 2.67-2.70 (m, 2H), 2.09 (s, 3H), 1.76-1.85 (m, 4H), 1.66-1.70 (m, 2H); LCMS (ESI) m/z: 357.1 [M+H]+.

Compound 327: ¹H NMR (400 MHz, DMSO-d6) δ 7.45 (br. s., 1H), 7.39-7.19 (m, 4H), 7.18-6.68 (m, 4H), 6.16-6.01 (m, 2H), 5.55-5.25 (m, 1H), 4.09-3.72 (m, 2H), 2.43-2.30 (m, 1H), 2.07-1.70 (m, 3H); LCMS (ESI) m/z: 363.2 [M+H]+.

Compound 328: 1HNMR (400 MHz, DMSO-d6) δ 7.54 (d, J=1.6 Hz, 1H), 7.50 (dd, J1=8.0 Hz, J2=1.6 Hz, 1H), 7.42-7.37 (m, 2H), 7.33-7.30 (m, 3H), 7.10 (d, J=8.2 Hz, 1H), 8.14 (s, 2H), 5.15 (s, 2H), 4.90 (s, 2H); LCMS (ESI) m/z: 335.1 [M+H]+.

Compound 329: ¹H NMR (400 MHz, DMSO-d6) δ 7.54-7.45 (m, 2H), 7.36-7.31 (m, 4H), 7.28-7.22 (m, 2H), 7.09 (dd, J=6.0, 8.2 Hz, 1H), 6.13 (d, J=4.0 Hz, 2H), 4.22 (m, 0.5H), 4.07-3.96 (m, 1H), 3.84-3.74 (m, 1H), 3.69-3.60 (m, 0.5H), 3.60-3.42 (m, 2H), 2.37-2.25 (m, 1H), 2.13-1.99 (m, 1H); LCMS (ESI) m/z: 363.2 [M+H]+.

Compound 330: ¹H NMR (400 MHz, DMSO-d6) δ 7.94 (ddd, J=2.0, 7.6, 9.3 Hz, 2H), 7.61-7.49 (m, 3H), 7.38-7.30 (m, 5H), 7.28-7.21 (m, 1H), 4.24 (dd, J=7.5, 10.5 Hz, 0.5H), 4.11-3.98 (m, 1H), 3.86-3.75 (m, 1H), 3.69-3.54 (m, 1H), 3.53-3.41 (m, 1.5H), 2.38-2.25 (m, 1H), 2.13-1.99 (m, 1H); LCMS (ESI) m/z: 319.2 [M+H]+.

Compound 331: 1HNMR (400 MHz, CDCl3) δ=7.57 (d, J=7.6 Hz, 0.5H), 7.51 (d, J=7.6 Hz, 0.5H), 7.44-7.20 (m, 4H), 7.15-7.12 (m, 1H), 7.10-7.02 (m, 1H), 6.96-6.91 (m, 0.3H), 6.90 (d, J=8.0 Hz, 0.4H), 6.82 (d, J=8.0 Hz, 0.4H), 6.72 (s, 0.5H), 6.46 (s, 0.5H), 6.03 (s, 1H), 6.00 (s, 1H), 5.94-5.92 (m, 0.5H), 5.48-5.45 (m, 0.5H), 4.26 (t, J=7.2 Hz, 1H), 4.06-3.93 (m, 1H), 2.55-2.43 (m, 1H), 2.22-2.11 (m, 1H), 2.04-1.87 (m, 2H); LCMS (ESI) m/z: 413.0 [M+H]+.

Compound 332: ¹H NMR (400 MHz, DMSO-d6) δ 9.08 (d, J=6.8 Hz, 1H), 7.99 (d, J=1.1 Hz, 1H), 7.25 (d, J=3.5 Hz, 1H), 7.09 (s, 1H), 6.76 (dd, J=1.8, 3.5 Hz, 1H), 4.49-4.34 (m, 1H), 3.59-3.47 (m, 1H), 3.45-3.35 (m, 1H), 3.32-3.16 (m, 2H), 2.17-2.02 (m, 1H), 1.96-1.85 (m, 1H), 1.40 (s, 9H); LCMS (ESI) m/z: 292.1 [M+H]+.

Compound 333: ¹H NMR (400 MHz, DMSO-d6) δ 7.96 (ddd, J=2.0, 7.4, 12.0 Hz, 1H), 7.74-7.67 (m, 1H), 7.62-7.52 (m, 2H), 7.35 (dd, J=4.2, 7.3 Hz, 4H), 7.31 (d, J=3.1 Hz, 1H), 7.28-7.22 (m, 1H), 4.24 (dd, J=7.7, 10.6 Hz, 0.5H), 4.11-3.99 (m, 1H), 3.86-3.78 (m, 1H), 3.72-3.63 (m, 0.5H), 3.62-3.41 (m, 2H), 2.38-2.27 (m, 1H), 2.14-2.01 (m, 1H); LCMS (ESI) m/z: 353.1 [M+H]+.

Compound 334: ¹H NMR (400 MHz, DMSO-d6) δ 7.99-7.88 (m, 2H), 7.60-7.47 (m, 3H), 7.44-7.30 (m, 3H), 7.16 (dt, J=6.8, 8.8 Hz, 2H), 4.23 (dd, J=7.5, 10.6 Hz, 0.5H), 4.11-3.94 (m, 1H), 3.87-3.72 (m, 1H), 3.66-3.59 (m, 0.5H), 3.59-3.48 (m, 1H), 3.48-3.39 (m, 1H), 2.37-2.21 (m, 1H), 2.13-1.94 (m, 1H); LCMS (ESI) m/z: 337.1 [M+H]+.

Compound 335: ¹H NMR (400 MHz, CDCl3) δ 7.81 (dd, J=2.0, 7.7 Hz, 1H), 7.71-7.64 (m, 1H), 7.53-7.39 (m, 3H), 7.27-7.27 (m, 2H), 7.26-7.14 (m, 1H), 7.12-6.98 (m, 1H), 6.93 (s, 0.5H), 6.70 (s, 0.5H), 6.06 (br d, J=7.0 Hz, 0.5H), 5.59 (dd, J=4.2, 8.1 Hz, 0.5H), 4.34-4.09 (m, 1H), 4.05-3.82 (m, 1H), 2.53-2.35 (m, 1H), 2.14-1.89 (m, 3H); LCMS (ESI) m/z: 337.1 [M+H]+.

Compound 336: ¹H NMR (400 MHz, DMSO-d6) δ 9.22 (br d, J=6.8 Hz, 3H), 8.00 (d, J=1.1 Hz, 1H), 7.26 (d, J=3.3 Hz, 1H), 7.16 (s, 1H), 6.76 (dd, J=1.8, 3.5 Hz, 1H), 4.65-4.50 (m, 1H), 3.47-3.35 (m, 2H), 3.27-3.15 (m, 2H), 2.24-2.13 (m, 1H), 2.07-1.93 (m, 1H); LCMS (ESI) m/z: 248.0 [M+H]+.

Compound 337: ¹H NMR (400 MHz, CHLOROFORM-d) δ 7.57 (s, 1H), 7.33 (d, J=3.9 Hz, 4H), 7.26 (br s, 1H), 7.12 (br d, J=7.0 Hz, 1H), 6.95 (d, J=3.1 Hz, 1H), 6.84 (s, 1H), 6.55 (br d, J=1.8 Hz, 1H), 4.68-4.59 (m, 1H), 3.69-3.59 (m, 2H), 2.91-2.84 (m, 1H), 2.68 (d, J=4.4 Hz, 2H), 2.40-2.31 (m, 2H), 1.81-1.72 (m, 1H); LCMS (ESI) m/z: 338.1 [M+H]+.

Compound 338: ¹H NMR (400 MHz, CHLOROFORM-d) δ 7.55 (br d, J=3.5 Hz, 1H), 7.36-7.28 (m, 2H), 7.24 (br d, J=6.1 Hz, 3H), 6.92 (dd, J=3.1, 8.3 Hz, 1H), 6.84 (d, J=5.7 Hz, 1H), 6.53 (br s, 1H), 4.41 (dd, J=7.9, 11.4 Hz, 0.5H), 4.19 (br dd, J=7.7, 12.1 Hz, 1H), 4.01-3.91 (m, 1H), 3.82 (t, J=10.7 Hz, 0.5H), 3.76-3.68 (m, 0.5H), 3.67-3.61 (m, 0.5H), 3.52-3.40 (m, 1H), 2.37 (br d, J=17.5 Hz, 1H), 2.17-2.04 (m, 1H); LCMS (ESI) m/z: 309.1 [M+H]+.

Compound 339: ¹H NMR (400 MHz, CDCl3) δ 7.82 (dt, J=1.8, 7.2 Hz, 2H), 7.54-7.46 (m, 3H), 7.37-7.29 (m, 1H), 7.07 (br t, J=6.7 Hz, 1H), 7.03-6.91 (m, 3H), 4.50 (dd, J=7.5, 11.5 Hz, 0.5H), 4.33-4.18 (m, 1H), 4.08-3.97 (m, 1H), 3.88 (br t, J=10.6 Hz, 0.5H), 3.81-3.61 (m, 1H), 3.56-3.42 (m, 1H), 2.52-2.34 (m, 1H), 2.23-2.03 (m, 1H); LCMS (ESI) m/z: 337.1 [M+H]+.

Compound 340: ¹H NMR (400 MHz, MeOD) δ=7.92-7.85 (m, 2H), 7.59-7.48 (m, 3H), 7.09 (d, J=4.0 Hz, 1H), 4.06 (t, J=6.9 Hz, 1H), 4.00 (s, 1H), 3.79 (t, J=7.2 Hz, 1H), 3.72 (s, 1H), 3.51-3.33 (m, 4H), 2.18-2.07 (m, 4H); LCMS (ESI) m/z: 298.1 [M+H]+.

Compound 341: ¹H NMR (400 MHz, MeOD) δ=7.92-7.85 (m, 2H), 7.59-7.48 (m, 3H), 7.09 (d, J=4.0 Hz, 1H), 4.06 (t, J=6.9 Hz, 1H), 4.00 (s, 1H), 3.79 (t, J=7.2 Hz, 1H), 3.72 (s, 1H), 3.51-3.33 (m, 4H), 2.18-2.07 (m, 4H); LCMS (ESI) m/z: 374.2 [M+H]+.

Compound 342: ¹H NMR (400 MHz, CDCl3) δ 7.85-7.75 (m, 2H), 7.52-7.43 (m, 3H), 6.94 (d, J=8.2 Hz, 1H), 4.06-3.96 (m, 1H), 3.95-3.81 (m, 1H), 3.79-3.71 (m, 1H), 3.70-3.58 (m, 1H), 2.75-2.56 (m, 2H), 2.56-2.46 (m, 2H), 2.38-2.32 (m, 3H), 2.13-1.76 (m, 4H); LCMS (ESI) m/z: 312.2 [M+H]+.

Compound 343: ¹H NMR (400 MHz, CDCl-d) δ 7.59 (s, 1H), 7.29 (br s, 1H), 7.25 (br s, 1H), 7.06-6.95 (m, 2H), 6.88 (s, 1H), 6.75 (br t, J=7.3 Hz, 1H), 6.65-6.52 (m, 3H), 4.83 (br s, 1H), 3.68 (dd, J=6.1, 9.8 Hz, 1H), 3.59-3.49 (m, 1H), 3.46-3.29 (m, 2H), 2.48-2.36 (m, 1H), 2.14 (br d, J=5.1 Hz, 1H); LCMS (ESI) m/z: 324.1 [M+H]+.

Compound 344: ¹H NMR (400 MHz, CHLOROFORM-d) δ 7.80 (dd, J=2.1, 7.5 Hz, 2H), 7.56-7.45 (m, 3H), 6.95 (s, 1H), 4.73 (s, 2H), 4.34 (s, 2H), 4.13 (s, 4H), 1.46 (s, 9H); LCMS (ESI) m/z: 370.1 [M+H]+.

Compound 345: ¹H NMR (400 MHz, CHLOROFORM-d) δ 7.86-7.76 (m, 2H), 7.56-7.42 (m, 3H), 6.94 (s, 1H), 4.71 (s, 2H), 4.33 (s, 2H), 3.85 (s, 4H); LCMS (ESI) m/z: 270.1 [M+H]+.

Compound 346: ¹H NMR (400 MHz, MeOD) δ 7.92 (br t, J=6.6 Hz, 1H), 7.86-7.69 (m, 3H), 7.40-7.29 (m, 4H), 7.28-7.20 (m, 1H), 6.98 (d, J=2.2 Hz, 1H), 4.39 (dd, J=7.6, 11.4 Hz, 0.5H), 4.25-4.10 (m, 1H), 4.03-3.89 (m, 1H), 3.83 (t, J=10.6 Hz, 0.5H), 3.76-3.66 (m, 0.5H), 3.63-3.46 (m, 1.5H), 2.47-2.33 (m, 1H), 2.24-2.05 (m, 1H); LCMS (ESI) m/z: 387.1 [M+H]+.

Compound 347: ¹H NMR (400 MHz, CHLOROFORM-d) δ 8.95-8.99 (m, 1H) 7.38-7.31 (m, 4H), 7.30-7.26 (m, 2H) 4.17-4.16 (m, 0.5H), 4.04-4.03 (m, 0.5H), 3.96-3.77 (m, 0.5H), 3.61-3.59 (m, 1H), 3.58-3.47 (m, 1H), 3.47-3.43 (m, 1.5H), 2.80-2.78 (m, 3H), 2.32-2.31 (m, 1H), 2.07-1.99 (m, 1H); LCMS (ESI) m/z: 300.1 [M+H]+.

Compound 348: ¹H NMR (400 MHz, DMSO-d6) δ 8.40 (br d, J=9.7 Hz, 1H), 8.04 (br d, J=7.7 Hz, 1H), 7.36-7.31 (m, 5H), 7.25 (td, J=4.4, 8.7 Hz, 1H), 4.18 (dd, J=7.6, 10.5 Hz, 0.5H), 4.08-3.92 (m, 1H), 3.85-3.71 (m, 1H), 3.67-3.53 (m, 1H), 3.51-3.41 (m, 1.5H), 2.36-2.25 (m, 1H), 2.13-1.99 (m, 1H); LCMS (ESI) m/z: 286.0 [M+H]+.

Compound 349: ¹H NMR (300 MHz, DMSO-d6) δ 7.37-7.13 (m, 5H), 6.53 (dd, J=1.7, 0.9 Hz, 1H), 4.15 (dd, J=10.6, 7.2 Hz, 1H), 4.07-3.84 (m, 1H), 3.84-3.65 (m, 1H), 3.65-3.37 (m, 3H), 3.20-3.01 (m, 1H), 2.27 (s, 1H), 2.04 (t, J=10.7 Hz, 1H), 1.27 (dd, J=6.9, 6.1 Hz, 6H); LCMS (ESI) m/z: 285.2 [M+H]+.

Compound 350: ¹H NMR (300 MHz, DMSO-d6) δ 7.45-7.28 (m, 1H), 7.18 (q, J=7.4, 6.9 Hz, 2H), 7.08 (ddd, J=9.1, 7.6, 2.5 Hz, 1H), 6.53 (t, J=1.2 Hz, 1H), 4.01-3.89 (m, 1H), 3.82-3.66 (m, 1H), 3.65-3.38 (m, 2H), 3.13 (dq, J=13.6, 6.8 Hz, 1H), 2.38-2.21 (m, 1H), 2.12-1.96 (m, 1H), 1.27 (dd, J=6.9, 5.4 Hz, 6H); LCMS (ESI) m/z: 303.2 [M+H]+.

Compound 351: ¹H NMR (300 MHz, DMSO-d6) δ 8.75 (tt, J=4.7, 1.5 Hz, 1H), 8.12-7.96 (m, 2H), 7.58-7.48 (m, 1H), 7.44-7.16 (m, 6H), 4.22 (dd, J=10.6, 7.4 Hz, 1H), 4.11-3.89 (m, 1H), 3.81 (td, J=10.1, 6.7 Hz, 1H), 3.73-3.39 (m, 3H), 2.18-2.00 (m, 1H); LCMS (ESI) m/z: 320.3 [M+H]+.

Compound 352: ¹H NMR (300 MHz, DMSO-d6) δ 8.75 (tt, J=4.7, 1.4 Hz, 1H), 8.09-7.96 (m, 2H), 7.55 (dddd, J=6.8, 5.0, 3.5, 1.9 Hz, 1H), 7.46-7.29 (m, 2H), 7.21 (ddt, J=10.9, 8.7, 4.8 Hz, 2H), 7.08 (s, 1H), 4.23 (dd, J=10.5, 7.4 Hz, 1H), 4.14-3.93 (m, 1H), 3.80 (td, J=10.2, 6.8 Hz, 1H), 3.72-3.39 (m, 3H), 2.33 (s, 1H), 2.10 (s, 1H); LCMS (ESI) m/z: 338.3 [M+H]+.

Compound 353: ¹H NMR (400 MHz, DMSO-d6) δ 7.51-7.32 (m, 2H), 7.17-6.94 (m, 2H), 6.24-6.00 (m, 3H), 5.80-5.24 (m, 1H), 4.01-3.60 (m, 2H), 2.31 (br. s., 1H), 2.21-2.10 (m, 3H), 2.02 (d, J=8.4 Hz, 3H); LCMS (ESI) m/z: 368.2 [M+H]+.

Compound 354: ¹H NMR (400 MHz, DMSO-d6) δ 7.51-7.41 (m, 1H), 7.38-7.19 (m, 4H), 7.18-7.03 (m, 2H), 7.02-6.68 (m, 1H), 6.21-6.01 (m, 3H), 5.58-5.19 (m, 1H), 4.10-3.74 (m, 2H), 2.46-2.29 (m, 1H), 2.03-1.76 (m, 3H); LCMS (ESI) m/z: 363.1 [M+H]+.

Compound 355: ¹H NMR (400 MHz, DMSO-d6) δ 7.50-7.25 (m, 2H), 7.24-6.98 (m, 4H), 6.97-6.67 (m, 2H), 6.20-6.02 (m, 2H), 5.55-5.07 (m, 1H), 4.11-3.67 (m, 2H), 2.45-2.16 (m, 3H), 2.01-1.76 (m, 3H); LCMS (ESI) m/z: 377.2 [M+H]+.

Compound 356: ¹H NMR (400 MHz, DMSO-d6) δ 7.50-7.25 (m, 2H), 7.22-6.85 (m, 5H), 6.83-6.64 (m, 1H), 6.16-6.04 (m, 2H), 5.50-5.16 (m, 1H), 4.06-3.78 (m, 2H), 3.77-3.59 (m, 3H), 2.34 (d, J=12.3 Hz, 1H), 1.93 (d, J=6.2 Hz, 3H); LCMS (ESI) m/z: 393.2 [M+H]+.

Compound 357: ¹H NMR (400 MHz, DMSO-d6) δ 7.93 (br. s., 1H), 7.25-7.11 (m, 1H), 7.02-6.82 (m, 1H), 6.73 (br. s., 1H), 6.26-6.03 (m, 1H), 5.75-5.32 (m, 1H), 3.99-3.74 (m, 2H), 2.33 (br. s., 1H), 2.24-2.11 (m, 3H), 2.04 (d, J=6.6 Hz, 3H); LCMS (ESI) m/z: 314.1 [M+H]+.

Compound 358: ¹H NMR (400 MHz, DMSO-d6) δ 7.49-7.41 (m, 1H), 7.37-7.19 (m, 5H), 7.18-6.67 (m, 3H), 6.18-5.99 (m, 2H), 5.59-5.18 (m, 1H), 4.05-3.71 (m, 2H), 2.46-2.29 (m, 1H), 2.06-1.73 (m, 3H); LCMS (ESI) m/z: 363.2 [M+H]+.

Compound 359: ¹H NMR (400 MHz, DMSO-d6) δ 7.43 (br. s., 1H), 7.31-7.12 (m, 2H), 7.09-6.94 (m, 2H), 6.92-6.63 (m, 3H), 6.08 (d, J=7.9 Hz, 2H), 5.45-5.19 (m, 1H), 4.01-3.57 (m, 5H), 2.31 (br. s., 1H), 2.01-1.75 (m, 3H); LCMS (ESI) m/z: 393.2 [M+H]+.

Compound 360: ¹H NMR (400 MHz, DMSO-d6) δ 7.44 (br. s., 1H), 7.28 (br. s., 1H), 7.19 (d, J=7.5 Hz, 1H), 7.11-6.96 (m, 2H), 6.94-6.63 (m, 3H), 6.10 (d, J=8.4 Hz, 2H), 5.49-5.18 (m, 1H), 4.03-3.59 (m, 5H), 2.35 (d, J=12.3 Hz, 1H), 1.95 (br. s., 3H); LCMS (ESI) m/z: 393.2 [M+H]+.

Compound 361: ¹H NMR (400 MHz, MeOD-d4) δ 8.49 (d, J=6.2 Hz, 1H), 8.45-8.39 (m, 1H), 7.42 (s, 1H), 7.40-7.32 (m, 2H), 7.24 (d, J=5.7 Hz, 1H), 7.19 (d, J=1.8 Hz, 0.2H), 6.96 (d, J=7.9 Hz, 0.6H), 6.91 (s, 0.9H), 6.72 (s, 0.3H), 6.09-5.95 (m, 2H), 5.80-5.72 (m, 0.4H), 5.33-5.25 (m, 0.6H), 4.25-4.05 (m, 1H), 4.00-3.84 (m, 1H), 2.51 (dd, J=7.9, 12.3 Hz, 1H), 2.12-1.83 (m, 3H); LCMS (ESI) m/z: 364.1 [M+H]+.

Compound 362: ¹H NMR (400 MHz, DMSO-d6) δ 8.53 (d, J=2.1 Hz, 1H), 8.45 (dd, J=1.6, 4.7 Hz, 1H), 8.36 (dt, J=2.0, 4.6 Hz, 1H), 7.70-7.64 (m, 0.6H), 7.55 (d, J=7.9 Hz, 0.4H), 7.52-7.44 (m, 1H), 7.40-7.32 (m, 1H), 7.31-7.25 (m, 0.4H), 7.21 (s, 0.6H), 7.09 (d, J=8.2 Hz, 0.6H), 7.03 (d, J=8.2 Hz, 0.2H), 6.96 (s, 0.2H), 6.15-6.07 (m, 2H), 5.60 (s, 1H), 5.24 (dd, J=4.4, 7.9 Hz, 1H), 4.05 (s, 1H), 3.94 (s, 1H), 2.40 (dd, J=7.5, 12.3 Hz, 1H), 1.95 (t, J=6.7 Hz, 2H); LCMS (ESI) m/z: 364.2 [M+H]+.

Compound 363: ¹H NMR (400 MHz, MeOD-d4) δ 8.49 (d, J=6.2 Hz, 1H), 8.45-8.39 (m, 1H), 7.42 (s, 1H), 7.40-7.32 (m, 2H), 7.24 (d, J=5.7 Hz, 1H), 7.19 (d, J=1.8 Hz, 0.2H), 6.96 (d, J=7.9 Hz, 0.6H), 6.91 (s, 0.9H), 6.72 (s, 0.3H), 6.09-5.95 (m, 2H), 5.80-5.72 (m, 0.4H), 5.33-5.25 (m, 0.6H), 4.25-4.05 (m, 1H), 4.00-3.84 (m, 1H), 2.51 (dd, J=7.9, 12.3 Hz, 1H), 2.12-1.83 (m, 3H); LCMS (ESI) m/z: 364.2 [M+H]+.

Compound 364: ¹H NMR (400 MHz, MeOD-d4) δ 7.43 (dd, J=1.6, 8.0 Hz, 0.5H), 7.34 (d, J=1.5 Hz, 0.5H), 7.26-7.19 (m, 1H), 7.18-7.10 (m, 1H), 7.06 (d, J=7.5 Hz, 0.5H), 7.01-6.79 (m, 4H), 6.42 (s, 0.5H), 6.03 (d, J=14.8 Hz, 2H), 5.77 (dd, J=2.7, 7.6 Hz, 0.5H), 5.56 (dd, J=3.5, 8.1 Hz, 0.5H), 4.23-4.14 (m, 0.5H), 4.05-3.76 (m, 4.5H), 2.43-2.28 (m, 1H), 2.07-1.80 (m, 3H); LCMS (ESI) m/z: 393.2 [M+H]+.

Compound 365: ¹H NMR (400 MHz, METHANOL-d4) δ 7.43 (dd, J=1.5, 8.2 Hz, 0.6H), 7.34 (d, J=1.3 Hz, 0.5H), 7.27-7.21 (m, 1H), 7.18-7.11 (m, 1H), 6.96 (d, J=7.9 Hz, 0.6H), 6.91-6.87 (m, 1H), 6.86-6.77 (m, 1.7H), 6.71-6.64 (m, 1H), 6.59 (s, 0.5H), 6.44 (s, 0.5H), 6.03 (d, J=13.2 Hz, 2H), 5.57-5.52 (m, 0.5H), 5.28 (dd, J=4.2, 7.7 Hz, 0.6H), 4.19-3.86 (m, 2H), 3.78 (s, 1.5H), 3.68 (s, 1.5H), 2.49-2.38 (m, 1H), 2.07-1.90 (m, 3H); LCMS (ESI) m/z: 393.1 [M+H]+.

Compound 366: ¹H NMR (400 MHz, DMSO-d6) δ 7.52-7.46 (m, 1.3H), 7.39-7.32 (m, 1H), 7.31-7.26 (m, 0.7H), 7.24-7.18 (m, 2H), 7.18-7.12 (m, 1H), 7.11-7.05 (m, 1.5H), 7.04-6.98 (m, 0.8H), 6.15-6.06 (m, 2H), 5.78 (d, J=6.2 Hz, 0.4H), 5.37 (dd, J=4.2, 8.2 Hz, 0.7H), 4.09-3.70 (m, 2H), 2.43-2.32 (m, 1H), 1.94 (m, 3H); LCMS (ESI) m/z: 381.1 [M+H]+.

Compound 367: ¹H NMR (400 MHz, MeOD-d4) δ 7.43 (d, J=8.4 Hz, 0.7H), 7.37-7.31 (m, 1H), 7.27 (d, J=7.1 Hz, 1H), 7.19-7.17 (m, 0.4H), 7.10 (d, J=7.5 Hz, 0.7H), 6.91 (s, 3.6H), 6.57 (s, 0.4H), 6.04 (d, J=12.8 Hz, 2H), 5.66 (d, J=7.5 Hz, 0.5H), 5.30 (dd, J=4.4, 7.5 Hz, 0.6H), 4.21-3.85 (m, 2H), 2.51-2.41 (m, 1H), 2.06-1.90 (m, 3H); LCMS (ESI) m/z: 381.1 [M+H]+.

Compound 368: ¹H NMR (400 MHz, MeOD-d4) δ 7.43 (dd, J=1.5, 8.2 Hz, 0.6H), 7.36-7.23 (m, 2H), 7.17 (s, 0.4H), 7.14-7.02 (m, 2H), 7.00-6.88 (m, 2H), 6.52 (s, 0.6H), 6.04 (d, J=12.3 Hz, 2H), 5.61 (d, J=4.9 Hz, 0.6H), 5.29 (dd, J=4.4, 7.9 Hz, 0.7H), 4.19-4.15 (m, 0.5H), 4.08-4.01 (m, 0.7H), 3.95-3.87 (m, 1H), 2.45 (d, J=7.1 Hz, 1H), 2.05-1.88 (m, 3H); LCMS (ESI) m/z: 381.0 [M+H]+.

Compound 369: ¹H NMR (400 MHz, MeOD-d4) δ 7.45-7.39 (m, 1H), 7.36-7.31 (m, 1H), 6.96 (d, J=8.4 Hz, 1H), 6.88 (s, 1H), 6.05 (s, 2H), 4.70-4.62 (m, 0.4H), 4.38-4.29 (m, 0.7H), 3.91-3.63 (m, 2H), 2.18-1.67 (m, 4H), 1.33 (d, J=6.2 Hz, 2H), 1.20 (d, J=6.6 Hz, 1H); LCMS (ESI) m/z: 301.1 [M+H]+.

Compound 370: ¹H NMR (400 MHz, MeOD-d4) δ 7.45-7.39 (m, 1H), 7.36-7.31 (m, 1H), 6.96 (d, J=8.4 Hz, 1H), 6.88 (s, 1H), 6.05 (s, 2H), 4.70-4.62 (m, 0.4H), 4.38-4.29 (m, 0.7H), 3.91-3.63 (m, 2H), 2.18-1.67 (m, 4H), 1.33-1.20 (m, 3H); LCMS (ESI) m/z: 301.1 [M+H]+.

Compound 371: ¹H NMR (400 MHz, MeOD-d4) δ 7.41 (dd, J=1.3, 7.9 Hz, 1H), 7.32 (d, J=1.3 Hz, 1H), 6.95 (d, J=7.9 Hz, 1H), 6.79 (s, 1H), 6.05 (s, 2H), 3.89 (t, J=6.8 Hz, 2H), 2.09-1.96 (m, 6H), 0.63 (d, J=1.8 Hz, 2H); LCMS (ESI) m/z: 313.1 [M+H]+.

Compound 372: ¹H NMR (400 MHz, MeOD-d4) δ 7.44 (dd, J=1.8, 8.4 Hz, 1H), 7.35 (d, J=1.3 Hz, 1H), 7.00-6.94 (m, 2H), 6.05 (s, 2H), 5.73-5.64 (m, 0.4H), 5.10-4.99 (m, 0.8H), 4.02-3.60 (m, 2H), 2.39-2.00 (m, 4H); LCMS (ESI) m/z: 355.1 [M+H]+.

Compound 373: ¹H NMR (400 MHz, MeOD-d4) δ 7.44 (dd, J=1.5, 8.2 Hz, 1H), 7.35 (d, J=1.3 Hz, 1H), 7.01-6.91 (m, 2H), 6.06 (s, 2H), 5.73-5.64 (m, 0.4H), 5.11-5.02 (m, 0.8H), 3.96-3.63 (m, 2H), 2.40-2.04 (m, 4H); LCMS (ESI) m/z: 355.1 [M+H]+.

Compound 374: ¹H NMR (400 MHz, DMSO-d6) δ 7.54-7.45 (m, 1H), 7.39-7.29 (m, 1H), 7.24 (br. s., 0.5H), 7.20-7.09 (m, 1.5H), 7.08-6.96 (m, 1.2H), 6.94-6.86 (m, 1.4H), 6.79 (d, J=7.5 Hz, 0.7H), 5.53 (d, J=6.6 Hz, 0.4H), 5.20 (br. s., 0.5H), 4.00 (br. s., 0.7H), 3.92-3.79 (m, 6H), 3.73 (br. s., 2.3H), 3.65 (br. s., 1H), 2.41-2.25 (m, 1H), 2.11-1.71 (m, 3H); LCMS (ESI) m/z: 409.2 [M+H]+.

Compound 375: ¹H NMR (400 MHz, DMSO-d6) δ 7.47 (d, J=11.7 Hz, 2H), 7.35-7.27 (m, 0.7H), 7.26-7.16 (m, 1.5H), 7.14-6.96 (m, 1.7H), 6.94-6.74 (m, 2.2H), 5.45 (d, J=4.7 Hz, 0.4H), 5.23 (br. s., 0.5H), 4.04-3.88 (m, 1H), 3.88-3.73 (m, 5H), 3.66 (br. s., 1H), 2.42-2.28 (m, 1H), 2.02-1.76 (m, 3H); LCMS (ESI) m/z: 379.2 [M+H]+.

Compound 376: ¹H NMR (400 MHz, DMSO-d6) δ 7.85 (d, J=8.2 Hz, 1H), 7.68 (d, J=7.8 Hz, 1H), 7.19 (d, J=7.8 Hz, 1H), 7.15-6.96 (m, 3H), 6.93-6.84 (m, 1H), 6.83-6.74 (m, 1H), 6.66 (br. s., 1H), 5.52-5.39 (m, 1H), 5.22 (br. s., 1H), 4.04-3.87 (m, 1H), 3.87-3.71 (m, 5H), 3.66 (br. s., 1H), 2.42-2.29 (m, 1H), 2.01-1.76 (m, 3H); LCMS (ESI) m/z: 379.2 [M+H]+.

Compound 377: δ¹H NMR (400 MHz, DMSO-d6) 7.91 (d, J=5.5 Hz, 1H), 7.75 (br. s., 1H), 7.52 (d, J=20.0 Hz, 3H), 7.26-7.14 (m, 2H), 7.01 (d, J=7.4 Hz, 1H), 6.89 (d, J=7.8 Hz, 1H), 6.84-6.73 (m, 1H), 5.44 (br. s., 0.5H), 5.23 (br. s., 0.5H), 4.05-3.85 (m, 2H), 3.84-3.72 (m, 2H), 3.65 (br. s., 1H), 2.35 (d, J=16.4 Hz, 1H), 1.95 (d, J=5.9 Hz, 3H); LCMS (ESI) m/z: 349.2 [M+H]+.

Compound 378: ¹H NMR (400 MHz, DMSO-d6) δ 8.09 (t, J=9.0 Hz, 1H), 7.99-7.79 (m, 1H), 7.71-7.54 (m, 1H), 7.40 (br. s., 1H), 7.17 (d, J=7.9 Hz, 1H), 7.08-6.95 (m, 1H), 6.88 (d, J=7.5 Hz, 1H), 6.77 (d, J=7.9 Hz, 1H), 5.47 (d, J=6.6 Hz, 0.4H), 5.20 (br. s., 0.6H), 4.00 (br. s., 1H), 3.73 (br. s., 3H), 3.63 (br. s., 1H), 2.32 (dd, J=8.6, 18.7 Hz, 1H), 1.99-1.71 (m, 3H); LCMS (ESI) m/z: 385.1 [M+H]+.

Compound 379: ¹H NMR (400 MHz, DMSO-d6) δ 7.91 (d, J=7.5 Hz, 0.5H), 7.78 (d, J=7.5 Hz, 0.5H), 7.57-7.45 (m, 1H), 7.29-6.98 (m, 4H), 6.89 (d, J=7.5 Hz, 1H), 6.80 (d, J=7.9 Hz, 1H), 6.65 (s, 1H), 5.44 (d, J=6.6 Hz, 0.5H), 5.19 (br. s., 0.5H), 4.11-3.54 (m, 8H), 2.41-2.26 (m, 1H), 1.99-1.71 (m, 3H); LCMS (ESI) m/z: 397.2 [M+H]+.

Compound 380: ¹H NMR (400 MHz, DMSO-d6) δ 8.06 (d, J=7.9 Hz, 1H), 7.89 (d, J=7.5 Hz, 1H), 7.59-7.42 (m, 2H), 7.28 (s, 1H), 7.20 (d, J=7.9 Hz, 1H), 7.00 (d, J=7.1 Hz, 1H), 6.89 (d, J=8.8 Hz, 1H), 6.78 (d, J=7.5 Hz, 1H), 5.42 (br. s., 0.5H), 5.23 (br. s., 0.5H), 4.07-3.58 (m, 5H), 2.33 (br. s., 1H), 1.95 (d, J=5.7 Hz, 3H); LCMS (ESI) m/z: 433.2 [M+H]+.

Compound 381: ¹H NMR (400 MHz, DMSO-d6) δ 8.15 (d, J=7.5 Hz, 1H), 8.04-7.81 (m, 3H), 7.42 (s, 1H), 7.20 (d, J=7.9 Hz, 1H), 7.00 (br. s., 1H), 6.90 (d, J=7.5 Hz, 1H), 6.77 (d, J=7.1 Hz, 1H), 5.42 (br. s., 0.5H), 5.24 (br. s., 0.5H), 4.07-3.56 (m, 5H), 2.35 (d, J=19.0 Hz, 1H), 2.02-1.78 (m, 3H); LCMS (ESI) m/z: 417.2 [M+H]+.

Compound 382: ¹H NMR (400 MHz, DMSO-d6) δ 7.82-7.67 (m, 1H), 7.63-7.52 (m, 1H), 7.39-7.25 (m, 1H), 7.23-7.11 (m, 2H), 6.99 (d, J=7.1 Hz, 1H), 6.89 (d, J=7.5 Hz, 1H), 6.78 (d, J=9.3 Hz, 1H), 5.43 (br. s., 0.5H), 5.22 (br. s., 0.5H), 4.02-3.59 (m, 8H), 2.41-2.27 (m, 1H), 1.95 (br. s., 3H); LCMS (ESI) m/z: 397.2 [M+H]+.

Compound 383: ¹H NMR (400 MHz, DMSO-d6) δ 7.68 (d, J=7.5 Hz, 1H), 7.50 (br. s., 1H), 7.42-7.12 (m, 3H), 7.01 (d, J=7.9 Hz, 1H), 6.94-6.72 (m, 2H), 5.46 (br. s., 0.5H), 5.23 (br. s., 0.5H), 4.05-3.57 (m, 8H), 2.33 (br. s., 1H), 2.04-1.75 (m, 3H); LCMS (ESI) m/z: 397.2 [M+H]+.

Compound 384: ¹H NMR (400 MHz, MeOD) δ 7.24-7.18 (m, 1H), 7.16-7.01 (m, 3H), 6.94 (d, J=7.5 Hz, 1H), 6.41-6.33 (s, 0.6H), 5.89 (s, 0.4H), 5.45-5.41 (m, 0.5H), 5.22-5.13 (m, 0.5H), 4.06-3.97 (m, 0.7H), 3.92-3.85 (m, 0.7H), 3.78-3.72 (m, 0.8H), 2.62 (d, J=7.1 Hz, 1H), 2.43-2.38 (m, 1H), 2.37-2.26 (m, 1.3H), 1.95-1.75 (m, 3.5H), 1.02-0.94 (m, 0.6H), 0.78-0.70 (m., 0.6H), 0.49 (d, J=6.6 Hz, 1H), 0.41-0.35 (m, 1H), 0.16 (d, J=5.3 Hz, 1H), 0.01 (d, J=4.9 Hz, 1H); LCMS (ESI) m/z: 297.2 [M+H]+.

Compound 385: ¹H NMR (400 MHz, DMSO-d6) δ 7.94 (dd, J=1.8, 7.7 Hz, 1H), 7.77 (dd, J=2.9, 6.7 Hz, 1H), 7.60-7.52 (m, 2H), 7.49 (dd, J=1.8, 5.0 Hz, 1H), 7.37-7.29 (m, 2H), 7.28-7.20 (m, 2H), 7.17-7.05 (m, 1H), 6.98 (s, 1H), 5.56 (d, J=5.5 Hz, 0.4H), 5.24 (dd, J=4.0, 7.9 Hz, 0.6H), 4.09-3.99 (m, 1H), 3.96-3.72 (m, 1H), 2.45-2.30 (m, 1H), 1.98-1.73 (m, 3H); LCMS (ESI) m/z: 319.2 [M+H]+.

Compound 386: $^1$H NMR (400 MHz, MeOD-d4) δ 7.88 (dd, J=2.0, 7.7 Hz, 1H), 7.71-7.65 (m, 1H), 7.57-7.43 (m, 3H), 7.37-7.21 (m, 3H), 7.16-7.06 (m, 1H), 7.03 (s, 1H), 6.58 (s, 1H), 5.68-5.58 (m, 0.5H), 5.33 (dd, J=4.3, 7.8 Hz, 0.5H), 4.27-4.13 (m, 0.5H), 4.06 (td, J=7.2, 11.4 Hz, 0.5H), 3.98-3.82 (m, 1H), 2.57-2.35 (m, 1H), 2.16-1.85 (m, 3H); LCMS (ESI) m/z: 319.2 [M+H]+.

Compound 387: $^1$H NMR (400 MHz, DMSO-d6) δ 7.95 (dd, J=1.8, 7.5 Hz, 1H), 7.80-7.75 (m, 1H), 7.55 (s, 2H), 7.53-7.47 (m, 1H), 7.36-7.31 (m, 2H), 7.29-7.19 (m, 2H), 7.16-7.07 (m, 1H), 7.00 (s, 1H), 5.59-5.54 (m, 0.4H), 5.25 (dd, J=4.0, 7.9 Hz, 0.6H), 4.11-3.98 (m, 0.6H), 3.96-3.81 (m, 1H), 3.81-3.72 (m, 0.4H), 2.44-2.29 (m, 1H), 1.97-1.74 (m, 3H); LCMS (ESI) m/z: 319.2 [M+H]+.

Compound 388: $^1$H NMR (400 MHz, DMSO-d6) δ 7.56-7.19 (m, 6H), 7.09 (d, J=7.9 Hz, 1H), 6.95 (s, 1H), 6.17-6.06 (m, 2H), 5.60-5.50 (m, 0.3H), 5.25-5.15 (m, 0.7H), 4.12-3.99 (m, 1H), 3.97-3.70 (m, 1H), 2.37 (dd, J=7.7, 12.1 Hz, 1H), 1.91 (d, J=6.6 Hz, 3H); LCMS (ESI) m/z: 441.1 [M+H]+.

Compound 389: $^1$H NMR (400 MHz, DMSO-d6) δ 7.56-7.40 (m, 3H), 7.38 (d, J=1.3 Hz, 1H), 7.27-7.18 (m, 2H), 7.12-6.91 (m, 2H), 6.18-6.05 (m, 2H), 5.55 (s, 0.4H), 5.18 (d, J=3.1 Hz, 0.6H), 4.01 (s, 1H), 3.90 (d, J=11.0 Hz, 1H), 2.44-2.28 (m, 1H), 1.91 (br. s., 3H); LCMS (ESI) m/z: 441.1 [M+H]+.

Compound 390: $^1$H NMR (400 MHz, DMSO-d6) δ 7.52 (br. s., 2H), 7.40-6.90 (m, 6H), 6.22-6.02 (m, 2H), 5.90-5.73 (m, 0.4H), 5.40 (d, J=4.0 Hz, 0.6H), 4.15 (d, J=4.0 Hz, 1H), 3.95 (d, J=7.5 Hz, 1H), 2.44-2.33 (m, 1H), 2.03-1.62 (m, 3H); LCMS (ESI) m/z: 441.1 [M+H]+.

Compound 391: $^1$H NMR (400 MHz, MeOD-d4) δ 9.15-9.02 (m, 1H), 7.84-7.75 (m, 1.3H), 7.70 (d, J=3.3 Hz, 0.6H), 7.40 (dd, J=1.7, 8.0 Hz, 0.7H), 7.33-7.24 (m, 1H), 7.18 (d, J=1.8 Hz, 0.3H), 6.94 (d, J=8.2 Hz, 0.6H), 6.90-6.86 (m, 1H), 6.74 (s, 0.3H), 6.05-5.99 (m, 2H), 5.94 (dd, J=2.5, 8.0 Hz, 0.3H), 5.47 (dd, J=4.9, 8.4 Hz, 0.6H), 4.26-4.12 (m, 1.3H), 4.03-3.86 (m, 0.7H), 2.65-2.49 (m, 1H), 2.22-1.93 (m, 3H); LCMS (ESI) m/z: 365.2 [M+H]+.

Compound 392: $^1$H NMR (400 MHz, MeOD-d4) δ 8.10 (d, J=8.8 Hz, 1H), 7.91 (d, J=8.8 Hz, 1H), 7.84-7.73 (m, 2H), 7.22-7.16 (m, 1.5H), 6.97 (d, J=8.6 Hz, 1H), 6.87 (d, J=8.6 Hz, 1H), 6.75-6.69 (m, 1.5H), 5.46 (m, 0.5H), 5.30-5.24 (m, 0.5H), 4.21-4.12 (m, 0.5H), 4.07-3.99 (m, 0.5H), 3.88 (t, J=7.1 Hz, 1H), 3.75 (s, 1.5H), 3.59 (s, 1.5H), 2.48-2.35 (m, 1H), 2.08-1.84 (m, 3H); LCMS (ESI) m/z: 467.2 [M+H]+.

Compound 393: $^1$H NMR (400 MHz, CDCl3) δ 7.60-7.51 (m, 1H), 7.46-7.37 (m, 1H), 7.24-7.18 (m, 1.4H), 7.14 (d, J=8.4 Hz, 0.4H), 7.03 (d, J=8.7 Hz, 1H), 6.92-6.87 (m, 1.59H), 6.79 (d, J=8.8 Hz, 1H), 6.53 (s, 0.5H), 5.77-5.70 (m, 0.5H), 5.36 (dd, J=4.1, 7.5 Hz, 0.5H), 4.30-4.12 (m, 1H), 3.94 (br d, J=8.2 Hz, 1H), 3.84-3.70 (m, 3H), 2.49-2.32 (m, 1H), 2.17-1.93 (m, 3H); LCMS (ESI) m/z: 429.2 [M+H]+.

Compound 394: $^1$H NMR (400 MHz, DMSO-d6) δ 8.20 (s, 0.4H), 8.22-8.18 (m, 0.3H), 8.05 (s, 1H), 7.84 (d, J=8.4 Hz, 1H), 7.61 (dd, J=1.3, 8.4 Hz, 0.5H), 7.45 (dd, J=1.3, 8.4 Hz, 0.5H), 7.38 (s, 0.5H), 7.16 (d, J=8.6 Hz, 1H), 7.03-6.96 (m, 1H), 6.86 (d, J=8.6 Hz, 1H), 6.75 (d, J=8.8 Hz, 1H), 5.52-5.48 (m, 0.5H), 5.21-5.16 (m, 0.5H), 3.99 (d, J=15.2 Hz, 3H), 3.70 (s, 2H), 3.81-3.70 (s, 3H), 3.3 (s, 2H), 2.45 (m, 1H), 2.39-2.23 (m, 1H), 1.89-1.80 (m, 3H); LCMS (ESI) m/z: 417.3 [M+H]+.

Compound 395: $^1$H NMR (400 MHz, DMSO-d6) δ 7.80-7.64 (m, 2H), 7.50-7.42 (m, 2H), 7.38-7.24 (m, 1H), 7.12-6.97 (m, 1.6H), 6.82 (s, 0.4H), 6.12-6.07 (m, 2H), 5.60 (br d, J=6.2 Hz, 0.3H), 5.33-5.24 (m, 0.7H), 4.08-3.78 (m, 2H), 2.43 (br dd, J=7.4, 12.5 Hz, 1H), 2.01-1.77 (m, 3H); LCMS (ESI) m/z: 388.2 [M+H]+.

Compound 396: $^1$H NMR (400 MHz, DMSO-d6) δ 7.75-7.42 (m, 5H), 7.30 (br s, 1H), 7.15-6.98 (m, 1.5H), 6.82 (br s, 0.5H), 6.15-6.06 (m, 2H), 5.57 (br s, 0.3H), 5.27 (br s, 0.7H), 4.13-3.77 (m, 2H), 2.47-2.37 (m, 1H), 2.03-1.79 (m, 3H); LCMS (ESI) m/z: 388.1 [M+H]+.

Compound 397: $^1$H NMR (400 MHz, CDCl3-d) δ=7.63 (br d, J=6.8 Hz, 1H), 7.51-7.28 (m, 5H), 7.24 (s, 1H), 6.92 (br d, J=7.9 Hz, 1H), 6.76 (d, J=1.5 Hz, 1H), 6.06 (d, J=1.5 Hz, 2H), 5.84 (br s, 1H), 4.63-4.33 (m, 2H), 4.00 (br d, J=7.5 Hz, 2H), 3.74 (br t, J=11.8 Hz, 1H), 3.47 (br s, 1H), 3.15 (br s, 0.6H), 1.58 (d, J=1.5 Hz, 0.4H); LCMS (ESI) m/z: 379.2 [M+H]+.

Compound 398: $^1$H NMR (400 MHz, DMSO-d6) δ 7.78 (br d, J=7.7 Hz, 1H), 7.72-7.54 (m, 1H), 7.47-7.41 (m, 2H), 7.38-7.26 (m, 1H), 7.10-6.95 (m, 2H), 6.83 (s, 1H), 6.12-6.05 (m, 2H), 5.78 (br d, J=6.0 Hz, 0.3H), 5.38 (br t, J=6.7 Hz, 0.7H), 4.14-3.79 (m, 2H), 2.57-2.50 (m, 1H), 2.07-1.77 (m, 3H); LCMS (ESI) m/z: 388.2 [M+H]+.

Compound 399: $^1$H NMR (400 MHz, CDCl3) δ 7.61 (d, J=1.4 Hz, 0.5H), 7.54 (dd, J=1.6, 8.2 Hz, 0.5H), 7.48 (d, J=1.4 Hz, 0.5H), 7.40 (dd, J=1.6, 8.2 Hz, 0.5H), 7.34-7.23 (m, 1H), 7.13 (d, J=8.7 Hz, 1H), 6.95 (d, J=8.5 Hz, 1H), 6.79 (d, J=8.7 Hz, 1H), 6.75 (s, 1H), 6.69 (d, J=8.8 Hz, 1H), 6.38 (s, 0.5H), 5.69-5.63 (m, 0.5H), 5.27 (dd, J=4.0, 7.7 Hz, 0.5H), 4.09 (s, 1H), 3.85 (br d, J=7.3 Hz, 1H), 3.74-3.59 (m, 3H), 3.17 (d, J=6.5 Hz, 6H), 2.38-2.23 (m, 1H), 2.08-1.83 (m, 3H); LCMS (ESI) m/z: 433.2 [M+H]+.

Compound 400: $^1$H NMR (400 MHz, DMSO-d6) δ 8.89 (d, J=10.9 Hz, 1H), 8.43 (d, J=1.4 Hz, 0.5H), 8.27 (s, 0.3H), 8.09-8.03 (m, 0.5H), 8.00-7.96 (m, 0.5H), 7.95-7.87 (m, 1H), 7.43 (s, 0.5H), 7.20 (d, J=8.7 Hz, 1H), 7.07 (s, 0.3H), 7.02 (d, J=8.7 Hz, 0.7H), 6.90 (d, J=8.8 Hz, 1H), 6.79 (d, J=8.8 Hz, 1H), 5.51 (dd, J=2.4, 7.2 Hz, 0.4H), 5.22 (dd, J=4.0, 7.8 Hz, 0.5H), 4.09-4.01 (m, 0.5H), 3.96-3.88 (m, 0.5H), 3.86-3.79 (m, 0.5H), 3.76-3.61 (m, 3H), 2.33 (br dd, J=7.8, 12.3 Hz, 1H), 1.98-1.76 (m, 3H); LCMS (ESI) m/z: 390.2 [M+H]+.

Compound 401: $^1$H NMR (400 MHz, CDCl3) δ 8.11 (d, J=11.3 Hz, 1H), 7.98 (s, 0.5H), 7.83 (m, 1H), 7.78-7.72 (m, 1H), 7.60 (m, 0.5H), 7.13 (br d, J=8.4 Hz, 1H), 6.98-6.89 (m, 1.4H), 6.80 (br d, J=8.5 Hz, 1H), 6.69 (br d, J=8.5 Hz, 1H), 6.54 (s, 0.4H), 5.66 (m, 0.5H), 5.28 (m, 0.5H), 4.22-4.07 (m, 1H), 3.93-3.82 (m, 1H), 3.76-3.58 (m, 3H), 2.42-2.22 (m, 1H), 2.09-1.83 (m, 3H); LCMS (ESI) m/z: 390.0 [M+H]+.

Compound 402: $^1$H NMR (400 MHz, DMSO-d6) δ 8.16-7.80 (m, 3H), 7.79-7.64 (m, 1H), 7.43-7.07 (m, 5H), 6.99 (s, 1H), 5.50 (br d, J=6.0 Hz, 0.4H), 5.29 (br dd, J=4.4, 7.5 Hz, 0.6H), 4.13-3.80 (m, 2H), 2.46-2.34 (m, 1H), 2.03-1.81 (m, 3H); LCMS (ESI) m/z: 344.2 [M+H]+.

Compound 403: $^1$H NMR (400 MHz, DMSO-d6) δ 8.39 (s, 1H), 8.24 (br d, J=8.2 Hz, 1H), 8.06 (br d, J=7.5 Hz, 1H), 8.00-7.88 (m, 1H), 7.82-7.66 (m, 1H), 7.42 (s, 1H), 7.38-7.20 (m, 3H), 7.18-7.02 (m, 1H), 5.53 (br d, J=7.1 Hz, 0.4H), 5.28 (br dd, J=3.7, 7.7 Hz, 0.6H), 4.07-3.88 (m, 1H), 3.84 (br s, 1H), 2.47-2.34 (m, 1H), 2.02-1.79 (m, 3H); LCMS (ESI) m/z: 344.2 [M+H]+.

Compound 404: $^1$H NMR (400 MHz, DMSO-d6) δ 8.11 (br d, J=7.9 Hz, 1H), 8.04-7.87 (m, 3H), 7.45 (s, 1H), 7.36-7.19 (m, 3H), 7.16-7.01 (m, 2H), 5.50 (br d, J=7.5 Hz, 0.4H), 5.27 (br s, 0.6H), 4.06-3.77 (m, 2H), 2.46-2.34 (m, 1H), 2.04-1.80 (m, 3H). LCMS (ESI) for m/z: 344.2 [M+H]+.

Compound 405: $^1$H NMR (400 MHz, DMSO-d6) δ=9.13 (br s, 0.5H), 8.95 (br s, 0.5H), 8.76-8.63 (m, 1H), 8.29 (br d, J=7.5 Hz, 1H), 8.12 (br d, J=7.1 Hz, 1H), 7.63-7.46 (m, 1H), 7.41-7.20 (m, 4H), 7.16-6.98 (m, 1H), 5.52 (br d, J=6.0 Hz, 0.4H), 5.28 (br s, 0.6H), 4.08-3.90 (m, 1H), 3.84 (br s, 1H), 2.47-2.33 (m, 1H), 2.01-1.77 (m, 3H). LCMS (ESI) m/z: 320.2 [M+H]+.

Compound 406: $^1$H NMR (400 MHz, CDCl3) δ 7.45-7.37 (m, 3H), 7.33 (br d, J=1.6 Hz, 2H), 7.27-7.21 (m, 2H), 7.16-7.11 (m, 0.3H), 6.96-6.85 (m, 1H), 6.81 (s, 0.6H), 6.57 (s, 0.3H), 6.10-6.00 (m, 2H), 5.88-5.83 (m, 0.3H), 5.65 (d, J=4.4 Hz, 1.3H), 5.58-5.53 (m, 0.3H), 5.41-5.34 (m, 1H), 4.42 (dd, J=6.7, 8.8 Hz, 1H), 4.16-4.11 (m, 0.3H), 4.06 (m, 0.7H); LCMS (ESI) m/z: 365.1 [M+H]+.

Compound 407: 1 HNMR (400 MHz, DMSO-d6) δ 7.50 (t, J=1.6 Hz, 1H), 7.46 (td, J1=8.0 Hz, J2=2.0 Hz, 1H), 7.17-7.16 (m, 1H), 7.09-7.07 (m, 1H), 6.13 (s, 2H), 4.04 (t, J=8.0 Hz, 0.35H), 3.90-3.86 (m, 0.65H), 3.78-3.72 (m, 0.65H), 3.68-3.56 (m, 1.35H), 2.05-1.97 (m, 1.4H), 1.93-1.79 (m, 2H), 1.74-1.68 (m, 0.7H), 1.08-1.02 (m, 0.65H), 0.94-0.90 (m, 0.35H), 0.63-0.58 (m, 0.65H), 0.48-0.45 (m, 0.65H), 0.40-0.21 (m, 2H), 0.11-0.07 (m, 0.35H), –0.20-0.26 (m, 0.35H); LCMS (ESI) m/z: 327.2 [M+H]+.

Compound 408: $^1$H NMR (400 MHz, DMSO-d6) δ=8.79-8.63 (m, 1H), 8.07-7.83 (m, 2H), 7.59-7.43 (m, 1H), 7.38-7.19 (m, 4H), 7.18-7.05 (m, 1H), 6.89 (s, 1H), 5.52 (br d, J=6.4 Hz, 0.4H), 5.28 (br dd, J=4.1, 7.2 Hz, 0.6H), 4.09-3.78 (m, 2H), 2.47-2.33 (m, 1H), 2.04-1.78 (m, 3H). LCMS (ESI) m/z: 320.2 [M+H]+.

Compound 409: $^1$H NMR (400 MHz, DMSO-d6) δ 8.81-8.67 (m, 2H), 7.86 (br d, J=5.5 Hz, 1H), 7.69 (br d, J=4.9 Hz, 1H), 7.51 (s, 1H), 7.39-7.19 (m, 4H), 7.16-7.05 (m, 1H), 5.50 (br d, J=7.5 Hz, 0.4H), 5.27 (br dd, J=3.7, 7.5 Hz, 0.6H), 4.08-3.76 (m, 2H), 2.47-2.36 (m, 1H), 2.01-1.77 (m, 3H). LCMS (ESI) m/z: 320.2 [M+H]+.

Compound 410: $^1$H NMR (400 MHz, DMSO-d6) δ 8.75 (s, 0.5H), 8.57 (br s, 0.5H), 8.19 (br d, J=7.1 Hz, 0.6H), 8.02 (br d, J=7.7 Hz, 0.4H), 7.39-7.07 (m, 5H), 7.01-6.88 (m, 1H), 6.83 (s, 1H), 5.53 (br d, J=6.4 Hz, 0.4H), 5.27 (br dd, J=4.1, 7.4 Hz, 0.6H), 4.07-3.89 (m, 4H), 3.82 (br d, J=6.2 Hz, 1H), 2.46-2.34 (m, 1H), 2.01-1.79 (m, 3H); LCMS (ESI) m/z: 350.2 [M+H]+.

Compound 411: $^1$H NMR (400 MHz, CDCl3) δ 7.28-7.20 (m, 1H), 7.17-7.12 (m, 1H), 6.86-6.79 (m, 1H), 6.72 (m, 0.6H), 6.67 (m, 0.4H), 6.00-5.96 (m, 2H), 5.91 (m, 0.3H), 5.76 (m, 0.6H), 5.56 (s, 0.3H), 5.33 (m, 0.6H), 4.16-4.08 (m, 1H), 3.98 (br s, 1H), 3.89-3.82 (m, 3H), 3.81-3.66 (m, 1H), 2.27-2.15 (m, 2H), 2.07-1.95 (m, 2H); LCMS (ESI) m/z: 384.1 [M+H]+.

Compound 412: $^1$H NMR (400 MHz, CDCl3) δ 7.29-7.20 (m, 1H), 7.17-7.11 (m, 1H), 6.86-6.79 (m, 1H), 6.74-6.68 (m, 1H), 6.23 (m, 0.6H), 6.07-6.02 (m, 0.6H), 5.99-5.96 (m, 2H), 5.43 (dd, J=2.9, 7.6 Hz, 0.6H), 4.20-3.68 (m, 2H), 2.30-1.98 (m, 4H); LCMS (ESI) m/z: 431.9, 433.9 [M+H]+.

Compound 413: $^1$H NMR (400 MHz, CDCl3) δ 7.40-7.32 (m, 1H), 7.28-7.24 (m, 1H), 6.96-6.90 (m, 1H), 6.82-6.76 (m, 1H), 6.10-6.04 (m, 2H), 4.96-4.78 (m, 0.2H), 4.35 (m, 0.7H), 4.34-3.78 (m, 3H), 3.78-3.80 (1H), 3.43-3.38 (m, 1H), 2.33-2.34 (m, 1H), 2.09-1.91 (m, 4.6H), 1.58-1.33 (m, 5H); LCMS (ESI) m/z: 371.2 [M+H]+.

Compound 414: $^1$H NMR (400 MHz, DMSO-d6) δ 7.68-7.52 (m, 0.5H), 7.49-7.39 (m, 1H), 7.36-6.95 (m, 7H), 6.63-6.54 (m, 0.5H), 6.16-6.04 (m, 2H), 5.52-5.37 (m, 0.3H), 5.32-5.15 (m, 0.7H), 5.03-4.83 (m, 1H), 4.38 (br s, 1H), 4.20-3.97 (m, 0.8H), 3.92-3.79 (m, 0.8H), 3.76-3.68 (m, 0.5H), 3.59 (br s, 0.2H), 2.66 (br d, J=1.8 Hz, 0.3H), 2.43-2.31 (m, 0.7H), 2.09-1.75 (m, 3H); LCMS (ESI) m/z: 379.2 [M+H]+.

Compound 415: $^1$H NMR (400 MHz, DMSO-d6) δ 8.48-8.34 (m, 1H), 7.97 (d, J=8.6 Hz, 0.6H), 7.83 (br d, J=8.8 Hz, 0.4H), 7.61-7.45 (m, 1H), 7.35-7.01 (m, 4H), 6.81 (s, 1H), 5.73 (br d, J=7.9 Hz, 0.4H), 5.41 (br dd, J=5.0, 7.6 Hz, 0.6H), 4.09-3.78 (m, 5H), 2.46-2.36 (m, 1H), 2.06-1.75 (m, 3H); LCMS (ESI) m/z: 368.0 [M+H]+; LCMS (ESI) m/z: 368.0 [M+H]+.

Compound 416: $^1$H NMR (400 MHz, DMSO-d6) δ=8.47-8.34 (m, 1H), 7.97 (br d, J=8.6 Hz, 1H), 7.80 (br d, J=8.8 Hz, 1H), 7.60-7.46 (m, 1H), 7.39-7.19 (m, 3H), 7.16-7.04 (m, 1H), 6.73 (s, 1H), 5.52 (br d, J=7.1 Hz, 0.5H), 5.30-5.21 (m, 0.5H), 4.06-3.97 (m, 1H), 3.95-3.87 (m, 3H), 3.82 (br s, 1H), 2.46-2.34 (m, 1H), 2.00-1.79 (m, 3H); LCMS (ESI) m/z: 350.0 [M+H]+.

Compound 417: 1 HNMR (400 MHz, DMSO-d6) δ 7.50 (d, J=2.0 Hz, 0.6H), 7.47 (dd, J1=8.0 Hz, J2=2.4 Hz, 0.6H), 7.42 (d, J=2.0 Hz, 0.3H), 7.39 (dd, J1=8.4 Hz, J2=2.0 Hz, 0.3H), 7.28 (d, J=2.0 Hz, 0.5H), 7.20 (s, 0.6H), 7.19 (d, J=2.0 Hz, 0.3H), 7.08 (d, J=8.4 Hz, 0.6H), 7.04 (d, J=8.0 Hz, 0.3H), 7.00 (s, 0.4H), 6.12-6.10 (m, 2H), 6.09 (d, J=2.0 Hz, 0.6H), 5.94 (d, J=2.0 Hz, 0.4H), 5.80-5.70 (m, 0.4H), 5.35-5.32 (m, 0.6H), 4.01-3.95 (m, 0.6H), 3.91-3.92 (m, 3H), 3.72 (s, 1H), 3.68-3.61 (m, 0.4H), 2.33-2.26 (m, 1H), 2.05-1.82 (m, 3H); LCMS (ESI) m/z: 367.0 [M+H]+.

Compound 418: 1HNMR (400 MHz, DMSO-d6) δ 7.50 (d, J=2.0 Hz, 0.6H), 7.47 (dd, J1=8.4 Hz, J2=2.0 Hz, 0.6H), 7.39 (d, J=1.6 Hz, 0.3H), 7.35 (dd, J1=8.0 Hz, J2=1.6 Hz, 0.3H), 7.19 (s, 0.6H), 7.08 (d, J=8.0 Hz, 0.7H), 7.02 (d, J=8.0 Hz, 0.3H), 6.99 (s, 0.3H), 6.18-6.08 (m, 2H), 5.65 (dd, J1=8.0 Hz, J2=2.8 Hz, 0.3H), 5.28 (dd, J1=8.0 Hz, J2=4.4 Hz, 0.7H), 4.06-3.95 (m, 1.4H), 3.83-3.74 (m, 0.7H), 2.43-2.32 (m, 1H), 2.10-1.91 (m, 3H); LCMS (ESI) m/z: 365.0 [M+H]+.

Compound 419: $^1$H NMR (400 MHz, CDCl3) δ 7.74 (s, 0.5H), 7.68-7.57 (m, 1.4H), 7.40 (br d, J=8.4 Hz, 0.8H), 7.36-7.27 (m, 3H), 7.26-7.20 (m, 1.5H), 7.15 (m, 0.5H), 6.94 (s, 0.5H), 6.71 (s, 0.2H), 5.78 (m, 0.3H), 5.59 (m, 1.3H), 5.49 (m, 0.2H), 5.36-5.27 (m, 1H), 4.38-4.31 (m, 1H), 4.09-4.03 (m, 0.4H), 4.01-3.92 (m, 3.5H), 2.59-2.44 (m, 3H); LCMS (ESI) m/z: 389.2 [M+H]+.

Compound 420: $^1$H NMR (400 MHz, DMSO-d6) δ=7.49-6.95 (m, 8.7H), 6.56 (br s, 0.3H), 6.15-6.05 (m, 2H), 5.48 (br s, 1H), 5.41-5.26 (m, 1H), 4.37-3.90 (m, 2H), 2.76 (br s, 1H), 2.28-2.04 (m, 1H); LCMS (ESI) m/z: 381.2 [M+H]+.

Compound 421: $^1$H NMR (400 MHz, DMSO-d6) 7.65-7.44 (m, 2H), 7.33-7.23 (m, 3H), 7.21-6.98 (m, 3.8H), 6.70 (s, 0.2H), 6.14-6.06 (m, 2H), 5.43 (dd, J=5.3, 8.4 Hz, 0.3H), 5.18-5.05 (m, 1.7H), 4.43-4.28 (m, 1H), 4.16-3.99 (m, 1H), 3.73 (dd, J=5.7, 11.2 Hz, 0.7H), 3.56 (dd, J=4.7, 12.5 Hz, 0.3H), 2.67-2.54 (m, 1H), 1.92-1.69 (m, 1H); LCMS (ESI) m/z: 379.1 [M+H]+.

Compound 422: $^1$H NMR (400 MHz, DMSO-d6) δ 7.53-7.44 (m, 1H), 7.35-7.12 (m, 5H), 7.11-6.99 (m, 2H), 6.65 (s, 1H), 6.16-6.06 (m, 2H), 5.44 (t, J=7.5 Hz, 1H), 5.23-5.09 (m, 1H), 4.41-4.30 (m, 1H), 4.02 (dd, J=3.6, 11.8 Hz, 1H), 3.89-3.75 (m, 1H), 2.40-2.30 (m, 1H), 2.02-1.81 (m, 1H); LCMS (ESI) m/z: 379.1 [M+H]+.

Compound 423: 1 HNMR (400 MHz, DMSO-d6) δ=8.03 (d, J=0.8 Hz, 0.5H), 7.99 (d, J=0.8 Hz, 0.3H), 7.52 (d, J=1.6 Hz, 0.5H), 7.49 (d, J=1.6 Hz, 0.3H), 7.46 (dd, J1=5.6 Hz, J2=1.6 Hz, 0.6H), 7.41 (dd, J1=8.0 Hz, J2=2.0 Hz, 0.3H), 7.22 (s, 0.6H), 7.15 (d, J=0.8 Hz, 0.5H), 7.12 (s, 0.4H), 7.10 (s, 0.3H), 7.08 (s, 0.3H), 7.06 (m, 0.4H), 7.04 (s, 0.2H), 6.13-6.11 (m, 2H), 5.71 (dd, J1=7.6 Hz, J2=2.0 Hz, 0.35H), 5.30 (dd, J1=8.0 Hz, J2=3.2 Hz, 0.6H), 4.00-3.85 (m, 1.3H), 3.79-3.73 (m, 0.4H), 3.69-3.62 (m, 0.4H), 2.40-2.27 (m, 1H), 2.12-1.96 (m, 2.7H), 1.90-1.77 (m, 0.4H). LCMS (ESI) m/z: 354.1 [M+H]+.

Compound 424: 1 HNMR (400 MHz, DMSO-d6) δ 7.48-7.45 (m, 1H), 7.46 (dd, J1=8.0 Hz, J2=1.8 Hz, 1H), 7.19-7.17 (m, 1H), 7.09-7.07 (m, 1H), 6.13 (s, 2H), 4.41-4.14 (m, 1H), 3.74-3.53 (m, 2H), 2.80-2.66 (m, 2H), 2.15-2.02 (3H), 1.90-1.59 (m, 7H), 1.51-1.44 (m, 2H), 1.36-1.24 (m, 2H); LCMS (ESI) m/z: 384.2 [M+H]+.

Compound 425: $^1$H NMR (400 MHz, DMSO-d6) δ 8.04 (s, 0.4H), 7.96 (s, 0.3H), 7.62 (dd, J=1.0, 7.8 Hz, 0.5H), 7.54 (d, J=7.3 Hz, 0.3H), 7.51-7.45 (m, 1H), 7.31 (d, J=1.8 Hz, 0.4H), 7.26 (dd, J=1.8, 8.2 Hz, 0.4H), 7.21 (s, 0.4H), 7.10-6.99 (m, 2H), 6.98-6.92 (m, 0.8H), 6.56 (d, J=7.5 Hz, 0.4H), 6.15-6.05 (m, 2H), 6.04 (d, J=5.7 Hz, 0.4H), 4.28 (d, J=17.2 Hz, 3H), 4.18 (dt, J=4.0, 7.4 Hz, 0.5H), 4.02-3.90 (m, 1H), 3.81-3.73 (m, 0.5H), 2.55 (br d, J=11.5 Hz, 1H), 2.06-1.79 (m, 3H); LCMS (ESI) m/z: 417.2 [M+H]+.

Compound 426: $^1$H NMR (400 MHz, CDCl3) δ 8.41-8.26 (m, 1H), 7.37-7.17 (m, 2H), 6.97-6.86 (m, 1H), 6.75 (s, 0.3H), 6.42 (d, J=1.5 Hz, 0.6H), 6.24 (d, J=1.5 Hz, 0.3H), 6.09-6.03 (m, 2.3H), 5.56 (dd, J=4.0, 6.7 Hz, 1H), 4.23-4.03 (m, 2H), 3.92-3.82 (m, 1H), 2.41-2.26 (m, 2H), 2.16-2.03 (m, 1H); LCMS (ESI) m/z: 354.2 [M+H]+.

Compound 427: $^1$H NMR (400 MHz, DMSO-d6) δ 7.52-6.96 (m, 8H), 6.82 (br s, 1H), 6.11 (br s, 2H), 5.76 (br s, 0.3H), 5.56-5.34 (m, 1.7H), 4.36-4.00 (m, 2H), 2.87-2.59 (m, 1H), 2.38-2.18 (m, 1H); LCMS (ESI) m/z: 381.2 [M+H]+.

Compound 428: $^1$H NMR (400 MHz, DMSO-d6) δ=7.89-7.72 (m, 1H), 7.43 (s, 1H), 7.38-7.21 (m, 3H), 7.18-7.01 (m, 1H), 6.92 (s, 1H), 6.76-6.65 (m, 1H), 6.49 (br d, J=6.8 Hz, 1H), 5.48 (br d, J=7.3 Hz, 0.4H), 5.28 (br dd, J=4.0, 7.5 Hz, 0.6H), 4.06-3.80 (m, 2H), 3.53-3.42 (m, 3H), 2.46-2.35 (m, 1H), 2.02-1.79 (m, 3H); LCMS (ESI) m/z: 350.0 [M+H]+.

Compound 429: $^1$H NMR (400 MHz, DMSO-d6) δ 8.44 (br s, 0.6H), 8.29 (br s, 0.4H), 7.86 (br d, J=9.3 Hz, 0.6H), 7.69 (br d, J=8.2 Hz, 0.4H), 7.36-7.19 (m, 4H), 7.18-7.05 (m, 1H), 6.96 (s, 0.6H), 6.63 (s, 0.4H), 6.56-6.44 (m, 1H), 5.54 (br d, J=6.4 Hz, 0.4H), 5.26 (br dd, J=4.2, 7.3 Hz, 0.6H), 4.04-3.76 (m, 2H), 3.56-3.46 (m, 3H), 2.47-2.31 (m, 1H), 2.01-1.78 (m, 3H); LCMS (ESI) m/z: 350.2 [M+H]+.

Compound 430: 1 HNMR (400 MHz, DMSO-d6) δ=7.51 (d, J=2.0 Hz, 0.6H) 7.48, (dd, J1=8.0 Hz, J2=2.0 Hz, 0.6H), 7.37 (d, J=1.6 Hz, 0.4H), 7.33 (dd, J1=8.0 Hz, J2=1.6 Hz, 0.4H), 7.20 (s, 0.6H), 7.09 (d, J=8.0 Hz, 0.6H), 7.05-6.98 (m, 1H), 6.96-6.87 (m, 1.4H), 6.82 (dd, J1=8.4 Hz, J2=2.4 Hz, 0.3H), 6.70 (td, J1=8.4 Hz, J2=2.4 Hz, 0.6H), 6.63 (td, J1=8.4 Hz, J2=2.4 Hz, 0.4H), 6.17-6.05 (m, 2H), 5.65 (dd, J1=8.0 Hz, J2=2.0 Hz, 0.4H), 5.35 (dd, J1=8.0 Hz, J2=3.2 Hz, 0.6H), 4.08-4.02 (m, 0.6H), 3.88-3.67 (m, 4.4H), 2.33-2.21 (m, 1H), 1.96-1.66 (m, 3H); LCMS (ESI) m/z: 411.2 [M+H]+.

Compound 431: $^1$H NMR (400 MHz, DMSO-d6) δ 8.74 (d, J=5.1 Hz, 1H), 8.68 (d, J=4.9 Hz, 1H), 7.52-7.43 (m, 1H), 7.39-7.25 (m, 2H), 7.15 (m, 0.5H), 7.06-7.08 (d, J=8.2 Hz, 0.5H), 7.02-6.95 (m, 0.5H), 6.97 (s, 0.4H), 6.09 (d, J=11.9 Hz, 2H), 5.62 (dd, J=2.4, 8.2 Hz, 0.4H), 5.22 (dd, J=4.4, 8.2 Hz, 0.5H), 4.04-3.92 (m, 1H), 3.83-3.66 (m, 1H), 2.45-2.32 (m, 1H), 2.13-1.69 (m, 3H); LCMS (ESI) m/z: 365.2 [M+H]+.

Compound 432: $^1$H NMR (400 MHz, CHLOROFORM-d) δ 8.73-8.61 (m, 1H), 8.43 (d, J=13.7 Hz, 1H), 8.24 (s, 0.5H), 8.07 (s, 0.5H), 7.43-7.32 (m, 1H), 7.28 (br s, 1H), 7.27-7.23 (m, 2H), 7.19-7.09 (m, 1H), 6.76 (s, 1H), 5.82-5.76 (m, 0.5H), 5.41 (dd, J=4.0, 7.6 Hz, 0.5H), 4.33-4.15 (m, 1H), 4.04-3.89 (m, 1H), 2.56-2.34 (m, 1H), 2.18-1.95 (m, 3H); LCMS (ESI) m/z: 360.2 [M+H]+.

Compound 433: $^1$H NMR (400 MHz, DMSO-d6) δ 9.41-9.27 (m, 1H), 8.34 (dd, J=1.5, 8.5 Hz, 0.6H), 8.18 (dd, J=1.5, 8.5 Hz, 0.4H), 7.99-7.83 (m, 1H), 7.62 (s, 1H), 7.39-7.19 (m, 4H), 7.16-7.06 (m, 1H), 5.54 (dd, J=2.4, 7.5 Hz, 0.4H), 5.26 (dd, J=4.2, 7.8 Hz, 0.6H), 4.11-4.03 (m, 0.5H), 3.93 (td, J=7.2, 10.9 Hz, 0.5H), 3.87-3.70 (m, 1H), 2.45-2.34 (m, 1H), 2.03-1.71 (m, 3H); LCMS (ESI) m/z: 321.2 [M+H]+.

Compound 434: $^1$H NMR (400 MHz, DMSO-d6) δ 7.54-7.45 (m, 2H), 7.36-7.29 (m, 1H), 7.28-7.20 (m, 3H), 7.19-7.06 (m, 3H), 6.13 (s, 2H), 4.66 (br s, 0.4H), 4.35 (br s, 0.6H), 3.72-3.53 (m, 2H), 3.15 (dd, J=3.0, 12.9 Hz, 0.6H), 2.88 (dd, J=4.3, 13.1 Hz, 0.4H), 2.76-2.58 (m, 1H), 2.05-1.61 (m, 4H); LCMS (ESI) m/z: 377.1 [M+H]+.

Compound 435: $^1$H NMR (400 MHz, DMSO-d6) δ 9.23-9.08 (m, 1H), 8.60-8.45 (m, 1H), 8.26 (d, J=8.4 Hz, 0.6H), 8.09 (d, J=8.2 Hz, 0.4H), 7.57 (s, 1H), 7.37-7.30 (m, 1H), 7.29-7.17 (m, 3H), 7.14-7.07 (m, 1H), 5.50 (dd, J=2.6, 7.5 Hz, 0.4H), 5.24 (dd, J=4.3, 7.8 Hz, 0.6H), 4.04 (td, J=6.4, 10.9 Hz, 1H), 3.95-3.74 (m, 1H), 2.47-2.32 (m, 1H), 1.99-1.75 (m, 3H); LCMS (ESI) m/z: 345.1 [M+H]+.

Compound 436: $^1$H NMR (400 MHz, DMSO-d6) δ 8.00-7.90 (m, 2H), 7.62-7.50 (m, 3H), 7.37-7.29 (m, 2H), 7.28-7.21 (m, 2H), 7.19-7.09 (m, 2H), 4.68 (br s, 0.4H), 4.37 (br s, 0.6H), 3.74-3.55 (m, 2H), 3.16 (dd, J=3.2, 12.9 Hz, 0.6H), 2.89 (dd, J=4.6, 12.8 Hz, 0.4H), 2.77-2.60 (m, 1H), 2.08-1.67 (m, 4H); LCMS (ESI) m/z: 333.1 [M+H]+.

Compound 437: $^1$H NMR (400 MHz, CDCl3) δ 8.10-7.98 (m, 1H), 7.32-7.26 (m, 0.5H), 7.20 (d, J=1.3 Hz, 0.5H), 7.16-7.09 (m, 1.4H), 7.07-6.95 (m, 1H), 6.89-6.78 (m, 1H), 6.72 (s, 0.5H), 6.38 (s, 0.3H), 6.00 (d, J=10.8 Hz, 2H), 5.96 (d, J=2.6 Hz, 0.2H), 5.68 (dd, J=4.2, 7.9 Hz, 0.5H), 4.27-4.15 (m, 1H), 4.07-3.99 (m, 0.4H), 3.90-3.77 (m, 3.3H), 2.42-2.29 (m, 1H), 2.21-2.12 (m, 1H), 2.03-1.90 (m, 2H); LCMS (ESI) m/z: 394.0 [M+H]+.

Compound 438: 1 HNMR (400 MHz, DMSO-d6) δ 7.88 (d, J=8.8 Hz, 0.6H), 7.82 (d, J=8.8 Hz, 0.4H), 7.77 (d, J=9.2 Hz, 0.6H), 7.58 (d, J=9.2 Hz, 0.4H), 7.50-7.46 (m, 0.6H), 7.41-7.37 (m, 0.4H), 7.34-7.27 (m, 2.5H), 7.26-7.08 (m, 3.5H), 5.73 (d, J=8.0 Hz, 0.4H), 5.30 (dd, J1=8.0 Hz, J2=4.8 Hz, 0.6H), 4.33-4.27 (m, 0.6H), 4.15-4.09 (m, 0.6H), 3.99-3.90 (m, 0.4H), 3.87-3.79 (m, 0.4H), 2.40-2.33 (m, 0.6H), 2.03-1.77 (m, 3.4H); LCMS (ESI) m/z: 393.0 [M+H]+.

Compound 439: 1 HNMR (400 MHz, DMSO-d6) δ=8.62-8.18 (m, 1H), 7.54-7.37 (m, 2H), 7.25-7.17 (m, 0.7H), 7.13-6.97 (m, 1.3H), 6.17-6.07 (m, 2H), 5.74-5.66 (m, 0.3H), 5.37 (dd, J=4.8, 8.0 Hz, 0.6H), 4.03-3.86 (m, 1.3H), 3.81-3.68 (m, 0.6H), 2.43-2.26 (m, 1H), 2.20-1.89 (m, 5.2H), 1.79 (s, 0.8H); LCMS (ESI) m/z: 368.0 [M+H]+.

Compound 440: $^1$H NMR (400 MHz, CDCl3) δ9.16-9.09 (m, 1H), 8.68-8.58 (m, 1H), 7.33-7.26 (m, 1H), 7.23-7.10 (m, 2H), 6.92-6.80 (m, 1H), 6.76-6.66 (m, 1H), 6.06-5.94 (m, 2H), 5.84 (br d, J=8.6 Hz, 0.3H), 5.30 (dd, J=3.3, 8.4 Hz, 0.6H), 4.29-4.12 (m, 1H), 3.96-3.86 (m, 1H), 2.53-2.37 (m, 1H), 2.22-1.93 (m, 3H); LCMS (ESI) m/z: 365.2 [M+H]+.

Compound 441: $^1$H NMR (400 MHz, DMSO-d6) δ 9.71 (s, 0.5H), 9.56 (s, 0.5H), 8.69-8.58 (m, 1H), 8.18 (dd, J=1.4, 9.4 Hz, 1H), 8.08-7.94 (m, 1H), 7.54 (s, 1H), 7.37-7.30 (m, 1H), 7.29-7.21 (m, 3H), 7.17-7.08 (m, 1H), 5.59 (br d, J=6.8 Hz, 0.4H), 5.26 (dd, J=4.2, 7.7 Hz, 0.6H), 4.11-4.03 (m, 1H), 3.98-3.71 (m, 1H), 2.46-2.31 (m, 1H), 1.97-1.75 (m, 3H); LCMS (ESI) m/z: 360.0 [M+H]+.

Compound 442: $^1$H NMR (400 MHz, CDCl3-d) δ 7.35-7.29 (m, 1H), 7.25-7.19 (m, 1H), 6.93-6.86 (m, 1H), 6.80 (s, 1H), 6.74 (s, 1H), 6.07-5.96 (m, 2H), 5.83 (s, 0.4H), 5.45 (br d, J=6.4 Hz, 0.6H), 4.21-4.00 (m, 1H), 3.91-3.77 (m, 1H), 2.43-2.33 (m, 3H), 2.32-2.16 (m, 3H), 2.14-1.95 (m, 1H); LCMS (ESI) m/z: 368.1 [M+H]+.

Compound 443: $^1$H NMR (400 MHz, DMSO-d6) δ 7.83 (dd, J=1.8, 12.1 Hz, 0.6H), 7.75-7.64 (m, 1H), 7.57 (br d, J=9.0 Hz, 0.4H), 7.37-7.20 (m, 5H), 7.16-7.05 (m, 1H), 6.95 (s, 1H), 5.57 (br d, J=6.2 Hz, 0.4H), 5.24 (dd, J=4.0, 7.9 Hz, 0.6H), 4.17 (qd, J=7.0, 14.1 Hz, 2H), 4.07-3.69 (m, 2H), 2.45-2.30 (m, 1H), 1.97-1.73 (m, 3H), 1.42-1.31 (m, 3H); LCMS (ESI) m/z: 381.0 [M+H]+.

Compound 444: $^1$H NMR (400 MHz, CDCl3-d) δ 7.58 (d, J=8.2 Hz, 1H), 7.44-7.39 (m, 1H), 7.37-7.31 (m, 1H), 7.30-7.27 (m, 1H), 7.27-7.21 (m, 2H), 7.20-7.10 (m, 1.5H), 6.92 (s, 0.5H), 6.58 (s, 1H), 5.81 (br d, J=6.6 Hz, 0.5H), 5.45-5.37 (m, 0.5H), 4.33-4.11 (m, 1H), 4.04-3.87 (m, 1H), 3.46 (d, J=19.2 Hz, 3H), 2.56-2.34 (m, 1H), 2.14-1.95 (m, 3H); LCMS (ESI) m/z: 390.2 [M+H]+.

Compound 445: 1H NMR (300 MHz, Chloroform-d) δ 9.23 (s, 1H), 7.76 (d, J=8.8 Hz, 2H), 7.37-7.24 (m, 2H), 7.03-6.85 (m, 2H), 6.79 (s, 1H), 6.70 (d, J=9 Hz, 2H), 4.19 (dd, J=2 Hz, 1H), 3.86 (s, 3H), 3.81 (dd, J=9 Hz, 1H), 3.35-3.23 (m, 1H), 2.43-2.33 (m, 2H), 2.19-1.98 (m, 2H); LCMS (ESI) m/z: 364.0 [M+H]+.

Compound 446: $^1$H NMR (400 MHz, CDCl3) δ 7.29 (dd, J=8.4, 2.1 Hz, 0.7H), 7.22 (dd, J=8.0, 2.0 Hz, 0.3H), 7.20 (d, J=1.6 Hz, 0.7H), 7.13 (d, J=1.2 Hz, 0.3H), 6.97 (d, J=1.2 Hz, 0.7H), 6.92-6.85 (m, 1.3H), 6.78 (d, J=1.2 Hz, 0.7H), 6.72 (s, 0.7H), 6.65 (d, J=1.2 Hz, 0.3H), 6.54 (s, 0.3H), 6.04 (s, 1.7H), 6.03 (s, 0.3H), 5.77 (dd, J=8.0, 3.6 Hz, 0.3H), 5.31 (dd, J=7.6, 5.2 Hz, 0.7H), 2.62-2.51 (m, 0.8H), 2.36-2.25 (m, 2H), 2.12-2.00 (m, 1.2H); LCMS (ESI) m/z: 367.0 [M+H]+.

Compound 447: $^1$H NMR (400 MHz, CDCl3) δ 8.44-8.33 (m, 1H), 7.84-7.71 (m, 1H), 7.28 (m, 0.5H), 7.21-7.15 (m, 0.4H), 7.09 (d, J=1.3 Hz, 1H), 7.04-6.92 (m, 1H), 6.90-6.79 (m, 1H), 6.73 (s, 0.5H), 6.53 (s, 0.4H), 6.14-6.07 (m, 0.3H), 6.00 (d, J=11.9 Hz, 2H), 5.72 (dd, J=4.4, 7.7 Hz, 0.56H), 4.32-4.19 (m, 1H), 4.12-4.04 (m, 0.4H), 3.90-3.82 (m, 0.4H), 2.55-2.39 (m, 1H), 2.18 (m, 0.6H), 2.08-1.92 (m, 2.6H); LCMS (ESI) m/z: 441.9 [M+H]+.

Compound 448: $^1$H NMR (400 MHz, CDCl3) δ 8.69 (dd, J=1.5, 4.9 Hz, 0.6H), 8.61 (br d, J=3.5 Hz, 0.4H), 7.95-7.88 (m, 0.85H), 7.30-7.25 (m, 1H), 7.22-7.17 (m, 1H), 7.11 (s, 0.23H), 6.90-6.78 (m, 1H), 6.74-6.62 (m, 1H), 6.17 (br d, J=7.5 Hz, 0.3H), 6.05-5.96 (m, 2H), 5.64-5.57 (m, 0.7H), 4.31-4.22 (m, 1.4H), 4.09-4.03 (m, 0.3H), 3.94-3.85 (m, 0.3H), 2.63-2.46 (m, 1H), 2.32-2.20 (m, 1H), 2.12-1.96 (m, 2H); LCMS (ESI) m/z: 389.0 [M+H]+.

Compound 449: $^1$H NMR (400 MHz, MeOD) δ 8.01 (s, 0.4H) 7.89 (d, J=8.60 Hz, 0.4H) 7.79 (s, 0.4H) 7.58 (d, J=8.38 Hz, 0.9H) 7.20-7.44 (m, 2.9H) 6.93-7.11 (m, 2.4H) 5.59 (dd, J=7.39, 4.52 Hz, 0.5H) 5.39 (dd, J=7.83, 4.30 Hz, 0.5H) 4.20-4.29 (m, 0.5H) 4.06-4.15 (m, 0.5H) 3.98-4.10 (m, 1H) 2.40-2.58 (m, 1H) 1.90-2.13 (m, 3H); LCMS (ESI) m/z: 371.0 [M+H]+.

Compound 450: $^1$H NMR (400 MHz, DMSO-d6) δ 9.07-8.99 (m, 2H), 8.68 (d, J=1.8 Hz, 1H), 8.53-8.39 (m, 1H), 8.31-8.17 (m, 1H), 7.69 (s, 1H), 7.39-7.20 (m, 4H), 7.12 (br d, J=7.9 Hz, 1H), 5.58 (br d, J=6.6 Hz, 0.4H), 5.27 (dd, J=3.9, 7.9 Hz, 0.6H), 4.13-4.03 (m, 1H), 4.00-3.73 (m, 1H), 2.47-2.34 (m, 1H), 2.01-1.74 (m, 3H); LCMS (ESI) m/z: 371.0 [M+H]+.

Compound 451: $^1$H NMR (400 MHz, DMSO-d6) δ 8.10 (d, J=2.0 Hz, 0.6H), 7.97-7.89 (m, 1H), 7.77 (dd, J=2.5, 9.6 Hz, 0.4H), 7.36-7.29 (m, 1H), 7.28-7.20 (m, 3H), 7.18-7.06 (m, 1.7H), 6.80 (s, 0.3H), 6.52-6.39 (m, 1H), 5.57 (br d, J=6.2 Hz, 0.4H), 5.23 (dd, J=4.1, 7.8 Hz, 0.6H), 4.05-3.95 (m, 1H), 3.92-3.69 (m, 1H), 2.44-2.31 (m, 1H), 1.97-1.72 (m, 3H); LCMS (ESI) m/z: 336.1 [M+H]+.

Compound 452: $^1$H NMR (400 MHz, CDCl3) δ 7.30 (dd, J=1.5, 8.2 Hz, 1H), 7.22-7.17 (m, 1H), 7.11 (s, 0.3H), 7.04 (t, J=8.5 Hz, 0.6H), 6.91-6.80 (m, 1.4H), 6.75 (s, 0.6H), 6.64-6.48 (m, 2.3H), 6.01 (d, J=11.7 Hz, 2H), 5.90 (m, 0.4H), 5.46 (m, 0.6H), 4.23-4.05 (m, 1H), 3.97-3.84 (m, 1H), 3.72 (d, J=19.8 Hz, 3H), 2.40-2.28 (m, 1H), 2.08-1.87 (m, 3H); LCMS (ESI) m/z: 410.9 [M+H]+.

Compound 453: $^1$H NMR (400 MHz, CDCl3) δ 7.27 (dd, J=1.5, 8.2 Hz, 0.6H), 7.18 (d, J=1.3 Hz, 0.6H), 7.16-7.07 (m, 1H), 7.04-6.93 (m, 1H), 6.88-6.79 (m, 1H), 6.72-6.60 (m, 2H), 6.52-6.42 (m, 1H), 6.06 (s, 0.3H), 6.02-5.98 (m, 2H), 5.73 (t, J=7.2 Hz, 0.3H), 5.59 (t, J=7.7 Hz, 0.6H), 4.27-4.19 (m, 0.7H), 4.06-3.92 (m, 1H), 3.85 (s, 2H), 3.79-3.71 (m, 1.6H), 2.41-2.27 (m, 1H), 2.16-1.89 (m, 3H); LCMS (ESI) m/z: 411.2 [M+H]+.

Compound 454: $^1$H NMR (400 MHz, MeOD) δ8.09 (d, J=8.38 Hz, 0.5H) 7.90 (s, 0.5H) 7.78 (d, J=8.16 Hz, 0.5H) 7.67-7.69 (m, 0.5H) 7.50-7.59 (m, 1.6H) 7.29-7.44 (m, 2.5H) 7.21-7.29 (m, 0.5H) 7.02-7.12 (m, 2H) 6.96 (s, 0.5H) 6.52 (d, J=1.98 Hz, 0.5H) 6.45 (d, J=1.76 Hz, 0.5H) 5.64 (dd, J=7.61, 4.74 Hz, 0.5H) 5.39-5.45 (m, 0.5H) 4.23-4.32 (m, 0.5H) 4.09-4.19 (m, 0.5H) 3.91-4.04 (m, 2.5H) 3.87 (s, 1.5H) 2.40-2.62 (m, 1H) 1.89-2.15 (m, 3H); LCMS (ESI) m/z: 373.0 [M+H]+.

Compound 455: 1HNMR (400 MHz, CDCl3) δ 9.31 (s, 0.8H), 8.19 (s, 0.2H), 7.55 (d, J=7.6 Hz, 0.8H), 7.51 (d, J=8.4 Hz, 0.2H), 7.36-7.25 (m, 4H), 7.09 (t, J=7.6 Hz, 1H), 6.92 (d, J=8.4 Hz, 0.8H), 6.88 (d, J=8.0 Hz, 0.2H), 6.06 (s, 1.6H), 6.04 (s, 0.4H), 6.21 (br d, J=8.4 Hz, 0.2H), 5.00 (br d, J=6.0 Hz, 0.8H), 4.12-3.85 (m, 2H), 2.66-2.62 (m, 1H), 2.32-2.20 (m, 1H), 2.14-2.05 (m, 1H), 2.01-1.92 (m, 1H); LCMS (ESI) m/z: 406.2 [M+H]+.

Compound 456: $^1$H NMR (400 MHz, CDCl3) δ 8.31 (m, 0.5H), 8.01 (m, 0.5H), 7.95 (s, 0.4H), 7.76 (s, 0.4H), 7.60 (m, 0.52H), 7.49 (m, 0.4H), 7.35-7.29 (m, 1H), 7.27 (m, 1.2H), 7.23 (m, 0.2H), 7.14-7.08 (m, 1H), 7.05-6.97 (m, 1.32H), 5.80-5.69 (m, 0.5H), 5.42 (dd, J=4.2, 7.5 Hz, 0.5H), 4.32 (m, 0.6H), 4.23-4.13 (m, 0.6H), 4.05-3.94 (m, 1H), 2.51-2.36 (m, 1H), 2.16-1.91 (m, 3H); LCMS (ESI) m/z: 318.2 [M+H]+.

Compound 457: $^1$H NMR (400 MHz, CDCl3) δ 8.34-8.23 (m, 1H), 7.36 (m, 0.5H), 7.31-7.27 (m, 1H), 7.22-7.15 (m, 2H), 7.12-7.07 (m, 1H), 6.90-6.81 (m, 1H), 6.74 (s, 0.5H), 6.56 (s, 0.3H), 6.08 (m, 0.4H), 6.04-5.96 (m, 2H), 5.61 (m, 0.0.6H), 4.24 (t, J=6.6 Hz, 1.4H), 4.05 (m, 0.3H), 3.93-3.83 (m, 0.3H), 2.54-2.36 (m, 1H), 2.29-2.18 (m, 1H), 2.11-1.96 (m, 3H); LCMS (ESI) m/z: 381.9 [M+H]+.

Compound 458: $^1$H NMR (400 MHz, CDCl3) δ 9.17-9.04 (m, 2H), 7.80 (s, 0.6H), 7.74-7.64 (m, 1.3H), 7.46 (d, J=8.4 Hz, 0.6H), 7.38-7.30 (m, 1H), 6.99-6.90 (m, 1H), 5.97 (m, 0.3H), 5.32 (m, 0.6H), 4.32-4.17 (m, 1.3H), 4.07-3.99 (m, 3H), 3.98-3.90 (m, 0.4H), 2.60-2.52 (m, 3H), 2.53-2.43 (m, 1H), 2.14-2.01 (m, 2H), 1.99-1.82 (m, 1H); LCMS (ESI) m/z: 389.2 [M+H]+.

Compound 459: $^1$H NMR (400 MHz, CDCl3) δ 8.13-8.03 (m, 1H), 7.34-7.19 (m, 2H), 7.08-6.93 (m, 1H), 6.91-6.81 (m, 1H), 6.77-6.69 (m, 1H), 6.09 (m, 0.3H), 6.06-5.98 (m, 2H), 5.49 (dd, J=5.1, 8.2 Hz, 0.7H), 4.28-4.14 (m, 1H), 3.99-3.85 (m, 1H), 2.56-2.39 (m, 1H), 2.11-1.83 (m, 3H); LCMS (ESI) m/z: 460.1 [M+H]+.

Compound 460: $^1$H NMR (400 MHz, CDCl3) δ 8.43-8.38 (m, 1H), 8.35-8.25 (m, 1H), 7.31 (dd, J=1.5, 8.2 Hz, 1H), 7.23-7.17 (m, 1H), 7.13-6.96 (m, 1H), 6.91-6.81 (m, 1H), 6.78-6.65 (m, 1H), 6.10 (m, 0.3H), 6.04-5.94 (m, 2H), 5.52 (m, 0.6H), 4.28-4.11 (m, 1H), 3.99-3.85 (m, 1H), 2.46 (m, 1H), 2.10-1.89 (m, 3H); LCMS (ESI) m/z: 381.9 [M+H]+.

Compound 461: ¹H NMR (400 MHz, CDCl3-d) δ 7.74-7.64 (m, 1H), 7.57-7.45 (m, 1H), 7.36-7.28 (m, 3H), 7.25-7.20 (m, 1H), 7.13 (d, J=1.6 Hz, 0.3H), 6.90 (d, J=8.1 Hz, 0.7H), 6.86-6.75 (m, 1H), 6.14 (dd, J=1.9, 7.5 Hz, 0.4H), 6.08-5.98 (m, 2H), 5.57 (dd, J=3.2, 7.9 Hz, 0.6H), 4.42-4.31 (m, 0.7H), 4.26-4.05 (m, 1H), 3.87 (td, J=8.4, 12.1 Hz, 0.3H), 2.54-2.26 (m, 3H), 2.22-2.03 (m, 1H); LCMS (ESI) m/z: 404.4 [M+H]+.

Compound 462: ¹H NMR (400 MHz, CDCl3) 6.05-8.96 (m, 1H), 7.74 (s, 1H), 7.67-7.58 (m, 1H), 7.46 (br d, J=8.6 Hz, 1H), 7.42-7.36 (m, 1H), 7.33-7.28 (m, 1H), 6.91-6.80 (m, 1H), 6.03 (m, 0.3H), 5.49 (m, 0.6H), 4.29-4.11 (m, 1H), 4.03-3.91 (m, 4H), 2.54-2.48 (m, 3H), 2.47-2.36 (m, 1H), 2.35-2.18 (m, 2H), 2.11-1.99 (m, 1H); LCMS (ESI) m/z: 389.4 [M+H]+.

Compound 463: ¹H NMR (400 MHz, CDCl3-d) δ 7.37-7.29 (m, 2H), 7.27-7.18 (m, 2H), 7.11 (d, J=7.7 Hz, 1H), 5.74 (br d, J=6.4 Hz, 0.5H), 5.46 (s, 0.5H), 5.37 (dd, J=3.5, 8.1 Hz, 0.5H), 5.09 (s, 0.5H), 4.20-4.03 (m, 1H), 3.95-3.86 (m, 1H), 3.86-3.80 (m, 2H), 3.74 (t, J=4.7 Hz, 2H), 3.40-3.33 (m, 2H), 3.24-3.10 (m, 2H), 2.48-2.28 (m, 1H), 2.11-1.88 (m, 3H); LCMS (ESI) m/z: 328.1 [M+H]+.

Compound 464: ¹H NMR (400 MHz, CDCl3-d) δ 8.53 (s, 1H), 7.66 (dd, J=0.8, 8.3 Hz, 1H), 7.42 (s, 1H), 7.40-7.34 (m, 3H), 7.27-7.23 (m, 2H), 7.02 (dd, J=1.3, 8.2 Hz, 1H), 5.03 (d, J=16.3 Hz, 1H), 4.96 (dd, J=6.1, 8.9 Hz, 1H), 4.54 (t, J=8.8 Hz, 1H), 4.17 (dd, J=6.0, 8.8 Hz, 1H), 4.13 (s, 0.5H), 4.09 (s, 0.5H), 4.04 (s, 3H), 2.58 (s, 3H); LCMS (ESI) m/z: 389.2 [M+H]+.

Example 137. Stearoyl-CoA Desaturase (SCD) is the Target of the Compounds of the Invention A. Materials and Methods: Compound Profiling Methods Strains expressing SCD1 or SCD5 as the sole desaturase, the human SCD1 and SCD5 genes were used to evaluate inhibition of SCD1/SCD5 using reduced growth as a surrogate for SCD inhibition. These yeast strains express human SCD1 or SCD5 from a plasmid harbored in a strain in which the yeast OLE1 gene is deleted.

All compound profiling experiments were performed using the same basic protocol. Yeast were cultured using standard techniques in complete synthetic media lacking uracil and containing yeast nitrogen base supplemented with 2% (w/v) glucose (SD-Ura) Starter cultures were inoculated in 3 mL SD-Ura media containing 0.01% tween and 0.2 mM palmitoleic and oleic acid. Cultures were incubated overnight in a 30° C. shaker incubator (225 rpm). Saturated morning cultures were centrifuged, washed in SD-Ura media lacking TWEEN-20 and fatty acids, and then diluted 1:20 in fresh SD-Ura media also lacking TWEEN-20 and fatty acids. Cells were grown for 6 h to an $OD_{600}$ (optical density) of 0.4-0.8 at 30° C. with shaking.

Compound stocks (10 mM in 100% DMSO) were arrayed into 384-round well, v-bottom polypropylene plates and diluted according to indicated dilution factors. Compound administration was performed in two separate steps. First, 15 μL of SD-Ura was dispensed into clear 384-well assay plates using a MULTIDROP™ Combi reagent dispenser. The diluted compound stock plates were then applied to the assay plates using an automated workstation (Perkin Elmer JANUS™) outfitted with a 384-pin tool containing slotted pins that deliver 100 nL of compound. The cultures described above were centrifuged and washed with media lacking TWEEN-20 or oleic and palmitoleic acids. Cultures were then resuspended at a 2-fold concentrated OD600 of 0.02 (final $OD_{600}$ of 0.0.01) in SD-Ura. 15 μL of diluted culture was then dispensed into the pinned assay plate to achieve 30 μL of the $1 \times OD_{600}$ culture (0.01) and a top drug concentration of 33.3 μM.

After yeast delivery, assay plates were incubated under humidified conditions at 30° C. for 40 h. Yeast growth was monitored by reading the $OD_{600}$ of each well using a microplate reader (Perkin Elmer EnVision™). Data were analyzed as follows. Raw data were processed by background subtracting and converting values to a percent of the nontreated condition for that strain [(EXP-0.035)/(DMSO-0.035)×100%].

B. Results

Using the methods described above, the inhibition of SCD1 and SCD5 was tested for compounds of the invention. The results are shown in Table 2.

TABLE 2

Inhibition of SCD1 and SCD5 by Compounds of the Invention

| Compound No. | SCD1 IC50 (μM) | SCD5 IC50 (μM) |
|---|---|---|
| 1 | >45 | >45 |
| 2 | 32.83 | 38.64 |
| 3 | >45 | 7.15 |
| 4 | 0.09 | 0.07 |
| 5 | >45 | 15 |
| 6 | >45 | 0.03 |
| 7 | 0.47 | 0.09 |
| 8 | 0.7 | 0.55 |
| 9 | >45 | 15.67 |
| 10 | >45 | >45 |
| 11 | 0.05 | 0.03 |
| 12 | >45 | >45 |
| 13 | >45 | 21.49 |
| 14 | >45 | 0.04 |
| 15 | >45 | >45 |
| 16 | >45 | >45 |
| 17 | >45 | 4.87 |
| 18 | >45 | 0.08 |
| 19 | 0.36 | 0.49 |
| 20 | >45 | 0.2 |
| 21 | >45 | >45 |
| 22 | >45 | 0.02 |
| 23 | >45 | 0.08 |
| 24 | >45 | >45 |
| 25 | >45 | >45 |
| 26 | >45 | 31 |
| 27 | >45 | >45 |
| 28 | >45 | 0.09 |
| 29 | >45 | >45 |
| 30 | 0.01 | 0.03 |
| 31 | >45 | >45 |
| 32 | >45 | >45 |
| 33 | >45 | >45 |
| 34 | >45 | 6.42 |
| 35 | 3.24 | >45 |
| 36 | >45 | 0.01 |
| 37 | 0.26 | 0.58 |
| 38 | >45 | 0.65 |
| 39 | >45 | >45 |
| 40 | >45 | >45 |
| 41 | >45 | >45 |
| 42 | >45 | >45 |
| 43 | >45 | >45 |
| 44 | >45 | >45 |
| | >45 | >45 |
| 45 | 23.12 | >45 |
| 46 | 22.63 | >45 |
| 47 | >45 | >45 |
| 48 | >45 | >45 |
| 49 | >45 | 2.65 |
| 50 | 25.48 | >45 |
| 51 | >45 | >45 |
| 52 | >45 | >45 |
| 53 | 0.07 | >45 |
| 54 | 2.04 | >45 |
| 55 | 0.59 | >45 |

TABLE 2-continued

Inhibition of SCD1 and SCD5 by Compounds of the Invention

| Compound No. | SCD1 IC50 (μM) | SCD5 IC50 (μM) |
|---|---|---|
| 56 | 2.41 | 2.69 |
| 57 | >45 | >45 |
| 58 | 0.02 | 0.91 |
| 59 | >45 | >45 |
| 60 | 0.03 | 0.77 |
| 61 | 25.46 | >45 |
| 62 | >45 | 33.15 |
| 63 | >45 | >45 |
| 64 | >45 | >45 |
| 65 | >45 | >45 |
| 66 | 1.83 | >45 |
| 67 | 0.99 | 7.89 |
| 68 | >45 | >45 |
| 69 | 0.19 | 7.9 |
| 70 | >45 | >45 |
| 71 | >45 | >45 |
| 72 | 0.084 | >45 |
| 73 | >45 | >45 |
| 74 | >45 | >45 |
| 75 | >45 | >45 |
| 76 | >45 | >45 |
| 77 | >45 | >45 |
| 78 | >45 | >45 |
| 79 | >45 | >45 |
| 80 | >45 | >45 |
| 81 | 0.232 | 1.6 |
| 82 | >45 | >45 |
| 83 | 0.066 | 0.276 |
| 84 | >45 | >45 |
| 85 | 0.011 | 0.327 |
| 86 | 0.188 | 0.688 |
| 87 | 15 | >45 |
| 88 | >45 | >45 |
| 89 | 12 | >45 |
| 90 | 1.1 | 9.5 |
| 91 | 0.439 | 0.058 |
| 92 | >45 | >45 |
| 93 | >45 | >45 |
| 94 | >45 | >45 |
| 95 | >45 | >45 |
| 96 | >45 | >45 |
| 97 | >45 | >45 |
| 98 | >45 | >45 |
| 99 | >45 | >45 |
| 100 | 3.1 | 20 |
| 101 | 0.220 | 1.2 |
| 102 | 0.036 | 0.073 |
| 103 | >45 | >45 |
| 104 | 0.066 | 1 |
| 105 | 3.9 | 9.1 |
| 106 | 0.048 | 1.9 |
| 107 | >45 | >45 |
| 108 | 1.2 | 1.8 |
| 109 | >45 | >45 |
| 110 | 8.9 | 11.0 |
| 111 | 9.4 | 16.0 |
| 112 | >45 | >45 |
| 113 | >45 | >45 |
| 114 | >45 | 0.71 |
| 115 | 0.34 | 6.4 |
| 116 | >45 | >45 |
| 117 | 0.026 | 0.48 |
| 118 | 0.15 | 2.7 |
| 119 | 0.11 | 2 |
| 120 | 0.94 | 19 |
| 121 | 0.21 | 19 |
| 122 | 4.7 | 21 |
| 123 | >45 | >45 |
| 124 | 5.7 | 7 |
| 125 | >45 | 11 |
| 126 | 6.97 | >45 |
| 127 | 4.62 | >45 |
| 128 | 0.98 | >45 |
| 129 | >45 | >45 |
| 130 | >45 | >45 |
| 131 | >45 | >45 |
| 132 | >45 | >45 |
| 133 | >45 | >45 |
| 134 | 5.32 | 4.96 |
| 135 | >45 | >45 |
| 136 | >45 | >45 |
| 137 | >45 | >45 |
| 138 | >45 | >45 |
| 139 | 0.737 | 6.968 |
| 140 | 5.116 | 12.522 |
| 141 | >45 | >45 |
| 142 | >45 | >45 |
| 143 | >45 | >45 |
| 144 | >45 | >45 |
| 145 | >45 | >45 |
| 146 | 11 | >45 |
| 147 | >45 | 7.4 |
| 148 | 4 | 0.35 |
| 149 | >45 | 6.4 |
| 150 |  |  |
| 151 | >45 | >45 |
| 152 | >45 | >45 |
| 153 | 9 | 7 |
| 154 | 1.6 | 5.2 |
| 155 | >45 | >45 |
| 156 | 0.01 | 0.71 |
| 157 | >45 | >45 |
| 158 | 0.6 | 1.8 |
| 159 | 0.058 | 0.386 |
| 160 | >45 | 2.3 |
| 161 | 25 | 1.4 |
| 162 | >45 | >45 |
| 163 | >45 | >45 |
| 164 | 11 | 10 |
| 165 | >45 | >45 |
| 166 | >45 | 3.9 |
| 167 | >45 | >45 |
| 168 | >45 | >45 |
| 169 | >45 | >45 |
| 170 | 0.131 | 0.48 |
| 171 | 19 | 10 |
| 172 | >45 | >45 |
| 173 | >45 | >45 |
| 174 | 8.2 | >45 |
| 175 | >45 | >45 |
| 176 | >45 | >45 |
| 177 | >45 | >45 |
| 178 | 0.01 | 0.05 |
| 179 | >45 | >45 |
| 180 | >45 | >45 |
| 181 | 5.8 | >45 |
| 182 | >45 | 0.42 |
| 183 | >45 | >45 |
| 184 | 29 | >45 |
| 185 | 0.012 | 0.052 |
| 186 | 2 | 7.6 |
| 187 | 15 | >45 |
| 188 | 0.074 | 0.16 |
| 189 | 0.065 | 0.345 |
| 190 | >45 | >45 |
| 191 | >45 | >45 |
| 192 | >45 | >45 |
| 193 | 0.01 | 0.047 |
| 194 | 25 | 0.696 |
| 195 | >45 | >45 |
| 196 | >45 | >45 |
| 197 | >45 | 14 |
| 198 | >45 | 2.3 |
| 199 | >45 | 6 |
| 200 | 6 | 6.3 |
| 201 | >45 | 34 |
| 202 | >45 | >45 |
| 203 | 0.025 | 2.5 |
| 204 | 30 | 3.5 |
|  | 33.87 | 2.28 |
| 205 | 0.23 | 0.63 |
| 206 | 0.28 | 1.4 |

TABLE 2-continued

Inhibition of SCD1 and SCD5 by Compounds of the Invention

| Compound No. | SCD1 IC50 (μM) | SCD5 IC50 (μM) |
|---|---|---|
| 207 | 2.56 | 1.14 |
| 208 | >45 | >45 |
| 209 | >45 | >45 |
| 210 | >45 | >45 |
| 211 | 0.12 | 0.81 |
| 212 | 4.52 | 1.62 |
| 213 | 0.49 | >45 |
| 214 | >45 | >45 |
| 215 | 1.86 | 1.36 |
| 216 | >45 | 1.13 |
| 217 | 1.57 | 0.32 |
| 218 | >45 | >45 |
| 219 | >45 | >45 |
| 220 | >45 | 2.92 |
| 221 | >45 | >45 |
| 222 | >45 | >45 |
| 223 | >45 | 3.26 |
| 224 | >45 | 0.95 |
| 225 | >45 | 6.41 |
| 226 | 11.98 | 0.95 |
| 227 | >45 | 8.87 |
| 228 | 37.08 | 18.6 |
| 229 | 0.66 | 7.17 |
| 230 | >45 | >45 |
| 231 | >45 | 5.89 |
| 232 | >45 | 1.63 |
| 233 | 2.61 | 3.12 |
| 234 | 15.48 | 5.08 |
| 235 | >45 | 5.16 |
| 236 | 3.33 | 1.55 |
| 237 | >45 | >45 |
| 238 | >45 | >45 |
| 239 | 0.866 | 1.92 |
| 240 | >45 | >45 |
| 241 | 3.38 | 0.629 |
| 242 | 0.264 | 0.305 |
| 243 | 1.6 | 1.5 |
| 244 | >45 | >45 |
| 245 | >45 | >45 |
| 246 | >45 | 22 |
| 247 | >45 | >45 |
| 248 | 33 | 27 |
| 249 | >45 | 26 |
| 250 | >45 | >45 |
| 251 | >45 | 16 |
| 252 | >45 | 7.5 |
| 253 | >45 | 13 |
| 254 | >45 | 35 |
| 255 | 23 | 1.8 |
| 256 | >45 | 17 |
| 257 | 0.321 | 3.14 |
| 258 | 2.5 | 1 |
| 259 | >45 | 5 |
| 260 | >45 | >45 |
| 261 | >45 | >45 |
| 262 | >45 | 41.28 |
| 263 | >45 | >45 |
| 264 | >45 | 30.69 |
| 265 | >45 | 2.48 |
| 266 | 0.73 | 13.27 |
| 267 | >45 | 20.47 |
| 268 | 36.01 | 29.49 |
| 269 | >45 | >45 |
| 270 | >45 | 4.>45 |
| 271 | >45 | 4.71 |
| 272 | >45 | >45 |
| 273 | >45 | 39.16 |
| 274 | >45 | 34.83 |
| 275 | >45 | 1.13 |
| 276 | >45 | >45 |
| 277 | >45 | 16.06 |
|  | >45 | 35 |
| 278 | >45 | >45 |
| 279 | >45 | >45 |
| 280 | >45 | 11.2 |
| 281 | >45 | >45 |
| 282 | >45 | >45 |
| 283 | >45 | >45 |
| 284 | >45 | >45 |
| 285 | >45 | >45 |
| 286 | >45 | >45 |
| 287 | >45 | >45 |
| 288 | >45 | 4.16 |
| 289 | >45 | 11.02 |
| 290 | >45 | 2.94 |
| 291 | >45 | 4.75 |
| 292 | >45 | 1.82 |
| 293 | >45 | >45 |
| 294 | 0.21 | >45 |
| 295 | >45 | 29.36 |
| 296 | >45 | >45 |
| 297 | 18.96 | 5.58 |
| 298 | 6.22 | 2.92 |
| 299 | >45 | 8.68 |
| 300 | >45 | 18.58 |
| 301 | >45 | 6.58 |
| 302 | >45 | 2.56 |
| 303 | >45 | >45 |
| 304 | 0.38 | 0.09 |
| 305 | 4.8 | 0.09 |
| 306 | 3.27 | 0.46 |
| 307 | >45 | 0.15 |
| 308 | >45 | 4.74 |
| 309 | >45 | 1.01 |
| 310 | >45 | 1.05 |
| 311 | >45 | >45 |
| 312 | >45 | >45 |
| 313 | 0.41 | 1.54 |
| 314 | >45 | 1.63 |
| 315 | 3.84 | 1.06 |
| 316 | >45 | 0.7 |
| 317 | >45 | >45 |
| 318 | >45 | 14.12 |
| 319 | >45 | >45 |
| 320 | >45 | >45 |
| 321 | >45 | 16 |
| 322 | >45 | >45 |
| 323 | >45 | 17.53 |
| 324 | >45 | 3.8 |
| 325 | 0.16 | 5.5 |
| 326 | >45 | 5.7 |
| 327 | 33.54 | 6.15 |
| 328 | >45 | >45 |
| 329 | >45 | >45 |
| 330 | >45 | 2.6 |
| 331 | >45 | 6.18 |
| 332 | >45 | >45 |
| 333 | >45 | 13.66 |
| 334 | >45 | >45 |
| 335 | >45 | >45 |
| 336 | >45 | >45 |
| 337 | >45 | >45 |
| 338 | >45 | 2.79 |
| 339 | >45 | 0.94 |
| 340 | >45 | >45 |
| 341 | >45 | 34 |
| 342 | >45 | >45 |
| 343 | >45 | 28.06 |
| 344 | >45 | >45 |
| 345 | >45 | >45 |
| 346 | >45 | 7.35 |
| 347 | 4.19 | 5.28 |
| 348 | 7.61 | >45 |
| 349 | >45 | >45 |
| 350 | >45 | 21 |
| 351 | >45 | 21 |
| 352 | >45 | 9 |
| 353 | >45 | >45 |
| 354 | >45 | >45 |
| 355 | >45 | 43.33 |
| 356 | >45 | >45 |
| 357 | >45 | >45 |

TABLE 2-continued

Inhibition of SCD1 and SCD5 by Compounds of the Invention

| Compound No. | SCD1 IC50 (µM) | SCD5 IC50 (µM) |
|---|---|---|
| 358 | >45 | 30.73 |
| 359 | >45 | >45 |
| 360 | >45 | 33.51 |
| 361 | >45 | >45 |
| 362 | >45 | >45 |
| 363 | >45 | >45 |
| 364 | >45 | 19.98 |
| 365 | >45 | 24.77 |
| 366 | >45 | >45 |
| 367 | >45 | 32.17 |
| 368 | >45 | 21.>45 |
| 369 | >45 | 30.97 |
| 370 | >45 | 19.82 |
| 371 | 30.38 | 4.92 |
| 372 | >45 | 30.01 |
| 373 | >45 | >45 |
| 374 | 32.18 | >45 |
| 375 | >45 | 39.62 |
| 376 | >45 | >45 |
| 377 | >45 | >45 |
| 378 | >45 | >45 |
| 379 | >45 | 15.78 |
| 380 | >45 | 33.33 |
| 381 | >45 | >45 |
| 382 | 43.54 | >45 |
| 383 | 36.63 | 22.85 |
| 384 | 30 | >45 |
| 385 | >45 | 10.16 |
| 386 | 30.49 | 18 |
| 387 | >45 | 30.03 |
| 388 | >45 | 20.55 |
| 389 | >45 | 19.13 |
| 390 | >45 | 18.58 |
| 391 | >45 | >45 |
| 392 | >45 | >45 |
| 393 | >45 | 41.67 |
| 394 | >45 | 17.88 |
| 395 | >45 | 33.07 |
| 396 | 38.9 | 22.44 |
| 397 | >45 | 16.95 |
| 398 | >45 | >45 |
| 399 | 14.98 | 2.89 |
| 400 | >45 | >45 |
| 401 | >45 | >45 |
| 402 | >45 | 36.75 |
| 403 | 31.05 | 20.1 |
| 404 | >45 | >45 |
| 405 | 33.3 | >45 |
| 406 | >45 | >45 |
| 407 | >45 | 10.28 |
| 408 | >45 | 34.3 |
| 409 | 22.99 | >45 |
| 410 | 27.07 | 28.13 |
| 411 | 30 | >45 |
| 412 | >45 | 32.4 |
| 413 | >45 | 40.89 |
| 414 | 30 | >45 |
| 415 | 40.24 | 16.41 |
| 416 | 23.07 | 14.13 |
| 417 | >45 | >45 |
| 418 | >45 | >45 |
| 419 | >45 | 28.15 |
| 420 | >45 | 36.41 |
| 421 | >45 | >45 |
| 422 | >45 | >45 |
| 423 | >45 | 39.83 |
| 424 | >45 | >45 |
| 425 | >45 | >45 |
| 426 | >45 | 27.31 |
| 427 | 30.02 | 19.66 |
| 428 | 29.37 | >45 |
| 429 | 36.34 | 40.68 |
| 430 | >45 | 30 |
| 431 | >45 | >45 |
| 432 | 40 | >45 |
| 433 | 36.75 | >45 |
| 434 | >45 | 4.67 |
| 435 | >45 | 41.67 |
| 436 | >45 | 8.9 |
| 437 | >45 | >45 |
| 438 | >45 | >45 |
| 439 | >45 | >45 |
| 440 | >45 | >45 |
| 441 | 32.39 | >45 |
| 442 | >45 | >45 |
| 443 | >45 | >45 |
| 444 | >45 | 25.88 |
| 445 | >45 | >45 |
| 446 | >45 | 33.33 |
| 447 | >45 | >45 |
| 448 | >45 | >45 |
| 449 | >45 | 41.67 |
| 450 | >45 | >45 |
| 451 | 37.16 | >45 |
| 452 | >45 | 40.56 |
| 453 | >45 | 13.72 |
| 454 | >45 | 22.89 |
| 455 | >45 | >45 |
| 456 | >45 | >45 |
| 457 | >45 | >45 |
| 458 | >45 | >45 |
| 459 | >45 | 23.22 |
| 460 | >45 | 27.94 |
| 461 | >45 | 27.63 |
| 462 | >45 | >45 |
| 463 | >45 | 40 |
| 464 | >45 | >45 |

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:
1. A compound having the structure of Formula I:

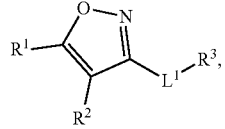

Formula I wherein
$R^1$ is H, halo, CN, $NO_2$, hydroxyl, optionally substituted amino, optionally substituted $C_1$-$C_6$ alkyl, optionally substituted $C_1$-$C_6$ heteroalkyl, optionally substituted $C_1$-$C_6$ alkenyl, optionally substituted $C_1$-$C_6$ heteroalk-

481 enyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl, $R^2$ is H or optionally substituted $C_1$-$C_6$ alkyl, or $R^1$ and $R^2$, together with the atoms to which each is attached, combine to form an optionally substituted $C_3$-$C_{10}$ carbocyclylene, optionally substituted $C_2$-$C_9$ heterocyclylene, optionally substituted $C_6$-$C_{10}$ arylene, or optionally substituted $C_2$-$C_9$ heteroarylene;

$L^1$ is optionally substituted $C_1$-$C_6$ alkylene or optionally substituted $C_1$-$C_6$ heteroalkylene; and $R^3$ is optionally substituted $C_2$-$C_9$ heteroaryl, or a pharmaceutically acceptable salt thereof.

2. The compound of claim 1, wherein $R^3$ is a heteroaryl having the structure of Formula Ia:

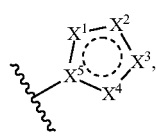

Formula Ia wherein each of $X^1$, $X^2$, $X^3$, and $X^4$ is, independently, O, $NR^4$, or $CR^5$, wherein each $R^4$ is, independently, H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl, each $R^5$ is, independently, H, CN, optionally substituted $C_1$-$C_6$ alkyl, or optionally substituted $C_1$-$C_6$ heteroalkyl, and if one of $X^1$, $X^2$, $X^3$, or $X^4$ is O, then the adjacent atoms are N or $CR^5$; and $X^5$ is N or C, wherein 1, 2, or 3 of $X^1$, $X^2$, $X^3$, $X^4$, or $X^5$ is O or N.

3. The compound of claim 1, wherein $R^3$ is

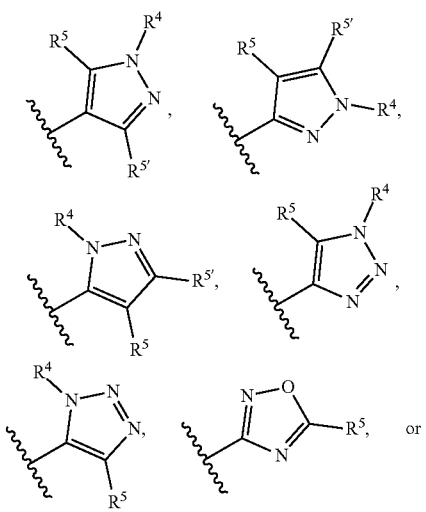

482

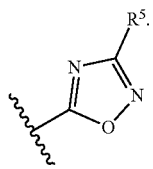

4. The compound of claim 1, wherein each of $R^5$ is, independently, H, CN, or optionally substituted $C_1$-$C_6$ alkyl.

5. The compound of claim 1, wherein $R^4$ is H.

6. The compound of claim 1, wherein $R^4$ is optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

7. The compound of claim 1, wherein $R^2$ is H or optionally substituted $C_1$-$C_6$ alkyl.

8. The compound of claim 1, wherein $R^1$ is H, halo, CN, $NO_2$, hydroxyl, optionally substituted amino, optionally substituted $C_1$-$C_6$ alkyl, optionally substituted $C_1$-$C_6$ heteroalkyl, optionally substituted $C_1$-$C_6$ alkenyl, optionally substituted $C_1$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

9. The compound of claim 8, wherein $R^1$ is is F, Cl, Br, I, CN, $NO_2$, $NH_2$,

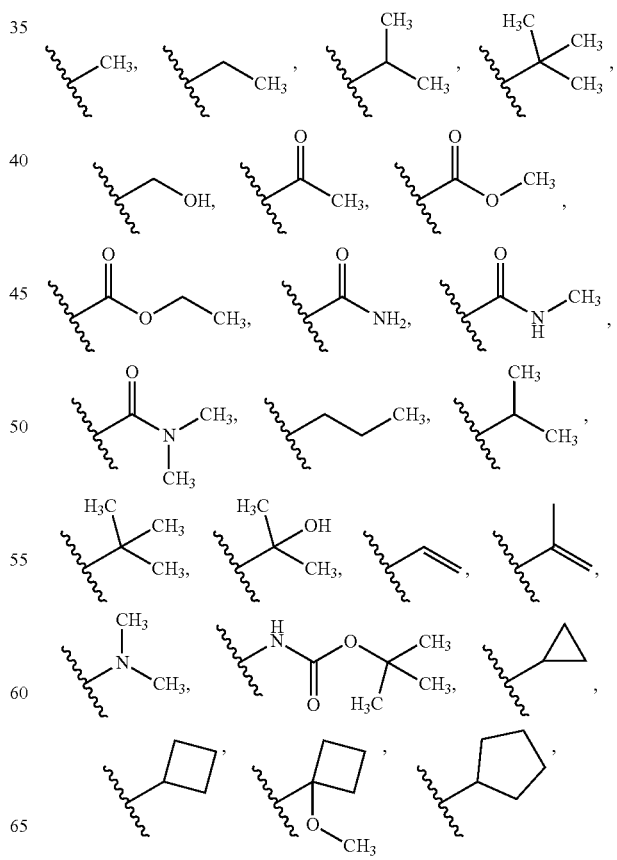

483
-continued
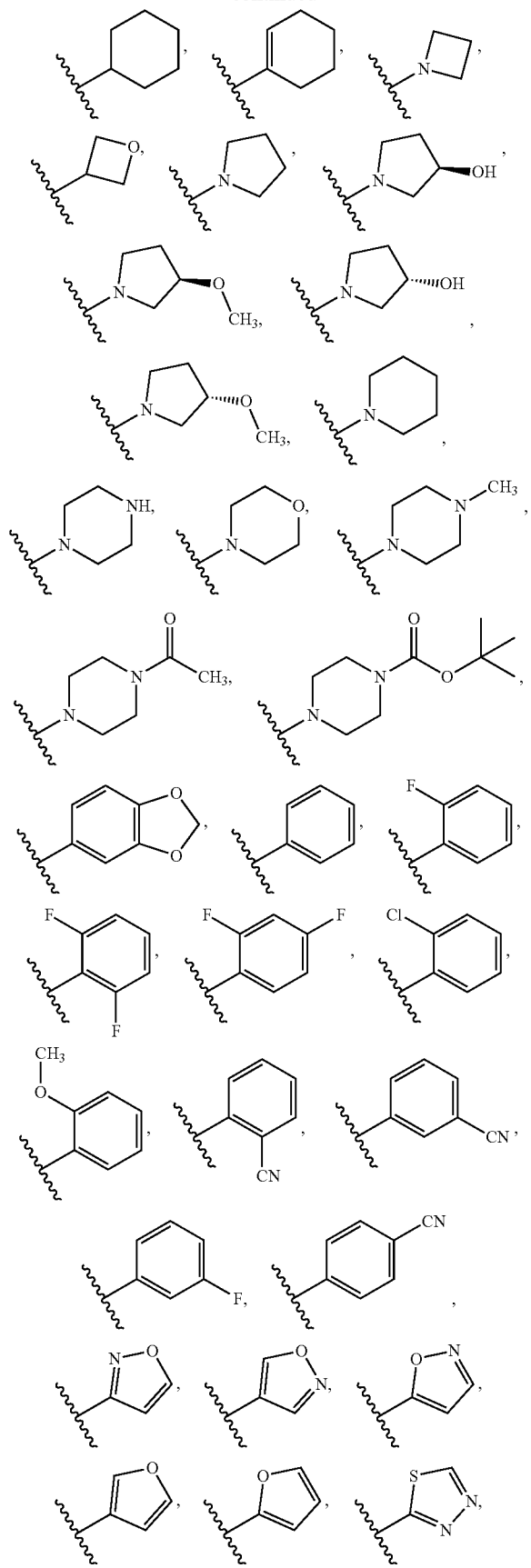
484
-continued
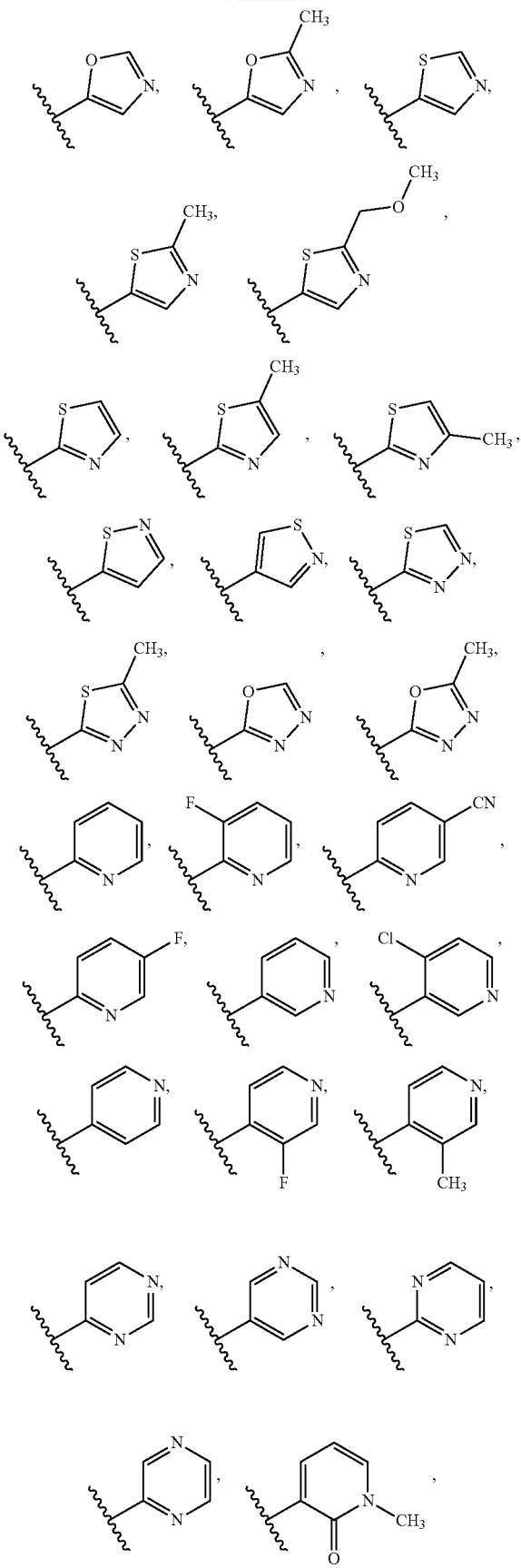

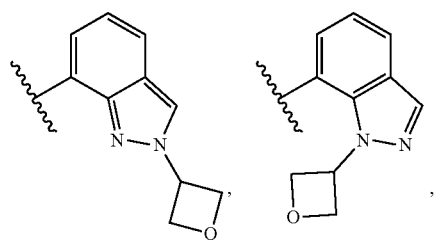

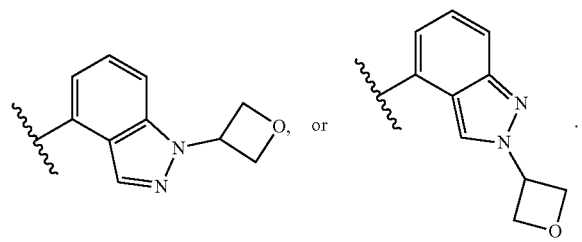

10. The compound of claim 1, wherein R¹ and R², together with the atoms to which each is attached, combine to form an optionally substituted $C_3$-$C_{10}$ carbocyclylene, optionally substituted $C_2$-$C_9$ heterocyclylene, optionally substituted $C_6$-$C_{10}$ arylene, or optionally substituted $C_2$-$C_9$ heteroarylene.

11. The compound of claim 1, wherein $L^1$ is optionally substituted $C_1$-$C_6$ heteroalkylene.

12. A compound selected from the group consisting of:

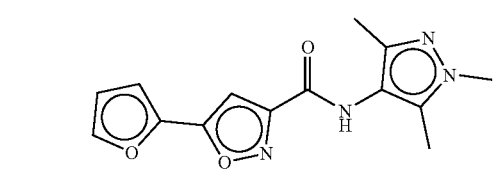

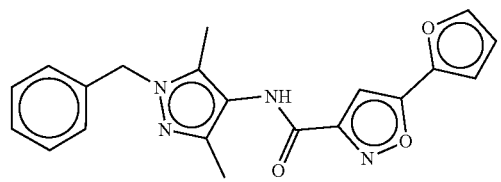

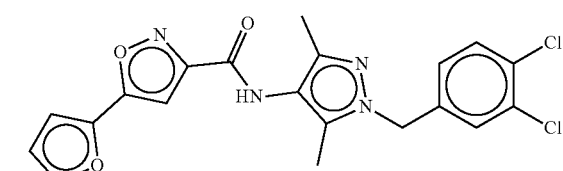

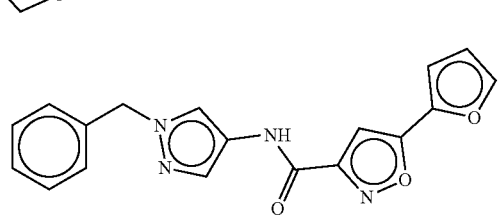

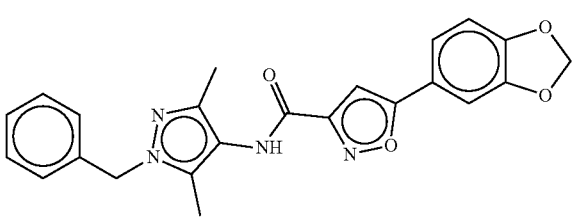

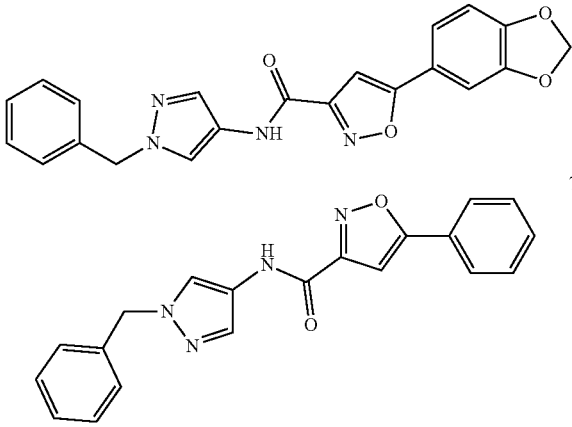

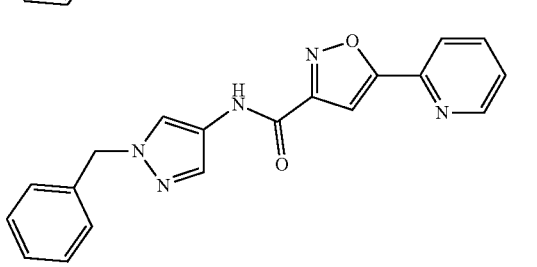

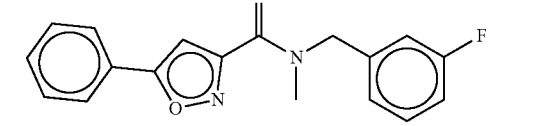

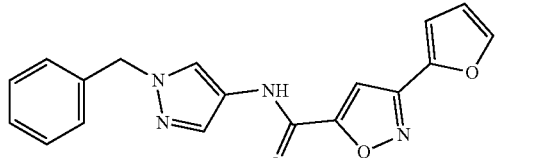

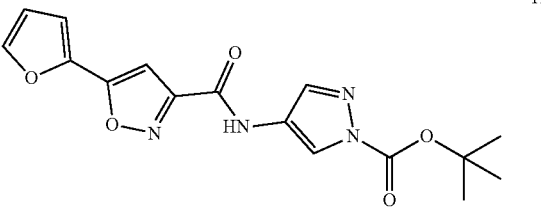

-continued

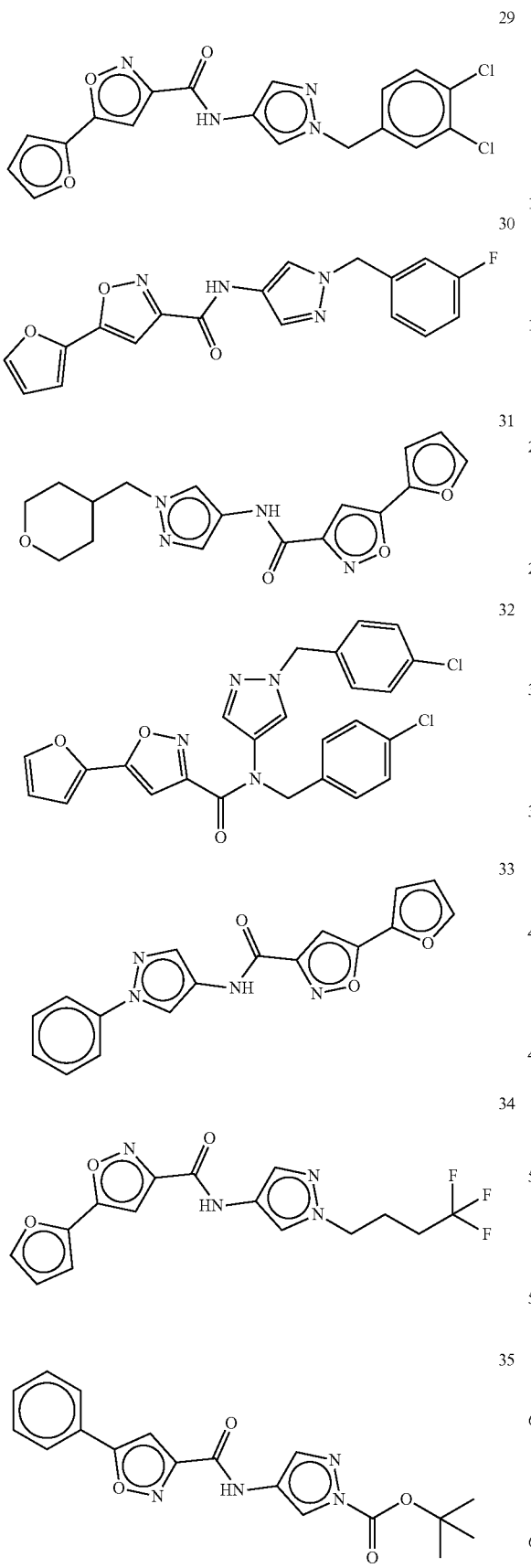
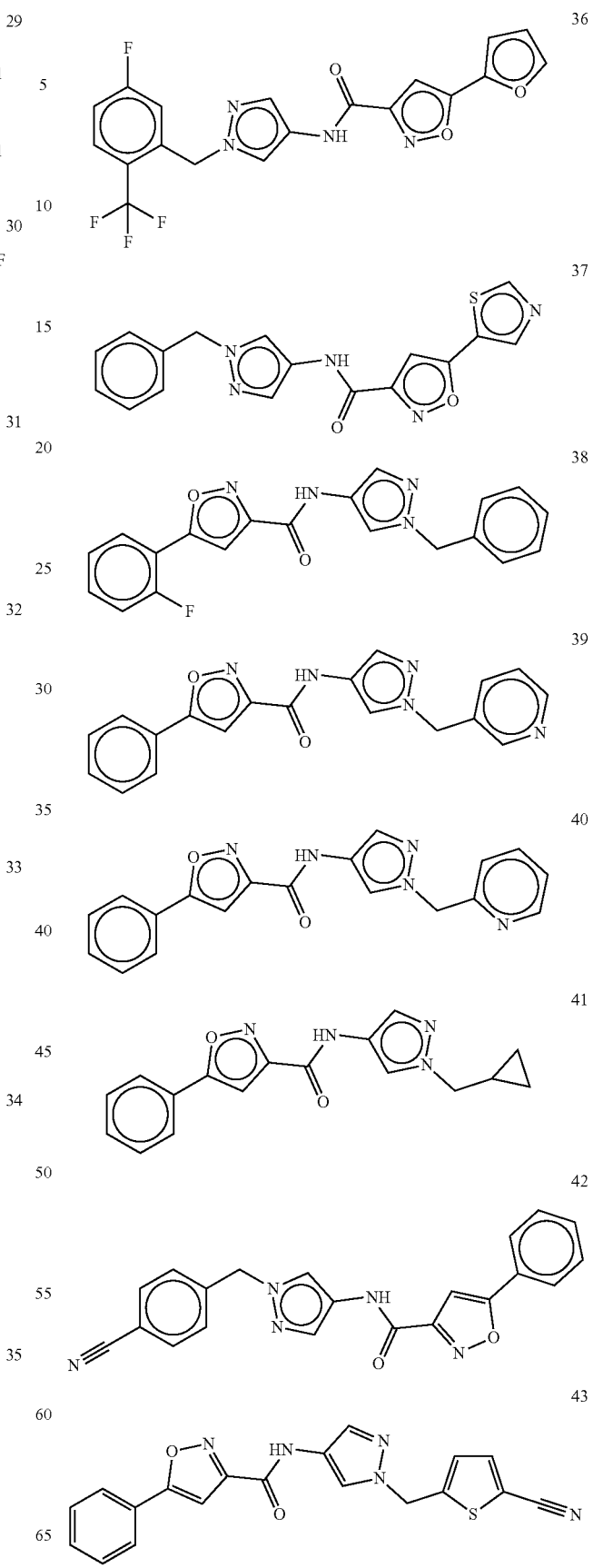

491
-continued
44
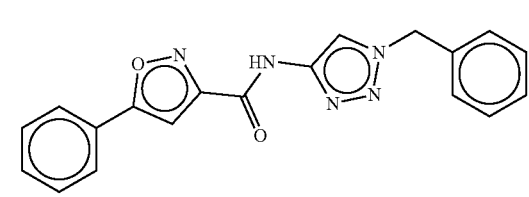
45
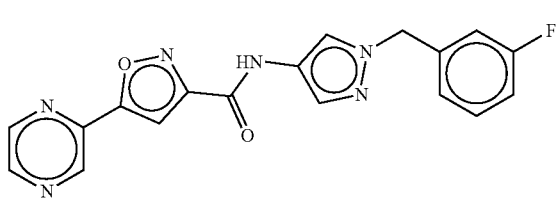
46
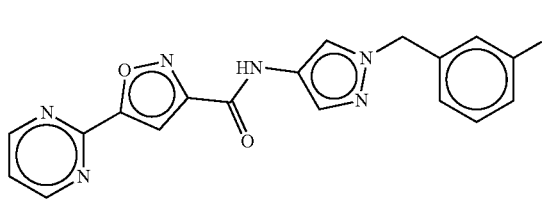
47
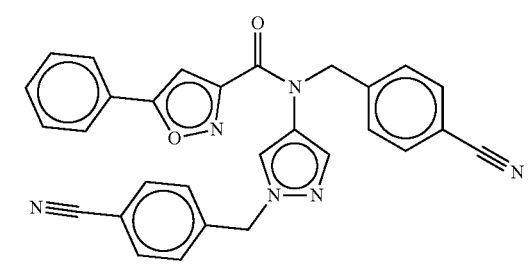
48
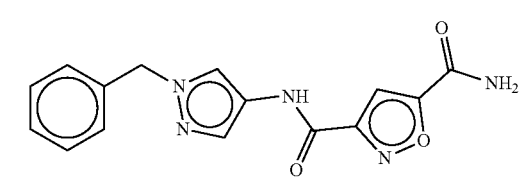
49
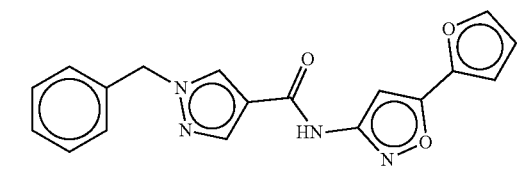
50
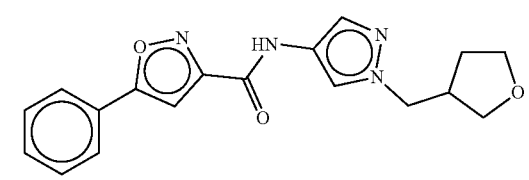
51
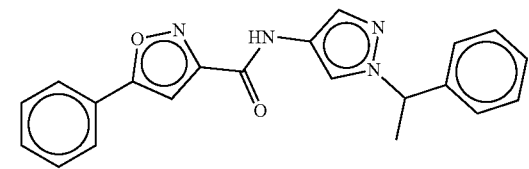
492
-continued
52
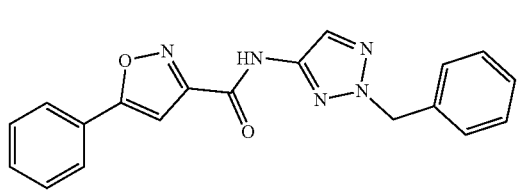
53
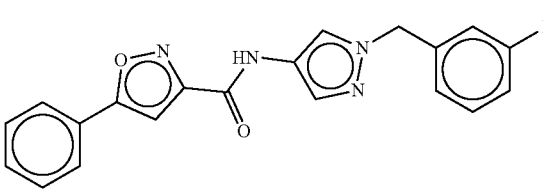
54
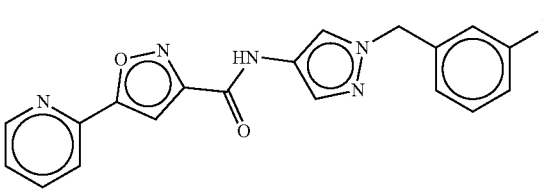
55
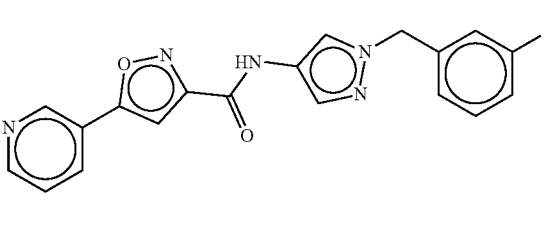
56
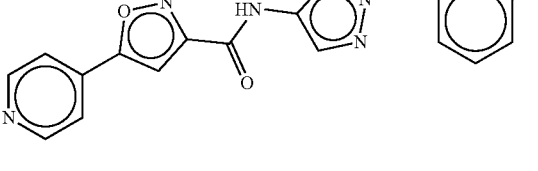
57
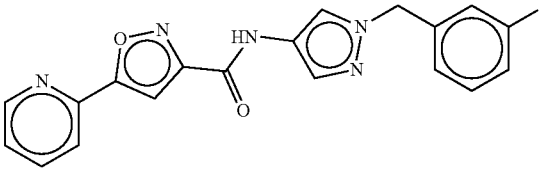
58
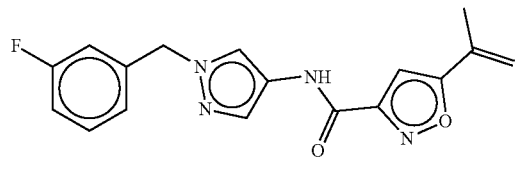
59
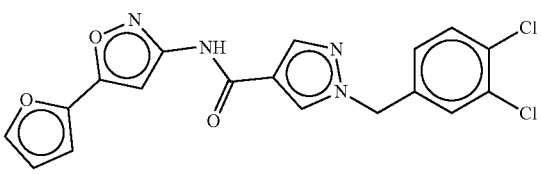

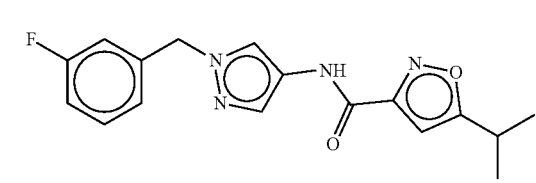
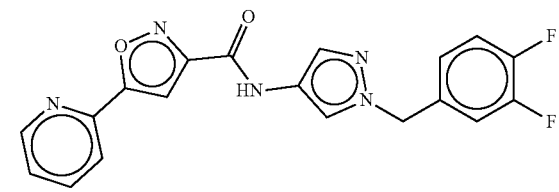
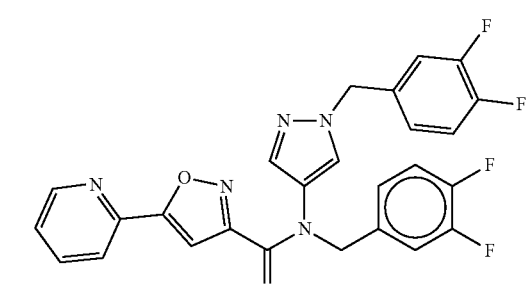
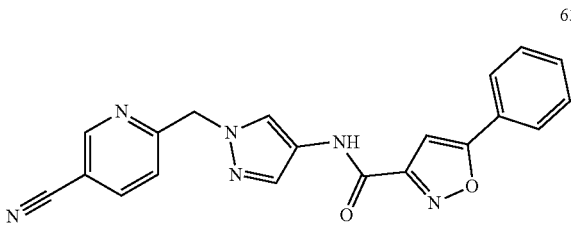
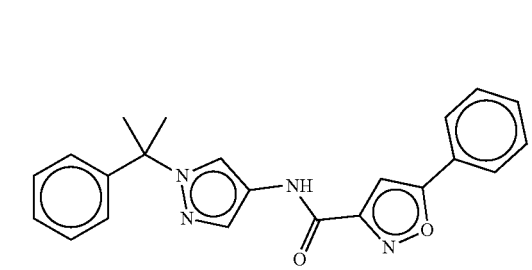
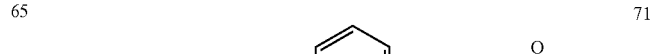
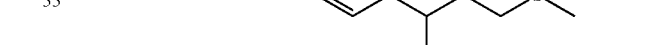
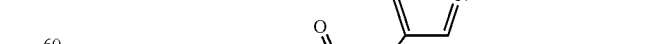
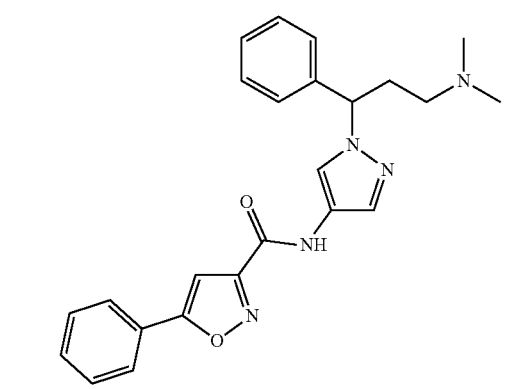
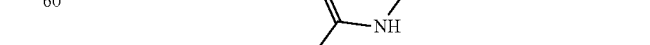
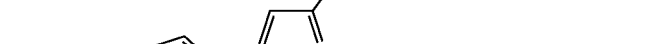
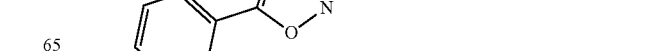

495
-continued
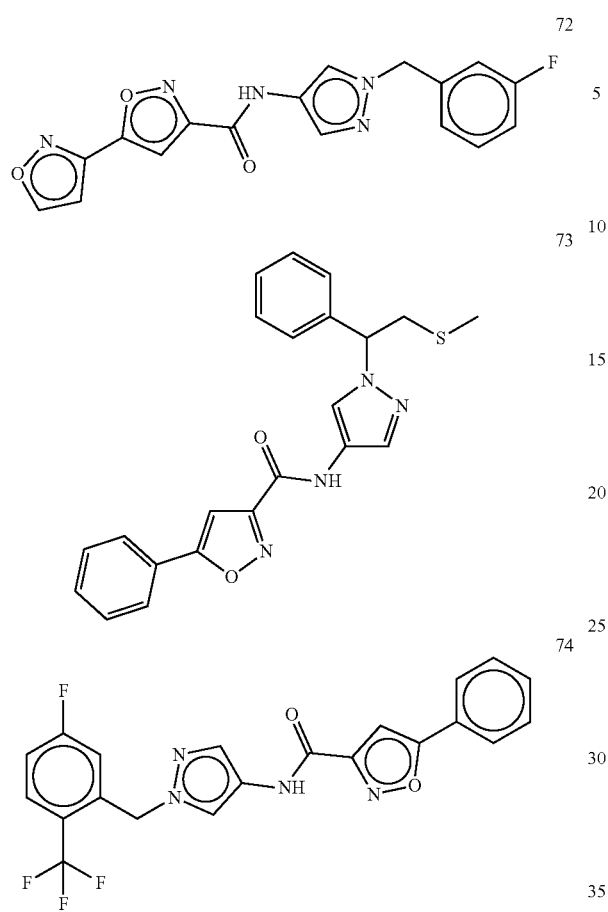
496
-continued
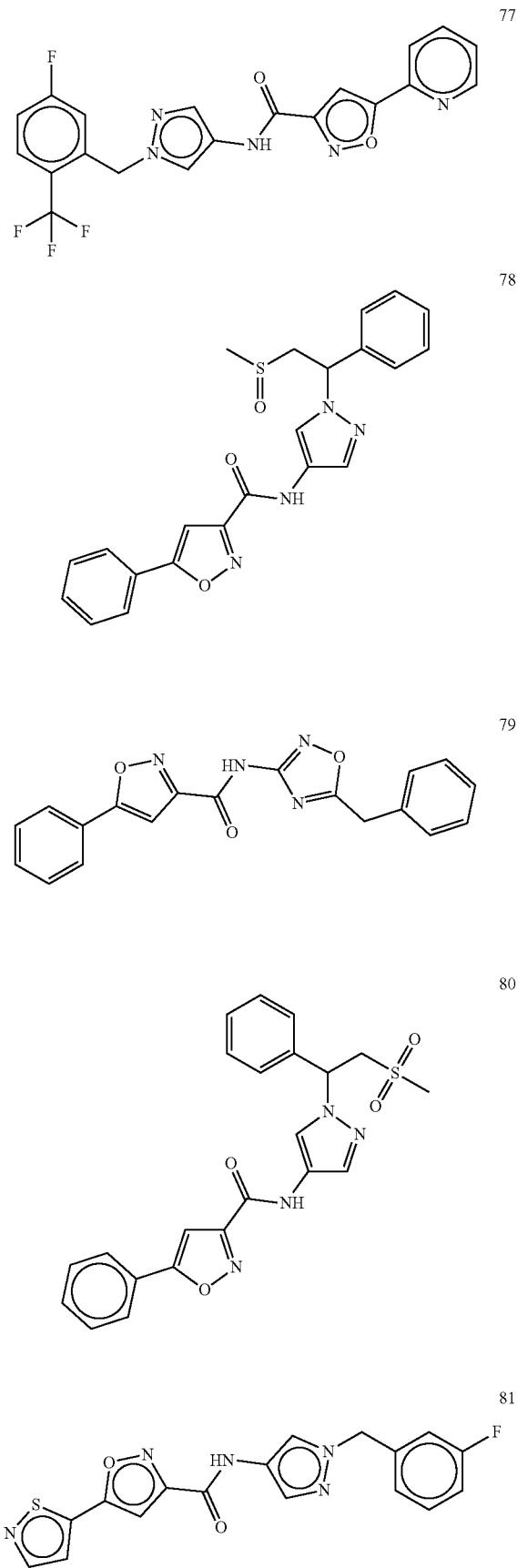

82
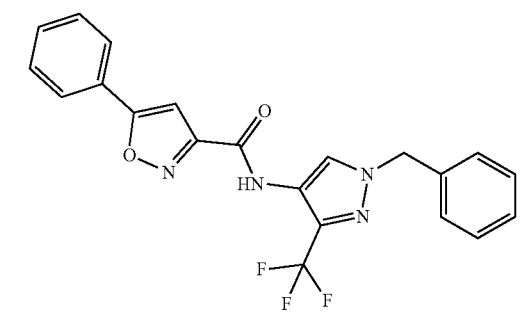
83
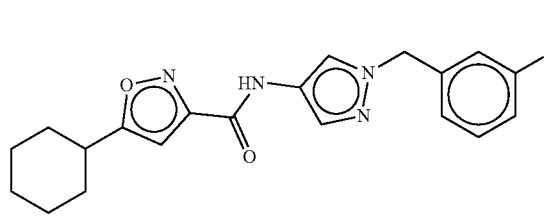
84
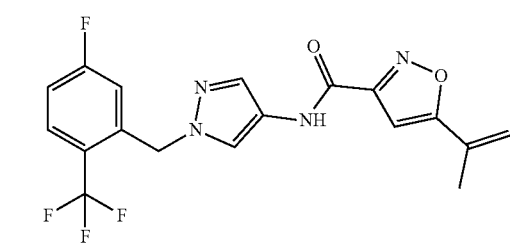
85
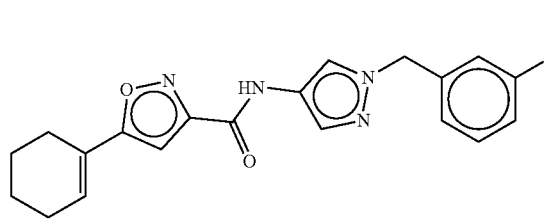
86
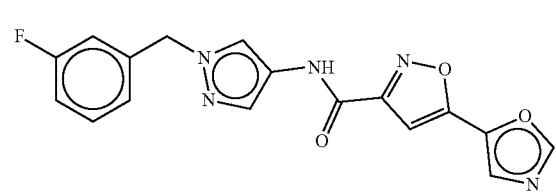
87
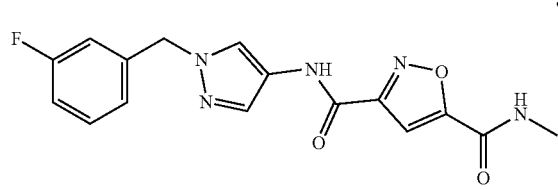
88
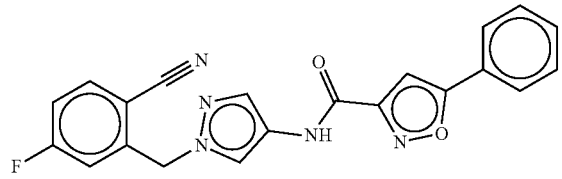
89
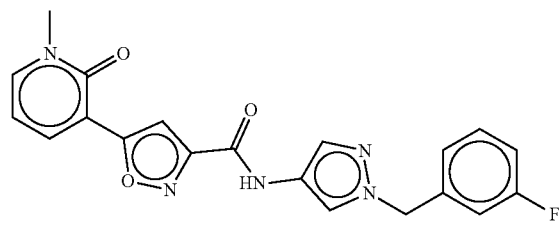
90
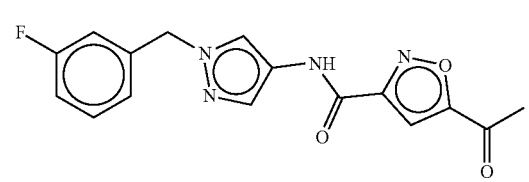
91
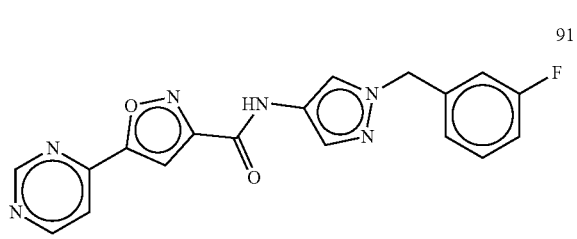
92
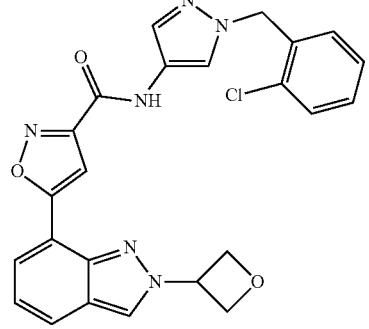
93
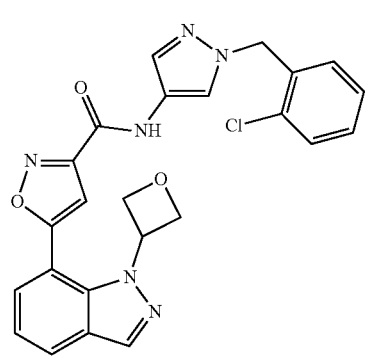

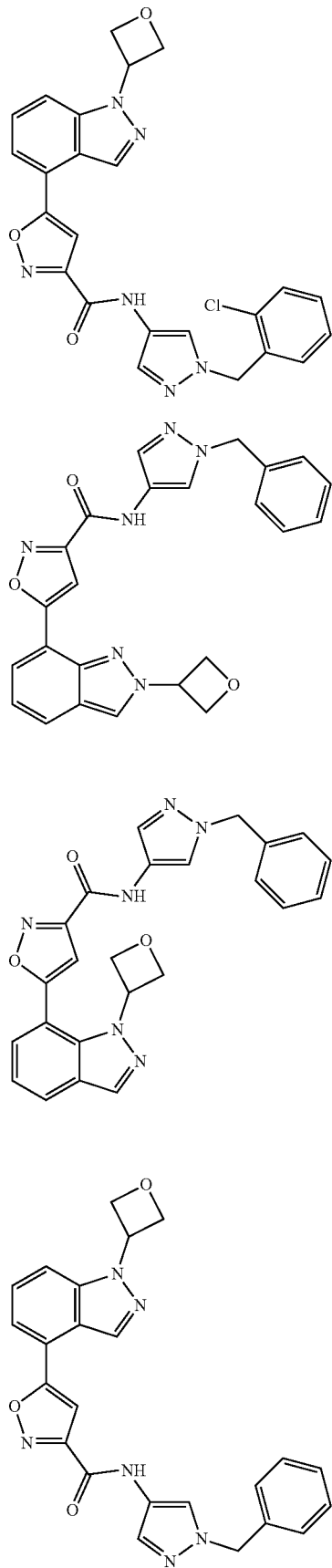
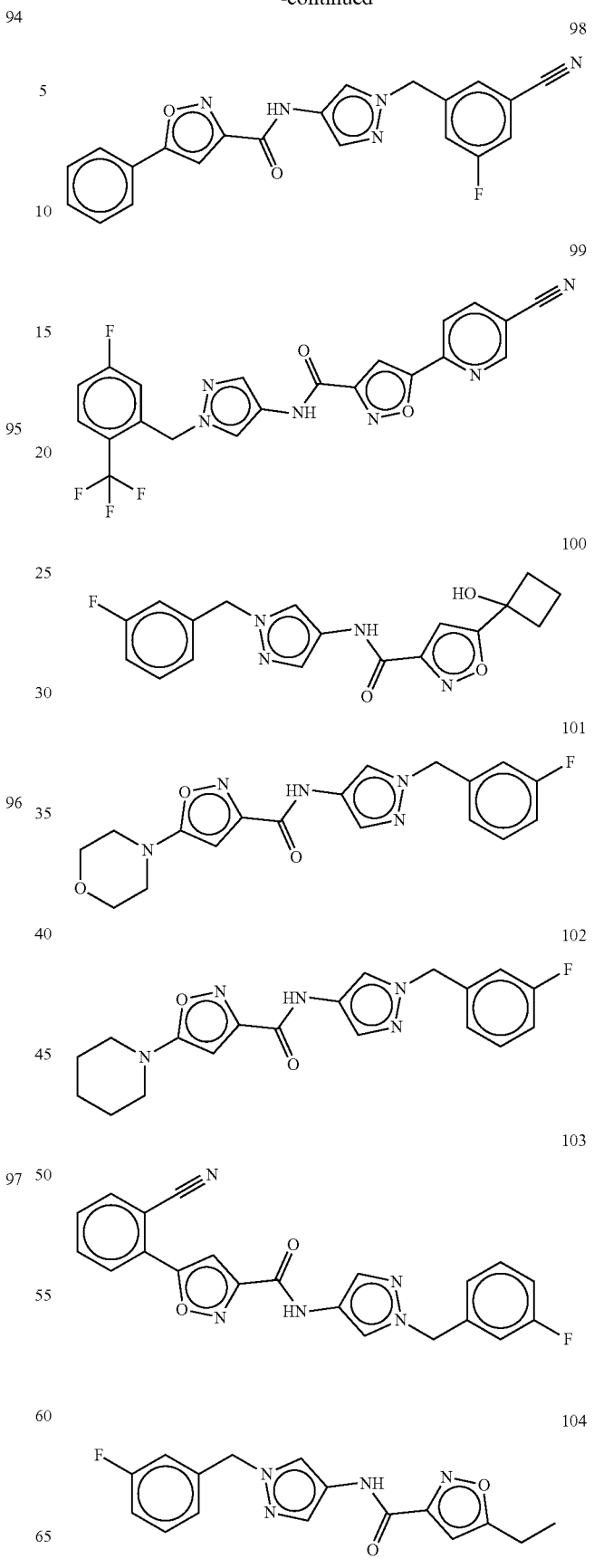

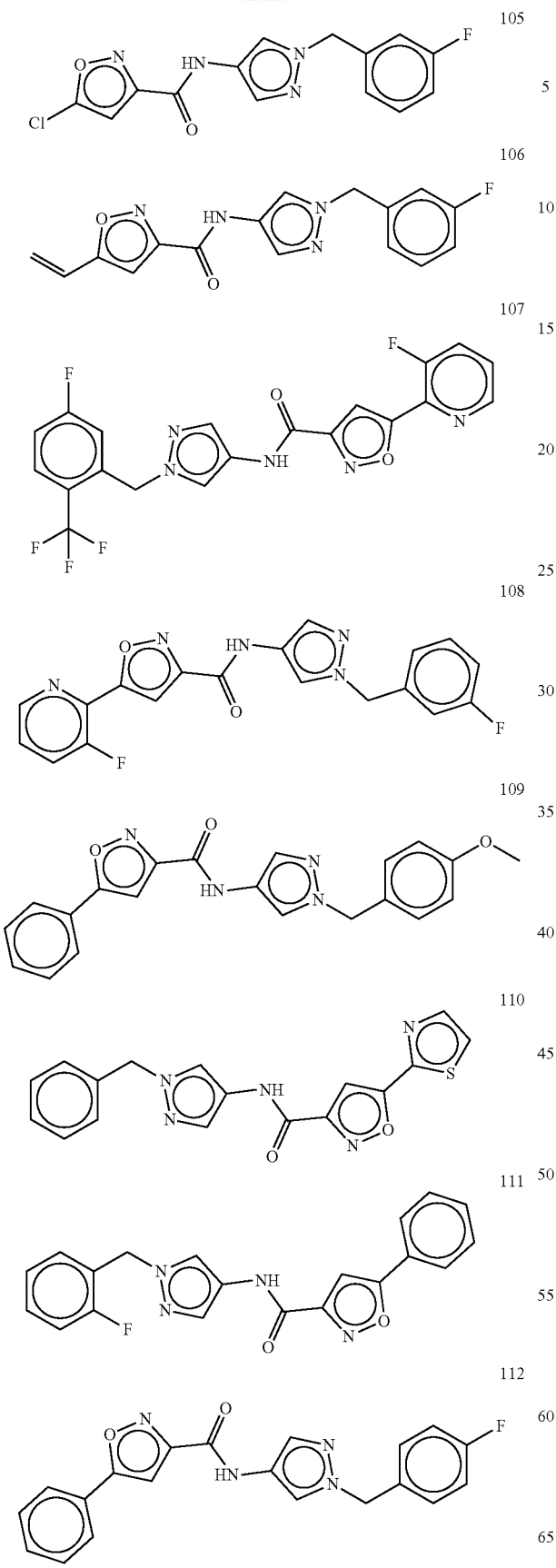
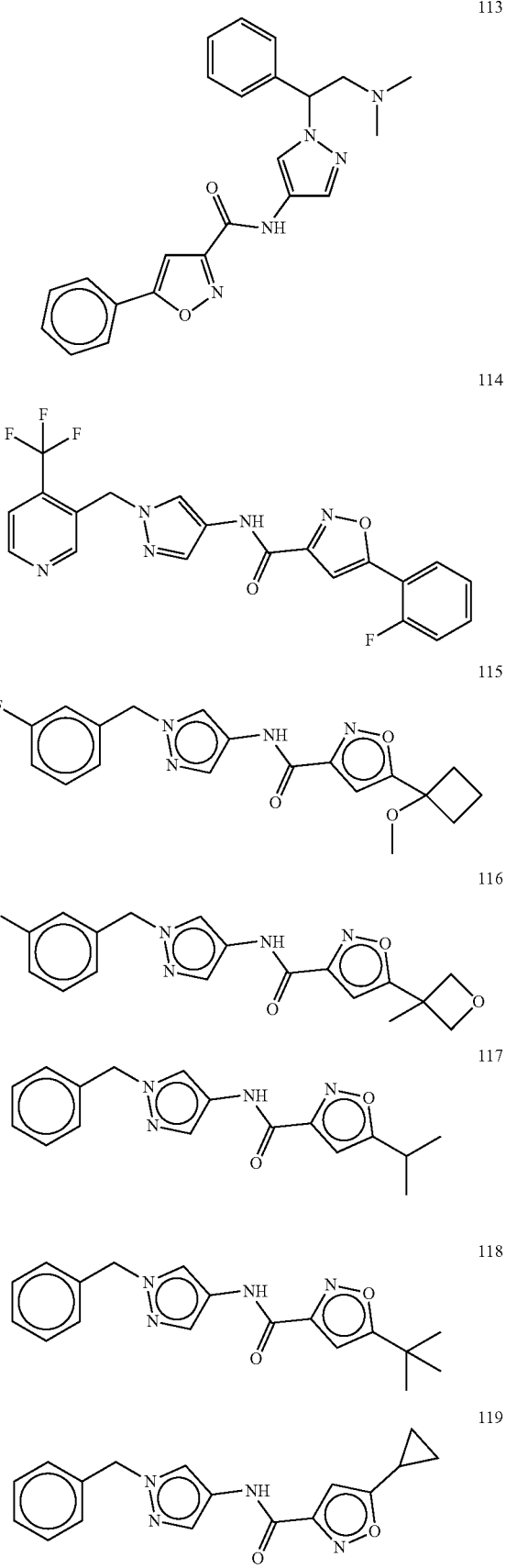

136 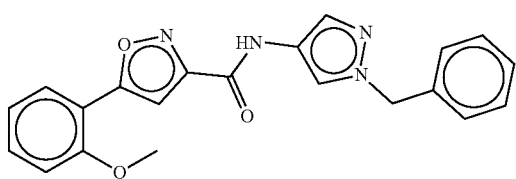
144 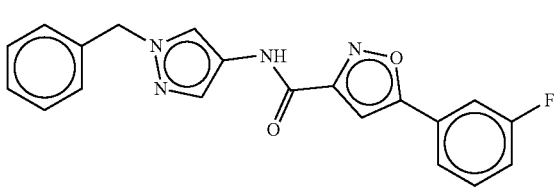
137 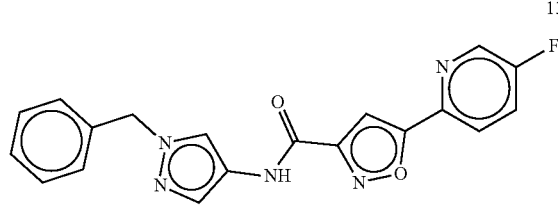
145 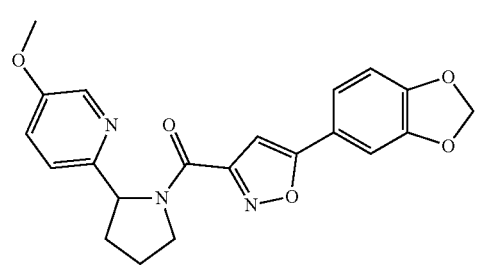
138 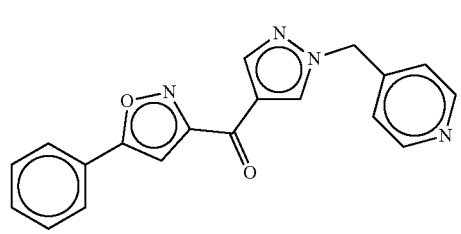
146 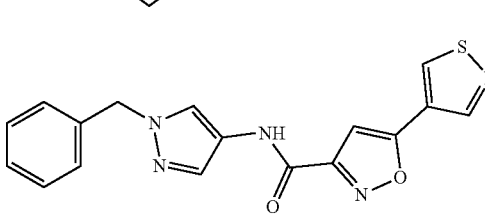
139 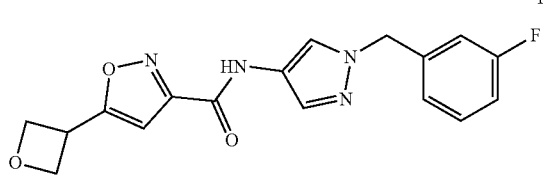
147 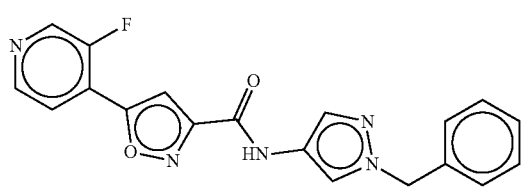
140 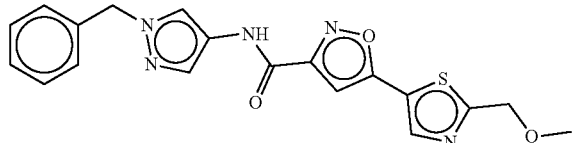
148 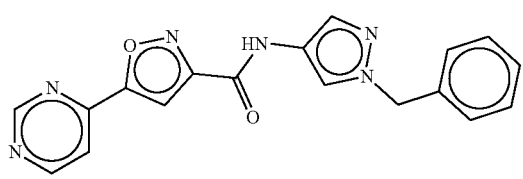
141 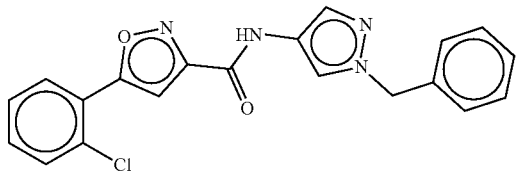
149 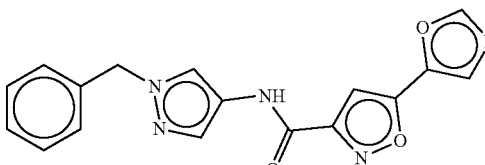
142 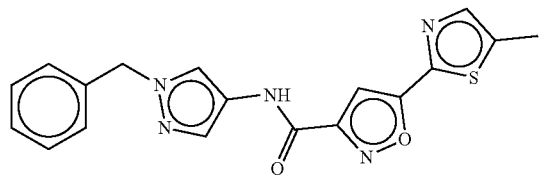
150 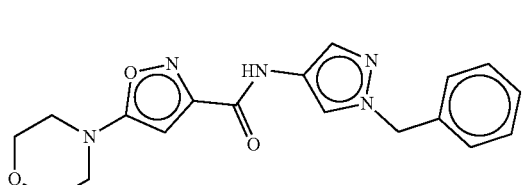
143 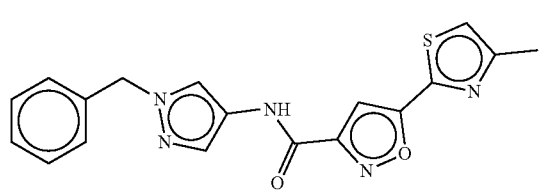
151 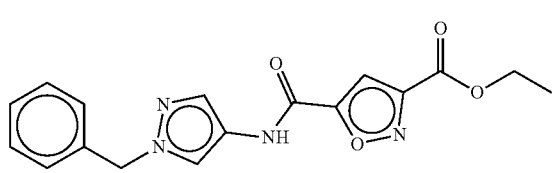

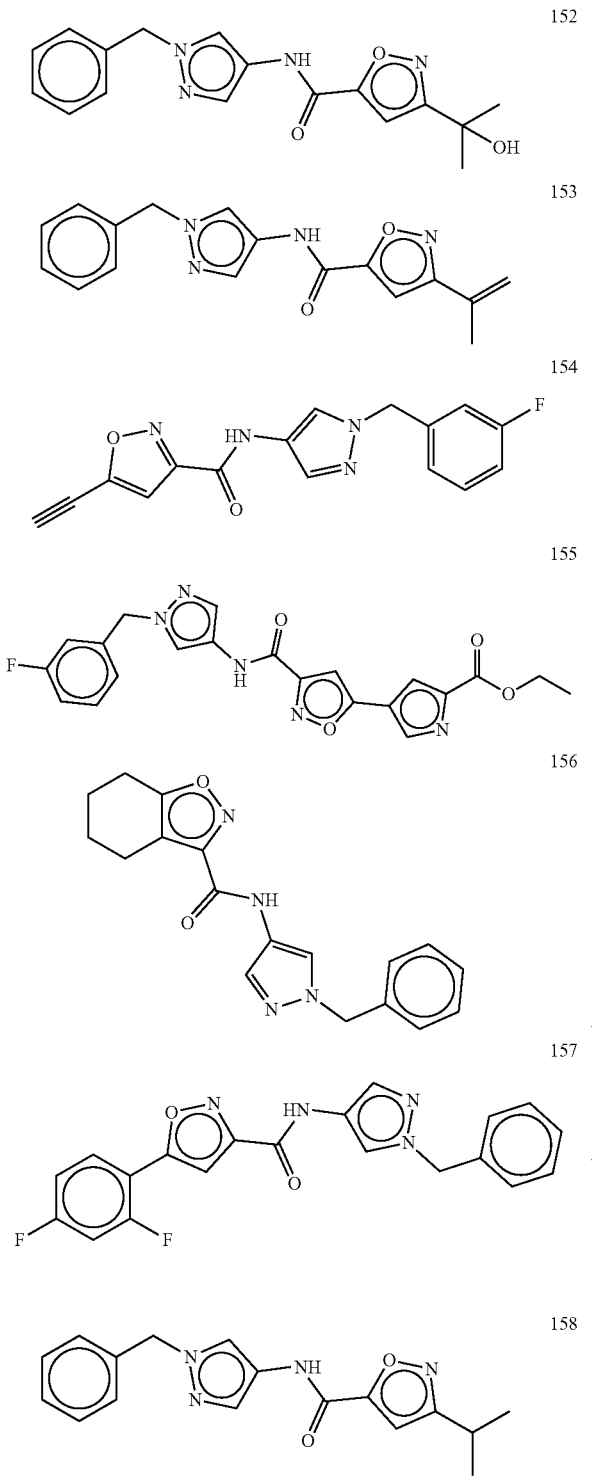
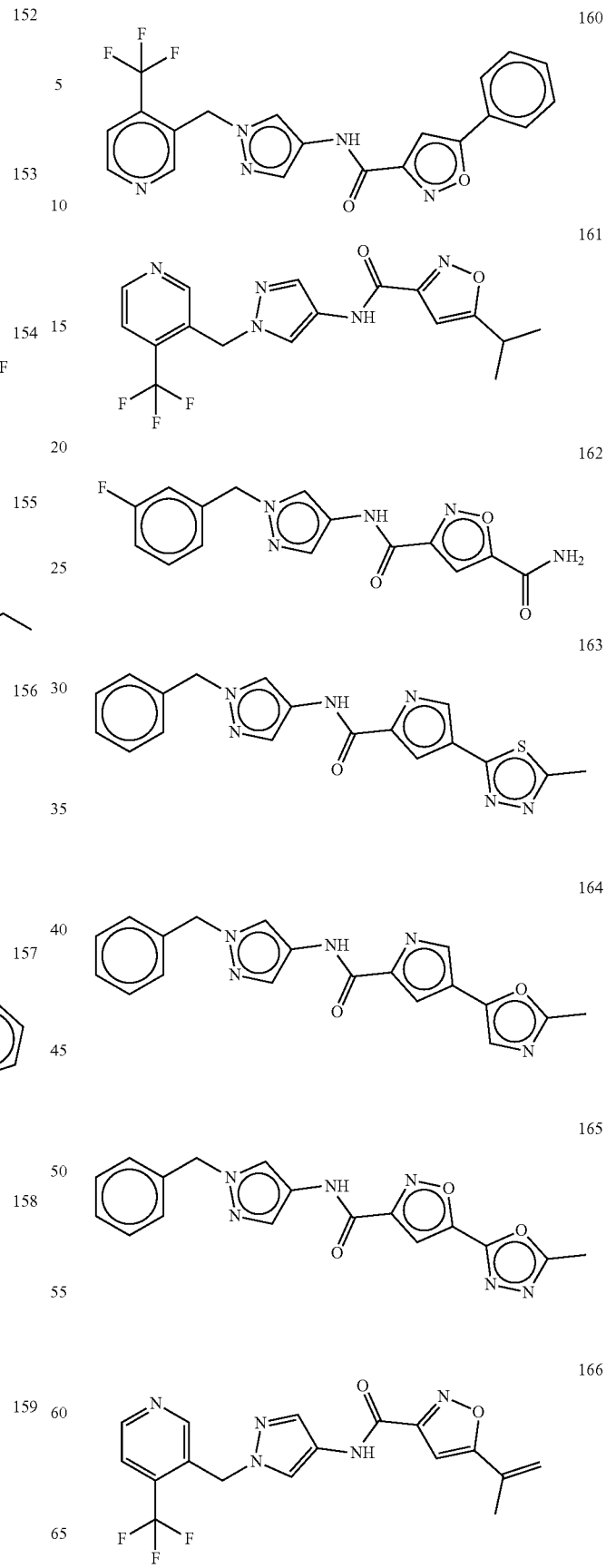

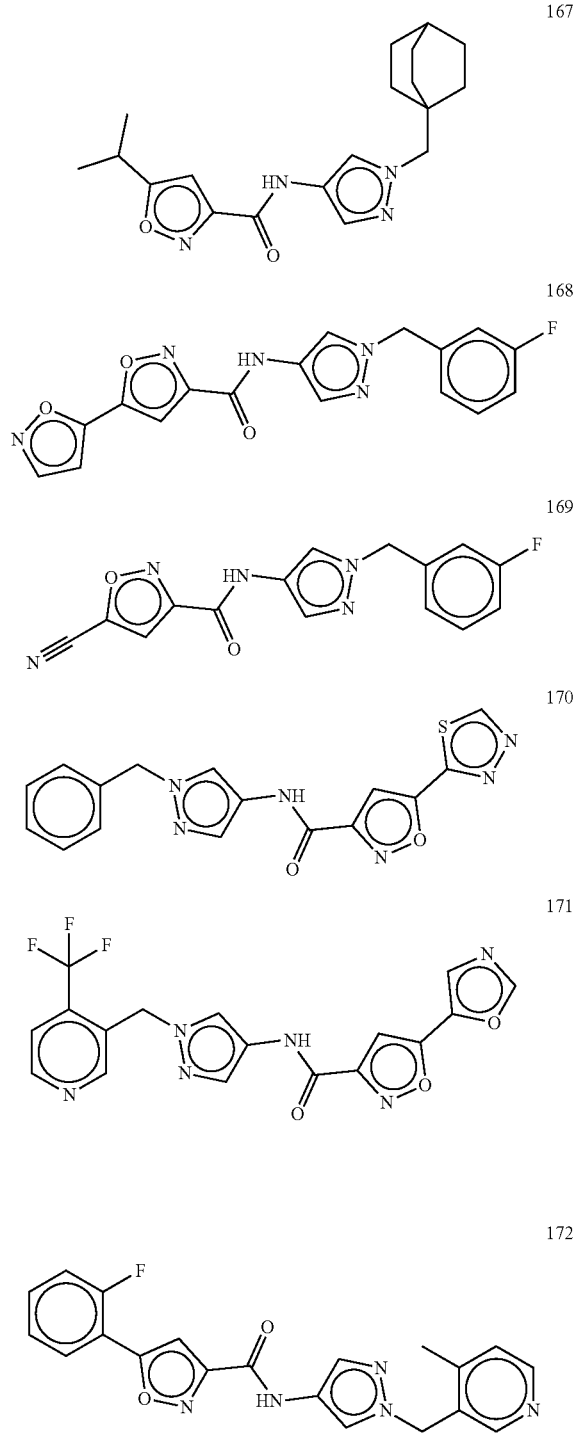
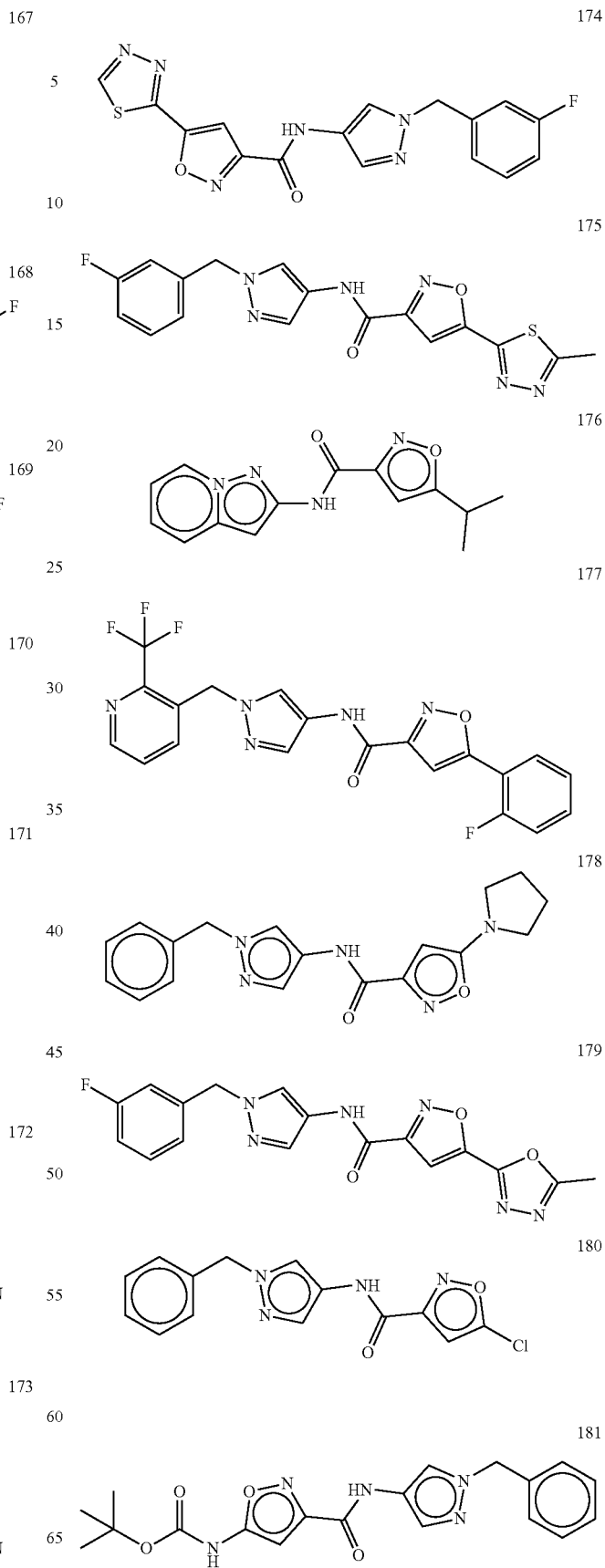

182
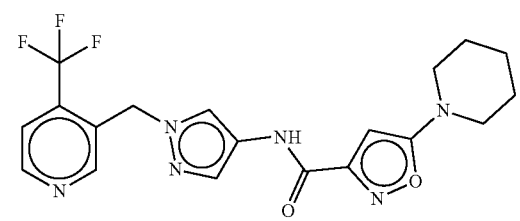
183
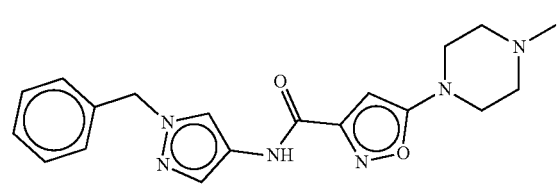
184
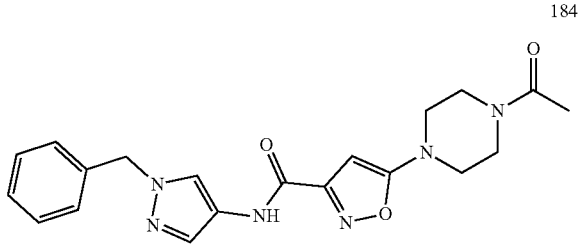
185
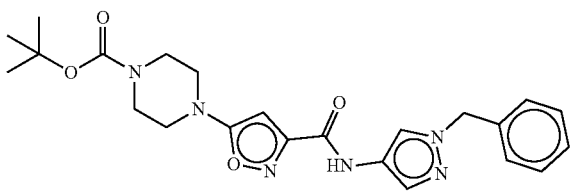
186
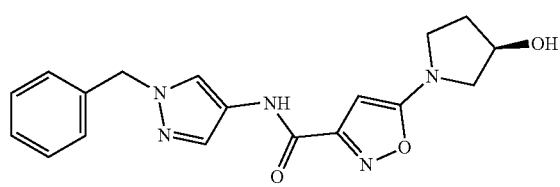
187
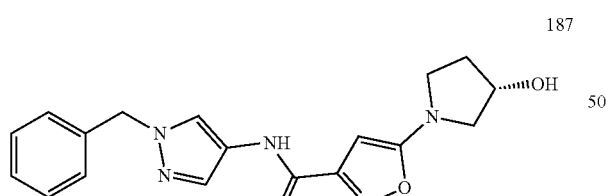
188
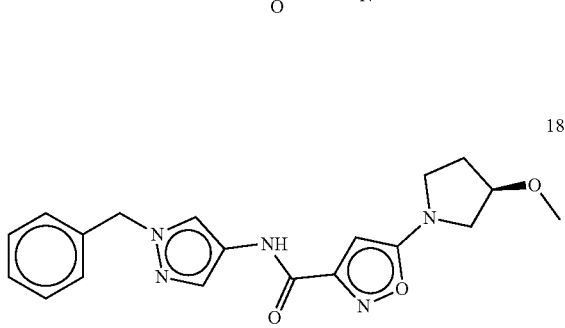
189
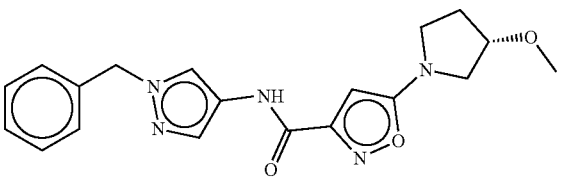
190
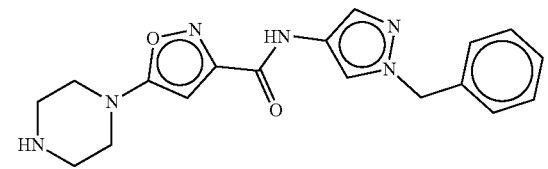
191
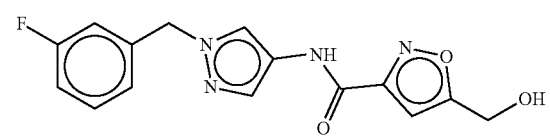
192
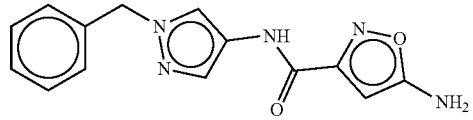
193
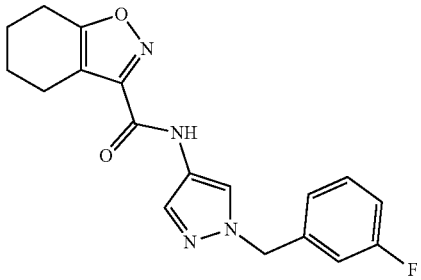
194
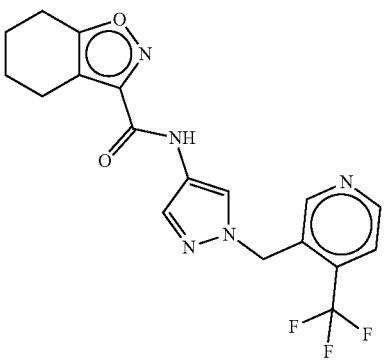
195
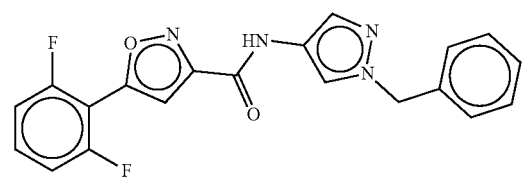

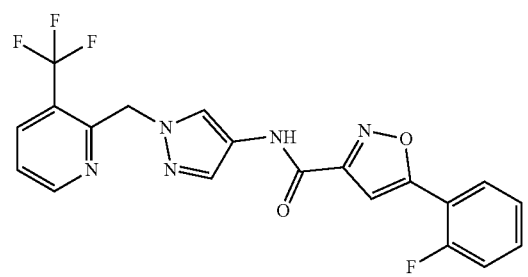
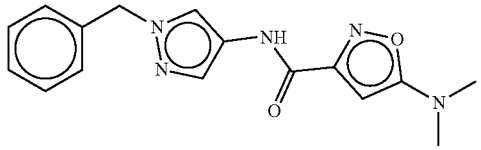
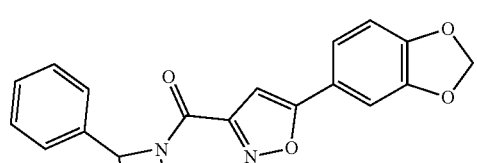
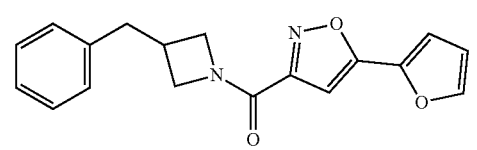
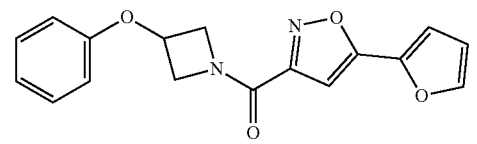
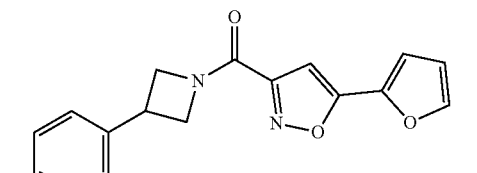
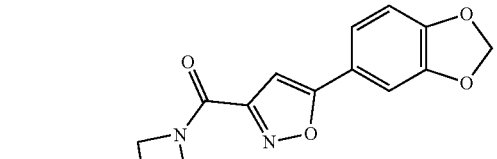
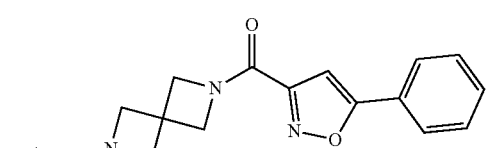
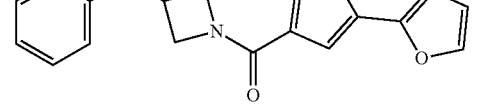

| | |
|---|---|
| 211 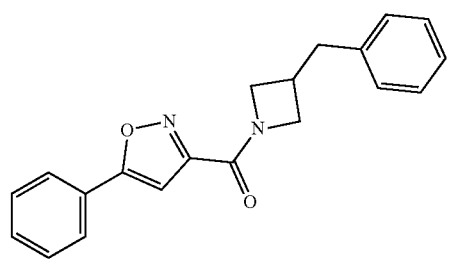 | 217 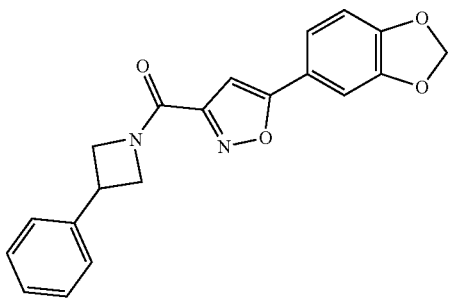 |
| 212 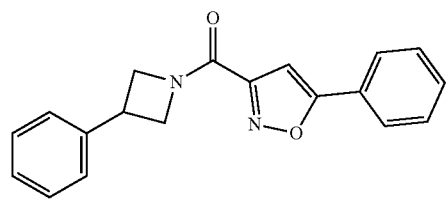 | 218 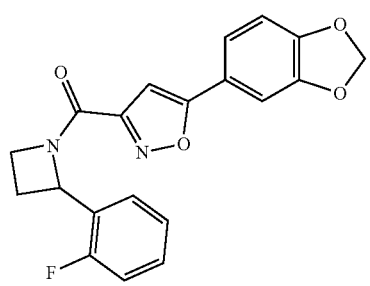 |
| 213 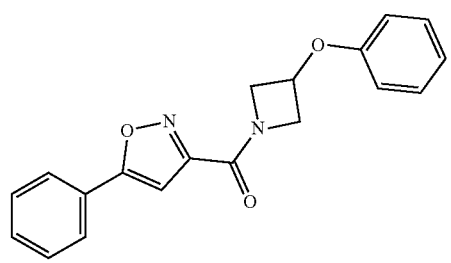 | 219 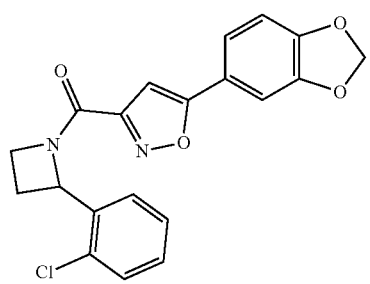 |
| 214 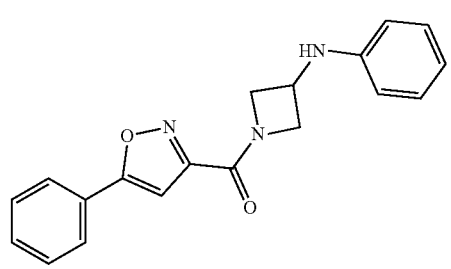 | 220 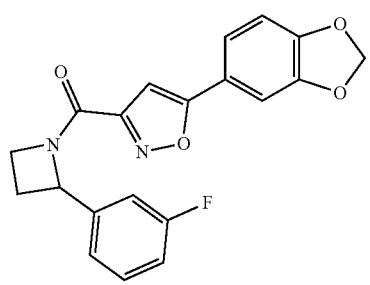 |
| 215 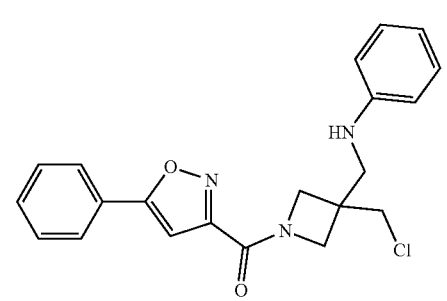 | |
| 216 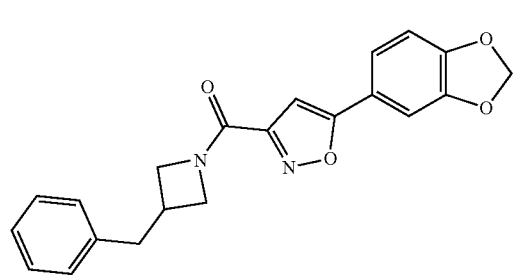 | 221 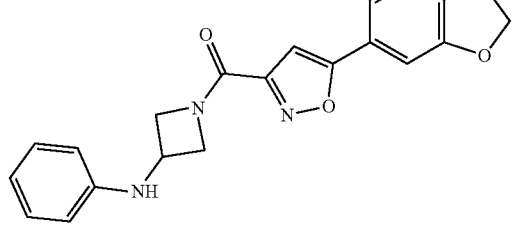 |

517
-continued
222
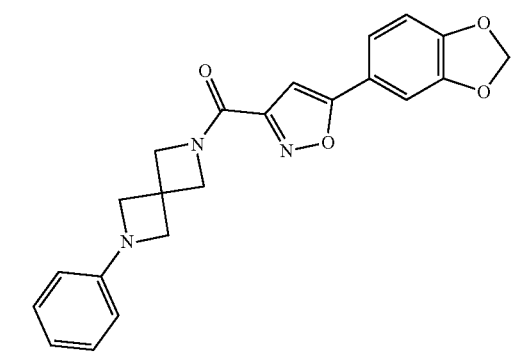
223
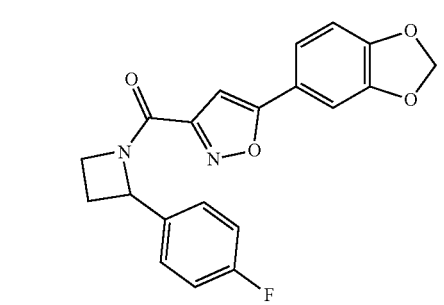
224
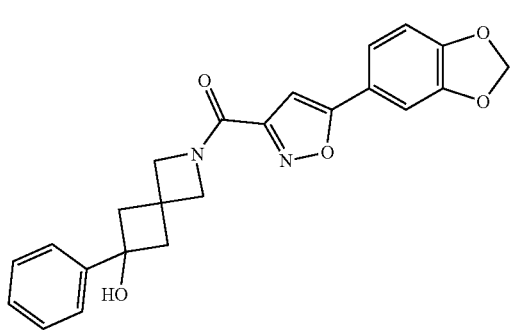
225
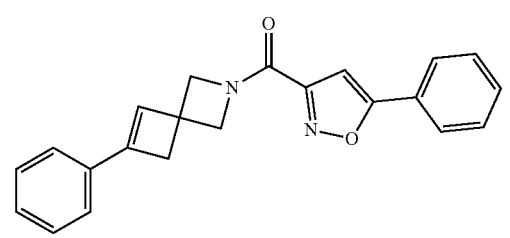
226
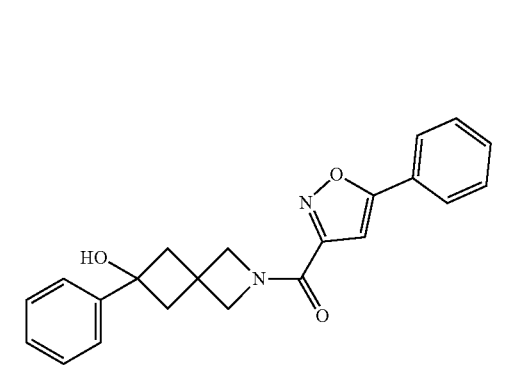
518
-continued
227
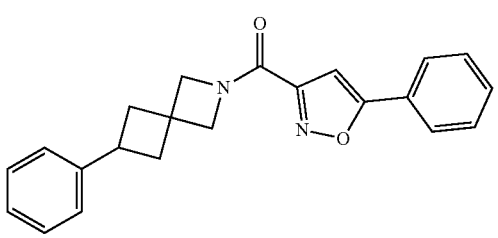
228
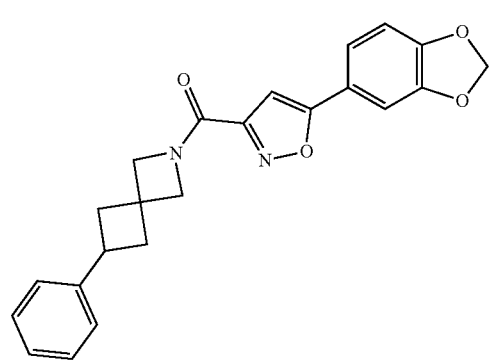
229
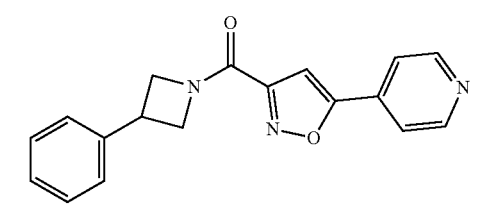
230
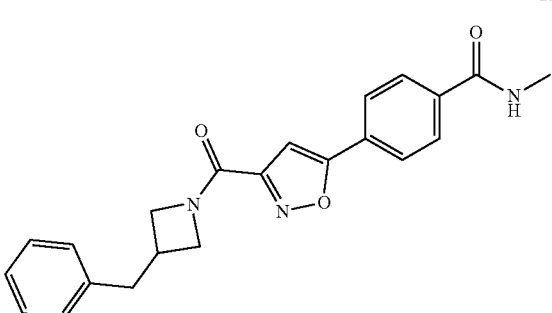
231
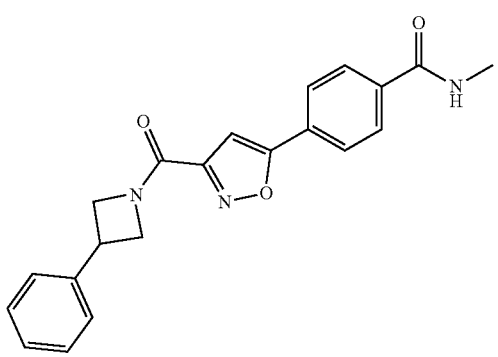

232 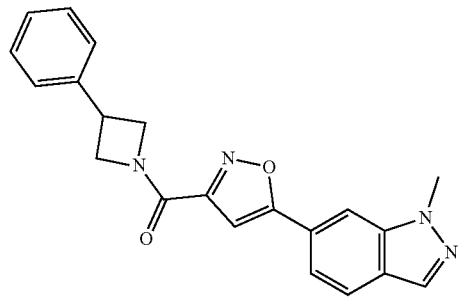
233 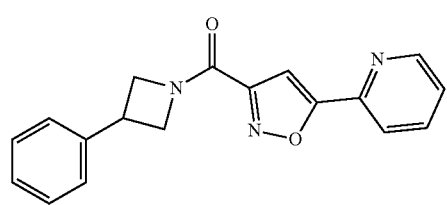
234 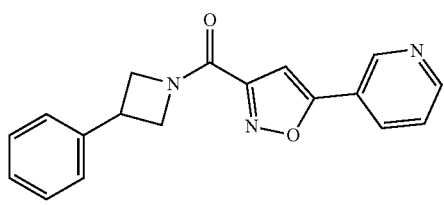
235 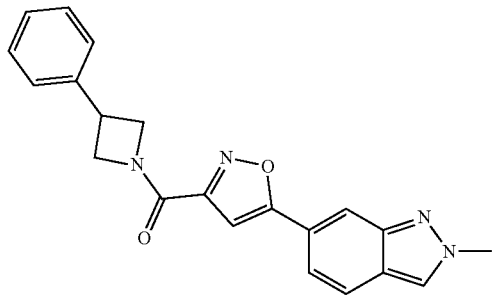
236 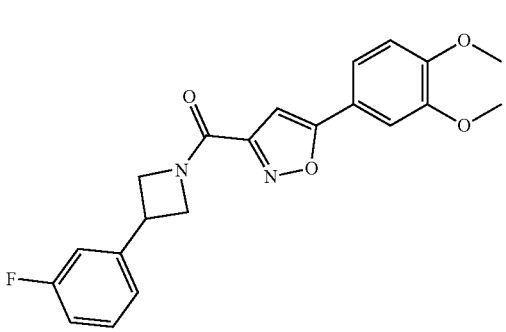
237 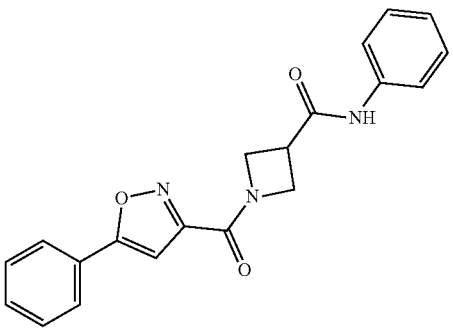
238 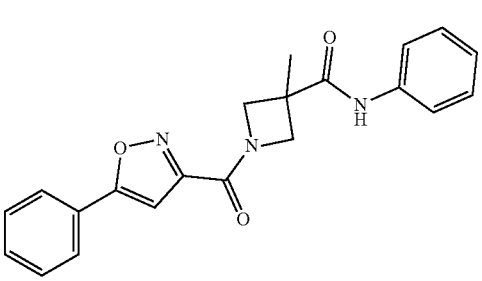
239 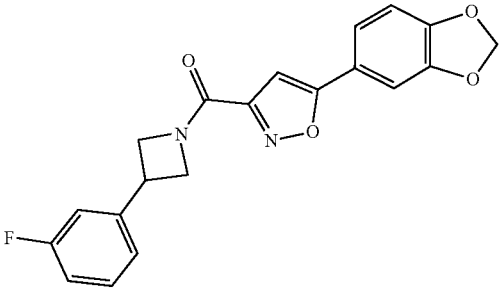
240 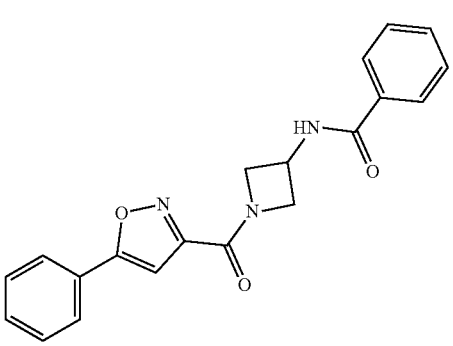
241 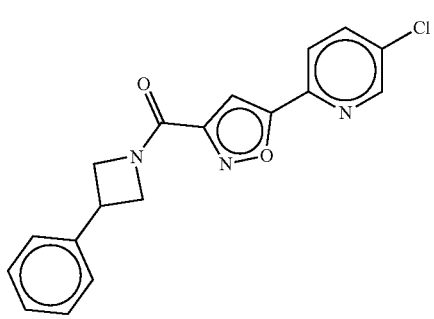

242 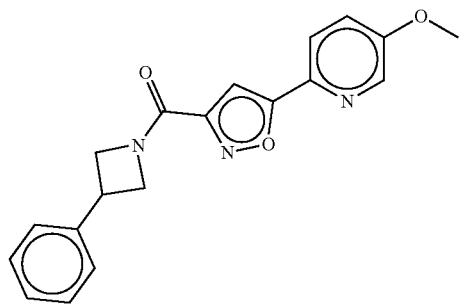
243 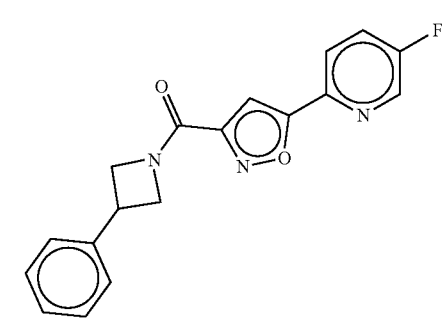
244 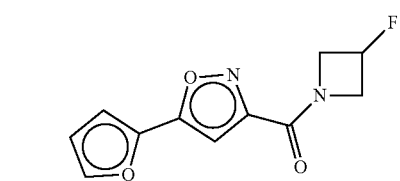
245 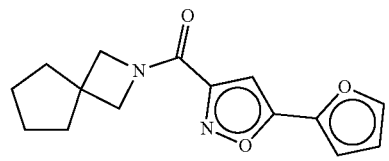
246 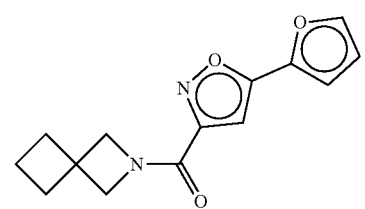
247 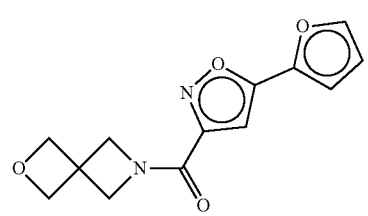
248 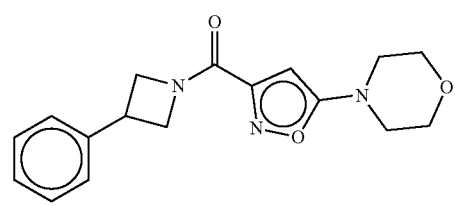
249 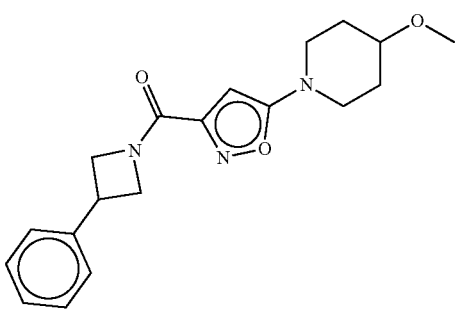
250 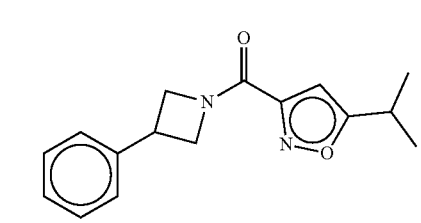
251 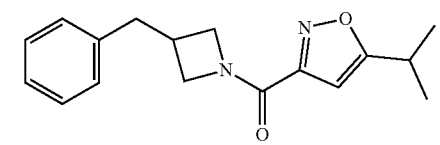
252 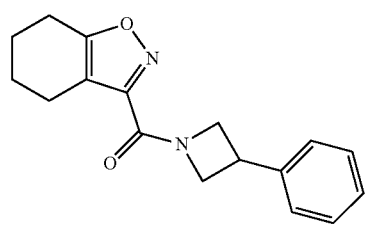
253 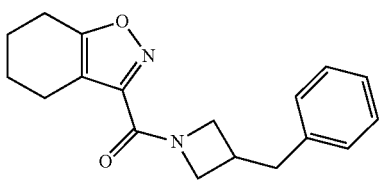
254 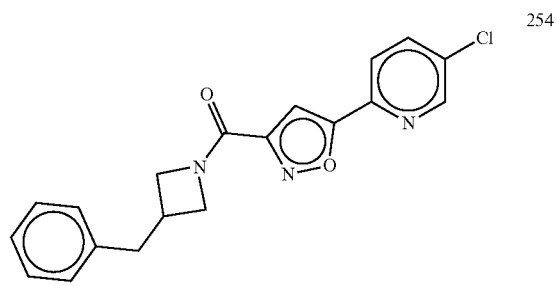

255
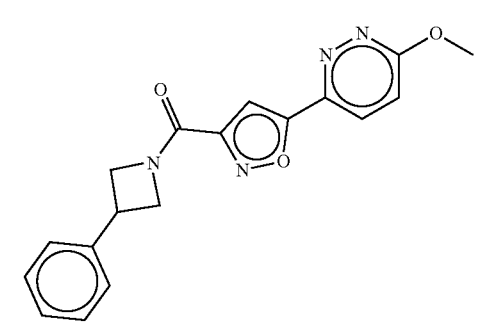
256
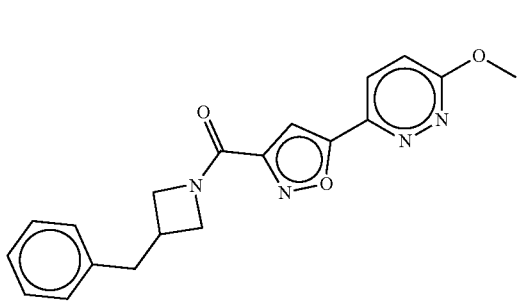
257
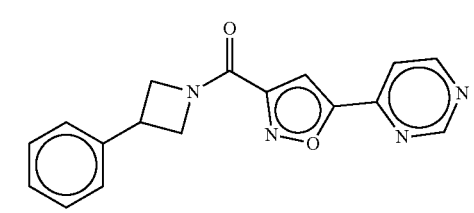
258
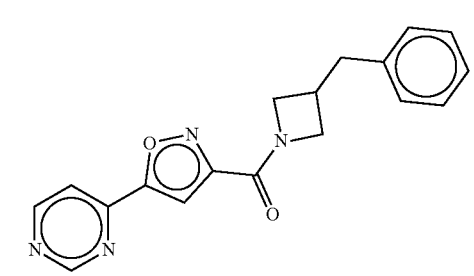
259
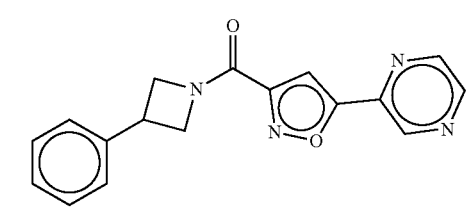
260
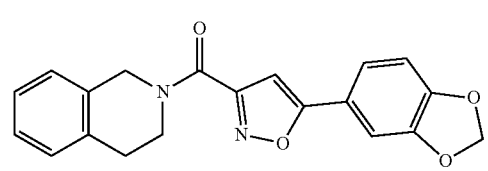
261
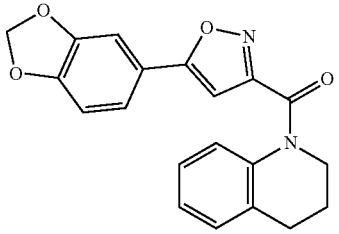
262
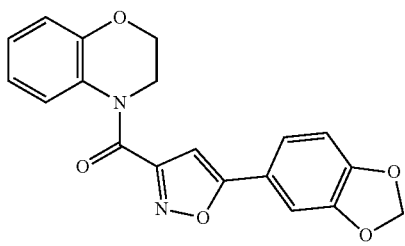
263
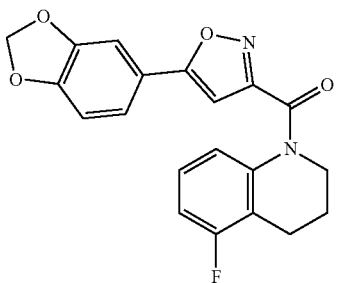
264
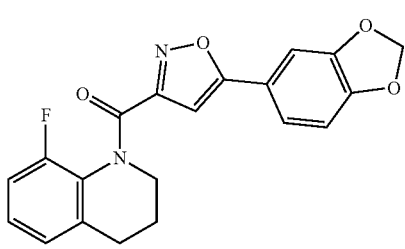
265
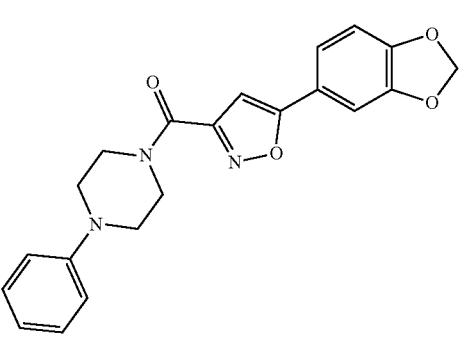
266
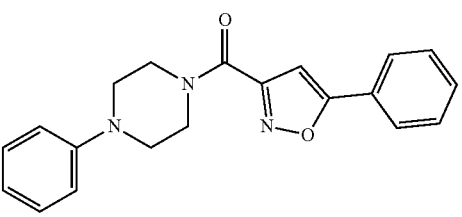

267 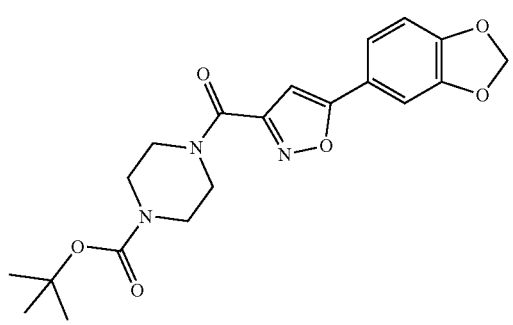
268 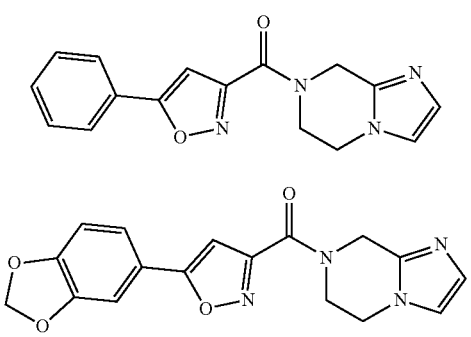
269 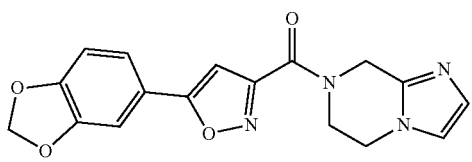
270 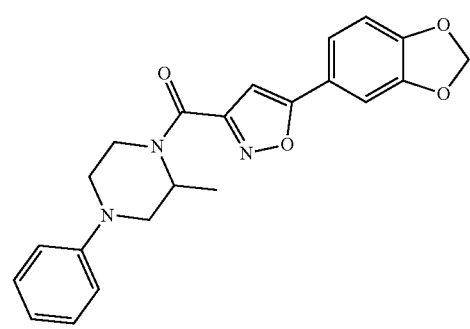
271 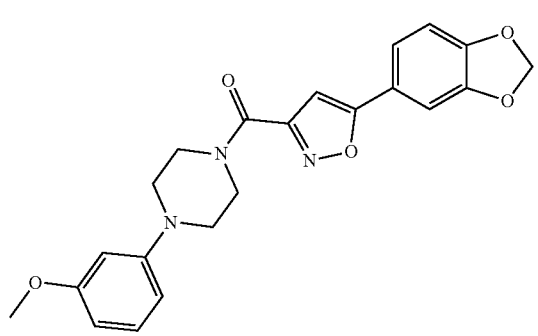
272 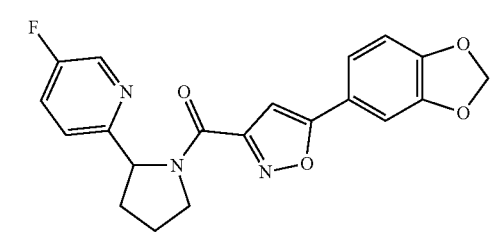
273 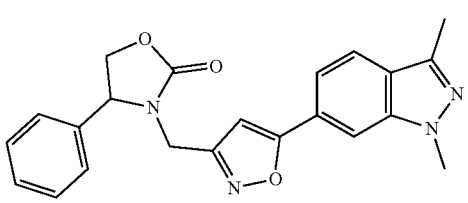
274 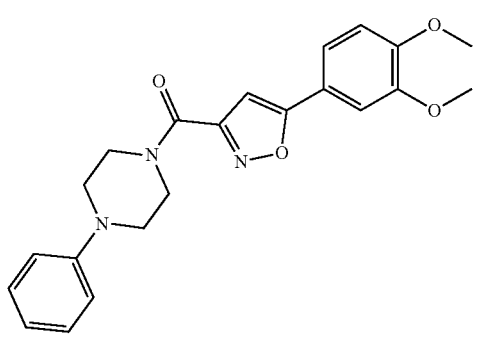
275 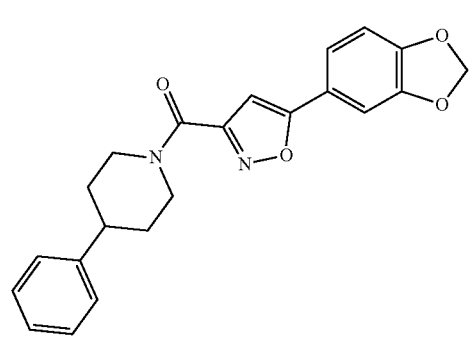
276 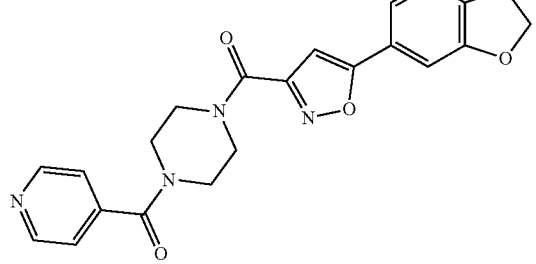
277 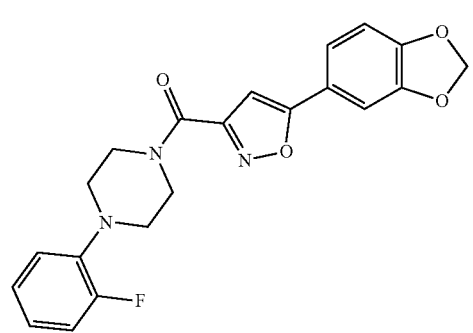

278 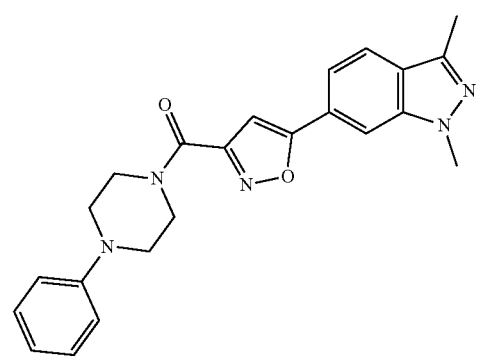
279 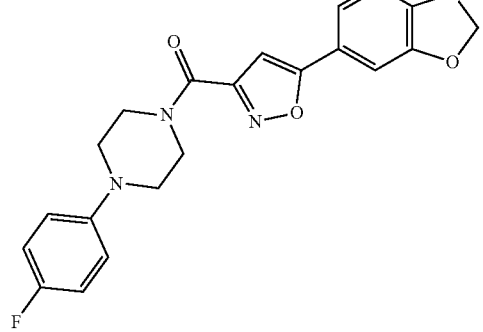
280 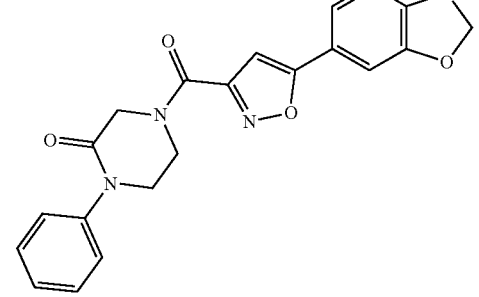
281 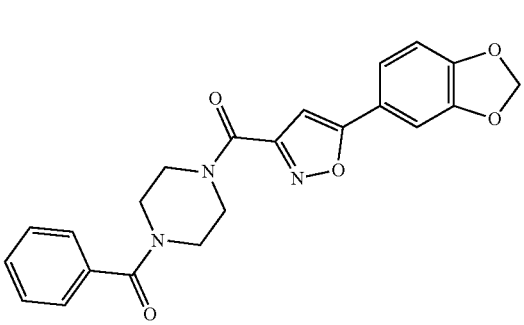
282 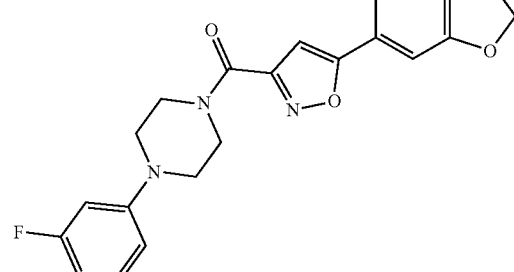
283 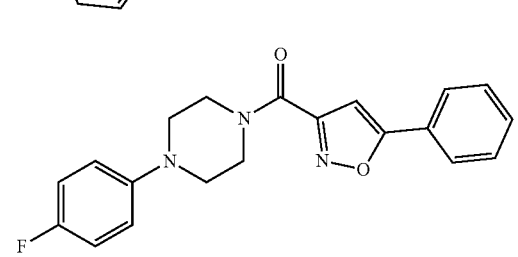
284 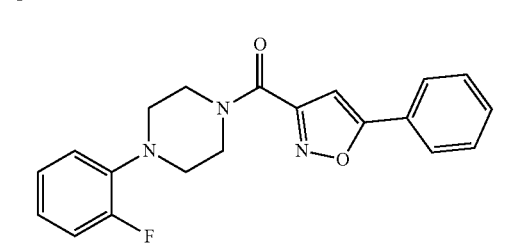
285 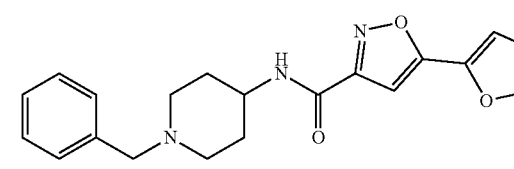
286 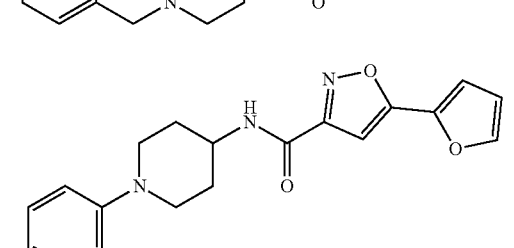
287 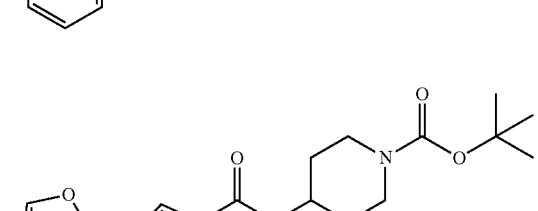
288 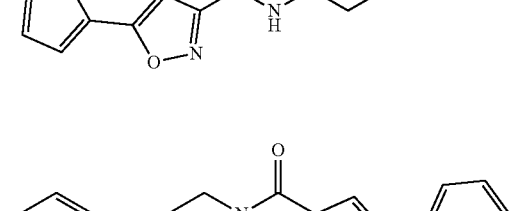

289 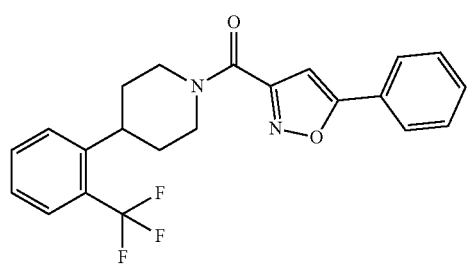
290 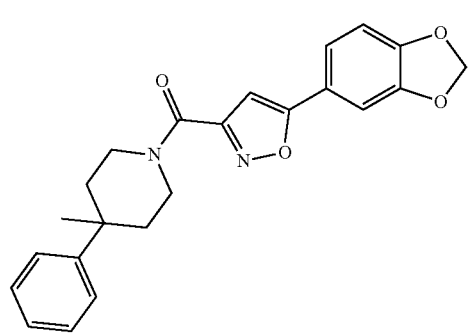
291 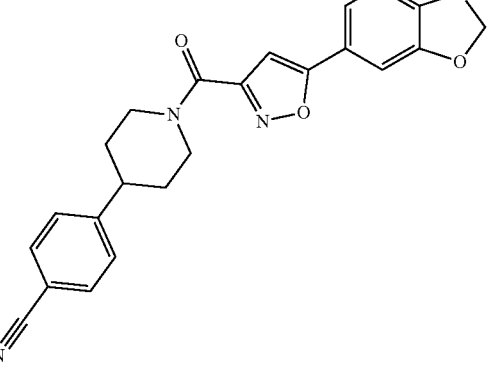
292 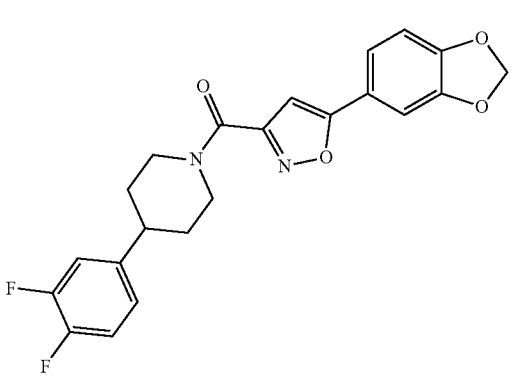
293 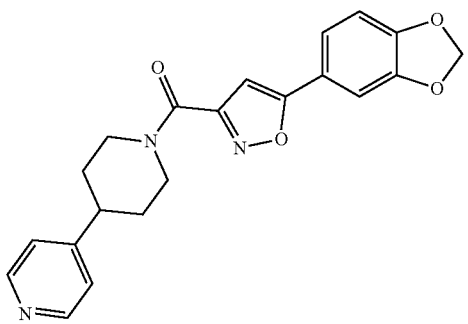
294 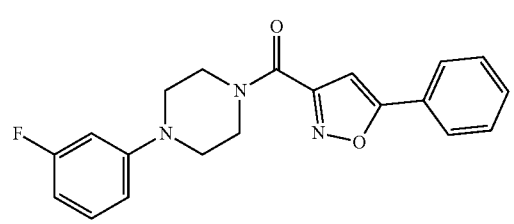
295 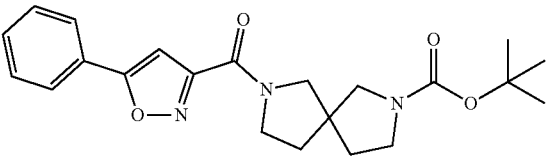
296 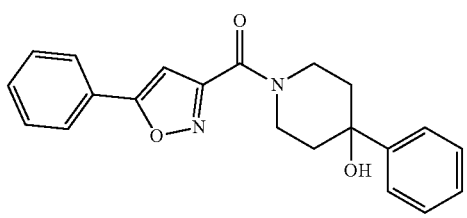
297 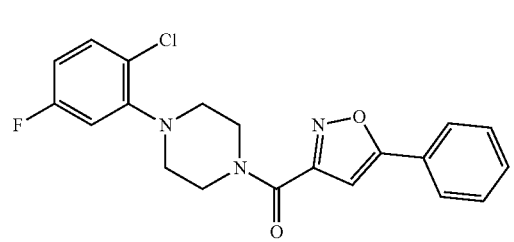
298 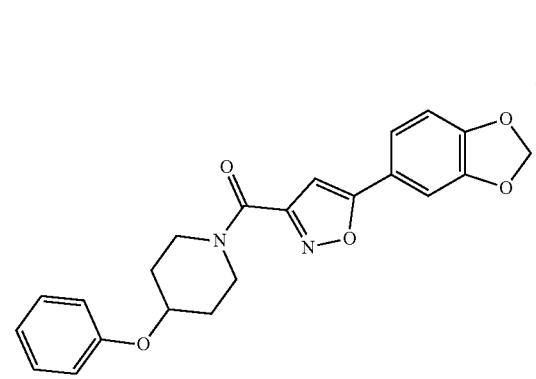

-continued
299
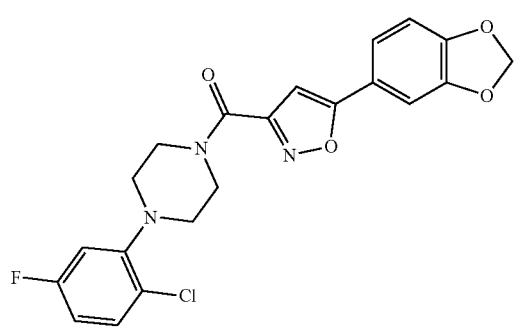
300
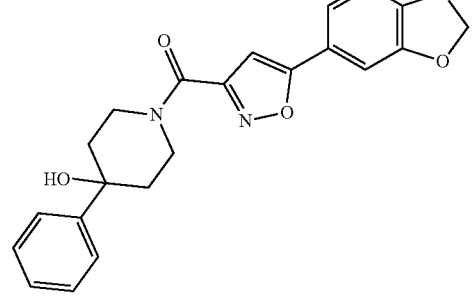
301
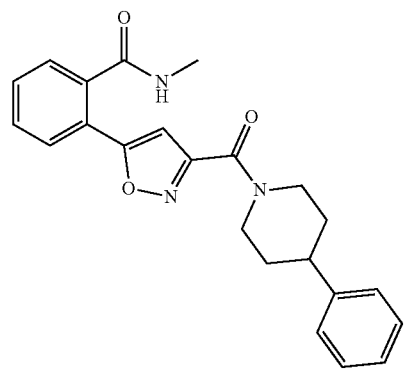
302
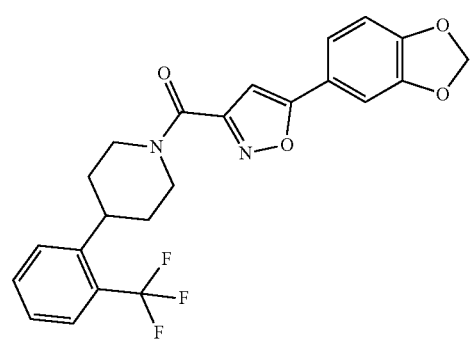
-continued
303
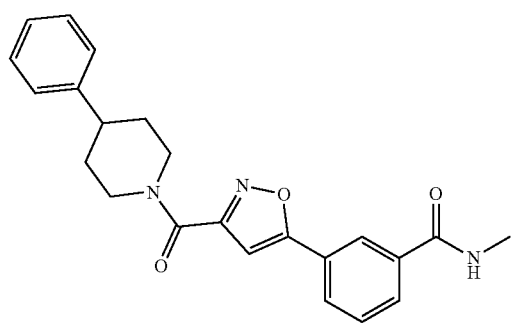
304
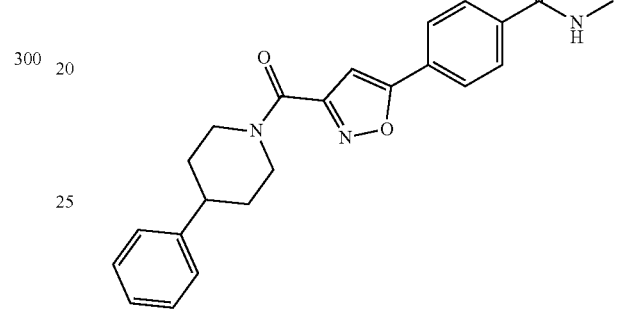
305
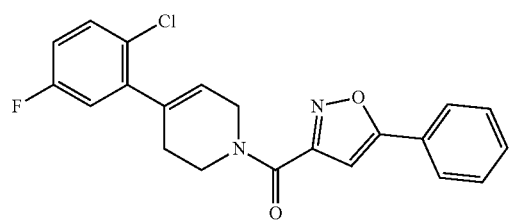
306
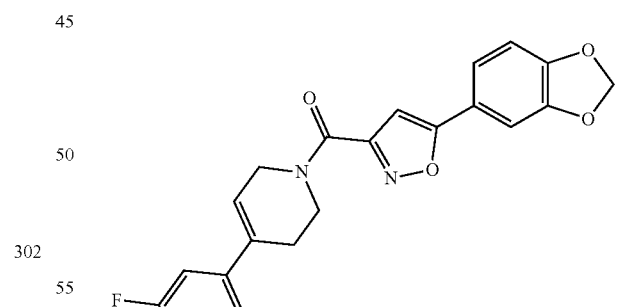
307
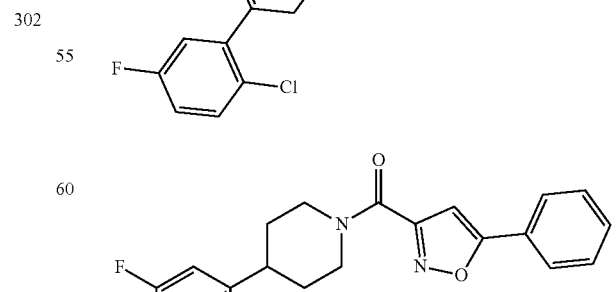

308 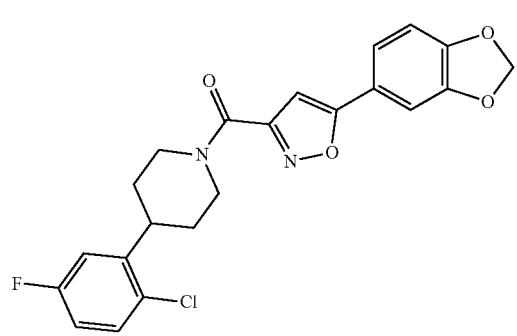
309 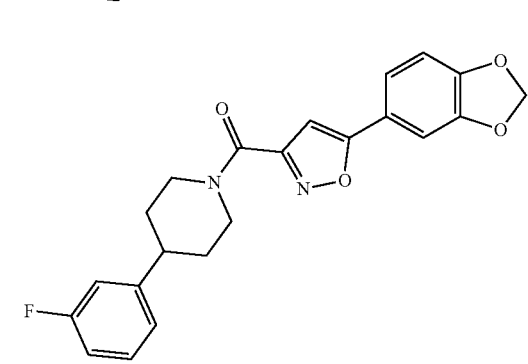
310 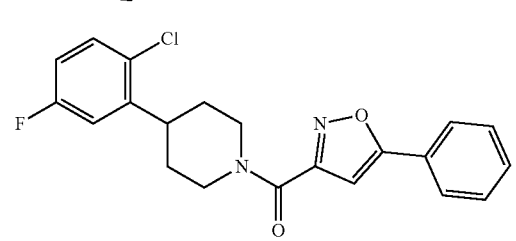
311 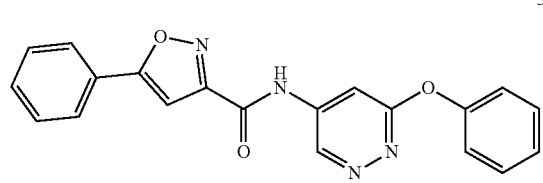
312 
313 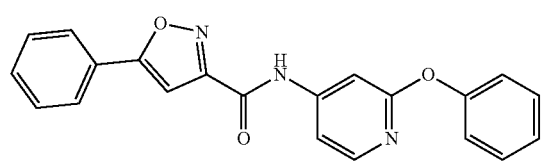
314 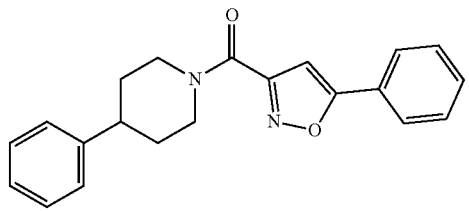
315 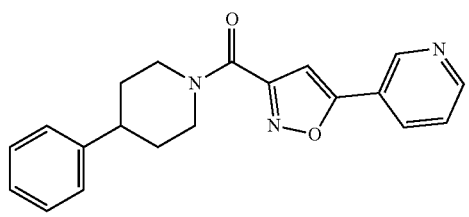
316 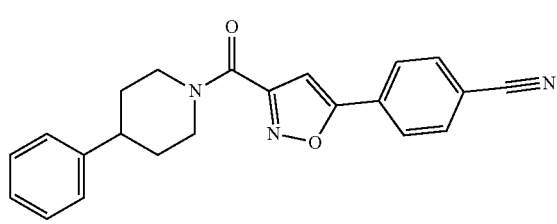
317 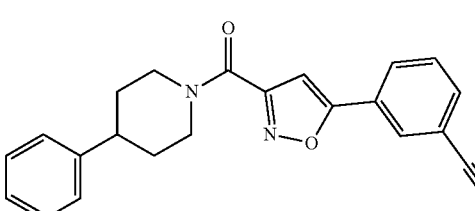
318 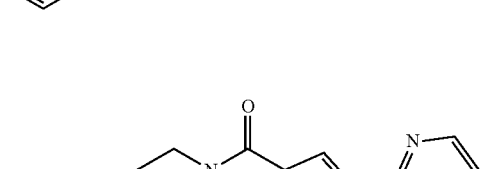
319 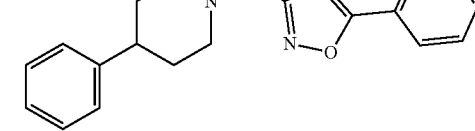

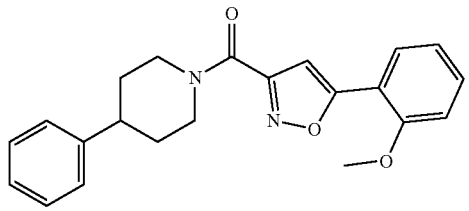
320
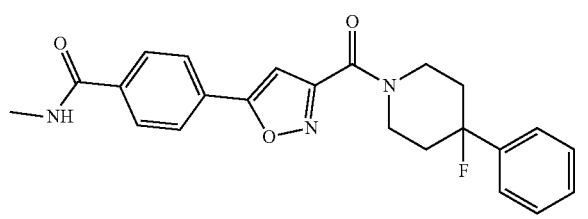
321
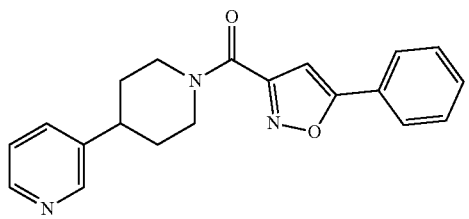
322
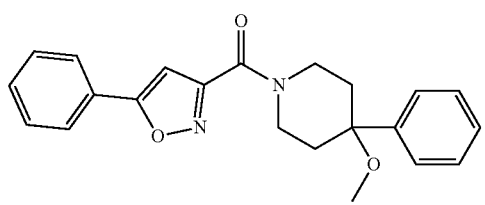
323
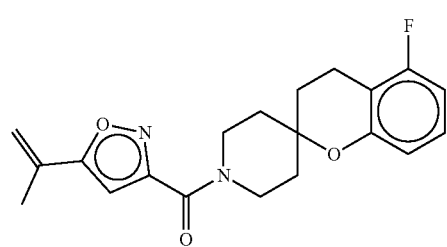
324
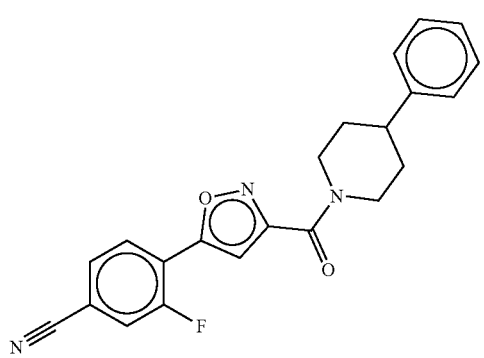
325
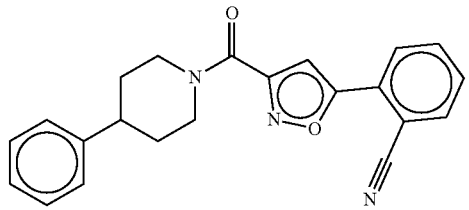
326

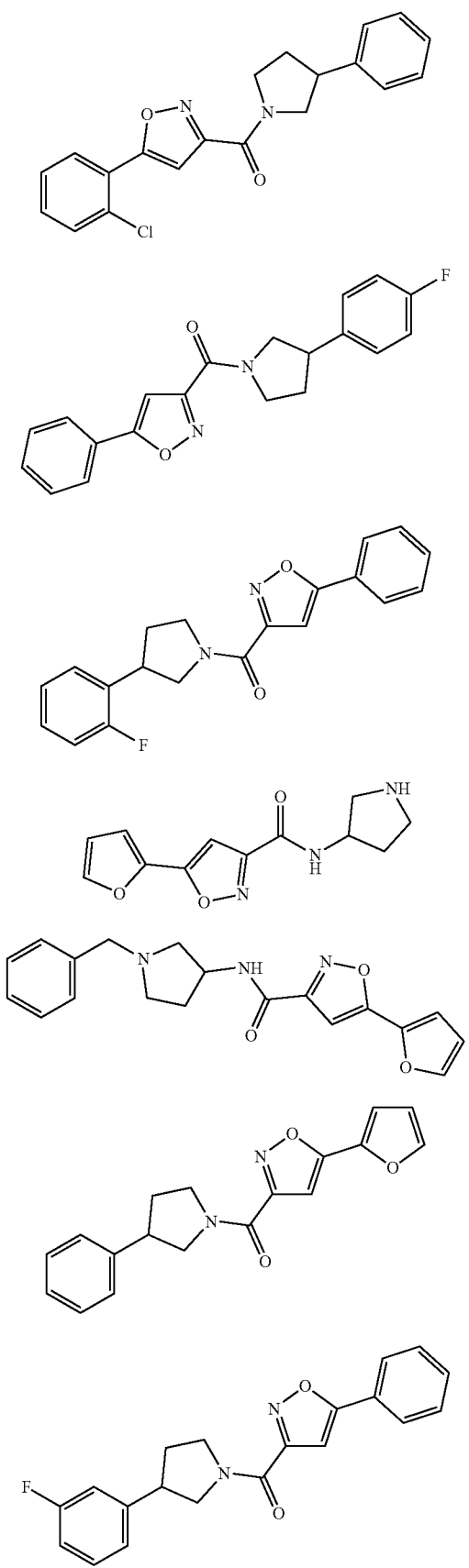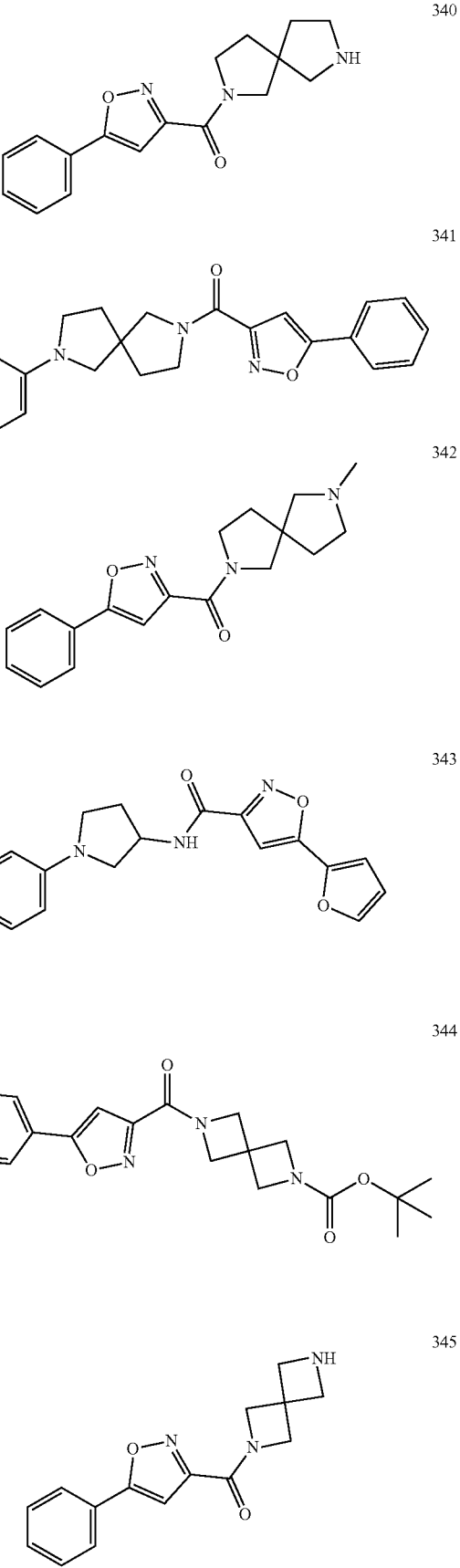

| 346 | 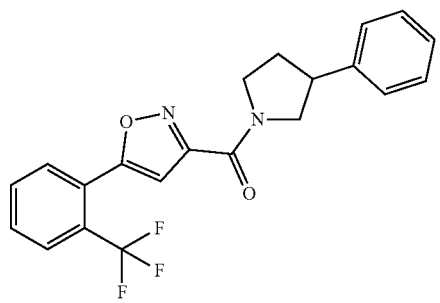 | 352 | 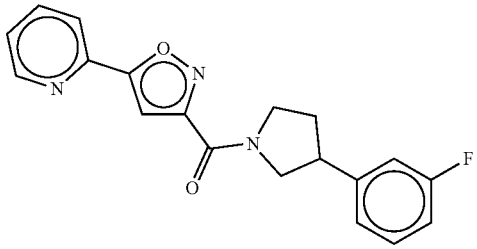 |
| 347 | 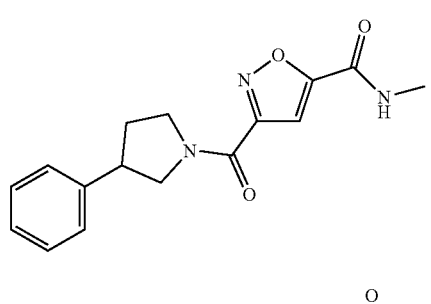 | 353 | 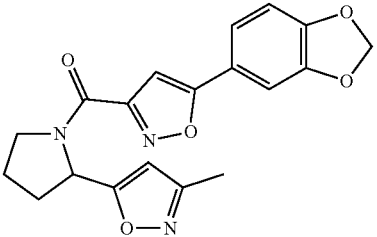 |
| 348 | 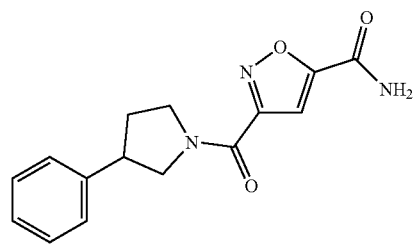 | 354 | 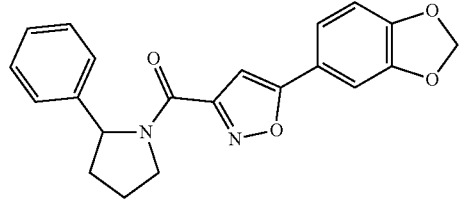 |
| 349 | 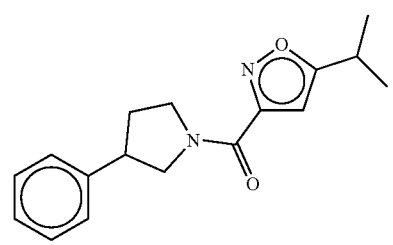 | 355 | 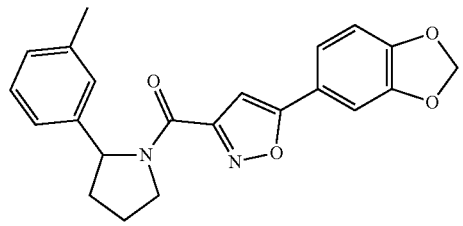 |
| 350 | 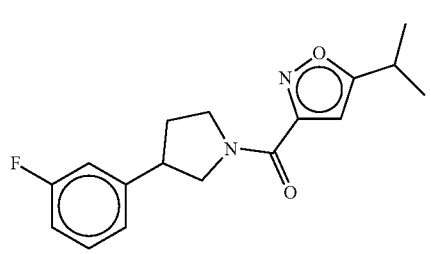 | 356 | 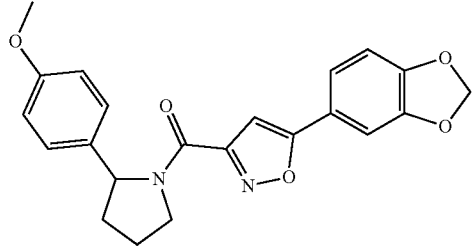 |
| 351 | 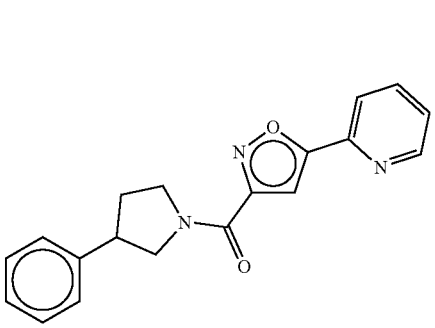 | 357 | 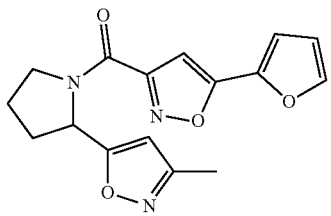 |

541
-continued
358
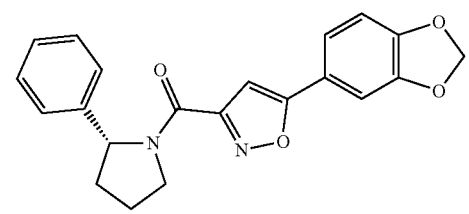
359
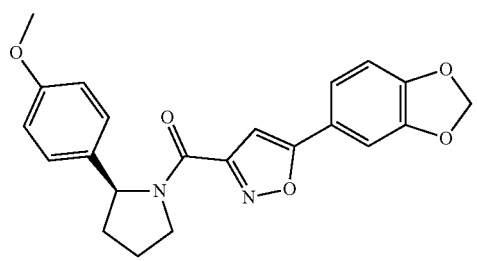
360
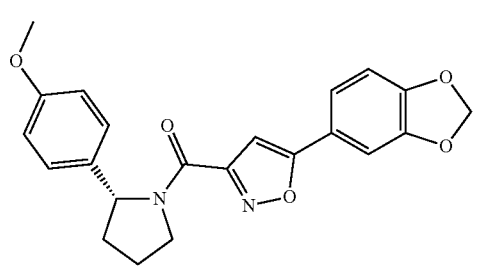
361
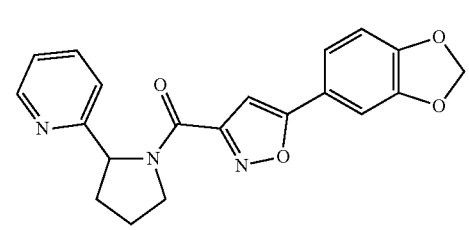
362
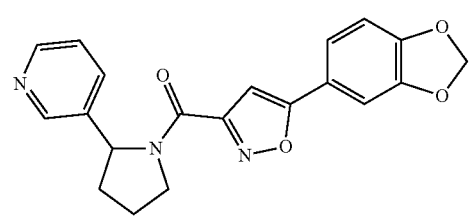
363
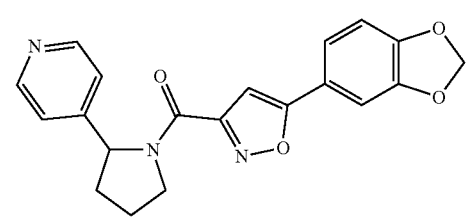
364
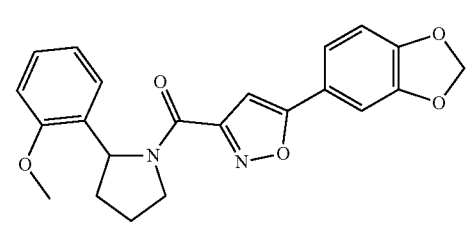
542
-continued
365
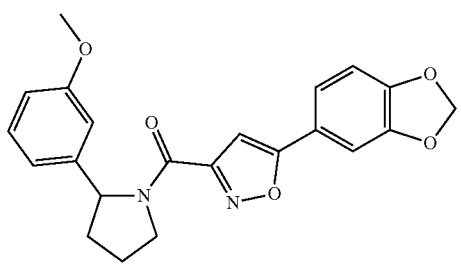
366
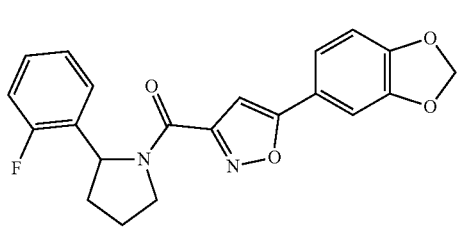
367
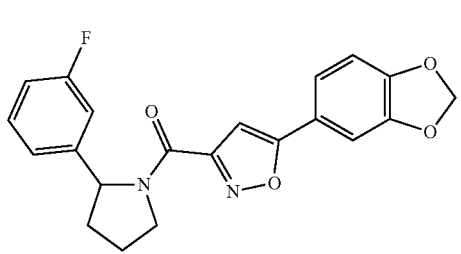
368
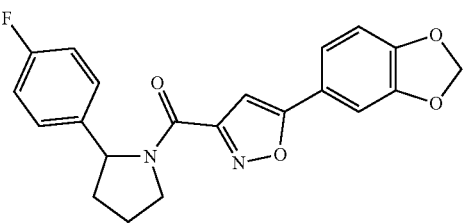
369
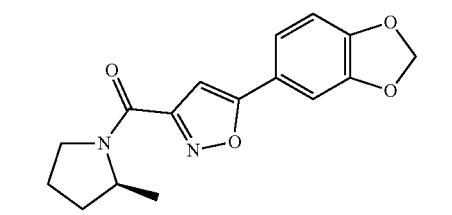
370
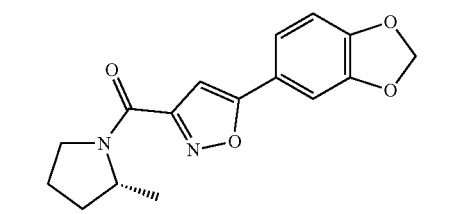
371
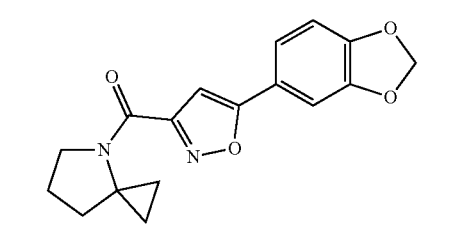

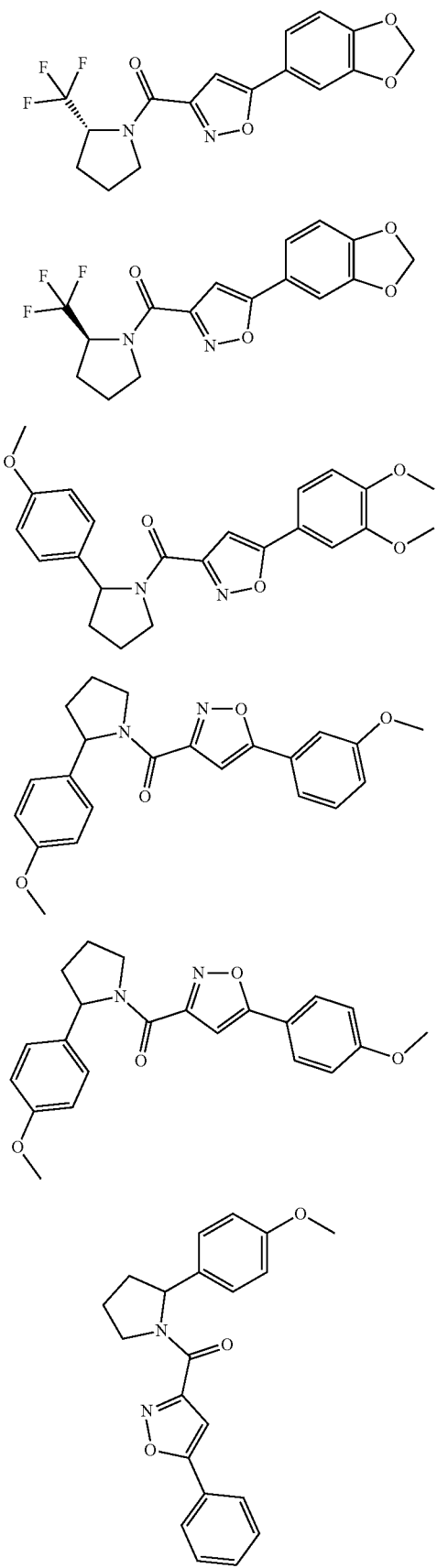
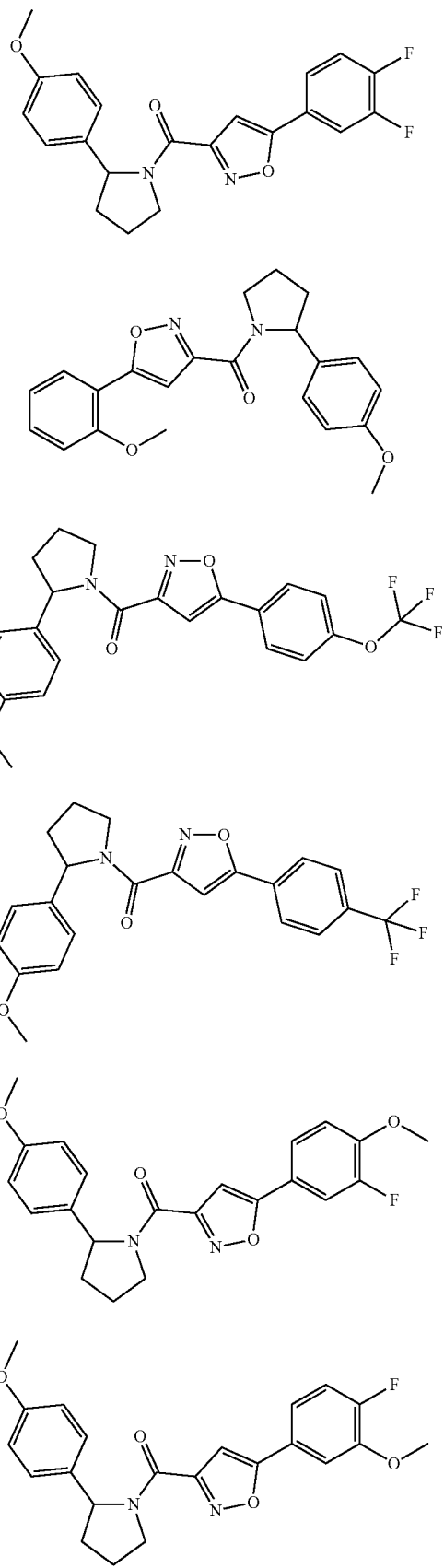

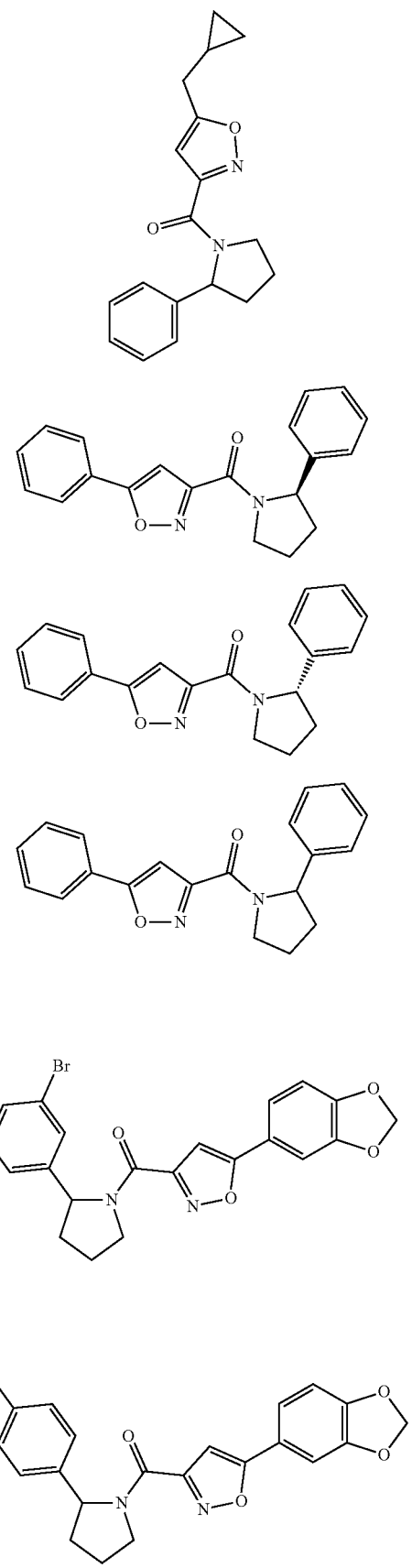
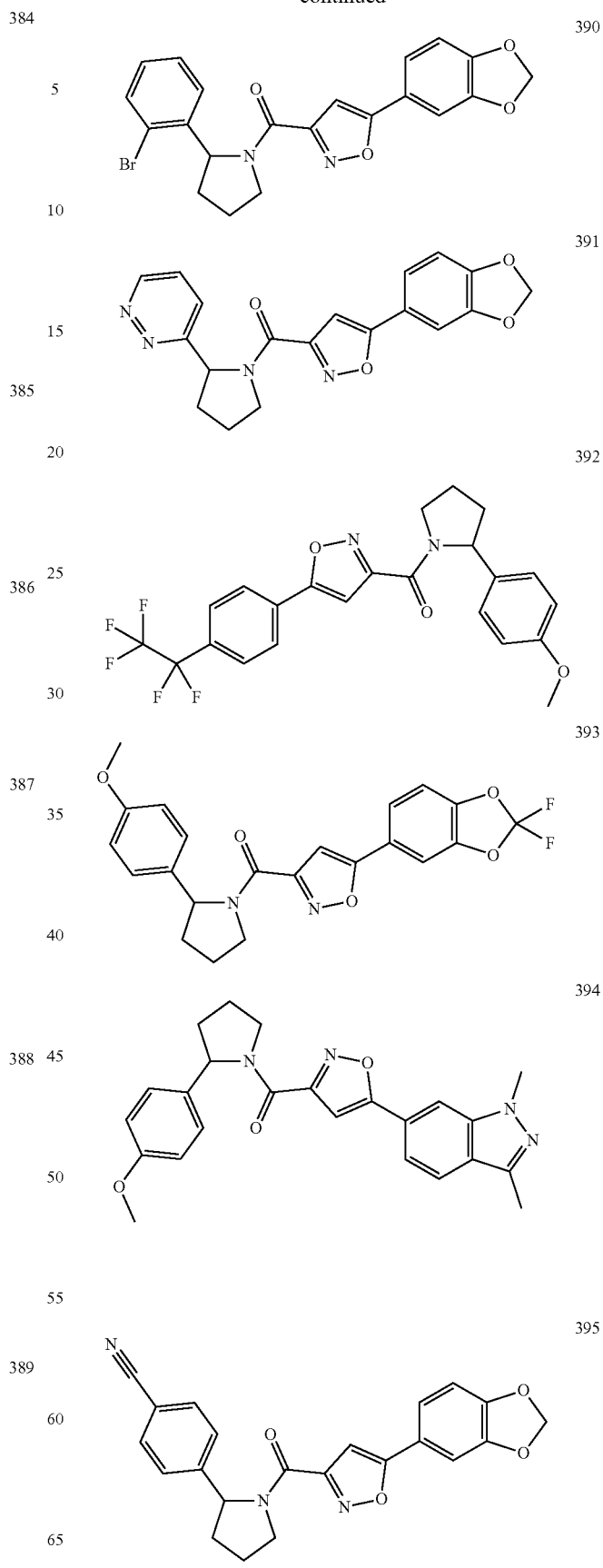

547
-continued
396
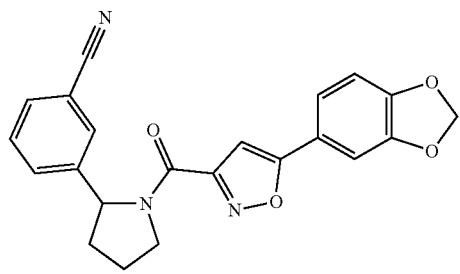
397
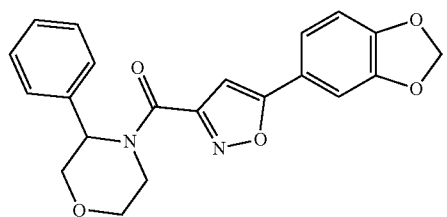
398
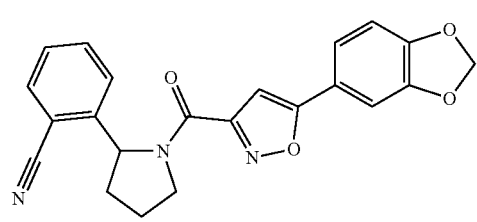
399
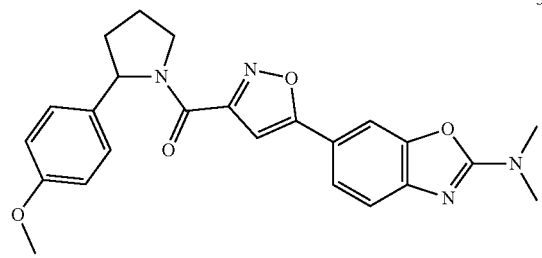
400
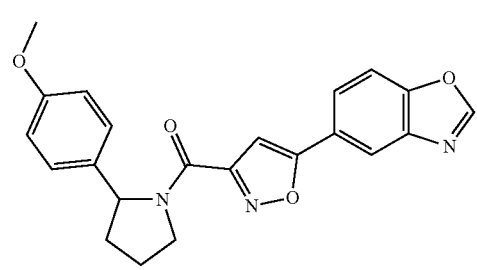
401
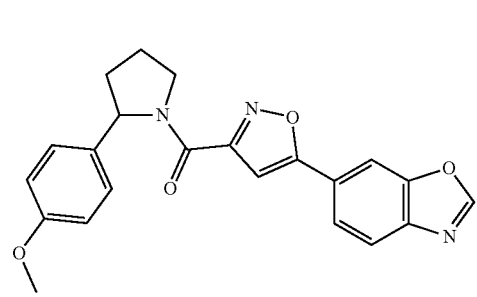
548
-continued
402
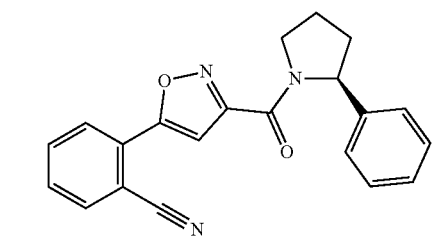
403
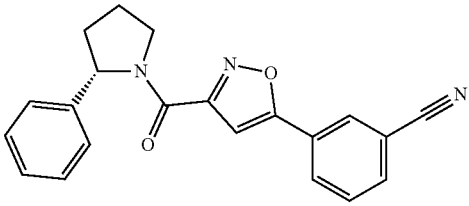
404
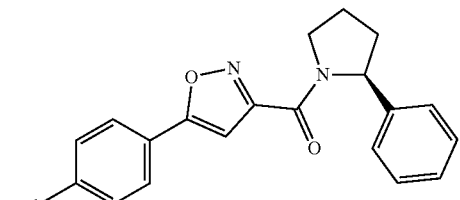
405
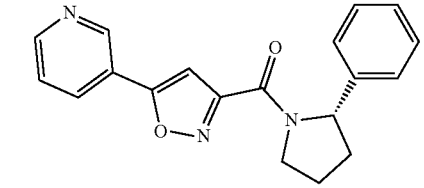
406
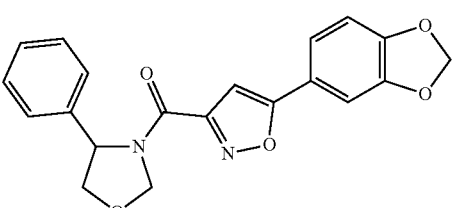
407
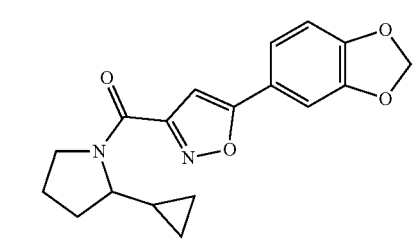
408
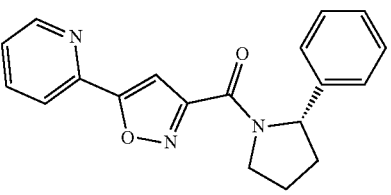

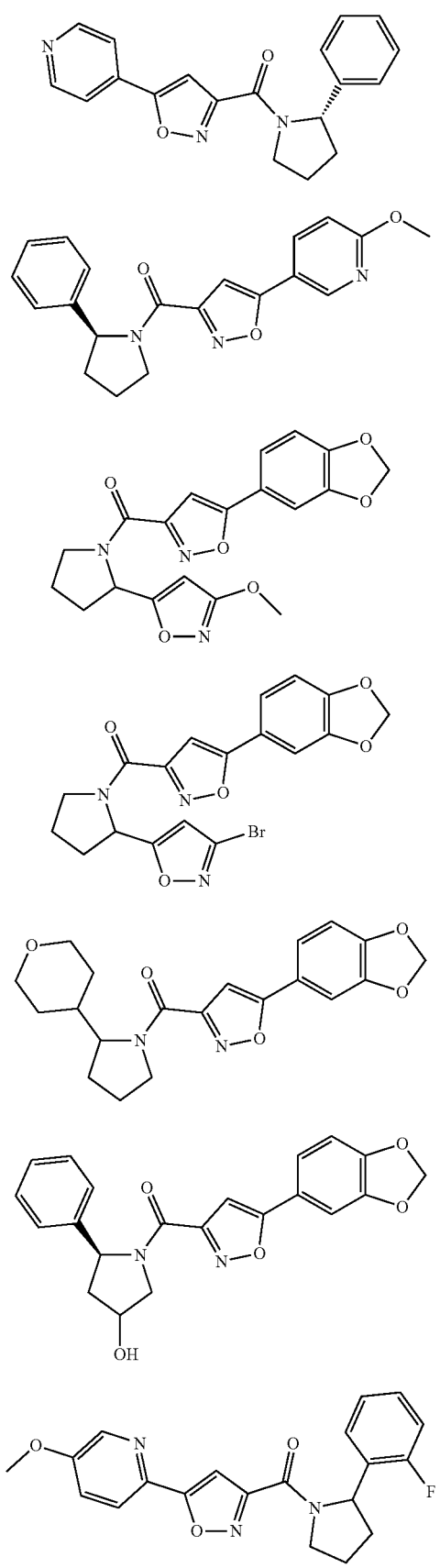
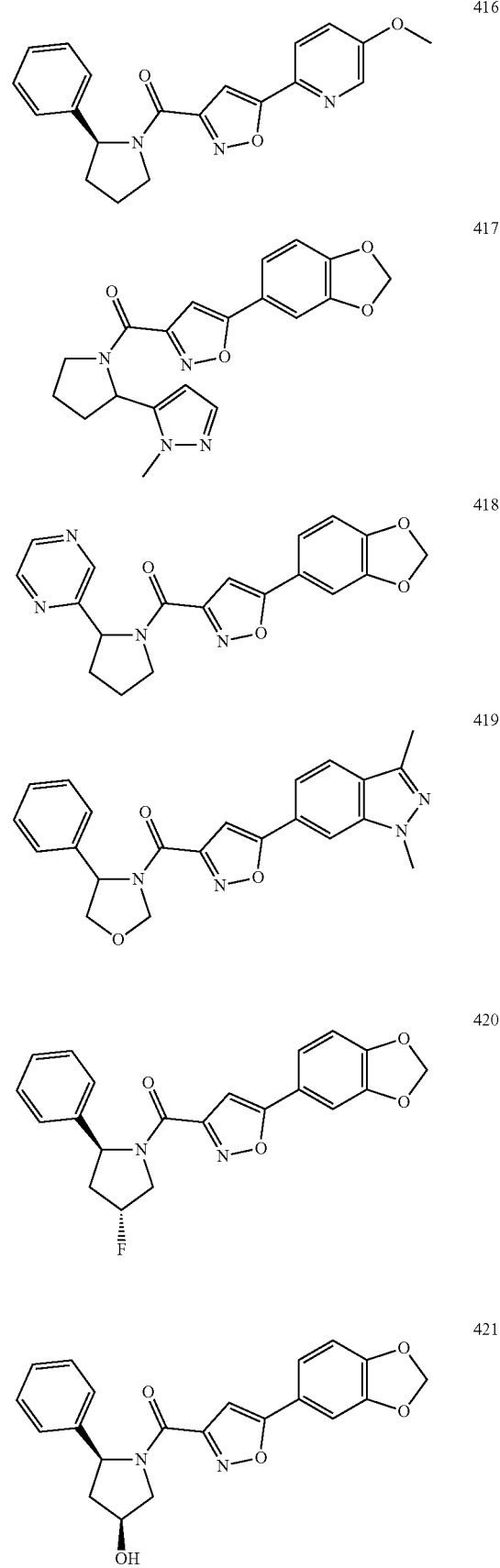

| 551 -continued | | 552 -continued | |
|---|---|---|---|
| 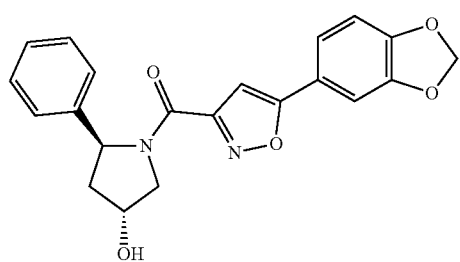 | 422 | 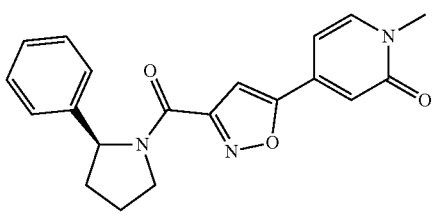 | 428 |
| 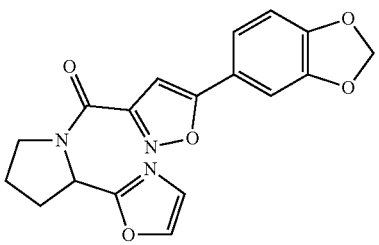 | 423 | 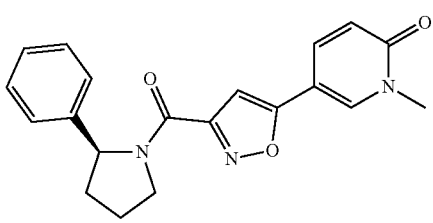 | 429 |
| 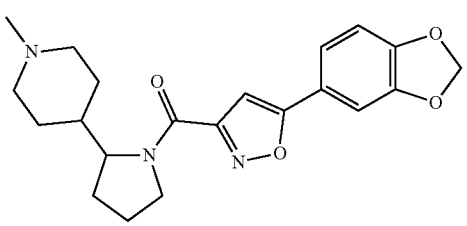 | 424 | 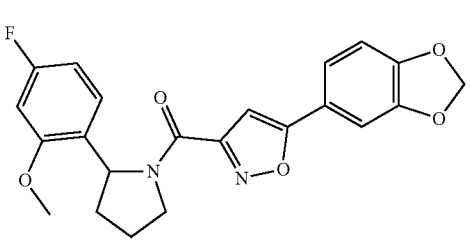 | 430 |
| 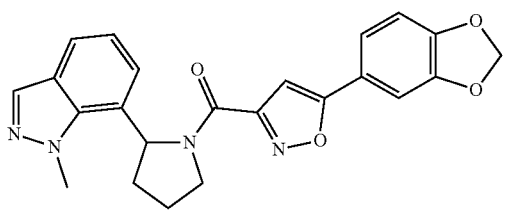 | 425 | 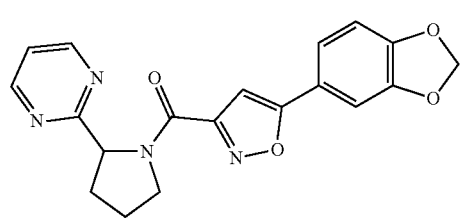 | 431 |
| 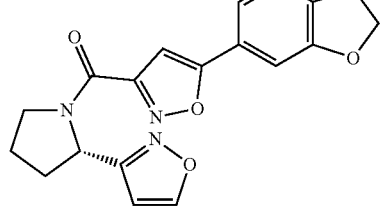 | 426 | 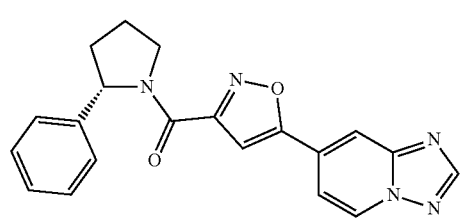 | 432 |
| 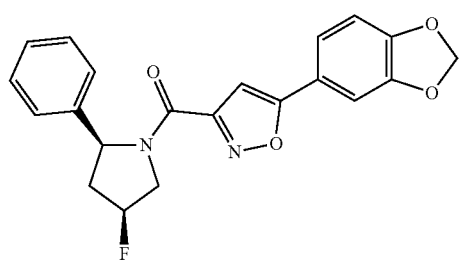 | 427 | 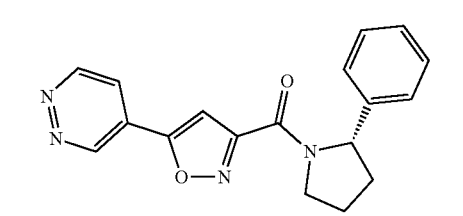 | 433 |
| | | 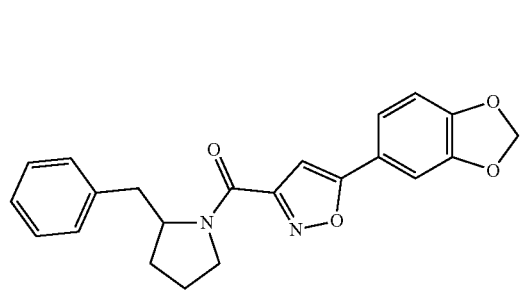 | 434 |

| 435 | 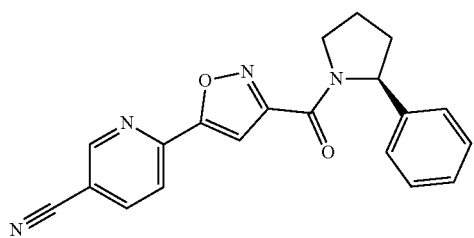 | 441 | 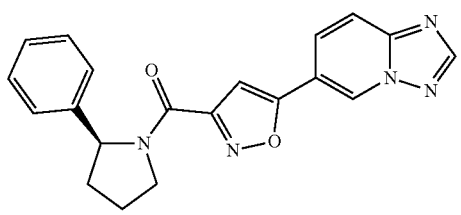 |
| 436 | 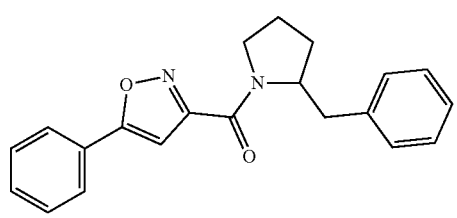 | 442 | 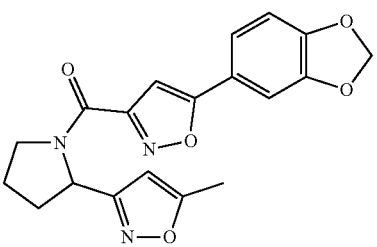 |
| 437 | 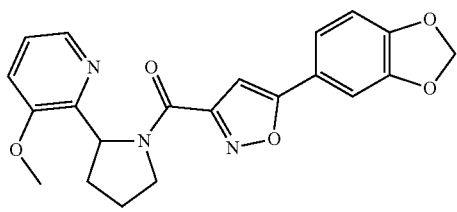 | 443 | 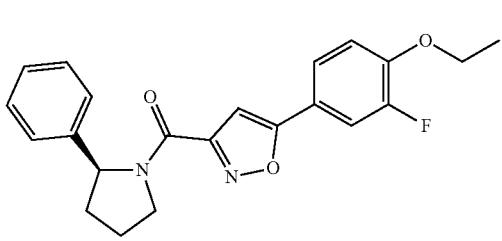 |
| 438 | 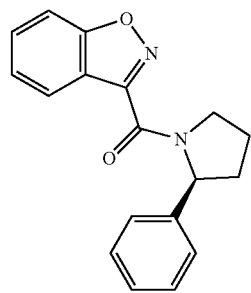 | 444 | 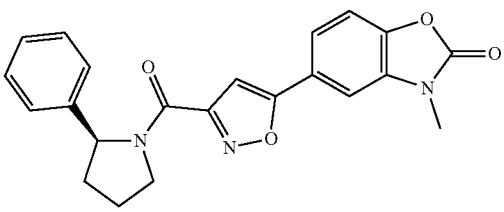 |
| | | 445 | 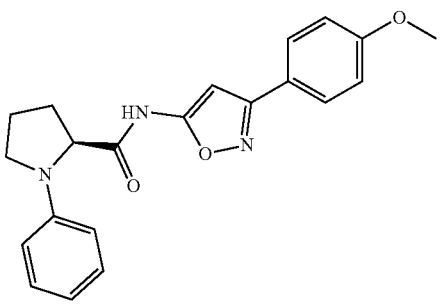 |
| 439 | 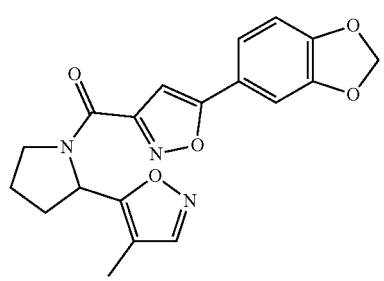 | | |
| 440 | 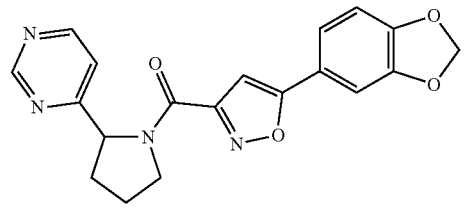 | 446 | 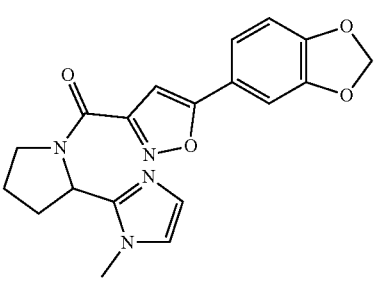 |

| | |
|---|---|
| 447 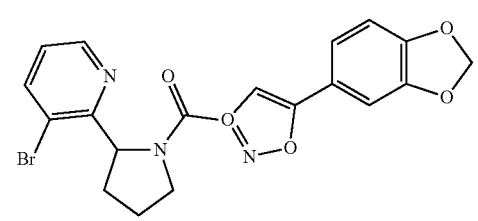 | 454 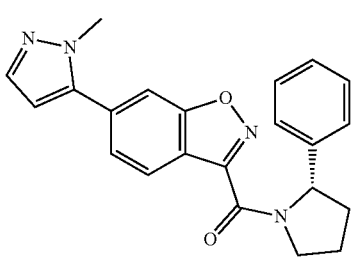 |
| 448 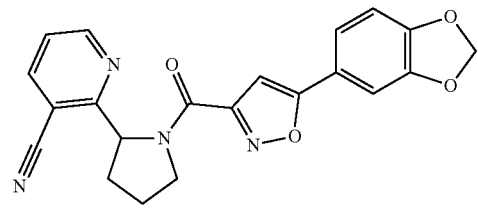 | 455 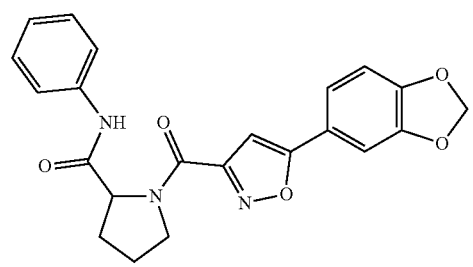 |
| 449 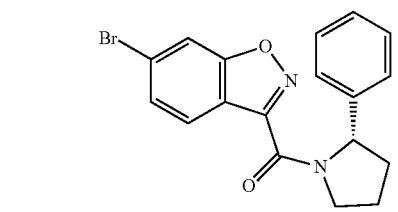 | 456 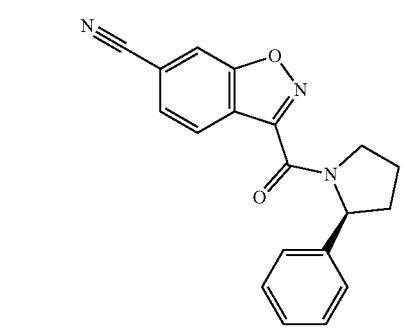 |
| 450 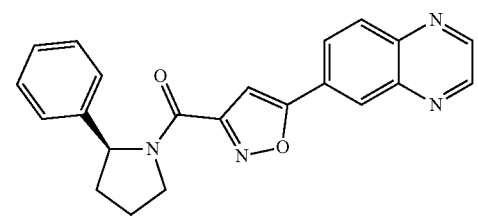 | 457 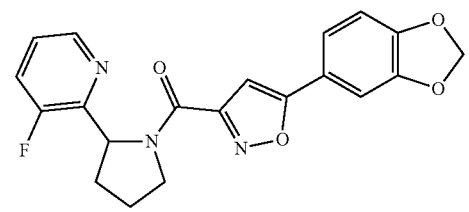 |
| 451 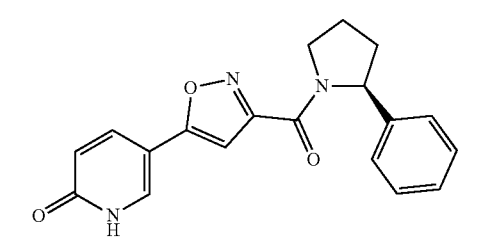 | 458 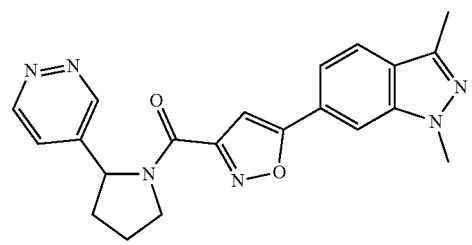 |
| 452 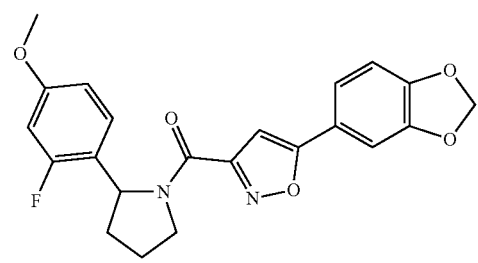 | 459 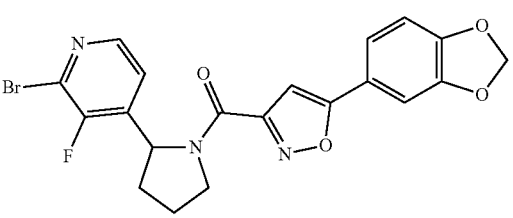 |
| 453 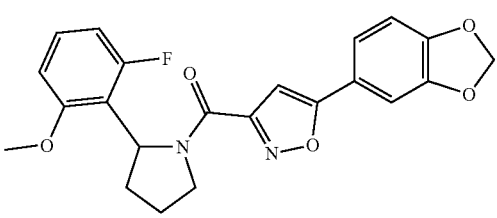 | |

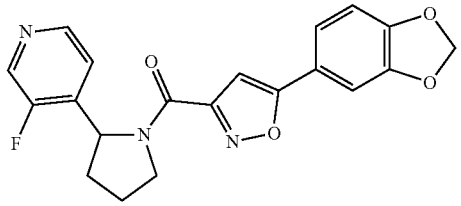

460

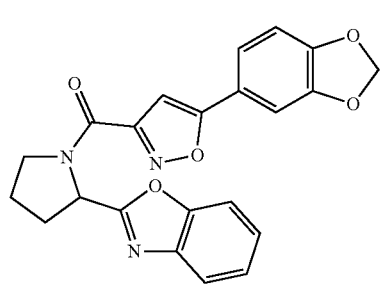

461

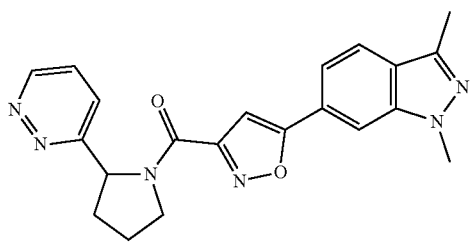

462

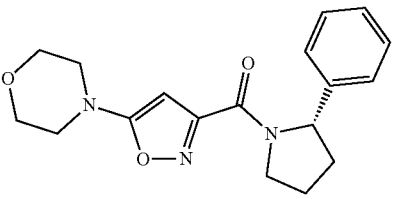

463

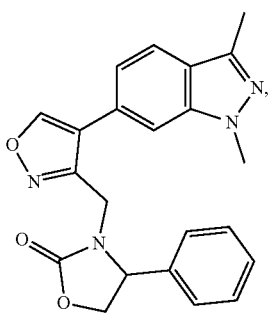

464 and pharmaceutically acceptable salts thereof.

13. A pharmaceutical composition comprising a compound, or pharmaceutically acceptable salt thereof, of claim 1, and a pharmaceutically acceptable excipient.

14. A method of inhibiting toxicity in a cell related to a protein, the method comprising administering an effective amount of a compound of claim 1.

15. A method of inhibiting SCD5, the method comprising contacting a cell with an effective amount of a compound of claim 1.

16. A method of inhibiting SCD1, the method comprising contacting a cell with an effective amount of a compound of claim 1.

* * * * *

UNITED STATES PATENT AND TRADEMARK OFFICE
CERTIFICATE OF CORRECTION

PATENT NO. : 10,919,885 B2
APPLICATION NO. : 16/393183
DATED : February 16, 2021
INVENTOR(S) : Iwona Wrona et al.

It is certified that error appears in the above-identified patent and that said Letters Patent is hereby corrected as shown below:

In the Claims

Column 507, Lines 22-29, replace

"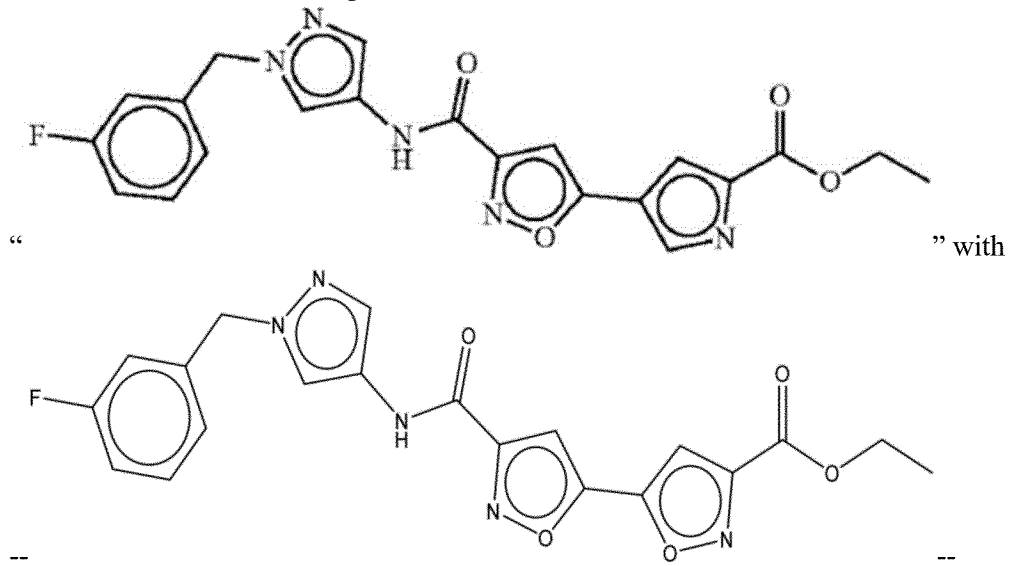" with

--  --

Column 508, Lines 30-35, replace

"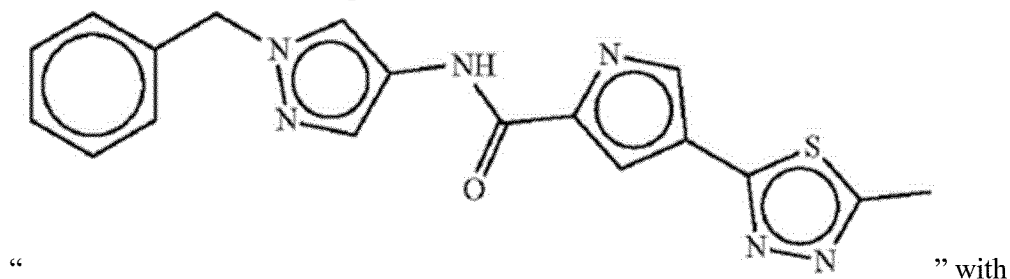" with

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,919,885 B2

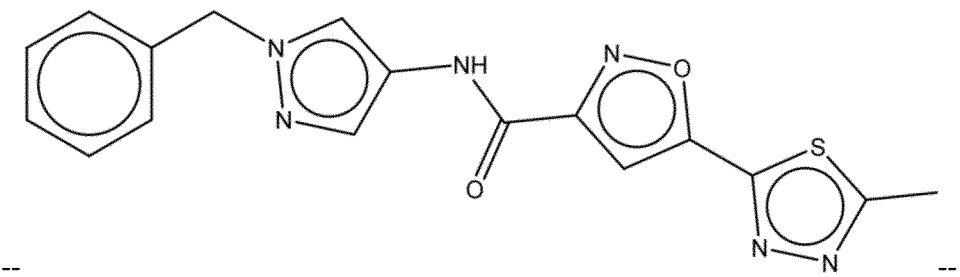

Column 508, Lines 40-45, replace

" 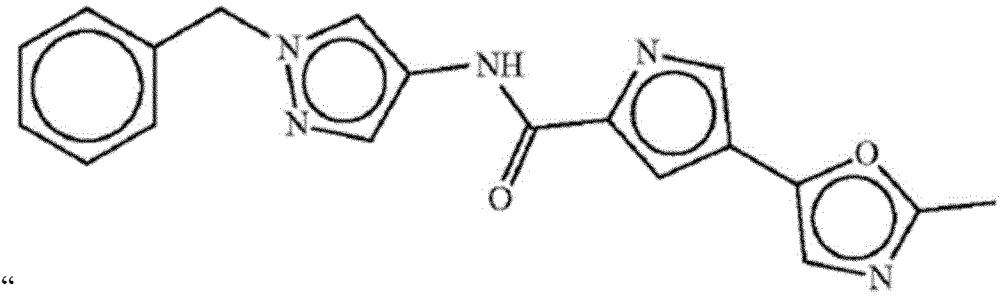 " with

-- 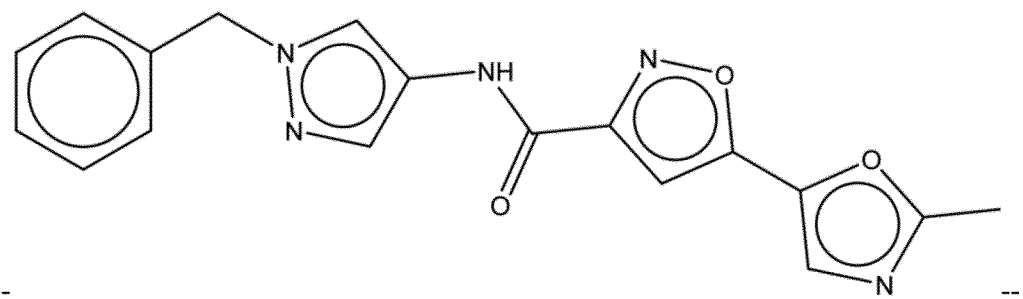 --